US012522601B2

(12) United States Patent
Lee et al.

(10) Patent No.: US 12,522,601 B2
(45) Date of Patent: Jan. 13, 2026

(54) 1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

(71) Applicant: CHONG KUN DANG PHARMACEUTICAL CORP., Seoul (KR)

(72) Inventors: Chang Kon Lee, Yongin-si (KR); Moo Sung Ko, Yongin-si (KR); Seok Hyoun Yun, Yongin-si (KR); Seo Young Lee, Yongin-si (KR); Hyunjin Michael Kim, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 689 days.

(21) Appl. No.: 17/904,809

(22) PCT Filed: Feb. 25, 2021

(86) PCT No.: PCT/KR2021/002364
§ 371 (c)(1),
(2) Date: Aug. 23, 2022

(87) PCT Pub. No.: WO2021/172887
PCT Pub. Date: Sep. 2, 2021

(65) Prior Publication Data

US 2023/0271955 A1 Aug. 31, 2023

(30) Foreign Application Priority Data

Feb. 25, 2020 (KR) ........................ 10-2020-0023251

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
USPC ..................................................... 514/210.16
See application file for complete search history.

(56) References Cited

U.S. PATENT DOCUMENTS

| | | | | |
|---|---|---|---|---|
| 6,936,608 | B2 * | 8/2005 | Bettati | A61P 25/00 514/243 |
| 2010/0120761 | A1 | 5/2010 | Berdini et al. | |
| 2012/0041000 | A1 | 2/2012 | Saxty et al. | |
| 2018/0023114 | A1 | 1/2018 | Morin et al. | |
| 2018/0215743 | A1 | 8/2018 | Lee et al. | |
| 2018/0230113 | A1 | 8/2018 | Lee et al. | |
| 2018/0230114 | A1 | 8/2018 | Lee et al. | |

FOREIGN PATENT DOCUMENTS

| | | | |
|---|---|---|---|
| AU | 2016299484 | B2 | 8/2019 |
| KR | 20120034635 | A | 4/2012 |
| RU | 2695227 | C1 | 7/2019 |
| RU | 2700696 | C2 | 9/2019 |
| RU | 2709207 | C2 | 12/2019 |
| TW | 201712007 | A | 4/2017 |
| TW | 202146409 | A | 12/2021 |
| WO | 2009002534 | A1 | 12/2008 |
| WO | 2011011186 | A2 | 1/2011 |
| WO | 2011038086 | A2 | 3/2011 |
| WO | 2011091213 | A2 | 7/2011 |
| WO | 2013008162 | A1 | 1/2013 |
| WO | 2013041407 | A1 | 3/2013 |
| WO | 2013052110 | A1 | 4/2013 |
| WO | 2013066833 | A1 | 5/2013 |
| WO | 2013066835 | A2 | 5/2013 |
| WO | 2013066838 | A1 | 5/2013 |
| WO | 2013066839 | A2 | 5/2013 |
| WO | 2013080120 | A1 | 6/2013 |
| WO | 2013134467 | A1 | 9/2013 |
| WO | 2017018804 | A1 | 2/2017 |
| WO | 2017030938 | A1 | 2/2017 |
| WO | 2017222950 | A1 | 12/2017 |
| WO | 2017222951 | A1 | 12/2017 |
| WO | 2019110663 | A1 | 6/2019 |
| WO | 2021127643 | A1 | 6/2021 |
| WO | 2021172886 | A1 | 9/2021 |

OTHER PUBLICATIONS

Bolden et al. "Anticancer activities of histone deacetylase inhibitors" Nature Reviews Drug Discovery, 5:769-784 (2006).
Chen et al. "Computational Exploration of Zinc Binding Groups for HDAC Inhibition" The Journal of Organic Chemistry, 78(10):5051-5055 (2013).
Hassig et al. "Nuclear histone acetylases and deacetylases and transcriptional regulation: HATs off to HDACs" Current Opinion in Chemical Biology, 1:300-308 (1997).
International Search Report and the Written Opinion of the International Searching Authority corresponding to International Patent Application No. PCT/KR2021/002364 (10 pages) (mailed Jun. 11, 2021).

(Continued)

*Primary Examiner* — Niloofar Rahmani
(74) *Attorney, Agent, or Firm* — Myers Bigel, P.A.

(57) ABSTRACT

The present invention relates to a novel compound having a histone deacetylase 6 (HDAC6) inhibitory activity, an isomer thereof or a pharmaceutically acceptable salt thereof, the use thereof for preparing a therapeutic medicament; a pharmaceutical composition containing the same, and a treatment method using the composition; and a preparation method thereof. The novel compound, the isomer thereof, or the pharmaceutically acceptable salt thereof according to the present invention has the HDAC6 inhibitory activity, which is effective in the prevention or treatment of HDAC6-mediated diseases including cancer, inflammatory diseases, autoimmune diseases, neurological or neurodegenerative diseases.

13 Claims, No Drawings

(56) References Cited

OTHER PUBLICATIONS

Kovacs et al. "HDAC6 Regulates Hsp90 Acetylation and Chaperone-Dependent Activation of Glucocorticoid Receptor" Molecular Cell, 18:601-607 (2005).
Li et al. "Discovery of a new class of histone deacetylase inhibitors with a novel zinc binding group" MedChemComm, 6:613-618 (2015).
Li et al. "HDAC6 α-tubulin deacetylase: A potential therapeutic target in neurodegenerative diseases" Journal of the Neurological Sciences, 304:1-8 (2011).
Methot et al. "Exploration of the internal cavity of histone deacetylase (HDAC) with selective HDAC1/HDAC2 Inhibitors (SHI-1:2)" Bioorganic & Medicinal Chemistry Letters, 18:973-978 (2008).
Santo et al. "Preclinical activity, pharmacodynamic, and pharmacokinetic properties of a selective HDAC6 inhibitor, ACY-1215, in combination with bortezomib in multiple myeloma" Blood, 119(11):2579-2589 (2012).
Subramanian et al. "Clinical Toxicities of Histone Deacetylase Inhibitors" Pharmaceuticals, 3:2751-2767 (2010).
Vishwakarma et al. "Tubastatin, a selective histone deacetylase 6 inhibitor shows anti-inflammatory and anti-rheumatic effects" International Immunopharmacology, 16:72-78 (2013).
Warrell et al. "Therapeutic Targeting of Transcription in Acute Promyelocytic Leukemia by Use of an Inhibitor of Histone Deacetylase" Journal of the National Cancer Institute, 90(21):1621-1625 (1998).
Witt et al. "HDAC family: What are the cancer relevant targets?" Cancer Letters, 277:8-21 (2009).
Yu et al. "Design, Synthesis, and Biological Evaluation of Imidazo[1,2-alpha]pyridine Derivatives as Novel PI3K/mTOR Dual Inhibitors" Journal of Medicinal Chemistry, 63:3028-3046 (2020).
Zhang et al. "Mice Lacking Histone Deacetylase 6 Have Hyperacetylated Tubulin but Are Viable and Develop Normally" Molecular and Cellular Biology, 28(5):1688-1701 (2008).
U.S. Appl. No. 17/904,806, filed Aug. 23, 2022, Lee et al.

* cited by examiner

1,3,4-OXADIAZOLE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present invention relates to a 1,3,4-oxadiazole derivative compound having a histone deacetylase 6 (HDAC6) inhibitory activity, an optical isomer thereof, a pharmaceutically acceptable salt thereof; the use for preparing a therapeutic medicament; a treatment method using the same; a pharmaceutical composition containing the same; and a preparation method thereof.

BACKGROUND ART

Post-translational modifications such as acetylation in cells are very important regulatory modules at the center of biological processes and are strictly controlled by a number of enzymes. Histones are core proteins that make up the chromatin, acting as spools around which DNA winds to help condensation of DNA. In addition, the balance between acetylation and deacetylation of histones plays a very important role in gene expression.

Histone deacetylases (HDACs) are enzymes that remove the acetyl group of the histone protein lysine residues constituting the chromatin, which are known to be associated with gene silencing and to induce cell cycle arrest, angiogenesis inhibition, immune regulation, cell death, and the like (Hassig et al., Curr. Opin. Chem. Biol. 1997, 1, 300-308). Further, it has been reported that inhibition of HDAC enzyme function induces cancer cell death by reducing the activity of cancer cell survival-related factors and activating cancer cell death-related factors in vivo (Warrell et al, J. Natl. Cancer Inst. 1998, 90, 1621-1625).

In humans, 18 HDACs are known and are classified into 4 groups depending on their homology with yeast HDACs. Here, 11 HDACs using zinc as a cofactor can be divided into three groups of Class I (HDACs 1, 2, 3, and 8), Class II (IIa: HDACs 4, 5, 7, and 9; IIb: HDACs 6 and 10) and Class IV (HDAC11). Further, 7 HDACs of Class III (SIRT 1-7) employ $NAD^+$ as a cofactor instead of zinc (Bolden et al., Nat. Rev. Drug. Discov. 2006, 5 (9), 769-784).

Various HDAC inhibitors are in the preclinical or clinical development stage. However, until now, only non-selective HDAC inhibitors are known as anticancer agents, wherein vorinostat (SAHA) and romidepsin (FK228) have been approved as treatments for cutaneous T-cell lymphoma, and panobinostat (LBH-589) has been approved as a treatment for multiple myeloma. However, non-selective HDACs inhibitors are generally known to cause side effects such as fatigue and nausea, and the like, at high doses (Piekarz et al., Pharmaceuticals 2010, 3, 2751-2767). These side effects are reported to be caused by inhibition of Class I HDACs, and due to these side effects, non-selective HDACs inhibitors have been limited in drug development in fields other than anticancer agents (Witt et al., Cancer Letters 277 (2009) 8.21).

Meanwhile, it has been reported that selective Class II HDAC inhibition may not show the toxicity seen in Class I HDAC inhibition, and if a selective Class II HDAC inhibitor is developed, side effects such as toxicity caused by the non-selective HDAC inhibition may be solved, and thus the selective HDAC inhibitor has the potential to be developed as effective therapeutic agent for various diseases (Matthias et al., Mol. Cell. Biol. 2008, 28, 1688-1701). HDAC6, one of the Class IIb HDACs, is mainly present in the cytoplasma and is known to be involved in deacetylation of a number of non-histone substrates (HSP90, cortactin, and the like) including tubulin proteins (Yao et al., Mol. Cell 2005, 18, 601-607). The HDAC6 has two catalytic domains, and the C-terminal of zinc-finger domain may bind to ubiquitinated proteins. Since the HDAC6 has a large number of non-histone proteins as substrates, it is known to play an important role in various diseases such as cancer, inflammatory diseases, autoimmune diseases, neurological diseases, and neurodegenerative disorders, and the like (Santo et al., Blood 2012 119:2579-258; Vishwakarma et al., International Immunopharmacology 2013, 16, 72-78; Hu et al., J. Neurol. Sci. 2011, 304, 1-8).

A common structural feature of various HDAC inhibitors is that they consist of a cap group, a linker group, and a zinc-binding group (ZBG), as shown in the structure of vorinostat below. Many researchers have studied the inhibitory activity and selectivity for enzymes through structural modifications of the cap group and linker group. Among the groups, the zinc-binding group is known to play a more important role in the enzyme inhibitory activity and selectivity (Wiest et al., J. Org. Chem. 2013 78:5051-5065; Methot et al., Bioorg. Med. Chem. Lett. 2008, 18, 973-978).

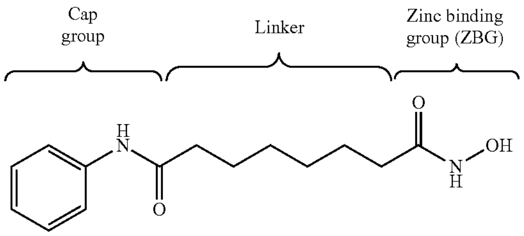 [SMILES: O=C(CCCCCCC(=O)Nc1ccccc1)NO]

Most of the zinc-binding groups are hydroxamic acid or benzamide, and among them, hydroxamic acid derivatives exhibit a strong HDAC inhibitory effect, but have problems such as low bioavailability and severe off-target activity. Since benzamide contains aniline, there is a problem that toxic metabolites may be caused in vivo (Woster et al., Med. Chem. Commun. 2015, online publication).

Therefore, for the treatment of cancer, inflammatory diseases, autoimmune diseases, neurological diseases, and neurodegenerative disorders, and the like, there is a need to develop a selective HDAC6 inhibitor having a zinc-binding group with improved bioavailability without side effects, unlike non-selective inhibitors with side effects.

DISCLOSURE

Technical Problem

An object of the present invention is to provide a 1,3,4-oxadiazole derivative compound having a selective histone deacetylase 6 (HDAC6) inhibitory activity, an optical isomer thereof, or a pharmaceutically acceptable salt thereof.

Another object of the present invention is to provide a pharmaceutical composition including a 1,3,4-oxadiazole derivative compound having a selective HDAC6 inhibitory activity, an optical isomer thereof, or a pharmaceutically acceptable salt thereof.

Still another object of the present invention is to provide a preparation method thereof.

Still another object of the present invention is to provide a pharmaceutical composition including the compounds for preventing or treating histone deacetylase 6 (HDAC6)-mediated diseases including infectious diseases; neoplasm; endocrine, nutritional and metabolic diseases; mental and behavioral disorders; neurological diseases; diseases of eyes and adnexa; circulatory diseases; respiratory diseases; digestive diseases; skin and subcutaneous tissue diseases; musculoskeletal and connective tissue diseases; or congenital malformations, alterations, or chromosomal abnormalities.

Still another object of the present invention is to provide the use of the compounds for preparing a medicament for preventing or treating HDAC6-mediated diseases.

Still another object of the present invention is to provide a method for preventing or treating HDAC6-mediated diseases including administering a therapeutically effective amount of the composition including the compounds as described above.

Technical Solution

The present inventors found a 1,3,4-oxadiazole derivative compound having a histone deacetylase 6 (HDAC6) inhibitory activity to inhibit or treat HDAC6-mediated diseases, and completed the present invention.

1,3,4-Oxadiazole Derivative Compound

In one general aspect, the present invention provides a 1,3,4-oxadiazole derivative compound represented by Chemical Formula I below, an optical isomer thereof, or a pharmaceutically acceptable salt thereof:

[Chemical Formula I]

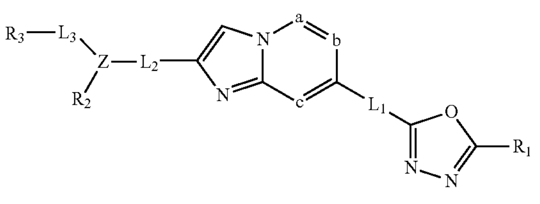

in the Chemical Formula I, $L_1$, $L_2$ and $L_3$ are each independently —($C_0$-$C_2$alkyl)-;

a, b and c are each independently N or $CR_4$ {wherein a, b and c cannot be N at the same time, and $R_4$ is —H, —X or —O($C_1$-$C_4$alkyl)};

Z is N, O, S, or nothing (null) {wherein when Z is nothing (null), $R_2$ is also nothing (null), and $L_2$ and $L_3$ are directly linked};

$R_1$ is —$CX_2$H or —$CX_3$;

$R_2$ is —H, —($C_1$-$C_4$alkyl), —C(═O)—$R^A$, —C(═O)—$OR^B$ or —C(═O)—$NR^CR^D$ {wherein when Z is O or S, $R_2$ is nothing (null)};

$R^A$ is —($C_1$-$C_4$alkyl), —($C_1$-$C_4$alkyl)-O—($C_1$-$C_4$alkyl), —($C_1$-$C_4$alkyl)-C(═O)—O($C_1$-$C_4$alkyl), -aryl, -heteroaryl, —$NR^{A1}R^{A2}$,

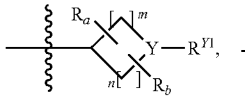
,
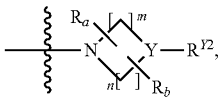
,
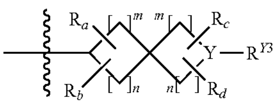
or

-continued

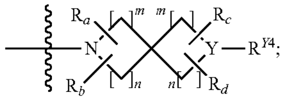
;

$R^B$ to $R^D$ are each independently —H, —($C_1$-$C_4$alkyl), —($C_1$-$C_4$alkyl)-O—($C_1$-$C_4$alkyl), —($C_1$-$C_4$alkyl)-C(═O)—O($C_1$-$C_4$alkyl), —($C_3$-$C_7$cycloalkyl), -aryl or -heteroaryl;

Y is N, CH, O or S(═O)$_2$, when Y is N or CH, $R^{Y1}$ to $R^{Y4}$ are each independently —H, —X, —OH, —($C_1$-$C_4$alkyl), —($C_3$-$C_7$cycloalkyl), —($C_2$-$C_6$heterocycloalkyl), —($C_1$-$C_4$alkyl)-O—($C_1$-$C_4$alkyl), —($C_1$-$C_4$alkyl)-C(═O)—O($C_1$-$C_4$alkyl), —C(═O)—($C_1$-$C_4$alkyl), —C(═O)—O($C_1$-$C_4$alkyl), —C(═O)—$NR^{A3}R^{A4}$, —C(═O)—($C_3$-$C_7$cycloalkyl), —C(═O)—($C_2$-$C_6$heterocycloalkyl), —S(═O)$_2$—($C_1$-$C_4$alkyl), -aryl, —($C_1$-$C_4$alkyl)-aryl, -heteroaryl, —($C_1$-$C_4$alkyl)-heteroaryl, an amine protecting group, or

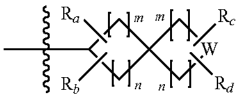

{wherein at least one H of —($C_1$-$C_4$alkyl), —($C_3$-$C_7$cycloalkyl), —($C_1$-$C_4$alkyl)-O—($C_1$-$C_4$alkyl), —($C_1$-$C_4$alkyl)-C(═O)—O($C_1$-$C_4$alkyl), —C(═O)—($C_1$-$C_4$alkyl), —C(═O)—($C_3$-$C_7$cycloalkyl), —C(═O)—($C_2$-$C_6$heterocycloalkyl) and —S(═O)$_2$—($C_1$-$C_4$alkyl) may be substituted with —X or —OH; at least one H of the aryl, —($C_1$-$C_4$alkyl)-aryl, heteroaryl and —($C_1$-$C_4$alkyl)-heteroaryl may be substituted with —($C_1$-$C_4$alkyl), —O—($C_1$-$C_4$alkyl), —X, —OH or —$CF_3$; —($C_2$-$C_6$heterocycloalkyl), -heteroaryl or —($C_1$-$C_4$alkyl) heteroaryl may contain N, O or S atoms in the ring; and W is NH, $CH_2$ or O};

when Y is O or S(═O)$_2$, $R^{Y1}$ to $R^{Y4}$ are nothing (null);

m and n are each independently an integer of 1, 2 or 3;

$R_a$ to $R_d$ are each independently —H or —($C_1$-$C_4$alkyl);

$R_3$ is —H, —($C_1$-$C_4$alkyl), —($C_1$-$C_4$alkyl)-O($C_1$-$C_4$alkyl), —($C_1$-$C_4$alkyl)-C(═O)—O($C_1$-$C_4$alkyl), —C(═O)—O($C_1$-$C_4$alkyl), —($C_3$-$C_7$cycloalkyl), —($C_2$-$C_6$heterocycloalkyl), -adamantyl, -aryl or -heteroaryl {wherein at least one H of —($C_1$-$C_4$alkyl) may be substituted with —X or —OH; at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C═O)—($C_1$-$C_4$alkyl), —C(═O)—O($C_1$-$C_4$alkyl), —$CF_3$, —$CF_2$H, —$OCF_3$, —$NR^{A5}R^{A6}$, —S(═O)$_2$—($C_1$-$C_4$alkyl), -aryl or -heteroaryl};

$R^{A1}$ to $R^{A6}$ are each independently —H or —($C_1$-$C_4$alkyl); and

X is F, Cl, Br or I.

According to an embodiment of the present invention, in the Chemical Formula I above, $L_1$, $L_2$ and $L_3$ are each independently —($C_0$-$C_4$alkyl)-;

a, b and c are each independently N or $CR_4$ {wherein a, b and c cannot be N at the same time, and $R_4$ is —H or —X};

Z is N, O, or nothing (null) {wherein when Z is nothing (null), $R_2$ is also nothing (null), and $L_2$ and $L_3$ are directly linked};

$R_1$ is —$CX_2H$ or —$CX_3$;

$R_2$ is —H, —($C_1$-$C_4$alkyl) or —C(═O)—$R^A$ {wherein when Z is O, Rz is nothing (null)};

$R^A$ is —$NR^{A1}R^{A2}$,

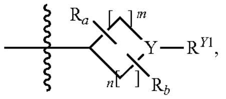

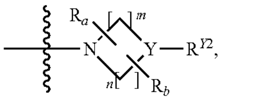

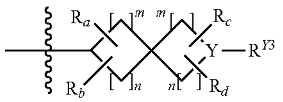

or

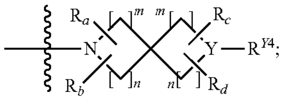

Y is N, CH, O or S(═O)$_2$;

when Y is N or CH, $R^{Y1}$ to $R^{Y4}$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—O($C_1$-$C_4$alkyl), —C(═O)—$NR^{A3}R^{A4}$, —C(═O)—($C_3$-$C_7$cycloalkyl), —C(═O)—($C_2$-$C_6$heterocycloalkyl), —S(═O)$_2$—($C_1$-$C_4$alkyl), -aryl, -heteroaryl, or

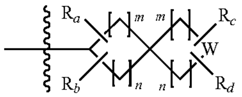

{wherein at least one H of —($C_1$-$C_4$alkyl), —($C_3$-$C_7$cycloalkyl), —C(═O)—($C_1$-$C_4$alkyl), —C(═O)—($C_3$-$C_7$cycloalkyl), —C(═O)—($C_2$-$C_6$heterocycloalkyl) and —S(═O)$_2$—($C_1$-$C_4$alkyl) may be substituted with —X or —OH; at least one H of the aryl and heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is NH, $CH_2$ or O};

when Y is O or S(═O)$_2$, $R^{Y1}$ to $R^{Y4}$ are nothing (null);

m and n are each independently an integer of 1 or 2;

$R_a$ to $R_d$ are each independently —H or —($C_1$-$C_4$alkyl);

$R_3$ is —($C_3$-$C_7$cycloalkyl), —($C_2$-$C_6$heterocycloalkyl), -adamantyl, -aryl or -heteroaryl {wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C═O)—($C_1$-$C_4$alkyl), —C(═O)—O($C_1$-$C_4$alkyl), —$CF_3$, —$CF_2H$, —$OCF_3$, —$NR^{A5}R^{A6}$, —S(═O)$_2$—($C_1$-$C_4$alkyl), -aryl, or -heteroaryl};

$R^{A1}$ to $R^{A6}$ are each independently —H or —($C_1$-$C_4$alkyl); and

X may be F, Cl or Br.

Further, according to another embodiment of the present invention, in the Chemical Formula I above, $L_1$ and $L_3$ are each independently —($C_0$alkyl)-;

$L_2$ is —($C_4$alkyl)-;

a, b and c are each independently $CR_4$ {wherein $R_4$ is —H or —X};

Z is N, O, or nothing (null) {wherein when Z is nothing (null), $R_2$ is also nothing (null), and $L_2$ and $L_3$ are directly linked};

$R_1$ is —$CF_2H$ or —$CF_3$;

$R_2$ is —H or —C(═O)—$R^A$ {wherein when Z is O, $R_2$ is nothing (null)};

$R^A$ is

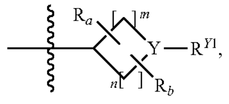

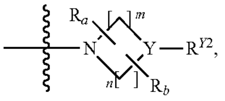

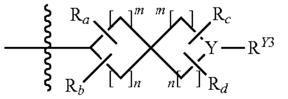

or

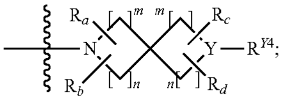

Y is N;

$R^{Y1}$ to $R^{Y4}$ are each independently —($C_1$-$C_4$alkyl), —($C_3$-$C_7$cycloalkyl), —($C_2$-$C_6$heterocycloalkyl), —C(═O)—($C_1$-$C_4$alkyl), —C(═O)—O($C_1$-$C_4$alkyl), —C(═O)—$NR^{A3}R^{A4}$, —C(═O)—($C_3$-$C_7$cycloalkyl), —C(═O)—($C_2$-$C_6$heterocycloalkyl), —S(═O)$_2$—($C_1$-$C_4$alkyl), -heteroaryl, or

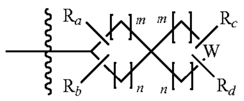

{wherein at least one H of —($C_1$-$C_4$alkyl), —($C_3$-$C_7$cycloalkyl), —C(═O)—($C_1$-$C_4$alkyl), —C(═O)—($C_3$-$C_7$cycloalkyl), —C(═O)—($C_2$-$C_6$heterocycloalkyl) and —S(═O)$_2$—($C_1$-$C_4$alkyl) may be substituted with —X or —OH; —($C_2$-$C_6$heterocycloalkyl) may contain N, O or S atoms in the ring; and W is $CH_2$ or O};

m and n are each independently an integer of 1 or 2;

$R_a$ to $R_d$ are each independently —H or —($C_1$-$C_4$alkyl);

$R_3$ is —($C_3$-$C_7$cycloalkyl), -adamantyl, -aryl or -heteroaryl {wherein at least one —H of —($C_3$-$C_7$cycloalkyl), -adamantyl, -aryl and -heteroaryl may each independently be substituted with —X, —($C_1$-$C_4$alkyl), —O($C_1$-$C_4$alkyl), —(C═O)—($C_1$-$C_4$alkyl), —$CF_3$, or —S(═O)$_2$—($C_1$-$C_4$alkyl)};

$R^{A1}$ to $R^{A6}$ are each independently —H or —($C_1$-$C_4$alkyl); and

X may be F or Cl.

Further, according to still another embodiment of the present invention, in the Chemical Formula I above, $L_1$, $L_2$ or $L_3$ is each independently —($C_0$-$C_4$alkyl)-;

a, b and c are each independently N or $CR_4$ {wherein a, b and c cannot be N at the same time, and $R_4$ is —H or —X};

Z is N;

$R_1$ is —$CX_2H$ or —$CX_3$;

$R_2$ is —C(═O)—$R^A$;

$R^A$ is

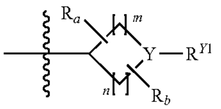 or 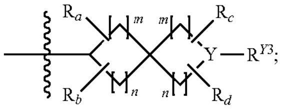

Y is N, CH, O or $S(=O)_2$;

when Y is N or CH, $R^{Y1}$ and $R^{Y3}$ are each independently —H, —($C_1$-$C_4$alkyl), —($C_3$-$C_7$cycloalkyl), —($C_2$-$C_6$heterocycloalkyl), —C(=O)—($C_1$-$C_4$alkyl), —C(=O)—O($C_1$-$C_4$alkyl), —C(=O)—$NR^{A3}R^{A4}$, —C(=O)—($C_3$-$C_7$cycloalkyl), —C(=O)—($C_2$-$C_6$heterocycloalkyl), —$S(=O)_2$—($C_1$-$C_4$alkyl), -aryl, -heteroaryl, or

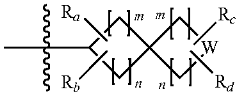

{wherein at least one H of —($C_1$-$C_4$alkyl), —($C_3$-$C_7$cycloalkyl), —C(=O)—($C_1$-$C_4$alkyl), —C(=O)—($C_3$-$C_7$cycloalkyl), —C(=O)—($C_2$-$C_6$heterocycloalkyl) and —$S(=O)_2$—($C_1$-$C_4$alkyl) may be substituted with —X or —OH; at least one H of the aryl and heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is NH, $CH_2$ or O};

when Y is O or $S(=O)_2$, $R^{Y1}$ and $R^{Y3}$ are nothing (null);

m and n are each independently an integer of 1 or 2;

$R_a$ to $R_d$ are each independently —H or —($C_1$-$C_4$alkyl);

$R_3$ is —C(=O)—O($C_1$-$C_4$alkyl), —($C_3$-$C_7$cycloalkyl), —($C_2$-$C_6$heterocycloalkyl), -adamantyl, -aryl or -heteroaryl {wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C=O)—($C_1$-$C_4$alkyl), —C(=O)—O($C_1$-$C_4$alkyl), —$CF_3$, —$CF_2H$, —$OCF_3$, —$NR^{A5}R^{A6}$, —$S(=O)_2$—($C_1$-$C_4$alkyl), -aryl, or -heteroaryl};

$R^{A3}$ to $R^{A6}$ are each independently —H or —($C_1$-$C_4$alkyl); and

X may be F, Cl or Br.

Further, according to still another embodiment of the present invention, in the Chemical Formula I above, $L_1$, $L_2$ and $L_3$ are each independently —($C_0$-$C_1$alkyl)-;

a, b and c are each independently N or $CR_4$ {wherein a, b and c cannot be N at the same time, and $R_4$ is —H or —X};

Z is N;

$R_1$ is —$CX_2H$ or —$CX_3$;

$R_2$ is —C(=O)—$R^A$;

$R^A$ is —$NR^{A1}R^{A2}$,

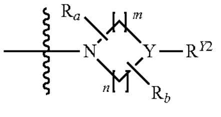 or 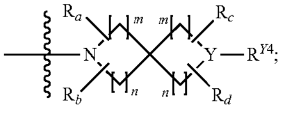

m and n are each independently an integer of 1 or 2;

$R_a$ to $R_d$ are each independently —H or —($C_1$-$C_4$alkyl);

Y is N, CH, O or $S(=O)_2$;

when Y is N or CH, $R^{Y2}$ and $R^{Y4}$ are each independently —H, —($C_1$-$C_4$alkyl), —($C_3$-$C_7$cycloalkyl), —($C_2$-$C_6$heterocycloalkyl), —C(=O)—($C_1$-$C_4$alkyl), —C(=O)—O($C_1$-$C_4$alkyl), —C(=O)—$NR^{A3}R^{A4}$, —C(=O)—($C_3$-$C_7$cycloalkyl), —C(=O)—($C_2$-$C_6$heterocycloalkyl), —$S(=O)_2$—($C_1$-$C_4$alkyl), -aryl, or -heteroaryl {wherein at least one H of —($C_1$-$C_4$alkyl), —($C_3$-$C_7$cycloalkyl), —C(=O)—($C_1$-$C_4$alkyl), —C(=O)—($C_3$-$C_7$cycloalkyl), —C(=O)—($C_2$-$C_6$heterocycloalkyl) and —$S(=O)_2$—($C_1$-$C_4$alkyl) may be substituted with —X or —OH; at least one H of the aryl and heteroaryl may be substituted with —($C_1$-$C_4$alkyl), —O—($C_1$-$C_4$alkyl), —X, —OH or —$CF_3$; and —($C_2$-$C_6$heterocycloalkyl) or -heteroaryl may contain N, O or S atoms in the ring};

when Y is O or $S(=O)_2$, $R^{Y2}$ and $R^{Y4}$ are nothing (null);

$R_3$ is —C(=O)—O($C_1$-$C_4$alkyl), —($C_3$-$C_7$cycloalkyl), —($C_2$-$C_6$heterocycloalkyl), -adamantyl, -aryl or -heteroaryl {wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C=O)—($C_1$-$C_4$alkyl), —C(=O)—O($C_1$-$C_4$alkyl), —$CF_3$, —$CF_2H$, —$OCF_3$, —$NR^{A5}R^{A6}$, —$S(=O)_2$—($C_1$-$C_4$alkyl), -aryl, or -heteroaryl};

$R^{A1}$ to $R^{A6}$ are each independently —H or —($C_1$-$C_4$alkyl); and

X may be F, Cl or Br.

Further, according to still another embodiment of the present invention, in the Chemical Formula I above, $L_1$, $L_2$ and $L_3$ are each independently —($C_0$-$C_4$alkyl)-;

a, b and c are each independently N or $CR_4$ {wherein a, b and c cannot be N at the same time, and $R^A$ is —H or —X};

Z is N, O, or nothing (null) {wherein when Z is nothing (null), $R_2$ is also nothing (null), and $L_2$ and $L_3$ are directly linked};

$R_1$ is —$CX_2H$ or —$CX_3$;

$R_2$ is —H, —($C_1$-$C_4$alkyl) {wherein when Z is O, $R_2$ is nothing (null)};

$R_3$ is —C(=O)—O($C_1$-$C_4$alkyl), —($C_3$-$C_7$cycloalkyl), —($C_2$-$C_6$heterocycloalkyl), -adamantyl, -aryl or -heteroaryl {wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C=O)—($C_1$-$C_4$alkyl), —C(=O)—O($C_1$-$C_4$alkyl), —$CF_3$, —$CF_2H$, —$OCF_3$, —$NR^{A5}R^{A6}$, —$S(=O)_2$—($C_1$-$C_4$alkyl), -aryl, or -heteroaryl};

$R^{A5}$ and $R^{A6}$ are each independently —H or —($C_1$-$C_4$alkyl); and

X may be F, Cl or Br.

Specific compounds represented by Chemical Formula I of the present invention are shown in Table 1 below.

TABLE 1
| Ex | Comp | Structure |
| --- | --- | --- |
| 1 | 3009 | 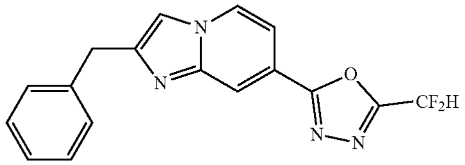 [SMILES: FC(F)c1nnc(-c2ccn3cc(Cc4ccccc4)nc3c2)o1] |
| 2 | 3585 | 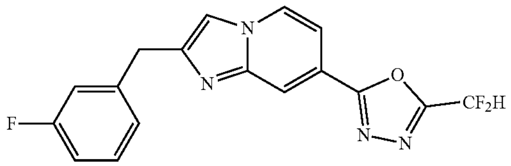 [SMILES: Fc1cccc(Cc2cn3ccc(-c4nnc(C(F)F)o4)cc3n2)c1] |
| 3 | 3586 | 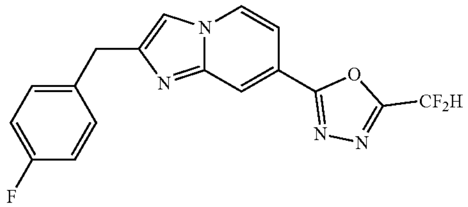 [SMILES: Fc1ccc(Cc2cn3ccc(-c4nnc(C(F)F)o4)cc3n2)cc1] |
| 4 | 3587 | 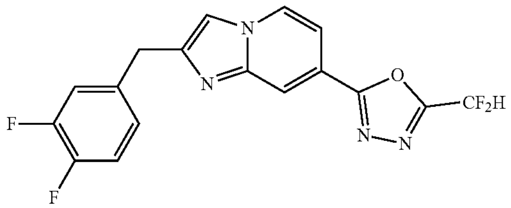 [SMILES: Fc1ccc(Cc2cn3ccc(-c4nnc(C(F)F)o4)cc3n2)cc1F] |
| 5 | 3588 | 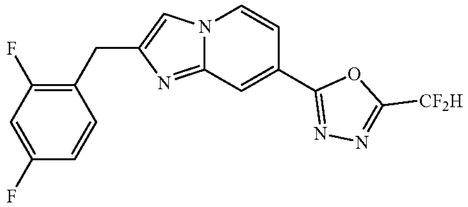 [SMILES: Fc1ccc(Cc2cn3ccc(-c4nnc(C(F)F)o4)cc3n2)c(F)c1] |
| 6 | 3589 | 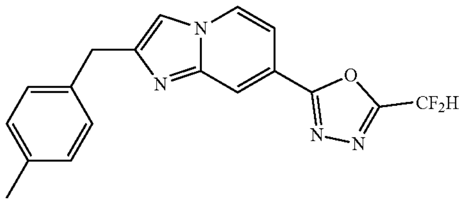 [SMILES: Cc1ccc(Cc2cn3ccc(-c4nnc(C(F)F)o4)cc3n2)cc1] |
| 7 | 3590 | 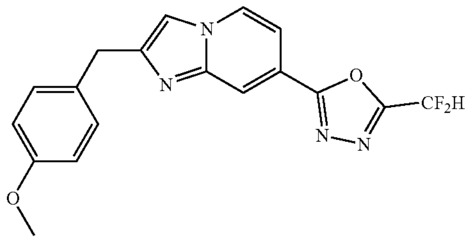 [SMILES: COc1ccc(Cc2cn3ccc(-c4nnc(C(F)F)o4)cc3n2)cc1] |

TABLE 1-continued
| Ex | Comp | Structure |
|---|---|---|
| 8 | 3591 | 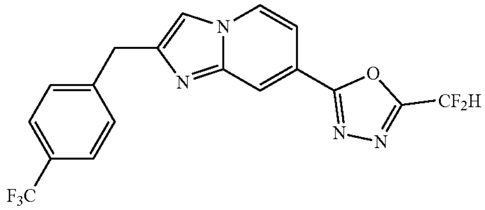 |
| 9 | 3592 | 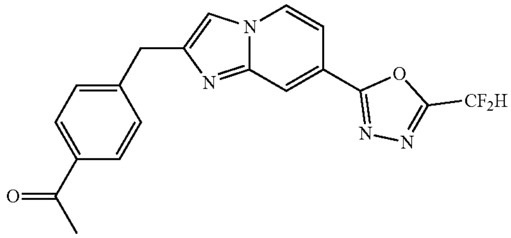 [SMILES: CC(=O)c1ccc(Cc2cn3ccc(-c4nnc(C(F)F)o4)cc3n2)cc1] |
| 10 | 3593 | 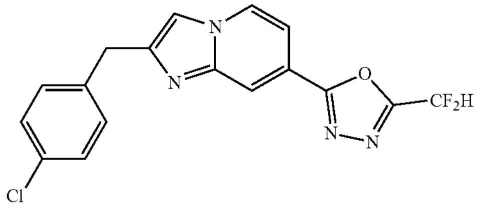 [SMILES: FC(F)c1nnc(-c2ccn3cc(Cc4ccc(Cl)cc4)nc3c2)o1] |
| 11 | 3594 | 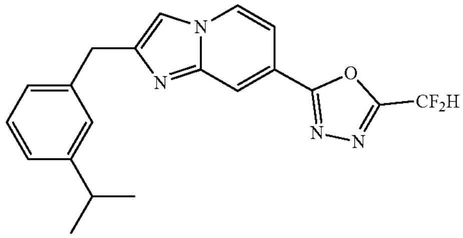 [SMILES: CC(C)c1cccc(Cc2cn3ccc(-c4nnc(C(F)F)o4)cc3n2)c1] |
| 12 | 3595 | 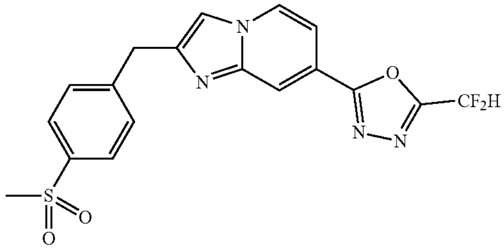 [SMILES: CS(=O)(=O)c1ccc(Cc2cn3ccc(-c4nnc(C(F)F)o4)cc3n2)cc1] |
| 13 | 3596 | 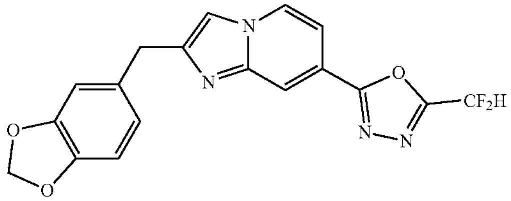 [SMILES: FC(F)c1nnc(-c2ccn3cc(Cc4ccc5c(c4)OCO5)nc3c2)o1] |
| 14 | 3668 | 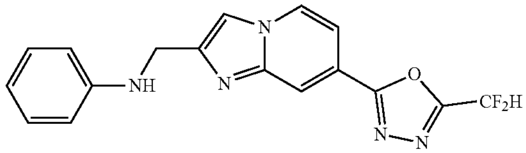 |

TABLE 1-continued
| Ex | Comp | Structure |
|---|---|---|
| 15 | 3669 | 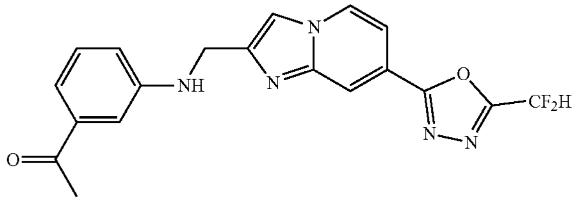 |
| 16 | 3670 | 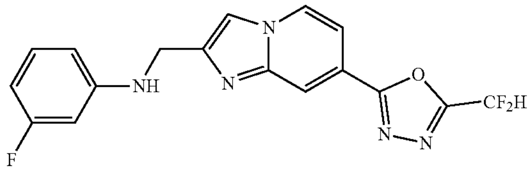 [SMILES: Fc1cccc(NCc2cn3ccc(-c4nnc(C(F)F)o4)cc3n2)c1] |
| 17 | 3671 | 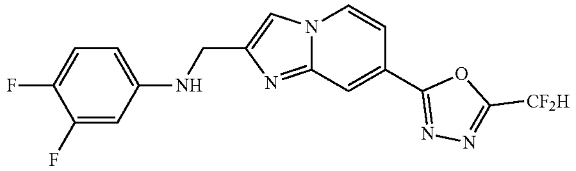 |
| 18 | 3672 | 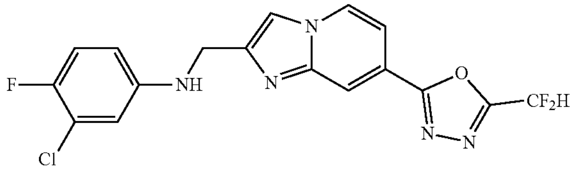 [SMILES: Fc1ccc(NCc2cn3ccc(-c4nnc(C(F)F)o4)cc3n2)cc1Cl] |
| 19 | 3673 | 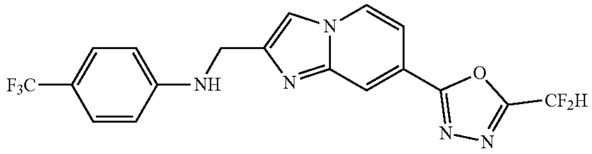 |
| 20 | 3674 | 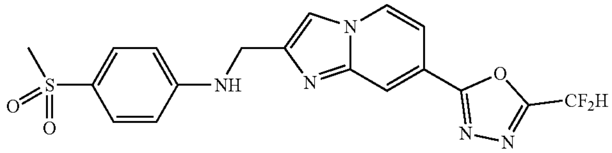 [SMILES: CS(=O)(=O)c1ccc(NCc2cn3ccc(-c4nnc(C(F)F)o4)cc3n2)cc1] |
| 21 | 3675 | 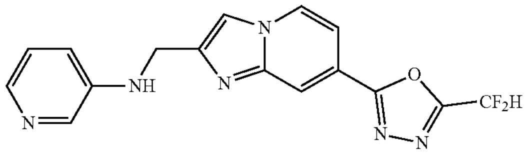 |
| 22 | 3676 | 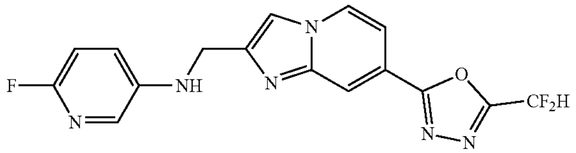 [SMILES: Fc1ccc(NCc2cn3ccc(-c4nnc(C(F)F)o4)cc3n2)cn1] |
| 23 | 3677 | 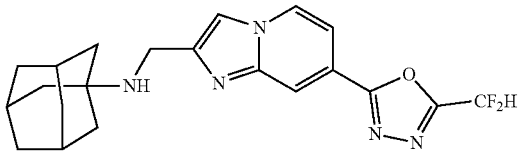 [SMILES: FC(F)c1nnc(-c2ccn3cc(CNC45CC6CC(CC(C6)C4)C5)nc3c2)o1] |

TABLE 1-continued
| Ex | Comp | Structure |
|---|---|---|
| 24 | 3678 | 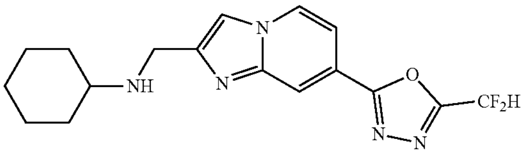 [SMILES: FC(F)c1nnc(-c2ccn3cc(CNC4CCCCC4)nc3c2)o1] |
| 25 | 3679 | 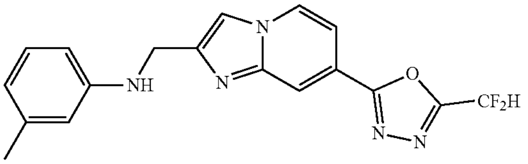 [SMILES: Cc1cccc(NCc2cn3ccc(-c4nnc(C(F)F)o4)cc3n2)c1] |
| 26 | 3719 | 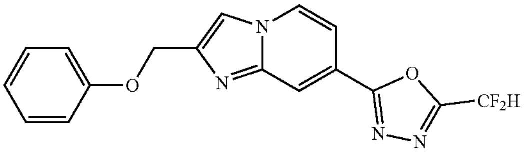 [SMILES: FC(F)c1nnc(-c2ccn3cc(COc4ccccc4)nc3c2)o1] |
| 27 | 3720 | 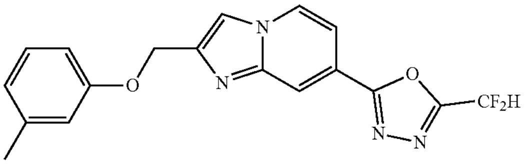 [SMILES: Cc1cccc(OCc2cn3ccc(-c4nnc(C(F)F)o4)cc3n2)c1] |
| 28 | 3721 | 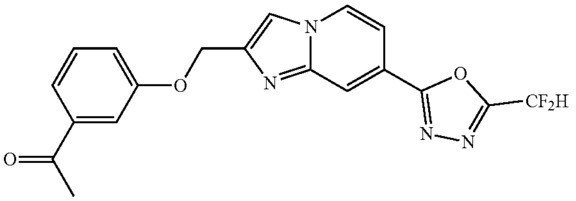 |
| 29 | 3722 | 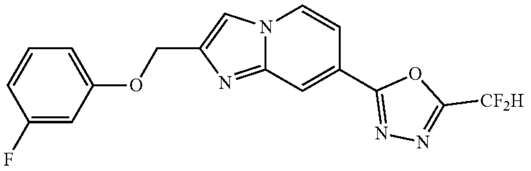 [SMILES: Fc1cccc(OCc2cn3ccc(-c4nnc(C(F)F)o4)cc3n2)c1] |
| 30 | 3723 | 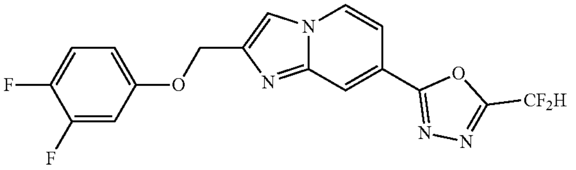 [SMILES: Fc1ccc(OCc2cn3ccc(-c4nnc(C(F)F)o4)cc3n2)cc1F] |
| 31 | 3724 | 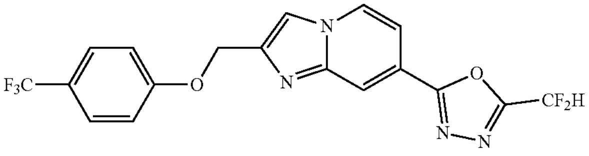 [SMILES: FC(F)c1nnc(-c2ccn3cc(COc4ccc(C(F)(F)F)cc4)nc3c2)o1] |
| 32 | 3725 | 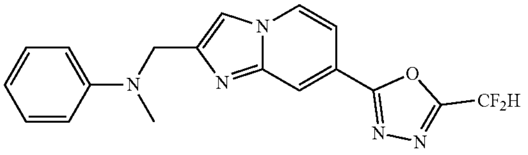 [SMILES: CN(Cc1cn2ccc(-c3nnc(C(F)F)o3)cc2n1)c1ccccc1] |

TABLE 1-continued
| Ex | Comp | Structure |
|---|---|---|
| 33 | 3782 | 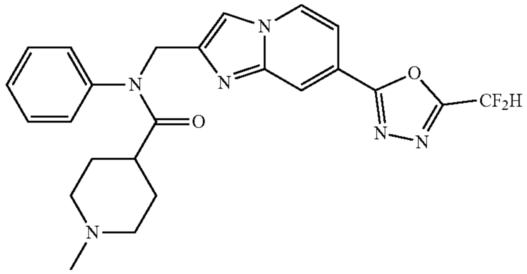 [SMILES: CN1CCC(C(=O)N(Cc2cn3ccc(-c4nnc(C(F)F)o4)cc3n2)c2ccccc2)CC1] |
| 34 | 3783 | 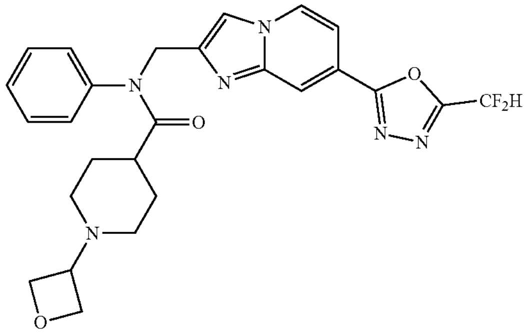 |
| 35 | 3784 | 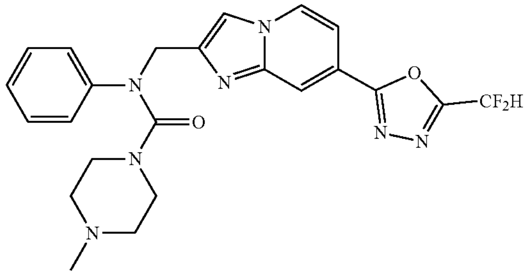 |
| 36 | 3785 | 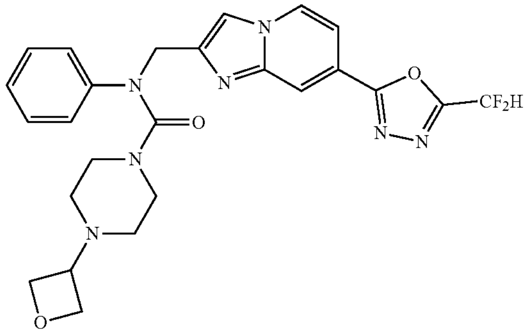 |
| 37 | 4033 | 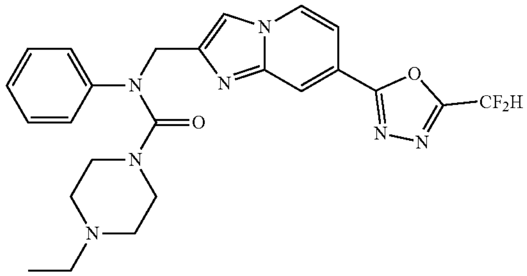 |

TABLE 1-continued
| Ex | Comp | Structure |
| --- | --- | --- |
| 38 | 4034 | 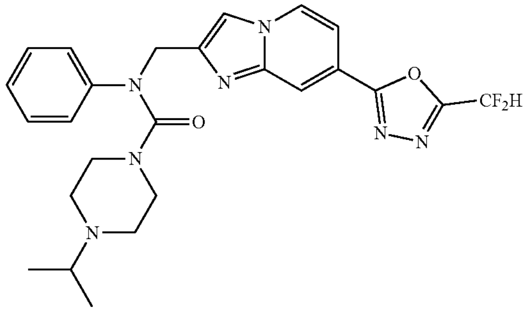 [SMILES: CC(C)N1CCN(C(=O)N(Cc2cn3ccc(-c4nnc(C(F)F)o4)cc3n2)c2ccccc2)CC1] |
| 39 | 4035 | 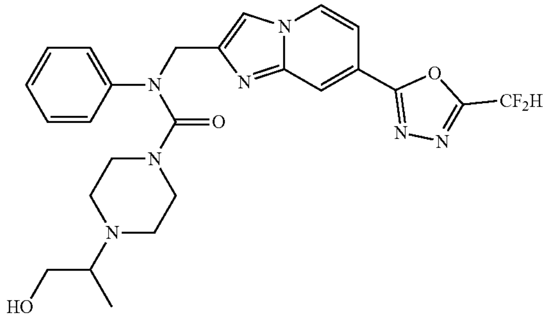 [SMILES: CC(CO)N1CCN(C(=O)N(Cc2cn3ccc(-c4nnc(C(F)F)o4)cc3n2)c2ccccc2)CC1] |
| 40 | 4036 | 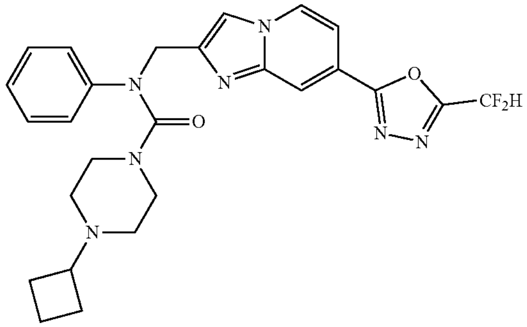 |
| 41 | 4037 | 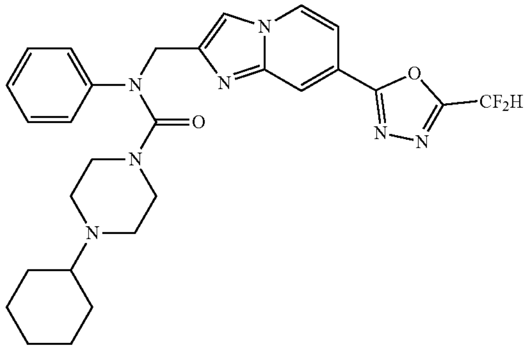 |

TABLE 1-continued
| Ex | Comp | Structure |
|---|---|---|
| 42 | 4038 | 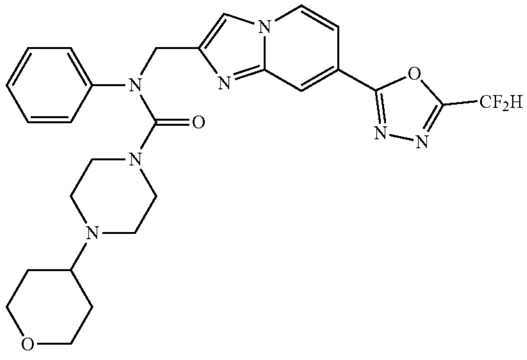 |
| 43 | 4039 | 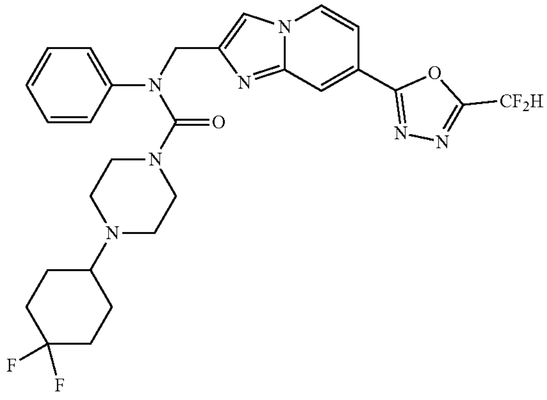 [SMILES: O=C(N1CCN(C2CCC(F)(F)CC2)CC1)N(Cc1cn2ccc(-c3nnc(C(F)F)o3)cc2n1)c1ccccc1] |
| 44 | 4040 | 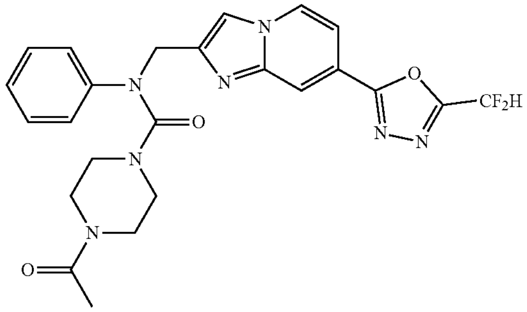 [SMILES: CC(=O)N1CCN(C(=O)N(Cc2cn3ccc(-c4nnc(C(F)F)o4)cc3n2)c2ccccc2)CC1] |
| 45 | 4041 | 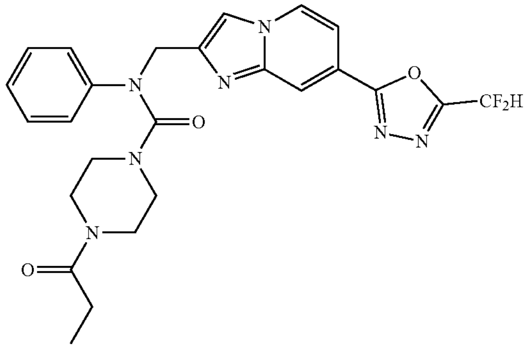 |

TABLE 1-continued
| Ex | Comp | Structure |
| --- | --- | --- |
| 46 | 4042 | 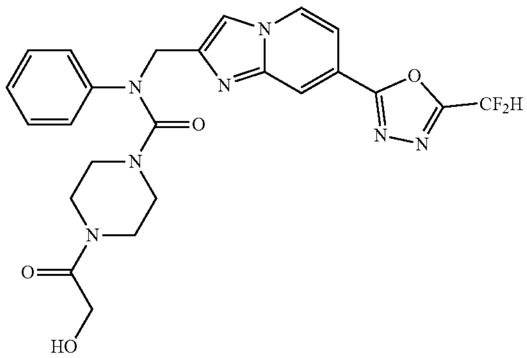 |
| 47 | 4043 | 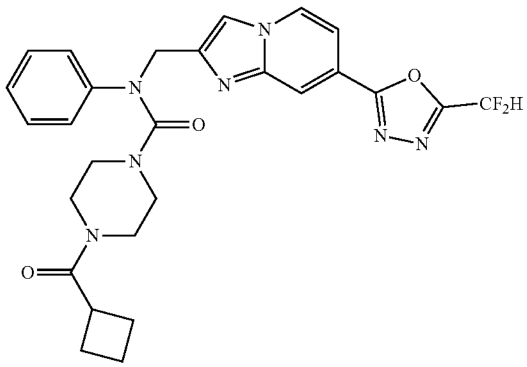 |
| 48 | 4044 | 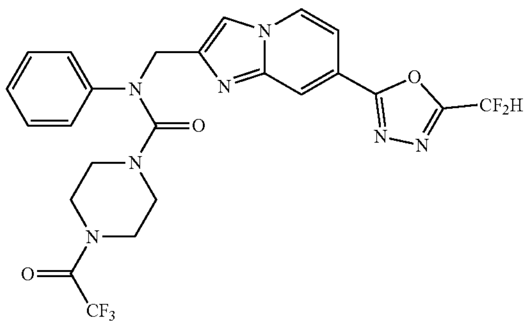 [SMILES: O=C(N1CCN(C(=O)C(F)(F)F)CC1)N(Cc1cn2ccc(-c3nnc(C(F)F)o3)cc2n1)c1ccccc1] |
| 49 | 4045 | 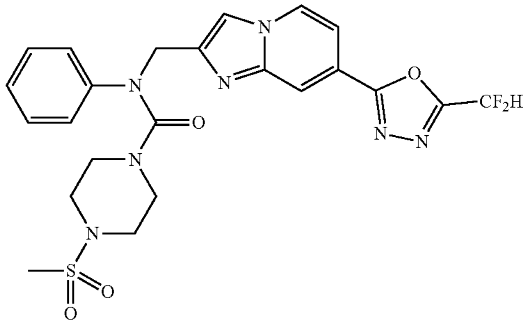 |

TABLE 1-continued
| Ex | Comp | Structure |
|---|---|---|
| 50 | 4046 | 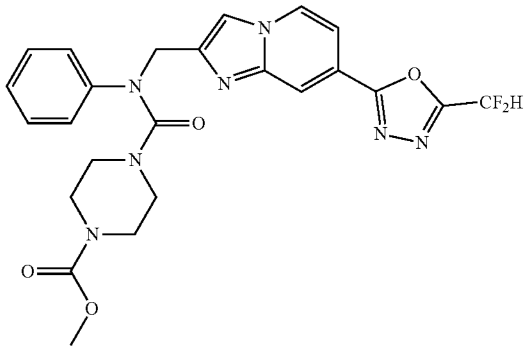 |
| 51 | 4047 | 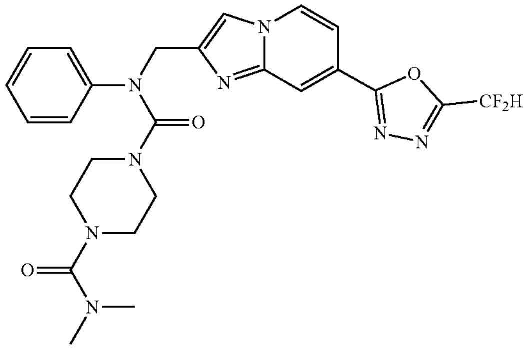 [SMILES: CN(C)C(=O)N1CCN(C(=O)N(Cc2cn3ccc(-c4nnc(C(F)F)o4)cc3n2)c2ccccc2)CC1] |
| 52 | 4048 | 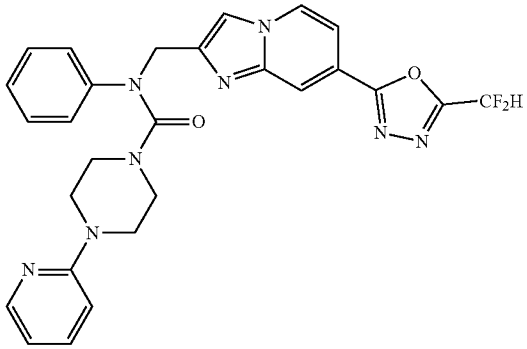 |
| 53 | 4049 | 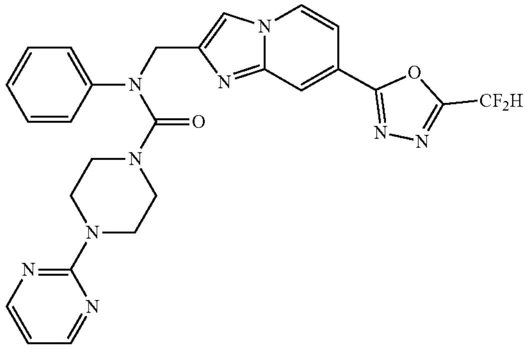 |

TABLE 1-continued
| Ex | Comp | Structure |
|---|---|---|
| 54 | 4083 | 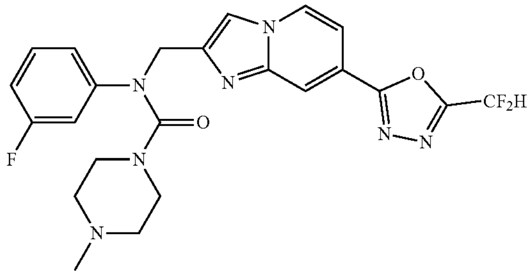 |
| 55 | 4084 | 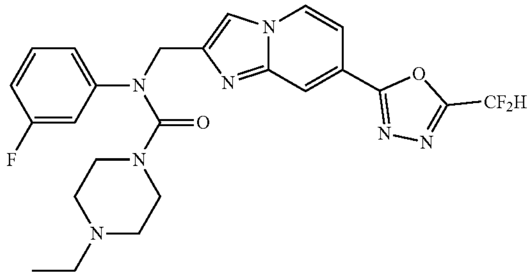 [SMILES: CCN1CCN(C(=O)N(Cc2cn3ccc(-c4nnc(C(F)F)o4)cc3n2)c2cccc(F)c2)CC1] |
| 56 | 4085 | 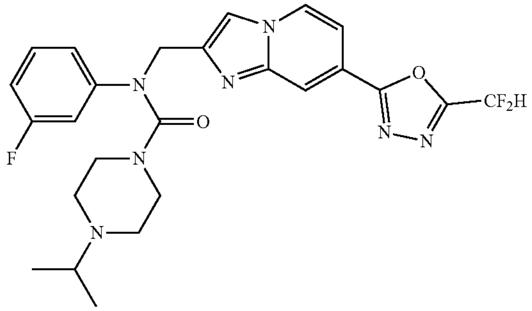 |
| 57 | 4086 | 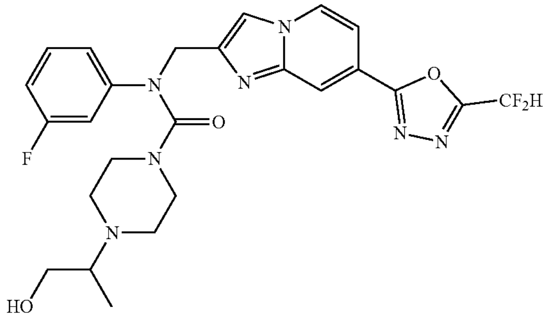 |
| 58 | 4087 | 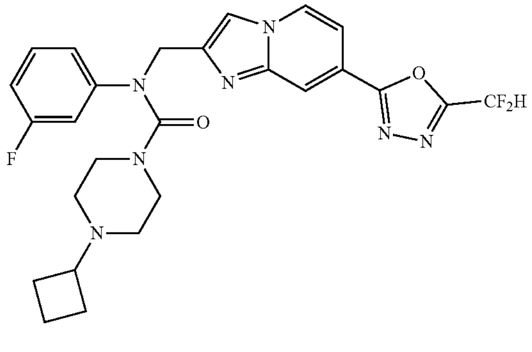 |

TABLE 1-continued
| Ex | Comp | Structure |
|---|---|---|
| 59 | 4088 | 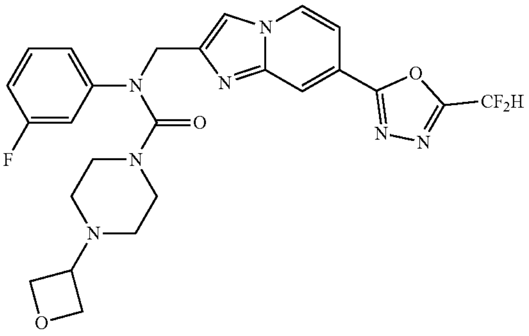 [SMILES: O=C(N1CCN(C2COC2)CC1)N(Cc1cn2ccc(-c3nnc(C(F)F)o3)cc2n1)c1cccc(F)c1] |
| 60 | 4089 | 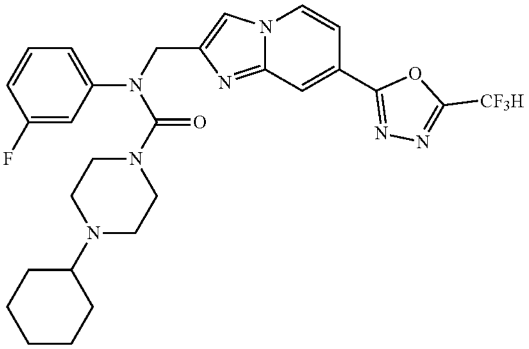 |
| 61 | 4090 | 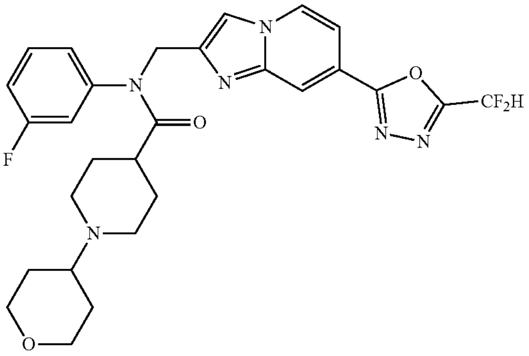 [SMILES: O=C(C1CCN(C2CCOCC2)CC1)N(Cc1cn2ccc(-c3nnc(C(F)F)o3)cc2n1)c1cccc(F)c1] |
| 62 | 4091 | 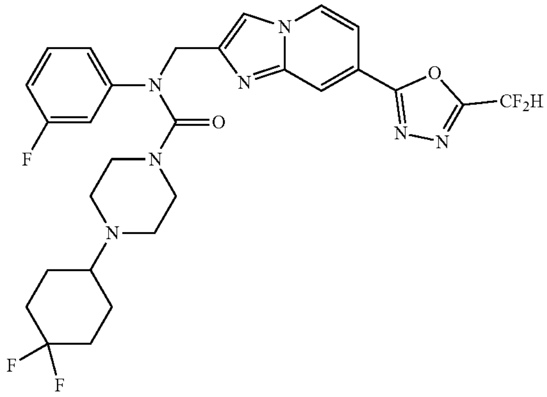 [SMILES: O=C(N1CCN(C2CCC(F)(F)CC2)CC1)N(Cc1cn2ccc(-c3nnc(C(F)F)o3)cc2n1)c1cccc(F)c1] |

TABLE 1-continued
| Ex | Comp | Structure |
|---|---|---|
| 63 | 4092 | 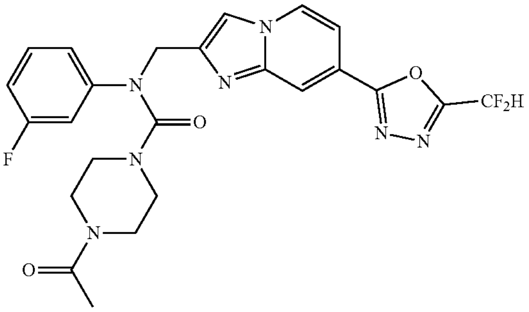 |
| 64 | 4093 | 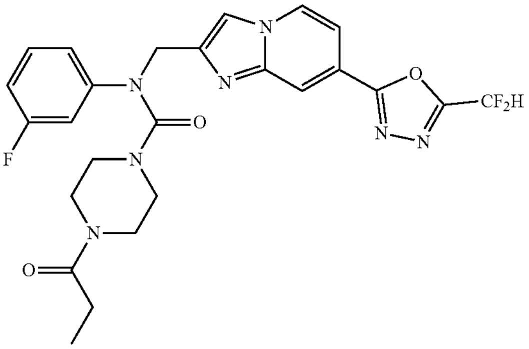 |
| 65 | 4094 | 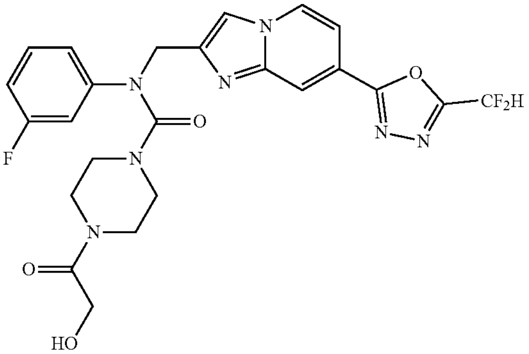 [SMILES: O=C(CO)N1CCN(C(=O)N(Cc2cn3ccc(-c4nnc(C(F)F)o4)cc3n2)c2cccc(F)c2)CC1] |
| 66 | 4095 | 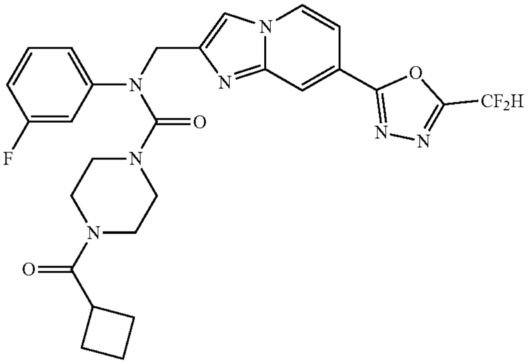 [SMILES: O=C(C1CCC1)N1CCN(C(=O)N(Cc2cn3ccc(-c4nnc(C(F)F)o4)cc3n2)c2cccc(F)c2)CC1] |

TABLE 1-continued
| Ex | Comp | Structure |
|---|---|---|
| 67 | 4096 | 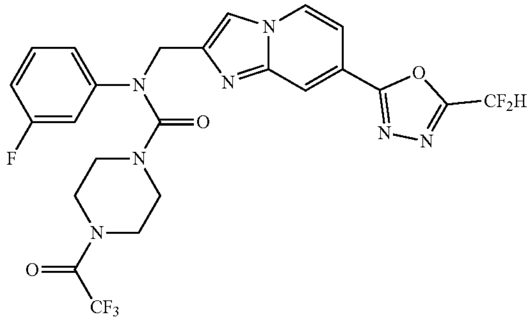 |
| 68 | 4097 | 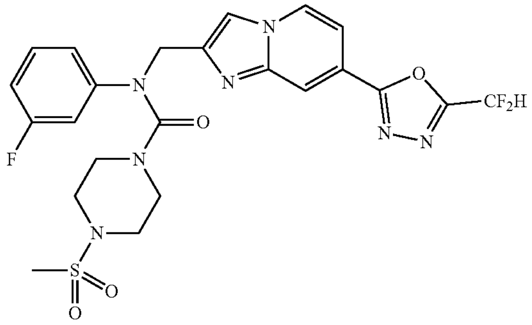 |
| 69 | 4098 | 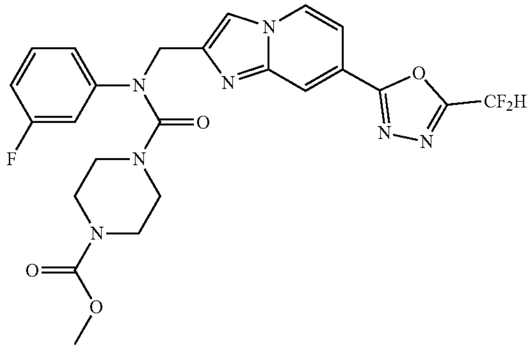 |
| 70 | 4099 | 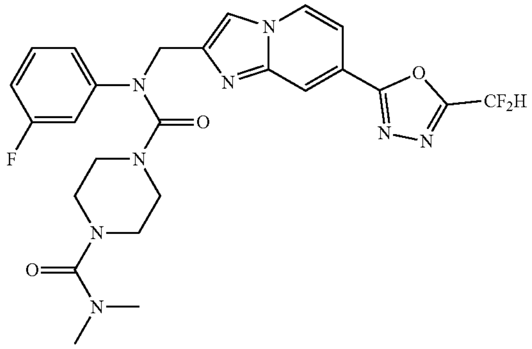 |

TABLE 1-continued
| Ex | Comp | Structure |
|---|---|---|
| 71 | 4100 | 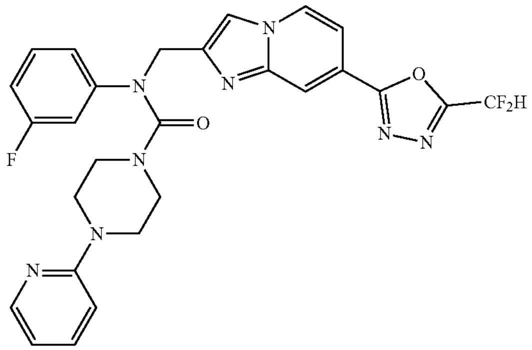 |
| 72 | 4101 | 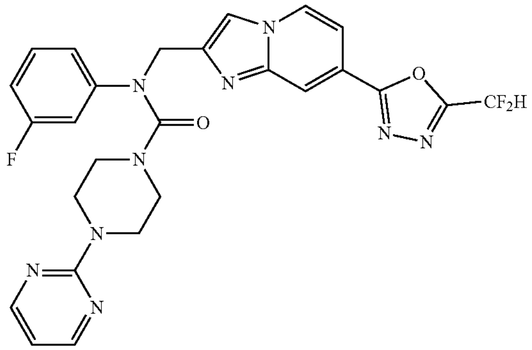 |
| 73 | 4102 | 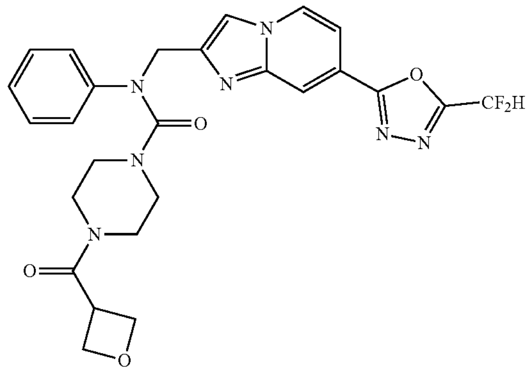 |
| 74 | 4103 | 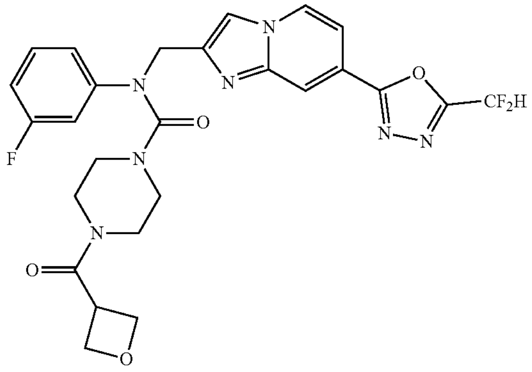 |

TABLE 1-continued
| Ex | Comp | Structure |
|---|---|---|
| 75 | 4115 | 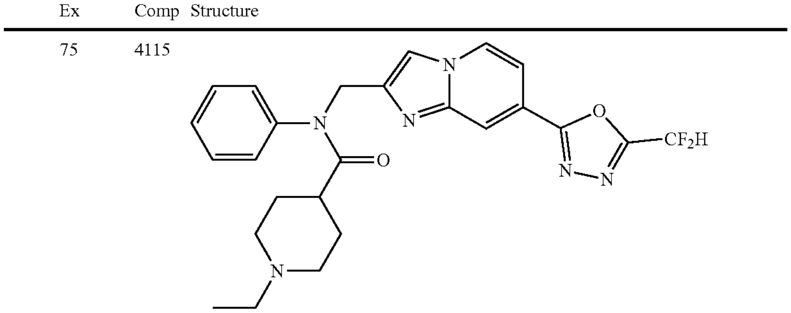 |
| 76 | 4116 | 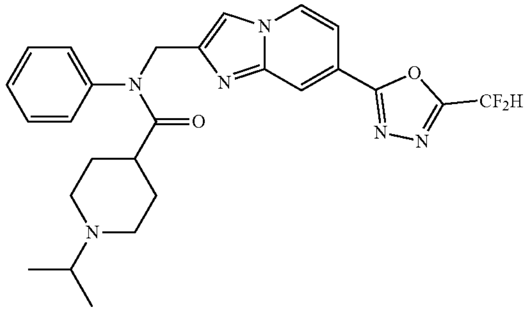 |
| 77 | 4117 | 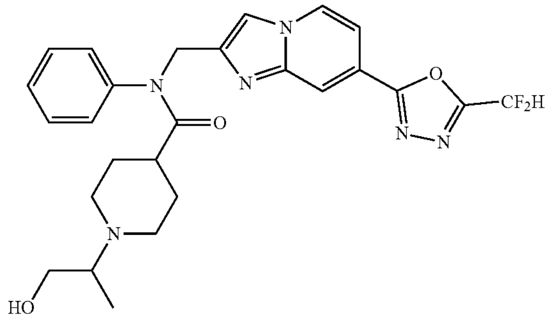 [SMILES: CC(CO)N1CCC(C(=O)N(Cc2cn3ccc(-c4nnc(C(F)F)o4)cc3n2)c2ccccc2)CC1] |
| 78 | 4118 | 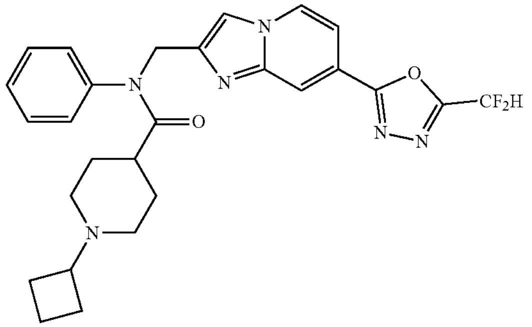 |
| 79 | 4119 | 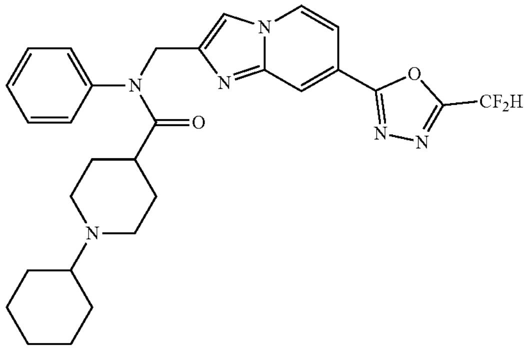 |

TABLE 1-continued
| Ex | Comp | Structure |
| --- | --- | --- |
| 80 | 4120 | 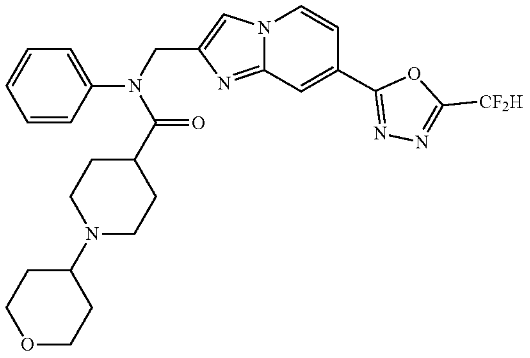 [SMILES: O=C(C1CCN(C2CCOCC2)CC1)N(Cc1cn2ccc(-c3nnc(C(F)F)o3)cc2n1)c1ccccc1] |
| 81 | 4121 | 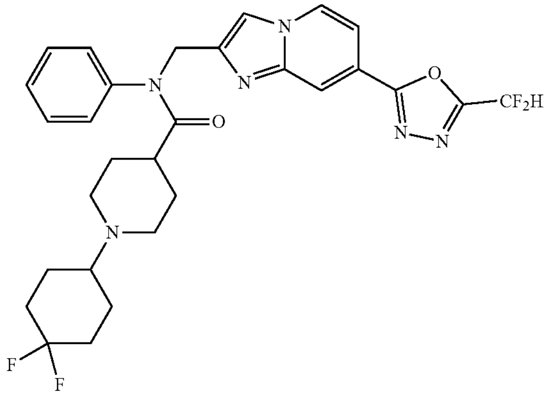 |
| 82 | 4122 | 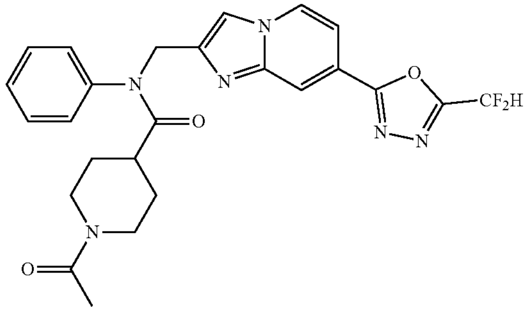 |
| 83 | 4123 | 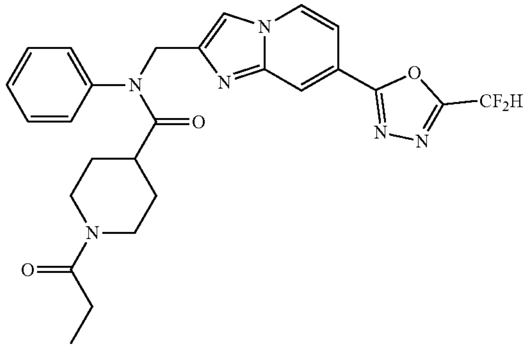 |

TABLE 1-continued
| Ex | Comp | Structure |
|---|---|---|
| 84 | 4124 | 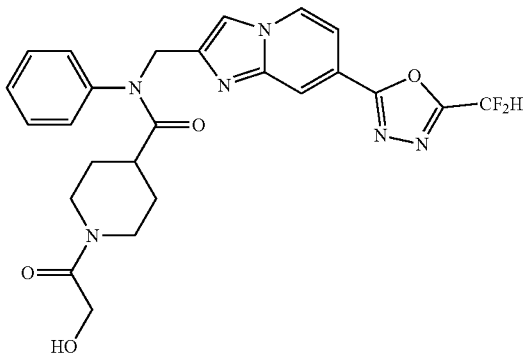 [SMILES: O=C(CO)N1CCC(C(=O)N(Cc2cn3ccc(-c4nnc(C(F)F)o4)cc3n2)c2ccccc2)CC1] |
| 85 | 4125 | 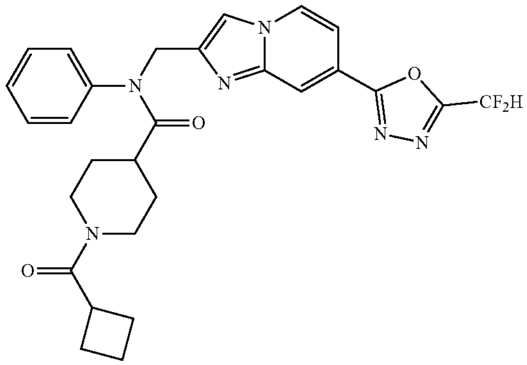 [SMILES: O=C(C1CCC1)N1CCC(C(=O)N(Cc2cn3ccc(-c4nnc(C(F)F)o4)cc3n2)c2ccccc2)CC1] |
| 86 | 4126 | 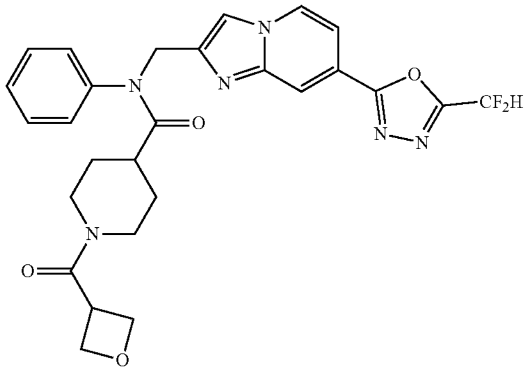 [SMILES: O=C(C1COC1)N1CCC(C(=O)N(Cc2cn3ccc(-c4nnc(C(F)F)o4)cc3n2)c2ccccc2)CC1] |
| 87 | 4127 | 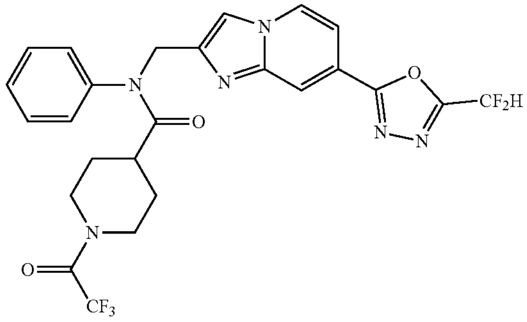 [SMILES: O=C(C1CCN(C(=O)C(F)(F)F)CC1)N(Cc1cn2ccc(-c3nnc(C(F)F)o3)cc2n1)c1ccccc1] |

TABLE 1-continued
| Ex | Comp | Structure |
| --- | --- | --- |
| 88 | 4128 | 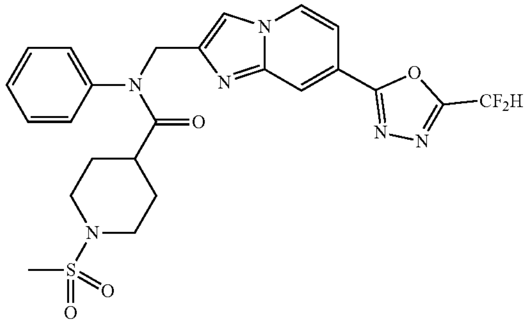 [SMILES: CS(=O)(=O)N1CCC(C(=O)N(Cc2cn3ccc(-c4nnc(C(F)F)o4)cc3n2)c2ccccc2)CC1] |
| 89 | 4129 | 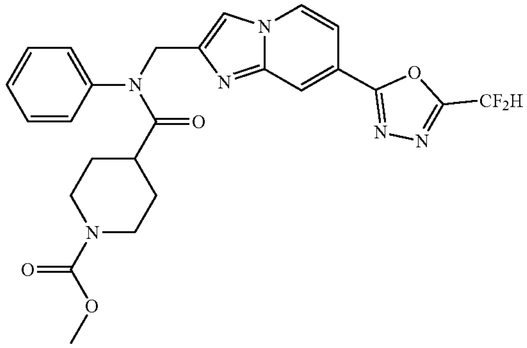 |
| 90 | 4130 | 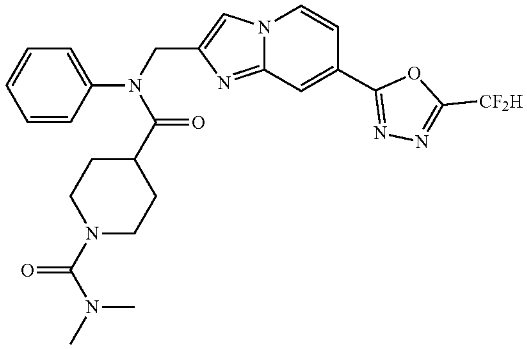 |
| 91 | 4131 | 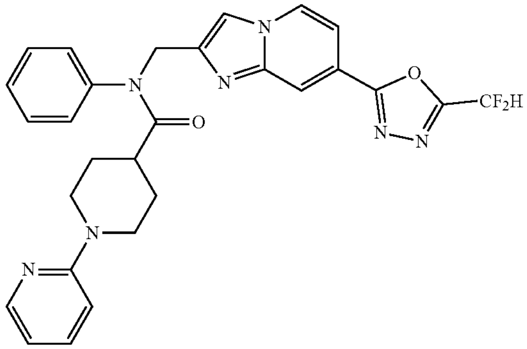 |

TABLE 1-continued
| Ex | Comp | Structure |
|---|---|---|
| 92 | 4132 | 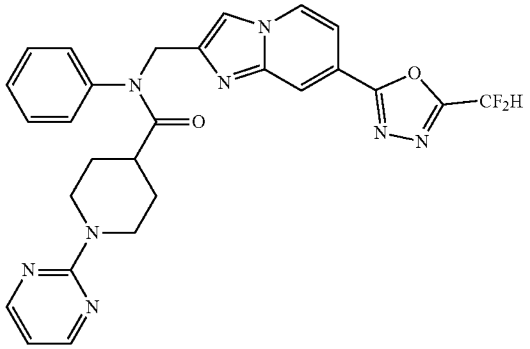 [SMILES: O=C(C1CCN(c2ncccn2)CC1)N(Cc1cn2ccc(-c3nnc(C(F)F)o3)cc2n1)c1ccccc1] |
| 93 | 4137 | 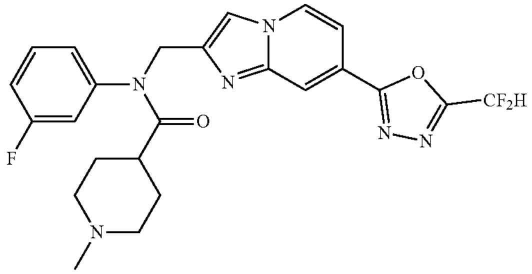 |
| 94 | 4138 | 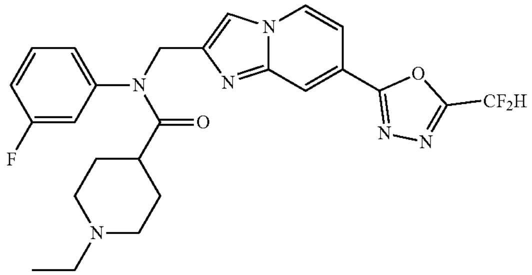 |
| 95 | 4139 | 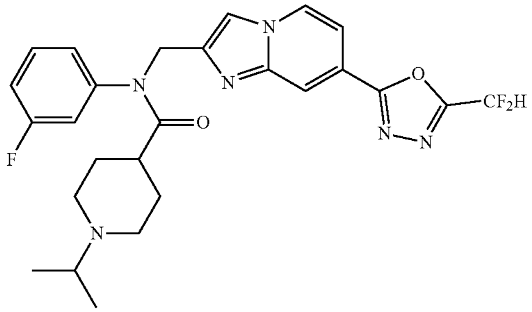 |
| 96 | 4140 | 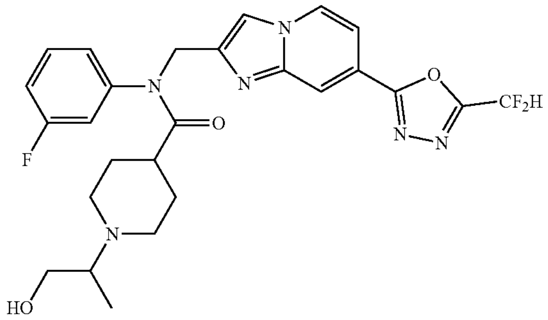 |

TABLE 1-continued
| Ex | Comp | Structure |
|---|---|---|
| 97 | 4141 | 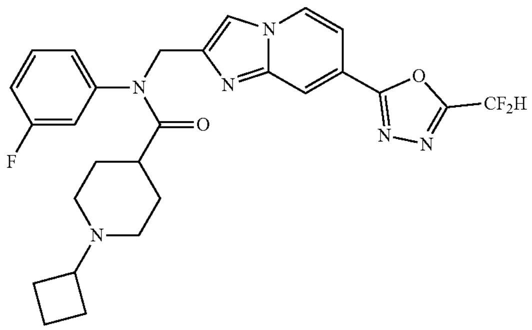 |
| 98 | 4142 | 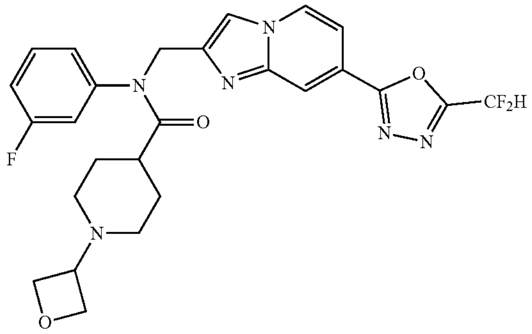 |
| 99 | 4143 | 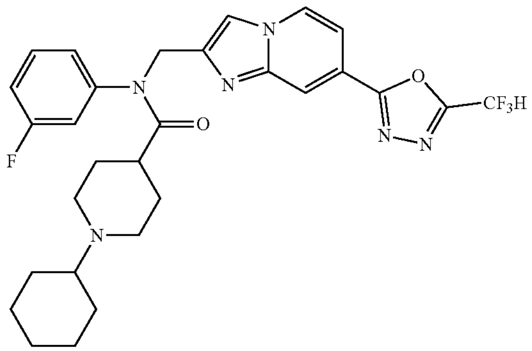 |
| 100 | 4144 | 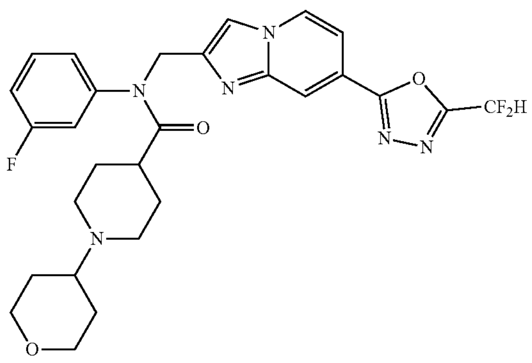 |

TABLE 1-continued
| Ex | Comp | Structure |
|---|---|---|
| 101 | 4145 | 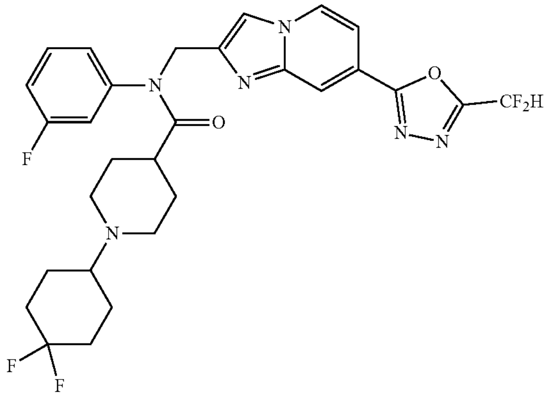 [SMILES: O=C(C1CCN(C2CCC(F)(F)CC2)CC1)N(Cc1cn2ccc(-c3nnc(C(F)F)o3)cc2n1)c1cccc(F)c1] |
| 102 | 4146 | 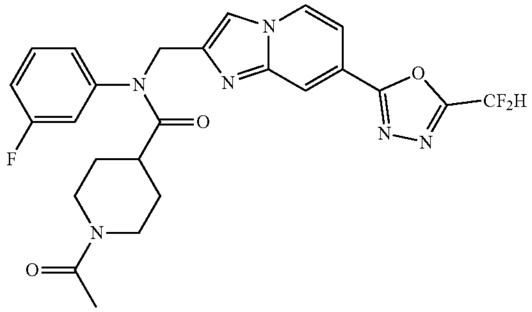 |
| 103 | 4147 | 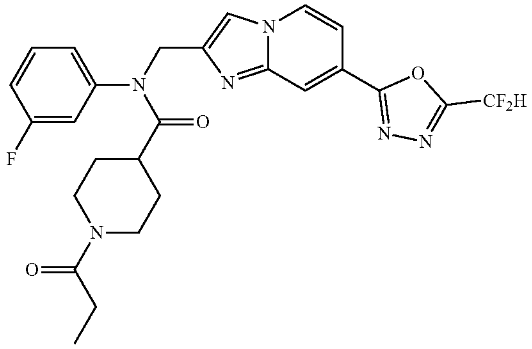 |
| 104 | 4149 | 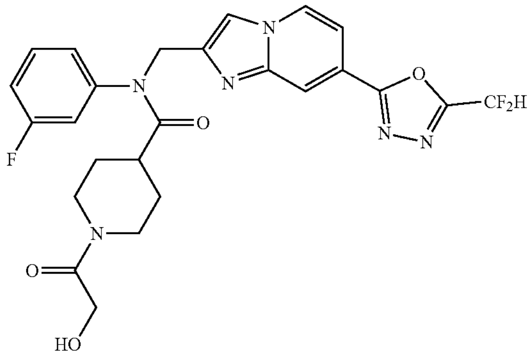 |

TABLE 1-continued
| Ex | Comp | Structure |
| --- | --- | --- |
| 105 | 4150 | 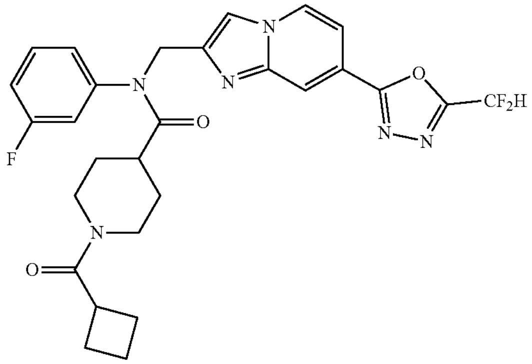 |
| 106 | 4151 | 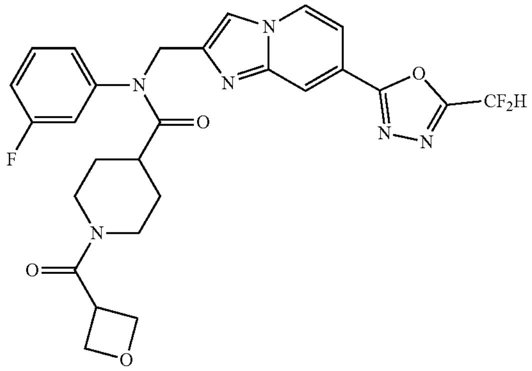 [SMILES: O=C(C1COC1)N1CCC(C(=O)N(Cc2cn3ccc(-c4nnc(C(F)F)o4)cc3n2)c2cccc(F)c2)CC1] |
| 107 | 4152 | 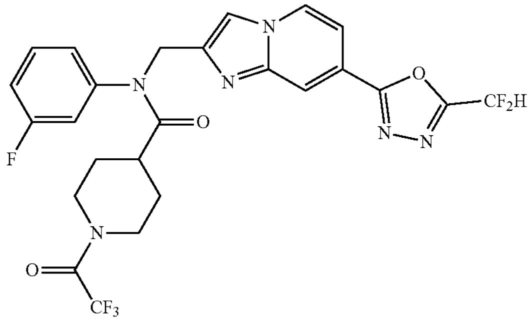 |
| 108 | 4153 | 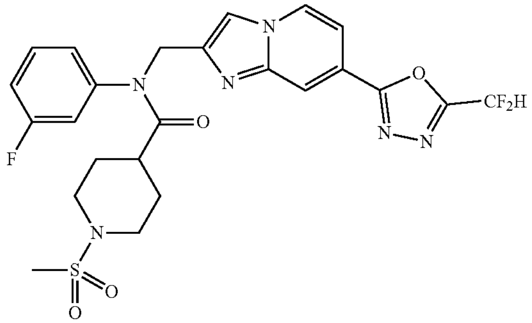 [SMILES: CS(=O)(=O)N1CCC(C(=O)N(Cc2cn3ccc(-c4nnc(C(F)F)o4)cc3n2)c2cccc(F)c2)CC1] |

TABLE 1-continued
| Ex | Comp | Structure |
|---|---|---|
| 109 | 4154 | 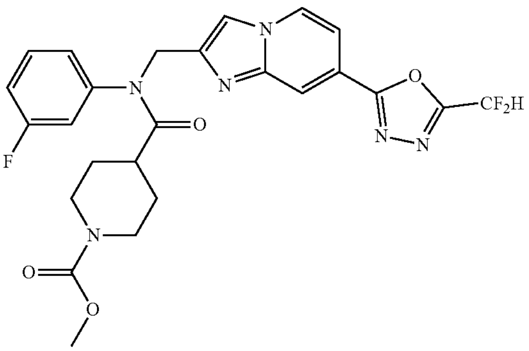 [SMILES: COC(=O)N1CCC(C(=O)N(Cc2cn3ccc(-c4nnc(C(F)F)o4)cc3n2)c2cccc(F)c2)CC1] |
| 110 | 4155 | 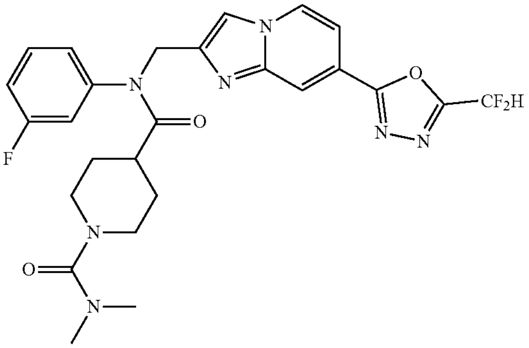 |
| 111 | 4156 | 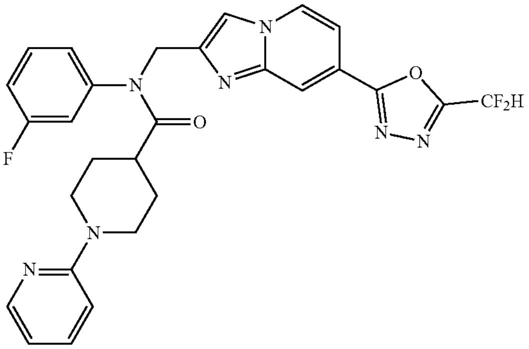 |
| 112 | 4157 | 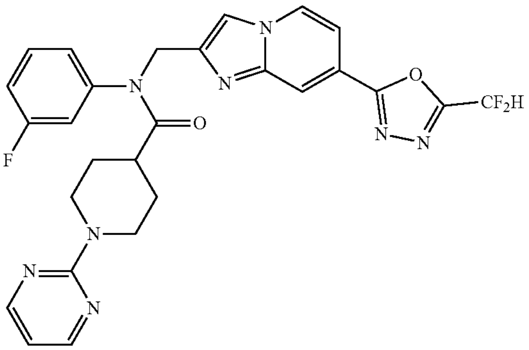 |

TABLE 1-continued
| Ex | Comp | Structure |
|---|---|---|
| 113 | 4158 | 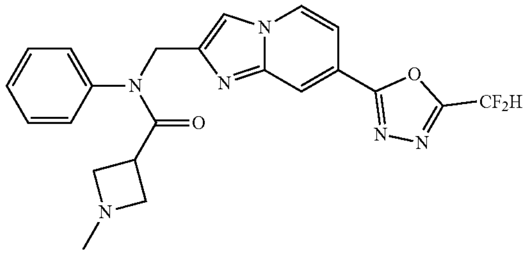 [SMILES: CN1CC(C(=O)N(Cc2cn3ccc(-c4nnc(C(F)F)o4)cc3n2)c2ccccc2)C1] |
| 114 | 4159 | 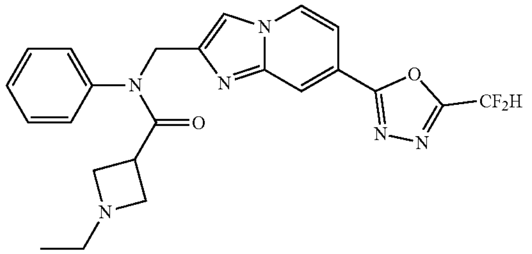 [SMILES: CCN1CC(C(=O)N(Cc2cn3ccc(-c4nnc(C(F)F)o4)cc3n2)c2ccccc2)C1] |
| 115 | 4160 | 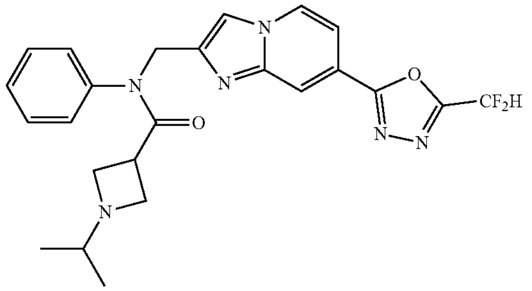 |
| 116 | 4161 | 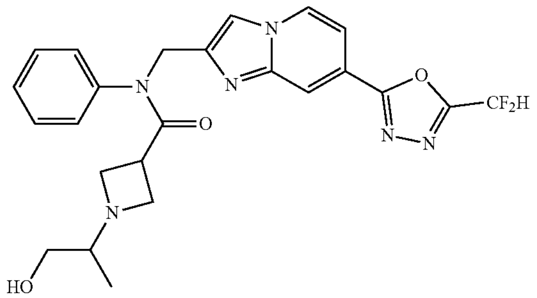 [SMILES: CC(CO)N1CC(C(=O)N(Cc2cn3ccc(-c4nnc(C(F)F)o4)cc3n2)c2ccccc2)C1] |
| 117 | 4162 | 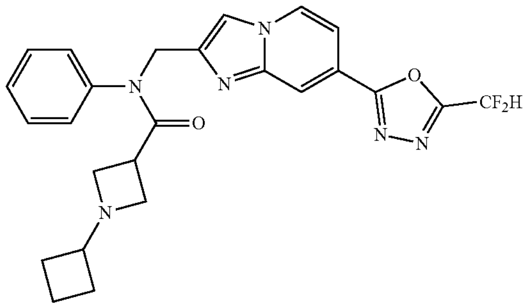 [SMILES: O=C(C1CN(C2CCC2)C1)N(Cc1cn2ccc(-c3nnc(C(F)F)o3)cc2n1)c1ccccc1] |

TABLE 1-continued
| Ex | Comp | Structure |
|---|---|---|
| 118 | 4163 | 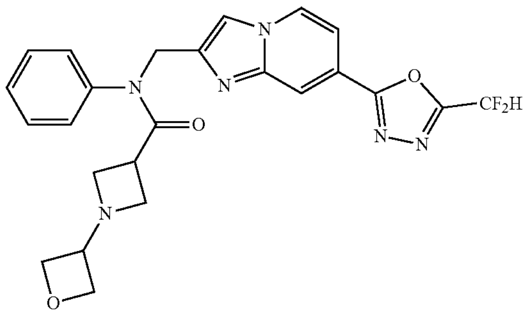 [SMILES: O=C(C1CN(C2COC2)C1)N(Cc1cn2ccc(-c3nnc(C(F)F)o3)cc2n1)c1ccccc1] |
| 119 | 4164 | 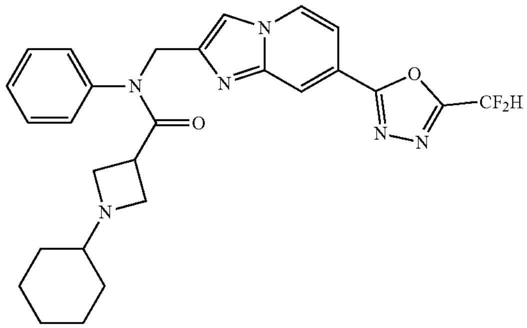 [SMILES: O=C(C1CN(C2CCCCC2)C1)N(Cc1cn2ccc(-c3nnc(C(F)F)o3)cc2n1)c1ccccc1] |
| 120 | 4165 | 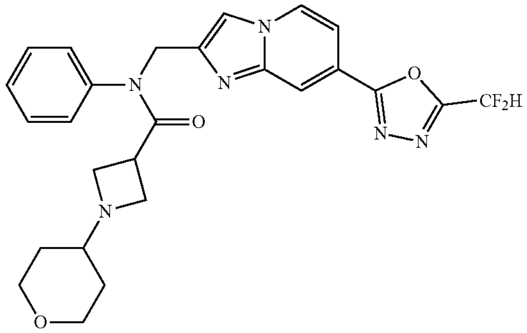 [SMILES: O=C(C1CN(C2CCOCC2)C1)N(Cc1cn2ccc(-c3nnc(C(F)F)o3)cc2n1)c1ccccc1] |
| 121 | 4166 | 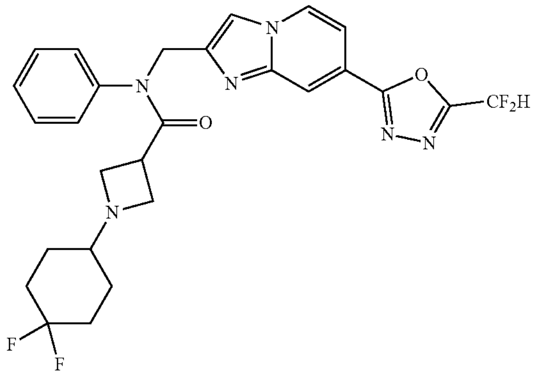 [SMILES: O=C(C1CN(C2CCC(F)(F)CC2)C1)N(Cc1cn2ccc(-c3nnc(C(F)F)o3)cc2n1)c1ccccc1] |

TABLE 1-continued
| Ex | Comp | Structure |
|---|---|---|
| 122 | 4167 | 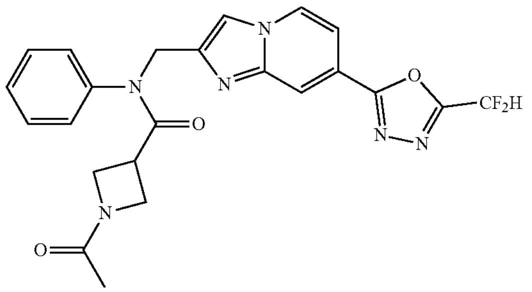 [SMILES: CC(=O)N1CC(C(=O)N(Cc2cn3ccc(-c4nnc(C(F)F)o4)cc3n2)c2ccccc2)C1] |
| 123 | 4168 | 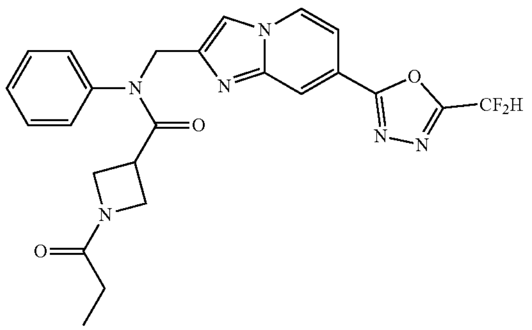 [SMILES: CCC(=O)N1CC(C(=O)N(Cc2cn3ccc(-c4nnc(C(F)F)o4)cc3n2)c2ccccc2)C1] |
| 124 | 4169 | 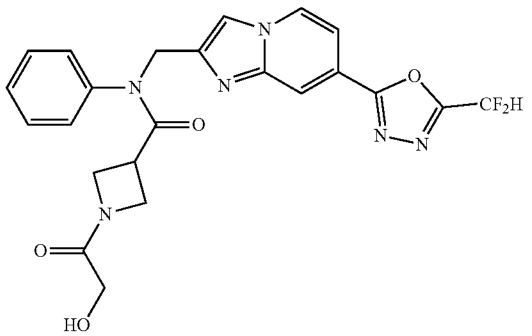 [SMILES: O=C(CO)N1CC(C(=O)N(Cc2cn3ccc(-c4nnc(C(F)F)o4)cc3n2)c2ccccc2)C1] |
| 125 | 4170 | 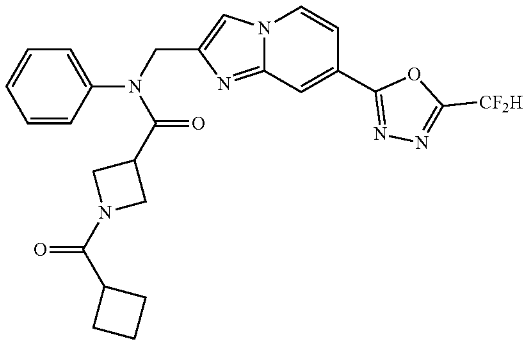 [SMILES: O=C(C1CCC1)N1CC(C(=O)N(Cc2cn3ccc(-c4nnc(C(F)F)o4)cc3n2)c2ccccc2)C1] |

TABLE 1-continued
| Ex | Comp | Structure |
|---|---|---|
| 126 | 4171 | 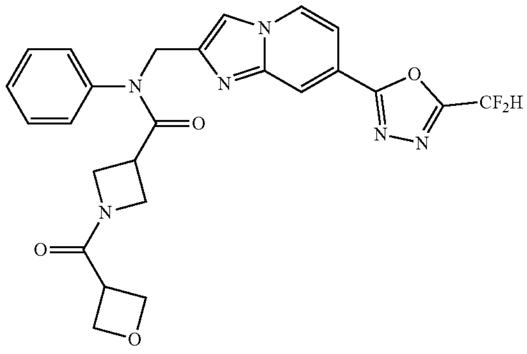 [SMILES: O=C(C1COC1)N1CC(C(=O)N(Cc2cn3ccc(-c4nnc(C(F)F)o4)cc3n2)c2ccccc2)C1] |
| 127 | 4172 | 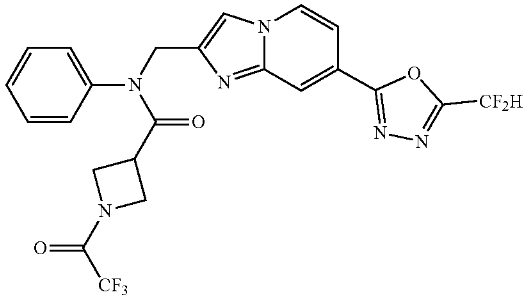 [SMILES: O=C(C1CN(C(=O)C(F)(F)F)C1)N(Cc1cn2ccc(-c3nnc(C(F)F)o3)cc2n1)c1ccccc1] |
| 128 | 4173 | 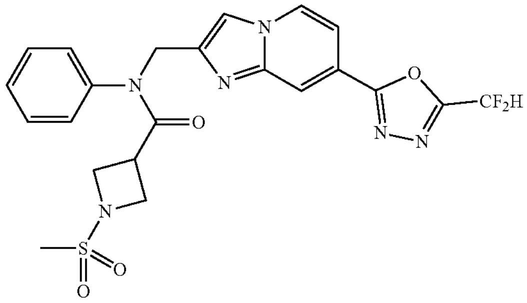 [SMILES: CS(=O)(=O)N1CC(C(=O)N(Cc2cn3ccc(-c4nnc(C(F)F)o4)cc3n2)c2ccccc2)C1] |
| 129 | 4174 | 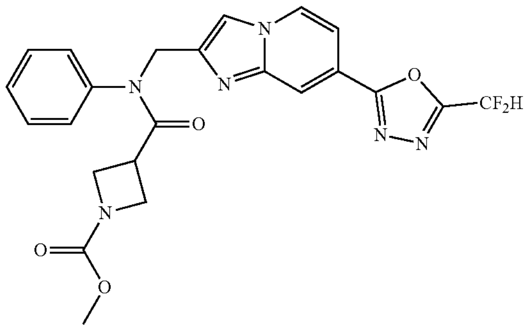 |

TABLE 1-continued
| Ex | Comp | Structure |
|---|---|---|
| 130 | 4175 | 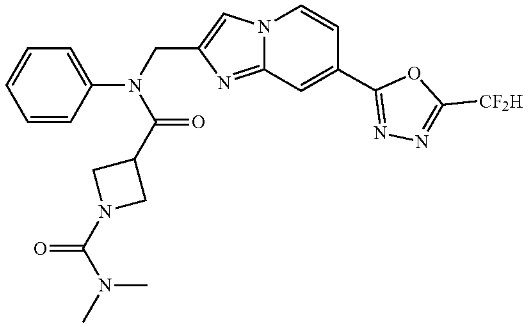 [SMILES: CN(C)C(=O)N1CC(C(=O)N(Cc2cn3ccc(-c4nnc(C(F)F)o4)cc3n2)c2ccccc2)C1] |
| 131 | 4176 | 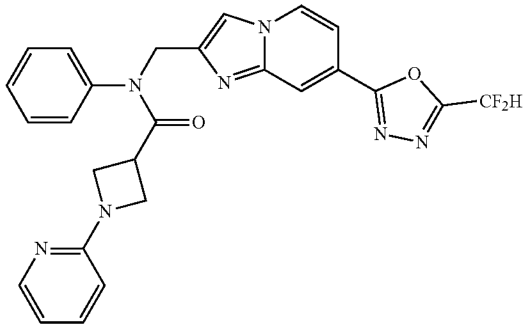 [SMILES: O=C(C1CN(c2ccccn2)C1)N(Cc1cn2ccc(-c3nnc(C(F)F)o3)cc2n1)c1ccccc1] |
| 132 | 4177 | 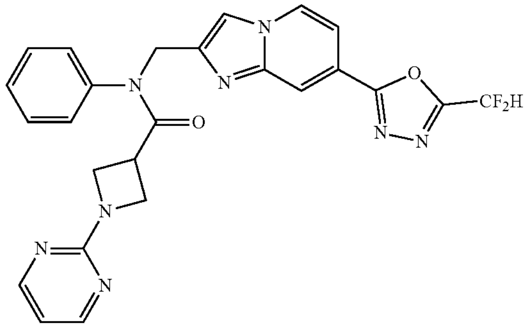 [SMILES: O=C(C1CN(c2ncccn2)C1)N(Cc1cn2ccc(-c3nnc(C(F)F)o3)cc2n1)c1ccccc1] |
| 133 | 4188 | 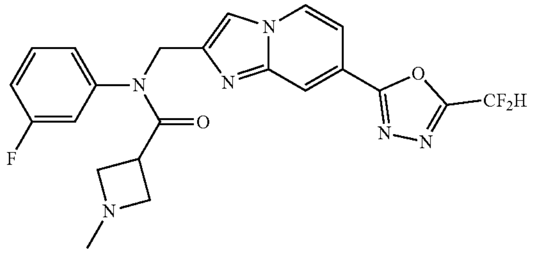 [SMILES: CN1CC(C(=O)N(Cc2cn3ccc(-c4nnc(C(F)F)o4)cc3n2)c2cccc(F)c2)C1] |
| 134 | 4189 | 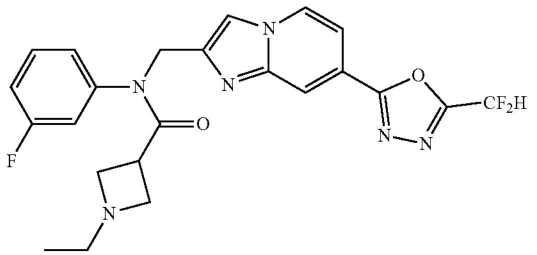 |

TABLE 1-continued
| Ex | Comp | Structure |
|---|---|---|
| 135 | 4190 | 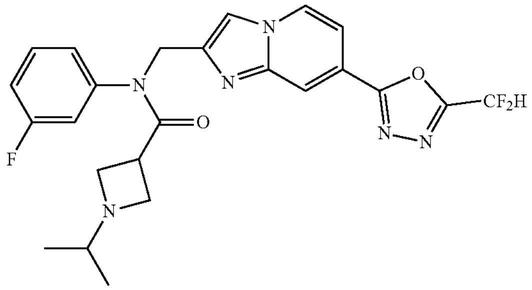 |
| 136 | 4191 | 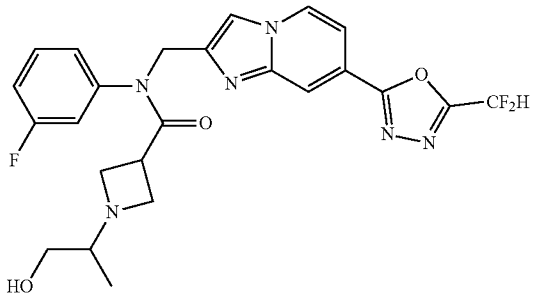 [SMILES: CC(CO)N1CC(C(=O)N(Cc2cn3ccc(-c4nnc(C(F)F)o4)cc3n2)c2cccc(F)c2)C1] |
| 137 | 4192 | 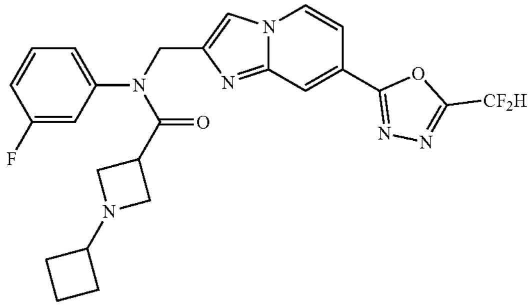 [SMILES: O=C(C1CN(C2CCC2)C1)N(Cc1cn2ccc(-c3nnc(C(F)F)o3)cc2n1)c1cccc(F)c1] |
| 138 | 4193 | 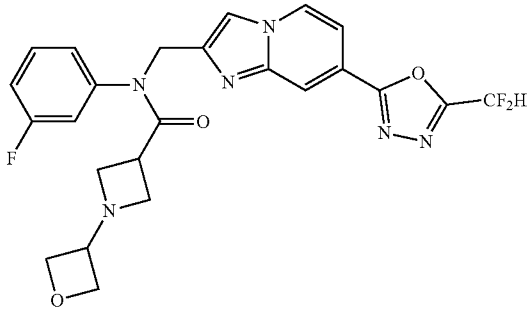 [SMILES: O=C(C1CN(C2COC2)C1)N(Cc1cn2ccc(-c3nnc(C(F)F)o3)cc2n1)c1cccc(F)c1] |
| 139 | 4194 | 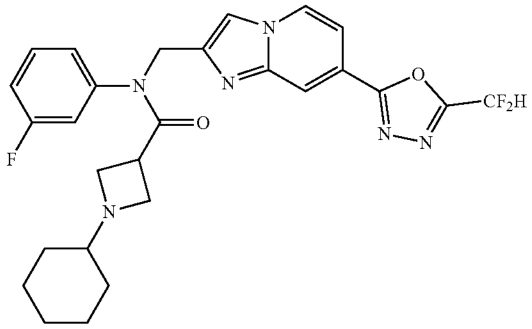 [SMILES: O=C(C1CN(C2CCCCC2)C1)N(Cc1cn2ccc(-c3nnc(C(F)F)o3)cc2n1)c1cccc(F)c1] |

TABLE 1-continued
| Ex | Comp | Structure |
|---|---|---|
| 140 | 4195 | 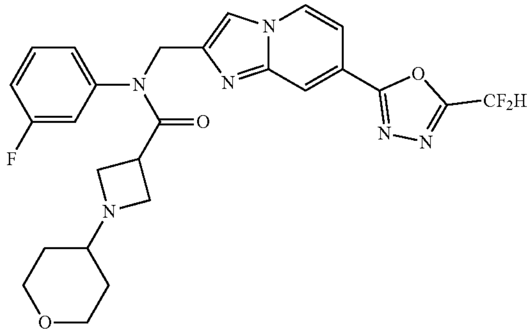 [SMILES: O=C(C1CN(C2CCOCC2)C1)N(Cc1cn2ccc(-c3nnc(C(F)F)o3)cc2n1)c1cccc(F)c1] |
| 141 | 4196 | 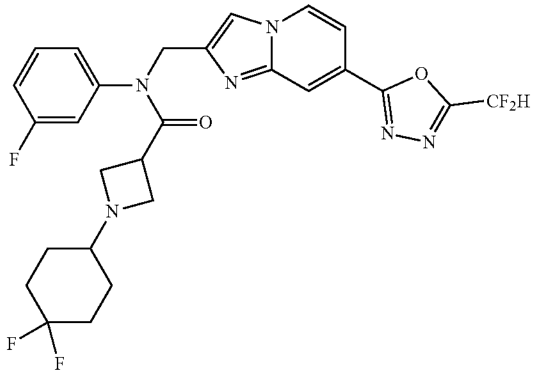 [SMILES: O=C(C1CN(C2CCC(F)(F)CC2)C1)N(Cc1cn2ccc(-c3nnc(C(F)F)o3)cc2n1)c1cccc(F)c1] |
| 142 | 4197 | 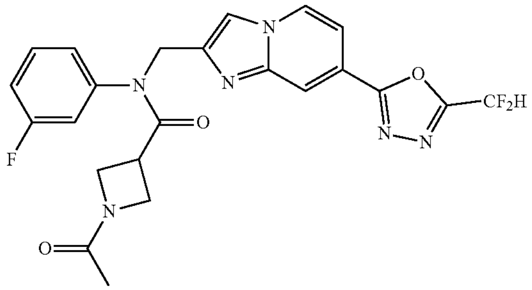 |
| 143 | 4198 | 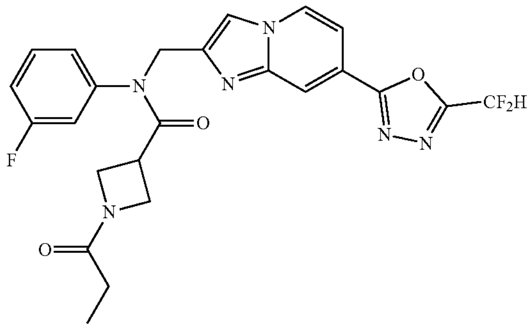 |

TABLE 1-continued
| Ex | Comp | Structure |
|---|---|---|
| 144 | 4199 | 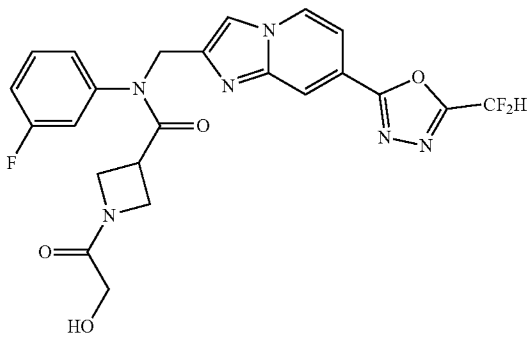 [SMILES: O=C(CO)N1CC(C(=O)N(Cc2cn3ccc(-c4nnc(C(F)F)o4)cc3n2)c2cccc(F)c2)C1] |
| 145 | 4200 | 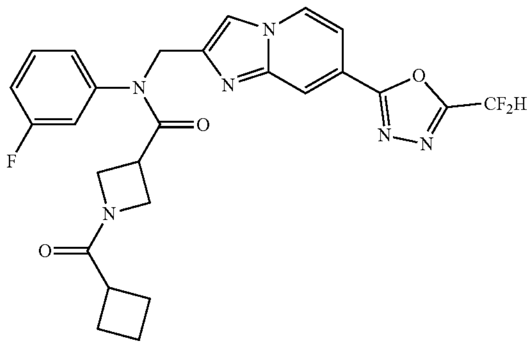 [SMILES: O=C(C1CCC1)N1CC(C(=O)N(Cc2cn3ccc(-c4nnc(C(F)F)o4)cc3n2)c2cccc(F)c2)C1] |
| 146 | 4201 | 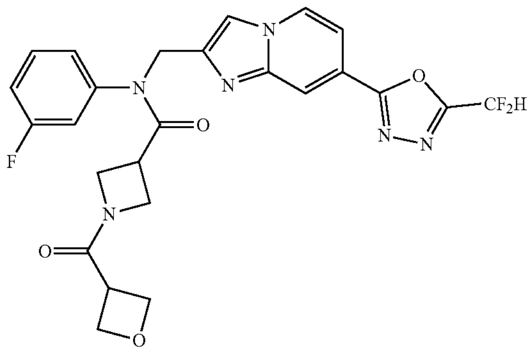 [SMILES: O=C(C1COC1)N1CC(C(=O)N(Cc2cn3ccc(-c4nnc(C(F)F)o4)cc3n2)c2cccc(F)c2)C1] |
| 147 | 4202 | 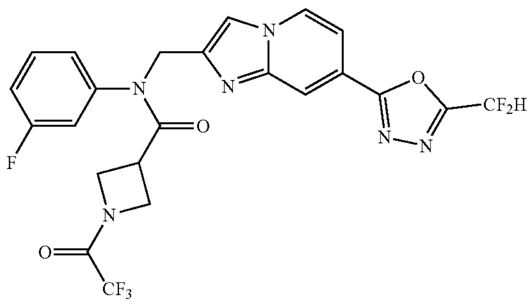 [SMILES: O=C(C1CN(C(=O)C(F)(F)F)C1)N(Cc1cn2ccc(-c3nnc(C(F)F)o3)cc2n1)c1cccc(F)c1] |

TABLE 1-continued
| Ex | Comp | Structure |
|---|---|---|
| 148 | 4203 | 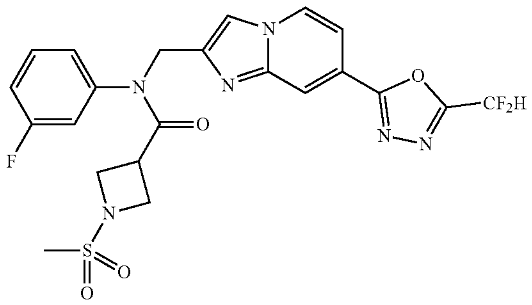 [SMILES: CS(=O)(=O)N1CC(C(=O)N(Cc2cn3ccc(-c4nnc(C(F)F)o4)cc3n2)c2cccc(F)c2)C1] |
| 149 | 4204 | 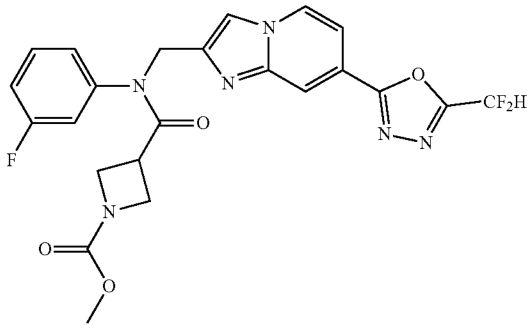 |
| 150 | 4205 | 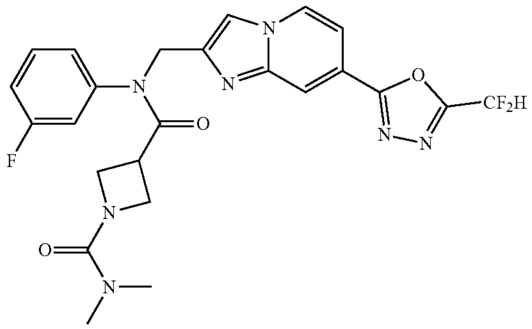 [SMILES: CN(C)C(=O)N1CC(C(=O)N(Cc2cn3ccc(-c4nnc(C(F)F)o4)cc3n2)c2cccc(F)c2)C1] |
| 151 | 4206 | 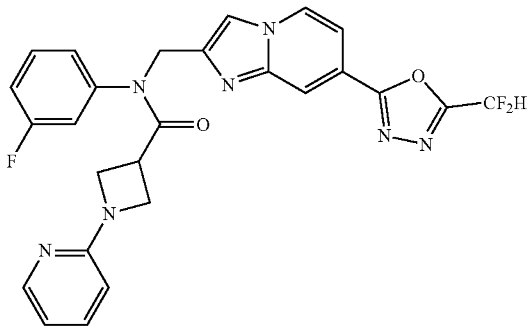 |

TABLE 1-continued
| Ex | Comp | Structure |
|---|---|---|
| 152 | 4207 | 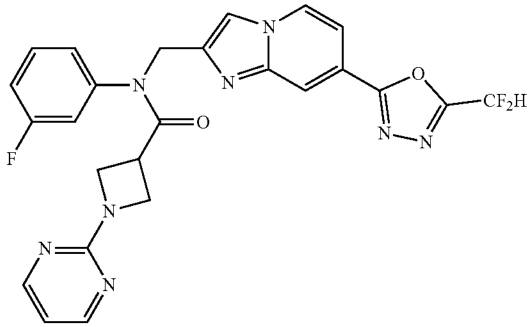 |
| 153 | 4618 | 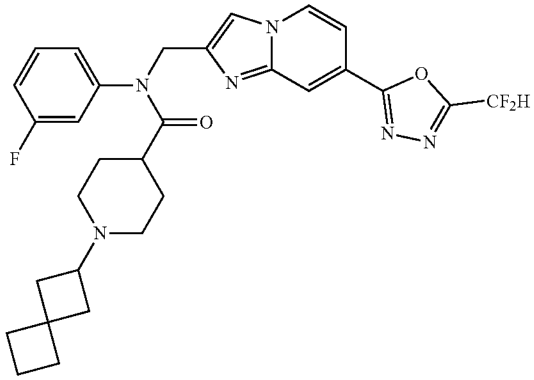 |
| 154 | 4619 | 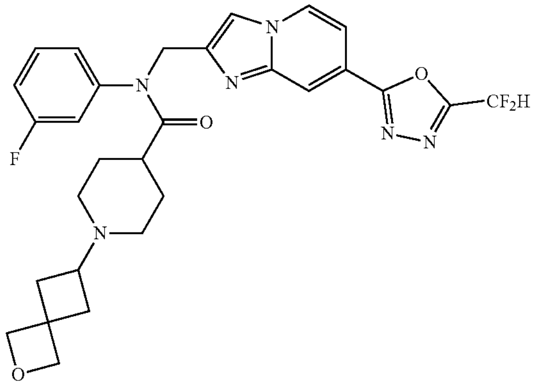 |
| 155 | 4620 | 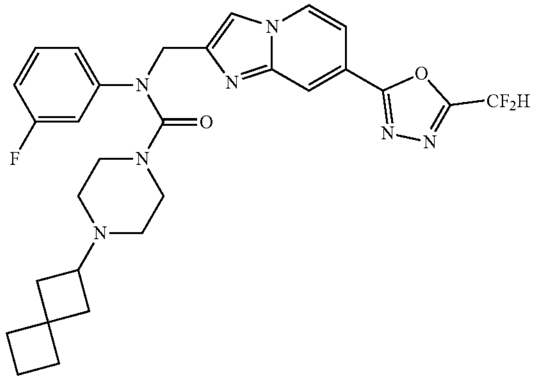 [SMILES: O=C(N1CCN(C2CC3(CCC3)C2)CC1)N(Cc1cn2ccc(-c3nnc(C(F)F)o3)cc2n1)c1cccc(F)c1] |

TABLE 1-continued
| Ex | Comp | Structure |
| --- | --- | --- |
| 156 | 4621 | 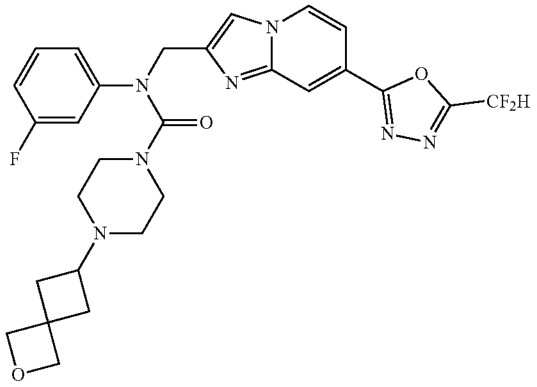 |
| 157 | 4625 | 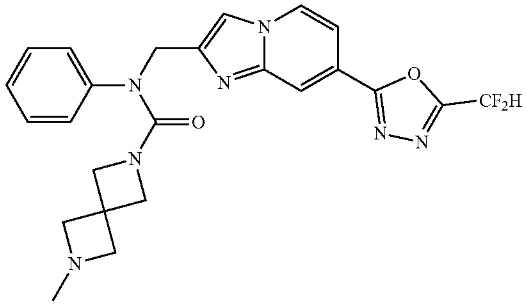 [SMILES: CN1CC2(C1)CN(C(=O)N(Cc1cn3ccc(-c4nnc(C(F)F)o4)cc3n1)c1ccccc1)C2] |
| 158 | 6892 | 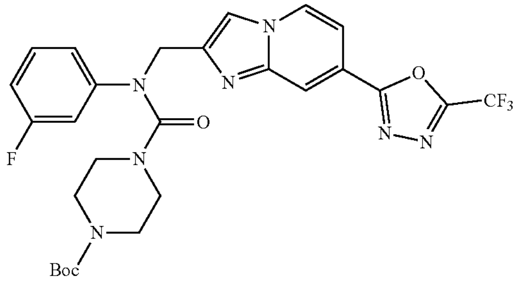 [SMILES: CC(C)(C)OC(=O)N1CCN(C(=O)N(Cc2cn3ccc(-c4nnc(C(F)(F)F)o4)cc3n2)c2cccc(F)c2)CC1] |
According to an embodiment of the present invention, specific compounds represented by Chemical Formula I of the present invention may be shown in Table 2 below:
TABLE 2
| Ex | Comp | Structure |
| --- | --- | --- |
| 33 | 3782 | 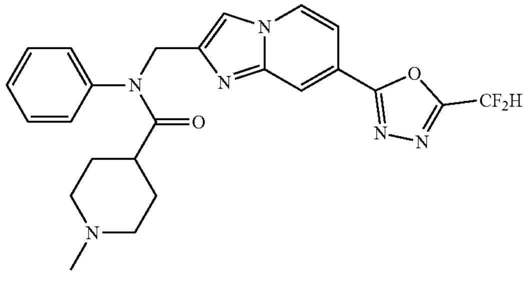 [SMILES: CN1CCC(C(=O)N(Cc2cn3ccc(-c4nnc(C(F)F)o4)cc3n2)c2ccccc2)CC1] |

TABLE 2-continued
| Ex | Comp | Structure |
|---|---|---|
| 34 | 3783 | 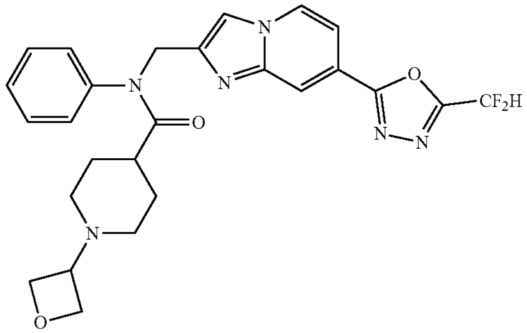 |
| 40 | 4036 | 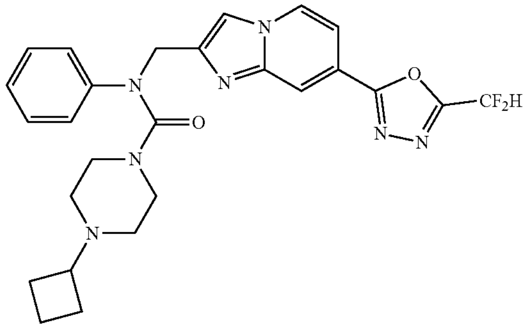 [SMILES: O=C(N1CCN(C2CCC2)CC1)N(Cc1cn2ccc(-c3nnc(C(F)F)o3)cc2n1)c1ccccc1] |
| 75 | 4115 | 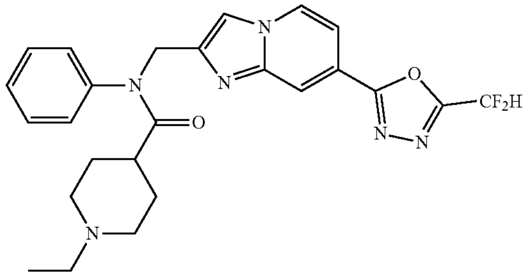 [SMILES: CCN1CCC(C(=O)N(Cc2cn3ccc(-c4nnc(C(F)F)o4)cc3n2)c2ccccc2)CC1] |
| 76 | 4116 | 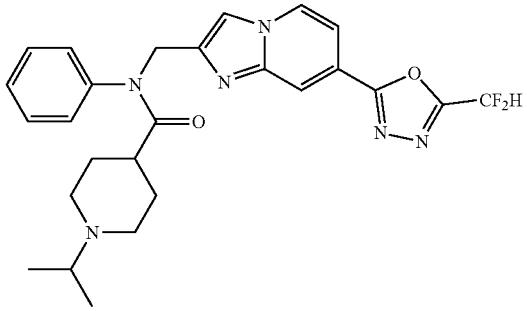 [SMILES: CC(C)N1CCC(C(=O)N(Cc2cn3ccc(-c4nnc(C(F)F)o4)cc3n2)c2ccccc2)CC1] |
| 77 | 4117 | 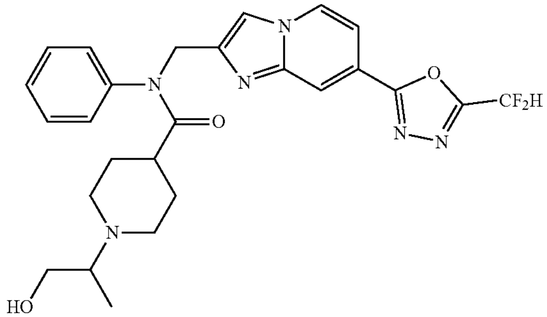 |

TABLE 2-continued
| Ex | Comp | Structure |
|---|---|---|
| 78 | 4118 | 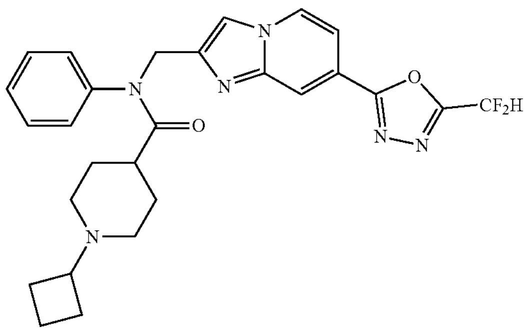 [SMILES: O=C(C1CCN(C2CCC2)CC1)N(Cc1cn2ccc(-c3nnc(C(F)F)o3)cc2n1)c1ccccc1] |
| 79 | 4119 | 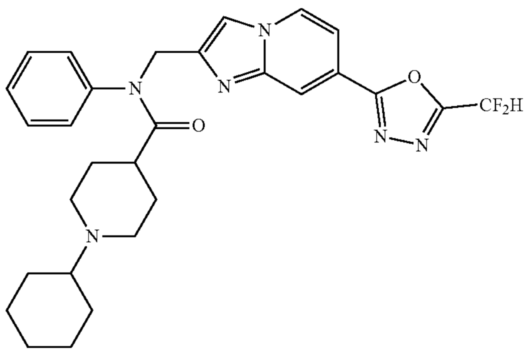 [SMILES: O=C(C1CCN(C2CCCCC2)CC1)N(Cc1cn2ccc(-c3nnc(C(F)F)o3)cc2n1)c1ccccc1] |
| 80 | 4120 | 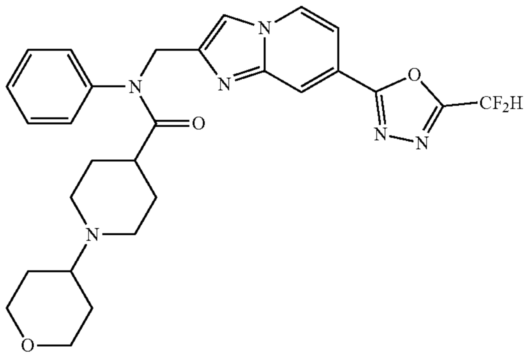 [SMILES: O=C(C1CCN(C2CCOCC2)CC1)N(Cc1cn2ccc(-c3nnc(C(F)F)o3)cc2n1)c1ccccc1] |
| 81 | 4121 | 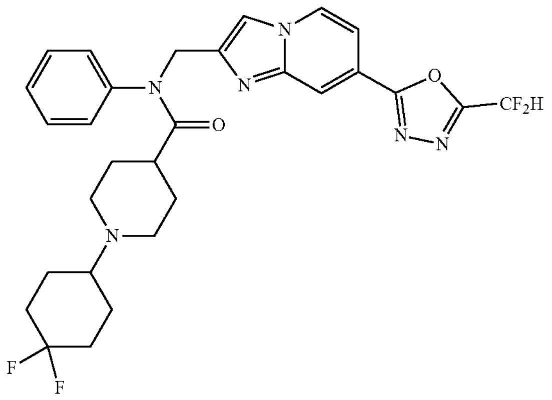 |

TABLE 2-continued
| Ex | Comp | Structure |
|---|---|---|
| 82 | 4122 | 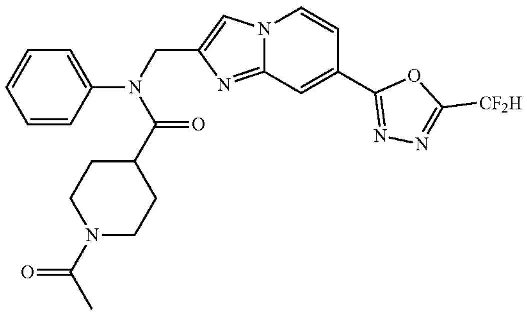 |
| 83 | 4123 | 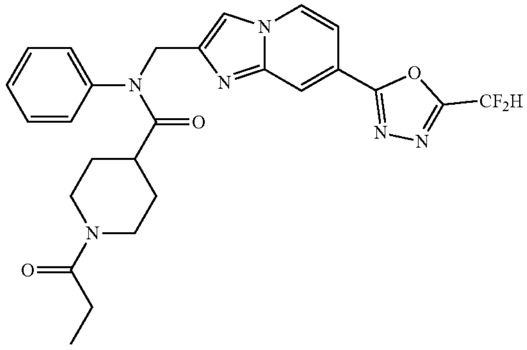 |
| 84 | 4124 | 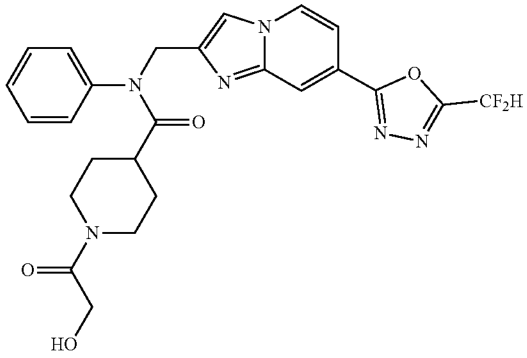 |
| 85 | 4125 | 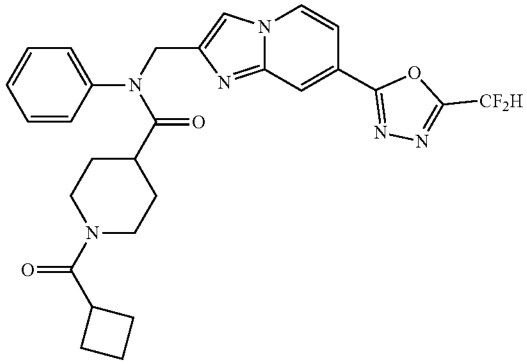 [SMILES: O=C(C1CCC1)N1CCC(C(=O)N(Cc2cn3ccc(-c4nnc(C(F)F)o4)cc3n2)c2ccccc2)CC1] |

TABLE 2-continued
| Ex | Comp | Structure |
|---|---|---|
| 86 | 4126 | 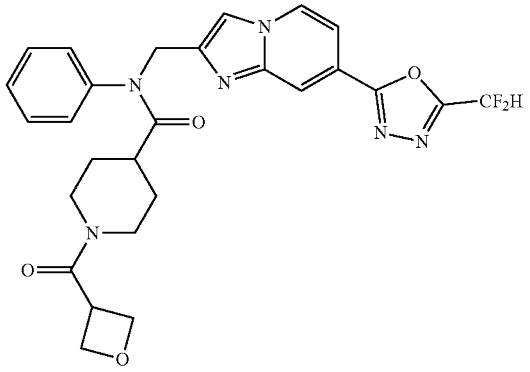 [SMILES: O=C(C1COC1)N1CCC(C(=O)N(Cc2cn3ccc(-c4nnc(C(F)F)o4)cc3n2)c2ccccc2)CC1] |
| 87 | 4127 | 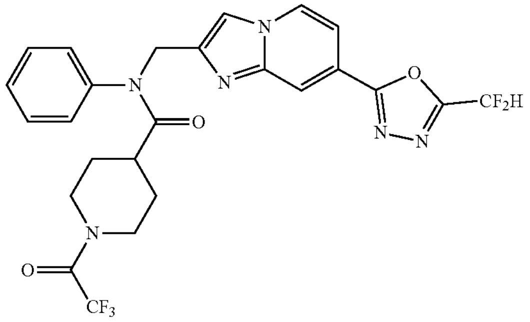 [SMILES: O=C(C1CCN(C(=O)C(F)(F)F)CC1)N(Cc1cn2ccc(-c3nnc(C(F)F)o3)cc2n1)c1ccccc1] |
| 88 | 4128 | 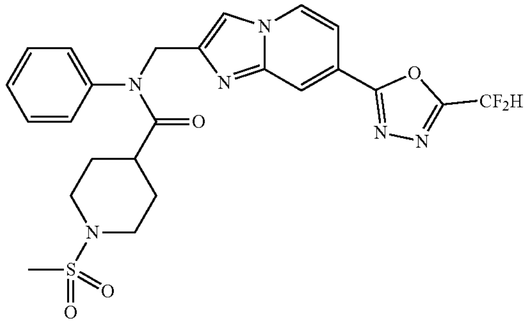 [SMILES: CS(=O)(=O)N1CCC(C(=O)N(Cc2cn3ccc(-c4nnc(C(F)F)o4)cc3n2)c2ccccc2)CC1] |
| 89 | 4129 | 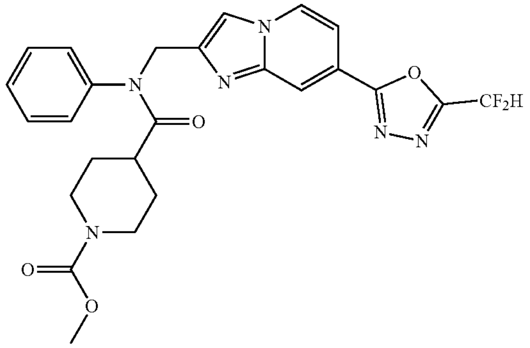 |

TABLE 2-continued
| Ex | Comp | Structure |
|---|---|---|
| 90 | 4130 | 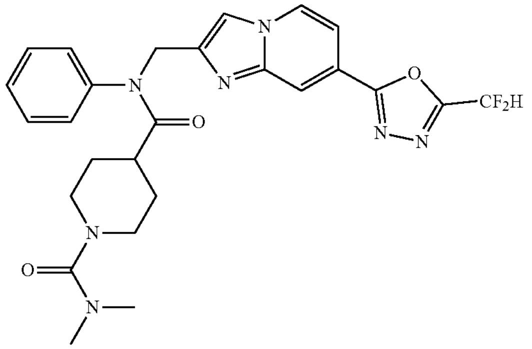 |
| 91 | 4131 | 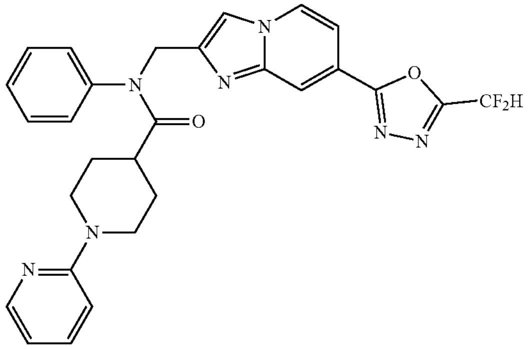 [SMILES: O=C(C1CCN(c2ccccn2)CC1)N(Cc1cn2ccc(-c3nnc(C(F)F)o3)cc2n1)c1ccccc1] |
| 92 | 4132 | 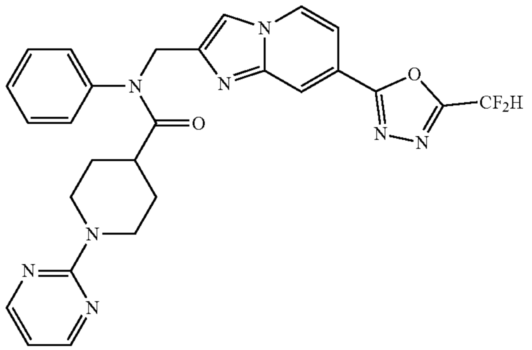 [SMILES: O=C(C1CCN(c2ncccn2)CC1)N(Cc1cn2ccc(-c3nnc(C(F)F)o3)cc2n1)c1ccccc1] |
| 93 | 4137 | 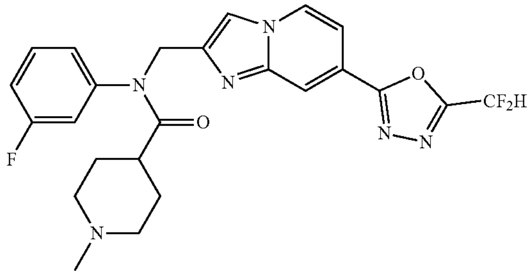 |

TABLE 2-continued
| Ex | Comp | Structure |
|---|---|---|
| 94 | 4138 | 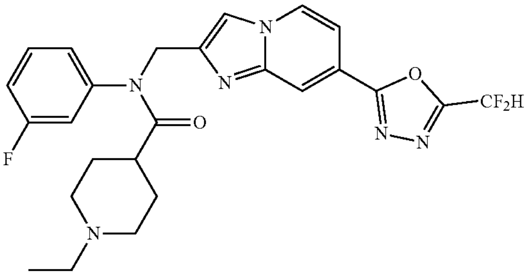 |
| 95 | 4139 | 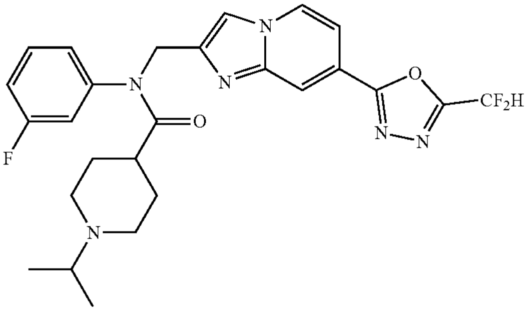 |
| 96 | 4140 | 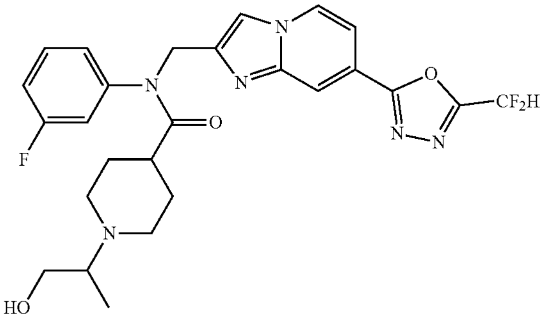 |
| 97 | 4141 | 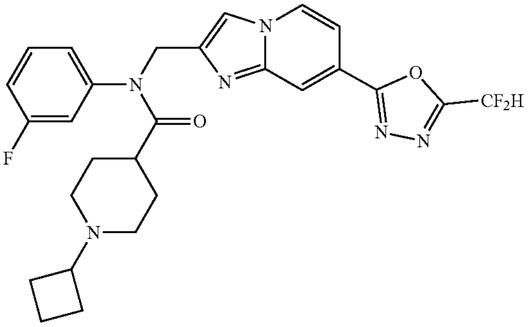 |
| 98 | 4142 | 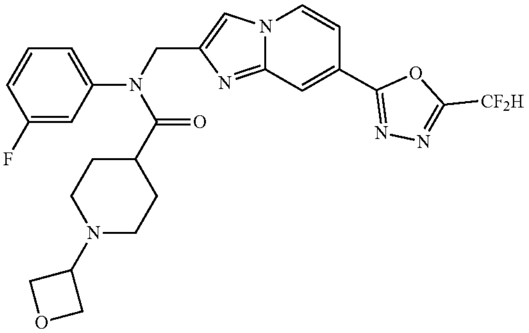 |

TABLE 2-continued
| Ex | Comp | Structure |
|---|---|---|
| 99 | 4143 | 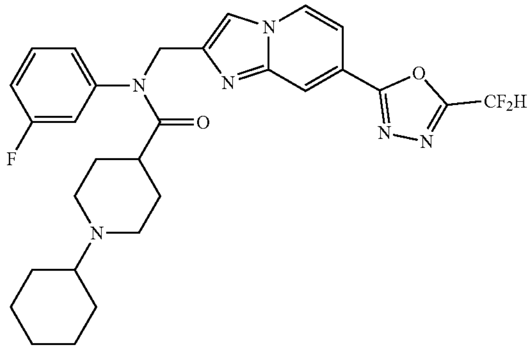 |
| 100 | 4144 | 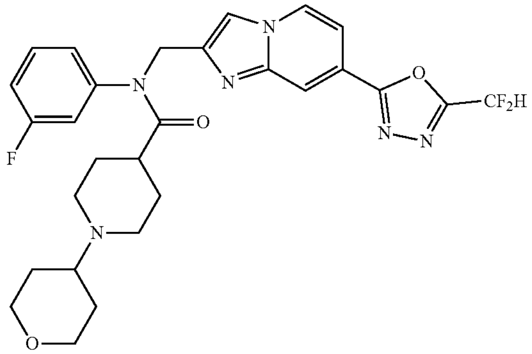 [SMILES: O=C(C1CCN(C2CCOCC2)CC1)N(Cc1cn2ccc(-c3nnc(C(F)F)o3)cc2n1)c1cccc(F)c1] |
| 101 | 4145 | 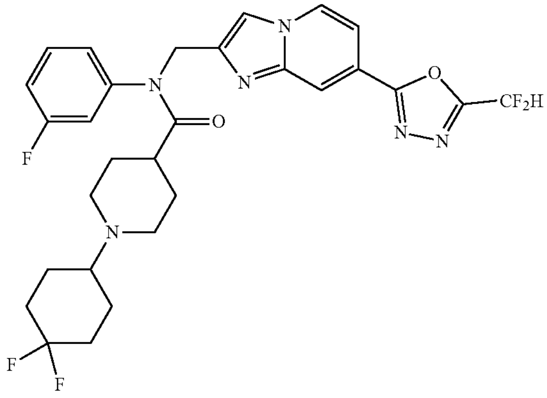 [SMILES: O=C(C1CCN(C2CCC(F)(F)CC2)CC1)N(Cc1cn2ccc(-c3nnc(C(F)F)o3)cc2n1)c1cccc(F)c1] |
| 102 | 4146 | 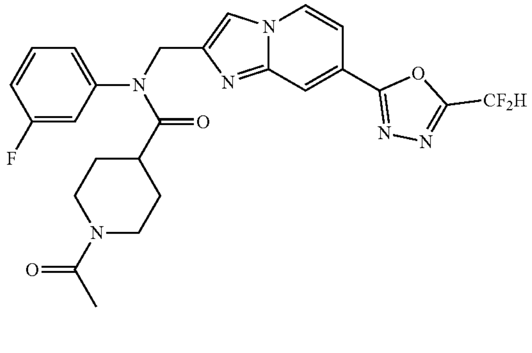 |

TABLE 2-continued
| Ex | Comp | Structure |
|---|---|---|
| 103 | 4147 | 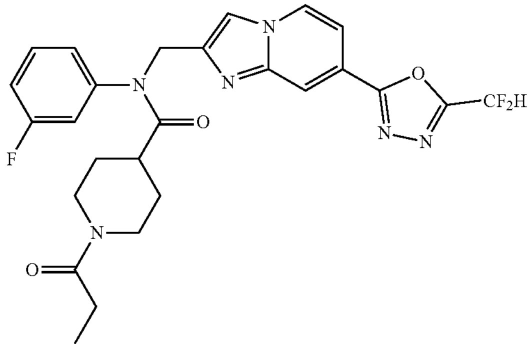 |
| 104 | 4149 | 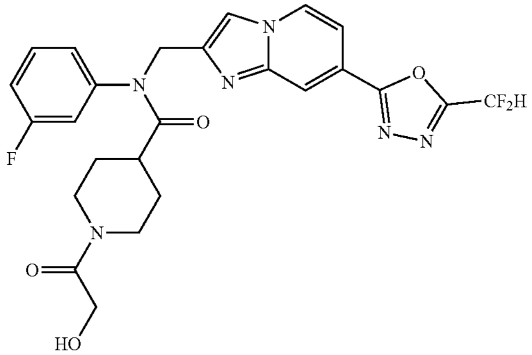 |
| 105 | 4150 | 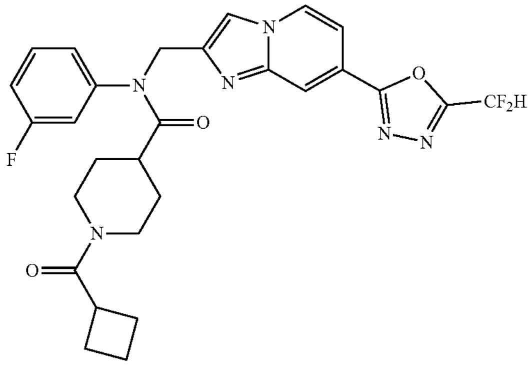 |
| 106 | 4151 | 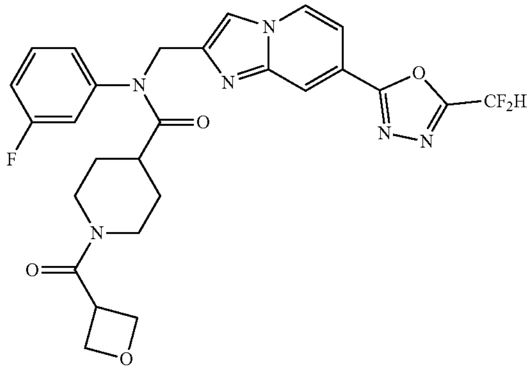 |

TABLE 2-continued
| Ex | Comp | Structure |
|---|---|---|
| 107 | 4152 | 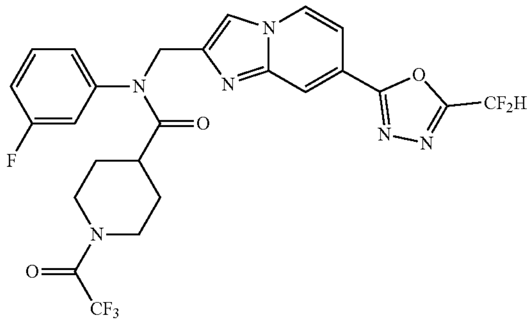 |
| 108 | 4153 | 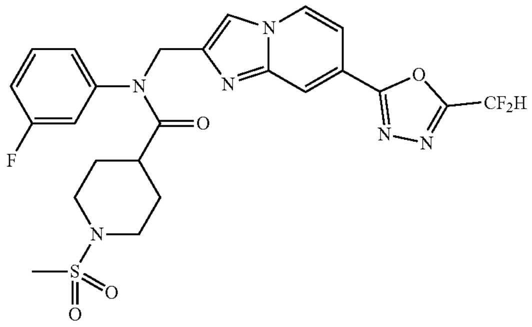 [SMILES: CS(=O)(=O)N1CCC(C(=O)N(Cc2cn3ccc(-c4nnc(C(F)F)o4)cc3n2)c2cccc(F)c2)CC1] |
| 109 | 4154 | 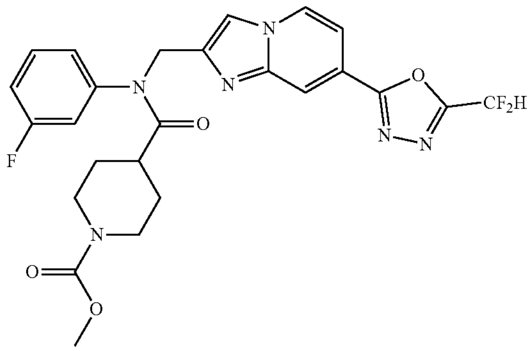 [SMILES: COC(=O)N1CCC(C(=O)N(Cc2cn3ccc(-c4nnc(C(F)F)o4)cc3n2)c2cccc(F)c2)CC1] |
| 110 | 4155 | 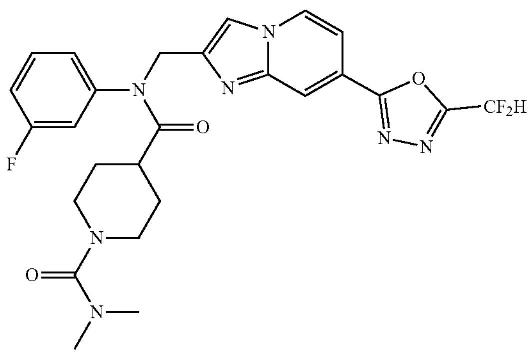 [SMILES: CN(C)C(=O)N1CCC(C(=O)N(Cc2cn3ccc(-c4nnc(C(F)F)o4)cc3n2)c2cccc(F)c2)CC1] |

TABLE 2-continued
| Ex | Comp | Structure |
|---|---|---|
| 111 | 4156 | 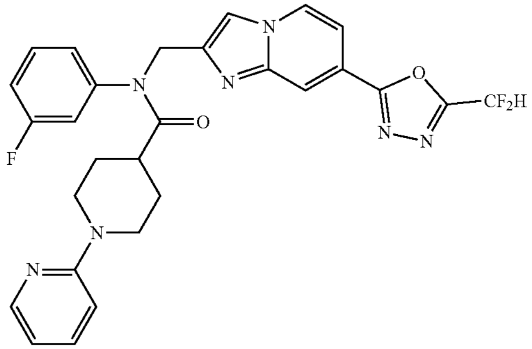 [SMILES: O=C(C1CCN(c2ccccn2)CC1)N(Cc1cn2ccc(-c3nnc(C(F)F)o3)cc2n1)c1cccc(F)c1] |
| 112 | 4157 | 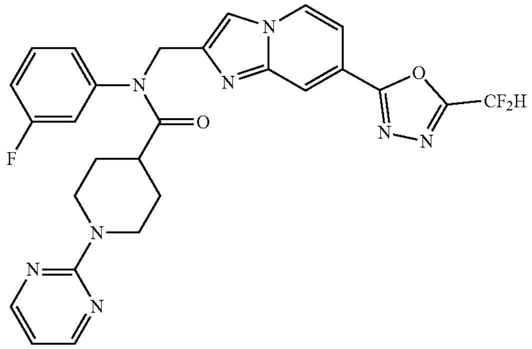 |
| 113 | 4158 | 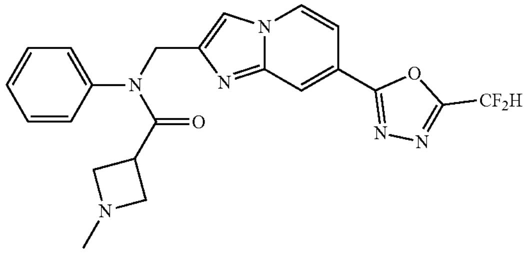 [SMILES: CN1CC(C(=O)N(Cc2cn3ccc(-c4nnc(C(F)F)o4)cc3n2)c2ccccc2)C1] |
| 114 | 4159 | 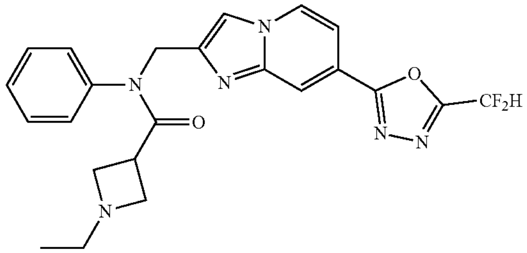 [SMILES: CCN1CC(C(=O)N(Cc2cn3ccc(-c4nnc(C(F)F)o4)cc3n2)c2ccccc2)C1] |
| 115 | 4160 | 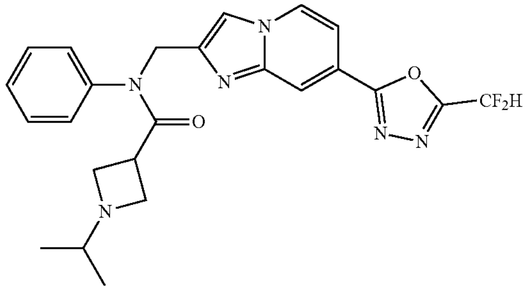 [SMILES: CC(C)N1CC(C(=O)N(Cc2cn3ccc(-c4nnc(C(F)F)o4)cc3n2)c2ccccc2)C1] |

TABLE 2-continued
| Ex | Comp | Structure |
|---|---|---|
| 116 | 4161 | 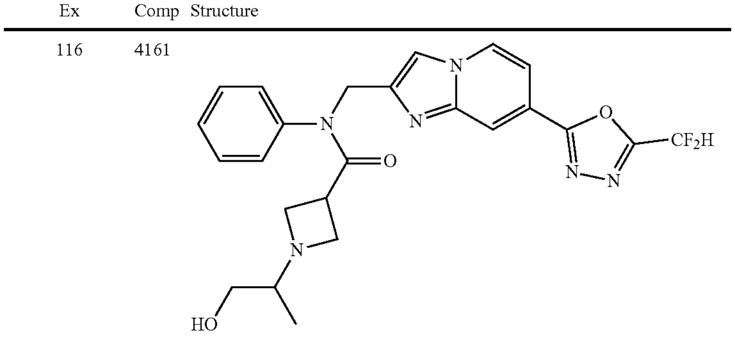 |
| 117 | 4162 | 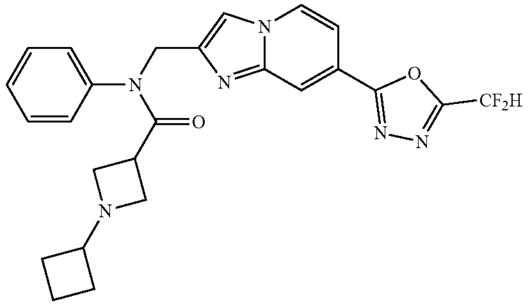 [SMILES: O=C(C1CN(C2CCC2)C1)N(Cc1cn2ccc(-c3nnc(C(F)F)o3)cc2n1)c1ccccc1] |
| 118 | 4163 | 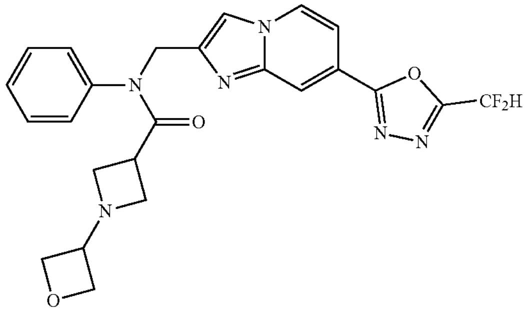 [SMILES: O=C(C1CN(C2COC2)C1)N(Cc1cn2ccc(-c3nnc(C(F)F)o3)cc2n1)c1ccccc1] |
| 119 | 4164 | 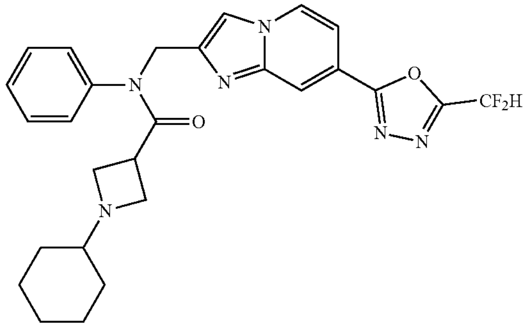 [SMILES: O=C(C1CN(C2CCCCC2)C1)N(Cc1cn2ccc(-c3nnc(C(F)F)o3)cc2n1)c1ccccc1] |
| 120 | 4165 | 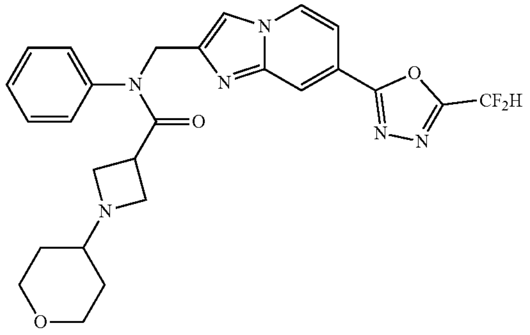 [SMILES: O=C(C1CN(C2CCOCC2)C1)N(Cc1cn2ccc(-c3nnc(C(F)F)o3)cc2n1)c1ccccc1] |

TABLE 2-continued
| Ex | Comp | Structure |
|---|---|---|
| 121 | 4166 | 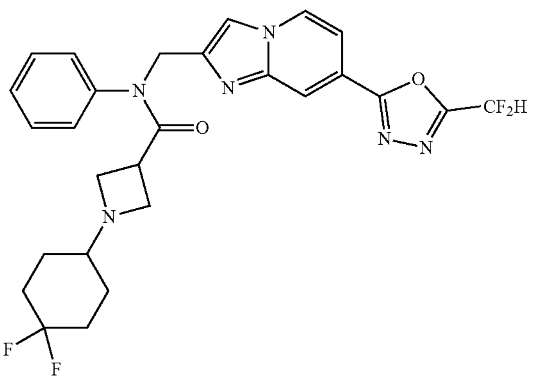 [SMILES: O=C(C1CN(C2CCC(F)(F)CC2)C1)N(Cc1cn2ccc(-c3nnc(C(F)F)o3)cc2n1)c1ccccc1] |
| 122 | 4167 | 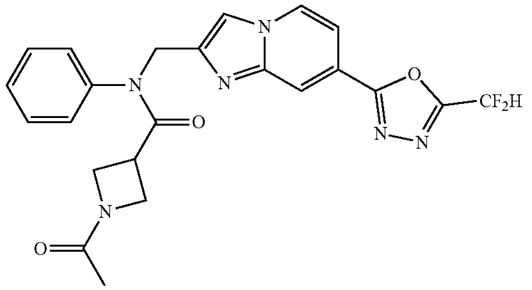 [SMILES: CC(=O)N1CC(C(=O)N(Cc2cn3ccc(-c4nnc(C(F)F)o4)cc3n2)c2ccccc2)C1] |
| 123 | 4168 | 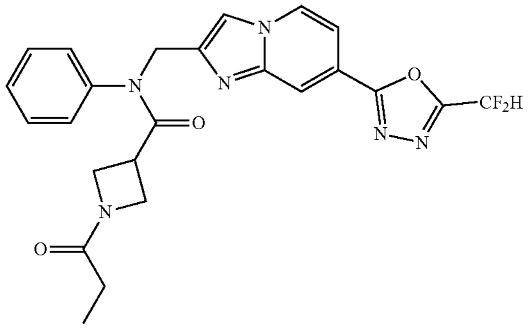 |
| 124 | 4169 | 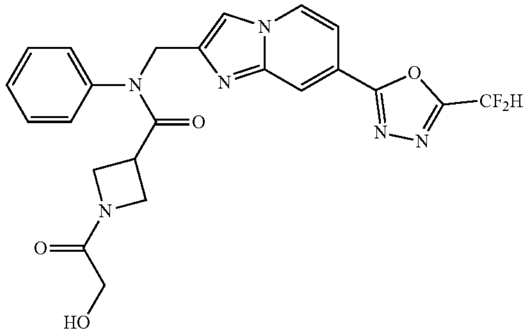 [SMILES: O=C(CO)N1CC(C(=O)N(Cc2cn3ccc(-c4nnc(C(F)F)o4)cc3n2)c2ccccc2)C1] |

TABLE 2-continued
| Ex | Comp | Structure |
|---|---|---|
| 125 | 4170 | 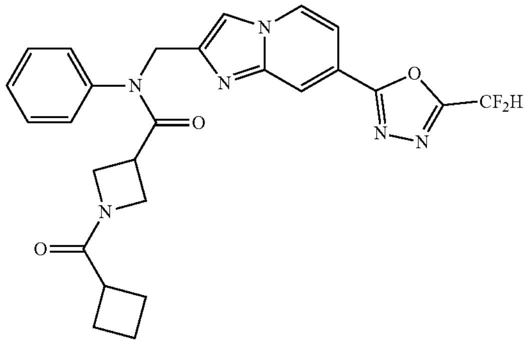 [SMILES: O=C(C1CCC1)N1CC(C(=O)N(Cc2cn3ccc(-c4nnc(C(F)F)o4)cc3n2)c2ccccc2)C1] |
| 126 | 4171 | 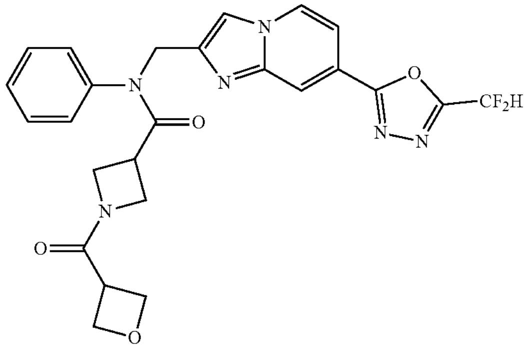 [SMILES: O=C(C1COC1)N1CC(C(=O)N(Cc2cn3ccc(-c4nnc(C(F)F)o4)cc3n2)c2ccccc2)C1] |
| 127 | 4172 | 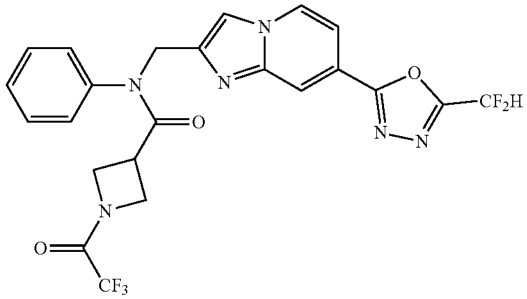 [SMILES: O=C(C1CN(C(=O)C(F)(F)F)C1)N(Cc1cn2ccc(-c3nnc(C(F)F)o3)cc2n1)c1ccccc1] |
| 128 | 4173 | 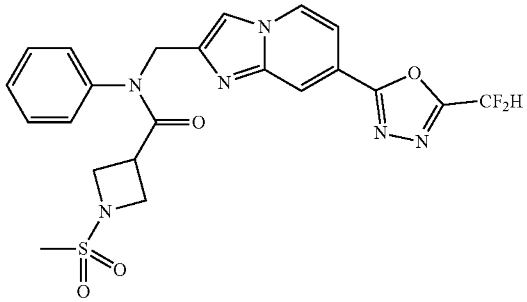 [SMILES: CS(=O)(=O)N1CC(C(=O)N(Cc2cn3ccc(-c4nnc(C(F)F)o4)cc3n2)c2ccccc2)C1] |

TABLE 2-continued
| Ex | Comp | Structure |
| --- | --- | --- |
| 129 | 4174 | 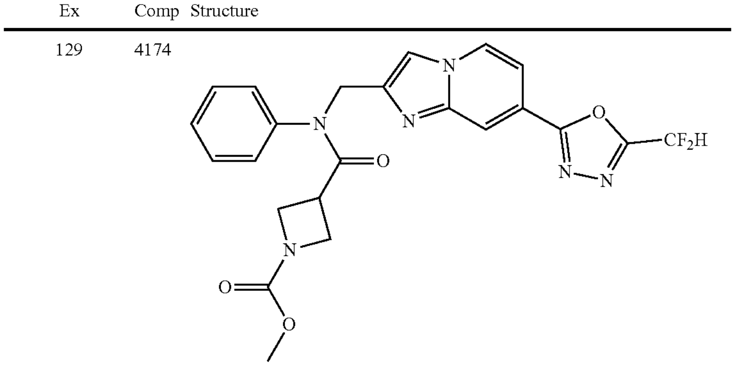 |
| 130 | 4175 | 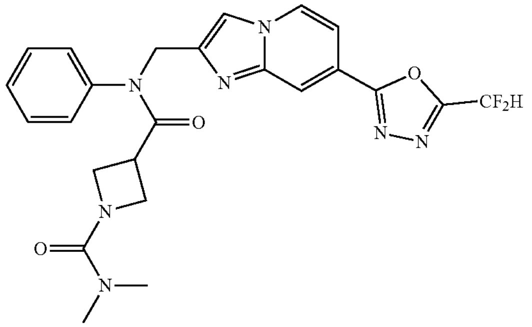 [SMILES: CN(C)C(=O)N1CC(C(=O)N(Cc2cn3ccc(-c4nnc(C(F)F)o4)cc3n2)c2ccccc2)C1] |
| 131 | 4176 | 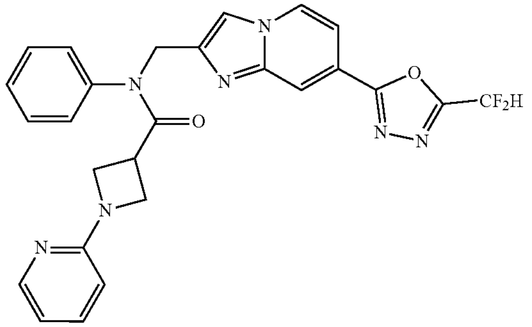 |
| 132 | 4177 | 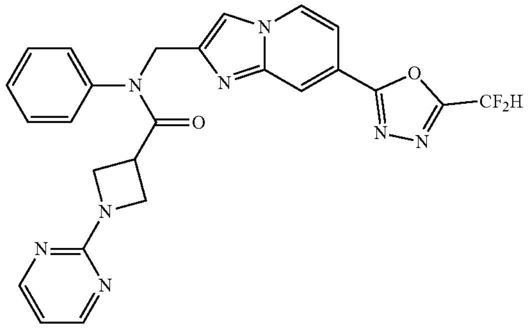 [SMILES: O=C(C1CN(c2ncccn2)C1)N(Cc1cn2ccc(-c3nnc(C(F)F)o3)cc2n1)c1ccccc1] |
| 133 | 4188 | 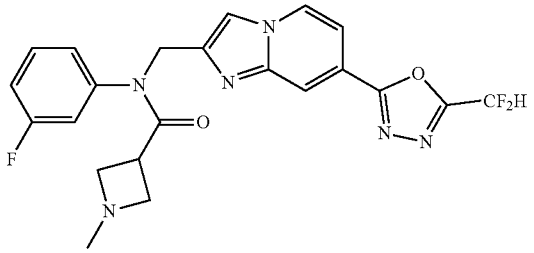 |

TABLE 2-continued
| Ex | Comp | Structure |
|---|---|---|
| 134 | 4189 | 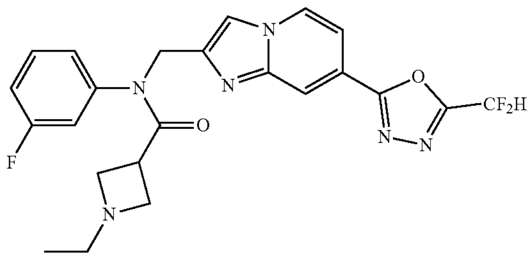 |
| 135 | 4190 | 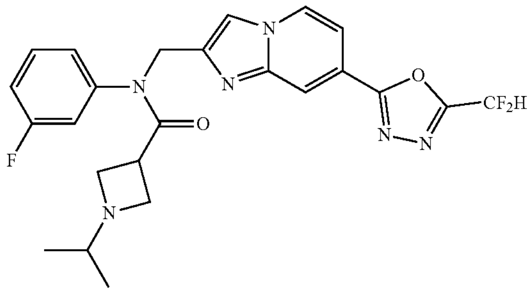 [SMILES: CC(C)N1CC(C(=O)N(Cc2cn3ccc(-c4nnc(C(F)F)o4)cc3n2)c2cccc(F)c2)C1] |
| 136 | 4191 | 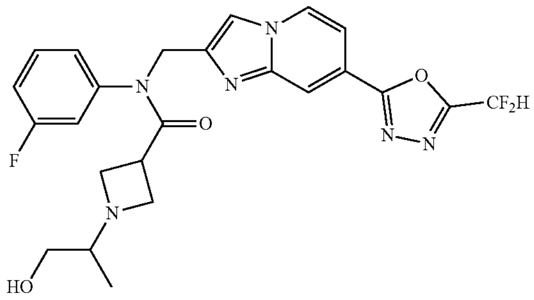 [SMILES: CC(CO)N1CC(C(=O)N(Cc2cn3ccc(-c4nnc(C(F)F)o4)cc3n2)c2cccc(F)c2)C1] |
| 137 | 4192 | 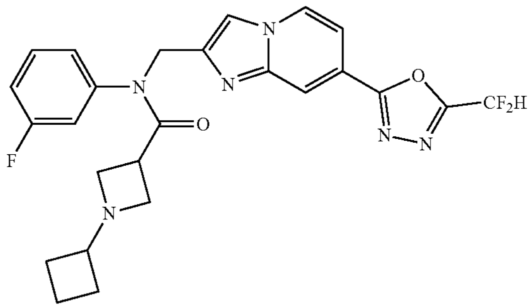 [SMILES: O=C(C1CN(C2CCC2)C1)N(Cc1cn2ccc(-c3nnc(C(F)F)o3)cc2n1)c1cccc(F)c1] |
| 138 | 4193 | 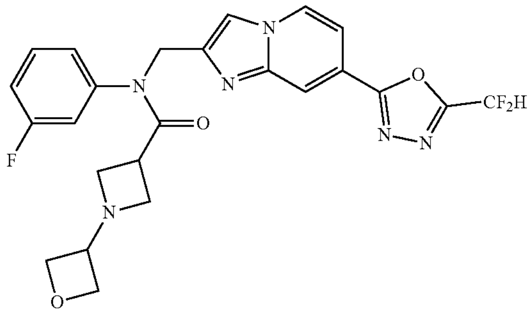 |

TABLE 2-continued
| Ex | Comp | Structure |
|---|---|---|
| 139 | 4194 | 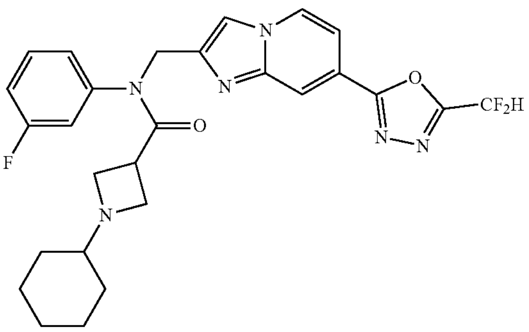 [SMILES: O=C(C1CN(C2CCCCC2)C1)N(Cc1cn2ccc(-c3nnc(C(F)F)o3)cc2n1)c1cccc(F)c1] |
| 140 | 4195 | 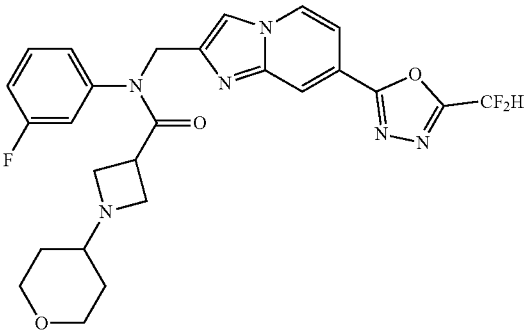 [SMILES: O=C(C1CN(C2CCOCC2)C1)N(Cc1cn2ccc(-c3nnc(C(F)F)o3)cc2n1)c1cccc(F)c1] |
| 141 | 4196 | 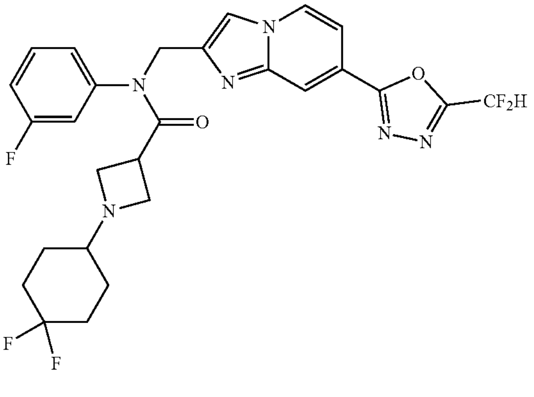 [SMILES: O=C(C1CN(C2CCC(F)(F)CC2)C1)N(Cc1cn2ccc(-c3nnc(C(F)F)o3)cc2n1)c1cccc(F)c1] |
| 142 | 4197 | 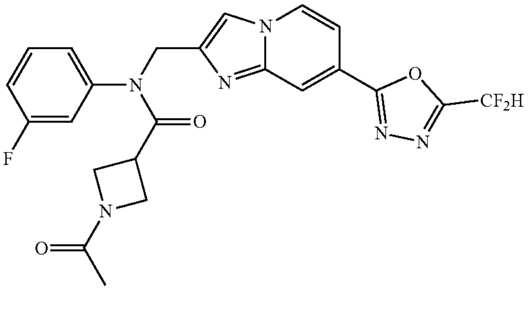 [SMILES: CC(=O)N1CC(C(=O)N(Cc2cn3ccc(-c4nnc(C(F)F)o4)cc3n2)c2cccc(F)c2)C1] |

TABLE 2-continued
| Ex | Comp | Structure |
|---|---|---|
| 143 | 4198 | 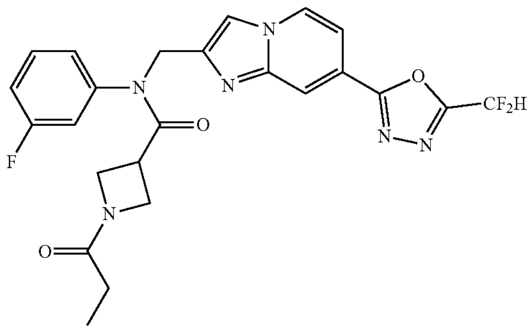 |
| 144 | 4199 | 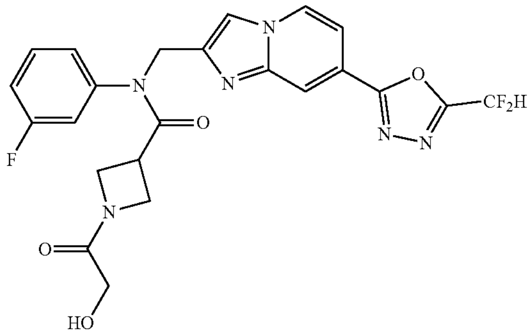 [SMILES: O=C(CO)N1CC(C(=O)N(Cc2cn3ccc(-c4nnc(C(F)F)o4)cc3n2)c2cccc(F)c2)C1] |
| 145 | 4200 | 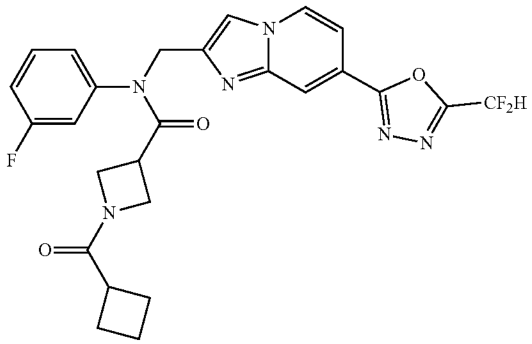 [SMILES: O=C(C1CCC1)N1CC(C(=O)N(Cc2cn3ccc(-c4nnc(C(F)F)o4)cc3n2)c2cccc(F)c2)C1] |
| 146 | 4201 | 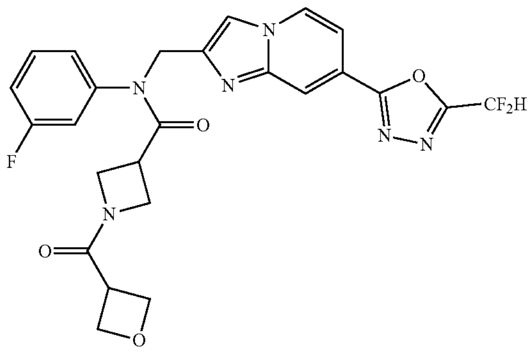 [SMILES: O=C(C1COC1)N1CC(C(=O)N(Cc2cn3ccc(-c4nnc(C(F)F)o4)cc3n2)c2cccc(F)c2)C1] |

TABLE 2-continued
| Ex | Comp | Structure |
| --- | --- | --- |
| 147 | 4202 | 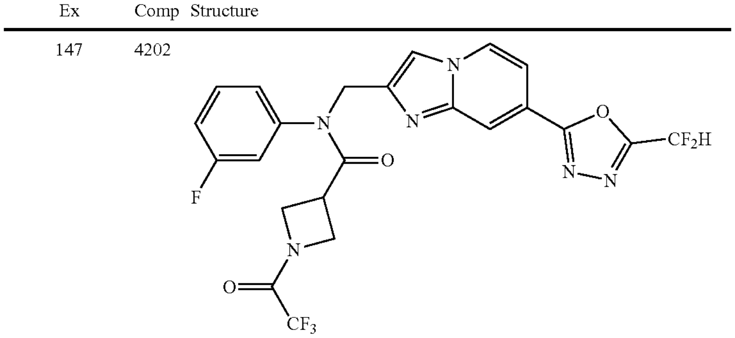 |
| 148 | 4203 | 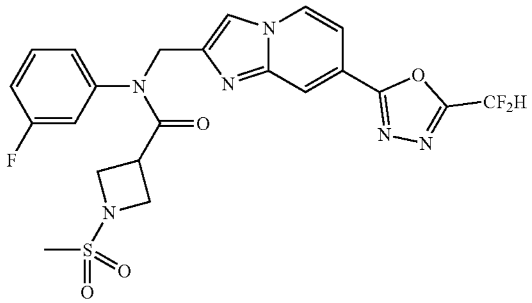 [SMILES: CS(=O)(=O)N1CC(C(=O)N(Cc2cn3ccc(-c4nnc(C(F)F)o4)cc3n2)c2cccc(F)c2)C1] |
| 149 | 4204 | 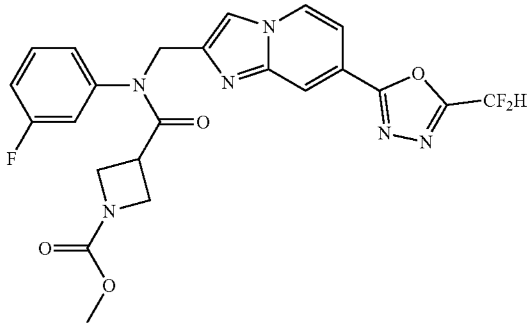 |
| 150 | 4205 | 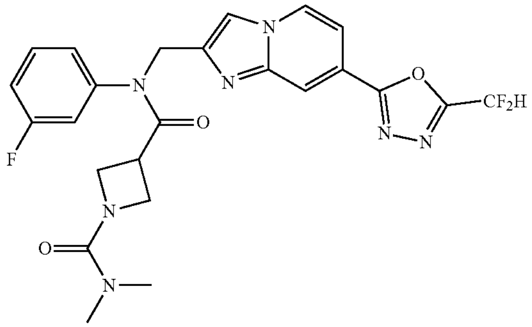 [SMILES: CN(C)C(=O)N1CC(C(=O)N(Cc2cn3ccc(-c4nnc(C(F)F)o4)cc3n2)c2cccc(F)c2)C1] |
| 151 | 4206 | 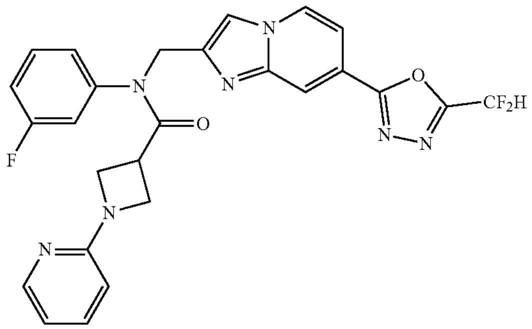 |

TABLE 2-continued
| Ex | Comp | Structure |
|---|---|---|
| 152 | 4207 | 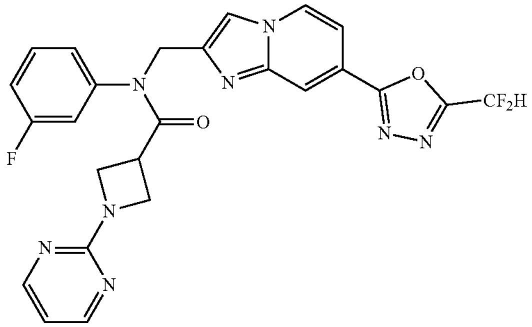 |
| 153 | 4618 | 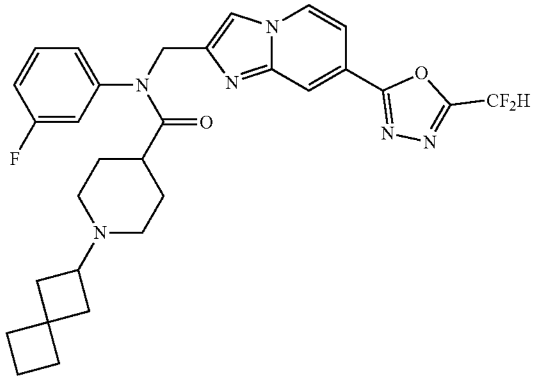 [SMILES: O=C(C1CCN(C2CC3(CCC3)C2)CC1)N(Cc1cn2ccc(-c3nnc(C(F)F)o3)cc2n1)c1cccc(F)c1] |
| 154 | 4619 | 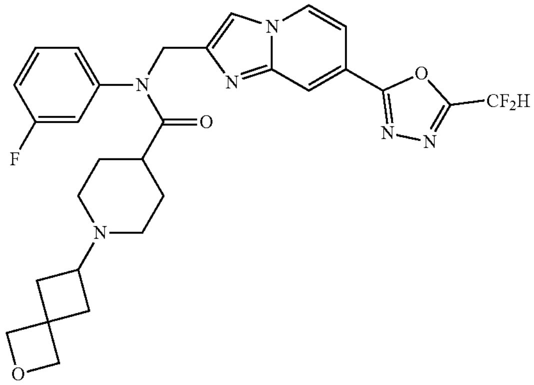 [SMILES: O=C(C1CCN(C2CC3(COC3)C2)CC1)N(Cc1cn2ccc(-c3nnc(C(F)F)o3)cc2n1)c1cccc(F)c1] |
According to another embodiment of the present invention, specific compounds represented by Chemical Formula I of the present invention may be shown in Table 3 below:
TABLE 3
| Ex | Comp | Structure |
|---|---|---|
| 35 | 3784 | 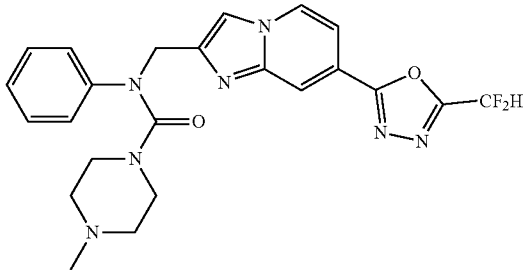 |

TABLE 3-continued
| Ex | Comp | Structure |
|---|---|---|
| 36 | 3785 | 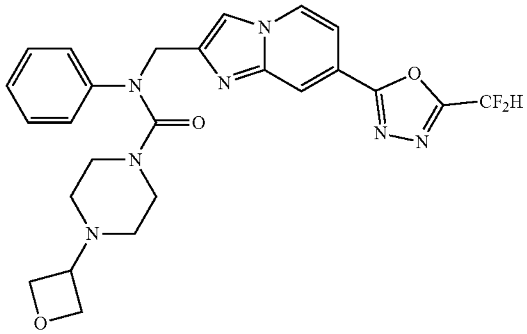 |
| 37 | 4033 | 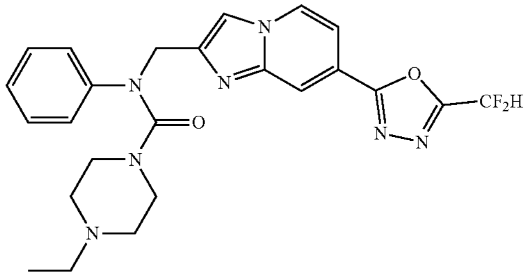 |
| 38 | 4034 | 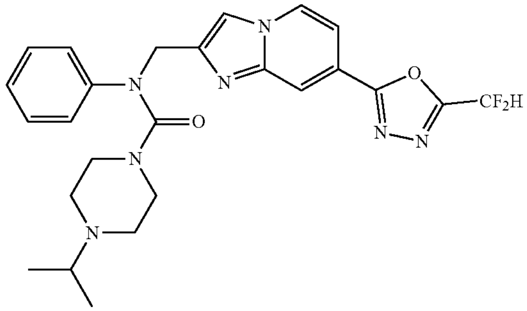 |
| 39 | 4035 | 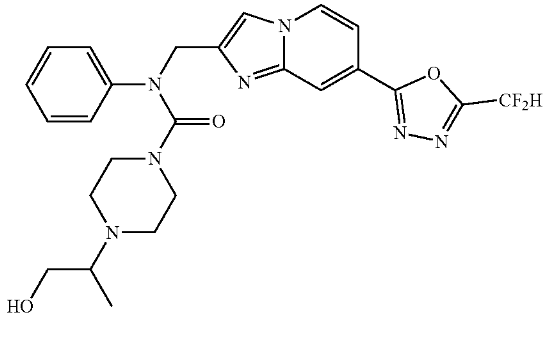 |

TABLE 3-continued
| Ex | Comp | Structure |
|---|---|---|
| 41 | 4037 | 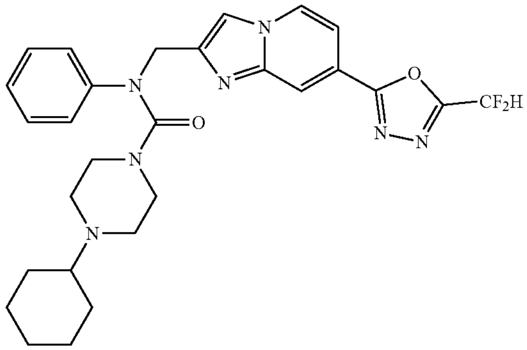 [SMILES: O=C(N1CCN(C2CCCCC2)CC1)N(Cc1cn2ccc(-c3nnc(C(F)F)o3)cc2n1)c1ccccc1] |
| 42 | 4038 | 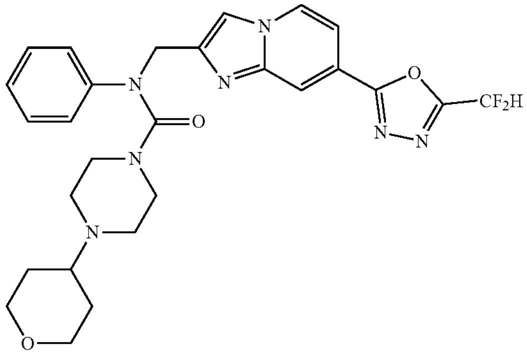 |
| 43 | 4039 | 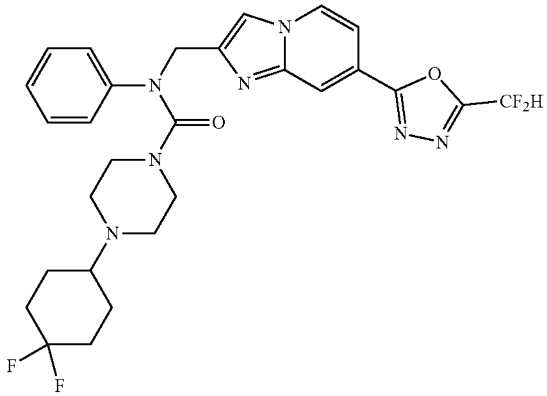 |
| 44 | 4040 | 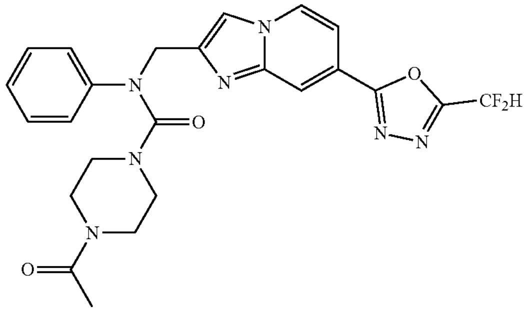 [SMILES: CC(=O)N1CCN(C(=O)N(Cc2cn3ccc(-c4nnc(C(F)F)o4)cc3n2)c2ccccc2)CC1] |

TABLE 3-continued
| Ex | Comp | Structure |
|---|---|---|
| 45 | 4041 | 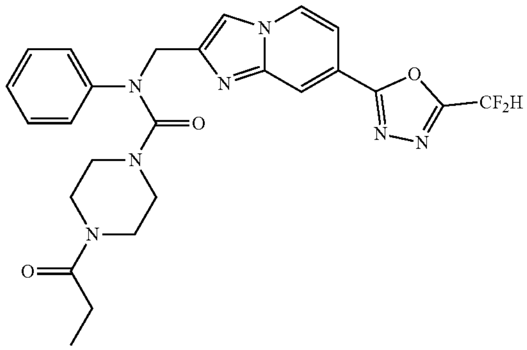 |
| 46 | 4042 | 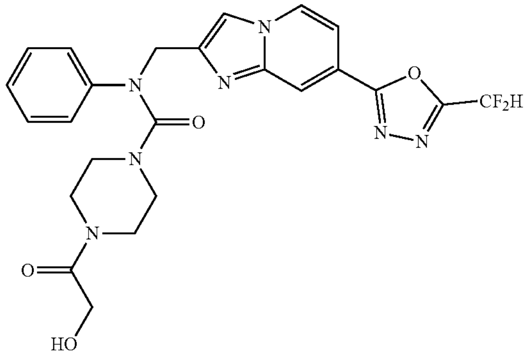 |
| 47 | 4043 | 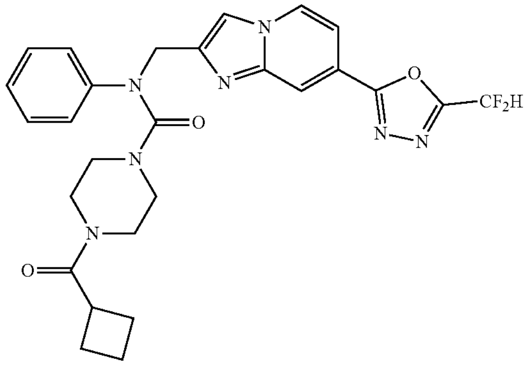 [SMILES: O=C(C1CCC1)N1CCN(C(=O)N(Cc2cn3ccc(-c4nnc(C(F)F)o4)cc3n2)c2ccccc2)CC1] |
| 48 | 4044 | 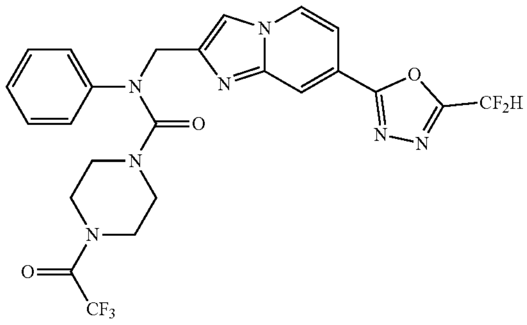 |

TABLE 3-continued
| Ex | Comp | Structure |
|---|---|---|
| 49 | 4045 | 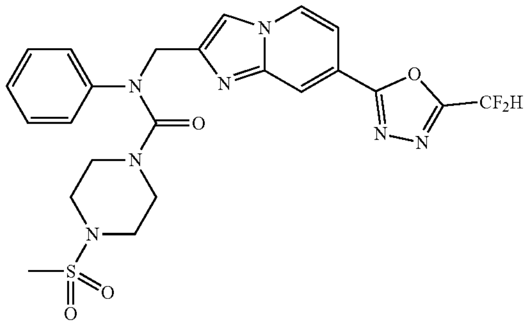 |
| 50 | 4046 | 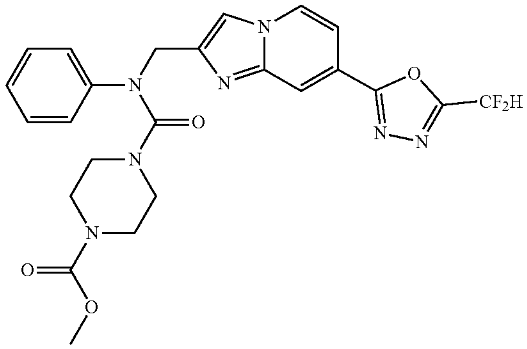 [SMILES: COC(=O)N1CCN(C(=O)N(Cc2cn3ccc(-c4nnc(C(F)F)o4)cc3n2)c2ccccc2)CC1] |
| 51 | 4047 | 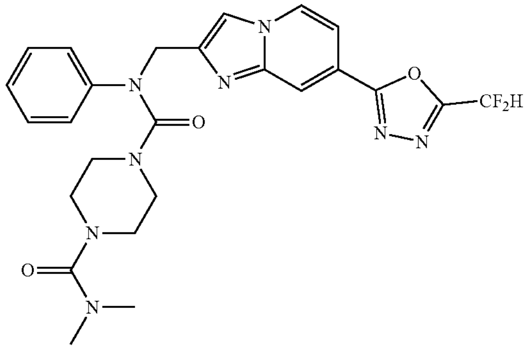 [SMILES: CN(C)C(=O)N1CCN(C(=O)N(Cc2cn3ccc(-c4nnc(C(F)F)o4)cc3n2)c2ccccc2)CC1] |
| 52 | 4048 | 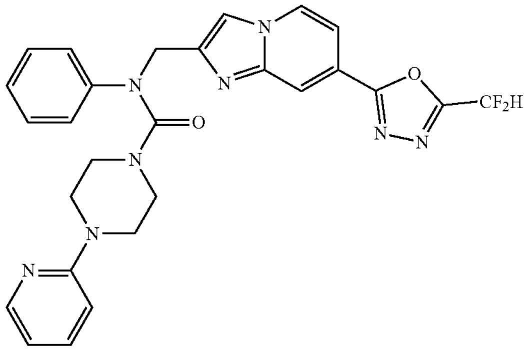 [SMILES: O=C(N1CCN(c2ccccn2)CC1)N(Cc1cn2ccc(-c3nnc(C(F)F)o3)cc2n1)c1ccccc1] |

TABLE 3-continued
| Ex | Comp | Structure |
|---|---|---|
| 53 | 4049 | 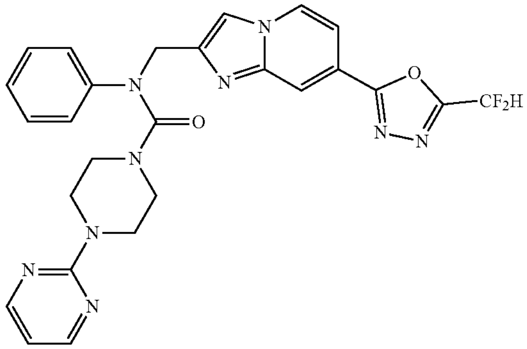 |
| 54 | 4083 | 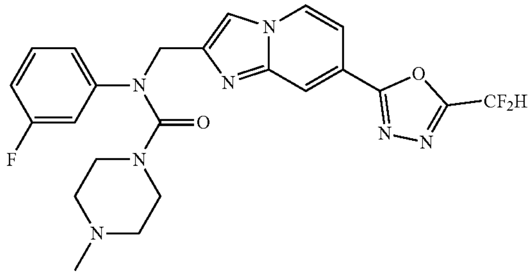 [SMILES: CN1CCN(C(=O)N(Cc2cn3ccc(-c4nnc(C(F)F)o4)cc3n2)c2cccc(F)c2)CC1] |
| 55 | 4084 | 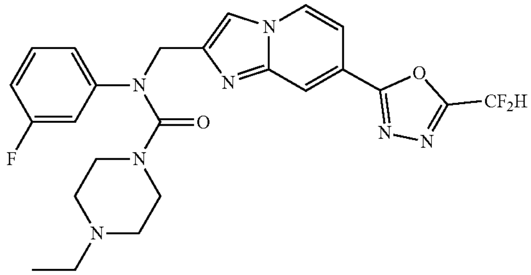 [SMILES: CCN1CCN(C(=O)N(Cc2cn3ccc(-c4nnc(C(F)F)o4)cc3n2)c2cccc(F)c2)CC1] |
| 56 | 4085 | 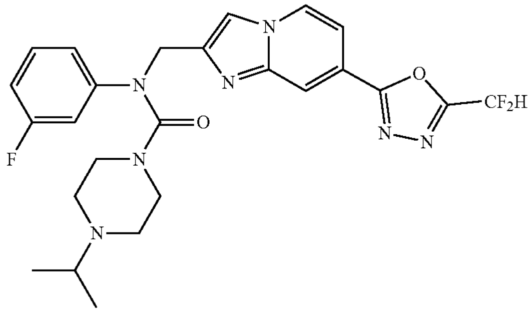 |
| 57 | 4086 | 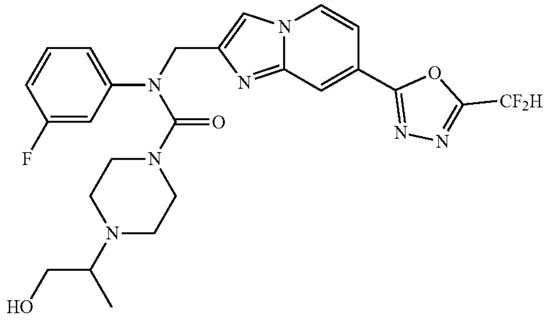 [SMILES: CC(CO)N1CCN(C(=O)N(Cc2cn3ccc(-c4nnc(C(F)F)o4)cc3n2)c2cccc(F)c2)CC1] |

TABLE 3-continued
| Ex | Comp | Structure |
|---|---|---|
| 58 | 4087 | 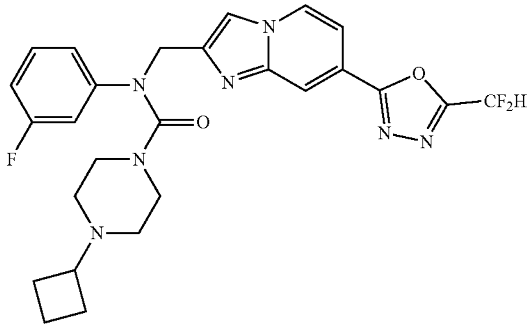 |
| 59 | 4088 | 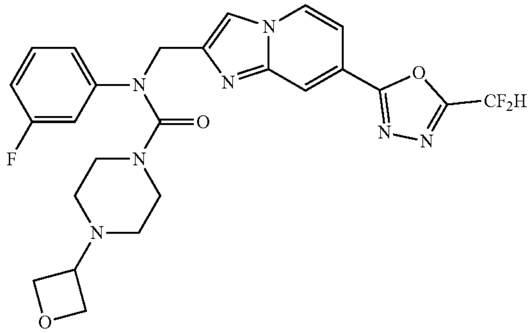 |
| 60 | 4089 | 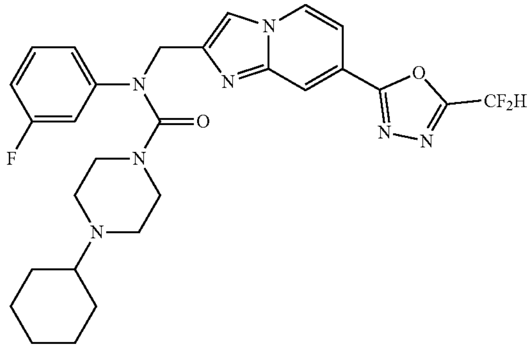 |
| 61 | 4090 | 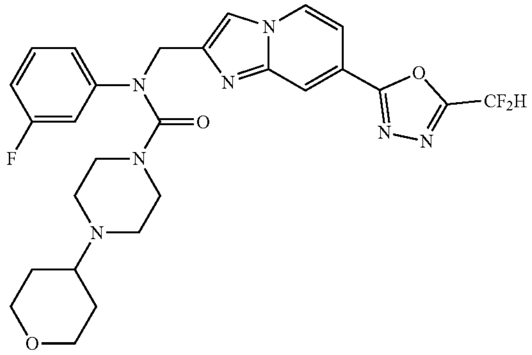 |

TABLE 3-continued
| Ex | Comp | Structure |
|---|---|---|
| 62 | 4091 | 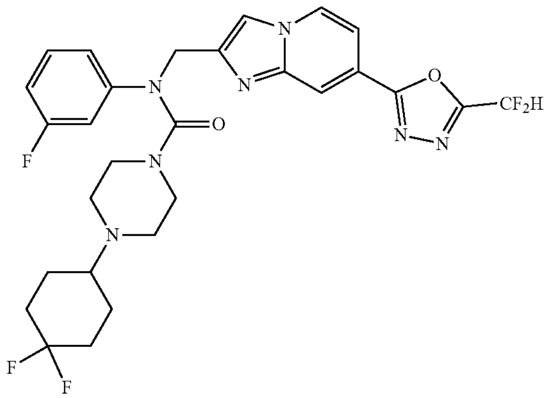 [SMILES: O=C(N1CCN(C2CCC(F)(F)CC2)CC1)N(Cc1cn2ccc(-c3nnc(C(F)F)o3)cc2n1)c1cccc(F)c1] |
| 63 | 4092 | 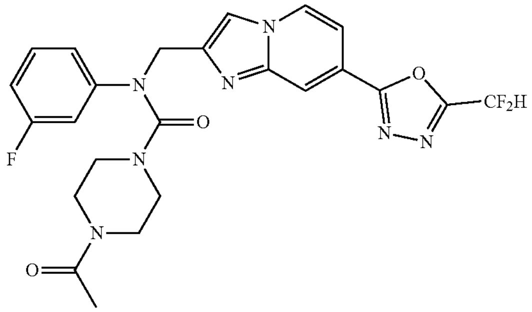 |
| 64 | 4093 | 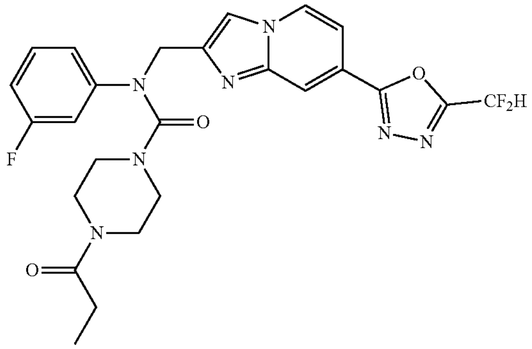 |
| 65 | 4094 | 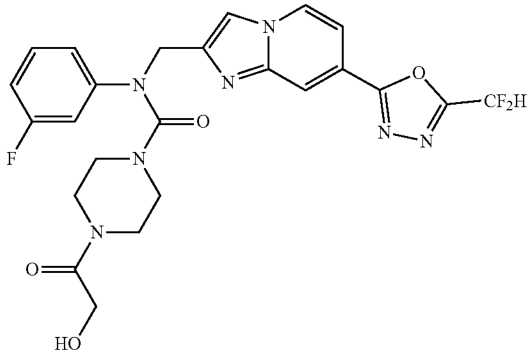 |

TABLE 3-continued
| Ex | Comp | Structure |
|---|---|---|
| 66 | 4095 | 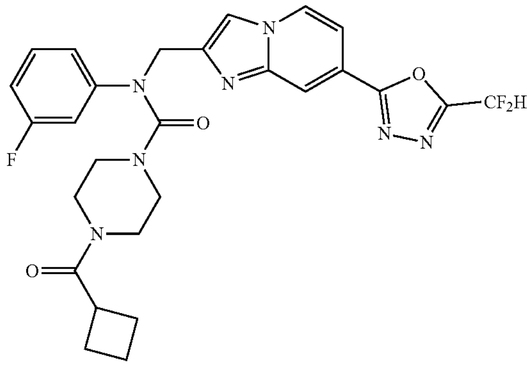 |
| 67 | 4096 | 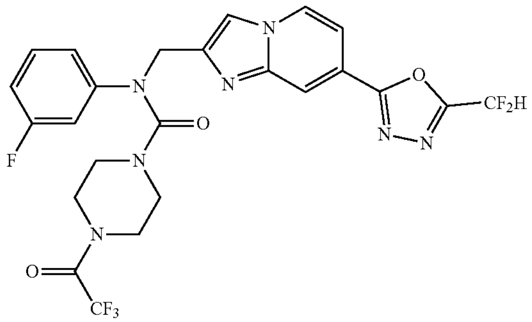 |
| 68 | 4097 | 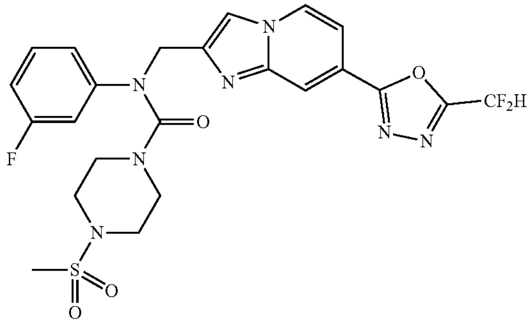 |
| 69 | 4098 | 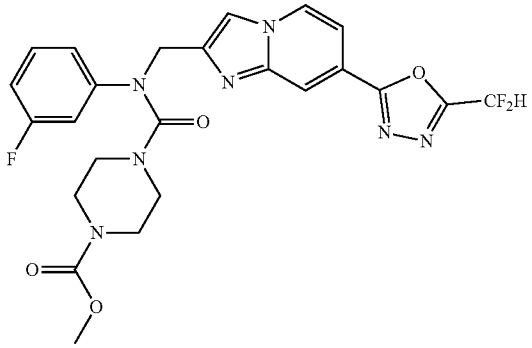 |

TABLE 3-continued
| Ex | Comp | Structure |
|---|---|---|
| 70 | 4099 | 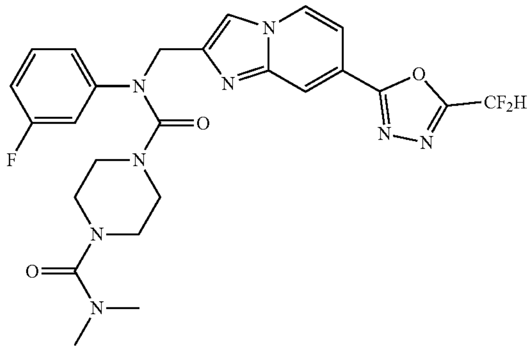 |
| 71 | 4100 | 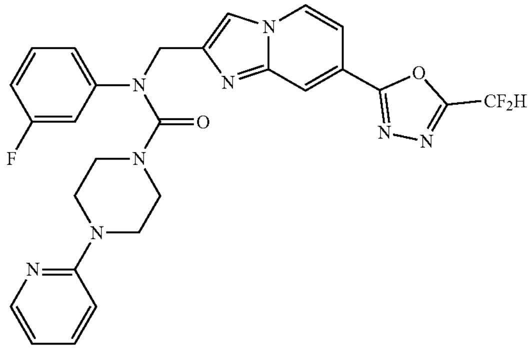 |
| 72 | 4101 | 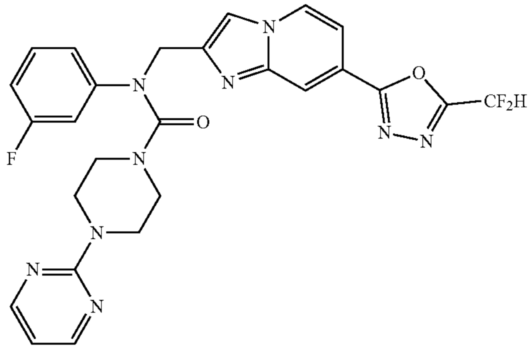 |
| 73 | 4102 | 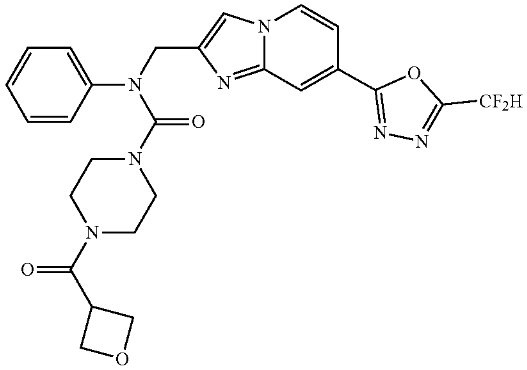 [SMILES: O=C(C1COC1)N1CCN(C(=O)N(Cc2cn3ccc(-c4nnc(C(F)F)o4)cc3n2)c2ccccc2)CC1] |

TABLE 3-continued
| Ex | Comp | Structure |
|---|---|---|
| 74 | 4103 | 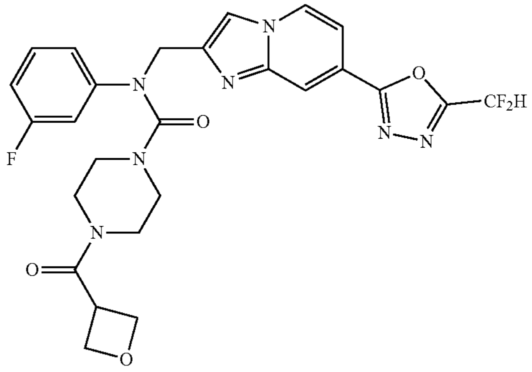 |
| 155 | 4620 | 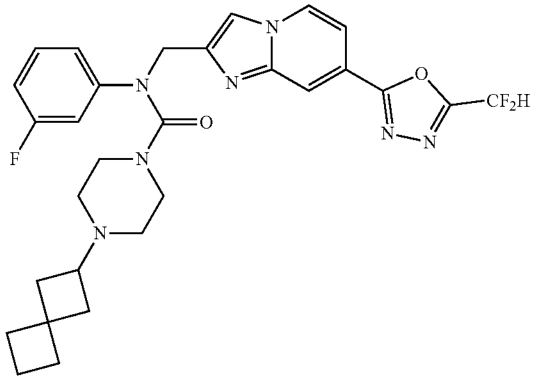 |
| 156 | 4621 | 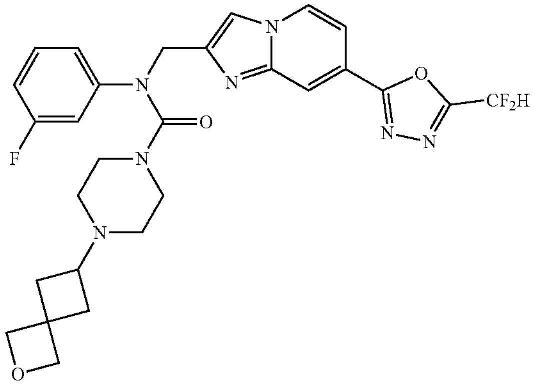 |
| 157 | 4625 | 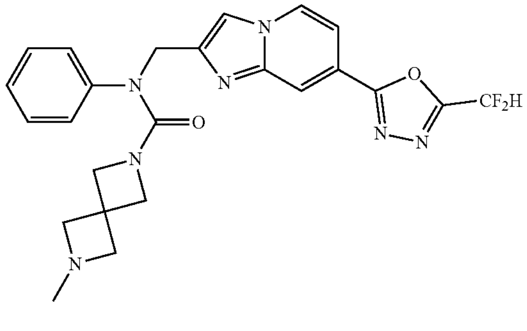 [SMILES: CN1CC2(C1)CN(C(=O)N(Cc1cn3ccc(-c4nnc(C(F)F)o4)cc3n1)c1ccccc1)C2] |

TABLE 3-continued
| Ex | Comp | Structure |
|---|---|---|
| 158 | 6892 | 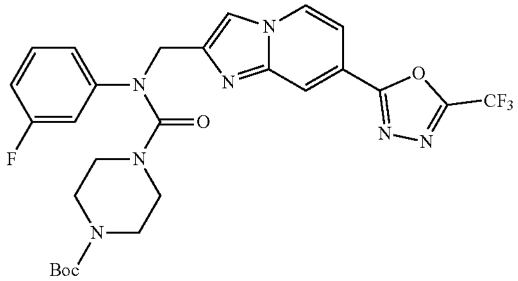 [SMILES: CC(C)(C)OC(=O)N1CCN(C(=O)N(Cc2cn3ccc(-c4nnc(C(F)(F)F)o4)cc3n2)c2cccc(F)c2)CC1] |
According to still another embodiment of the present invention, specific compounds represented by Chemical Formula I of the present invention may be shown in Table 4 below:
TABLE 4
| Ex | Comp | Structure |
|---|---|---|
| 1 | 3009 | 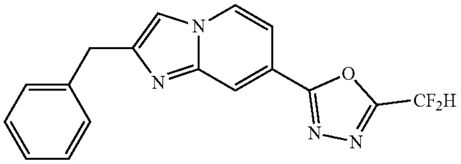 [SMILES: FC(F)c1nnc(-c2ccn3cc(Cc4ccccc4)nc3c2)o1] |
| 2 | 3585 | 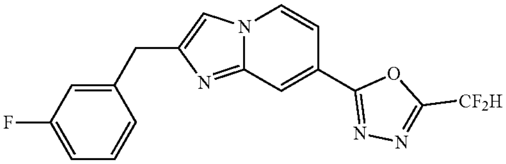 [SMILES: Fc1cccc(Cc2cn3ccc(-c4nnc(C(F)F)o4)cc3n2)c1] |
| 3 | 3586 | 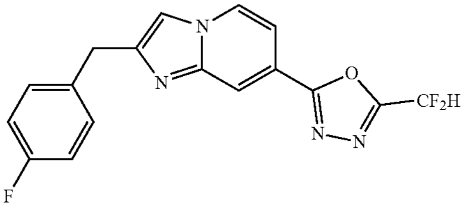 [SMILES: Fc1ccc(Cc2cn3ccc(-c4nnc(C(F)F)o4)cc3n2)cc1] |
| 4 | 3587 | 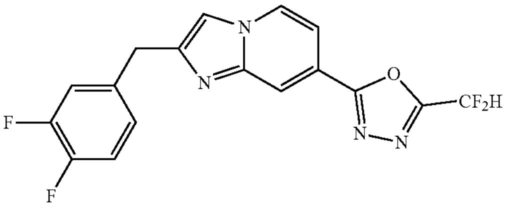 [SMILES: Fc1ccc(Cc2cn3ccc(-c4nnc(C(F)F)o4)cc3n2)cc1F] |
| 5 | 3588 | 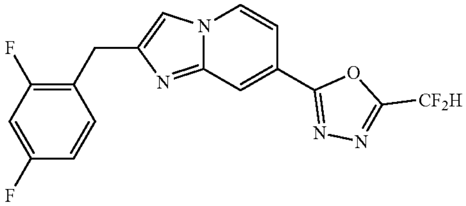 [SMILES: Fc1ccc(Cc2cn3ccc(-c4nnc(C(F)F)o4)cc3n2)c(F)c1] |

TABLE 4-continued
| Ex | Comp | Structure |
|---|---|---|
| 6 | 3589 | 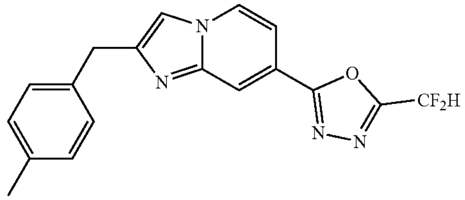 [SMILES: Cc1ccc(Cc2cn3ccc(-c4nnc(C(F)F)o4)cc3n2)cc1] |
| 7 | 3590 | 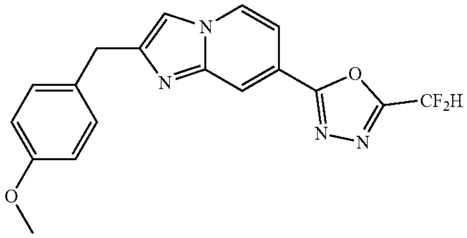 [SMILES: COc1ccc(Cc2cn3ccc(-c4nnc(C(F)F)o4)cc3n2)cc1] |
| 8 | 3591 | 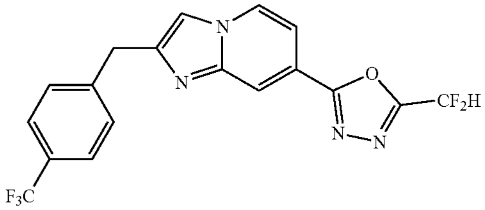 [SMILES: FC(F)c1nnc(-c2ccn3cc(Cc4ccc(C(F)(F)F)cc4)nc3c2)o1] |
| 9 | 3592 | 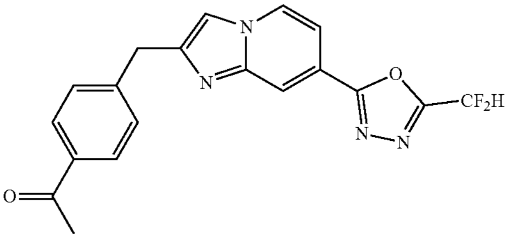 [SMILES: CC(=O)c1ccc(Cc2cn3ccc(-c4nnc(C(F)F)o4)cc3n2)cc1] |
| 10 | 3593 | 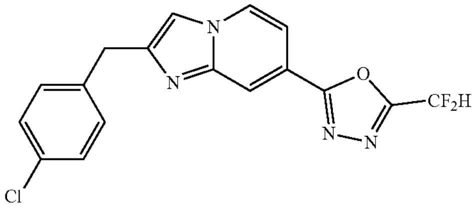 [SMILES: FC(F)c1nnc(-c2ccn3cc(Cc4ccc(Cl)cc4)nc3c2)o1] |
| 11 | 3594 | 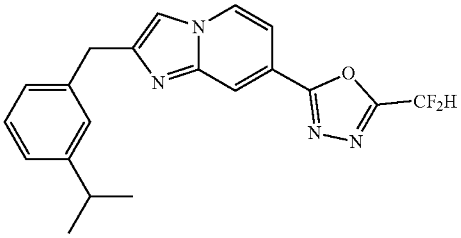 [SMILES: CC(C)c1cccc(Cc2cn3ccc(-c4nnc(C(F)F)o4)cc3n2)c1] |

TABLE 4-continued
| Ex | Comp | Structure |
|---|---|---|
| 12 | 3595 | 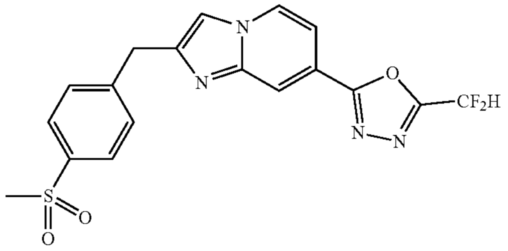 [SMILES: CS(=O)(=O)c1ccc(Cc2cn3ccc(-c4nnc(C(F)F)o4)cc3n2)cc1] |
| 13 | 3596 | 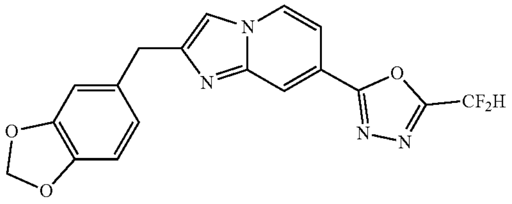 [SMILES: FC(F)c1nnc(-c2ccn3cc(Cc4ccc5c(c4)OCO5)nc3c2)o1] |
| 14 | 3668 | 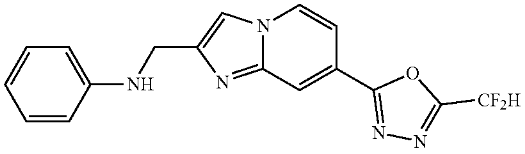 |
| 15 | 3669 | 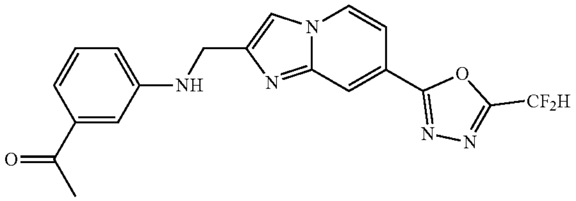 |
| 16 | 3670 | 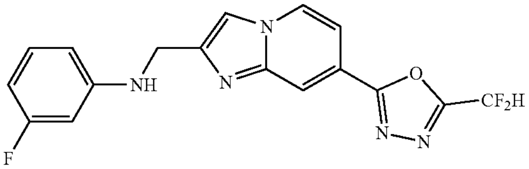 [SMILES: Fc1cccc(NCc2cn3ccc(-c4nnc(C(F)F)o4)cc3n2)c1] |
| 17 | 3671 | 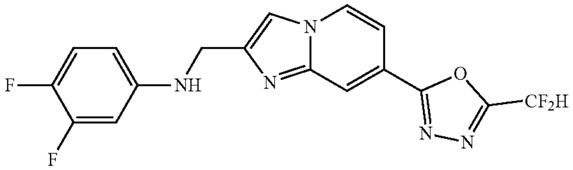 |
| 18 | 3672 | 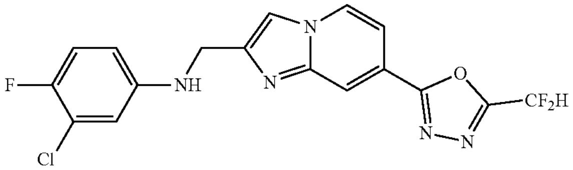 [SMILES: Fc1ccc(NCc2cn3ccc(-c4nnc(C(F)F)o4)cc3n2)cc1Cl] |
| 19 | 3673 | 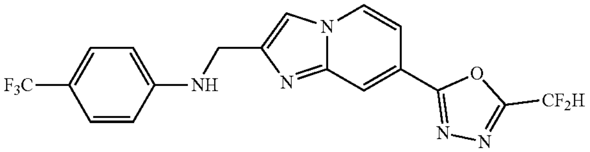 [SMILES: FC(F)c1nnc(-c2ccn3cc(CNc4ccc(C(F)(F)F)cc4)nc3c2)o1] |

TABLE 4-continued
| Ex | Comp | Structure |
| --- | --- | --- |
| 20 | 3674 | 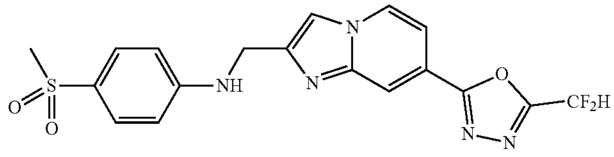 [SMILES: CS(=O)(=O)c1ccc(NCc2cn3ccc(-c4nnc(C(F)F)o4)cc3n2)cc1] |
| 21 | 3675 | 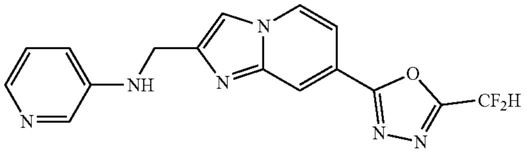 |
| 22 | 3676 | 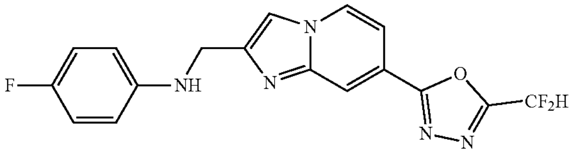 |
| 23 | 3677 | 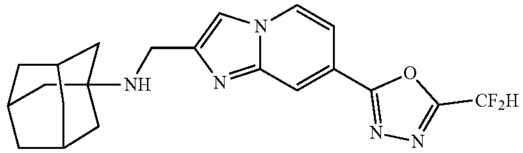 [SMILES: FC(F)c1nnc(-c2ccn3cc(CNC45CC6CC(CC(C6)C4)C5)nc3c2)o1] |
| 24 | 3678 | 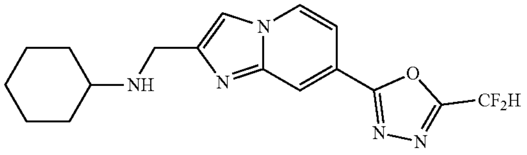 [SMILES: FC(F)c1nnc(-c2ccn3cc(CNC4CCCCC4)nc3c2)o1] |
| 25 | 3679 | 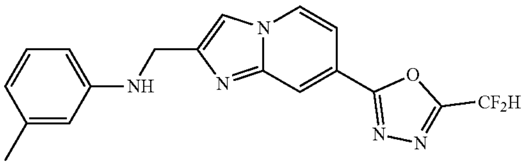 |
| 26 | 3719 | 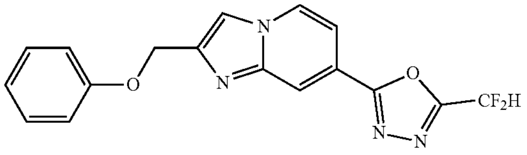 [SMILES: FC(F)c1nnc(-c2ccn3cc(COc4ccccc4)nc3c2)o1] |
| 27 | 3720 | 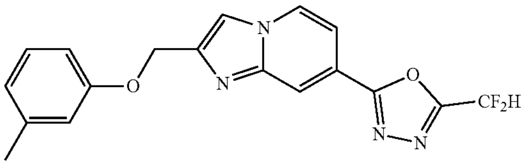 [SMILES: Cc1cccc(OCc2cn3ccc(-c4nnc(C(F)F)o4)cc3n2)c1] |
| 28 | 3721 | 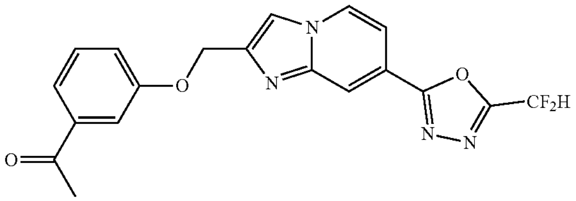 [SMILES: CC(=O)c1cccc(OCc2cn3ccc(-c4nnc(C(F)F)o4)cc3n2)c1] |

TABLE 4-continued

| Ex | Comp | Structure |
| --- | --- | --- |
| 29 | 3722 | 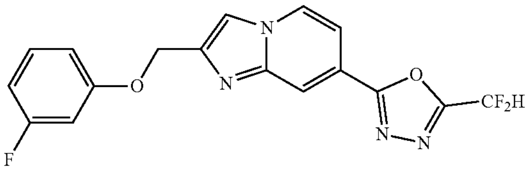 [SMILES: Fc1cccc(OCc2cn3ccc(-c4nnc(C(F)F)o4)cc3n2)c1] |
| 30 | 3723 | 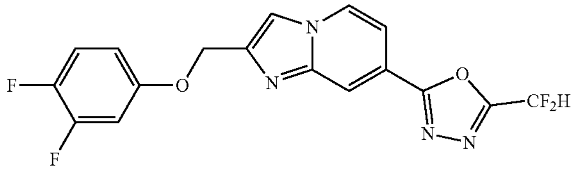 |
| 31 | 3724 | 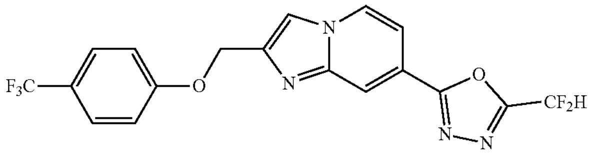 [SMILES: FC(F)c1nnc(-c2ccn3cc(COc4ccc(C(F)(F)F)cc4)nc3c2)o1] |
| 32 | 3725 | 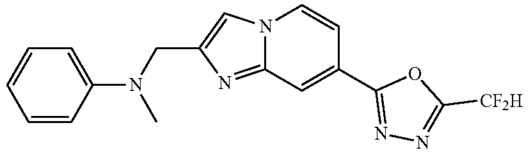 |

In the present invention, the pharmaceutically acceptable salt refers to a salt commonly used in the pharmaceutical industry, for example, may include inorganic ionic salts prepared from calcium, potassium, sodium, and magnesium, and the like, inorganic acid salts prepared from hydrochloric acid, nitric acid, phosphoric acid, bromic acid, iodic acid, perchloric acid, and sulfuric acid, and the like; organic acid salts prepared from acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like; sulfonic acid salts prepared from methanesulfonic acid, ethanesulfonic acid, benzenesulfonic acid, p-toluenesulfonic acid, and naphthalenesulfonic acid, and the like; amino acid salts prepared from glycine, arginine, lysine, and the like; and amine salts prepared with trimethylamine, triethylamine, ammonia, pyridine, picoline, and the like, but types of salts referred to in the present invention are not limited by these salts listed above.

Preferred salts in the present invention include hydrochloride, phosphate, sulfate, trifluoroacetate, citrate, bromate, maleate, or tartrate.

The compound represented by Chemical Formula I of the present invention may contain one or more asymmetric carbons, thereby being able to exist as a racemate, a racemic mixture, a single enantiomer, a diastereomeric mixture, and each diastereomer. These isomers may be separated using conventional techniques, for example, by partitioning, such as by column chromatography, HPLC, or the like, the compound represented by Chemical Formula I. Alternatively, stereoisomers of each of the compounds represented by Chemical Formula I may be stereospecifically synthesized using optically pure starting materials and/or reagents with known arrangement.

Method for Preparing 1,3,4-Oxadiazole Derivative Compound

The present invention provides a method for preparing a 1,3,4-oxadiazole derivative compound represented by Chemical Formula I, an optical isomer thereof, or a pharmaceutically acceptable salt thereof.

A preferred method for preparing the 1,3,4-oxadiazole derivative compound represented by Chemical Formula I, the optical isomer thereof, or the pharmaceutically acceptable salt thereof according to the present invention is the same as Reaction Schemes 1 to 4 below, which also includes preparation methods modified to a level obvious to those skilled in the art.

[Reaction Scheme 1]

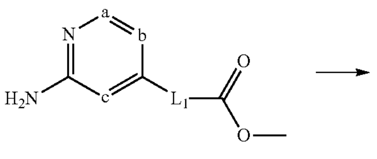

1-1

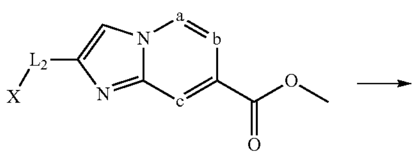

1-2

-continued

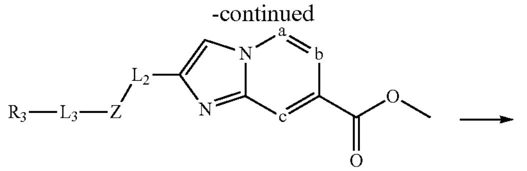

1-3

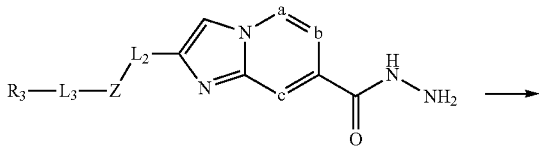

1-4

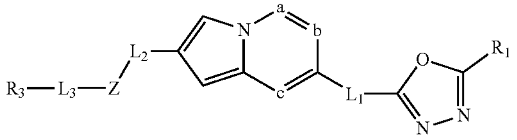

1-5

In Reaction Scheme 1, Compound 1-1 is reacted with 1,3-dichloropropan-2-one to synthesize bicyclic Compound 1-2, followed by substitution with various functional groups to synthesize Compound 1-3, followed by reaction with hydrazine to synthesize hydrazide Compound 1-4. Finally, a cyclization reaction with difluoroacetic anhydride is performed to synthesize title Compound 1-5.

A compound prepared by the Reaction Scheme above is Compound 3009.

[Reaction Scheme 2]

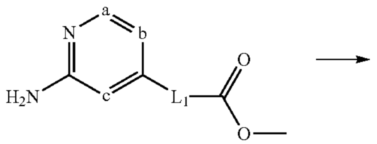

1-1

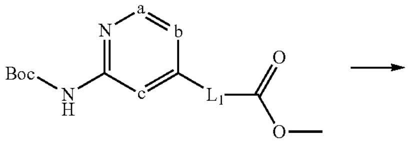

2-1

-continued

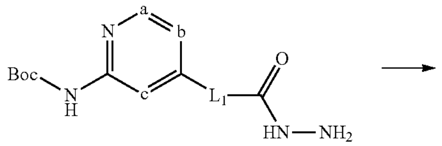

2-2

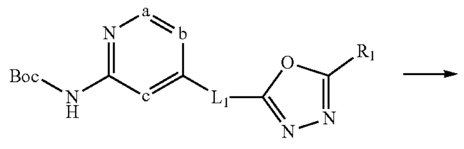

2-3

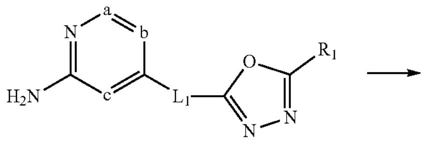

2-4

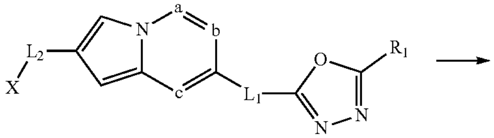

2-5

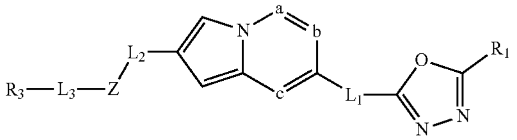

2-6

In Reaction Scheme 2, Compound 2-1 in which a protecting group is introduced into Compound 1-1 is synthesized, and then reacted with hydrazine to synthesize hydrazide Compound 2-2. A cyclization reaction with fluorine-substituted acetic anhydride is performed to synthesize Compound 2-3, and then the protecting group is removed under an acidic condition to synthesize Compound 2-4. By reacting with 1,3-dichloropropan-2-one, bicyclic Compound 2-5 is synthesized and reacted with various functional groups to synthesize title Compound 2-6.

Compounds prepared by the above Reaction Scheme are Compounds 3585, 3586, 3587, 3588, 3589, 3590, 3591, 3592, 3593, 3594, 3595, 3596, 3668, 3669, 3670, 3671, 3672, 3673, 3674, 3675, 3676, 3677, 3678, 3679, 3719, 3720, 3721, 3722, 3723, 3724, and 3725.

[Reaction Scheme 3]

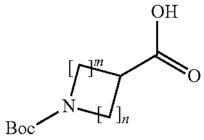

3-1

-continued

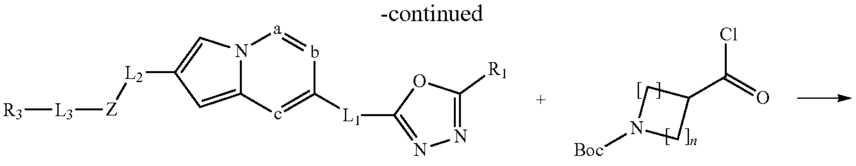

2-6 + 3-2

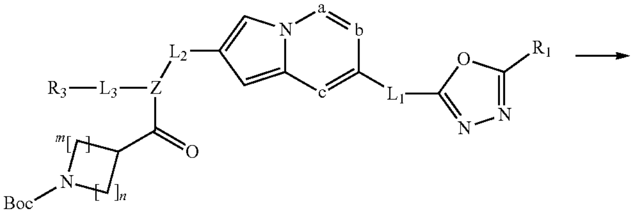

3-3

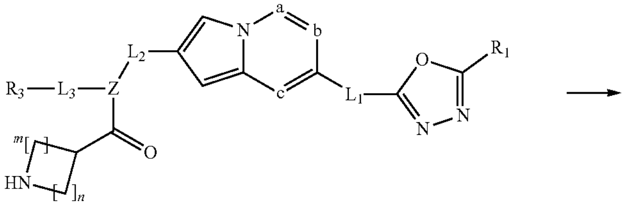

TFA 3-4

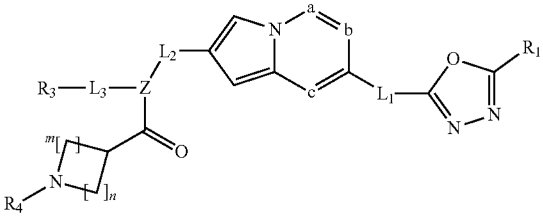

3-5

Reaction Scheme 3 shows a method for synthesizing a compound having an amide structure, wherein Compound 2-6 synthesized in Reaction Scheme 2 is reacted with Compound 3-2 having an acetyl chloride functional group under a basic condition, thereby synthesizing Compound 3-3. Compound 3-4 from which the protecting group is removed under an acid condition is synthesized and reacted with various functional groups to synthesize title Compound 3-5.

Compounds prepared by the above Reaction Scheme are Compounds 3782, 3783, 4115, 4116, 4117, 4118, 4119, 4120, 4121, 4122, 4123, 4124, 4125, 4126, 4127, 4128, 4129, 4130, 4131, 4132, 4137, 4138, 4139, 4140, 4141, 4142, 4143, 4144, 4145, 4146, 4147, 4148, 4150, 4151, 4152, 4153, 4154, 4155, 4156, 4157, 4158, 4159, 4160, 4161, 4162, 4163, 4164, 4165, 4166, 4167, 4168, 4169, 4170, 4171, 4172, 4173, 4174, 4175, 4176, 4177, 4188, 4189, 4190, 4191, 4192, 4193, 4194, 4195, 4196, 4197, 4198, 4199, 4200, 4201, 4202, 4203, 4204, 4205, 4206, 4207, 4618, and 4619.

[Reaction Scheme 4]

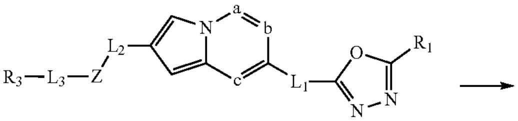

2-6

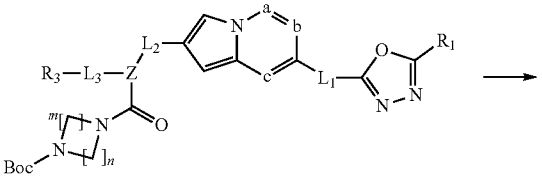

4-1

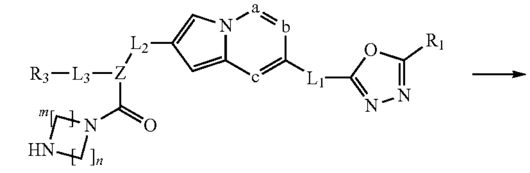

TFA 4-2

-continued

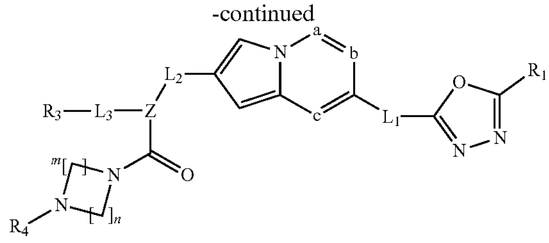

4-3

Reaction Scheme 4 shows a method for synthesizing a compound having a urea structure, wherein Compound 2-6 synthesized in Reaction Scheme 2 is reacted with triphosgene and an amine compound under a basic condition, thereby synthesizing Compound 4-1. Compound 4-2 from which the protecting group is removed under an acid condition is synthesized and reacted with various functional groups to synthesize title Compound 4-3.

Compounds prepared by the above Reaction Scheme are Compounds 3784, 3785, 4033, 4034, 4035, 4036, 4037, 4038, 4039, 4040, 4041, 4042, 4043, 4044, 4045, 4046, 4047, 4048, 4049, 4083, 4084, 4085, 4086, 4087, 4088, 4089, 4090, 4091, 4092, 4093, 4094, 4095, 4096, 4097, 4098, 4099, 4100, 4101, 4102, 4103, 4620, 4621, 4625, and 6892.

Composition Comprising 1,3,4-Oxadiazole Derivative Compound, Use Thereof, and Treatment Method Using the Same The present invention provides a pharmaceutical composition for preventing or treating histone deacetylase 6-mediated diseases containing the compound represented by Chemical Formula I below, the optical isomer thereof, or the pharmaceutically acceptable salt thereof as an active ingredient:

[Chemical Formula I]

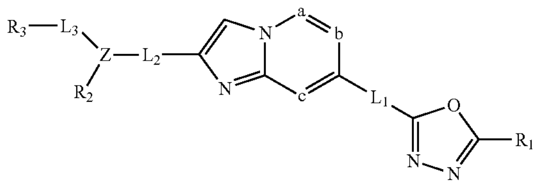

The Chemical Formula I is the same as defined above.

The pharmaceutical composition of the present invention exhibits a remarkable effect in the prevention or treatment of histone deacetylase 6-mediated diseases by selectively inhibiting a histone deacetylase 6.

The histone deacetylase 6-mediated diseases include infectious diseases such as prion disease; neoplasm such as benign tumors (e.g. myelodysplastic syndrome) or malignant tumors (e.g. multiple myeloma, lymphoma, leukemia, lung cancer, colorectal cancer, colon cancer, prostate cancer, urinary tract epithelial cell carcinoma, breast cancer, melanoma, skin cancer, liver cancer, brain cancer, stomach cancer, ovarian cancer, pancreatic cancer, head and neck cancer, oral cancer or glioma); endocrine, nutritional and metabolic diseases such as Wilson's disease, amyloidosis or diabetes; mental and behavioral disorders such as depression or Rett syndrome; neurological diseases such as central nervous system atrophy (e.g. Huntington's disease, spinal muscular atrophy (SMA), spinal cerebellar ataxia (SCA)), neurodegenerative diseases (e.g. Alzheimer's disease), movement disorders (e.g. Parkinson's disease), neuropathy (e.g. hereditary neuropathy (Charcot-Marie-Tooth disease), sporadic neuropathy, inflammatory neuropathy, drug-induced neuropathy), motor neuropathy (e.g. amyotrophic lateral sclerosis (ALS)), or central nervous system demyelination (e.g. multiple sclerosis (MS)); diseases of eyes and adnexa such as uveitis; circulatory diseases such as atrial fibrillation, stroke, and the like; respiratory diseases such as asthma; digestive diseases such as alcoholic liver disease, inflammatory bowel disease, Crohn's disease, ulcerative bowel disease, and the like; skin and subcutaneous tissue diseases such as psoriasis; musculoskeletal and connective tissue diseases such as rheumatoid arthritis, osteoarthritis, systemic lupus erythematosus (SLE), and the like; or congenital malformations, alterations, and chromosomal abnormalities such as autosomal dominant polycystic kidney disease, and also include symptoms or diseases related to abnormal functions of histone deacetylase.

The pharmaceutically acceptable salt is the same as described above in the pharmaceutically acceptable salt of the compound represented by Chemical Formula I of the present invention.

The pharmaceutical composition of the present invention may further include one or more pharmaceutically acceptable carriers for administration, in addition to the compound represented by Chemical Formula I, the optical isomer thereof, or the pharmaceutically acceptable salt thereof. The pharmaceutically acceptable carrier may be used by mixing saline, sterile water, Ringer's solution, buffered saline, dextrose solution, maltodextrin solution, glycerol, ethanol and one or more of these ingredients, and if necessary, other conventional additives such as antioxidants, buffers, bacteriostatic agents, and the like, may be added. Further, injectable formulations such as aqueous solutions, suspensions, emulsions, and the like, pills, capsules, granules or tablets may be formulated by further adding diluents, dispersants, surfactants, binders and lubricants. Accordingly, the composition of the present invention may be a patch, liquid, pill, capsule, granule, tablet, suppository, or the like. These formulations may be prepared by a conventional method used for formulation in the art or by a method disclosed in Remington's Pharmaceutical Science (latest edition), Mack Publishing Company, Easton PA, and formulated into various formulations depending on respective diseases or ingredients.

The composition of the present invention may be administered orally or parenterally (for example, intravenously, subcutaneously, intraperitoneally or topically) depending on the desired method, and the dosage range varies depending on the patient's weight, age, sex, health condition, diet, administration time, administration method, excretion rate, and severity of disease, and the like. The daily dose of the compound represented by Chemical Formula I of the present invention may be about 1 to 1000 mg/kg, preferably 5 to 100 mg/kg, and may be administered once a day or divided into several times a day.

The pharmaceutical composition of the present invention may further include one or more active ingredients exhibiting the same or similar medicinal effects in addition to the compound represented by Chemical Formula I above, the optical isomer thereof, or the pharmaceutically acceptable salt thereof.

The present invention provides a method for preventing or treating histone deacetylase 6-mediated diseases including administering a therapeutically effective amount of the compound represented by Chemical Formula I, the optical isomer thereof, or the pharmaceutically acceptable salt thereof.

The term "therapeutically effective amount" used in the present invention refers to an amount of the compound represented by Chemical Formula I that is effective for preventing or treating the histone deacetylase 6-mediated diseases.

In addition, the present invention provides a method for selectively inhibiting HDAC6 by administering the compound represented by Chemical Formula I, the optical isomer thereof, or the pharmaceutically acceptable salt thereof to a mammal including humans.

The method for preventing or treating the histone deacetylase 6-mediated diseases of the present invention also includes administering the compound represented by Chemical Formula I to treat the disease itself before the onset of the symptom, but also to inhibit or avoid the symptom thereof. In the management of the disease, prophylactic or therapeutic dose of a specific active ingredient will vary depending on the nature and severity of the disease or condition, and the route to which the active ingredient is administered. The dose and frequency of dose will vary depending on the age, weight and response of the individual patients. A suitable dosage regimen may be readily selected by a person having ordinary knowledge in the art considering these factors for granted. In addition, the method for preventing or treating histone deacetylase 6-mediated diseases of the present invention may further include administrating a therapeutically effective amount of an additional active agent useful for the treatment of the disease together with the compound represented by Chemical Formula I, wherein the additional active agent may exhibit synergistic or auxiliary effects together with the compound represented by Chemical Formula I.

The present invention also aims to provide the use of the compound represented by Chemical Formula I above, the optical isomer thereof, or the pharmaceutically acceptable salt thereof for preparing a medicament for treating histone deacetylase 6-mediated diseases. The compound represented by Chemical Formula I above for preparing the medicament may be mixed with acceptable adjuvants, diluents, carriers, and the like, and may be prepared as a complex formulation with other active agents to have a synergistic effect of active ingredients.

Matters mentioned in the uses, compositions and treatment methods of the present invention are applied equally as long as they are inconsistent with each other.

Advantageous Effects

The compound represented by Chemical Formula I above of the present invention, the optical isomer thereof, or the pharmaceutically acceptable salt thereof, is able to selectively inhibit histone deacetylase 6 (HDAC6), thereby having remarkably excellent preventive or therapeutic effects on HDAC6-mediated diseases.

BEST MODE

Hereinafter, the present invention will be described in more detail through Examples and Experimental Examples. However, they are only examples of the present invention, and the scope of the present invention is not limited thereto.

Preparation of 1,3,4-Oxadiazole Derivative Compounds of the Present Invention

A specific method for preparing the compound represented by Chemical Formula I is the same as follows.

Example 1: Synthesis of Compound 3009, 2-(2-benzylimidazo[1,2-a]pyridin-7-yl)-5-(difluoromethyl)-1,3,4-oxadiazole

[Step 1] Synthesis of methyl 2-(chloromethyl)imidazo[1,2-a]pyridin-7-carboxylate

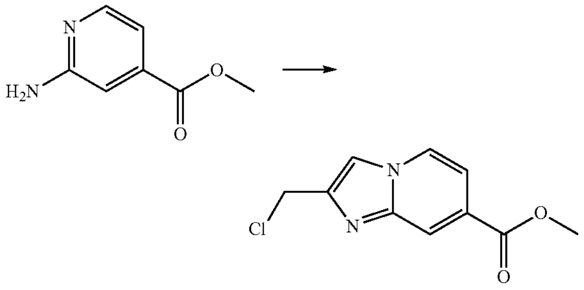

Methyl 2-aminoisonicotinate (1.000 g, 6.572 mmol) and 1,3-dichloropropan-2-one (1.085 g, 8.544 mmol) were dissolved in ethanol (5 mL)/1,2-dimethoxyethane (6 mL), and the resulting solution was stirred at room temperature for 1 hour and further stirred at 90° C. for 16 hours. Then, the temperature was lowered to room temperature to terminate the reaction. Water was poured into the reaction mixture, extracted with dichloromethane, and filtered through a plastic filter to remove a solid residue and an aqueous layer, and then concentrated under reduced pressure. The concentrate was purified by column chromatography ($SiO_2$, 24 g cartridge; ethyl acetate/hexane=5% to 70%) and concentrated to obtain the title compound (0.200 g, 13.5%) as a beige solid.

[Step 2] Synthesis of methyl 2-benzylimidazo[1,2-a]pyridin-7-carboxylate

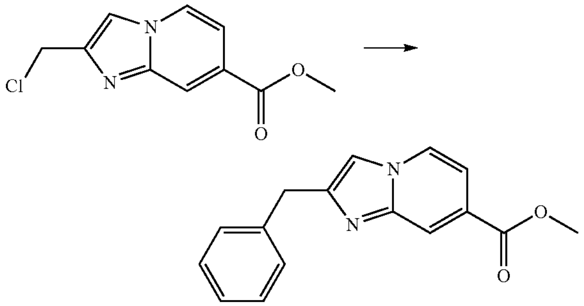

Methyl 2-(chloromethyl)imidazo[1,2-a]pyridin-7-carboxylate (0.200 g, 0.890 mmol) prepared in step 1, phenylboronic acid (0.217 g, 1.781 mmol), bis(triphenyl)phosphine)palladium(II) dichloride ($Pd(PPh_3)_2Cl_2$, 0.062 g, 0.089 mmol), and potassium carbonate (0.369 g, 2.671 mmol) were dissolved in 1,4-dioxane (8 mL)/water (2 mL) at room temperature, and the resulting solution was stirred at 105° C. for 16 hours. Then, the temperature was lowered to room temperature to terminate the reaction. Water was poured into the reaction mixture, extracted with dichloromethane, and filtered through a plastic filter to remove a solid residue and an aqueous layer, and then concentrated under reduced pressure. The concentrate was purified by column chromatography ($SiO_2$, 24 g cartridge; ethyl acetate/hexane=5% to 70%) and concentrated to obtain the title compound (0.076 g, 32.1%) as a white solid.

[Step 3] Synthesis of 2-benzylimidazo[1,2-a]pyridin-7-carbohydrazide

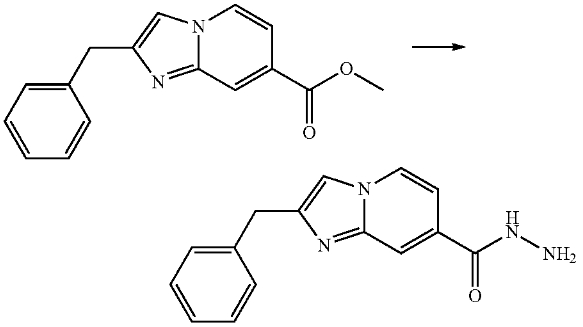

Methyl 2-benzylimidazo[1,2-a]pyridine-7-carboxylate (0.075 g, 0.282 mmol) prepared in step 2 and hydrazine monohydrate (0.068 mL, 1.408 mmol) were dissolved in ethanol (5 mL) at room temperature, and the resulting solution was heated to reflux for 16 hours. Then, the temperature was lowered to room temperature to terminate the reaction. Water was poured into the reaction mixture, extracted with dichloromethane, and filtered through a plastic filter to remove a solid residue and an aqueous layer, and then concentrated under reduced pressure to obtain the title compound (0.074 g, 98.7%) as a white solid.

[Step 4] Synthesis of Compound 3009

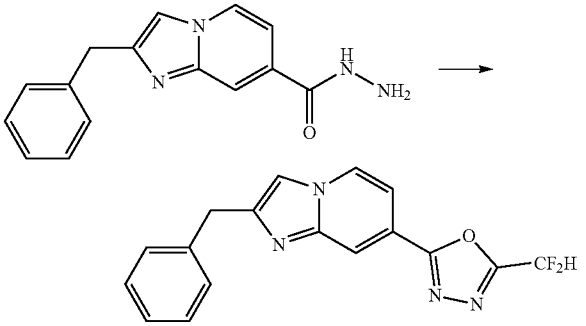

2-Benzylimidazo[1,2-a]pyridine-7-carbohydrazide (0.065 g, 0.244 mmol) prepared in step 3 and imidazole (0.050 g, 0.732 mmol) were dissolved in dichloromethane (5 mL), and 2,2-difluoroacetic anhydride (0.152 mL, 1.220 mmol) was added at room temperature and heated to reflux for 16 hours. Then, the temperature was lowered to room temperature to terminate the reaction. Water was poured into the reaction mixture, extracted with dichloromethane, and filtered through a plastic filter to remove a solid residue and an aqueous layer, and then concentrated under reduced pressure. The concentrate was purified by column chromatography ($SiO_2$, 4 g cartridge; ethyl acetate/hexane=5% to 60%) and concentrated to obtain the title compound (0.030 g, 37.7%) as a bright red solid.

$^1$H NMR (400 MHz, $CDCl_3$) δ 8.29 (m, 1H), 8.15-8.13 (m, 1H), 7.49-7.46 (m, 1H), 7.36-7.32 (m, 5H), 7.29-7.26 (m, 1H), 6.95 (t, J=51.7 Hz, 1H), 4.22 (s, 2H);

LRMS (ES) m/z 327.2 ($M^+$+1).

Example 2: Synthesis of Compound 3585, 2-(difluoromethyl)-5-(2-(3-fluorobenzyl)imidazo[1,2-a]pyridin-7-yl)-1,3,4-oxadiazole

[Step 1] Synthesis of methyl 2-((tert-butoxycarbonyl)amino)isonicotinate

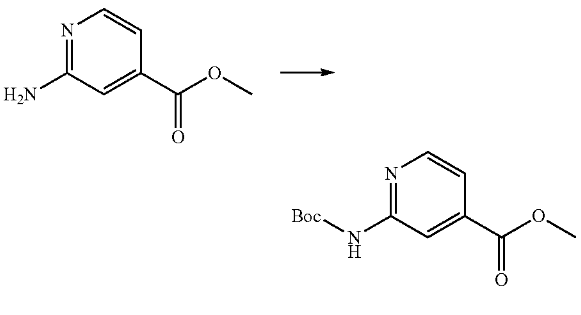

Methyl 2-aminoisonicotinate (20.000 g, 131.449 mmol) and di-tert-butyl dicarbonate (37.295 g, 170.884 mmol) were dissolved in tert-butanol (800 mL) at room temperature. The resulting solution was stirred at 60° C. for 16 hours, and then the temperature was lowered to room temperature to terminate the reaction. The precipitated solid was filtered, washed with ethanol, and dried to obtain the title compound (26.000 g, 78.4%) as a white solid.

[Step 2] Synthesis of tert-butyl (4-(hydrazinecarbonyl)pyridin-2-yl)carbamate

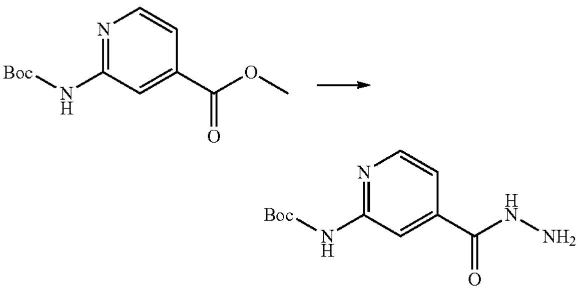

Methyl 2-((tert-butoxycarbonyl)amino)isonicotinate (26.000 g, 103.064 mmol) prepared in step 1 and hydrazine monohydrate (100.182 mL, 2.061 mol) were dissolved in methanol (800 mL) at room temperature. The resulting solution was stirred at the same temperature for 16 hours. Methanol (500 mL) was added to the obtained product, followed by filtration through a plastic filter to obtain an organic layer, and the obtained organic layer was concentrated to obtain the title compound (25.000 g, 96.2%) as a white solid.

[Step 3] Synthesis of tert-butyl (4-(5-(difluoromethyl)-1,3,4-oxadiazol-2-yl)pyridin-2-yl)carbamate

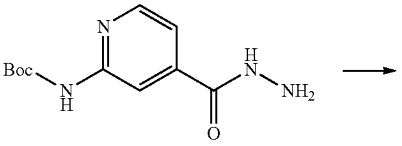

-continued

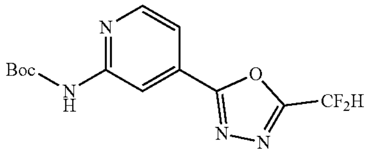

Tert-butyl (4-(hydrazinecarbonyl)pyridin-2-yl)carbamate (20.000 g, 79.280 mmol) prepared in step 2 and triethylamine (55.250 mL, 396.401 mmol) were dissolved in tetrahydrofuran (600 mL), and 2,2-difluoroacetic anhydride (49.281 mL, 396.401 mmol) was added at room temperature and heated to reflux for 16 hours. Then, the temperature was lowered to room temperature to terminate the reaction. A saturated aqueous ammonium chloride solution was poured into the reaction mixture, followed by extraction with ethyl acetate. The organic layer was washed with a saturated aqueous sodium chloride solution, dried over anhydrous magnesium sulfate, filtered, and concentrated under reduced pressure. Ethyl acetate (40 mL) and hexane (200 mL) were poured into the concentrate, suspended, and filtered to obtain a solid, and the obtained solid was washed with hexane and dried to obtain the title compound (11.500 g, 46.5%) as a white solid.

[Step 4] Synthesis of 4-(5-(difluoromethyl)-1,3,4-oxadiazol-2-yl)pyridin-2-amine

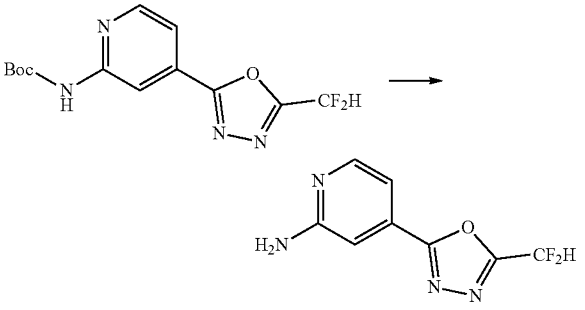

Tert-butyl (4-(5-(difluoromethyl)-1,3,4-oxadiazol-2-yl)pyridin-2-yl)carbamate (11.500 g, 36.826 mmol) prepared in step 3 was dissolved in dichloromethane (300 mL), and trifluoroacetic acid (28.199 mL, 368.259 mmol) was added at 0° C. and stirred at room temperature for 4 hours. After removing the solvent from the reaction mixture under reduced pressure, a saturated aqueous sodium hydrogen carbonate solution (150 mL) was poured into the concentrate and suspended, followed by filtration to obtain a solid. The obtained solid was washed with water and dried to obtain the title compound (7.500 g, 96.0%) as a white solid.

[Step 5] Synthesis of 2-(2-(chloromethyl)imidazo[1,2-a]pyridin-7-yl)-5-(difluoromethyl)-1,3,4-oxadiazole

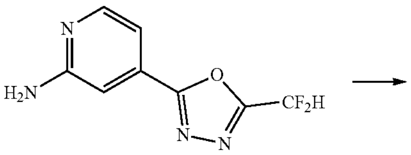

-continued

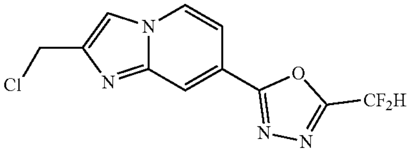

4-(5-(Difluoromethyl)-1,3,4-oxadiazol-2-yl)pyridin-2-amine (7.500 g, 35.351 mmol) prepared in step 4, 1,3-dichloropropan-2-one (6.732 g, 53.026 mmol), and sodium hydrogen carbonate (14.848 g, 176.753 mmol) were dissolved in 1,4-dioxane (250 mL) at room temperature. The resulting solution was heated to reflux for 16 hours, and then the temperature was lowered to room temperature to terminate the reaction. The reaction mixture was filtered through a plastic filter to remove solids, and the filtrate was purified by column chromatography ($SiO_2$, 80 g cartridge; ethyl acetate/hexane=10% to 90%) and concentrated to obtain the title compound (7.000 g, 69.6%) as a beige solid.

[Step 6] Synthesis of Compound 3585

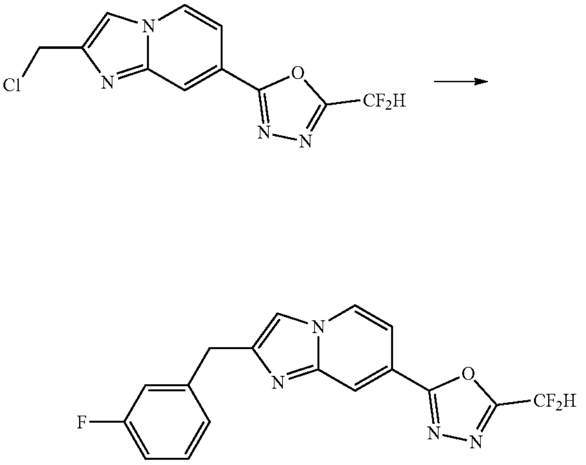

2-(2-(Chloromethyl)imidazo[1,2-a]pyridin-7-yl)-5-(difluoromethyl)-1,3,4-oxadiazole (0.050 g, 0.176 mmol) prepared in step 5, (3-fluorophenyl)boronic acid (0.049 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 4 g cartridge; ethyl acetate/hexane=0% to 70%) and concentrated to obtain the title compound (0.023 g, 38.0%) as a pink solid.

$^1H$ NMR (400 MHz, $CDCl_3$) δ 8.27-8.19 (m, 1H), 8.10 (dd, J=7.1, 1.0 Hz, 1H), 7.44 (dd, J=7.1, 1.7 Hz, 1H), 7.34 (s, 1H), 7.23 (td, J=8.0, 6.0 Hz, 1H), 7.05 (dt, J=7.6, 1.2 Hz, 1H), 7.00-6.70 (m, 3H), 4.13 (s, 2H);

LRMS (ES) m/z 345.9 ($M^+$+1).

Example 3: Synthesis of Compound 3586, 2-(difluoromethyl)-5-(2-(4-fluorobenzyl)imidazo[1,2-a]pyridin-7-yl)-1,3,4-oxadiazole

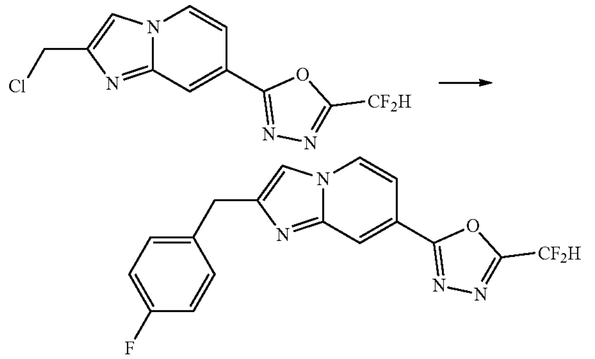

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (4-fluorophenyl)boronic acid (0.049 g, 0.351 mmol), bis(triphenylphosphine)palladium (II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 4 g cartridge; ethyl acetate/hexane=0% to 70%) and concentrated to obtain the title compound (0.030 g, 49.6%) as a pink solid.

$^1$H NMR (400 MHz, $CDCl_3$) δ 8.37-8.29 (m, 1H), 8.18 (dd, J=7.1, 1.0 Hz, 1H), 7.53 (dd, J=7.1, 1.7 Hz, 1H), 7.39 (d, J=0.9 Hz, 1H), 7.36-7.30 (m, 2H), 7.10-6.81 (m, 3H), 4.20 (s, 2H);

LRMS (ES) m/z 346.0 ($M^+$+1).

Example 4: Synthesis of Compound 3587, 2-(2-(3,4-difluorobenzyl)imidazo[1,2-a]pyridin-7-yl)-5-(difluoromethyl)-1,3,4-oxadiazole

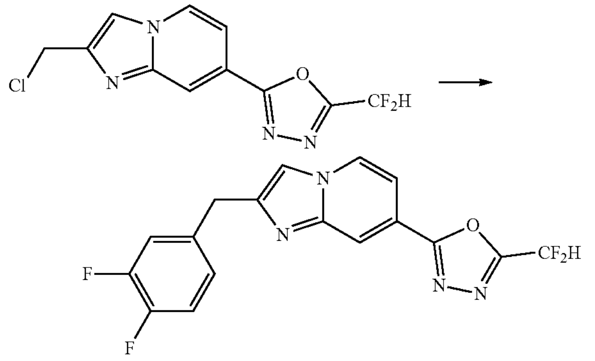

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (3,4-difluorophenyl)boronic acid (0.055 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 4 g cartridge; ethyl acetate/hexane=0% to 70%) and concentrated to obtain the title compound (0.033 g, 51.9%) as a pink solid.

$^1$H NMR (400 MHz, $CDCl_3$) δ 8.38-8.29 (m, 1H), 8.21 (dd, J=7.1, 1.0 Hz, 1H), 7.55 (dd, J=7.1, 1.7 Hz, 1H), 7.45 (s, 1H), 7.21-6.81 (m, 4H), 4.19 (s, 2H);

LRMS (ES) m/z 364.0 ($M^+$+1).

Example 5: Synthesis of Compound 3588, 2-(2-(2,4-difluorobenzyl)imidazo[1,2-a]pyridin-7-yl)-5-(difluoromethyl)-1,3,4-oxadiazole

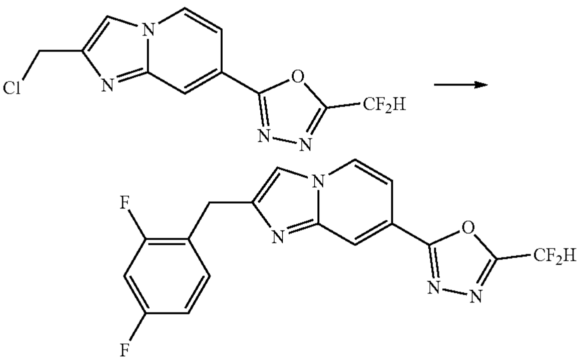

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (2,4-difluorophenyl)boronic acid (0.055 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 4 g cartridge; ethyl acetate/hexane=0% to 70%) and concentrated to obtain the title compound (0.031 g, 48.7%) as a pink solid.

$^1$H NMR (400 MHz, $CDCl_3$) δ 8.37-8.29 (m, 1H), 8.20 (dd, J=7.1, 1.0 Hz, 1H), 7.54 (dd, J=7.1, 1.7 Hz, 1H), 7.47 (s, 1H), 7.37 (td, J=8.7, 8.3, 6.4 Hz, 1H), 7.11-6.80 (m, 3H), 4.22 (s, 2H);

LRMS (ES) m/z 364.0 ($M^+$+1).

Example 6: Synthesis of Compound 3589, 2-(difluoromethyl)-5-(2-(4-methylbenzyl)imidazo[1,2-a]pyridin-7-yl)-1,3,4-oxadiazole

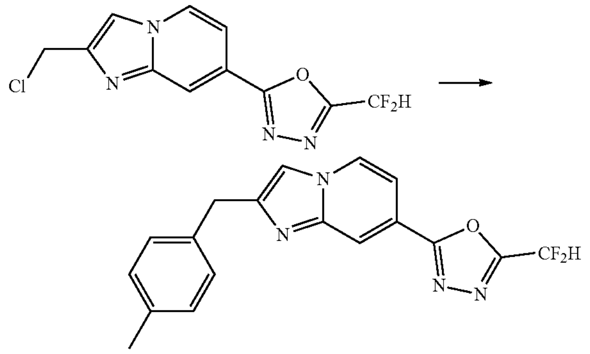

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, p-tolylboronic acid (0.048 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 4 g cartridge; ethyl acetate/hexane=0% to 70%) and concentrated to obtain the title compound (0.028 g, 46.8%) as a pink solid.

$^1H$ NMR (400 MHz, $CDCl_3$) δ 8.39-8.28 (m, 1H), 8.15 (dd, J=7.1, 1.0 Hz, 1H), 7.51 (dd, J=7.1, 1.7 Hz, 1H), 7.37 (t, J=0.8 Hz, 1H), 7.26 (d, J=8.0 Hz, 2H), 7.19-7.15 (m, 2H), 6.95 (t, J=51.7 Hz, 1H), 4.20 (s, 2H), 2.37 (s, 3H);

LRMS (ES) m/z 341.3 ($M^+$+1).

Example 7: Synthesis of Compound 3590, 2-(difluoromethyl)-5-(2-(4-methylbenzyl)imidazo[1,2-a]pyridin-7-yl)-1,3,4-oxadiazole

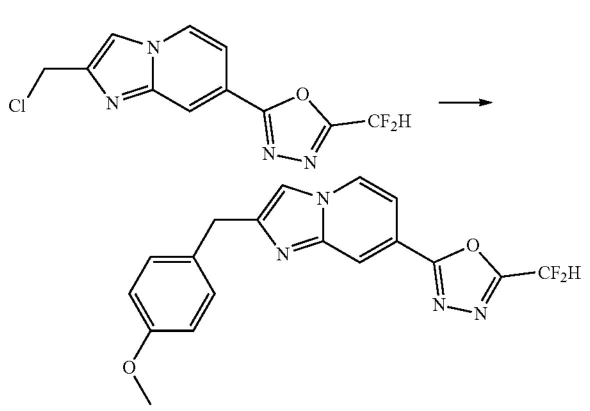

2-(2-(Chloromethyl)imidazo[1,2-a]pyridin-7-yl)-5-(difluoromethyl)-1,3,4-oxadiazole (0.050 g, 0.176 mmol)· prepared in step 5 of Example 2, (4-methoxyphenyl)boronic acid (0.053 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; ethyl acetate/hexane=0% to 70%) and concentrated to obtain the title compound (0.015 g, 24.0%) as a pink solid.

$^1H$ NMR (400 MHz, $CDCl_3$) δ 8.29-8.16 (m, 1H), 8.06 (dd, J=7.1, 1.0 Hz, 1H), 7.41 (dd, J=7.1, 1.7 Hz, 1H), 7.19 (t, J=4.3 Hz, 3H), 7.00-6.71 (m, 3H), 4.08 (s, 2H), 3.73 (s, 3H);

LRMS (ES) m/z 356.9 ($M^+$+1).

Example 8: Synthesis of Compound 3591, 2-(difluoromethyl)-5-(2-(4-trifluoromethyl)benzyl)imidazo[1,2-a]pyridin-7-yl)-1,3,4-oxadiazole

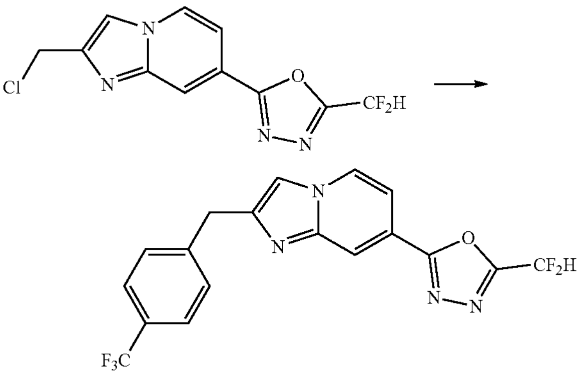

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (4-(trifluoromethyl)phenyl)boronic acid (0.067 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; ethyl acetate/hexane=0% to 70%) and concentrated to obtain the title compound (0.029 g, 41.9%) as a pink solid.

$^1H$ NMR (400 MHz, $CDCl_3$) δ 8.40-8.27 (m, 1H), 8.20 (dd, J=7.1, 0.9 Hz, 1H), 7.61 (d, J=8.0 Hz, 2H), 7.54 (dd, J=7.1, 1.7 Hz, 1H), 7.48 (d, J=8.0 Hz, 2H), 7.44 (s, 1H), 6.96 (t, J=51.7 Hz, 1H), 4.28 (s, 2H);

LRMS (ES) m/z 394.7 ($M^+$+1).

Example 9: Synthesis of Compound 3592, 1-(4-((7-(5-(difluoromethyl)-1,3,4-oxadiazol-2-yl)imidazo[1,2-a]pyridin-2-yl)methyl)phenyl)ethan-1-one

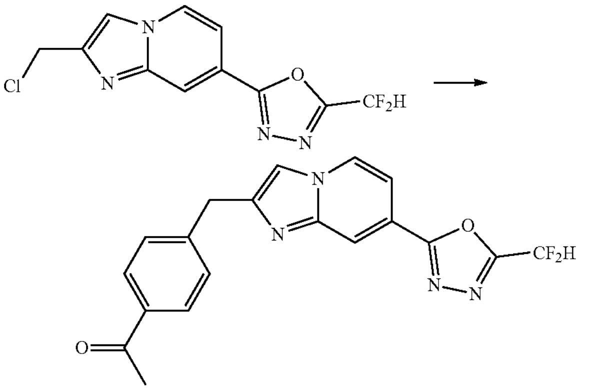

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (4-acetylphenyl)boronic acid (0.058 g, 0.351 mmol), bis(triphenylphosphine)palladium (II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; ethyl acetate/hexane=0% to 70%) and concentrated to obtain the title compound (0.021 g, 32.5%) as a pink solid.

$^1$H NMR (400 MHz, $CDCl_3$) δ 8.35-8.30 (m, 1H), 8.19 (dd, J=7.1, 1.0 Hz, 1H), 7.99-7.92 (m, 2H), 7.70 (ddd, J=12.0, 8.3, 1.4 Hz, 1H), 7.58-7.50 (m, 1H), 7.49-7.43 (m, 3H), 6.96 (t, J=51.7 Hz, 1H), 4.29 (s, 2H), 2.62 (s, 3H);

LRMS (ES) m/z 369.3 ($M^+$+1).

Example 10: Synthesis of Compound 3593, 2-(2-(4-chlorobenzyl)imidazo[1,2-a]pyridin-7-yl)-5-(difluoromethyl)-1,3,4-oxadiazole

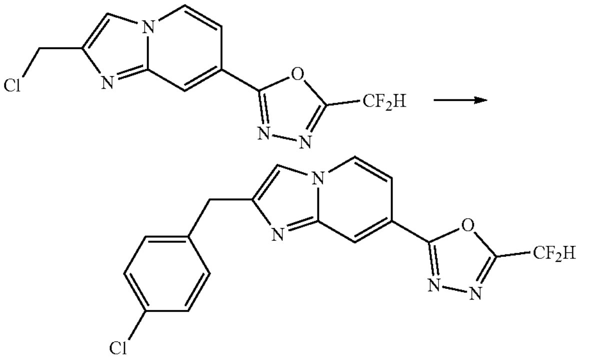

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (4-fluorophenyl)boronic acid (0.055 g, 0.351 mmol), bis(triphenylphosphine)palladium (II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; ethyl acetate/hexane=0% to 70%) and concentrated to obtain the title compound (0.012 g, 18.9%) as a pink solid.

$^1$H NMR (400 MHz, $CDCl_3$) δ 8.32 (dt, J=1.7, 0.8 Hz, 1H), 8.18 (dd, J=7.1, 0.9 Hz, 1H), 7.52 (dd, J=7.1, 1.7 Hz, 1H), 7.39 (q, J=0.8 Hz, 1H), 7.35-7.27 (m, 4H), 6.95 (t, J=51.7 Hz, 1H), 4.19 (s, 2H);

LRMS (ES) m/z 362.9 ($M^+$+1).

Example 11: Synthesis of Compound 3594, 2-(difluoromethyl)-5-(2-(3-isopropylbenzyl)imidazo[1,2-a]pyridin-7-yl)-1,3,4-oxadiazole

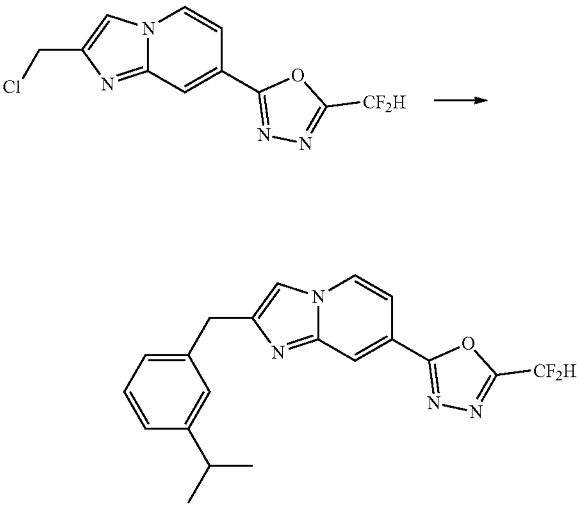

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (3-isopropylphenyl)boronic acid (0.058 g, 0.351 mmol), bis(triphenylphosphine)palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; ethyl acetate/hexane=0% to 70%) and concentrated to obtain the title compound (0.032 g, 49.5%) as a pink solid.

$^1$H NMR (400 MHz, $CDCl_3$) δ 8.33 (s, 1H), 8.17 (dd, J=7.1, 0.9 Hz, 1H), 7.52 (dd, J=7.1, 1.7 Hz, 1H), 7.37 (d, J=0.8 Hz, 1H), 7.32-7.26 (m, 1H), 7.23 (d, J=1.8 Hz, 1H), 7.20-7.13 (m, 2H), 6.95 (t, J=51.7 Hz, 1H), 4.22 (s, 2H), 2.92 (p, J=6.9 Hz, 1H), 1.28 (d, J=6.9 Hz, 6H);

LRMS (ES) m/z 370.0 ($M^+$+1).

Example 12: Synthesis of Compound 3595, 2-(difluoromethyl)-5-(2-(4-(methylsulfonyl)benzyl)imidazo[1,2-a]pyridin-7-yl)-1,3,4-oxadiazole

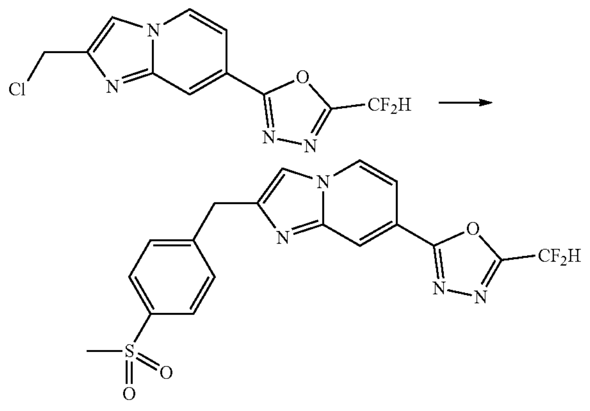

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (4-(methylsulfonyl)phenyl) boronic acid (0.070 g, 0.351 mmol), bis(triphenylphosphine) palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; dichloromethane/methanol=0% to 10%) and concentrated to obtain the title compound (0.033 g, 46.5%) as a pink solid.

$^1H$ NMR (400 MHz, $CDCl_3$) δ 8.33 (dt, J=1.7, 0.8 Hz, 1H), 8.22 (dd, J=7.1, 0.9 Hz, 1H), 7.95-7.87 (m, 2H), 7.56 (td, J=6.6, 1.8 Hz, 3H), 7.49 (d, J=0.8 Hz, 1H), 6.96 (t, J=51.7 Hz, 1H), 4.31 (s, 2H), 3.06 (s, 3H);

LRMS (ES) m/z 405.1 ($M^+$+1).

Example 13: Synthesis of Compound 3596, 2-(2-(benzo[d][1,3]dioxol-5-ylmethyl)imidazo[1,2-a]pyridin-7-yl)-5-(difluoromethyl)-1,3,4-oxadiazole

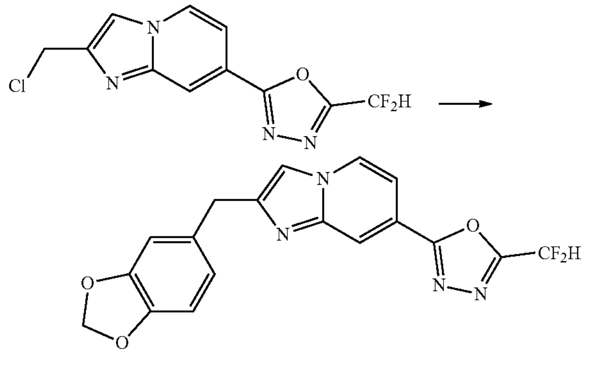

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, benzo[d][1,3]dioxol-5-ylboronic acid (0.058 g, 0.351 mmol), bis(triphenylphosphine) palladium(II) dichloride ($Pd(PPh_3)_2Cl_2$, 0.012 g, 0.018 mmol), and potassium carbonate (0.073 g, 0.527 mmol) were dissolved in 1,4-dioxane (4 mL)/water (1 mL) at room temperature, and the resulting solution was stirred at 100° C. for 1 hour. Then, the temperature was lowered to room temperature to terminate the reaction. After removing the solvent from the reaction mixture under reduced pressure, the concentrate was purified by chromatography ($SiO_2$ plate, 20×20×1 mm; dichloromethane/methanol=0% to 10%) and concentrated to obtain the title compound (0.041 g, 63.0%) as a pink solid.

$^1H$ NMR (400 MHz, $CDCl_3$) δ 8.32 (d, J=1.6 Hz, 1H), 8.18 (dd, J=7.1, 1.0 Hz, 1H), 7.52 (dd, J=7.1, 1.7 Hz, 1H), 7.41 (s, 1H), 7.10-6.77 (m, 4H), 5.96 (s, 2H), 4.15 (s, 2H);

LRMS (ES) m/z 372.0 ($M^+$+1).

Example 14: Synthesis of Compound 3668, N-((7-(5-(difluoromethyl)-1,3,4-oxadiazol-2-yl)imidazo[1,2-a]pyridin-2-yl)methyl)aniline

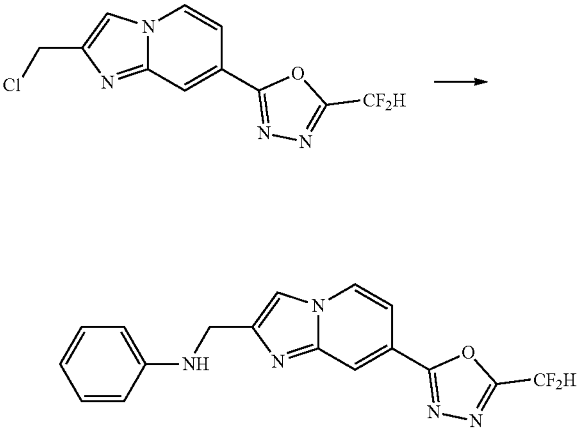

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, aniline (0.024 mL, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.050 g, 83.4%) as a yellow solid.

$^1H$ NMR (400 MHz, $CDCl_3$) δ 8.33 (dt, J=1.7, 0.8 Hz, 1H), 8.21 (dd, J=7.2, 1.0 Hz, 1H), 7.68 (d, J=0.9 Hz, 1H), 7.54 (dd, J=7.1, 1.7 Hz, 1H), 7.25-7.18 (m, 2H), 6.96 (t, J=51.7 Hz, 1H), 6.80-6.70 (m, 3H), 4.62 (d, J=0.8 Hz, 2H);

LRMS (ES) m/z 342.9 ($M^+$+1).

Example 15: Synthesis of Compound 3669, 1-(3-((7-(5-(difluoromethyl)-1,3,4-oxadiazol-2-yl)imidazo[1,2-a]pyridin-2-yl)methyl)amino)phenyl)ethan-1-one

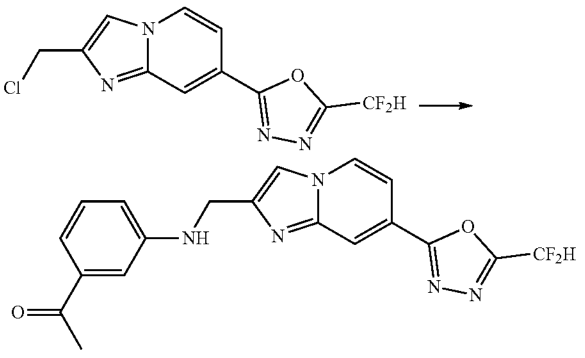

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, m-toluidine (0.036 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.040 g, 59.4%) as a yellow solid.

$^1H$ NMR (400 MHz, $CDCl_3$) δ 8.38-8.29 (m, 1H), 8.24 (dd, J=7.1, 1.0 Hz, 1H), 7.74-7.67 (m, 1H), 7.57 (dd, J=7.1, 1.7 Hz, 1H), 7.36-7.32 (m, 2H), 7.31-7.28 (m, 1H), 7.11-6.82 (m, 2H), 4.68-4.64 (m, 2H), 2.59 (s, 3H);

LRMS (ES) m/z 385.0 ($M^+$+1).

Example 16: Synthesis of Compound 3670, N-((7-(5-(difluoromethyl)-1,3,4-oxadiazol-2-yl)imidazo[1,2-a]pyridin-2-yl)methyl)-3-fluoroaniline

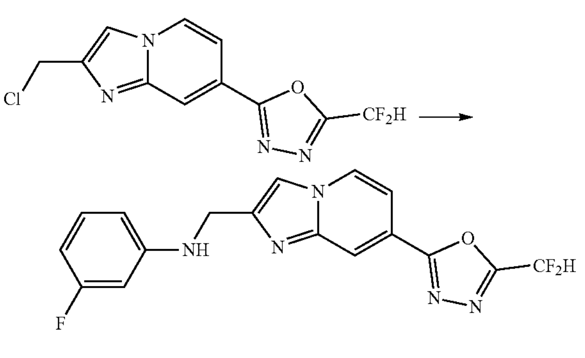

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 3-fluoroaniline (0.036 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.040 g, 59.4%) as a yellow solid.

$^1H$ NMR (400 MHz, $CDCl_3$) δ 8.34 (dt, J=1.7, 0.8 Hz, 1H), 8.23 (dd, J=7.1, 1.0 Hz, 1H), 7.68 (d, J=0.8 Hz, 1H), 7.57 (dd, J=7.1, 1.7 Hz, 1H), 7.18-6.76 (m, 2H), 6.54-6.32 (m, 3H), 4.59 (d, J=0.8 Hz, 2H);

LRMS (ES) m/z 360.9 ($M^+$+1).

Example 17: Synthesis of Compound 3671, N-((7-(5-(difluoromethyl)-1,3,4-oxadiazol-2-yl)imidazo[1,2-a]pyridin-2-yl)methyl)-3,4-difluoroaniline

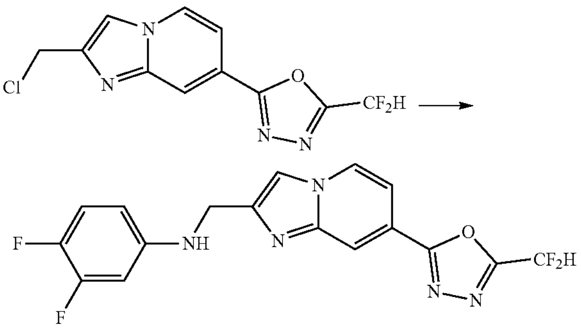

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 3,4-difluoroaniline (0.029 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.024 g, 38.0%) as a yellow solid.

$^1H$ NMR (400 MHz, $CDCl_3$) δ 8.38 (s, 1H), 8.27 (dd, J=7.1, 1.0 Hz, 1H), 7.69 (d, J=0.8 Hz, 1H), 7.63 (dd, J=7.1, 1.7 Hz, 1H), 7.11-6.80 (m, 2H), 6.52 (ddd, J=12.5, 6.6, 2.9 Hz, 1H), 6.42 (ddd, J=8.9, 3.2, 1.6 Hz, 1H), 4.57 (d, J=0.8 Hz, 2H);

LRMS (ES) m/z 378.1 ($M^+$+1).

Example 18: Synthesis of Compound 3672, 3-chloro-N-((7-(5-(difluoromethyl)-1,3,4-oxadiazol-2-yl)imidazo[1,2-a]pyridin-2-yl)methyl)-4-fluoroaniline

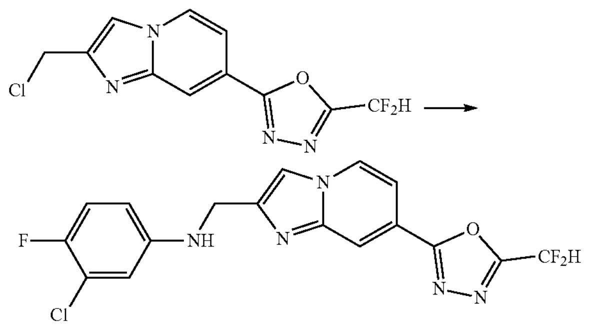

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 3-chloro-4-fluoroaniline (0.038 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.041 g, 59.3%) as a yellow solid.

$^1$H NMR (400 MHz, $CDCl_3$) δ 8.37 (d, J=1.5 Hz, 1H), 8.26 (dd, J=7.1, 1.0 Hz, 1H), 7.69 (d, J=0.8 Hz, 1H), 7.62 (dd, J=7.1, 1.7 Hz, 1H), 7.10-6.80 (m, 2H), 6.73 (dd, J=6.0, 2.9 Hz, 1H), 6.57 (ddd, J=8.9, 3.8, 2.9 Hz, 1H), 4.57 (d, J=0.8 Hz, 2H);

LRMS (ES) m/z 396.0 ($M^+$+1).

Example 19: Synthesis of Compound 3673, N-((7-(5-(difluoromethyl)-1,3,4-oxadiazol-2-yl)imidazo[1,2-a]pyridin-2-yl)methyl)-4-(trifluoromethyl)aniline

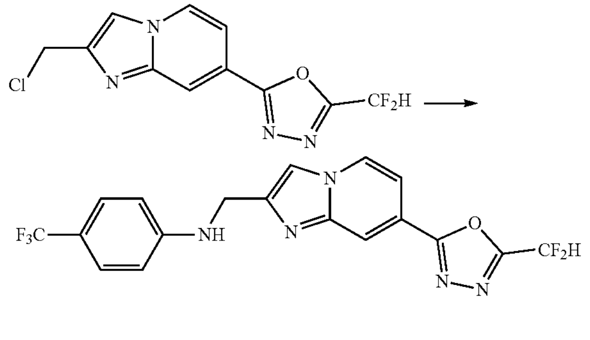

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 4-(trifluoromethyl)aniline (0.042 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.029 g, 40.3%) as a yellow solid.

$^1$H NMR (400 MHz, $CDCl_3$) δ 8.36 (dt, J=1.6, 0.7 Hz, 1H), 8.25 (dd, J=7.1, 1.0 Hz, 1H), 7.68 (d, J=0.7 Hz, 1H), 7.60 (dd, J=7.1, 1.7 Hz, 1H), 7.47-7.39 (m, 2H), 6.97 (t, J=51.7 Hz, 1H), 6.74 (d, J=8.6 Hz, 2H), 4.66 (s, 2H);

LRMS (ES) m/z 411.0 ($M^+$+1).

Example 20: Synthesis of Compound 3674, N-((7-(5-(difluoromethyl)-1,3,4-oxadiazol-2-yl)imidazo[1,2-a]pyridin-2-yl)methyl)-4-(methylsulfonyl)aniline

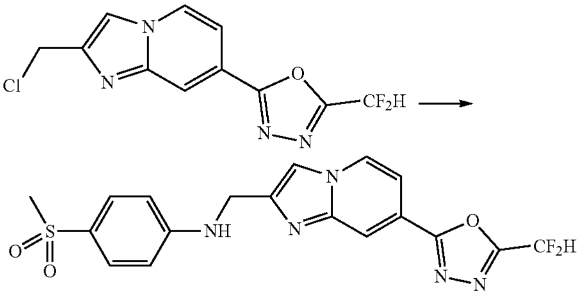

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 4-(methylsulfonyl)aniline (0.045 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; dichloromethane/methanol=0% to 10%) and concentrated to obtain the title compound (0.034 g, 46.2%) as a yellow solid.

$^1$H NMR (400 MHz, $CDCl_3$) δ 8.33 (dt, J=1.7, 0.8 Hz, 1H), 8.26 (dd, J=7.1, 1.0 Hz, 1H), 7.76-7.71 (m, 2H), 7.69 (d, J=0.8 Hz, 1H), 7.58 (dd, J=7.2, 1.7 Hz, 1H), 6.97 (t, J=51.7 Hz, 1H), 6.79-6.71 (m, 2H), 4.66 (d, J=4.3 Hz, 2H), 3.02 (s, 3H);

LRMS (ES) m/z 420.3 ($M^+$+1).

Example 21: Synthesis of Compound 3675, N-((7-(5-(difluoromethyl)-1,3,4-oxadiazol-2-yl)imidazo[1,2-a]pyridin-2-yl)methyl)pyridin-3-amine

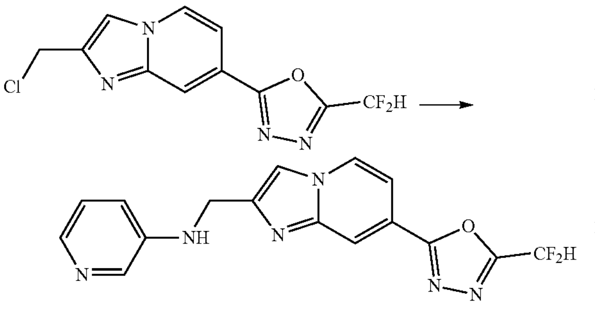

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, pyridine-3-amine (0.025 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; dichloromethane/methanol=0% to 10%) and concentrated to obtain the title compound (0.037 g, 61.5%) as a yellow solid.

$^1H$ NMR (400 MHz, $CDCl_3$) δ 8.33 (dt, J=1.7, 0.8 Hz, 1H), 8.24 (dd, J=7.1, 1.0 Hz, 1H), 8.19 (d, J=2.8 Hz, 1H), 8.05-7.99 (m, 1H), 7.70 (s, 1H), 7.56 (dd, J=7.1, 1.7 Hz, 1H), 7.17-6.82 (m, 3H), 4.62 (s, 2H);

LRMS (ES) m/z 343.1 ($M^+$+1).

Example 22: Synthesis of Compound 3676, N-((7-(5-(difluoromethyl)-1,3,4-oxadiazol-2-yl)imidazo[1,2-a]pyridin-2-yl)methyl)-6-fluoropyridin-3-amine

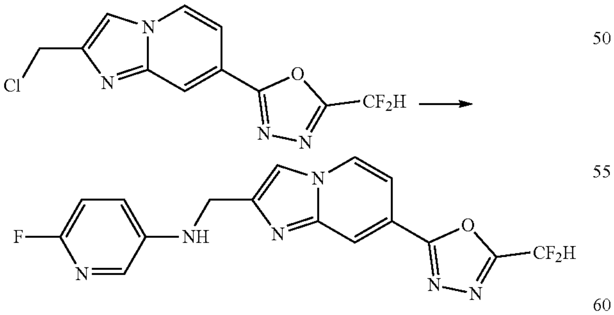

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, 6-fluoropyridin-3-amine (0.030 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; dichloromethane/methanol=0% to 10%) and concentrated to obtain the title compound (0.033 g, 52.1%) as a yellow solid.

$^1H$ NMR (400 MHz, $CDCl_3$) δ 8.35 (dt, J=1.7, 0.9 Hz, 1H), 8.26 (dd, J=7.1, 1.0 Hz, 1H), 7.73-7.68 (m, 1H), 7.66 (dd, J=3.1, 1.9 Hz, 1H), 7.60 (dd, J=7.1, 1.7 Hz, 1H), 7.16 (ddd, J=8.8, 6.7, 3.1 Hz, 1H), 6.97 (t, J=51.7 Hz, 1H), 6.79 (ddd, J=8.7, 3.4, 0.6 Hz, 1H), 4.59 (s, 2H);

LRMS (ES) m/z 362.1 ($M^+$+1).

Example 23: Synthesis of Compound 3677, (3s,5s,7s)-N-((7-(5-(difluoromethyl)-1,3,4-oxadiazol-2-yl)imidazo[1,2-a]pyridin-2-yl)methyl)adamantane-1-amine

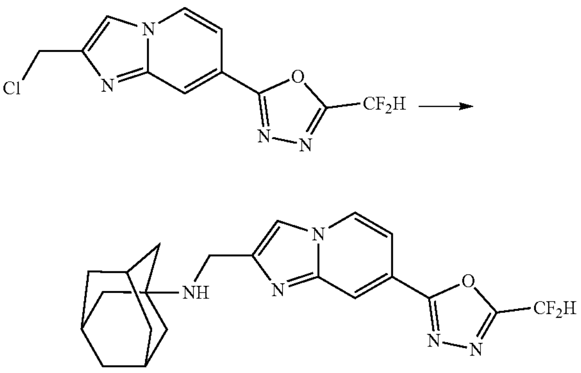

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, (3s,5s,7s)-adamantan-1-amine (0.040 g, 0.263 mmol), potassium carbonate (0.036 g, 0.263 mmol), and potassium iodide (0.015 g, 0.088 mmol) were added to N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 25%) and concentrated to obtain the title compound (0.023 g, 32.8%) as a yellow solid.

$^1H$ NMR (400 MHz, $CDCl_3$) δ 8.29 (p, J=0.8 Hz, 1H), 8.23 (dd, J=7.1, 0.9 Hz, 1H), 7.84 (s, 1H), 7.50 (dd, J=7.1, 1.7 Hz, 1H), 6.95 (t, J=51.7 Hz, 1H), 4.10 (s, 2H), 2.18-2.09 (m, 3H), 1.84 (d, J=2.9 Hz, 6H), 1.70 (q, J=12.8 Hz, 6H); LRMS (ES) m/z 399.8 ($M^+$+1).

Example 24: Synthesis of Compound 3678, N-((7-(5-(difluoromethyl)-1,3,4-oxadiazol-2-yl)imidazo[1,2-a]pyridin-2-yl)methyl)cyclohexanamine

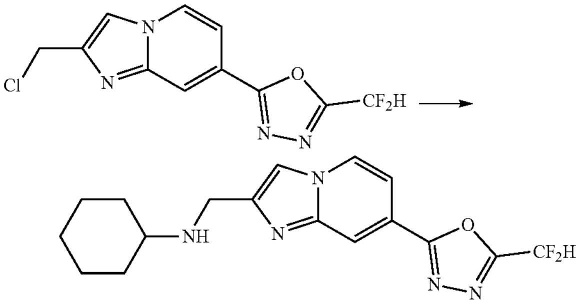

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, cyclohexanamine (0.026 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 25%) and concentrated to obtain the title compound (0.024 g, 39.3%) as a yellow solid.

$^1H$ NMR (400 MHz, $CDCl_3$) δ 8.30 (dt, J=1.7, 0.8 Hz, 1H), 8.24 (dd, J=7.1, 0.9 Hz, 1H), 7.74 (s, 1H), 7.53 (dd, J=7.1, 1.7 Hz, 1H), 6.96 (t, J=51.7 Hz, 1H), 4.09 (s, 2H), 2.61 (tt, J=10.0, 3.7 Hz, 1H), 2.39 (s, 1H), 2.01 (d, J=12.0 Hz, 2H), 1.85-1.71 (m, 2H), 1.70-1.59 (m, 1H), 1.39-1.13 (m, 4H);

LRMS (ES) m/z 347.7 ($M^+$+1).

Example 25: Synthesis of Compound 3679, N-((7-(5-(difluoromethyl)-1,3,4-oxadiazol-2-yl)imidazo[1,2-a]pyridin-2-yl)methyl)-3-methylaniline

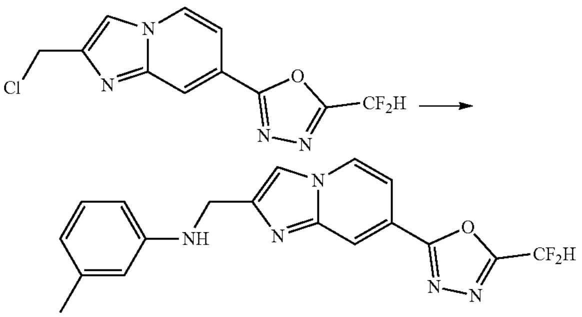

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, m-toluidine (0.028 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by column chromatography ($SiO_2$, 4 g cartridge; ethyl acetate/hexane=0% to 70%) and concentrated to obtain the title compound (0.032 g, 51.3%) as a yellow solid.

$^1H$ NMR (400 MHz, $CDCl_3$) δ 8.31 (p, J=0.8 Hz, 1H), 8.19 (dd, J=7.1, 1.0 Hz, 1H), 7.67 (d, J=0.9 Hz, 1H), 7.52 (dd, J=7.1, 1.7 Hz, 1H), 7.14-6.77 (m, 2H), 6.63-6.50 (m, 3H), 4.60 (d, J=0.9 Hz, 2H), 2.29 (s, 3H);

LRMS (ES) m/z 356.2 ($M^+$+1).

Example 26: Synthesis of Compound 3719, 2-(difluoromethyl)-5-(2-(phenoxymethyl)imidazo[1,2-a]pyridin-7-yl)-1,3,4-oxadiazole

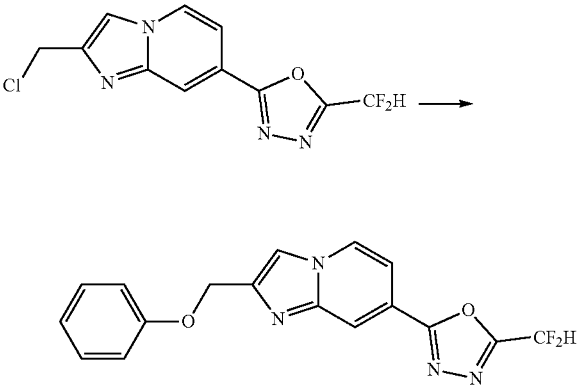

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, phenol (0.019 mL, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.032 g, 66.5%) as a white solid.

$^1H$ NMR (400 MHz, $CDCl_3$) δ 8.38 (d, J=1.6 Hz, 1H), 8.28 (dd, J=7.1, 1.0 Hz, 1H), 7.86-7.79 (m, 1H), 7.60 (dd, J=7.1, 1.7 Hz, 1H), 7.38-7.30 (m, 2H), 7.12-6.81 (m, 4H), 5.39-5.35 (m, 2H);

LRMS (ES) m/z 342.7 ($M^+$+1).

Example 27: Synthesis of Compound 3720, 2-(difluoromethyl)-5-(2-((m-tolyloxy)methyl)imidazo[1,2-a]pyridin-7-yl)-1,3,4-oxadiazole

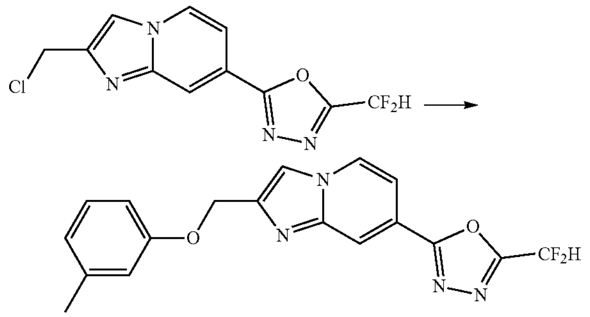

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, m-cresol (0.023 g, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.037 g, 73.9%) as a white solid.

$^1$H NMR (400 MHz, $CDCl_3$) δ 8.38 (dd, J=1.8, 0.9 Hz, 1H), 8.27 (dd, J=7.2, 1.0 Hz, 1H), 7.82 (d, J=0.9 Hz, 1H), 7.59 (dd, J=7.1, 1.7 Hz, 1H), 7.22 (t, J=7.8 Hz, 1H), 7.12-6.78 (m, 4H), 5.36 (d, J=0.8 Hz, 2H), 2.37 (s, 3H);

LRMS (ES) m/z 356.7 ($M^+$+1).

Example 28: Synthesis of Compound 3721, 1-(3-((7-(5-(difluoromethyl)-1,3,4-oxadiazol-2-yl)imidazo[1,2-a]pyridin-2-yl)methoxy)phenyl)ethan-1-one

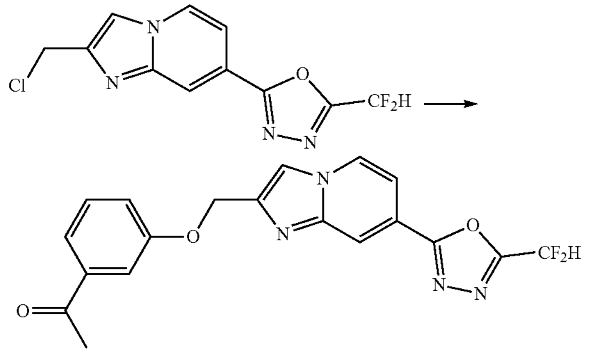

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, 1-(3-hydroxyphenyl)ethan-1-one (0.029 g, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.010 g, 18.5%) as a white solid.

$^1$H NMR (400 MHz, $CDCl_3$) δ 8.28 (dt, J=1.7, 0.8 Hz, 1H), 8.19 (dd, J=7.1, 1.0 Hz, 1H), 7.91-7.86 (m, 2H), 7.74 (d, J=0.8 Hz, 1H), 7.50 (dd, J=7.1, 1.7 Hz, 1H), 7.05-6.74 (m, 3H), 5.33 (d, J=0.7 Hz, 2H), 2.50 (s, 3H);

LRMS (ES) m/z 384.8 ($M^+$+1).

Example 29: Synthesis of Compound 3722, 2-(difluoromethyl)-5-(2-((3-fluorophenoxy)methyl)imidazo[1,2-a]pyridin-7-yl)-1,3,4-oxadiazole

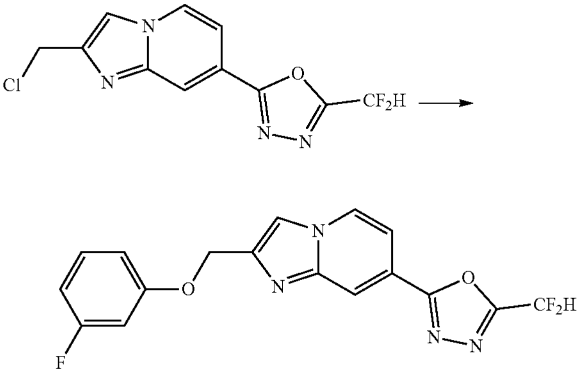

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, 3-fluorophenol (0.024 g, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.036 g, 71.1%) as a white solid.

$^1$H NMR (400 MHz, $CDCl_3$) δ 8.38 (dt, J=1.7, 0.8 Hz, 1H), 8.29 (dd, J=7.1, 0.9 Hz, 1H), 7.83 (t, J=0.8 Hz, 1H), 7.61 (dd, J=7.1, 1.7 Hz, 1H), 7.28 (d, J=6.9 Hz, 1H), 7.11-6.68 (m, 4H), 5.35 (d, J=0.8 Hz, 2H);

LRMS (ES) m/z 360.7 ($M^+$+1).

Example 30: Synthesis of Compound 3723, 2-(difluoromethyl)-5-(2-((3,4-difluorophenoxy)methyl)imidazo[1,2-a]pyridin-7-yl)-1,3,4-oxadiazole

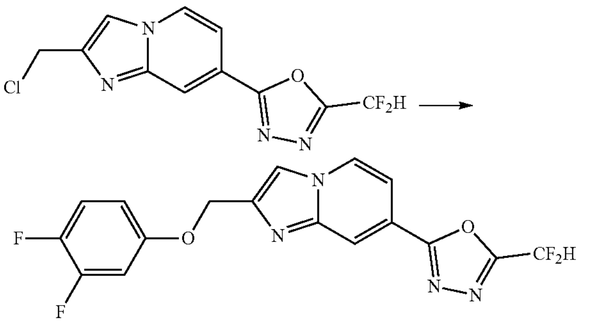

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, 3,4-difluorophenol (0.027 g, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.032 g, 60.2%) as a white solid.

$^1H$ NMR (400 MHz, $CDCl_3$) δ 8.37 (dt, J=1.7, 0.8 Hz, 1H), 8.29 (dd, J=7.1, 1.0 Hz, 1H), 7.82 (d, J=0.8 Hz, 1H), 7.60 (dd, J=7.1, 1.7 Hz, 1H), 7.15-6.73 (m, 4H), 5.30 (d, J=0.8 Hz, 2H);

LRMS (ES) m/z 378.7 ($M^+$+1).

Example 31: Synthesis of Compound 3724, 2-(difluoromethyl)-5-(2-((4-(trifluoromethyl)phenoxy)methyl)imidazo[1,2-a]pyridin-7-yl)-1,3,4-oxadiazole

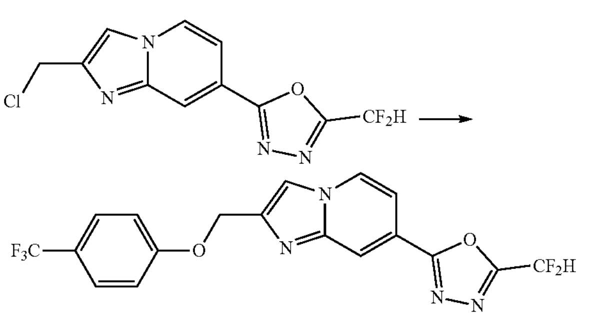

2-(2-(Chloromethyl)imidazo[1,2-a]pyridin-7-yl)-5-(difluoromethyl)-1,3,4-oxadiazole (0.040 g, 0.141 mmol) prepared in step 5 of Example 2, 4-(trifluoromethyl)phenol (0.034 g, 0.211 mmol), and potassium carbonate (0.039 g, 0.281 mmol) were dissolved in N,N-dimethylformamide (2 mL) at room temperature, and the resulting solution was stirred at the same temperature for 2 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 50%) and concentrated to obtain the title compound (0.051 g, 88.5%) as a white solid.

$^1H$ NMR (400 MHz, $CDCl_3$) δ 8.33-8.28 (m, 1H), 8.20 (dd, J=7.1, 1.0 Hz, 1H), 7.74 (d, J=0.8 Hz, 1H), 7.52 (ddd, J=10.9, 8.1, 1.3 Hz, 3H), 7.08-6.71 (m, 3H), 5.33 (d, J=0.8 Hz, 2H);

LRMS (ES) m/z 410.7 ($M^+$+1).

Example 32: Synthesis of Compound 3725, N-((7-(5-(difluoromethyl)-1,3,4-oxadiazol-2-yl)imidazo[1,2-a]pyridin-2-yl)methyl)-N-methylaniline

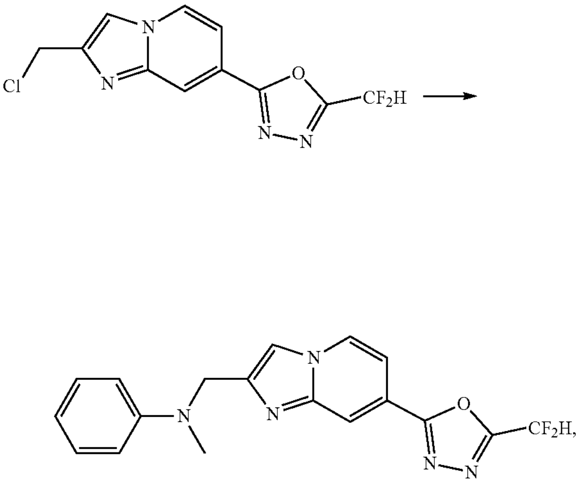

2-(2-(Chloromethyl)imidazo[1,2-a]pyridin-7-yl)-5-(difluoromethyl)-1,3,4-oxadiazole (0.050 g, 0.176 mmol) prepared in step 5 of Example 2, N-methylaniline (0.028 g, 0.263 mmol), potassium carbonate (0.036 g, 0.263 mmol), and potassium iodide (0.015 g, 0.088 mmol) were dissolved in N,N-dimethylformamide (3 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; hexane/ethyl acetate=0% to 50%) and concentrated to obtain the title compound (0.051 g, 81.7%) as a white solid.

$^1H$ NMR (400 MHz, $CDCl_3$) δ 8.33 (dt, J=1.7, 0.9 Hz, 1H), 8.15 (dd, J=7.1, 1.0 Hz, 1H), 7.53-7.48 (m, 2H), 7.30-7.23 (m, 2H), 7.10-6.75 (m, 4H), 4.80 (d, J=0.9 Hz, 2H), 3.16 (s, 3H);

LRMS (ES) m/z 355.7 ($M^+$+1).

Example 33: Synthesis of Compound 3782, N-((7-(5-(difluoromethyl)-1,3,4-oxadiazol-2-yl)imidazo[1,2-a]pyridin-2-yl)methyl)-1-methyl-N-phenylpiperidine-4-carboxamide

[Step 1] Synthesis of tert-butyl 4-(chlorocarbonyl)piperidine-1-carboxylate

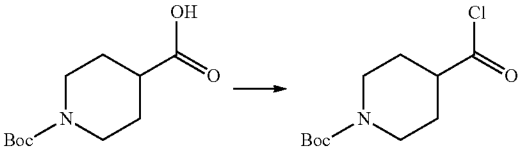 [SMILES: CC(C)(C)OC(=O)N1CCC(C(=O)O)CC1 ; CC(C)(C)OC(=O)N1CCC(C(=O)Cl)CC1]

1-(Tert-butoxycarbonyl)piperidine-4-carboxylic acid (0.200 g, 0.872 mmol) was dissolved in dichloromethane (10 mL), and oxalyl chloride (2.00 M solution, 0.567 mL, 1.134 mmol) and N,N-dimethylformamide (0.007 mL, 0.087 mmol) were added at 0° C. and stirred at room temperature for 2 hours. After removing the solvent from the reaction mixture under reduced pressure, the title compound (0.216 g, 100.0%) was obtained as a yellow solid without further purification.

[Step 2] Synthesis of tert-butyl 4-(((7-(5-(difluoromethyl)-1,3,4-oxadiazol-2-yl)imidazo[1,2-a]pyridin-2-yl)methyl)(phenyl)carbamoyl)piperidine-1-carboxylate

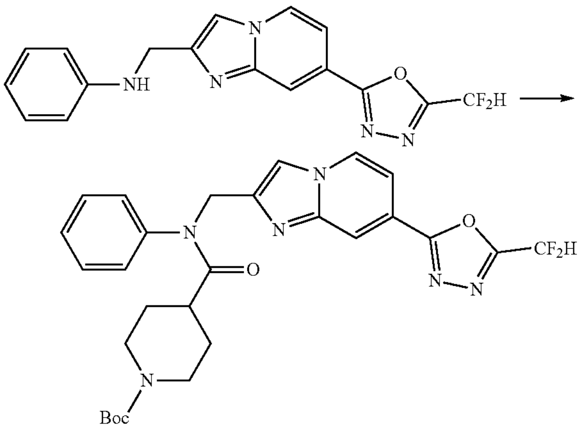

To a solution in which N-((7-(5-(difluoromethyl)-1,3,4-oxadiazol-2-yl)imidazo[1,2-a]pyridin-2-yl)methyl)aniline (0.200 g, 0.586 mmol) prepared in Example 14 was dissolved in dichloromethane (20 mL) at 0° C., tert-butyl 4-(chlorocarbonyl)piperidine-1-carboxylate (0.189 g, 0.762 mmol) prepared in step 1 and triethylamine (0.245 mL, 1.758 mmol) were added and stirred at room temperature for 16 hours. A saturated aqueous ammonium chloride solution was poured into the concentrate obtained by removing the solvent from the reaction mixture under reduced pressure, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.200 g, 61.8%) as a yellow solid.

[Step 3] Synthesis of N-((7-(5-(difluoromethyl)-1,3,4-oxadiazol-2-yl)imidazo[1,2-a]pyridin-2-yl)methyl)-N-phenylpiperidine-4-carboxamide

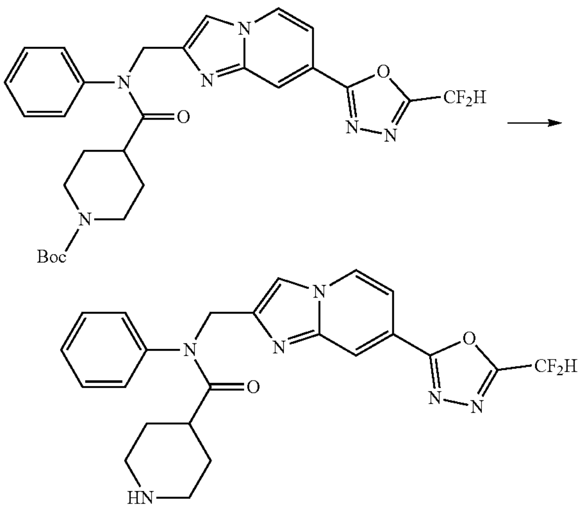

Tert-butyl 4-(((7-(5-(difluoromethyl)-1,3,4-oxadiazol-2-yl)imidazo[1,2-a]pyridin-2-yl)methyl)(phenyl)carbamoyl)piperidine-1-carboxylate (0.120 g, 0.217 mmol) prepared in step 2 and trifluoroacetic acid (0.333 mL, 4.343 mmol) were dissolved in dichloromethane (5 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (0.098 g, 99.7%) was obtained as a brown gel without further purification.

[Step 4] Synthesis of Compound 3782

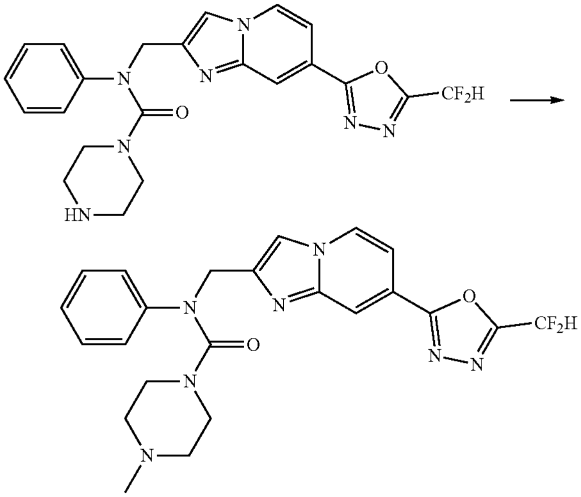

N-((7-(5-(difluoromethyl)-1,3,4-oxadiazol-2-yl)imidazo[1,2-a]pyridin-2-yl)methyl)-N-phenylpiperidine-4-carboxamide (0.050 g, 0.111 mmol) prepared in step 3, formaldehyde (0.007 g, 0.221 mmol), acetic acid (0.006 mL, 0.111 mmol), and sodium triacetoxyborohydride (0.070 g, 0.332 mmol) were dissolved in dichloromethane (3 mL) at room temperature, and the resulting solution was stirred at the same temperature for 18 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by chromatography ($SiO_2$ plate, 20×20×1 mm; dichloromethane/methanol=0% to 10%) and concentrated to obtain the title compound (0.038 g, 73.7%) as a white solid.

$^1H$ NMR (400 MHz, $CDCl_3$) δ 8.29 (dt, J=1.7, 0.8 Hz, 1H), 8.23 (dd, J=7.1, 1.0 Hz, 1H), 7.78 (s, 1H), 7.53 (dd, J=7.1, 1.7 Hz, 1H), 7.46-7.36 (m, 3H), 7.27-7.21 (m, 2H), 6.95 (t, J=51.7 Hz, 1H), 5.04 (s, 2H), 2.89 (s, 2H), 2.25 (s, 4H), 1.93 (q, J=11.6, 11.0 Hz, 3H), 1.71 (s, 3H);

LRMS (ES) m/z 468.1 ($M^+$+1).

Example 34: Synthesis of Compound 3783, N-((7-(5-(difluoromethyl)-1,3,4-oxadiazol-2-yl)imidazo[1,2-a]pyridin-2-yl)methyl)-1-(oxetan-3-yl)-N-phenylpiperidine-4-carboxamide

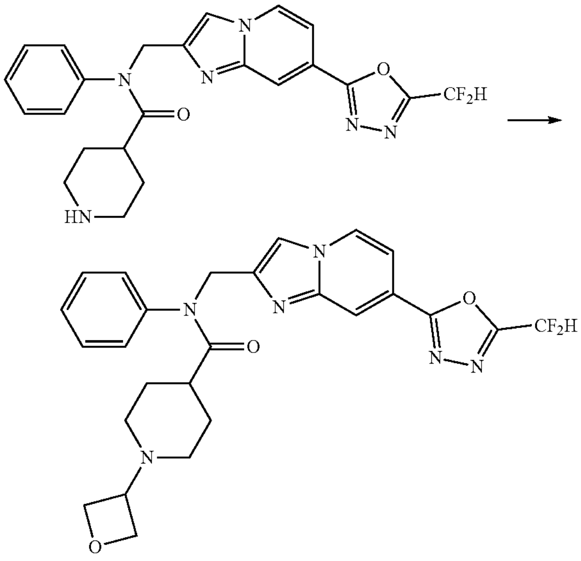

N-((7-(5-(difluoromethyl)-1,3,4-oxadiazol-2-yl)imidazo[1,2-a]pyridin-2-yl)methyl)-N-phenylpiperidine-4-carboxamide (0.050 g, 0.111 mmol) prepared in step 3 of Example 33, oxetan-3-one (0.016 g, 0.221 mmol), acetic acid (0.006 mL, 0.111 mmol), and sodium triacetoxyborohydride (0.070 g, 0.332 mmol) were dissolved in dichloromethane (3 mL) at room temperature, and the resulting solution was stirred at the same temperature for 18 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by chromatography ($SiO_2$ plate, 20×20×1 mm; dichloromethane/methanol=0% to 10%) and concentrated to obtain the title compound (0.042 g, 74.7%) as a white solid.

$^1H$ NMR (400 MHz, $CDCl_3$) δ 8.29 (dt, J=1.6, 0.8 Hz, 1H), 8.23 (dd, J=7.1, 0.9 Hz, 1H), 7.79 (s, 1H), 7.53 (dd, J=7.1, 1.7 Hz, 1H), 7.46-7.33 (m, 3H), 7.27-7.22 (m, 2H), 6.95 (t, J=51.7 Hz, 1H), 5.04 (s, 2H), 4.59 (d, J=6.6 Hz, 4H), 3.38 (s, 1H), 2.70 (s, 2H), 2.25 (d, J=12.0 Hz, 1H), 1.92 (q, J=11.8, 11.2 Hz, 2H), 1.67 (s, 4H);

LRMS (ES) m/z 508.9 ($M^+$+1).

Example 35: Synthesis of Compound 3784, N-((7-(5-(difluoromethyl)-1,3,4-oxadiazol-2-yl)imidazo[1,2-a]pyridin-2-yl)methyl)-4-methyl-N-phenylpiperazine-1-carboxamide

[Step 1] Synthesis of tert-butyl 4-(((7-(5-(difluoromethyl)-1,3,4-oxadiazol-2-yl)imidazo[1,2-a]pyridin-2-yl)methyl)(phenyl)carbamoyl)piperazine-1-carboxylate

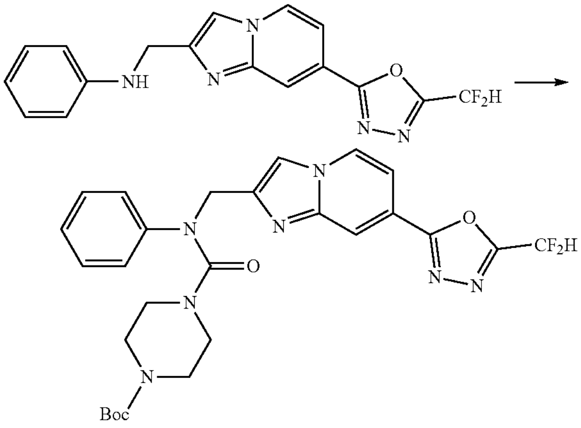

N-((7-(5-(difluoromethyl)-1,3,4-oxadiazol-2-yl)imidazo[1,2-a]pyridin-2-yl)methyl)aniline (0.200 g, 0.586 mmol) prepared in Example 14, triphosgene (0.174 g, 0.586 mmol), and N,N-diisopropylethylamine (0.510 mL, 2.930 mmol) were dissolved in dichloromethane (15 mL), and the resulting solution was stirred at room temperature for 10 minutes. Then, tert-butyl piperazine-1-carboxylate (0.142 g, 0.762 mmol) was added and further stirred at the same temperature for 16 hours. Water was poured into the reaction mixture, extracted with dichloromethane, and filtered through a plastic filter to remove a solid residue and an aqueous layer, and then concentrated under reduced pressure. The concentrate was purified by column chromatography ($SiO_2$, 12 g cartridge; ethyl acetate/hexane=5% to 50%) and concentrated to obtain the title compound (0.160 g, 49.3%) as a white solid.

[Step 2] Synthesis of N-((7-(5-(difluoromethyl)-1,3,4-oxadiazol-2-yl)imidazo[1,2-a]pyridin-2-yl)methyl)-N-phenylpiperazine-1-carboxamide

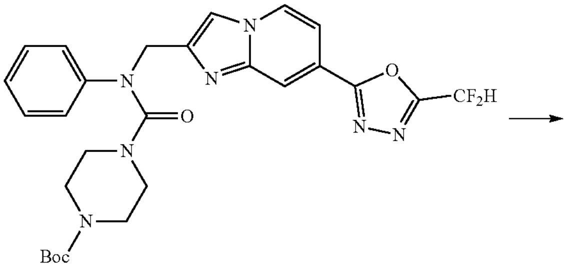

-continued

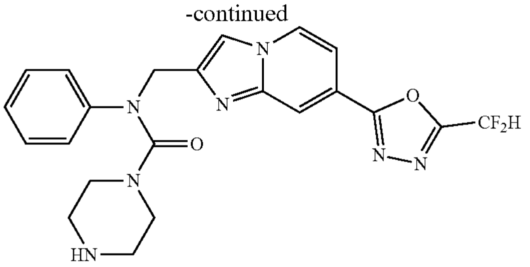

Tert-butyl 4-(((7-(5-(difluoromethyl)-1,3,4-oxadiazol-2-yl)imidazo[1,2-a]pyridin-2-yl)methyl)(phenyl)carbamoyl) piperazine-1-carboxylate (0.100 g, 0.181 mmol) prepared in step 1 was dissolved in dichloromethane (15 mL), and trifluoroacetic acid (0.277 mL, 3.613 mmol) was added at 0° C. and stirred at room temperature for 16 hours. A saturated aqueous sodium hydrogen carbonate solution was poured into the reaction mixture, extracted with dichloromethane, and then filtered through a plastic filter to remove a solid residue and an aqueous layer. After concentration under reduced pressure, the title compound (0.099 g, 96.6%) was obtained as a foam type solid without further purification.

[Step 3] Synthesis of Compound 3784

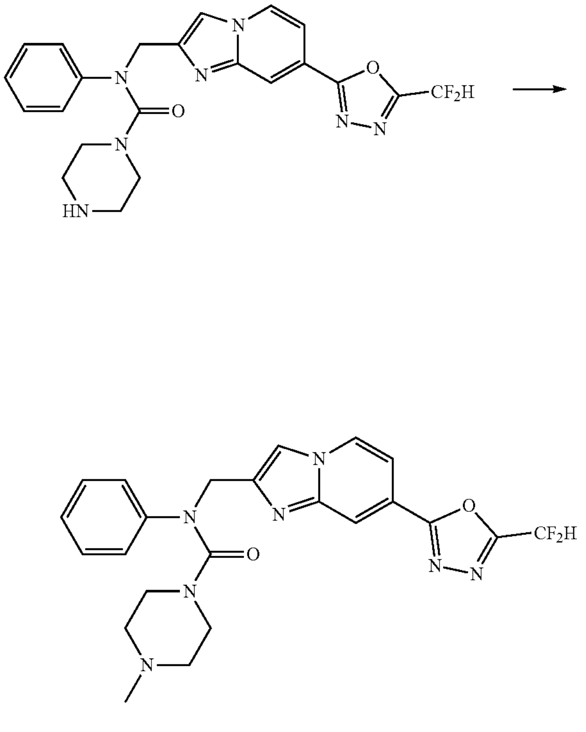

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2, paraformaldehyde (0.007 g, 0.221 mmol), and acetic acid (0.006 mL, 0.110 mmol) were dissolved in dichloromethane (5 mL), and the resulting solution was stirred at room temperature for 1 hour. Then, sodium triacetoxyborohydride (0.070 g, 0.331 mmol) was added and further stirred at the same temperature for 16 hours. Water was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=10%) and concentrated to obtain the title compound (0.030 g, 58.2%) as a white solid.

$^1$H NMR (400 MHz, MeOD) δ 8.59 (m, 1H), 8.20 (m, 1H), 7.97 (m, 1H), 7.56-7.54 (m, 1H), 7.39-7.35 (m, 2H), 7.26-7.13 (m, 4H), 5.03 (s, 2H), 3.32 (m, 4H), 2.36 (m, 4H), 2.29 (s, 3H);

LRMS (ES) m/z 468.3 ($M^+$+1).

Example 36: Synthesis of Compound 3785, N-((7-(5-(difluoromethyl)-1,3,4-oxadiazol-2-yl)imidazo[1,2-a]pyridin-2-yl)methyl)-4-(oxetan-3-yl)-N-phenylpiperazine-1-carboxamide

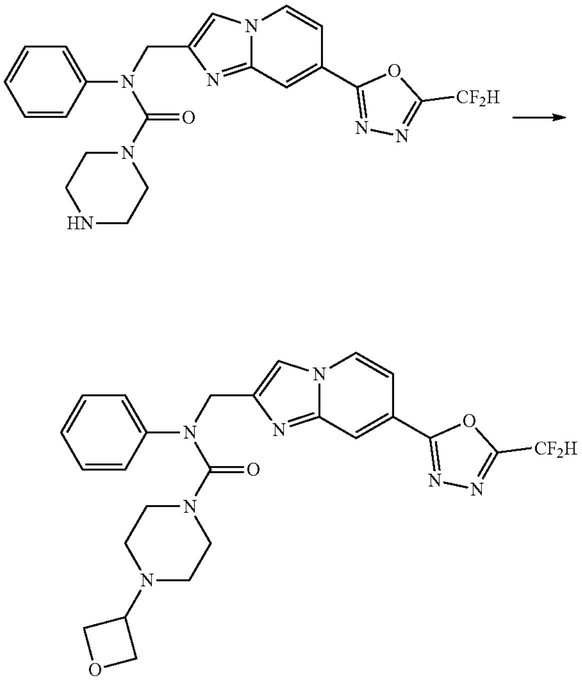

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2 of Example 35, oxetan-3-one (0.014 mL, 0.221 mmol), and acetic acid (0.006 mL, 0.110 mmol) were dissolved in dichloromethane (5 mL), and the resulting solution was stirred at room temperature for 1 hour. Then, sodium triacetoxyborohydride (0.070 g, 0.331 mmol) was added and further stirred at the same temperature for 16 hours. Water was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=10%) and concentrated to obtain the title compound (0.028 g, 49.8%) as a white solid.

$^1$H NMR (400 MHz, MeOD) δ 8.58 (m, 1H), 8.19 (m, 1H), 7.96 (s, 1H), 7.55-7.52 (m, 1H), 7.39-7.34 (m, 2H), 7.26-7.13 (m, 4H), 5.02 (s, 2H), 4.63 (m, 2H), 4.52 (m, 2H), 3.41 (m, 1H), 3.32 (m, 4H), 2.17 (m, 4H);

LRMS (ES) m/z 510.1 ($M^+$+1).

Example 37: Synthesis of Compound 4033, N-((7-(5-(difluoromethyl)-1,3,4-oxadiazol-2-yl)imidazo[1,2-a]pyridin-2-yl)methyl)-4-ethyl-N-phenylpiperazine-1-carboxamide

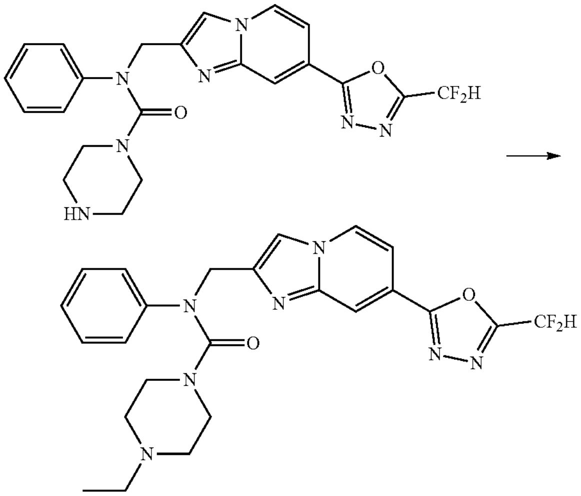

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, acetaldehyde (0.019 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.027 g, 25.4%) as a yellow solid.

$^1$H NMR (700 MHz, MeOD) δ 8.59 (dd, J=7.2, 1.0 Hz, 1H), 8.21 (dt, J=1.7, 0.8 Hz, 1H), 7.98 (d, J=0.8 Hz, 1H), 7.55 (dd, J=7.1, 1.7 Hz, 1H), 7.38-7.13 (m, 6H), 5.03 (d, J=0.8 Hz, 2H), 3.32-3.27 (m, 4H), 2.38 (q, J=7.3 Hz, 2H), 2.31 (t, J=5.1 Hz, 4H), 1.06 (t, J=7.2 Hz, 3H);

LRMS (ES) m/z 482.2 ($M^+$+1).

Example 38: Synthesis of Compound 4034, N-((7-(5-(difluoromethyl)-1,3,4-oxadiazol-2-yl)imidazo[1,2-a]pyridin-2-yl)methyl)-4-isopropyl-N-phenylpiperazine-1-carboxamide

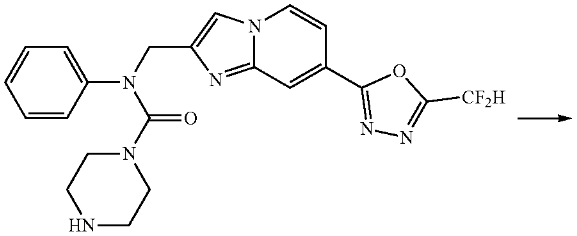

-continued

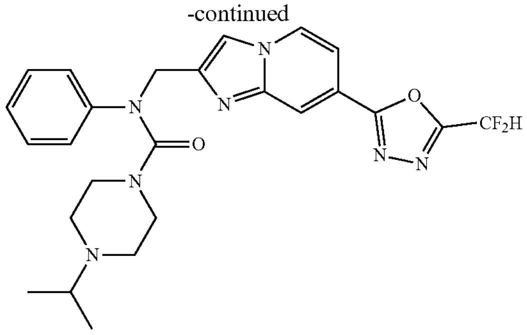

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2 of Example 35, propan-2-one (0.013 g, 0.221 mmol), acetic acid (0.006 mL, 0.110 mmol), and sodium triacetoxyborohydride (0.070 g, 0.331 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.030 g, 54.9%) as a yellow solid.

$^1$H NMR (400 MHz, MeOD) δ 8.53 (dd, J=7.1, 1.0 Hz, 1H), 8.22 (dt, J=1.8, 0.8 Hz, 1H), 7.92 (s, 1H), 7.55 (dd, J=7.1, 1.7 Hz, 1H), 7.39-7.02 (m, 6H), 5.02 (s, 2H), 3.30 (t, J=5.1 Hz, 4H), 2.65 (p, J=6.5 Hz, 1H), 2.40 (t, J=5.1 Hz, 4H), 1.02 (d, J=6.5 Hz, 6H);

LRMS (ES) m/z 496.5 ($M^+$+1).

Example 39: Synthesis of Compound 4035, N-((7-(5-(difluoromethyl)-1,3,4-oxadiazol-2-yl)imidazo[1,2-a]pyridin-2-yl)methyl)-4-(1-hydroxypropan-2-yl)-N-phenylpiperazine-1-carboxamide

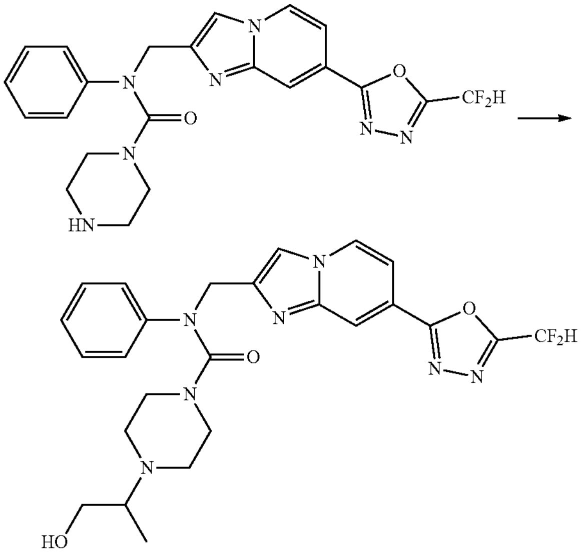

N-((7-(5-(difluoromethyl)-1,3,4-oxadiazol-2-yl)imidazo [1,2-a]pyridin-2-yl)methyl)-N-phenylpiperazine-1-carboxamide (0.100 g, 0.221 mmol) prepared in step 2 of Example 35, 1-hydroxypropan-2-one (0.033 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.011 g, 9.8%) as a yellow solid.

$^1H$ NMR (400 MHz, $CDCl_3$) δ 8.31-8.27 (m, 1H), 8.20 (dt, J=7.2, 1.4 Hz, 1H), 7.79-7.74 (m, 1H), 7.51 (tt, J=5.4, 1.7 Hz, 1H), 7.38-7.30 (m, 2H), 7.27-7.21 (m, 2H), 7.20-7.09 (m, 1H), 7.09-6.80 (m, 1H), 5.07 (s, 2H), 3.33 (d, J=23.0 Hz, 4H), 3.24-3.15 (m, 2H), 2.40 (s, 2H), 2.12 (s, 2H), 2.04 (s, 1H), 1.28 (s, 3H);

LRMS (ES) m/z 512.3 ($M^+$+1).

Example 40: Synthesis of Compound 4036, 4-cyclobutyl-N-((7-(5-(difluoromethyl)-1,3,4-oxadiazol-2-yl)imidazo[1,2-a]pyridin-2-yl)methyl)-N-phenylpiperazine-1-carboxamide

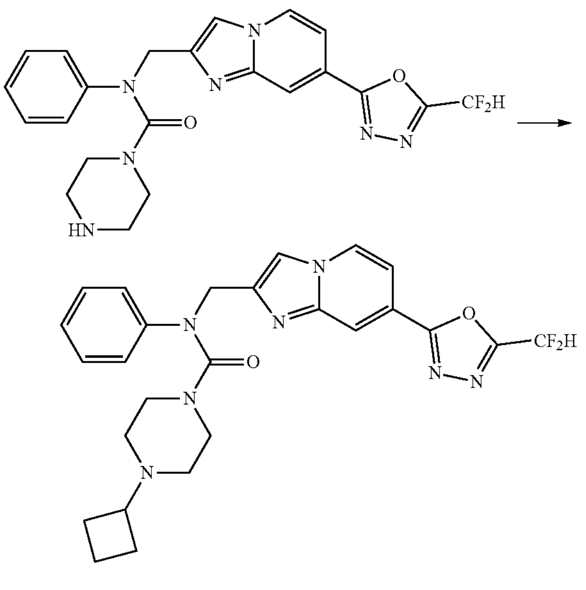

N-((7-(5-(difluoromethyl)-1,3,4-oxadiazol-2-yl)imidazo [1,2-a]pyridin-2-yl)methyl)-N-phenylpiperazine-1-carboxamide (0.100 g, 0.221 mmol) prepared in step 2 of Example 35, cyclobutanone (0.031 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.028 g, 25.0%) as a yellow solid.

$^1H$ NMR (700 MHz, MeOD) δ 8.60 (dd, J=7.1, 1.0 Hz, 1H), 8.21 (p, J=0.8 Hz, 1H), 7.98 (d, J=0.8 Hz, 1H), 7.56 (dd, J=7.1, 1.7 Hz, 1H), 7.40-7.14 (m, 6H), 5.03 (d, J=0.8 Hz, 2H), 3.29 (t, J=5.1 Hz, 4H), 2.73-2.66 (m, 1H), 2.18 (t, J=5.1 Hz, 4H), 2.06-1.98 (m, 2H), 1.89-1.79 (m, 2H), 1.70 (ddt, J=12.8, 10.0, 5.7 Hz, 2H);

LRMS (ES) m/z 508.3 ($M^+$+1).

Example 41: Synthesis of Compound 4037, 4-cyclohexyl-N-((7-(5-(difluoromethyl)-1,3,4-oxadiazol-2-yl)imidazo[1,2-a]pyridin-2-yl)methyl)-N-phenylpiperazine-1-carboxamide

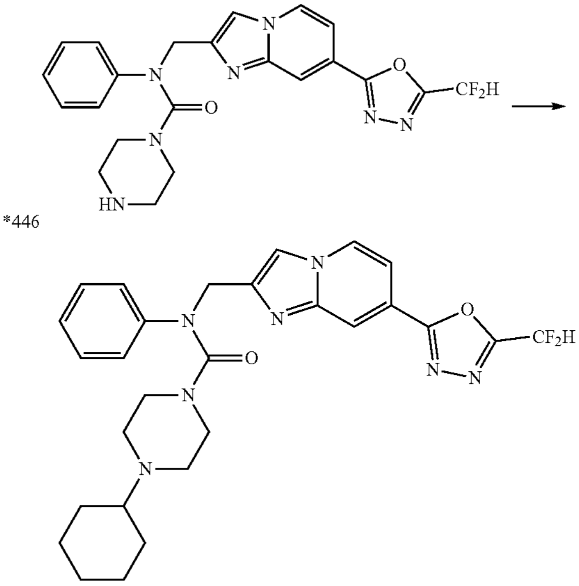

*446

N-((7-(5-(difluoromethyl)-1,3,4-oxadiazol-2-yl)imidazo [1,2-a]pyridin-2-yl)methyl)-N-phenylpiperazine-1-carboxamide (0.100 g, 0.221 mmol) prepared in step 2 of Example 35, cyclohexanone (0.043 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.031 g, 26.2%) as a yellow solid.

$^1H$ NMR (700 MHz, MeOD) δ 8.57 (d, J=7.1 Hz, 1H), 8.22-8.20 (m, 1H), 7.96 (s, 1H), 7.55 (dd, J=7.1, 1.7 Hz, 1H), 7.41-7.09 (m, 6H), 5.04-5.01 (m, 2H), 3.29 (t, J=5.1 Hz, 4H), 2.43 (t, J=5.0 Hz, 4H), 2.23 (tt, J=11.9, 3.6 Hz, 1H), 1.86-1.74 (m, 4H), 1.63 (dt, J=12.6, 3.3 Hz, 1H), 1.24 (qt, J=12.9, 3.2 Hz, 2H), 1.19-1.07 (m, 3H);

LRMS (ES) m/z 536.2 ($M^+$+1).

Example 42: Synthesis of Compound 4038, N-((7-(5-(difluoromethyl)-1,3,4-oxadiazol-2-yl)imidazo[1,2-a]pyridin-2-yl)methyl)-N-phenyl-4-(tetrahydro-2H-pyran-4-yl)piperazine-1-carboxamide

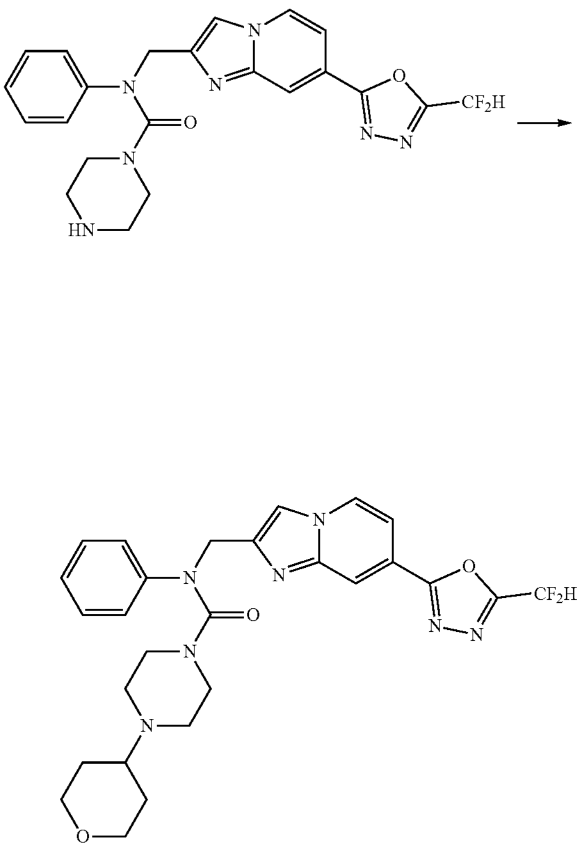

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, tetrahydro-4H-pyran-4-one (0.044 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.016 g, 13.5%) as a yellow solid.

$^1H$ NMR (700 MHz, MeOD) δ 8.53 (d, J=7.1 Hz, 1H), 8.23-8.20 (m, 1H), 7.92 (s, 1H), 7.55 (dd, J=7.1, 1.7 Hz, 1H), 7.36 (dd, J=8.5, 7.4 Hz, 2H), 7.29-7.05 (m, 4H), 5.02 (s, 2H), 3.97 (dd, J=11.3, 4.4 Hz, 2H), 3.36 (td, J=12.0, 1.9 Hz, 2H), 3.31-3.28 (m, 4H), 2.43 (t, J=5.1 Hz, 5H), 1.75 (ddd, J=12.4, 4.3, 2.1 Hz, 2H), 1.47 (qd, J=12.2, 4.5 Hz, 2H);

LRMS (ES) m/z 538.1 ($M^+$+1).

Example 43: Synthesis of Compound 4039, 4-(4,4-difluorocyclohexyl)-N-((7-(5-(difluoromethyl)-1,3,4-oxadiazol-2-yl)imidazo[1,2-a]pyridin-2-yl)methyl)-N-phenylpiperazine-1-carboxamide

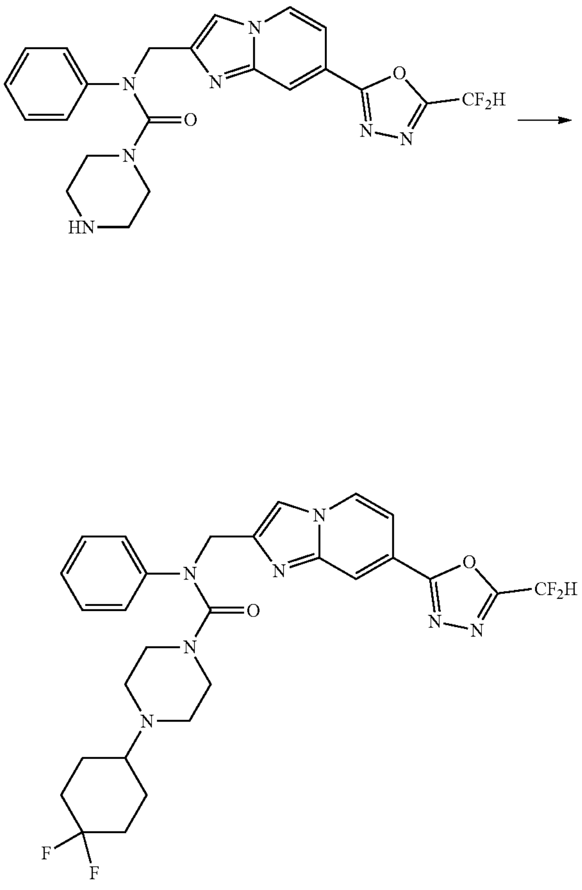

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, 4,4-difluorocyclohexan-1-one (0.059 g, 0.441 mmol), acetic acid (0.013 mL, 0.221 mmol), and sodium triacetoxyborohydride (0.140 g, 0.662 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.034 g, 27.0%) as a yellow solid.

$^1H$ NMR (700 MHz, MeOD) δ 8.47 (dd, J=7.1, 1.0 Hz, 1H), 8.21 (dt, J=1.7, 0.8 Hz, 1H), 7.88 (d, J=0.8 Hz, 1H), 7.54 (dd, J=7.1, 1.7 Hz, 1H), 7.37-7.32 (m, 2H), 7.25-7.00 (m, 4H), 5.01 (s, 2H), 3.30-3.26 (m, 4H), 2.47-2.27 (m, 5H), 2.08-2.04 (m, 2H), 1.81 (d, J=13.1 Hz, 2H), 1.72 (dddd, J=30.7, 17.4, 13.1, 4.2 Hz, 2H), 1.57-1.49 (m, 2H);

LRMS (ES) m/z 572.3 ($M^+$+1).

Example 44: Synthesis of Compound 4040, 4-acetyl-N-((7-(5-(difluoromethyl)-1,3,4-oxadiazol-2-yl)imidazo[1,2-a]pyridin-2-yl)methyl)-N-phenylpiperazine-1-carboxamide

*461

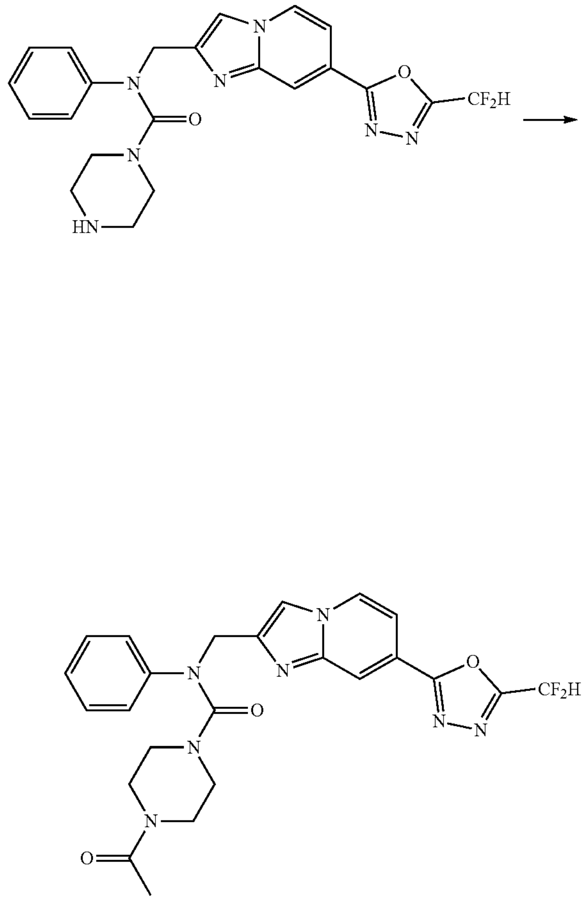

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, acetyl chloride (0.031 mL, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.018 g, 16.5%) as a yellow solid.

$^1$H NMR (400 MHz, $CDCl_3$) δ 8.37 (s, 1H), 8.24 (d, J=7.1 Hz, 1H), 7.79 (s, 1H), 7.59 (d, J=7.1 Hz, 1H), 7.37 (dd, J=8.4, 7.2 Hz, 2H), 7.33-7.28 (m, 2H), 7.21-7.13 (m, 1H), 6.95 (t, J=51.7 Hz, 1H), 5.07 (s, 2H), 3.43 (t, J=5.3 Hz, 2H), 3.30 (s, 4H), 3.23 (t, J=5.4 Hz, 2H), 2.04 (s, 3H);

LRMS (ES) m/z 496.0 ($M^+$+1).

Example 45: Synthesis of Compound 4041, N-((7-(5-(difluoromethyl)-1,3,4-oxadiazol-2-yl)imidazo[1,2-a]pyridin-2-yl)methyl)-N-phenyl-4-propionylpiperazine-1-carboxamide

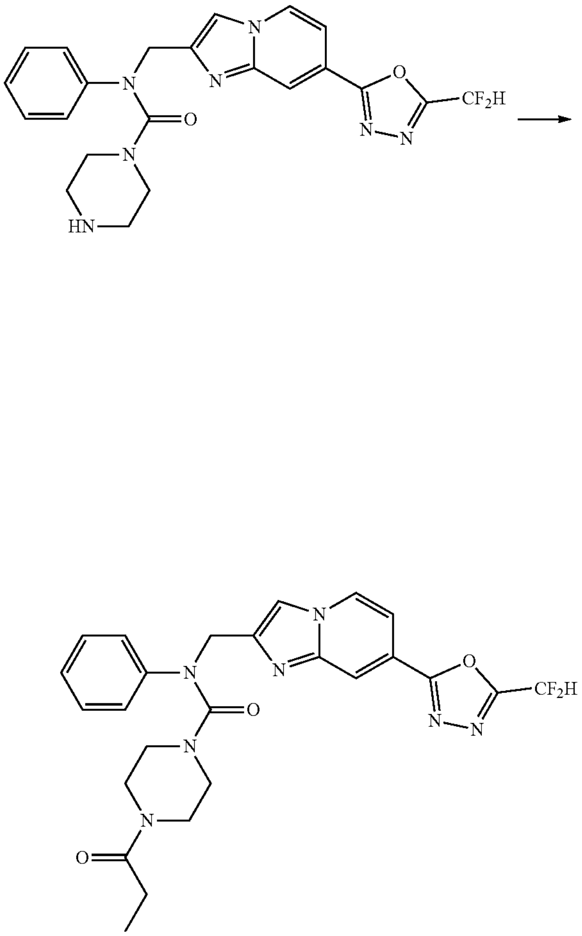

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, propionyl chloride (0.041 g, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.014 g, 12.5%) as a yellow solid.

$^1$H NMR (700 MHz, MeOD) § 8.58 (dd, J=7.1, 1.0 Hz, 1H), 8.20 (dt, J=1.7, 0.8 Hz, 1H), 8.00-7.98 (m, 1H), 7.54 (dd, J=7.1, 1.7 Hz, 1H), 7.40-7.14 (m, 6H), 5.06-5.03 (m, 2H), 3.44-3.38 (m, 4H), 3.32-3.24 (m, 4H), 2.35 (q, J=7.5 Hz, 2H), 1.07 (t, J=7.5 Hz, 3H);

LRMS (ES) m/z 510.3 ($M^+$+1).

Example 46: Synthesis of Compound 4042, N-((7-(5-(difluoromethyl)-1,3,4-oxadiazol-2-yl)imidazo[1,2-a]pyridin-2-yl)methyl)-4-(2-hydroxyacetyl)-N-phenylpiperazine-1-carboxamide

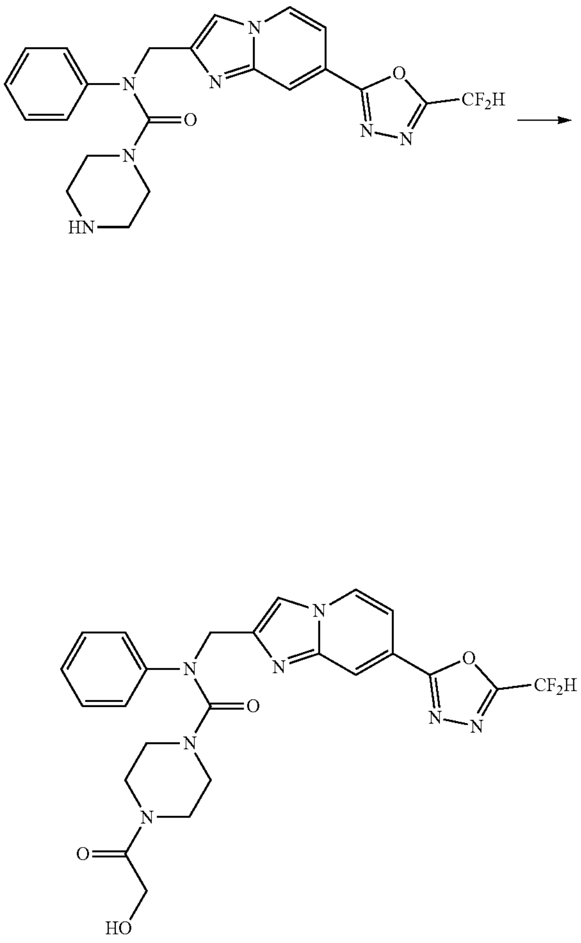

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, 2-hydroxyacetyl chloride (0.042 g, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.029 g, 25.7%) as a yellow solid.

$^1H$ NMR (400 MHz, $CDCl_3$) δ 8.42 (s, 1H), 8.26 (d, J=7.1 Hz, 1H), 7.80 (s, 1H), 7.64 (s, 1H), 7.43-7.30 (m, 4H), 7.24-7.16 (m, 1H), 6.95 (t, J=51.7 Hz, 1H), 5.07 (d, J=0.7 Hz, 2H), 4.09 (s, 2H), 3.50 (t, J=5.3 Hz, 2H), 3.29 (d, J=9.9. Hz, 4H), 3.10 (t, J=5.2 Hz, 2H);

LRMS (ES) m/z 513.2 ($M^+$+1).

Example 47: Synthesis of Compound 4043, 4-(cyclobutanecarbonyl)-N-((7-(5-(difluoromethyl)-1,3,4-oxadiazol-2-yl)imidazo[1,2-a]pyridine-2-yl)methyl)-N-phenylpiperazine-1-carboxamide

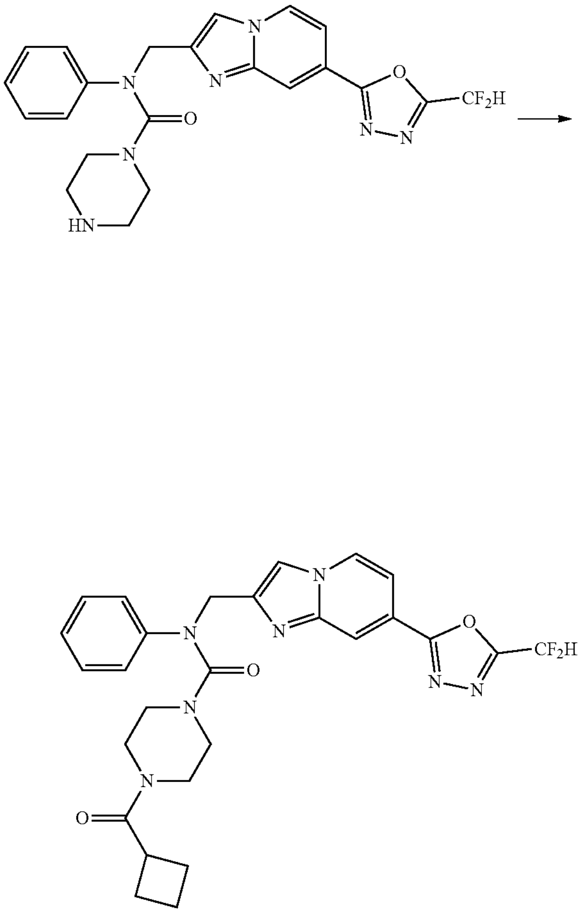

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, cyclobutanecarbonyl chloride (0.052 g, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.030 g, 25.4%) as a yellow solid.

$^1H$ NMR (700 MHz, MeOD) δ 8.59 (dd, J=7.1, 1.0 Hz, 1H), 8.21 (dt, J=1.7, 0.8 Hz, 1H), 8.02-7.98 (m, 1H), 7.56 (dd, J=7.1, 1.7 Hz, 1H), 7.44-7.14 (m, 6H), 5.06-5.03 (m, 2H), 3.42-3.36 (m, 2H), 3.29-3.22 (m, 6H), 2.28-2.17 (m, 3H), 2.14 (ddddd, J=12.2, 11.0, 8.8, 3.7, 1.8 Hz, 2H), 2.02-1.94 (m, 1H), 1.84-1.78 (m, 1H);

LRMS (ES) m/z 537.1 ($M^+$+1).

Example 48: Synthesis of Compound 4044, N-((7-(5-(difluoromethyl)-1,3,4-oxadiazol-2-yl)imidazo[1,2-a]pyridin-2-yl)methyl)-N-phenyl-4-(2,2,2-trifluoroacetyl)piperazine-1-carboxamide

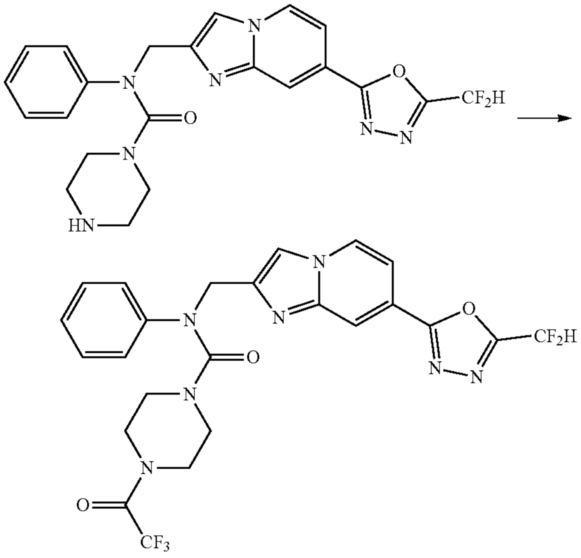

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2 of Example 35, 1,1,1,5,5,5-hexafluoropentane-2,4-dione (0.046 g, 0.221 mmol), and triethylamine (0.046 mL, 0.331 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.041 g, 67.7%) as a yellow solid.

$^1H$ NMR (400 MHz, MeOD) δ 8.59 (dd, J=7.2, 1.0 Hz, 1H), 8.22 (dt, J=1.7, 0.8 Hz, 1H), 8.00 (d, J=0.7 Hz, 1H), 7.56 (dd, J=7.2, 1.7 Hz, 1H), 7.44-7.09 (m, 6H), 5.06 (d, J=0.8 Hz, 2H), 3.51 (q, J=5.3 Hz, 4H), 3.36 (dd, J=6.7, 4.4 Hz, 4H);

LRMS (ES) m/z 550.4 ($M^+$+1).

Example 49: Synthesis of Compound 4045, N-((7-(5-(difluoromethyl)-1,3,4-oxadiazol-2-yl)imidazo[1,2-a]pyridin-2-yl)methyl)-4-(methylsulfonyl)-N-phenylpiperazine-1-carboxamide

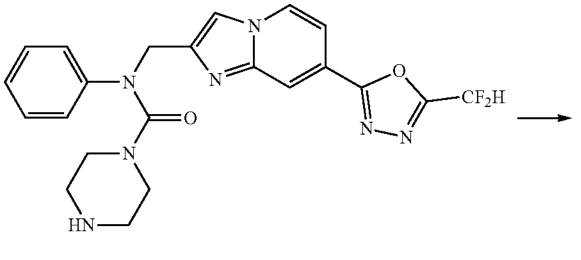

-continued

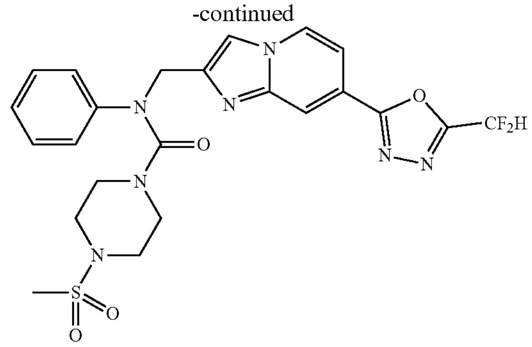

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2 of Example 35, methanesulfonyl chloride (0.017 mL, 0.221 mmol), and triethylamine (0.046 mL, 0.331 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.012 g, 20.5%) as a yellow solid.

$^1H$ NMR (400 MHz, MeOD) δ 8.59 (dd, J=7.1, 1.0 Hz, 1H), 8.22 (dt, J=1.7, 0.8 Hz, 1H), 7.99 (d, J=0.8 Hz, 1H), 7.56 (dd, J=7.1, 1.7 Hz, 1H), 7.45-7.06 (m, 6H), 5.04 (d, J=0.7 Hz, 2H), 3.39-3.35 (m, 4H), 3.07-3.02 (m, 4H), 2.80 (s, 3H);

LRMS (ES) m/z 532.4 ($M^+$+1).

Example 50: Synthesis of Compound 4046, methyl 4-(((7-(5-(difluoromethyl)-1,3,4-oxadiazol-2-yl)imidazo[1,2-a]pyridin-2-yl)methyl)(phenyl)carbamoyl)piperazine-1-carboxylate

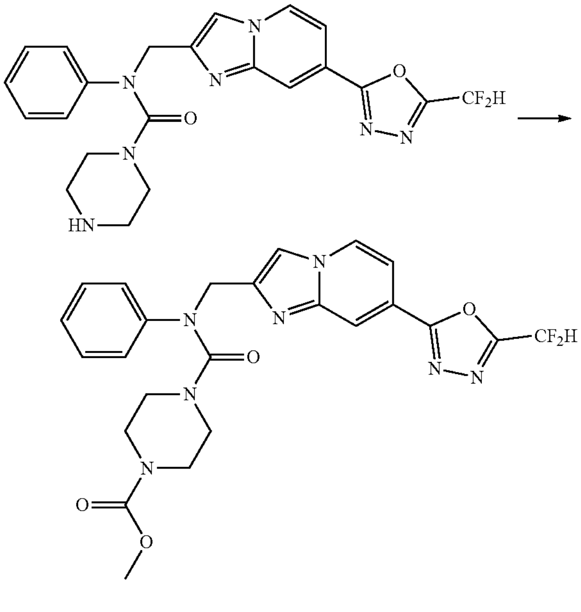

N-((7-(5-(difluoromethyl)-1,3,4-oxadiazol-2-yl)imidazo [1,2-a]pyridin-2-yl)methyl)-N-phenylpiperazine-1-carboxamide (0.100 g, 0.221 mmol) prepared in step 2 of Example 35, methyl carbonochloridate (0.042 g, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.034 g, 30.1%) as a yellow solid.

$^1H$ NMR (700 MHz, MeOD) δ 8.59 (dd, J=7.1, 1.0 Hz, 1H), 8.21 (dt, J=1.7, 0.8 Hz, 1H), 7.99 (d, J=0.8 Hz, 1H), 7.55 (dd, J=7.1, 1.7 Hz, 1H), 7.44-7.11 (m, 6H), 5.04 (d, J=0.8 Hz, 2H), 3.66 (s, 3H), 3.29 (d, J=5.9 Hz, 4H), 3.26 (dd, J=7.0, 3.5 Hz, 4H);

LRMS (ES) m/z 511.8 ($M^+$+1).

Example 51: Synthesis of Compound 4047, N1-((7-(5-(difluoromethyl)-1,3,4-oxadiazol-2-yl)imidazo[1,2-a]pyridin-2-yl)methyl)-N4,N4-dimethyl-N1-phenylpiperazine-1,4-dicarboxamide

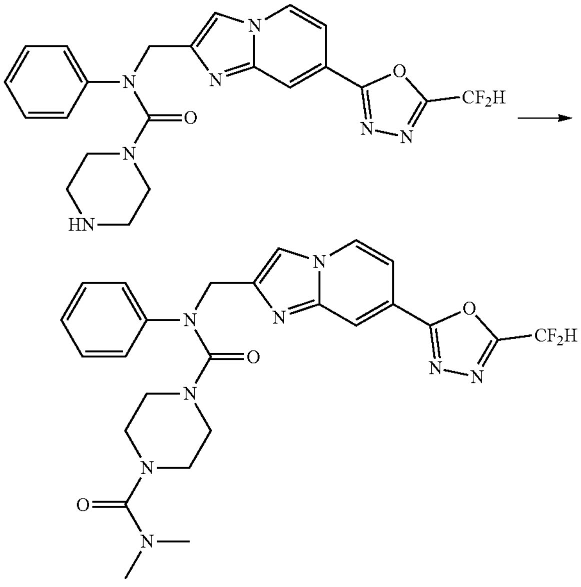

N-((7-(5-(difluoromethyl)-1,3,4-oxadiazol-2-yl)imidazo [1,2-a]pyridin-2-yl)methyl)-N-phenylpiperazine-1-carboxamide (0.100 g, 0.221 mmol) prepared in step 2 of Example 35, dimethylcarbamic chloride (0.047 g, 0.441 mmol), and triethylamine (0.092 mL, 0.662 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.028 g, 24.2%) as a yellow solid.

$^1H$ NMR (700 MHz, MeOD) δ 8.59 (dd, J=7.1, 1.0 Hz, 1H), 8.21 (dt, J=1.7, 0.8 Hz, 1H), 7.99 (d, J=0.8 Hz, 1H), 7.55 (dd, J=7.1, 1.7 Hz, 1H), 7.43-7.07 (m, 6H), 5.04 (d, J=0.8 Hz, 2H), 3.32-3.28 (m, 4H), 3.09-3.05 (m, 4H), 2.81 (s, 6H);

LRMS (ES) m/z 525.0 ($M^+$+1).

Example 52: Synthesis of Compound 4048, N-((7-(5-(difluoromethyl)-1,3,4-oxadiazol-2-yl)imidazo[1,2-a]pyridin-2-yl)methyl)-N-phenyl-4-(pyridin-2-yl)piperazine-1-carboxamide

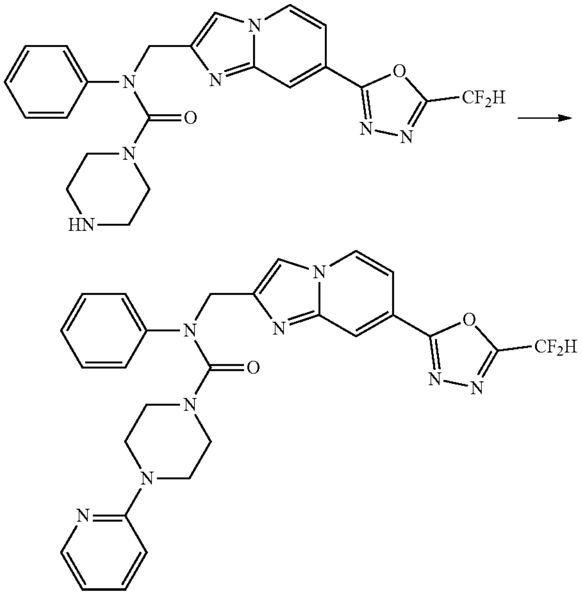

N-((7-(5-(difluoromethyl)-1,3,4-oxadiazol-2-yl)imidazo [1,2-a]pyridin-2-yl)methyl)-N-phenylpiperazine-1-carboxamide (0.065 g, 0.143 mmol) prepared in step 2 of Example 35, 2-chloropyridine (0.033 g, 0.287 mmol), cesium carbonate (0.093 g, 0.287 mmol), and RuPhos palladium G2 (0.006 g, 0.007 mmol) were dissolved in 1,4-dioxane (2 mL) at room temperature, and the resulting solution was stirred at 100° C. for 18 hours. Then, the temperature was lowered to room temperature to terminate the reaction. A saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 30%) and concentrated to obtain the title compound (0.011 g, 14.5%) as a white solid.

$^1H$ NMR (400 MHz, $CDCl_3$) δ 8.32 (s, 1H), 8.24 (d, J=7.1 Hz, 1H), 8.20-8.16 (m, 1H), 7.79 (s, 1H), 7.53 (d, J=7.1 Hz, 1H), 7.39-7.29 (m, 5H), 7.16 (t, J=7.1 Hz, 1H), 6.95 (t, J=51.7 Hz, 1H), 6.74 (s, 2H), 5.10 (d, J=2.3 Hz, 2H), 3.45 (s, 6H), 1.63 (s, 2H);

LRMS (ES) m/z 531.4 ($M^+$+1).

Example 53: Synthesis of Compound 4049, N-((7-(5-(difluoromethyl)-1,3,4-oxadiazol-2-yl)imidazo[1,2-a]pyridin-2-yl)methyl)-N-phenyl-4-(pyrimidin-2-yl)piperazine-1-carboxamide

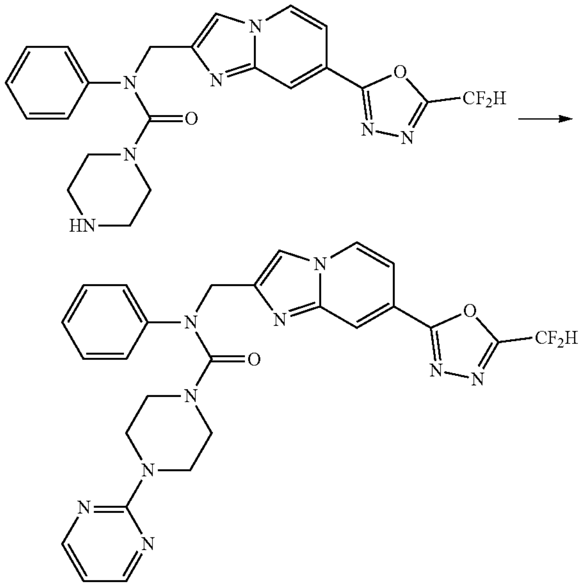

N-((7-(5-(difluoromethyl)-1,3,4-oxadiazol-2-yl)imidazo[1,2-a]pyridin-2-yl)methyl)-N-phenylpiperazine-1-carboxamide (0.100 g, 0.221 mmol) prepared in step 2 of Example 35, 2-chloropyrimidine (0.051 g, 0.441 mmol), and potassium carbonate (0.061 g, 0.441 mmol) were dissolved in acetonitrile (2 mL)/N,N-dimethylformamide (2 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.015 g, 12.8%) as a yellow solid.

$^1H$ NMR (700 MHz, MeOD) δ 8.56 (d, J=7.0 Hz, 1H), 8.31-8.23 (m, 2H), 7.97 (d, J=9.4 Hz, 1H), 7.76-7.73 (m, 1H), 7.59 (d, J=7.1 Hz, 1H), 7.40-7.08 (m, 6H), 6.58 (t, J=4.8 Hz, 1H), 5.06 (s, 2H), 3.66-3.62 (m, 4H), 3.36-3.34 (m, 4H);

LRMS (ES) m/z 532.0 ($M^+$+1).

Example 54: Synthesis of Compound 4083, N-((7-(5-(difluoromethyl)-1,3,4-oxadiazol-2-yl)imidazo[1,2-a]pyridin-2-yl)methyl)-N-(3-fluorophenyl)-4-methylpiperazine-1-carboxamide

[Step 1] Synthesis of tert-butyl 4-(((7-(5-(difluoromethyl)-1,3,4-oxadiazol-2-yl)imidazo[1,2-a]pyridin-2-yl)methyl)(3-fluorophenyl)carbamoyl)piperazine-1-carboxylate

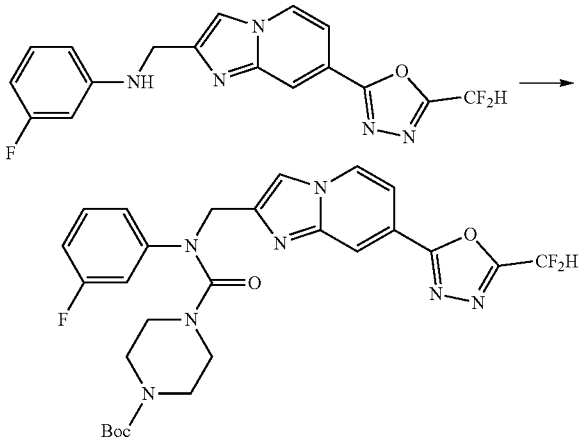

N-((7-(5-(difluoromethyl)-1,3,4-oxadiazol-2-yl)imidazo[1,2-a]pyridin-2-yl)methyl)-3-fluoroaniline (0.200 g, 0.557 mmol) prepared in Example 16, tert-butyl piperazine-1-carboxylate (0.135 g, 0.724 mmol), triphosgene (0.165 g, 0.557 mmol), and N,N-diisopropylethylamine (0.485 mL, 2.783 mmol) were dissolved in dichloromethane (15 mL), and the resulting solution was stirred at 0° C. for 1 hour and further stirred at room temperature for 18 hours. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 40 g cartridge; ethyl acetate/hexane=0% to 60%) and concentrated to obtain the title compound (0.240 g, 75.4%) as a white solid.

[Step 2] Synthesis of N-((7-(5-(difluoromethyl)-1,3,4-oxadiazol-2-yl)imidazo[1,2-a]pyridin-2-yl)methyl)-N-(3-fluorophenyl)piperazine-1-carboxamide

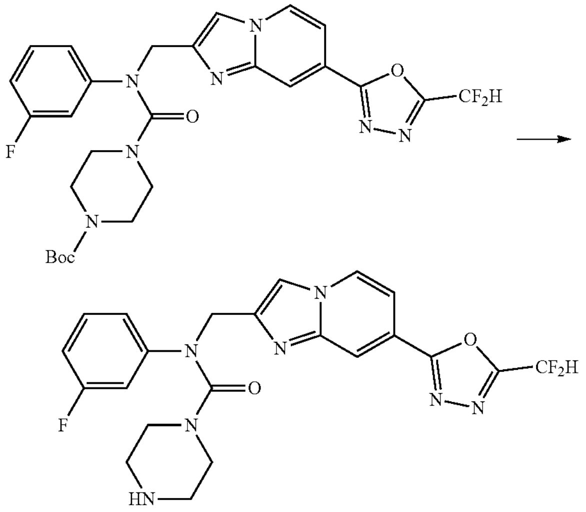

Tert-butyl 4-(((7-(5-(difluoromethyl)-1,3,4-oxadiazol-2-yl)imidazo[1,2-a]pyridin-2-yl)methyl)(3-fluorophenyl)carbamoyl)piperazine-1-carboxylate (2.000 g, 3.499 mmol) prepared in step 1, and trifluoroacetic acid (5.359 mL, 69.984 mmol) were dissolved in dichloromethane (30 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (1.650 g, 100.0%) was obtained as a brown gel without further purification.

[Step 3] Synthesis of Compound 4083

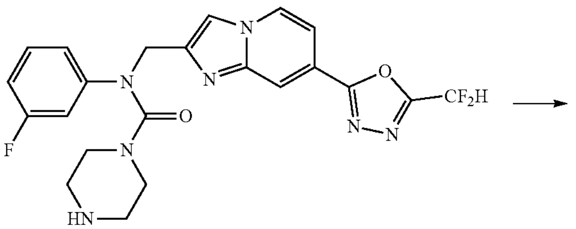

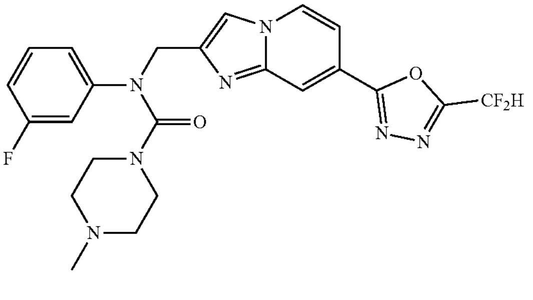

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2, formaldehyde (0.010 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.018 g, 21.8%) as a yellow solid.

$^1$H NMR (700 MHz, MeOD) δ 8.59 (dd, J=7.2, 1.0 Hz, 1H), 8.22 (dt, J=1.8, 0.9 Hz, 1H), 7.99 (d, J=0.7 Hz, 1H), 7.56 (dd, J=7.1, 1.7 Hz, 1H), 7.37 (td, J=8.4, 6.6 Hz, 1H), 7.26 (t, J=51.6 Hz, 1H), 7.09-7.03 (m, 2H), 6.90 (tdd, J=8.3, 2.5, 0.9 Hz, 1H), 5.04 (d, J=0.8 Hz, 2H), 3.32 (s, 2H), 3.28-3.25 (m, 2H), 2.31 (t, J=5.0 Hz, 4H), 2.25 (s, 3H);

LRMS (ES) m/z 486.1 ($M^+$+1).

Example 55: Synthesis of Compound 4084, N-((7-(5-(difluoromethyl)-1,3,4-oxadiazol-2-yl)imidazo[1,2-a]pyridin-2-yl)methyl)-4-ethyl-N-(3-fluorophenyl)piperazine-1-carboxamide

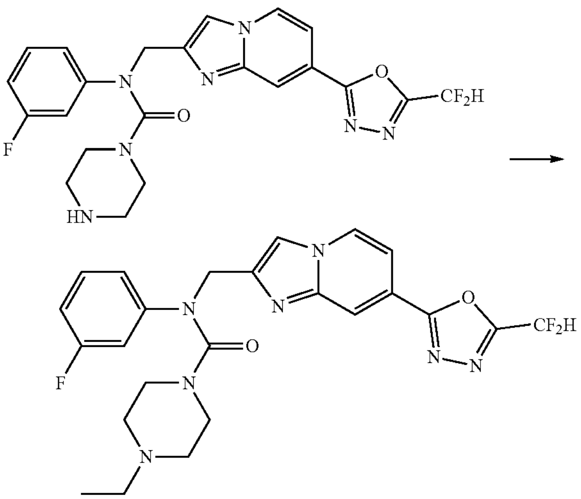

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, acetaldehyde (0.015 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.022 g, 26.0%) as a yellow solid.

$^1$H NMR (700 MHz, MeOD) δ 8.59 (dd, J=7.1, 1.0 Hz, 1H), 8.21 (dt, J=1.7, 0.8 Hz, 1H), 7.99 (d, J=0.8 Hz, 1H), 7.56 (dd, J=7.1, 1.7 Hz, 1H), 7.37 (td, J=8.3, 6.5 Hz, 1H), 7.27 (t, J=51.6 Hz, 1H), 7.09-7.04 (m, 2H), 6.90 (tdd, J=8.4, 2.4, 0.9 Hz, 1H), 5.04 (d, J=0.8 Hz, 2H), 3.33 (dd, J=3.6, 2.0 Hz, 4H), 2.40 (q, J=7.2 Hz, 2H), 2.35 (t, J=5.1 Hz, 4H), 1.07 (t, J=7.2 Hz, 3H);

LRMS (ES) m/z 500.1 ($M^+$+1).

Example 56: Synthesis of Compound 4085, N-((7-(5-(difluoromethyl)-1,3,4-oxadiazol-2-yl)imidazo[1,2-a]pyridin-2-yl)methyl)-N-(3-fluorophenyl)-4-isopropylpiperazine-1-carboxamide

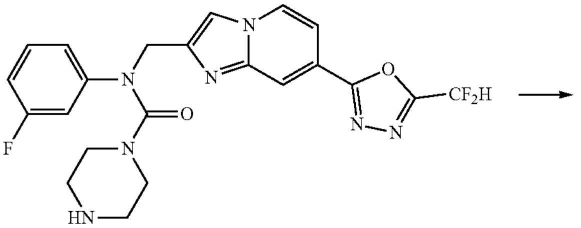

-continued

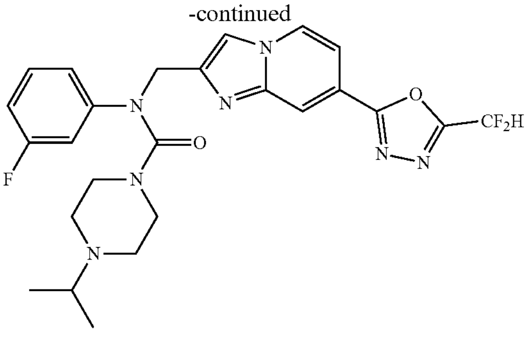

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, propan-2-one (0.020 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 27.5%) as a yellow solid.

$^1$H NMR (700 MHz, MeOD) δ 8.59 (dd, J=7.1, 1.0 Hz, 1H), 8.22 (dt, J=1.7, 0.8 Hz, 1H), 7.99 (d, J=0.8 Hz, 1H), 7.56 (dd, J=7.2, 1.7 Hz, 1H), 7.37 (td, J=8.3, 6.6 Hz, 1H), 7.27 (t, J=51.6 Hz, 1H), 7.08-7.04 (m, 2H), 6.90 (tdd, J=8.4, 2.4, 0.9 Hz, 1H), 5.04 (d, J=0.8 Hz, 2H), 3.33-3.31 (m, 4H), 2.65 (p, J=6.5 Hz, 1H), 2.42 (t, J=5.1 Hz, 4H), 1.03 (d, J=6.5 Hz, 6H);

LRMS (ES) m/z 514.4 ($M^+$+1).

Example 57: Synthesis of Compound 4086, N-((7-(5-(difluoromethyl)-1,3,4-oxadiazol-2-yl)imidazo[1,2-a]pyridin-2-yl)methyl)-N-(3-fluorophenyl)-4-(1-hydroxypropan-2-yl)piperazine-1-carboxamide

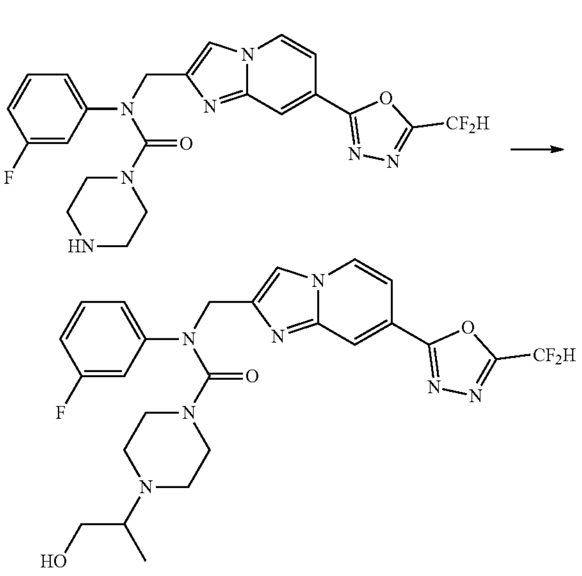

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, 1-hydroxypropan-2-one (0.025 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.022 g, 24.5%) as a yellow solid.

$^1$H NMR (700 MHz, MeOD) δ 8.60 (dd, J=7.1, 1.0 Hz, 1H), 8.23 (dt, J=1.8, 0.9 Hz, 1H), 8.00 (d, J=0.8 Hz, 1H), 7.56 (dd, J=7.1, 1.7 Hz, 1H), 7.36 (td, J=8.3, 6.6 Hz, 1H), 7.26 (t, J=51.7 Hz, 1H), 7.08-7.03 (m, 2H), 6.92-6.86 (m, 1H), 5.04 (d, J=0.8 Hz, 2H), 3.53 (dd, J=11.1, 6.8 Hz, 1H), 3.41 (dd, J=11.2, 5.6 Hz, 1H), 3.33-3.30 (m, 4H), 2.65 (td, J=6.8, 5.7 Hz, 1H), 2.50 (ddd, J=10.6, 6.3, 3.8 Hz, 2H), 2.43 (ddd, J=10.9, 6.3, 4.2 Hz, 2H), 0.96 (d, J=6.7 Hz, 3H);

LRMS (ES) m/z 530.1 ($M^+$+1).

Example 58: Synthesis of Compound 4087, 4-cyclobutyl-N-((7-(5-(difluoromethyl)-1,3,4-oxadiazol-2-yl)imidazo[1,2-a]pyridin-2-yl)methyl)-N-(3-fluorophenyl)piperazine-1-carboxamide

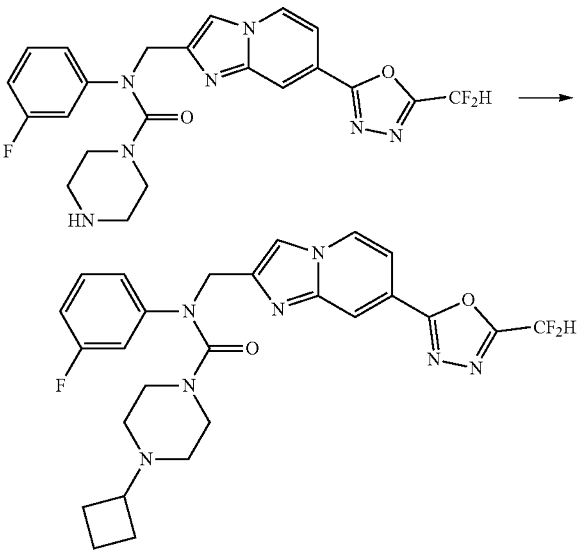

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, cyclobutanone (0.024 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.025 g, 28.0%) as a yellow solid.

$^1$H NMR (700 MHz, MeOD) δ 8.55 (dd, J=7.1, 1.0 Hz, 1H), 8.24-8.21 (m, 1H), 7.94 (s, 1H), 7.56 (dd, J=7.1, 1.7 Hz, 1H), 7.34 (td, J=8.4, 6.5 Hz, 1H), 7.20 (t, J=51.7 Hz, 1H), 7.05-6.99 (m, 2H), 6.90-6.85 (m, 1H), 5.03 (s, 2H), 3.31 (d, J=7.4 Hz, 4H), 2.74 (s, 1H), 2.24 (s, 4H), 2.06-2.00 (m, 2H), 1.90-1.79 (m, 2H), 1.71 (dtd, J=15.6, 10.8, 10.3, 8.2 Hz, 2H);

LRMS (ES) m/z 526.1 ($M^+$+1).

Example 59: Synthesis of Compound 4088, N-((7-(5-(difluoromethyl)-1,3,4-oxadiazol-2-yl)imidazo[1,2-a]pyridin-2-yl)methyl)-N-(3-fluorophenyl)-4-(oxetan-3-yl)piperazine-1-carboxamide

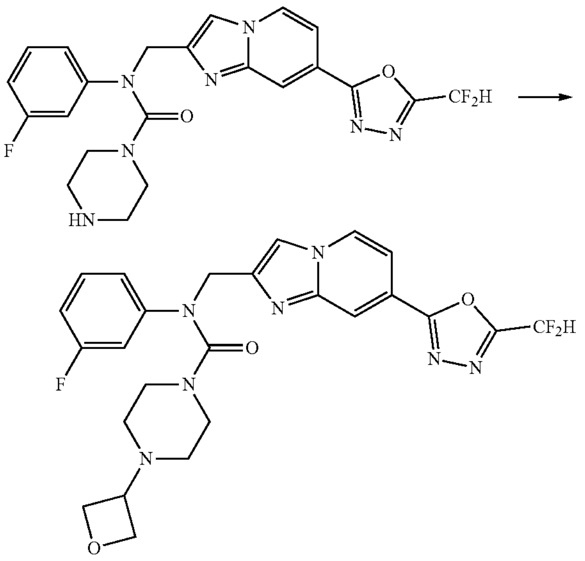

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, oxetan-3-one (0.024 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.019 g, 21.2%) as a yellow solid.

$^1$H NMR (700 MHz, MeOD) δ 8.54 (dd, J=7.1, 1.0 Hz, 1H), 8.23 (dt, J=1.8, 0.8 Hz, 1H), 7.94 (d, J=0.8 Hz, 1H), 7.56 (dd, J=7.1, 1.7 Hz, 1H), 7.34 (td, J=8.4, 6.4 Hz, 1H), 7.20 (t, J=51.6 Hz, 1H), 7.05-6.99 (m, H), 6.88 (tdd, J=8.3, 2.5, 0.9 Hz, 1H), 5.05-4.98 (m, 2H), 4.66 (t, J=6.7 Hz, 2H), 4.55 (t, J=6.2 Hz, 2H), 3.47 (s, 1H), 3.36-3.34 (m, 4H), 2.24 (s, 4H);

LRMS (ES) m/z 529.2 ($M^+$+1).

Example 60: Synthesis of Compound 4089, 4-cyclohexyl-N-((7-(5-(difluoromethyl)-1,3,4-oxadiazol-2-yl)imidazo[1,2-a]pyridin-2-yl)methyl)-N-(3-fluorophenyl)piperazine-1-carboxamide

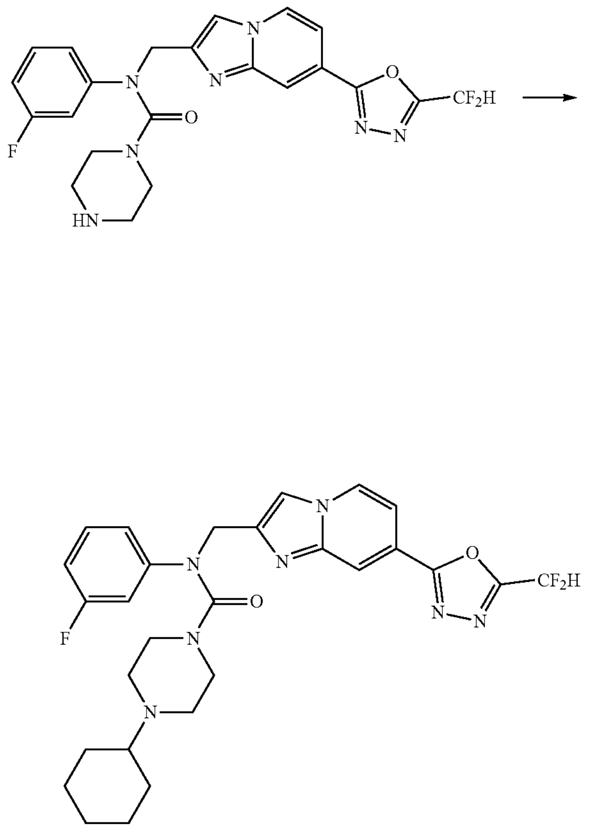

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, cyclohexanone (0.033 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.018 g, 19.2%) as a yellow solid.

$^1$H NMR (700 MHz, MeOD) δ 8.54 (dd, J=7.1, 1.0 Hz, 1H), 8.23 (t, J=1.1 Hz, 1H), 7.94 (s, 1H), 7.56 (dd, J=7.1, 1.7 Hz, 1H), 7.34 (td, J=8.5, 6.7 Hz, 1H), 7.20 (t, J=51.6 Hz, 1H), 7.07-6.95 (m, 2H), 6.87 (ddd, J=9.5, 8.0, 2.5 Hz, 1H), 5.03 (s, 2H), 3.32 (s, 4H), 2.50 (s, 4H), 2.28 (s, 1H), 1.84 (d, J=11.2 Hz, 2H), 1.82-1.76 (m, 2H), 1.64 (d, J=12.6 Hz, 1H), 1.24 (ddd, J=16.0, 11.2, 3.2 Hz, 2H), 1.21-1.13 (m, 2H), 1.11 (dt, J=12.9, 3.6 Hz, 1H);

LRMS (ES) m/z 554.4 ($M^+$+1).

Example 61: Synthesis of Compound 4090, N-((7-(5-(difluoromethyl)-1,3,4-oxadiazol-2-yl)imidazo[1,2-a]pyridin-2-yl)methyl)-N-(3-fluorophenyl)-4-(tetrahydro-2H-pyran-4-yl)piperazine-1-carboxamide

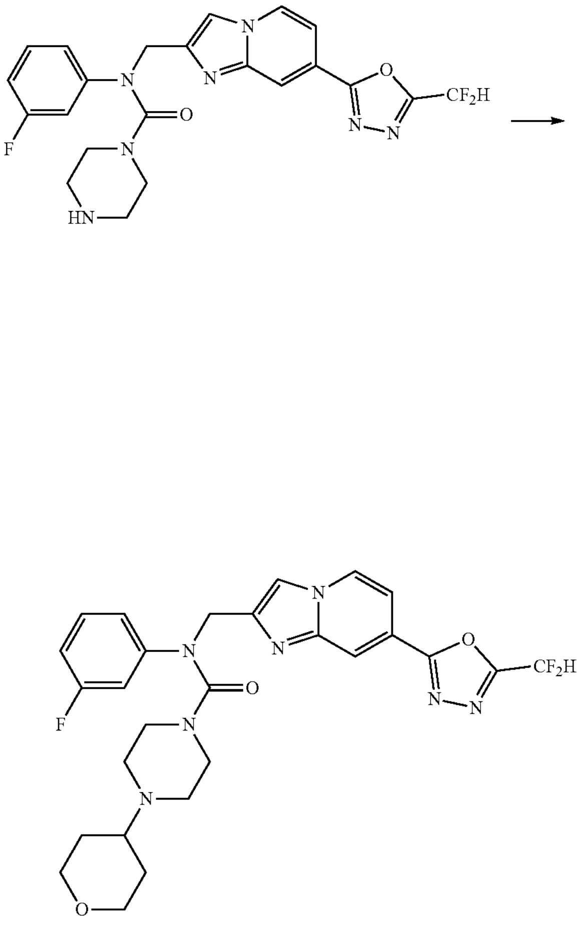

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, tetrahydro-4H-pyran-4-one (0.034 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.028 g, 29.7%) as a yellow solid.

$^1$H NMR (700 MHz, MeOD) δ 8.53 (dt, J=6.8, 3.2 Hz, 1H), 8.23 (s, 1H), 7.93 (d, J=2.5 Hz, 1H), 7.56 (d, J=7.0 Hz, 1H), 7.34 (q, J=7.8 Hz, 1H), 7.18 (tt, J=51:7, 2.9 Hz, 1H); 7.02 (t, J=10.6 Hz, 2H), 6.87 (td, J=8.3, 2.6 Hz, 1H), 5.03 (s, 2H), 4.00-3.96 (m, 2H), 3.41-3.32 (m, 7H), 2.48 (s, 4H), 1.77 (d, J=12.5 Hz, 2H), 1.50 (dd, J=12.2, 4.3 Hz, 2H);

LRMS (ES) m/z 556.1 ($M^+$+1).

Example 62: Synthesis of Compound 4091, 4-(4,4-difluorocyclohexyl)-N-((7-(5-(difluoromethyl)-1,3,4-oxadiazol-2-yl)imidazo[1,2-a]pyridin-2-yl)methyl)-N-(3-fluorophenyl)piperazine-1-carboxamide

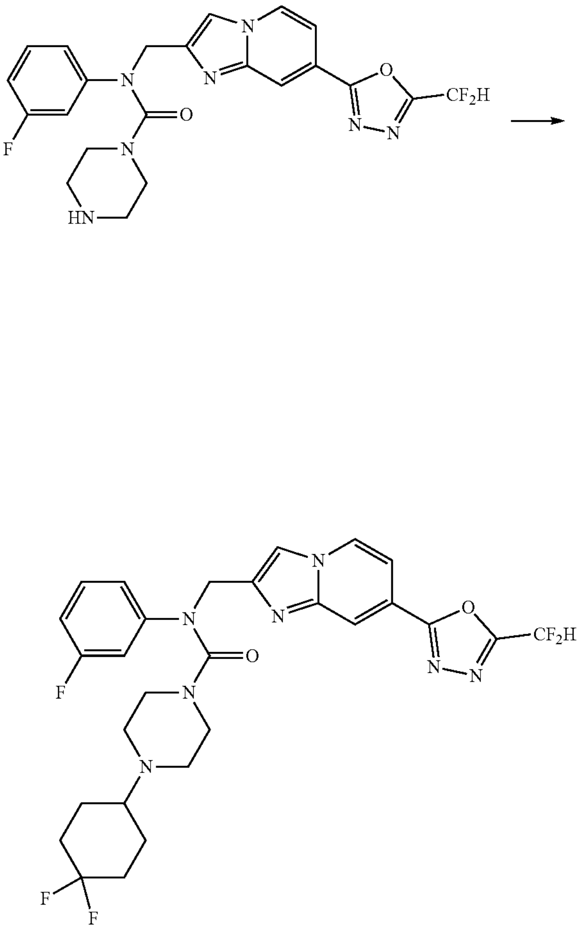

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, 4,4-difluorocyclohexan-1-one (0.046 g, 0.339 mmol), acetic acid (0.010 mL, 0.170 mmol), and sodium triacetoxyborohydride (0.108 g, 0.509 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.030 g, 30.0%) as a yellow solid.

$^1$H NMR (400 MHz, $CDCl_3$) δ 8.28 (s, 1H), 8.21 (d, J=7.0 Hz, 1H), 7.75 (d, J=0.8 Hz, 1H), 7.53 (d, J=7.2 Hz, 1H), 7.32 (d, J=7.8 Hz, 1H), 7.09-6.78 (m, 4H), 5.07 (s, 2H), 4.01-3.87 (m, 1H), 3.30 (s, 2H), 2.40 (s, 3H), 2.23-2.05 (m, 3H), 1.98-1.83 (m, 4H), 1.76 (dt, J=12.3, 6.3 Hz, 4H);

LRMS (ES) m/z 590.3 ($M^+$+1).

Example 63: Synthesis of Compound 4092, 4-acetyl-N-((7-(5-(difluoromethyl)-1,3,4-oxadiazol-2-yl)imidazo[1,2-a]pyridin-2-yl)methyl)-N-(3-fluorophenyl)piperazine-1-carboxamide

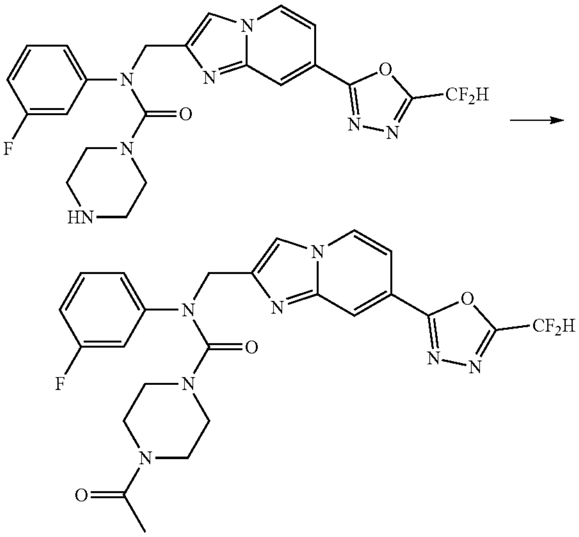

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, acetyl chloride (0.024 mL, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.037 g, 42.5%) as a yellow solid.

$^1H$ NMR (400 MHz, $CDCl_3$) δ 8.32 (s, 1H), 8.23 (dd, J=7.1, 1.0 Hz, 1H), 7.77 (s, 1H), 7.56 (dd, J=7.1, 1.7 Hz, 1H), 7.32 (td, J=8.2, 6.5 Hz, 1H), 7.13-6.79 (m, 4H), 5.07 (s, 2H), 3.47 (dd, J=6.6, 4.0 Hz, 2H), 3.33 (s, 4H), 3.26-3.22 (m, 2H), 2.05 (s, 3H);

LRMS (ES) m/z 514.3 ($M^+$+1).

Example 64: Synthesis of Compound 4093, N-((7-(5-(difluoromethyl)-1,3,4-oxadiazol-2-yl)imidazo[1,2-a]pyridin-2-yl)methyl)-N-(3-fluorophenyl)-4-propionylpiperazine-1-carboxamide

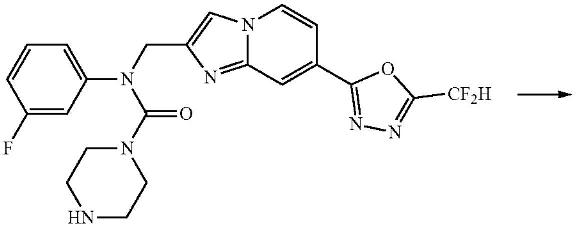

-continued

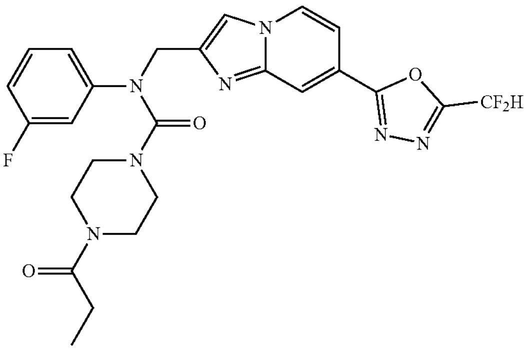

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, propionyl chloride (0.031 g, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.031 g, 34.6%) as a yellow solid.

$^1H$ NMR (700 MHz, MeOD) δ 8.59 (dd, J=7.1, 1.0 Hz, 1H), 8.21 (dt, J=1.7, 0.8 Hz, 1H), 8.02-7.99 (m, 1H), 7.55 (dd, J=7.1, 1.7 Hz, 1H), 7.37 (td, J=8.2, 6.4 Hz, 1H), 7.27 (t, J=51.7 Hz, 1H), 7.13-7.06 (m, 2H), 6.91 (tdd, J=8.4, 2.5, 0.9 Hz, 1H), 5.06 (d, J=0.8 Hz, 2H), 3.49-3.42 (m, 4H), 3.35-3.34 (m, 2H), 3.30-3.27 (m, 2H), 2.37 (q, J=7.5 Hz, 2H), 1.08 (t, J=7.5 Hz, 3H);

LRMS (ES) m/z 528.1 ($M^+$+1).

Example 65: Synthesis of Compound 4094, N-((7-(5-(difluoromethyl)-1,3,4-oxadiazol-2-yl)imidazo[1,2-a]pyridin-2-yl)methyl)-N-(3-fluorophenyl)-4-(2-hydroxyacetyl)piperazine-1-carboxamide

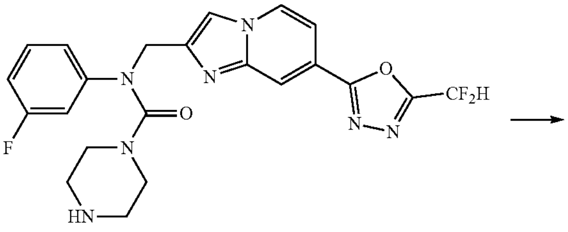

-continued

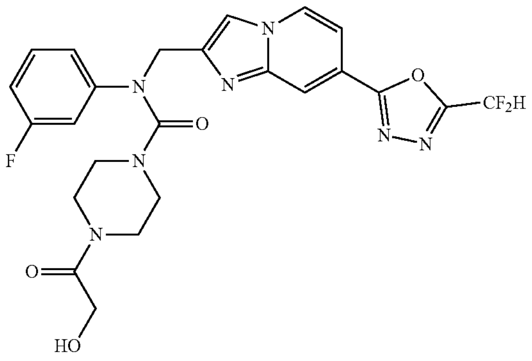

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, 2-hydroxyacetyl chloride (0.032 g, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.014 g, 15.6%) as a yellow solid.

$^1H$ NMR (700 MHz, MeOD) δ 8.60 (dd, J=7.1, 1.0 Hz, 1H), 8.23 (dt, J=1.7, 0.8 Hz, 1H), 8.01 (d, J=0.8 Hz, 1H), 7.57 (dd, J=7.1, 1.7 Hz, 1H), 7.38 (td, J=8.2, 6.5 Hz, 1H), 7.26 (t, J=51.7 Hz, 1H), 7.13-7.06 (m, 2H), 6.92 (tdd, J=8.3, 2.5, 0.9 Hz, 1H), 5.06 (d, J=0.8 Hz, 2H), 4.19 (s, 2H), 3.74 (p, J=6.6 Hz, 1H), 3.48 (t, J=5.3 Hz, 2H), 3.26-3.19 (m, 1H), 1.39 (d, J=6.7 Hz, 4H);

LRMS (ES) m/z 530.0 ($M^+$+1).

Example 66: Synthesis of Compound 4095, 4-(cyclobutanecarbonyl)-N-((7-(5-(difluoromethyl)-1,3,4-oxadiazol-2-yl)imidazo[1,2-a]pyridine-2-yl)methyl)-N-(3-fluorophenyl)piperazine-1-carboxamide

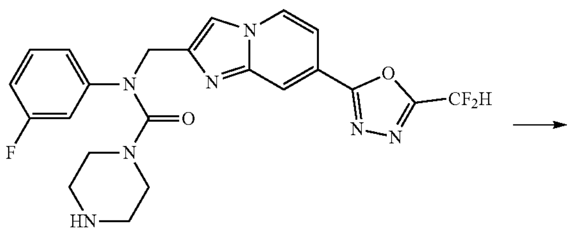

-continued

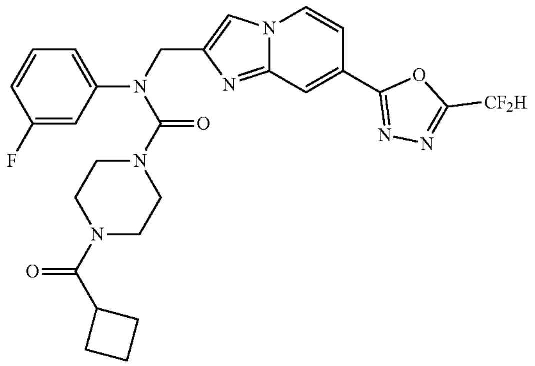

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, cyclobutanecarbonyl chloride (0.040 g, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.027 g, 28.7%) as a yellow solid.

$^1H$ NMR (700 MHz, MeOD) δ 8.60 (dd, J=7.1, 1.0 Hz, 1H), 8.24-8.21 (m, 1H), 8.01 (s, 1H), 7.57 (dd, J=7.1, 1.7 Hz, 1H), 7.37 (td, J=8.2, 6.5 Hz, 1H), 7.26 (t, J=51.7 Hz, 1H), 7.13-7.06 (m, 2H), 6.92 (tdd, J=8.4, 2.5, 0.9 Hz, 1H), 5.06 (s, 2H), 3.46-3.43 (m, 2H), 3.37 (td, J=8.7, 1.1 Hz, 1H), 3.32 (s, 1H), 3.30-3.26 (m, 4H), 2.28-2.19 (m, 3H), 2.17-2.10 (m, 2H), 2.04-1.95 (m, 1H), 1.84-1.78 (m, 1H);

LRMS (ES) m/z 553.9 ($M^+$+1).

Example 67: Synthesis of Compound 4096, N-((7-(5-(difluoromethyl)-1,3,4-oxadiazol-2-yl)imidazo[1,2-a]pyridin-2-yl)methyl)-N-(3-fluorophenyl)-4-(2,2,2-trifluoroacetyl)piperazine-1-carboxamide

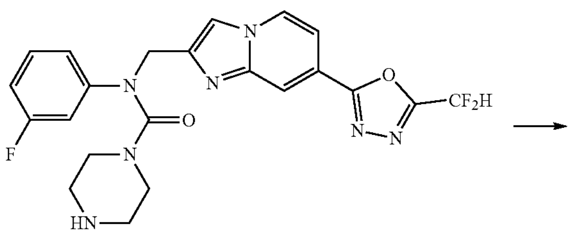

-continued

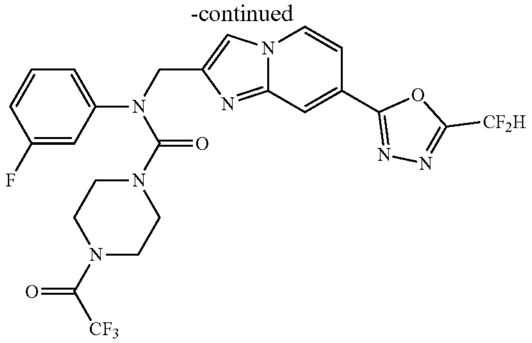

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.050 g, 0.106 mmol) prepared in step 2 of Example 54, 1,1,1,5,5,5-hexafluoropentane-2,4-dione (0.044 g, 0.212 mmol), and triethylamine (0.044 mL, 0.318 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.038 g, 63.1%) as a yellow solid.

$^1H$ NMR (400 MHz, MeOD) δ 8.59 (dd, J=7.2, 1.0 Hz, 1H), 8.23 (dt, J=1.6, 0.8 Hz, 1H), 8.01 (d, J=0.7 Hz, 1H), 7.57 (dd, J=7.2, 1.7 Hz, 1H), 7.42-6.86 (m, 5H), 5.07 (d, J=0.8 Hz, 2H), 3.56 (q, J=5.0 Hz, 4H), 3.38 (td, J=7.2, 6.2, 4.0 Hz, 4H);

LRMS (ES) m/z 568.4 ($M^+$+1).

Example 68: Synthesis of Compound 4097, N-((7-(5-(difluoromethyl)-1,3,4-oxadiazol-2-yl)imidazo[1,2-a]pyridin-2-yl)methyl)-N-(3-fluorophenyl)-4-(methylsulfonyl)piperazine-1-carboxamide

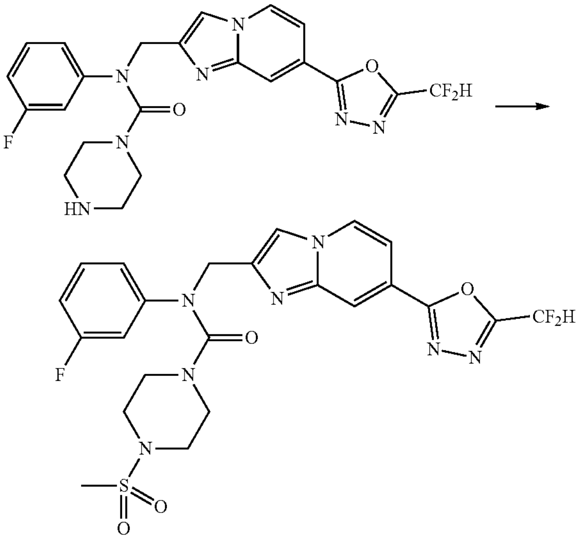

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.050 g, 0.106 mmol) prepared in step 2 of Example 54, methanesulfonyl chloride (0.016 mL, 0.212 mmol), and triethylamine (0.044 mL, 0.318 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.015 g, 25.7%) as a yellow solid.

$^1H$ NMR (400 MHz, MeOD) δ 8.60 (dd, J=7.2, 1.0 Hz, 1H), 8.23 (dt, J=1.7, 0.8 Hz, 1H), 8.01 (d, J=0.8 Hz, 1H), 7.57 (dd, J=7.1, 1.7 Hz, 1H), 7.46-6.87 (m, 5H), 5.06 (d, J=0.7 Hz, 2H), 3.43-3.36 (m, 4H), 3.13-3.06 (m, 4H), 2.81 (s, 3H);

LRMS (ES) m/z 550.4 ($M^+$+1).

Example 69: Synthesis of Compound 4098, methyl 4-(((7-(5-(difluoromethyl)-1,3,4-oxadiazol-2-yl)imidazo[1,2-a]pyridin-2-yl)methyl)(3-fluorophenyl)carbamoyl)piperazine-1-carboxylate

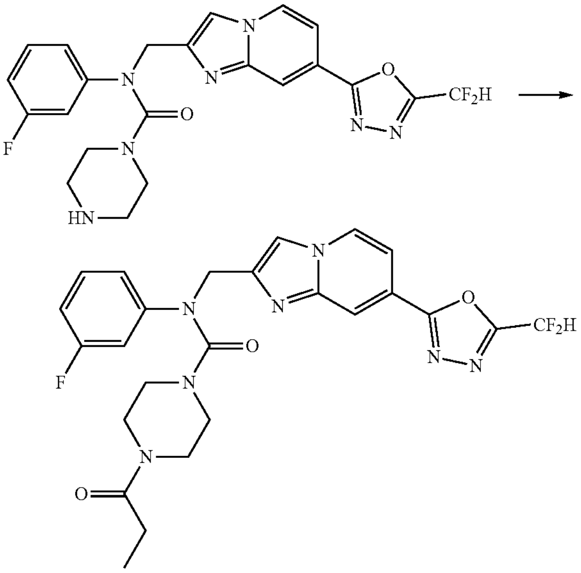

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, methyl carbonochloridate (0.032 g, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.032 g, 35.6%) as a yellow solid.

$^1H$ NMR (700 MHz, MeOD) & 8.55 (dd, J=7.1, 1.0 Hz, 1H), 8.24 (dt, J=1.8, 0.9 Hz, 1H), 7.96 (s, 1H), 7.57 (dd,

J=7.1, 1.7 Hz, 1H), 7.35 (td, J=8.4, 6.5 Hz, 1H), 7.20 (t, J=51.6 Hz, 1H), 7.07-7.02 (m, 2H), 6.92-6.86 (m, 1H), 5.05-5.02 (m, 2H), 3.67 (s, 3H), 3.36-3.34 (m, 4H), 3.28 (dd, J=6.6, 3.7 Hz, 4H);

LRMS (ES) m/z 531.3 ($M^{+}$+1).

Example 70: Synthesis of Compound 4099, N1-((7-(5-(difluoromethyl)-1,3,4-oxadiazol-2-yl)imidazo[1,2-a]pyridin-2-yl)methyl)-N1-(3-fluorophenyl)-N4,N4-dimethylpiperazine-1,4-dicarboxamide

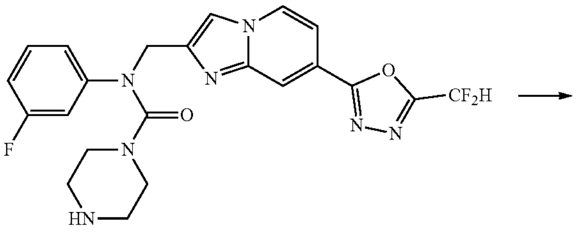

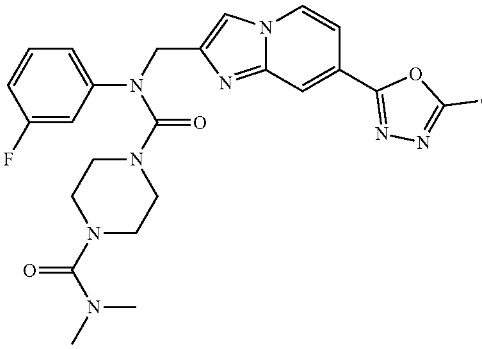

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, dimethylcarbamic chloride (0.036 g, 0.339 mmol), and triethylamine (0.071 mL, 0.509 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.018 g, 19.6%) as a yellow solid.

$^{1}$H NMR (700 MHz, MeOD) δ 8.58-8.55 (m, 1H), 8.26-8.24 (m, 1H), 7.97 (s, 1H), 7.59 (dd, J=7.1, 1.7 Hz, 1H), 7.36 (td, J=8.4, 6.4 Hz, 1H), 7.20 (t, J=51.7 Hz, 1H), 7.06-7.02 (m, 2H), 6.89 (tdd, J=8.3, 2.4, 1.0 Hz, 1H), 5.05 (s, 2H), 3.32-3.30 (m, 4H), 3.12-3.10 (m, 4H), 2.82 (s, 6H);

LRMS (ES) m/z 542.9 ($M^{+}$+1).

Example 71: Synthesis of Compound 4100, N-((7-(5-(difluoromethyl)-1,3,4-oxadiazol-2-yl)imidazo[1,2-a]pyridin-2-yl)methyl)-N-(3-fluorophenyl)-4-(pyridin-2-yl)piperazine-1-carboxamide

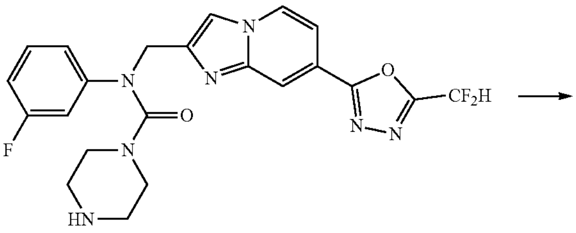

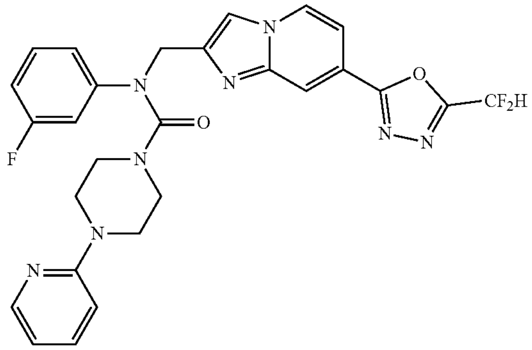

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.066 g, 0.140 mmol) prepared in step 2 of Example 54, 2-chloropyridine (0.032 g, 0.280 mmol), cesium carbonate (0.091 g, 0.280 mmol), and RuPhos palladium G2 (0.005 g, 0.007 mmol) were dissolved in 1,4-dioxane (2 mL) at room temperature, and the resulting solution was stirred at 100° C. for 18 hours. Then, the temperature was lowered to room temperature to terminate the reaction. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 30%) and concentrated to obtain the title compound (0.014 g, 18.2%) as a white solid.

$^{1}$H NMR (400 MHz, $CDCl_3$) δ 8.32 (s, 1H), 8.25 (d, J=7.0 Hz, 1H), 8.21-8.17 (m, 1H), 7.78 (s, 1H), 7.59-7.52 (m, 1H), 7.42 (ddt, J=10.9, 7.4, 1.6 Hz, 1H), 7.36-7.29 (m, 1H), 7.14-6.79 (m, 5H), 6.61 (d, J=8.3 Hz, 1H), 5.10 (s, 2H), 3.55 (d, J=57.6 Hz, 6H), 1.80-1.56 (m, 2H);

LRMS (ES) m/z 549.4 ($M^{+}$+1).

Example 72: Synthesis of Compound 4101, N-((7-(5-(difluoromethyl)-1,3,4-oxadiazol-2-yl)imidazo[1,2-a]pyridin-2-yl)methyl)-N-(3-fluorophenyl)-4-(pyrimidin-2-yl)piperazine-1-carboxamide

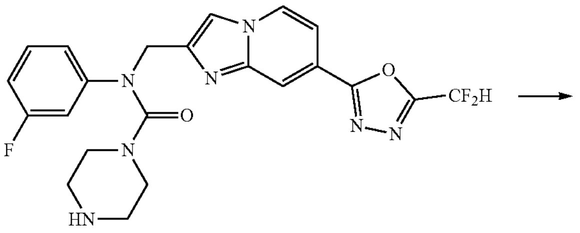

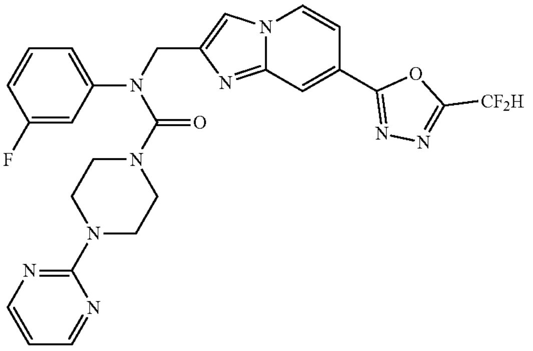

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.080 g, 0.170 mmol) prepared in step 2 of Example 54, 2-chloropyrimidine (0.039 g, 0.339 mmol), and potassium carbonate (0.047 g, 0.339 mmol) were dissolved in acetonitrile (2 mL)/N,N-dimethylformamide (2 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.015 g, 16.1%) as a yellow solid.

$^1$H NMR (700 MHz, MeOD) δ 8.50 (dd, J=7.1, 1.8 Hz, 1H), 8.28 (d, J=4.8 Hz, 1H), 8.24 (d, J=1.6 Hz, 1H), 7.93 (s, 1H), 7.56 (dd, J=7.1, 1.7 Hz, 1H), 7.34 (td, J=8.1, 6.4 Hz, 1H), 7.15 (td, J=51.7, 2.0 Hz, 1H), 7.07-7.02 (m, 2H), 6.87 (td, J=8.3, 2.4 Hz, 1H), 6.57 (t, J=4.7 Hz, 1H), 5.06 (s, 2H), 3.70-3.66 (m, 4H), 3.40-3.35 (m, 4H);

LRMS (ES) m/z 550.2 ($M^+$+1).

Example 73: Synthesis of Compound 4102, N-((7-(5-(difluoromethyl)-1,3,4-oxadiazol-2-yl)imidazo[1,2-a]pyridin-2-yl)methyl)-4-(oxetan-3-carbonyl)-N-phenylpiperazine-1-carboxamide

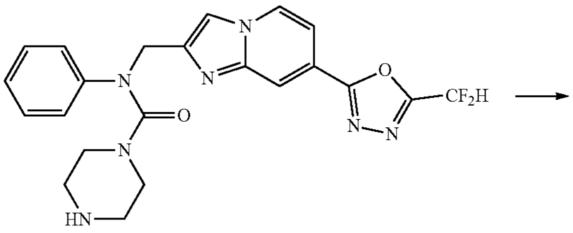

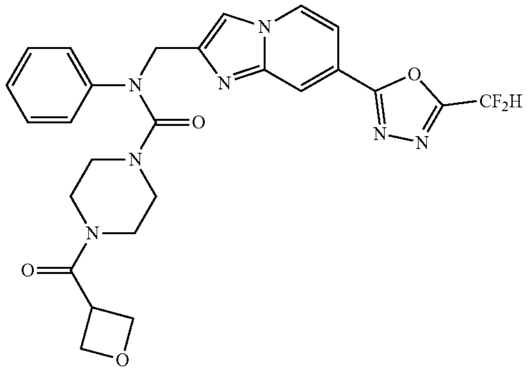

N-((7-(5-(difluoromethyl)-1,3,4-oxadiazol-2-yl)imidazo[1,2-a]pyridin-2-yl)methyl)-N-phenylpiperazine-1-carboxamide (0.050 g, 0.110 mmol) prepared in step 2 of Example 35, oxetane-3-carboxylic acid (0.023 g, 0.221 mmol), 1-[bis(dimethylamino)methylene]-1H-1, 2, 3-triazolo[4,5-b]pyridinium 3-oxide hexafluorophosphate (HATU, 0.050 g, 0.132 mmol), and triethylamine (0.043 mL, 0.331 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.015 g, 25.3%) as a white solid.

$^1$H NMR (400 MHz, $CDCl_3$) δ 8.34-8.29 (m, 1H), 8.24 (dt, J=7.1, 1.0 Hz, 1H), 7.77 (dd, J=5.3, 0.7 Hz, 1H), 7.55 (dd, J=7.2, 1.7 Hz, 1H), 7.36 (tt, J=7.4, 1.9 Hz, 2H), 7.28-7.25 (m, 2H), 7.21-7.13 (m, 1H), 6.95 (t, J=51.7 Hz, 1H), 5.07 (d, J=3.3 Hz, 2H), 4.85 (dd, J=7.1, 5.9 Hz, 1H), 4.76 (dd, J=8.7, 5.9 Hz, 1H), 3.44 (dt, J=10.2, 5.4 Hz, 2H), 3.31 (s, 2H), 3.24 (ddt, J=10.3, 7.4, 3.5 Hz, 4H), 3.01 (t, J=5.3 Hz, 1H), 2.04 (s, 2H);

LRMS (ES) m/z 538.5 ($M^+$+1).

Example 74: Synthesis of Compound 4103, N-((7-(5-(difluoromethyl)-1,3,4-oxadiazol-2-yl)imidazo[1,2-a]pyridin-2-yl)methyl)-N-(3-fluorophenyl)-4-(oxetan-3-carbonyl)piperazine-1-carboxamide

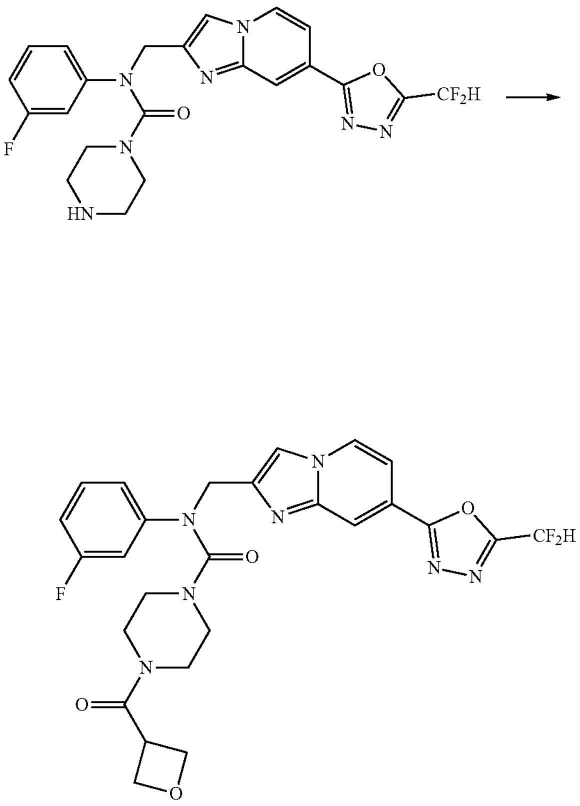

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.050 g, 0.106 mmol) prepared in step 2 of Example 54, oxetane-3-carboxylic acid (0.022 g, 0.212 mmol), 1-[bis(dimethylamino)methylene]-1H-1, 2, 3-triazolo[4,5-b]pyridinium 3-oxide hexafluorophosphate (HATU, 0.048 g, 0.127 mmol), and triethylamine (0.044 mL, 0.318 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.024 g, 40.7%) as a white solid.

$^1H$ NMR (400 MHz, $CDCl_3$) δ 8.31 (dd, J=1.7, 0.9 Hz, 1H), 8.23 (dd, J=7.1, 1.0 Hz, 1H), 7.76 (dd, J=4.5, 0.7 Hz, 1H), 7.55 (dd, J=7.1, 1.8 Hz, 1H), 7.32 (tdd, J=8.5, 6.6, 2.0 Hz, 1H), 7.11-6.79 (m, 4H), 5.07 (d, J=3.0 Hz, 2H), 4.87 (dd, J=7.1, 5.9 Hz, 1H), 4.77 (dd, J=8.7, 6.0 Hz, 1H), 3.48 (dt, J=10.5, 5.4 Hz, 2H), 3.34 (s, 2H), 3.31-3.16 (m, 4H), 3.05 (t, J=5.3 Hz, 1H), 2.06 (s, 2H);

LRMS (ES) m/z 556.5 ($M^+$+1).

Example 75: Synthesis of Compound 4115, N-((7-(5-(difluoromethyl)-1,3,4-oxadiazol-2-yl)imidazo[1,2-a]pyridin-2-yl)methyl)-1-ethyl-N-phenylpiperidine-4-carboxamide

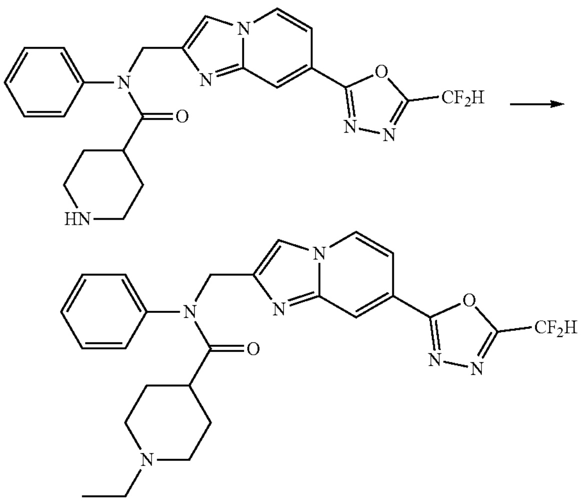

N-((7-(5-(difluoromethyl)-1,3,4-oxadiazol-2-yl)imidazo[1,2-a]pyridin-2-yl)methyl)-N-phenylpiperidine-4-carboxamide (0.040 g, 0.088 mmol) prepared in step 3 of Example 33, acetaldehyde (0.010 mL, 0.177 mmol), and acetic acid (0.005 mL, 0.088 mmol) were dissolved in dichloromethane (0.5 mL), and the resulting solution was stirred at room temperature for 1 hour. Then, sodium triacetoxyborohydride (0.056 g, 0.265 mmol) was added and further stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 20%) and concentrated to obtain the title compound (0.003 g, 7.8%) as a yellow gel.

$^1H$ NMR (400 MHz, $CDCl_3$) δ 8.30 (d, J=1.6 Hz, 1H), 8.24 (dd, J=0.9, 7.1 Hz, 1H), 7.77 (s, 1H), 7.54 (dd, J=1.8, 7.1 Hz, 1H), 7.46-7.36 (m, 3H), 7.27-7.21 (m, 2H), 6.95 (t, J=51.7 Hz, 1H), 5.04 (s, 2H), 3.09 (s, 2H), 2.55 (s, 2H), 2.41 (s, 1H), 2.02 (s, 1H), 1.97 (d, J=10.3 Hz, 3H), 1.80 (s, 2H), 1.28 (s, 1H), 1.15 (s, 3H);

LRMS (ES) m/z 481.3 ($M^+$+1).

Example 76: Synthesis of Compound 4116, N-((7-(5-(difluoromethyl)-1,3,4-oxadiazol-2-yl)imidazo[1,2-a]pyridin-2-yl)methyl)-1-isopropyl-N-phenylpiperidine-4-carboxamide

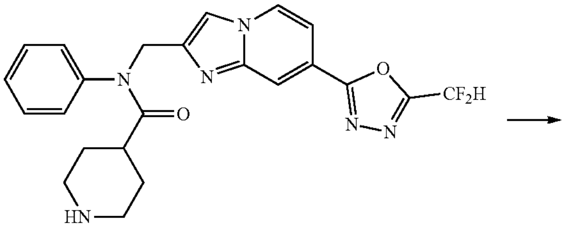

-continued

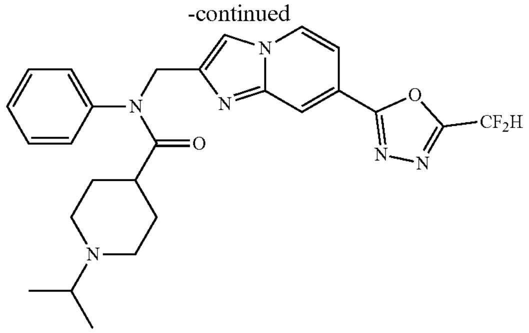

N-((7-(5-(difluoromethyl)-1,3,4-oxadiazol-2-yl)imidazo[1,2-a]pyridin-2-yl)methyl)-N-phenylpiperidine-4-carboxamide (0.024 g, 0.053 mmol) prepared in step 3 of Example 33, propan-2-one (0.006 g, 0.106 mmol), and acetic acid (0.003 mL, 0.053 mmol) were dissolved in dichloromethane (1 mL), and the resulting solution was stirred at room temperature for 1 hour. Then, sodium triacetoxyborohydride (0.034 g, 0.159 mmol) was added and further stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20x20x1 mm; methanol/dichloromethane=0% to 20%) and concentrated to obtain the title compound (0.006 g, 22.5%) as a yellow solid.

$^1$H NMR (700 MHz, MeOD) δ 8.58 (dd, J=1.0, 7.1 Hz, 1H), 8.23 (dt, J=0.8, 1.8 Hz, 1H), 7.94-7.89 (m, 1H), 7.58 (dd, J=1.7, 7.1 Hz, 1H), 7.47-7.38 (m, 3H), 7.32-7.27 (m, 2H), 5.11 (s, 2H), 3.40 (d, J=12.2 Hz, 2H), 2.78 (s, 2H), 2.65 (d, J=11.8 Hz, 1H), 2.12-2.05 (m, 2H), 2.04-1.99 (m, 2H), 1.96 (s, 1H), 1.27 (d, J=6.7 Hz, 6H);

LRMS (ES) m/z 495.4 ($M^+$+1).

Example 77: Synthesis of Compound 4117, N-((7-(5-(difluoromethyl)-1,3,4-oxadiazol-2-yl)imidazo[1,2-a]pyridin-2-yl)methyl)-1-(1-hydroxypropan-2-yl)-N-phenylpiperidine-4-carboxamide

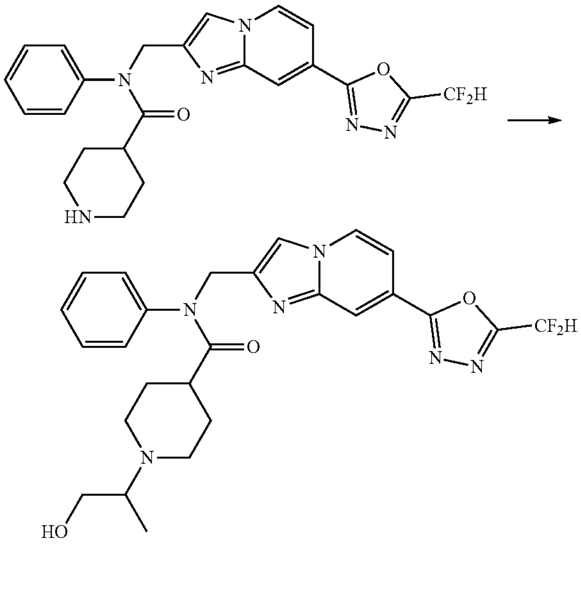

N-((7-(5-(difluoromethyl)-1,3,4-oxadiazol-2-yl)imidazo[1,2-a]pyridin-2-yl)methyl)-N-phenylpiperidine-4-carboxamide (0.040 g, 0.088 mmol) prepared in step 3 of Example 33, 1-hydroxypropan-2-one (0.012 m, 0.177 mmol), acetic acid (0.005 mL, 0.088 mmol), and sodium triacetoxyborohydride (0.056 g, 0.265 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20x20x1 mm; methanol/dichloromethane=0% to 20%) and concentrated to obtain the title compound (0.009 g, 19.1%) as a white solid.

$^1$H NMR (400 MHz, $CDCl_3$) δ 8.31 (s, 1H), 8.24 (d, J=7.1 Hz, 1H), 7.74 (s, 1H), 7.55 (dd, J=1.7, 7.1 Hz, 1H), 7.41 (td, J=5.8, 8.3 Hz, 3H), 7.26-7.18 (m, 2H), 6.96 (t, J=51.7 Hz, 1H), 5.04 (s, 2H), 3.71 (dd, J=4.2, 12.2 Hz, 1H), 3.48 (dd, J=8.6, 12.0 Hz, 1H), 3.30 (s, 1H), 3.14 (s, 2H), 2.80 (s, 1H), 2.50 (d, J=26.3 Hz, 2H), 2.05 (s, 2H), 1.97-1.82 (m, 2H), 1.06 (d, J=6.7 Hz, 3H);

LRMS (ES) m/z 510.55 ($M^+$+1).

Example 78: Synthesis of Compound 4118, 1-cyclobutyl-N-((7-(5-(difluoromethyl)-1,3,4-oxadiazol-2-yl)imidazo[1,2-a]pyridin-2-yl)methyl)-N-phenylpiperidine-4-carboxamide

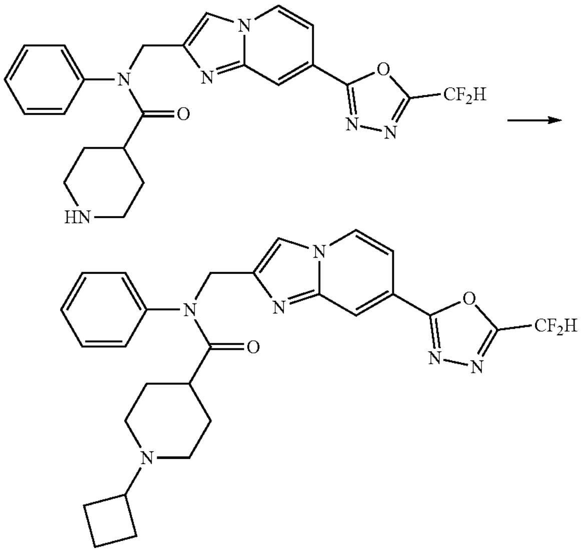

N-((7-(5-(difluoromethyl)-1,3,4-oxadiazol-2-yl)imidazo[1,2-a]pyridin-2-yl)methyl)-N-phenylpiperidine-4-carboxamide (0.040 g, 0.088 mmol) prepared in step 3 of Example 33, cyclobutanone (0.013 mL, 0.177 mmol), and acetic acid (0.005 mL, 0.088 mmol) were dissolved in dichloromethane (0.5 mL), and the resulting solution was stirred at room temperature for 1 hour. Then, sodium triacetoxyborohydride (0.056 g, 0.265 mmol) was added and further stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 20%) and concentrated to obtain the title compound (0.012 g, 27.2%) as a pale red solid.

$^1$H NMR (400 MHz, $CDCl_3$) δ 8.31 (s, 1H), 8.24 (d, J=7.1 Hz, 1H), 7.74 (s, 1H), 7.55 (dd, J=1.7, 7.1 Hz, 1H), 7.41 (td, J=5.8, 8.3 Hz, 3H), 7.26-7.18 (m, 2H), 6.96 (t, J=51.7 Hz, 1H), 5.04 (s, 2H), 3.71 (dd, J=4.2, 12.2 Hz, 1H), 3.48 (dd, J=8.6, 12.0 Hz, 1H), 3.30 (s, 1H), 3.14 (s, 2H), 2.80 (s, 1H), 2.50 (d, J=26.3 Hz, 2H), 2.05 (s, 2H), 1.97-1.82 (m, 2H), 1.06 (d, J=6.7 Hz, 3H);

LRMS (ES) m/z 507.3 ($M^+$+1).

Example 79: Synthesis of Compound 4119, 1-cyclohexyl-N-((7-(5-(difluoromethyl)-1,3,4-oxadiazol-2-yl)imidazo[1,2-a]pyridin-2-yl)methyl)-N-phenylpiperidine-4-carboxamide

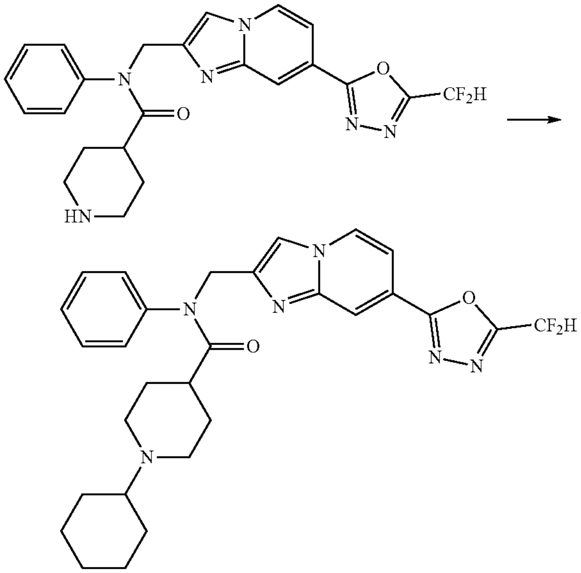

N-((7-(5-(difluoromethyl)-1,3,4-oxadiazol-2-yl)imidazo[1,2-a]pyridin-2-yl)methyl)-N-phenylpiperidine-4-carboxamide (0.040 g, 0.088 mmol) prepared in step 3 of Example 33, cyclohexanone (0.018 mL, 0.177 mmol), and acetic acid (0.005 mL, 0.088 mmol) were dissolved in dichloromethane (0.5 mL), and the resulting solution was stirred at room temperature for 1 hour. Then, sodium triacetoxyborohydride (0.056 g, 0.265 mmol) was added and further stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 20%) and concentrated to obtain the title compound (0.004 g, 7.6%) as a white solid.

$^1$H NMR (400 MHz, MeOD) δ 8.58 (dd, J=1.0, 7.1 Hz, 1H), 8.25-8.22 (m, 1H), 7.92 (s, 1H), 7.57 (dd, J=1.7, 7.1 Hz, 1H), 7.47-7.36 (m, 3H), 7.31-7.15 (m, 3H), 5.10 (s, 2H), 2.84 (s, 1H), 2.58 (dd, J=12.7, 22.7 Hz, 3H), 2.11-1.81 (m, 8H), 1.68 (d, J=13.0 Hz, 1H), 1.41-1.31 (m, 5H), 1.20 (dd, J=11.7, 23.7 Hz, 2H);

LRMS (ES) m/z 535.3 ($M^+$+1).

Example 80: Synthesis of Compound 4120, N-((7-(5-(difluoromethyl)-1,3,4-oxadiazol-2-yl)imidazo[1,2-a]pyridin-2-yl)methyl)-N-phenyl-1-(tetrahydro-2H-pyran-4-yl)piperidine-4-carboxamide

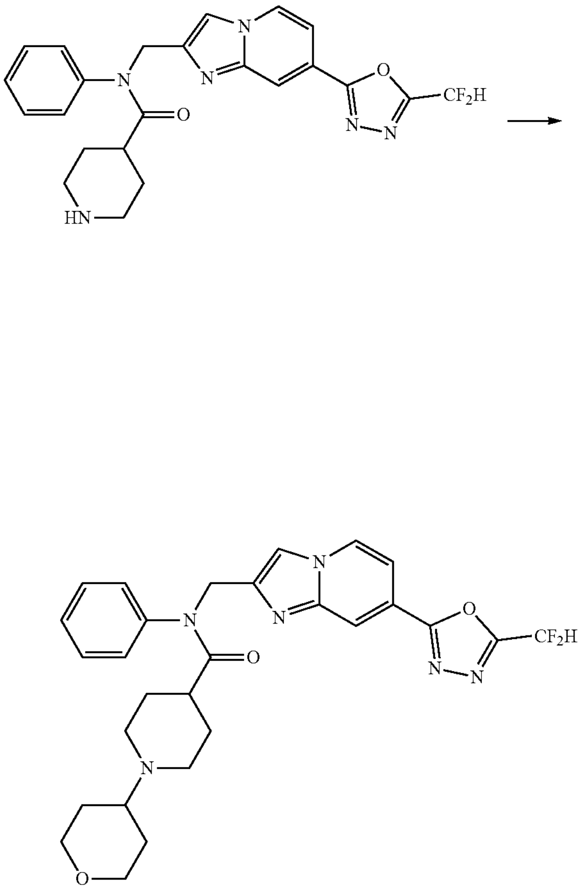

N-((7-(5-(difluoromethyl)-1,3,4-oxadiazol-2-yl)imidazo[1,2-a]pyridin-2-yl)methyl)-N-phenylpiperidine-4-carboxamide (0.050 g, 0.111 mmol) prepared in step 3 of Example 33, tetrahydro-4H-pyran-4-one (0.020 mL, 0.221 mmol), acetic acid (0.006 mL, 0.111 mmol) and sodium triacetoxyborohydride (0.070 g, 0.332 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 20%) and concentrated to obtain the title compound (0.012 g, 20.7%) as a white solid.

$^1$H NMR (400 MHz, $CDCl_3$) δ 8.31-8.28 (m, 1H), 8.23 (dd, J=1.0, 7.1 Hz, 1H), 7.78 (s, 1H), 7.53 (dd, J=1.7, 7.1 Hz, 1H), 7.46-7.32 (m, 3H), 7.27-7.20 (m, 2H), 6.95 (t, J=51.7 Hz, 1H), 5.04 (s, 2H), 3.99 (dd, J=4.2, 11.4 Hz, 2H), 3.34 (td, J=2.0, 11.8 Hz, 2H), 2.92 (s, 2H), 2.34 (d, J=64.4 Hz, 2H), 1.88 (d, J=14.6 Hz, 4H), 1.76-1.48 (m, 6H);

LRMS (ES) m/z 537.3 ($M^+$+1).

Example 81: Synthesis of Compound 4121, 1-(4,4-difluorocyclohexyl)-N-((7-(5-(difluoromethyl)-1,3,4-oxadiazol-2-yl)imidazo[1,2-a]pyridin-2-yl)methyl)-N-phenylpiperidine-4-carboxamide

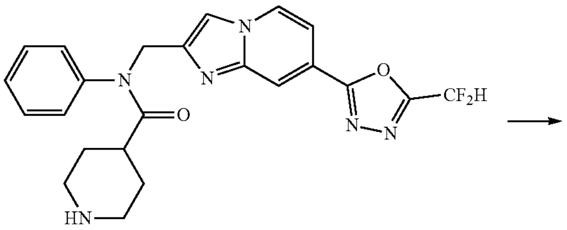

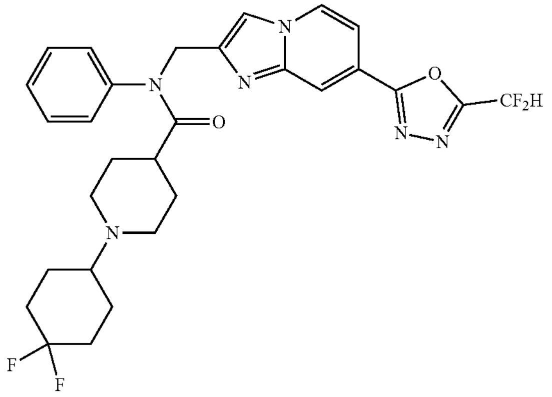

N-((7-(5-(difluoromethyl)-1,3,4-oxadiazol-2-yl)imidazo[1,2-a]pyridin-2-yl)methyl)-N-phenylpiperidine-4-carboxamide (0.040 g, 0.088 mmol) prepared in step 3 of Example 33, 4,4-difluorocyclohexan-1-one (0.024 g, 0.177 mmol), acetic acid (0.005 mL, 0.088 mmol), and sodium triacetoxyborohydride (0.056 g, 0.265 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 20%) and concentrated to obtain the title compound (0.014 g, 28.2%) as a white solid.

$^1$H NMR (400 MHz, $CDCl_3$) δ 8.29 (s, 1H), 8.23 (d, J=7.1 Hz, 1H), 7.78 (s, 1H), 7.53 (dd, J=1.8, 7.1 Hz, 1H), 7.46-7.32 (m, 3H), 7.27-7.19 (m, 2H), 5.04 (s, 2H), 3.93 (dt, J=3.5, 7.0 Hz, 1H), 2.85 (s, 2H), 2.41-1.51 (m, 15H);

LRMS (ES) m/z 571.4 ($M^+$+1).

Example 82: Synthesis of Compound 4122, 1-acetyl-N-((7-(5-(difluoromethyl)-1,3,4-oxadiazol-2-yl)imidazo[1,2-a]pyridin-2-yl)methyl)-N-phenylpiperidine-4-carboxamide

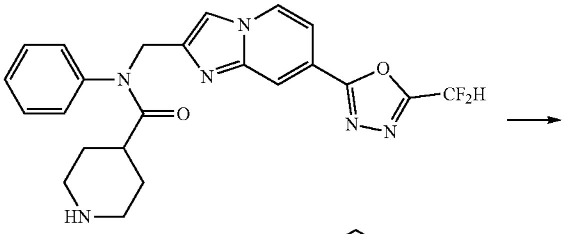

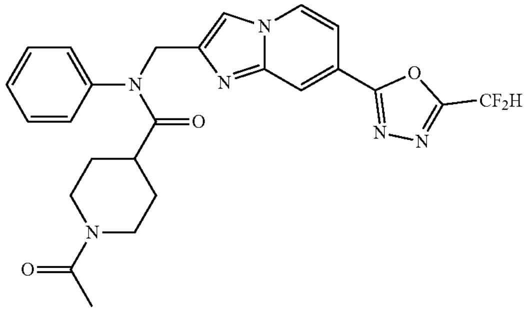

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, acetyl chloride (0.031 mL, 0.181 mmol), and triethylamine (0.038 mL, 0.272 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.012 g, 26.6%) as a white solid.

$^1$H NMR (400 MHz, $CDCl_3$) δ 8.30 (s, 1H), 8.23 (d, J=7.2 Hz, 1H), 7.77 (s, 1H), 7.54 (d, J=7.2 Hz, 1H), 7.41 (dq, J=7.0, 13.7 Hz, 3H), 7.31-7.22 (m, 3H), 6.95 (t, J=51.7 Hz, 1H), 5.14-4.95 (m, 2H), 4.53 (d, J=13.3 Hz, 1H), 3.77 (d, J=13.5 Hz, 1H), 2.84 (t, J=13.0 Hz, 1H), 2.49 (d, J=11.1 Hz, 1H), 2.34 (t, J=12.4 Hz, 1H), 2.06 (s, 3H), 1.75 (dd, J=14.2, 49.2 Hz, 4H);

LRMS (ES) m/z 494.9 ($M^+$+1).

Example 83: Synthesis of Compound 4123, N-((7-(5-(difluoromethyl)-1,3,4-oxadiazol-2-yl)imidazo[1,2-a]pyridin-2-yl)methyl)-N-phenyl-1-propionylpiperidine-4-carboxamide

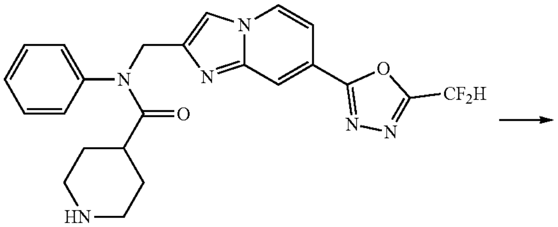

-continued

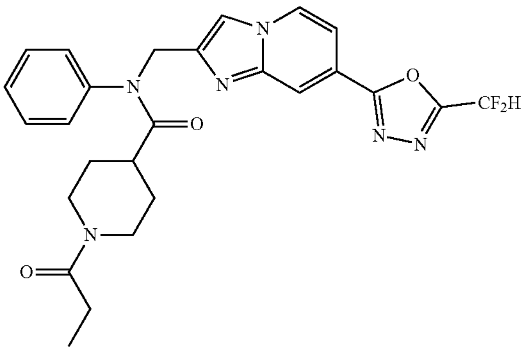

-continued

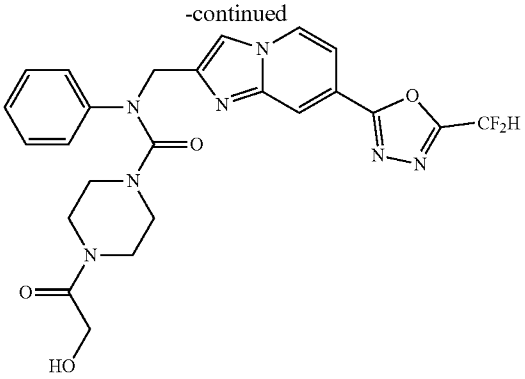

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, propionyl chloride (0.017 g, 0.181 mmol), and triethylamine (0.038 mL, 0.272 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.023 g, 49.0%) as an orange solid.

$^1H$ NMR (400 MHz, $CDCl_3$) δ 8.32-8.26 (m, 1H), 8.23 (dd, J=0.9, 7.1 Hz, 1H), 7.76 (s, 1H), 7.53 (dd, J=1.7, 7.1 Hz, 1H), 7.47-7.33 (m, 3H), 7.29-7.21 (m, 2H), 6.95 (t, J=51.7 Hz, 1H), 5.10-4.95 (m, 2H), 4.55 (d, J=13.4 Hz, 1H), 3.81 (d, J=13.6 Hz, 1H), 2.84-2.74 (m, 1H), 2.50 (ddt, J=4.3, 10.3, 15.0 Hz, 1H), 2.31 (pd, J=4.1, 7.5, 8.6 Hz, 3H), 1.85-1.59 (m, 4H), 1.12 (t, J=7.5 Hz, 3H);

LRMS (ES) m/z 509.2 ($M^+$+1).

Example 84: Synthesis of Compound 4124, N-((7-(5-(difluoromethyl)-1,3,4-oxadiazol-2-yl)imidazo[1,2-a]pyridin-2-yl)methyl)-1-(2-hydroxyacetyl)-N-phenylpiperidine-4-carboxamide

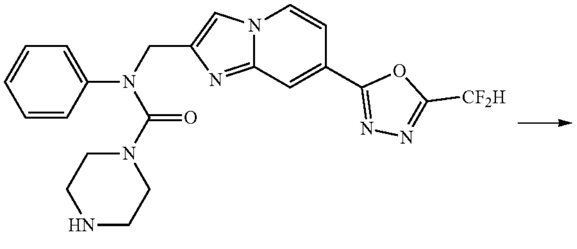

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, 2-hydroxyacetic acid (0.014 g, 0.181 mmol), triethylamine (0.038 mL, 0.272 mmol), and 1-[bis(dimethylamino)methylene]-1H-1, 2, 3-triazolo[4,5-b]pyridinium 3-oxide hexafluorophosphate (HATU, 0.052 g, 0.136 mmol) were dissolved in dichloromethane (1 mL) at room temperature, and the resulting solution was stirred at the same temperature for 18 hours. Water was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.012 g, 25.5%) as an orange solid.

$^1H$ NMR (400 MHz, $CDCl_3$) δ 8.33-8.29 (m, 1H), 8.23 (dd, J=0.9, 7.1 Hz, 1H), 7.76 (s, 1H), 7.54 (dd, J=1.7, 7.1 Hz, 1H), 7.47-7.38 (m, 3H), 7.27 (d, J=7.7 Hz, 3H), 6.95 (t, J=51.7 Hz, 1H), 5.03 (d, J=2.9 Hz, 2H), 4.48 (d, J=13.3 Hz, 1H), 4.18-4.03 (m, 2H), 3.62 (s, 1H), 3.47 (d, J=13.7 Hz, 1H), 2.83-2.72 (m, 1H), 2.54 (td, J=4.1, 10.1, 10.5 Hz, 2H), 1.85-1.64 (m, 4H);

LRMS (ES) m/z 511.3 ($M^+$+1).

Example 85: Synthesis of Compound 4125, 1-(cyclobutanecarbonyl)-N-((7-(5-(difluoromethyl)-1,3,4-oxadiazol-2-yl)imidazo[1,2-a]pyridine-2-yl)methyl)-N-phenylpiperidine-4-carboxamide

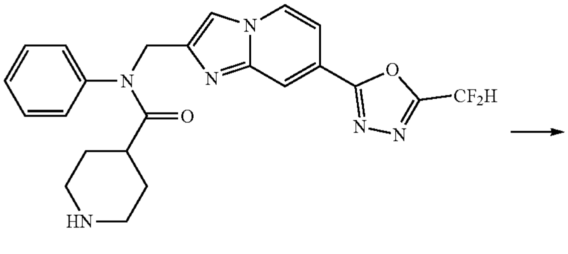

-continued

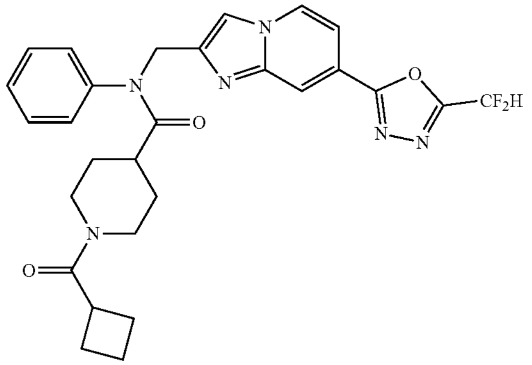

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, cyclobutanecarbonyl chloride (0.021 g, 0.181 mmol), and triethylamine (0.038 mL, 0.272 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 40.9%) as an orange gel.

$^1$H NMR (400 MHz, $CDCl_3$) δ 8.30 (dt, J=0.8, 1.7 Hz, 1H), 8.23 (dd, J=1.0, 7.1 Hz, 1H), 7.77 (s, 1H), 7.53 (dd, J=1.7, 7.1 Hz, 1H), 7.46-7.35 (m, 3H), 7.28-7.24 (m, 2H), 6.95 (t, J=51.7 Hz, 1H), 5.10-4.95 (m, 2H), 4.52 (d, J=13.6 Hz, 1H), 3.66 (d, J=13.4 Hz, 1H), 3.25-3.15 (m, 1H), 2.71 (t, J=11.7 Hz, 1H), 2.48 (ddt, J=4.4, 10.4, 15.0 Hz, 1H), 2.39-2.25 (m, 4H), 2.19-2.03 (m, 1H), 1.99-1.79 (m, 2H), 1.77-1.61 (m, 4H);

LRMS (ES) m/z 535.1 ($M^+$+1).

Example 86: Synthesis of Compound 4126, N-((7-(5-(difluoromethyl)-1,3,4-oxadiazol-2-yl)imidazo[1,2-a]pyridin-2-yl)methyl)-1-(oxetan-3-carbonyl)-N-phenylpiperidine-4-carboxamide

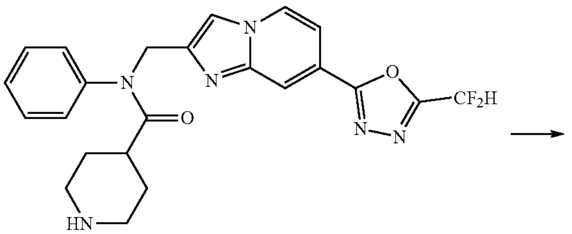

-continued

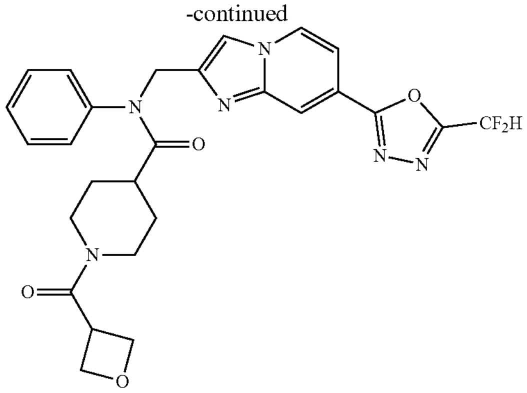

N-((7-(5-(difluoromethyl)-1,3,4-oxadiazol-2-yl)imidazo[1,2-a]pyridin-2-yl)methyl)-N-phenylpiperidine-4-carboxamide (0.050 g, 0.111 mmol) prepared in step 3 of Example 33, oxetane-3-carboxylic acid (0.023 g, 0.221 mmol), 1-[bis(dimethylamino)methylene]-1H-1, 2, 3-triazolo[4,5-b]pyridinium 3-oxide hexafluorophosphate (HATU, 0.063 g, 0.166 mmol), and triethylamine (0.043 mL, 0.332 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.007 g, 12.0%) as a white solid.

$^1$H NMR (400 MHz, $CDCl_3$) δ 8.31 (s, 1H), 8.23 (dd, J=1.0, 7.1 Hz, 1H), 7.76 (s, 1H), 7.55 (dd, J=1.7, 7.1 Hz, 1H), 7.48-7.35 (m, 3H), 7.30-7.23 (m, 2H), 7.02 (d, J=51.7 Hz, 1H), 5.03 (d, J=4.3 Hz, 2H), 4.93 (dd, J=5.9, 7.2 Hz, 1H), 4.85 (dd, J=5.9, 7.2 Hz, 1H), 4.76 (ddd, J=5.8, 8.7, 10.1 Hz, 2H), 4.52 (d, J=13.4 Hz, 1H), 3.96 (tt, J=7.2, 8.7 Hz, 1H), 3.30 (d, J=13.6 Hz, 1H), 2.78-2.70 (m, 1H), 2.50 (dq, J=4.8, 10.1 Hz, 1H), 2.46-2.38 (m, 1H), 1.75-1.62 (m, 4H);

LRMS (ES) m/z 537.2 ($M^+$+1).

Example 87: Synthesis of Compound 4127, N-((7-(5-(difluoromethyl)-1,3,4-oxadiazol-2-yl)imidazo[1,2-a]pyridin-2-yl)methyl)-N-phenyl-1-(2,2,2-trifluoroacetyl)piperidine-4-carboxamide

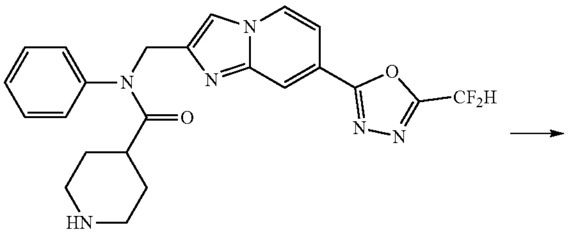

-continued

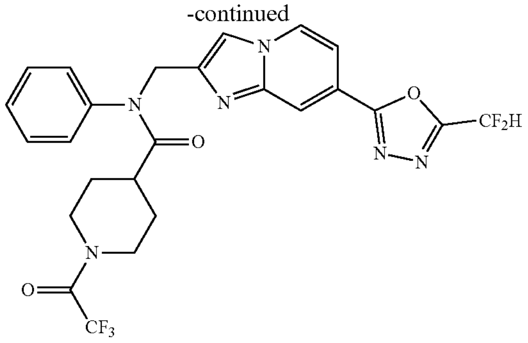

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, 2,2,2-trifluoroacetic anhydride (0.025 mL, 0.181 mmol), and triethylamine (0.038 mL, 0.272 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 40.0%) as a pale red solid.

$^1H$ NMR (400 MHz, $CDCl_3$) δ 8.33-8.26 (m, 1H), 8.23 (dd, J=0.9, 7.1 Hz, 1H), 7.77 (s, 1H), 7.54 (dd, J=1.7, 7.1 Hz, 1H), 7.43 (ddd, J=5.9, 7.9, 10.5 Hz, 3H), 7.28 (d, J=6.2 Hz, 2H), 6.95 (t, J=51.7 Hz, 1H), 5.03 (s, 2H), 4.45-4.33 (m, 1H), 3.97 (d, J=14.0 Hz, 1H), 3.01-2.88 (m, 1H), 2.72-2.53 (m, 2H), 1.94-1.65 (m, 4H);

LRMS (ES) m/z 549.3 ($M^+$+1).

Example 88: Synthesis of Compound 4128, N-((7-(5-(difluoromethyl)-1,3,4-oxadiazol-2-yl)imidazo[1,2-a]pyridin-2-yl)methyl)-1-(methylsulfonyl)-N-phenylpiperidine-4-carboxamide

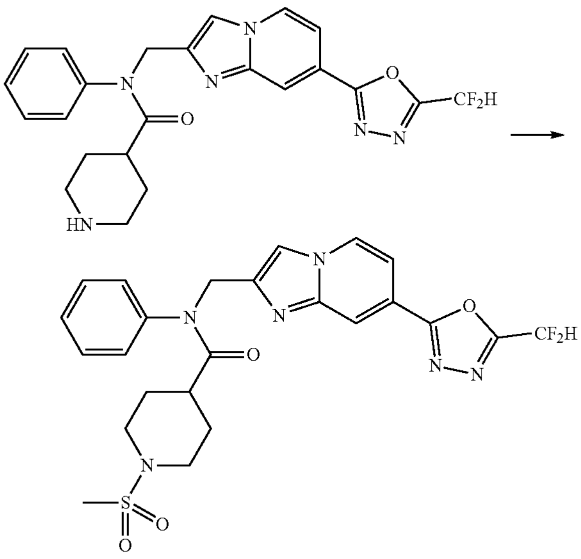

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, methanesulfonyl chloride (0.014 mL, 0.181 mmol), and triethylamine (0.038 mL, 0.272 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.008 g, 15.6%) as a white solid.

$^1H$ NMR (400 MHz, $CDCl_3$) δ 8.32 (s, 1H), 8.25 (dd, J=1.0, 7.1 Hz, 1H), 7.78 (s, 1H), 7.56 (dd, J=1.7, 7.1 Hz, 1H), 7.48-7.36 (m, 3H), 7.28-7.25 (m, 2H), 6.95 (t, J=51.7 Hz, 1H), 5.05 (s, 2H), 3.74 (dd, J=6.0, 10.1 Hz, 2H), 2.74 (s, 3H), 2.54 (td, J=2.9, 11.9 Hz, 2H), 2.43-2.34 (m, 1H), 2.00-1.86 (m, 2H), 1.75 (dd, J=3.6, 13.6 Hz, 2H);

LRMS (ES) m/z 531.1 ($M^+$+1).

Example 89: Synthesis of Compound 4129, methyl 4-(((7-(5-(difluoromethyl)-1,3,4-oxadiazol-2-yl)imidazo[1,2-a]pyridin-2-yl)methyl)(phenyl)carbamoyl)piperidine-1-carboxylate

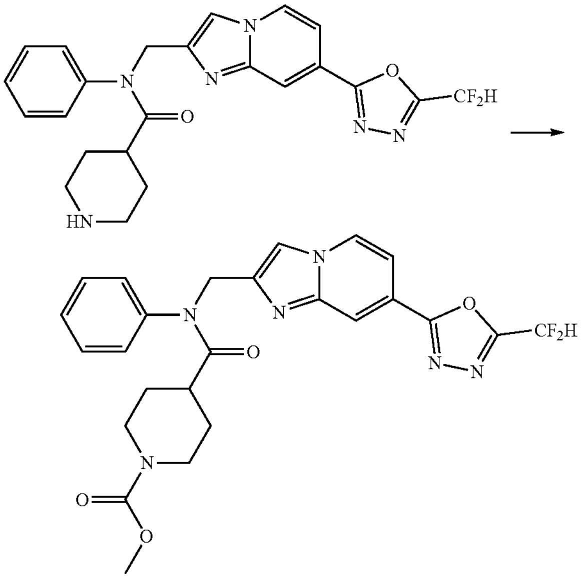

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, methyl carbonochloridate (0.017 g, 0.181 mmol), and triethylamine (0.025 mL, 0.181 mmol) were dissolved in dichloromethane (1 mL) at room temperature, and the resulting solution was stirred at the same temperature for 18 hours. Water was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 43.7%) as a pale orange solid.

$^1H$ NMR (400 MHz, $CDCl_3$) δ 8.29 (dt, J=0.9, 1.8 Hz, 1H), 8.23 (dd, J=0.9, 7.1 Hz, 1H), 7.77 (s, 1H), 7.53 (dd, J=1.7, 7.1 Hz, 1H), 7.46-7.35 (m, 3H), 7.26-7.23 (m, 2H), 6.95 (t, J=51.7 Hz, 1H), 5.03 (s, 2H), 4.09 (s, 2H), 3.67 (s, 3H), 2.53 (s, 2H), 2.43 (tt, J=3.8, 11.2 Hz, 1H), 1.76 (qd, J=4.4, 11.9, 12.4 Hz, 2H), 1.62 (d, J=12.8 Hz, 2H);

LRMS (ES) m/z 511.1 ($M^+$+1).

Example 90: Synthesis of Compound 4130, N4-((7-(5-(difluoromethyl)-1,3,4-oxadiazol-2-yl)imidazo[1,2-a]pyridin-2-yl)methyl)-N1,N1-dimethyl-N4-phenylpiperidine-1,4-dicarboxamide

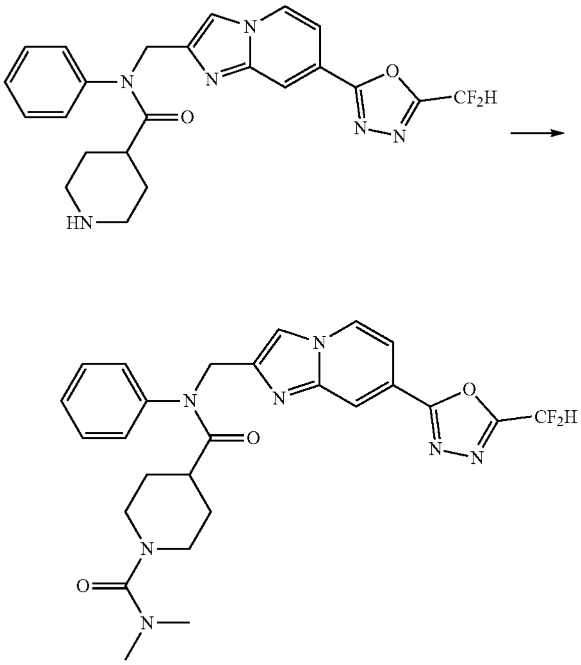

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, dimethylcarbamic chloride (0.019 g, 0.181 mmol), and triethylamine (0.025 mL, 0.181 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.024 g, 51.4%) as a red gel.

$^1H$ NMR (400 MHz, $CDCl_3$) δ 8.29 (dt, J=0.8, 1.7 Hz, 1H), 8.23 (dd, J=1.0, 7.1 Hz, 1H), 7.77 (s, 1H), 7.53 (dd, J=1.7, 7.1 Hz, 1H), 7.40 (dddd, J=2.3, 4.6, 6.8, 11.7 Hz, 3H), 7.27-7.23 (m, 2H), 6.95 (t, J=51.7 Hz, 1H), 5.03 (s, 2H), 3.59 (dd, J=3.8, 13.3 Hz, 2H), 2.79 (s, 6H), 2.44 (dtd, J=5.1, 11.5, 12.2, 16.5 Hz, 3H), 1.82 (qd, J=4.0, 12.6 Hz, 2H), 1.64 (dd, J=3.5, 13.7 Hz, 2H);

LRMS (ES) m/z 524.4 ($M^+$+1).

Example 91: Synthesis of Compound 4131, N-((7-(5-(difluoromethyl)-1,3,4-oxadiazol-2-yl)imidazo[1,2-a]pyridin-2-yl)methyl)-N-phenyl-1-(pyridin-2-yl)piperidine-4-carboxamide

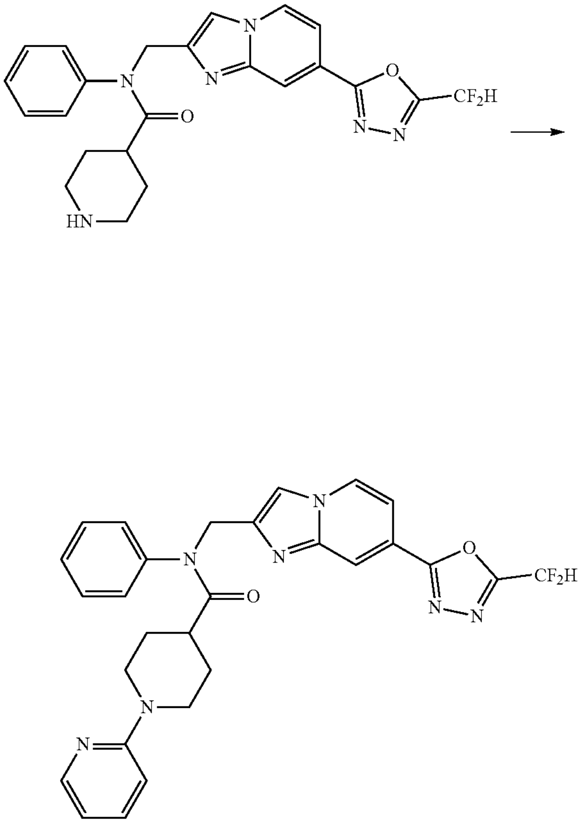

N-((7-(5-(difluoromethyl)-1,3,4-oxadiazol-2-yl)imidazo[1,2-a]pyridin-2-yl)methyl)-N-phenylpiperidine-4-carboxamide (0.025 g, 0.055 mmol) prepared in step 3 of Example 33, 2-bromopyridine (0.017 g, 0.111 mmol), cesium carbonate (0.036 g, 0.111 mmol), and RuPhos palladium G2 (0.002 g, 0.003 mmol) were dissolved in 1,4-dioxane (0.5 mL) at room temperature, and the resulting solution was stirred at 120° C. for 18 hours. Then, the temperature was lowered to room temperature to terminate the reaction. An saturated aqueous sodium hydrogen carbonate solution was poured into the reaction mixture, followed by extraction with ethyl acetate. The organic layer was washed with a saturated aqueous sodium chloride solution, dried over anhydrous magnesium sulfate, filtered, and concentrated under reduced pressure. The concentrate was purified by chromatography ($SiO_2$ plate, 20×20×1 mm; methanol/dichloromethane=0% to 7%) and concentrated to obtain the title compound (0.006 g, 19.1%) as a yellow solid.

$^1H$ NMR (400 MHz, $CDCl_3$) δ 8.30 (p, J=0.8 Hz, 1H), 8.23 (dd, J=1.0, 7.1 Hz, 1H), 8.15 (ddd, J=0.9, 2.0, 4.9 Hz, 1H), 7.79 (s, 1H), 7.54 (dd, J=1.7, 7.1 Hz, 1H), 7.48-7.37 (m, 4H), 7.31-7.26 (m, 2H), 6.95 (t, J=51.7 Hz, 1H), 6.63-6.55 (m, 2H), 5.05 (s, 2H), 4.25 (d, J=13.1 Hz, 2H), 2.57 (dt, J=11.9, 34.6 Hz, 3H), 1.90 (qd, J=4.2, 12.7 Hz, 2H), 1.73 (d, J=13.1 Hz, 2H);

LRMS (ES) m/z 530.3 ($M^+$+1).

Example 92: Synthesis of Compound 4132, N-((7-(5-(difluoromethyl)-1,3,4-oxadiazol-2-yl)imidazo[1,2-a]pyridin-2-yl)methyl)-N-phenyl-1-(pyrimidin-2-yl)piperidine-4-carboxamide

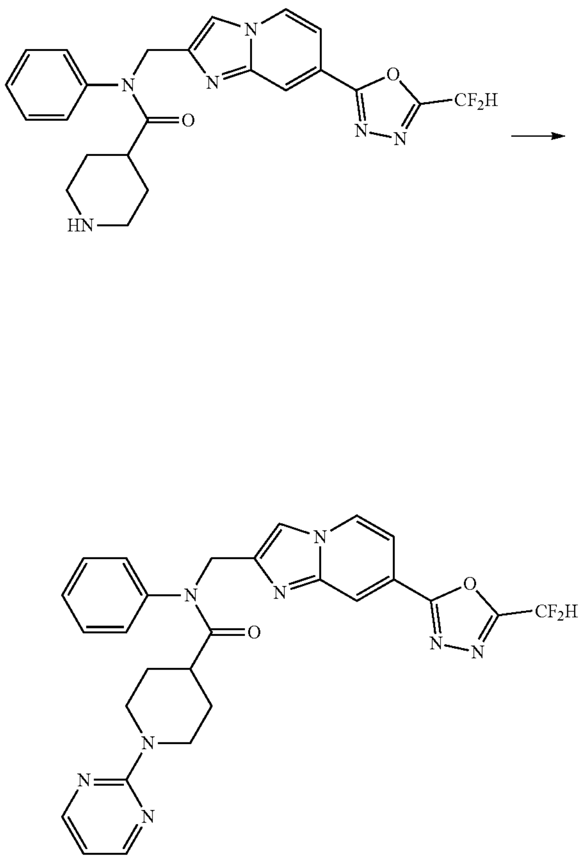 [SMILES: O=C(C1CCNCC1)N(Cc1cn2ccc(-c3nnc(C(F)F)o3)cc2n1)c1ccccc1 ; O=C(C1CCN(c2ncccn2)CC1)N(Cc1cn2ccc(-c3nnc(C(F)F)o3)cc2n1)c1ccccc1]

N-((7-(5-(difluoromethyl)-1,3,4-oxadiazol-2-yl)imidazo[1,2-a]pyridin-2-yl)methyl)-N-phenylpiperidine-4-carboxamide (0.041 g, 0.091 mmol) prepared in step 3 of Example 33, 2-chloropyrimidine (0.021 g, 0.181 mmol), and potassium carbonate (0.038 g, 0.272 mmol) were dissolved in N,N-dimethylformamide (0.5 mL)/acetonitrile (0.5 mL) at room temperature, and the resulting solution was stirred at the same temperature for 18 hours. An saturated aqueous sodium hydrogen carbonate solution was poured into the concentrate obtained by removing the solvent from the reaction mixture under reduced pressure, followed by extraction with ethyl acetate. The organic layer was washed with a saturated aqueous sodium chloride solution, dried over anhydrous magnesium sulfate, filtered, and concentrated under reduced pressure. The concentrate was purified by chromatography ($SiO_2$ plate, 20×20×1 mm; methanol/dichloromethane=0% to 7%) and concentrated to obtain the title compound (0.022 g, 45.6%) as a white solid.

$^1H$ NMR (400 MHz, $CDCl_3$) δ 8.29-8.25 (m, 3H), 8.22 (dd, J=1.0, 7.1 Hz, 1H), 7.78 (s, 1H), 7.52 (dd, J=1.7, 7.1 Hz, 1H), 7.47-7.36 (m, 3H), 7.29-7.26 (m, 2H), 6.95 (t, J=51.7 Hz, 1H), 6.44 (t, J=4.7 Hz, 1H), 5.04 (s, 2H), 4.71 (dt, J=3.4, 13.5 Hz, 2H), 2.70-2.52 (m, 3H), 1.83 (dq, J=5.8, 7.6, 19.8 Hz, 2H), 1.70 (dd, J=3.6, 13.9 Hz, 2H);

LRMS (ES) m/z 531.3 ($M^+$+1).

Example 93: Synthesis of Compound 4137, N-((7-(5-(difluoromethyl)-1,3,4-oxadiazol-2-yl)imidazo[1,2-a]pyridin-2-yl)methyl)-N-(3-fluorophenyl)-1-methylpiperidine-4-carboxamide

[Step 1] Synthesis of tert-butyl 4-(chlorocarbonyl)piperidine-1-carboxylate

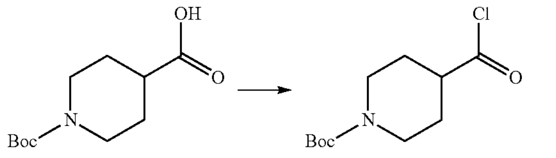 [SMILES: CC(C)(C)OC(=O)N1CCC(C(=O)O)CC1 ; CC(C)(C)OC(=O)N1CCC(C(=O)Cl)CC1]

1-(Tert-butoxycarbonyl)piperidine-4-carboxylic acid (1,000 g, 4.361 mmol), oxalyl chloride (2.00 M solution dry, in DCM, 2.835 mL, 5.670 mmol), and N,N-dimethylformamide (0.034 mL, 0.436 mmol) were dissolved in dichloromethane (25 mL) at 0° C., and the resulting solution was stirred at room temperature for 2 hours. After removing the solvent from the reaction mixture under reduced pressure, the title compound (1.080 g, 100.0%) was obtained as a yellow solid without further purification.

[Step 2] Synthesis of tert-butyl 4-(((7-(5-(difluoromethyl)-1,3,4-oxadiazol-2-yl)imidazo[1,2-a]pyridin-2-yl)methyl)(3-fluorophenyl)carbamoyl)piperidine-1-carboxylate

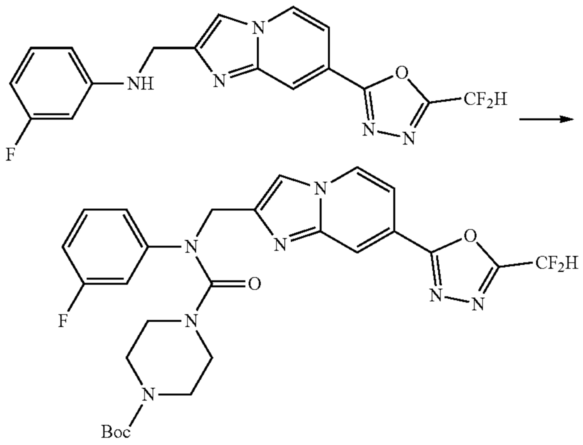

N-((7-(5-(difluoromethyl)-1,3,4-oxadiazol-2-yl)imidazo[1,2-a]pyridin-2-yl)methyl)-3-fluoroaniline (1.000 g, 2.783 mmol) prepared in Example 16, tert-butyl 4-(chlorocarbonyl)piperidine-1-carboxylate (1.034 g, 4.175 mmol), and triethylamine (1.164 mL, 8.349 mmol) were dissolved in dichloromethane (15 mL) at room temperature, and the resulting solution was stirred at the same temperature for 18 hours. An aqueous N-ammonium chloride solution was poured into the reaction mixture, followed by extraction with ethyl acetate. The organic layer was washed with a saturated aqueous sodium chloride solution, dried over anhydrous magnesium sulfate, filtered, and concentrated under reduced pressure. The concentrate was purified by column chromatography ($SiO_2$, 24 g cartridge; ethyl acetate/hexane=0% to 90%) and concentrated to obtain the title compound (0.680 g, 42.8%) as a pale orange solid.

[Step 3] Synthesis of N-((7-(5-(difluoromethyl)-1,3,4-oxadiazol-2-yl)imidazo[1,2-a]pyridin-2-yl)methyl)-N-(3-fluorophenyl)piperidine-4-carboxamide

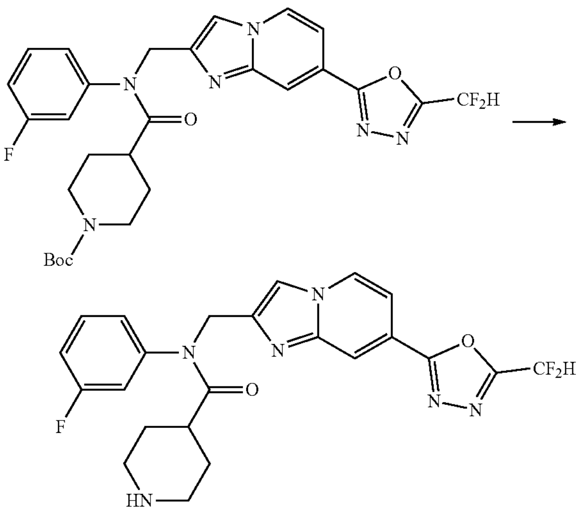

Tert-butyl 4-(((7-(5-(difluoromethyl)-1,3,4-oxadiazol-2-yl)imidazo[1,2-a]pyridin-2-yl)methyl)(3-fluorophenyl)carbamoyl)piperidine-1-carboxylate (1,000 g, 1.753 mmol) prepared in step 2, and trifluoroacetic acid (2.684 mL, 35.053 mmol) were dissolved in dichloromethane (30 mL) at room temperature, and the resulting solution was stirred at the same temperature for 3 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (0.824 g, 99.9%) was obtained as a brown gel without further purification.

[Step 4] Synthesis of Compound 4137

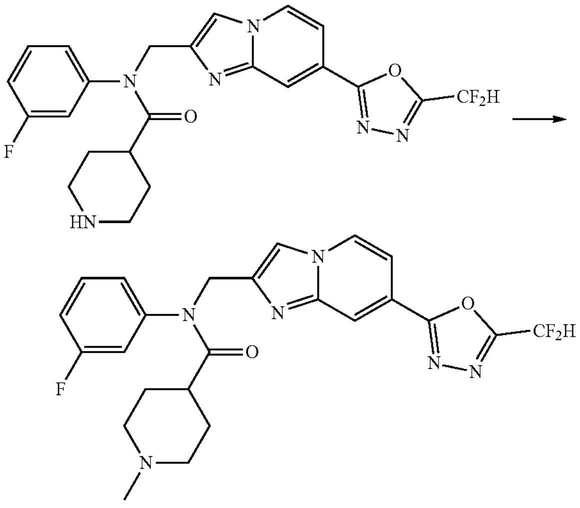

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3, formaldehyde (35.00%, 0.022 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.024 g, 38.8%) as a yellow solid.

$^1$H NMR (700 MHz, $CDCl_3$) δ 8.29 (d, J=1.7 Hz, 1H), 8.24 (dd, J=7.1, 1.0 Hz, 1H), 7.79 (s, 1H), 7.54 (dd, J=7.1, 1.7 Hz, 1H), 7.39 (td, J=8.1, 6.2 Hz, 1H), 7.12-6.86 (m, 4H), 5.01 (s, 2H), 2.92-2.80 (m, 2H), 2.29-2.16 (m, 5H), 1.94-1.86 (m, 2H), 1.82-1.72 (m, 3H);

LRMS (ES) m/z 485.3 ($M^+$+1).

Example 94: Synthesis of Compound 4138, N-((7-(5-(difluoromethyl)-1,3,4-oxadiazol-2-yl)imidazo[1,2-a]pyridin-2-yl)methyl)-1-ethyl-N-(3-fluorophenyl)piperidine-4-carboxamide

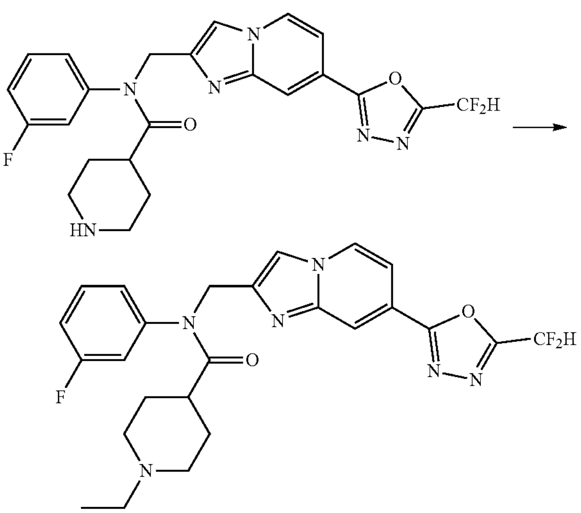

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, acetaldehyde (0.011 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.031 g, 48.8%) as a yellow solid.

$^1$H NMR (400 MHz, $CDCl_3$) δ 8.30 (dt, J=1.7, 0.8 Hz, 1H), 8.24 (ddd, J=7.1, 2.9, 1.0 Hz, 1H), 7.78 (d, J=8.3 Hz, 1H), 7.55 (dd, J=7.2, 1.7 Hz, 1H), 7.40 (tdd, J=8.2, 6.3, 1.8 Hz, 1H), 7.13-6.80 (m, 4H), 5.02 (s, 2H), 3.00 (s, 1H), 2.50-2.21 (m, 3H), 1.99-1.62 (m, 7H), 1.12 (s, 3H);

LRMS (ES) m/z 499.3 ($M^{+}$+1).

Example 95: Synthesis of Compound 4139, N-((7-(5-(difluoromethyl)-1,3,4-oxadiazol-2-yl)imidazo[1,2-a]pyridin-2-yl)methyl)-N-(3-fluorophenyl)-1-isopropylpiperidine-4-carboxamide

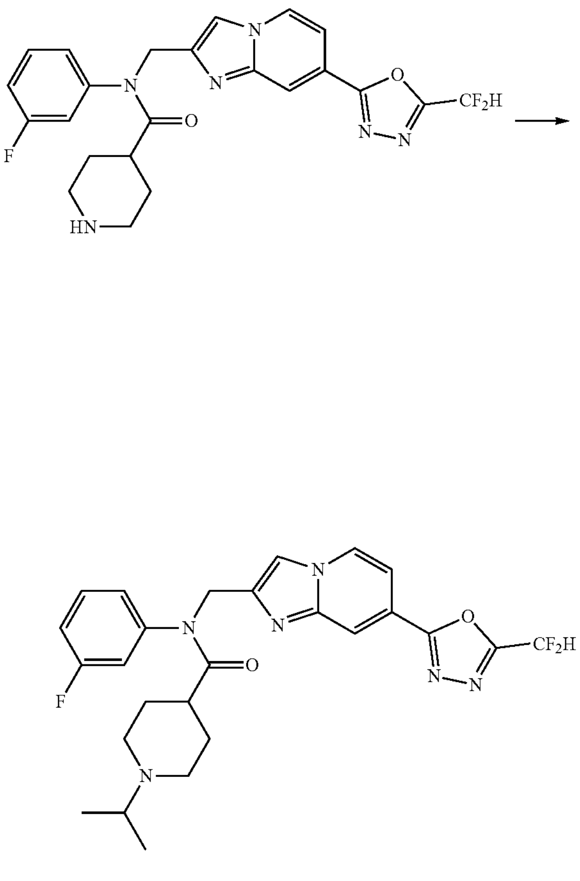

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, propan-2-one (0.015 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.018 g, 27.5%) as a yellow solid.

$^{1}$H NMR (700 MHz, $CDCl_3$) δ 8.30 (d, J=1.6 Hz, 1H), 8.24 (dd, J=7.1, 1.0 Hz, 1H), 7.78 (s, 1H), 7.55 (dd, J=7.1, 1.7 Hz, 1H), 7.39 (td, J=8.1, 6.3 Hz, 1H), 7.13-6.85 (m, 4H), 5.02 (s, 2H), 2.86 (s, 2H), 2.68 (s, 1H), 2.29-2.19 (m, 1H), 1.91 (s, 4H), 1.66 (s, 2H), 1.00 (s, 6H);

LRMS (ES) m/z 512.9 ($M^{+}$+1).

Example 96: Synthesis of Compound 4140, N-((7-(5-(difluoromethyl)-1,3,4-oxadiazol-2-yl)imidazo[1,2-a]pyridin-2-yl)methyl)-N-(3-fluorophenyl)-1-(1-hydroxypropan-2-yl)piperidine-4-carboxamide

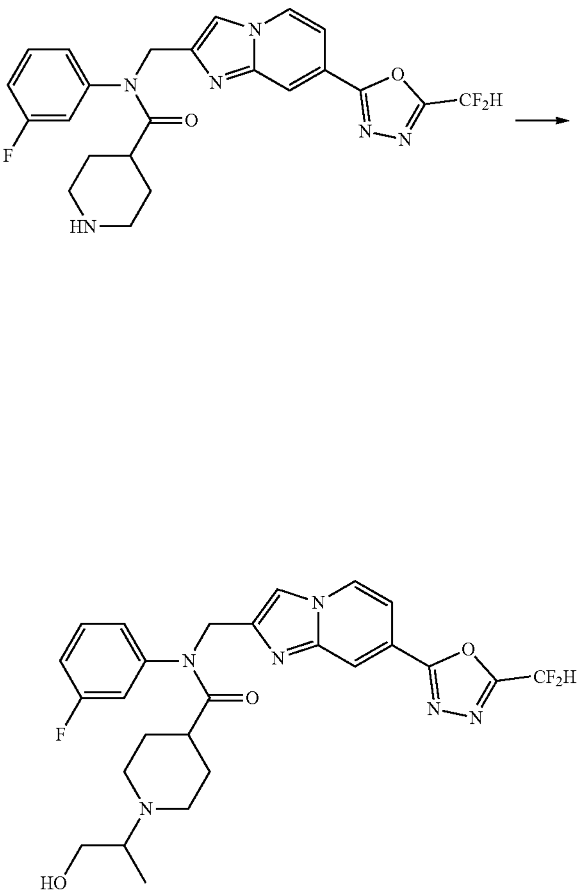

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, 1-hydroxypropan-2-one (0.019 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.019 g, 28.2%) as a yellow solid.

$^{1}$H NMR (700 MHz, $CDCl_3$) δ 8.31 (dt, J=1.7, 0.8 Hz, 1H), 8.25 (dd, J=7.1, 1.0 Hz, 1H), 7.78 (s, 1H), 7.56 (dd, J=7.1, 1.7 Hz, 1H), 7.41 (td, J=8.1, 6.3 Hz, 1H), 7.12 (dt, J=8.3, 4.6 Hz, 1H), 7.09-7.04 (m, 2H), 7.04-6.88 (m, 1H), 5.02 (s, 2H), 3.40 (d, J=64.6 Hz, 3H), 2.98-2.69 (m, 3H), 1.96 (d, J=11.2 Hz, 2H), 1.84 (s, 2H), 0.93-0.80 (m, 5H);

LRMS (ES) m/z 529.3 ($M^{+}$+1).

Example 97: Synthesis of Compound 4141, 1-cyclobutyl-N-((7-(5-(difluoromethyl)-1,3,4-oxadiazol-2-yl)imidazo[1,2-a]pyridin-2-yl)methyl)-N-(3-fluorophenyl)piperidine-4-carboxamide

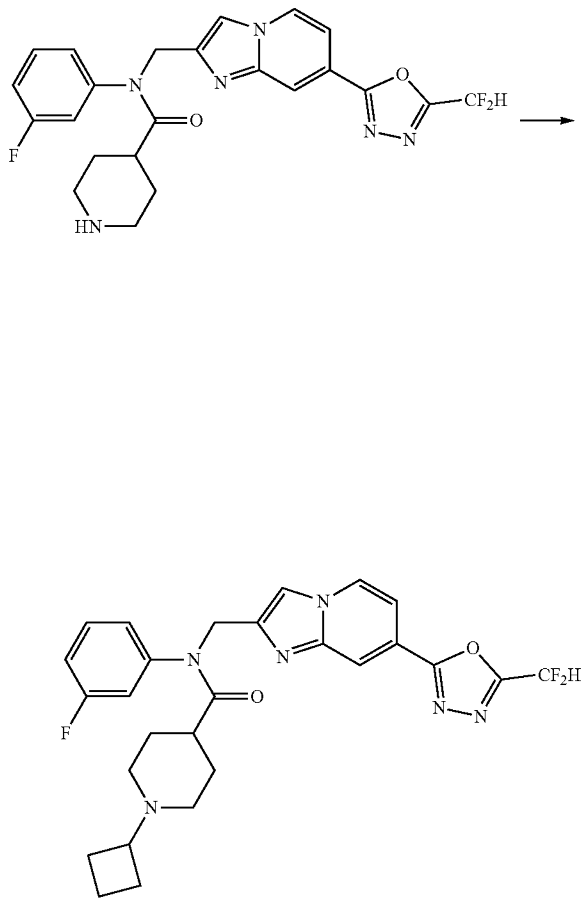

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, cyclobutanone (0.018 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.022 g, 32.9%) as a yellow solid.

$^1$H NMR (700 MHz, $CDCl_3$) δ 8.29 (d, J=1.6 Hz, 1H), 8.24 (dd, J=7.1, 1.0 Hz, 1H), 7.78 (s, 1H), 7.55 (dd, J=7.1, 1.7 Hz, 1H), 7.39 (td, J=8.1, 6.3 Hz, 1H), 7.10 (dt, J=8.7, 4.7 Hz, 1H), 7.07-6.87 (m, 3H), 5.02 (s, 2H), 2.87 (s, 2H), 2.61 (s, 1H), 2.30-2.19 (m, 1H), 1.98 (s, 2H), 1.90 (d, J=10.9 Hz, 4H), 1.65 (s, 4H), 1.56-1.44 (m, 2H);

LRMS (ES) m/z 525.2 ($M^+$+1).

Example 98: Synthesis of Compound 4142, N-((7-(5-(difluoromethyl)-1,3,4-oxadiazol-2-yl)imidazo[1,2-a]pyridin-2-yl)methyl)-N-(3-fluorophenyl)-1-(oxetan-3-yl)piperidine-4-carboxamide

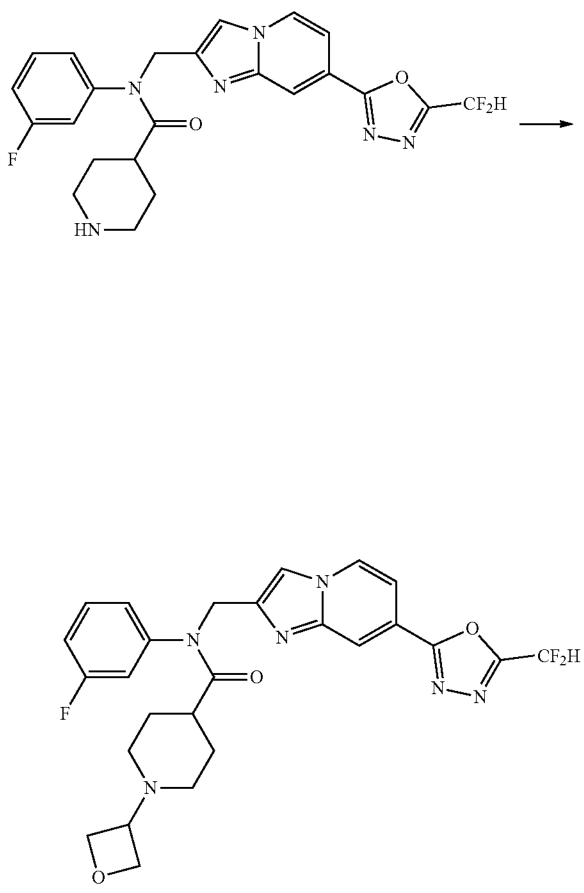

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, oxetan-3-one (0.018 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20x20x1 mm; dichloromethane/methanol=0% to 10%) and concentrated to obtain the title compound (0.032 g, 47.7%) as a yellow solid.

$^1$H NMR (700 MHz, $CDCl_3$) δ 8.30 (dd, J=1.8, 0.9 Hz, 1H), 8.24 (dd, J=7.1, 1.0 Hz, 1H), 7.78 (s, 1H), 7.55 (dd, J=7.1, 1.7 Hz, 1H), 7.40 (td, J=8.1, 6.3 Hz, 1H), 7.15-7.09 (m, 1H), 7.09-6.84 (m, 3H), 5.02 (s, 2H), 4.61 (s, 4H), 3.40 (s, 1H), 2.73 (s, 2H), 2.34-2.21 (m, 1H), 1.93 (d, J=12.2 Hz, 2H), 1.66 (s, 4H);

LRMS (ES) m/z 527.0 ($M^+$+1).

Example 99: Synthesis of Compound 4143, 1-cyclohexyl-N-((7-(5-(difluoromethyl)-1,3,4-oxadiazol-2-yl)imidazo[1,2-a]pyridin-2-yl)methyl)-N-(3-fluorophenyl)piperidine-4-carboxamide

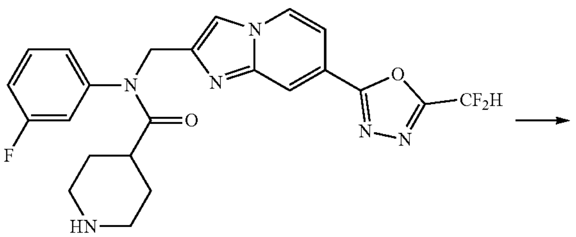

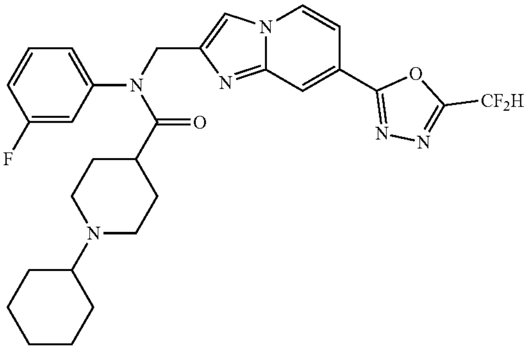

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, cyclohexanone (0.025 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.014 g, 19.9%) as a yellow solid.

$^1H$ NMR (700 MHz, $CDCl_3$) δ 8.32-8.26 (m, 1H), 8.23 (dd, J=7.1, 1.0 Hz, 1H), 7.78 (s, 1H), 7.53 (dd, J=7.1, 1.7 Hz, 1H), 7.38 (td, J=8.1, 6.3 Hz, 1H), 7.13-6.85 (m, 4H), 5.01 (s, 2H), 2.92 (s, 2H), 2.35-2.19 (m, 2H), 2.10-1.95 (m, 2H), 1.92-1.73 (m, 8H), 1.61 (d, J=13.1 Hz, 2H), 1.21 (d, J=14.6 Hz, 4H);

LRMS (ES) m/z 553.1 ($M^+$+1).

Example 100: Synthesis of Compound 4144, N-((7-(5-(difluoromethyl)-1,3,4-oxadiazol-2-yl)imidazo[1,2-a]pyridin-2-yl)methyl)-N-(3-fluorophenyl)-1-(tetrahydro-2H-pyran-4-yl)piperidine-4-carboxamide

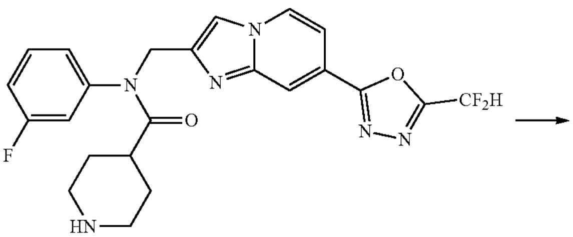

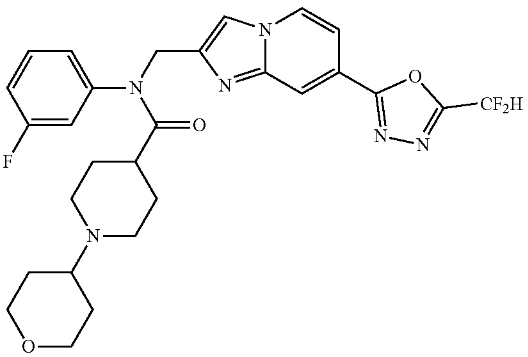

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, tetrahydro-4H-pyran-4-one (0.026 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.016 g, 22.6%) as a yellow solid.

$^1H$ NMR (700 MHz, $CDCl_3$) δ 8.33-8.27 (m, 1H), 8.24 (dd, J=7.1, 1.0 Hz, 1H), 7.83-7.74 (m, 1H), 7.55 (dd, J=7.1, 1.7 Hz, 1H), 7.40 (td, J=8.1, 6.3 Hz, 1H), 7.10 (ddd, J=8.4, 5.5, 2.2 Hz, 1H), 7.09-6.86 (m, 3H), 5.02 (s, 2H), 4.04-3.95 (m, 2H), 3.35 (t, J=11.7 Hz, 2H), 2.93 (s, 2H), 2.45 (d, J=22.4 Hz, 1H), 2.31-2.20 (m, 1H), 1.89 (d, J=10.6 Hz, 4H), 1.67 (s, 4H), 1.56 (d, J=11.5 Hz, 2H);

LRMS (ES) m/z 555.3 ($M^+$+1).

Example 101: Synthesis of Compound 4145, 1-(4,4-difluorocyclohexyl)-N-((7-(5-(difluoromethyl)-1,3,4-oxadiazol-2-yl)imidazo[1,2-a]pyridin-2-yl)methyl)-N-(3-fluorophenyl)piperidine-4-carboxamide

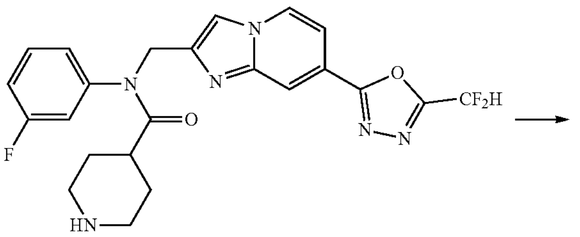

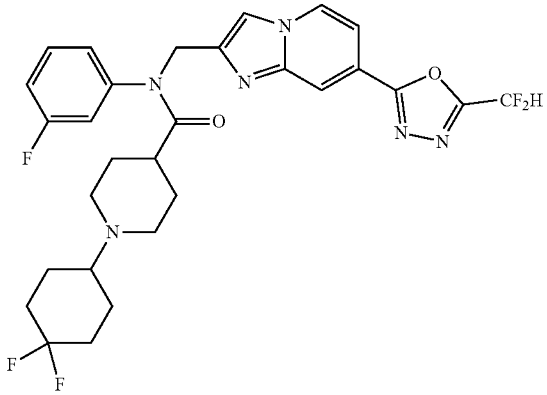

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, 4,4-difluorocyclohexan-1-one (0.034 g, 0.255 mmol), acetic acid (0.007 mL, 0.128 mmol), and sodium triacetoxyborohydride (0.081 g, 0.383 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.026 g, 34.6%) as a yellow solid.

$^1$H NMR (400 MHz, $CDCl_3$) δ 8.31-8.27 (m, 1H), 8.23 (dd, J=7.1, 1.0 Hz, 1H), 7.78 (s, 1H), 7.53 (dd, J=7.1, 1.7 Hz, 1H), 7.39 (td, J=8.1, 6.3 Hz, 1H), 7.15-6.77 (m, 4H), 5.01 (s, 2H), 2.87 (s, 2H), 2.36 (s, 1H), 2.30-2.21 (m, 1H), 2.10 (d, J=11.6 Hz, 2H), 1.96 (s, 2H), 1.92-1.54 (m, 10H);

LRMS (ES) m/z 589.2 ($M^+$+1).

Example 102: Synthesis of Compound 4146, 1-acetyl-N-((7-(5-(difluoromethyl)-1,3,4-oxadiazol-2-yl)imidazo[1,2-a]pyridin-2-yl)methyl)-N-(3-fluorophenyl)piperidine-4-carboxamide

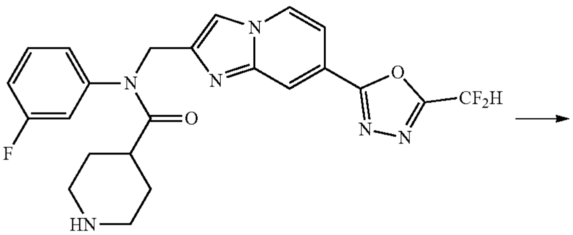

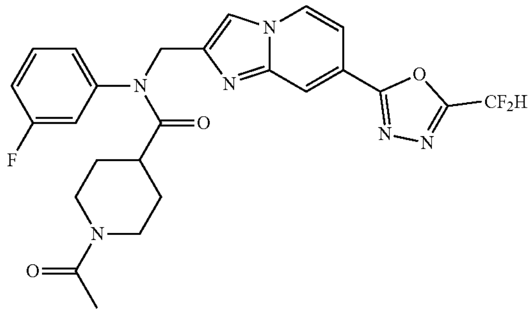

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, acetyl chloride (0.018 mL, 0.255 mmol), and triethylamine (0.053 mL, 0.383 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.021 g, 32.1%) as a yellow solid.

$^1$H NMR (700 MHz, $CDCl_3$) δ 8.46 (s, 1H), 8.34-8.26 (m, 1H), 7.82 (s, 1H), 7.69 (dd, J=7.1, 1.7 Hz, 1H), 7.45 (td, J=8.2, 6.3 Hz, 1H), 7.17-7.13 (m, 2H), 7.12-7.09 (m, 1H), 6.97 (t, J=51.7 Hz, 1H), 5.06 (s, 2H), 4.55 (d, J=13.6 Hz, 1H), 3.80 (d, J=13.6 Hz, 1H), 2.88 (t, J=13.8 Hz, 1H), 2.53 (d, J=11.2 Hz, 1H), 2.44-2.34 (m, 1H), 2.07 (s, 3H), 1.84-1.63 (m, 4H);

LRMS (ES) m/z 513.0 ($M^+$+1).

Example 103: Synthesis of Compound 4147, N-((7-(5-(difluoromethyl)-1,3,4-oxadiazol-2-yl)imidazo[1,2-a]pyridin-2-yl)methyl)-N-(3-fluorophenyl)-1-propionylpiperidine-4-carboxamide

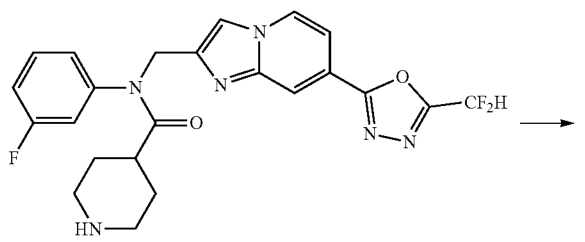

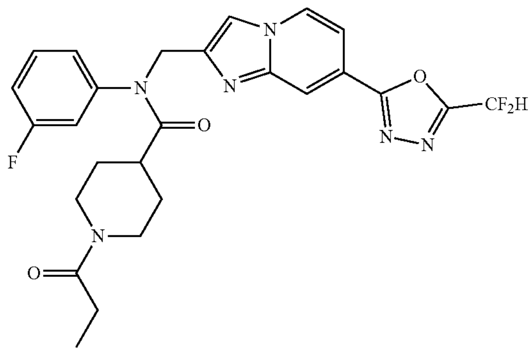

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, propionyl chloride (0.024 g, 0.255 mmol), and triethylamine (0.053 mL, 0.383 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.010 g, 14.9%) as a yellow solid.

$^1H$ NMR (700 MHz, $CDCl_3$) δ 8.33 (s, 1H), 8.25 (dd, J=7.1, 1.0 Hz, 1H), 7.78 (s, 1H), 7.57 (dd, J=7.2, 1.6 Hz, 1H), 7.42 (td, J=8.1, 6.2 Hz, 1H), 7.16-7.05 (m, 3H), 6.96 (t, J=51.7 Hz, 1H), 5.08-4.94 (m, 2H), 4.57 (dd, J=11.2, 6.8 Hz, 1H), 3.83 (d, J=13.7 Hz, 1H), 2.88-2.74 (m, 1H), 2.52 (td, J=11.8, 11.0, 5.7 Hz, 1H), 2.33 (dddd, J=23.0, 17.7, 15.3, 10.0 Hz, 4H), 1.83-1.74 (m, 1H), 1.74-1.61 (m, 2H), 1.13 (t, J=7.5 Hz, 3H);

LRMS (ES) m/z 527.0 ($M^+$+1).

Example 104: Synthesis of Compound 4149, N-((7-(5-(difluoromethyl)-1,3,4-oxadiazol-2-yl)imidazo[1,2-a]pyridin-2-yl)methyl)-N-(3-fluorophenyl)-1-(2-hydroxyacetyl)piperidine-4-carboxamide

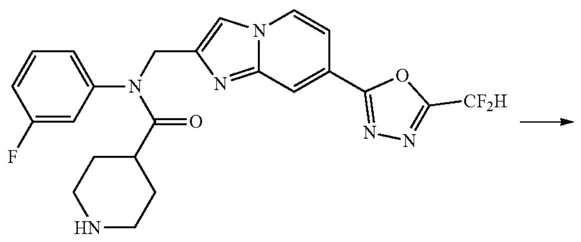

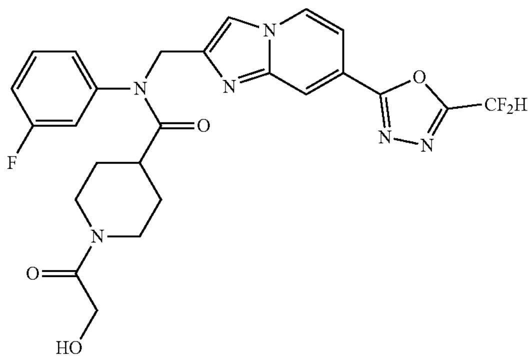

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.060 g, 0.128 mmol) prepared in step 3 of Example 93, 2-hydroxyacetyl chloride (0.024 g, 0.255 mmol), 1-[bis(dimethylamino)methylene]-1H-1, 2, 3-triazolo[4,5-b]pyridinium 3-oxide hexafluorophosphate (HATU, 0.097 g, 0.255 mmol), and N,N-diisopropylethylamine (0.044 mL, 0.255 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.017 g, 25.2%) as a yellow solid.

$^1H$ NMR (400 MHz, $CDCl_3$) δ 8.31 (dt, J=1.7, 0.9 Hz, 1H), 8.24 (dd, J=7.1, 1.0 Hz, 1H), 7.76 (s, 1H), 7.55 (dd, J=7.1, 1.7 Hz, 1H), 7.42 (td, J=8.3, 6.3 Hz, 1H), 7.16-6.78 (m, 4H), 5.01 (s, 2H), 4.48 (d, J=13.7 Hz, 1H), 4.18-4.01 (m, 2H), 3.48 (d, J=13.7 Hz, 1H), 2.86-2.73 (m, 1H), 2.63-2.44 (m, 2H), 1.84-1.62 (m, 4H);

LRMS (ES) m/z 529.0 ($M^+$+1).

Example 105: Synthesis of Compound 4150, 1-(cyclobutanecarbonyl)-N-((7-(5-(difluoromethyl)-1,3,4-oxadiazol-2-yl)imidazo[1,2-a]pyridine-2-yl)methyl)-N-(3-fluorophenyl)piperidine-4-carboxamide

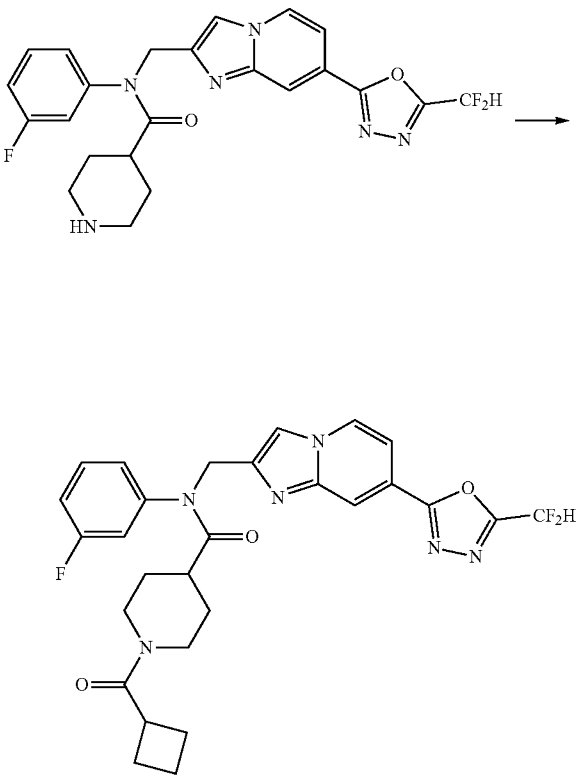

N-((7-(5-(difluoromethyl)-1,3,4-oxadiazol-2-yl)imidazo[1,2-a]pyridin-2-yl)methyl)-N-(3-fluorophenyl)piperidine-4-sulfonamide (0.050 g, 0.099 mmol) prepared in step 3 of Example 93, cyclobutanecarbonyl chloride (0.023 g, 0.197 mmol), and triethylamine (0.041 mL, 0.296 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.011 g, 20.0%) as a yellow gel.

$^1H$ NMR (400 MHz, $CDCl_3$) δ 8.31 (d, J=1.6 Hz, 1H), 8.24 (dd, J=1.0, 7.1 Hz, 1H), 7.77 (s, 1H), 7.55 (dt, J=1.2, 7.0 Hz, 1H), 7.41 (td, J=6.3, 8.3 Hz, 1H), 7.16-6.80 (m, 4H), 5.01 (d, J=3.4 Hz, 2H), 4.53 (d, J=13.3 Hz, 1H), 3.68 (d, J=13.6 Hz, 1H), 3.21 (p, J=8.5 Hz, 1H), 2.74 (t, J=12.7 Hz, 1H), 2.48 (d, J=12.2 Hz, 1H), 2.34 (ddd, J=9.3, 11.8, 20.7 Hz, 3H), 2.12 (ddt, J=3.6, 8.2, 11.8 Hz, 2H), 2.00-1.59 (m, 6H);

LRMS (ES) m/z 553.4 ($M^+$+1).

Example 106: Synthesis of Compound 4151, N-((7-(5-(difluoromethyl)-1,3,4-oxadiazol-2-yl)imidazo[1,2-a]pyridin-2-yl)methyl)-N-(3-fluorophenyl)-1-(oxetane-3-carbonyl)piperidine-4-carboxamide

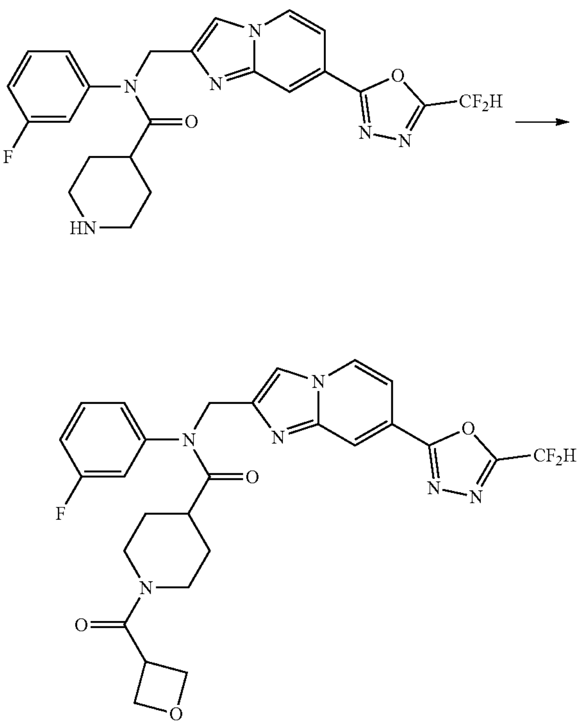

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, oxetane-3-carboxylic acid (0.022 g, 0.213 mmol), 1-[bis(dimethylamino)methylene]-1H-1, 2, 3-triazolo[4,5-b]pyridinium 3-oxide hexafluorophosphate (HATU, 0.061 g, 0.159 mmol), and triethylamine (0.044 mL, 0.319 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated, and then the obtained product was again purified by chromatography ($SiO_2$ plate, 20×20×1 mm; methanol/1%-dichloromethane aqueous solution=0% to 7%) and concentrated to obtain the title compound (0.016 g, 27.3%) as a yellow solid.

$^1H$ NMR (400 MHz, $CDCl_3$) δ 8.34-8.28 (m, 1H), 8.24 (dd, J=1.0, 7.1 Hz, 1H), 7.76 (s, 1H), 7.56 (dd, J=1.7, 7.2 Hz, 1H), 7.42 (td, J=6.2, 8.2 Hz, 1H), 7.16-6.82 (m, 4H), 5.01 (d, J=1.6 Hz, 2H), 4.93 (dd, J=5.9, 7.2 Hz, 1H), 4.86 (dd, J=5.9, 7.2 Hz, 1H), 4.77 (td, J=5.9, 8.6 Hz, 2H), 4.53 (d, J=13.4 Hz, 1H), 4.01-3.91 (m, 1H), 3.31 (d, J=13.5 Hz, 1H), 2.77 (t, J=11.9 Hz, 1H), 2.56-2.38 (m, 2H), 1.71 (d, J=18.8 Hz, 4H);

LRMS (ES) m/z 555.4 ($M^+$+1).

Example 107: Synthesis of Compound 4152, N-((7-(5-(difluoromethyl)-1,3,4-oxadiazol-2-yl)imidazo[1,2-a]pyridin-2-yl)methyl)-N-(3-fluorophenyl)-1-(2,2,2-trifluoroacetyl)piperidine-4-carboxamide

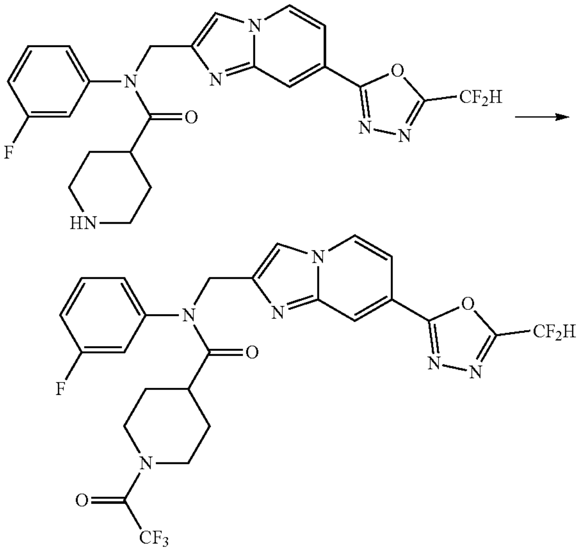

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, 2,2,2-trifluoroacetic anhydride (0.045 g, 0.213 mmol), and triethylamine (0.044 mL, 0.319 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.020 g, 33.6%) as a brown solid.

$^1$H NMR (400 MHz, $CDCl_3$) δ 8.33-8.28 (m, 1H), 8.24 (dd, J=1.0, 7.1 Hz, 1H), 7.77 (s, 1H), 7.56 (dd, J=1.7, 7.2 Hz, 1H), 7.43 (td, J=6.3, 8.3 Hz, 1H), 7.17-6.77 (m, 4H), 5.01 (s, 2H), 4.46-4.34 (m, 1H), 3.98 (d, J=14.0 Hz, 1H), 3.06-2.94 (m, 1H), 2.74-2.53 (m, 1H), 1.94-1.68 (m, 4H);

LRMS (ES) m/z 566.7 ($M^+$+1).

Example 108: Synthesis of Compound 4153, N-((7-(5-(difluoromethyl)-1,3,4-oxadiazol-2-yl)imidazo[1,2-a]pyridin-2-yl)methyl)-N-(3-fluorophenyl)-1-(methylsulfonyl)piperidine-4-carboxamide

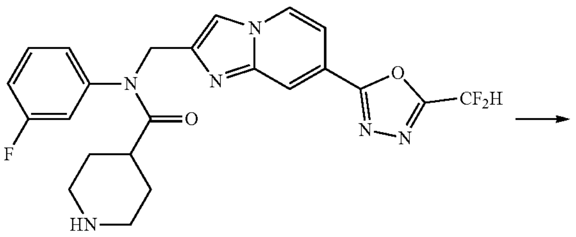

-continued

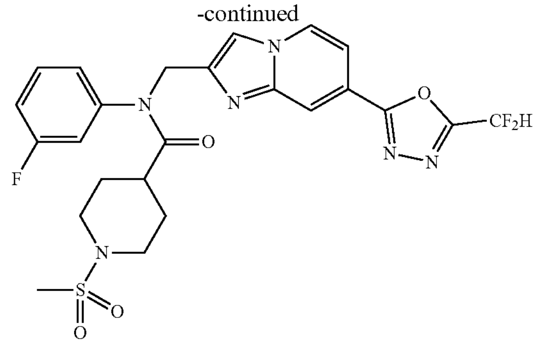

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, methanesulfonyl chloride (0.016 mL, 0.213 mmol), and triethylamine (0.044 mL, 0.319 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.005 g, 8.7%) as a brown solid.

$^1$H NMR (400 MHz, $CDCl_3$) δ 8.32 (d, J=1.5 Hz, 1H), 8.25 (dd, J=1.0, 7.2 Hz, 1H), 7.78 (s, 1H), 7.57 (dd, J=1.7, 7.1 Hz, 1H), 7.46-7.39 (m, 1H), 7.16-6.77 (m, 4H), 5.02 (s, 2H), 3.76 (d, J=12.3 Hz, 2H), 2.75 (s, 3H), 2.57 (t, J=11.6 Hz, 2H), 2.40 (d, J=11.4 Hz, 1H), 2.01-1.84 (m, 2H), 1.75 (d, J=13.5 Hz, 2H);

LRMS (ES) m/z 549.4 ($M^+$+1).

Example 109: Synthesis of Compound 4154, methyl 4-(((7-(5-(difluoromethyl)-1,3,4-oxadiazol-2-yl)imidazo[1,2-a]pyridin-2-yl)methyl)(3-fluorophenyl)carbamoyl)piperidine-1-carboxylate

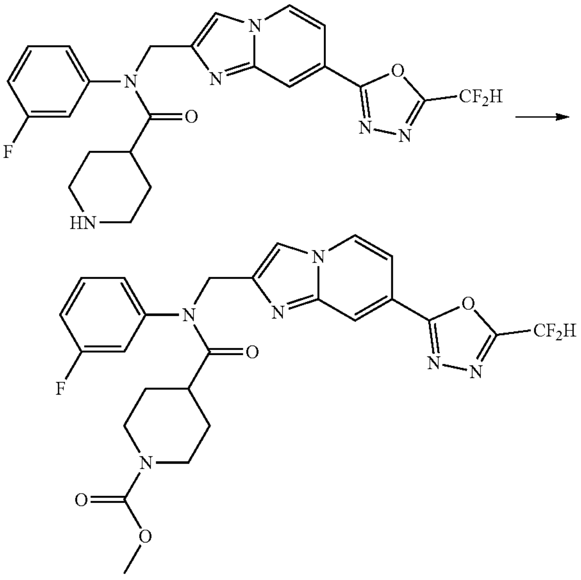

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, methyl carbonochloridate (0.020 g, 0.213 mmol), and triethylamine (0.044 mL, 0.319 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.021 g, 35.2%) as a red solid.

$^1$H NMR (400 MHz, $CDCl_3$) δ 8.32-8.27 (m, 1H), 8.23 (dd, J=1.0, 7.2 Hz, 1H), 7.77 (s, 1H), 7.54 (dd, J=1.7, 7.1 Hz, 1H), 7.40 (td, J=6.4, 8.3 Hz, 1H), 7.16-6.80 (m, 4H), 5.01 (s, 2H), 4.10 (s, 2H), 3.67 (s, 3H), 2.65-2.37 (m, 3H), 1.75 (qd, J=4.4, 11.9, 12.4 Hz, 2H), 1.62 (d, J=13.1 Hz, 2H);

LRMS (ES) m/z 529.1 ($M^+$+1).

Example 110: Synthesis of Compound 4155, N4-((7-(5-(difluoromethyl)-1,3,4-oxadiazol-2-yl)imidazo[1,2-a]pyridin-2-yl)methyl)-N4-(3-fluorophenyl)-N1,N1-dimethylpiperidine-1,4-dicarboxamide

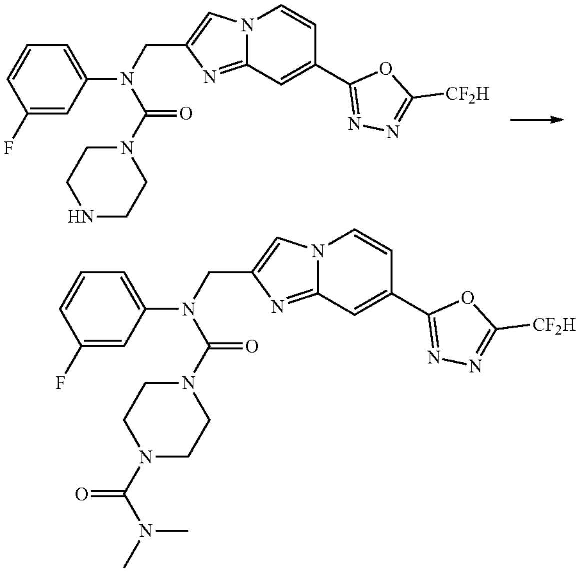

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, dimethylcarbamic chloride (0.023 g, 0.213 mmol), and triethylamine (0.044 mL, 0.319 mmol) were dissolved in dichloromethane (1 mL) at room temperature, and the resulting solution was stirred at the same temperature for 18 hours. An saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; methanol/dichloromethane=0% to 7%) and concentrated to obtain the title compound (0.019 g, 33.5%) as a pale red solid.

$^1$H NMR (400 MHz, $CDCl_3$) δ 8.32-8.28 (m, 1H), 8.24 (dd, J=1.0, 7.1 Hz, 1H), 7.78 (s, 1H), 7.55 (dd, J=1.7, 7.1 Hz, 1H), 7.41 (td, J=6.4, 8.3 Hz, 1H), 7.15-6.81 (m, 4H), 5.02 (s, 2H), 3.61 (d, J=13.2 Hz, 2H), 2.80 (s, 6H), 2.57-2.37 (m, 3H), 1.82 (qd, J=4.0, 12.6 Hz, 2H), 1.64 (d, J=12.8 Hz, 2H);

LRMS (ES) m/z 542.0 ($M^+$+1).

Example 111: Synthesis of Compound 4156, N-((7-(5-(difluoromethyl)-1,3,4-oxadiazol-2-yl)imidazo[1,2-a]pyridin-2-yl)methyl)-N-(3-fluorophenyl)-1-(pyridin-2-yl)piperidine-4-carboxamide

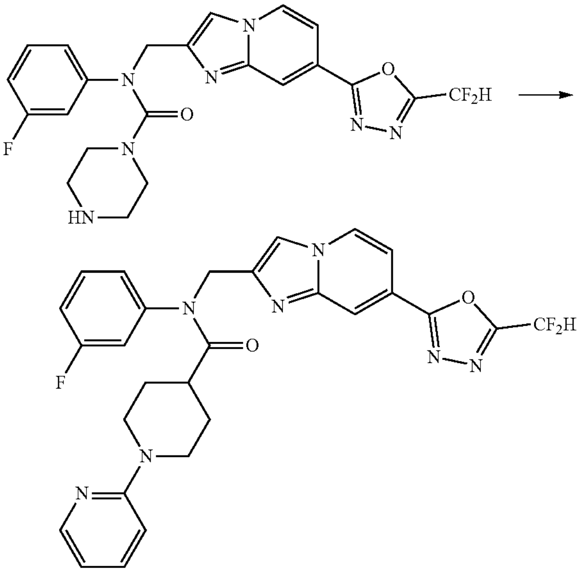

N-((7-(5-(Difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, 2-bromopyridine (0.034 g, 0.213 mmol), RuPhos palladium G2 (0.004 g, 0.005 mmol), and cesium carbonate (0.069 g, 0.213 mmol) were dissolved in 1,4-dioxane (1 mL) at room temperature, and the resulting solution was stirred at 120° C. for 18 hours. Then, the reaction was terminated by lowering the temperature to room temperature. An saturated aqueous sodium hydrogen carbonate solution was poured into the concentrate obtained by removing the solvent from the reaction mixture under reduced pressure, followed by extraction with ethyl acetate. The organic layer was washed with a saturated aqueous sodium chloride solution, dried over anhydrous magnesium sulfate, filtered, and concentrated under reduced pressure. The concentrate was purified by chromatography ($SiO_2$ plate, 20×20×1 mm; methanol/dichloromethane=0% to 7%) and concentrated to obtain the title compound (0.013 g, 22.2%) as a brown solid.

$^1$H NMR (400 MHz, $CDCl_3$) δ 8.33-8.29 (m, 1H), 8.23 (dd, J=1.0, 7.1 Hz, 1H), 8.16 (ddd, J=0.8, 2.0, 5.0 Hz, 1H), 7.79 (s, 1H), 7.55 (dd, J=1.7, 7.1 Hz, 1H), 7.48-7.36 (m, 2H), 7.16-6.80 (m, 4H), 6.65-6.55 (m, 2H), 5.03 (s, 2H), 4.26 (d, J=13.5 Hz, 2H), 2.65 (t, J=12.6 Hz, 2H), 2.53 (s, 1H), 1.89 (qd, J=4.1, 12.5 Hz, 2H), 1.72 (d, J=13.1 Hz, 2H);

LRMS (ES) m/z 548.2 ($M^+$+1).

Example 112: Synthesis of Compound 4157, N-((7-(5-(difluoromethyl)-1,3,4-oxadiazol-2-yl)imidazo[1,2-a]pyridin-2-yl)methyl)-N-(3-fluorophenyl)-1-(pyrimidin-2-yl)piperidine-4-carboxamide

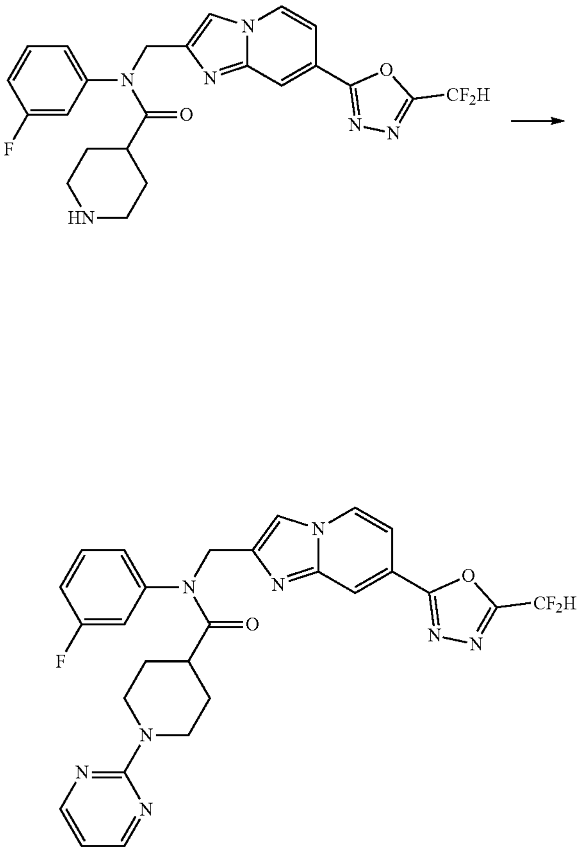

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.050 g, 0.106 mmol) prepared in step 3 of Example 93, 2-chloropyrimidine (0.024 g, 0.213 mmol), and potassium carbonate (0.044 g, 0.319 mmol) were dissolved in N,N-dimethylformamide (0.5 mL)/acetonitrile (0.5 mL) at room temperature, and the resulting solution was stirred at the same temperature for 18 hours. An saturated aqueous sodium hydrogen carbonate solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. Dichloromethane (3 mL) was added to the concentrate, followed by stirring, and the precipitated solid was filtered, washed with dichloromethane, and dried to obtain the title compound (0.018 g, 30.5%) as a white solid.

$^1$H NMR (400 MHz, $CDCl_3$) δ 8.31-8.26 (m, 3H), 8.23 (dd, J=0.9, 7.1 Hz, 1H), 7.78 (s, 1H), 7.54 (dd, J=1.7, 7.1 Hz, 1H), 7.43 (td, J=6.5, 8.3 Hz, 1H), 7.15-6.81 (m, 4H), 6.46 (t, J=4.7 Hz, 1H), 5.02 (s, 2H), 4.73 (dt, J=3.5, 13.4 Hz, 2H), 2.69 (t, J=13.0 Hz, 2H), 2.56 (d, J=11.5 Hz, 1H), 1.83 (qd, J=4.2, 12.0, 12.5 Hz, 2H), 1.71 (d, J=13.0 Hz, 2H);

LRMS (ES) m/z 549.4 ($M^+$+1).

Example 113: Synthesis of Compound 4158, N-((7-(5-(difluoromethyl)-1,3,4-oxadiazol-2-yl)imidazo[1,2-a]pyridin-2-yl)methyl)-1-methyl-N-phenylazetidine-3-carboxamide

[Step 1] Synthesis of tert-butyl 3-(chlorocarbonyl) azetidine-1-carboxylate

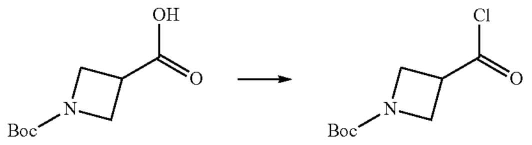 [SMILES: CC(C)(C)OC(=O)N1CC(C(=O)O)C1 ; CC(C)(C)OC(=O)N1CC(C(=O)Cl)C1]

1-(Tert-butoxycarbonyl) azetidine-3-carboxylic acid (1.200 g, 5.964 mmol) was dissolved in dichloromethane (150 mL), and oxalyl chloride (2.00 M solution in DCM, 3.578 mL, 7.156 mmol) and N,N-dimethylformamide (0.046 mL, 0.596 mmol) were added at 0° C. and stirred at room temperature for 2 hours. After removing the solvent from the reaction mixture under reduced pressure, the title compound (1.250 g, 95.4%) was obtained as a colorless oil without further purification.

[Step 2] Synthesis of tert-butyl 3-(((7-(5-(difluoromethyl)-1,3,4-oxadiazol-2-yl)imidazo[1,2-a]pyridin-2-yl)methyl)(phenyl)carbamoyl) azetidine-1-carboxylate

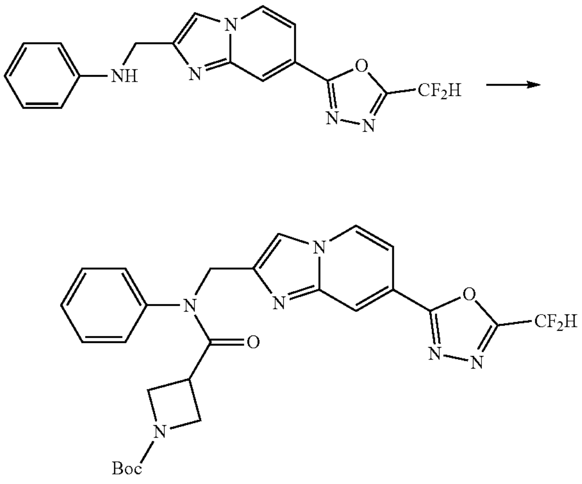 [SMILES: FC(F)c1nnc(-c2ccn3cc(CNc4ccccc4)nc3c2)o1 ; CC(C)(C)OC(=O)N1CC(C(=O)N(Cc2cn3ccc(-c4nnc(C(F)F)o4)cc3n2)c2ccccc2)C1]

To a solution in which N-((7-(5-(difluoromethyl)-1,3,4-oxadiazol-2-yl)imidazo[1,2-a]pyridin-2-yl)methyl)aniline (1.500 g, 4.395 mmol) prepared in Example 14 and triethylamine (1.838 mL, 13.184 mmol) were dissolved in dichloromethane (150 mL) at room temperature, tert-butyl 3-(chlorocarbonyl) azetidine-1-carboxylate (1.255 g, 5.713 mmol) was added and stirred at the same temperature for 16 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by column chromatography ($SiO_2$, 40 g cartridge; ethyl acetate/hexane=5% to 60%) and concentrated to obtain the title compound (1.600 g, 69.4%) as a beige solid.

[Step 3] Synthesis of N-((7-(5-(difluoromethyl)-1,3,4-oxadiazol-2-yl)imidazo[1,2-a]pyridin-2-yl)methyl)-N-phenylazetidine-3-carboxamide

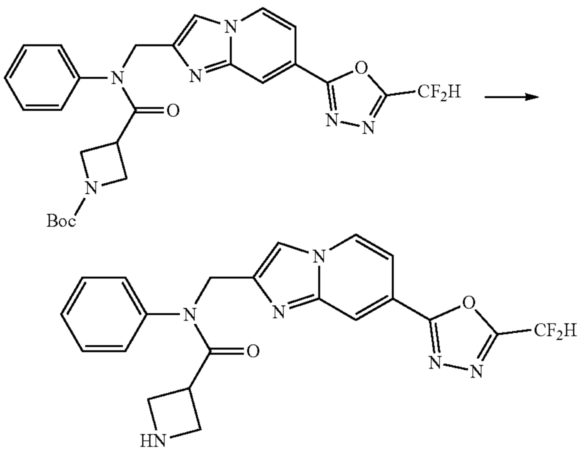

Tert-butyl 3-(((7-(5-(difluoromethyl)-1,3,4-oxadiazol-2-yl)imidazo[1,2-a]pyridin-2-yl)methyl)(phenyl)carbamoyl)azetidine-1-carboxylate (0.600 g, 1.144 mmol) prepared in step 2 and trifluoroacetic acid (1.752 mL, 22.878 mmol) were dissolved in dichloromethane (7 mL) at room temperature, and the resulting solution was stirred at the same temperature for 2 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (0.485 g, 99.9%) was obtained as a brown gel without further purification.

[Step 4] Synthesis of Compound 4158

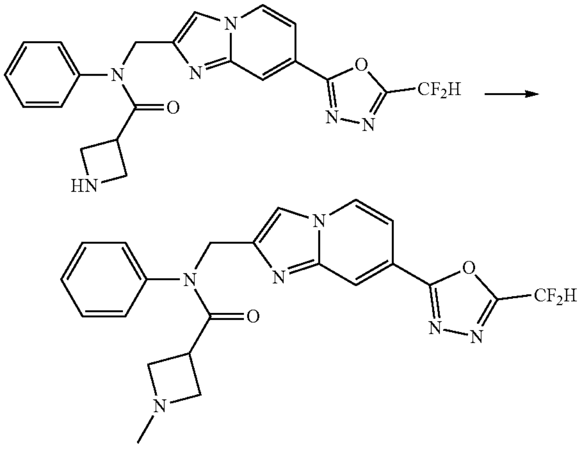

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3, formaldehyde (0.007 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.014 g, 27.1%) as a white solid.

$^1$H NMR (400 MHz, $CDCl_3$) δ 8.31 (dt, J=1.8, 0.8 Hz, 1H), 8.23 (dd, J=7.1, 1.0 Hz, 1H), 7.79 (s, 1H), 7.54 (dd, J=7.1, 1.7 Hz, 1H), 7.44-7.34 (m, 3H), 7.19-7.13 (m, 2H), 6.95 (t, J=51.7 Hz, 1H), 5.05 (s, 2H), 3.39-3.28 (m, 5H), 2.35 (s, 3H);

LRMS (ES) m/z 439.3 ($M^+$+1).

Example 114: Synthesis of Compound 4159, N-((7-(5-(difluoromethyl)-1,3,4-oxadiazol-2-yl)imidazo[1,2-a]pyridin-2-yl)methyl)-1-ethyl-N-phenylazetidine-3-carboxamide

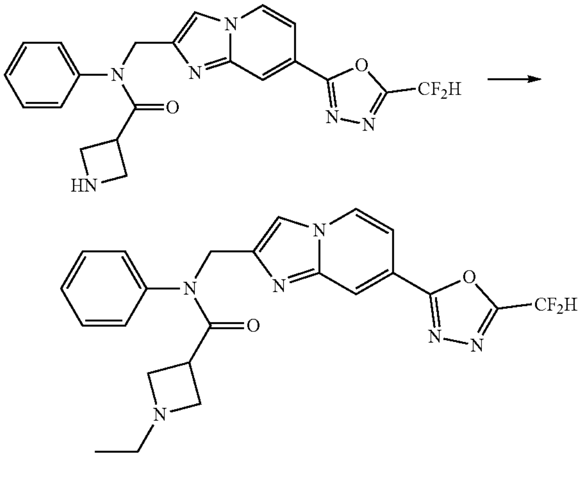

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, acetaldehyde (0.010 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.022 g, 41.3%) as a white solid.

$^1$H NMR (400 MHz, $CDCl_3$) δ 8.31 (dt, J=1.7, 0.8 Hz, 1H), 8.23 (dd, J=7.1, 1.0 Hz, 1H), 7.78 (s, 1H), 7.54 (dd, J=7.1, 1.7 Hz, 1H), 7.45-7.34 (m, 3H), 7.21-7.13 (m, 2H), 6.95 (t, J=51.7 Hz, 1H), 5.06 (s, 2H), 3.39 (s, 5H), 2.60 (s, 2H), 0.99 (t, J=7.1 Hz, 3H);

LRMS (ES) m/z 453.4 ($M^+$+1).

Example 115: Synthesis of Compound 4160, N-((7-(5-(difluoromethyl)-1,3,4-oxadiazol-2-yl)imidazo[1,2-a]pyridin-2-yl)methyl)-1-isopropyl-N-phenylazetidine-3-carboxamide

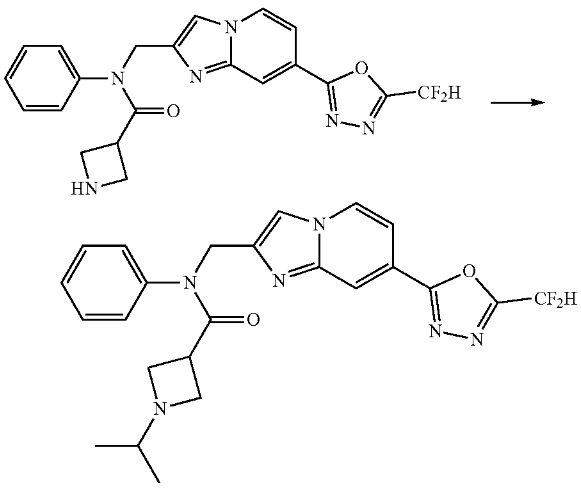

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, propan-2-one (0.014 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 43.7%) as a white solid.

$^1H$ NMR (400 MHz, $CDCl_3$) δ 8.31 (dt, J=1.8, 0.8 Hz, 1H), 8.23 (dd, J=7.2, 1.0 Hz, 1H), 7.76 (s, 1H), 7.54 (dd, J=7.1, 1.7 Hz, 1H), 7.44-7.35 (m, 3H), 7.20-7.13 (m, 2H), 6.95 (t, J=51.7 Hz, 1H), 5.06 (s, 2H), 3.40 (s, 5H), 2.63 (s, 1H), 1.01 (d, J=5.4 Hz, 6H);

LRMS (ES) m/z 467.4 ($M^+$+1).

Example 116: Synthesis of Compound 4161, N-((7-(5-(difluoromethyl)-1,3,4-oxadiazol-2-yl)imidazo[1,2-a]pyridin-2-yl)methyl)-1-(1-hydroxypropan-2-yl)-N-phenylazetidine-3-carboxamide

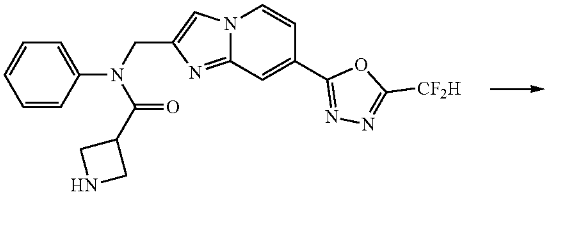

-continued

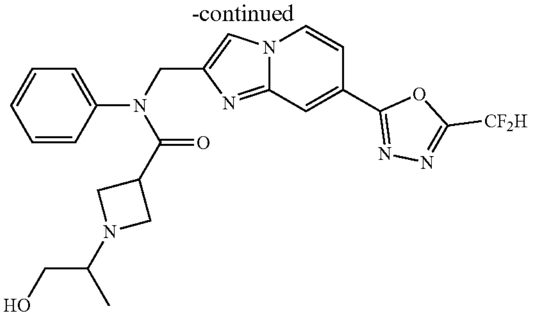

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, 1-hydroxypropan-2-one (0.017 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.029 g, 51.0%) as a white solid.

$^1H$ NMR (400 MHz, $CDCl_3$) δ 8.32 (dt, J=1.7, 0.8 Hz, 1H), 8.24 (dd, J=7.1, 1.0 Hz, 1H), 7.80-7.73 (m, 1H), 7.55 (dd, J=7.1, 1.7 Hz, 1H), 7.44-7.36 (m, 3H), 7.20-7.14 (m, 2H), 6.95 (t, J=51.7 Hz, 1H), 5.06 (s, 2H), 3.64-3.28 (m, 7H), 2.64 (s, 1H), 1.02 (d, J=6.5 Hz, 3H);

LRMS (ES) m/z 483.4 ($M^+$+1).

Example 117: Synthesis of Compound 4162, 1-cyclobutyl-N-((7-(5-(difluoromethyl)-1,3,4-oxadiazol-2-yl)imidazo[1,2-a]pyridin-2-yl)methyl)-N-phenylazetidine-3-carboxamide

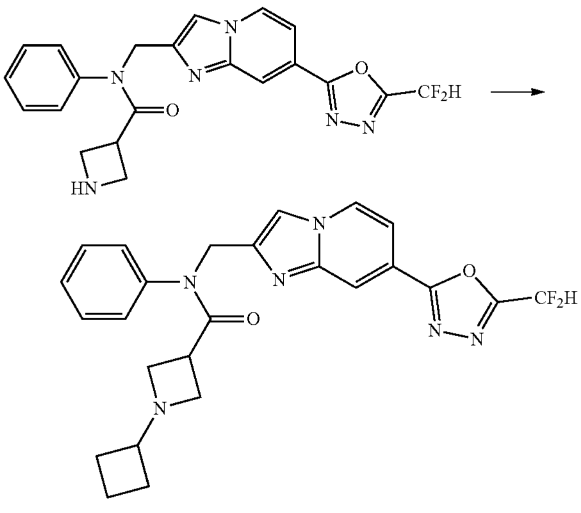

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, cyclobutanone (0.017 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.018 g, 31.9%) as a white solid.

$^1H$ NMR (400 MHz, $CDCl_3$) δ 8.32 (dt, J=1.7, 0.8 Hz, 1H), 8.23 (dd, J=7.2, 1.0 Hz, 1H), 7.76 (s, 1H), 7.55 (dd, J=7.1, 1.7 Hz, 1H), 7.44-7.35 (m, 3H), 7.16 (dd, J=7.8, 1.9 Hz, 2H), 6.95 (t, J=51.7 Hz, 1H), 5.06 (s, 2H), 3.60-3.28 (m, 5H), 2.04 (d, J=11.2 Hz, 4H), 1.84 (s, 1H), 1.71 (q, J=9.2 Hz, 2H);

LRMS (ES) m/z 479.0 ($M^+$+1).

Example 118: Synthesis of Compound 4163, N-((7-(5-(difluoromethyl)-1,3,4-oxadiazol-2-yl)imidazo[1,2-a]pyridin-2-yl)methyl)-1-(oxetan-3-yl)-N-phenylazetidine-3-carboxamide

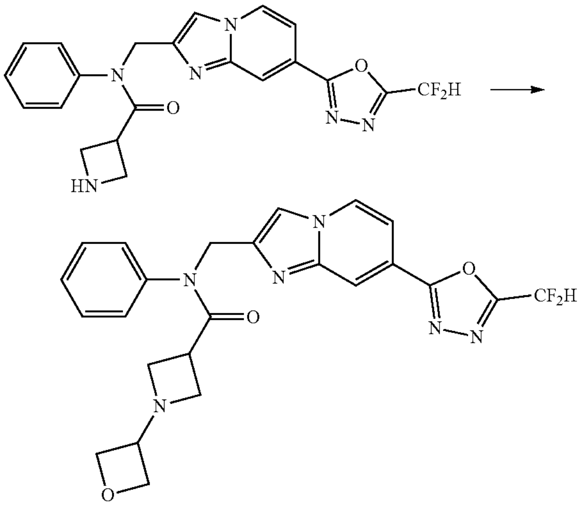

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, oxetan-3-one (0.017 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.019 g, 33.6%) as a white solid.

$^1H$ NMR (400 MHz, $CDCl_3$) δ 8.32 (dt, J=1.6, 0.8 Hz, 1H), 8.23 (dd, J=7.1, 1.0 Hz, 1H), 7.78 (s, 1H), 7.54 (dd, J=7.1, 1.7 Hz, 1H), 7.45-7.36 (m, 3H), 7.21-7.15 (m, 2H), 6.95 (t, J=51.7 Hz, 1H), 5.06 (s, 2H), 4.69 (t, J=6.8 Hz, 2H), 4.53 (t, J=6.1 Hz, 2H), 3.81 (s, 1H), 3.54-3.29 (m, 5H);

LRMS (ES) m/z 481.4 ($M^+$+1).

Example 119: Synthesis of Compound 4164, 1-cyclohexyl-N-((7-(5-(difluoromethyl)-1,3,4-oxadiazol-2-yl)imidazo[1,2-a]pyridin-2-yl)methyl)-N-phenylazetidine-3-carboxamide

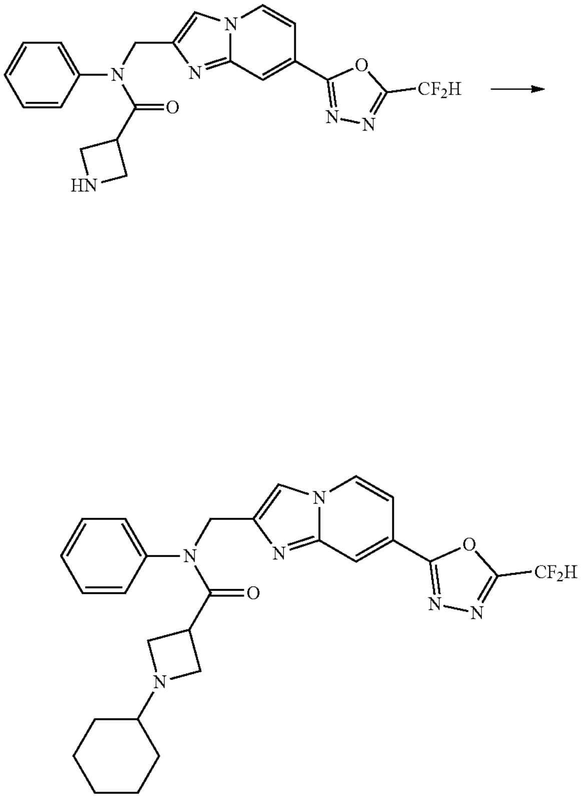

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, cyclohexanone (0.023 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.028 g, 46.9%) as a white solid.

$^1H$ NMR (400 MHz, $CDCl_3$) δ 8.34-8.29 (m, 1H), 8.23 (dd, J=7.2, 1.0 Hz, 1H), 7.77 (s, 1H), 7.54 (dd, J=7.1, 1.7 Hz, 1H), 7.44-7.34 (m, 3H), 7.17 (dd, J=8.0, 1.7 Hz, 2H), 6.95 (t, J=51.7 Hz, 1H), 5.06 (s, 2H), 3.40 (s, 4H), 1.73 (d, J=10.2 Hz, 5H), 1.61 (s, 2H), 1.17 (d, J=9.2 Hz, 5H);

LRMS (ES) m/z 507.4 ($M^+$+1).

Example 120: Synthesis of Compound 4165, N-((7-(5-(difluoromethyl)-1,3,4-oxadiazol-2-yl)imidazo[1,2-a]pyridin-2-yl)methyl)-N-phenyl-1-(tetrahydro-2H-pyran-4-yl) azetidine-3-carboxamide

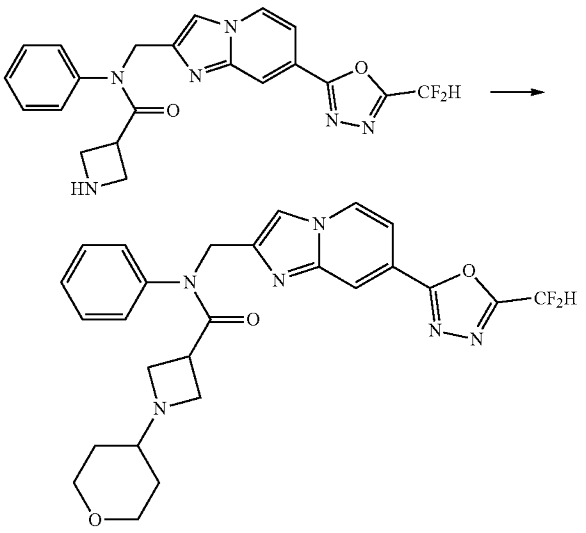

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, tetrahydro-4H-pyran-4-one (0.024 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.023 g, 38.4%) as a white solid.

$^1H$ NMR (400 MHz, $CDCl_3$) δ 8.32-8.30 (m, 1H), 8.23 (dd, J=7.1, 1.0 Hz, 1H), 7.77 (s, 1H), 7.54 (dd, J=7.1, 1.7 Hz, 1H), 7.44-7.34 (m, 3H), 7.20-7.14 (m, 2H), 6.95 (t, J=51.7 Hz, 1H), 5.06 (s, 2H), 3.94 (d, J=11.8 Hz, 2H), 3.35 (td, J=11.4, 2.3 Hz, 6H), 2.35 (s, 1H), 1.84-1.69 (m, 1H), 1.64 (d, J=12.8 Hz, 2H), 1.28 (s, 2H);

LRMS (ES) m/z 509.0 ($M^+$+1).

Example 121: Synthesis of Compound 4166, 1-(4,4-difluorocyclohexyl)-N-((7-(5-(difluoromethyl)-1,3,4-oxadiazol-2-yl)imidazo[1,2-a]pyridin-2-yl)methyl)-N-phenylazetidine-3-carboxamide

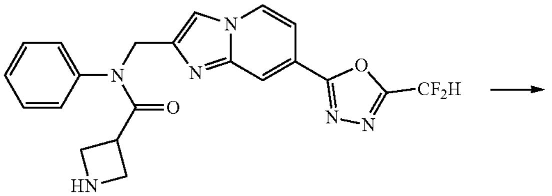

-continued

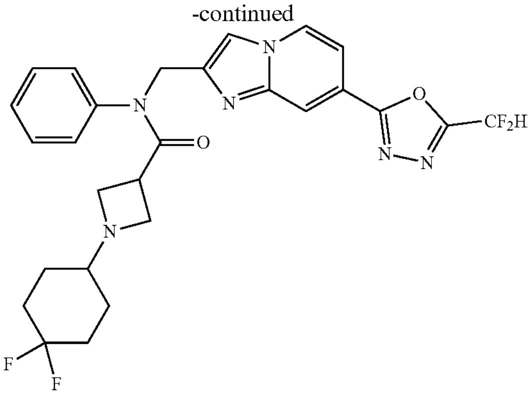

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, 4,4-difluorocyclohexan-1-one (0.032 g, 0.236 mmol), acetic acid (0.007 mL, 0.118 mmol), and sodium triacetoxyborohydride (0.075 g, 0.353 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.031 g, 48.5%) as a white solid.

$^1H$ NMR (400 MHz, $CDCl_3$) δ 8.31 (dt, J=1.7, 0.8 Hz, 1H), 8.23 (dd, J=7.1, 1.0 Hz, 1H), 7.78 (s, 1H), 7.54 (dd, J=7.1, 1.7 Hz, 1H), 7.44-7.34 (m, 3H), 7.22-7.16 (m, 2H), 6.95 (t, J=51.7 Hz, 1H), 5.05 (s, 2H), 3.28 (q, J=7.5, 6.9 Hz, 1H), 3.19 (s, 4H), 2.21 (s, 1H), 2.00 (s, 2H), 1.68 (q, J=14.1 Hz, 4H), 1.39 (s, 2H);

LRMS (ES) m/z 543.5 ($M^+$+1).

Example 122: Synthesis of Compound 4167, 1-acetyl-N-((7-(5-(difluoromethyl)-1,3,4-oxadiazol-2-yl)imidazo[1,2-a]pyridine-2-yl)methyl)-N-phenylazetidine-3-carboxamide

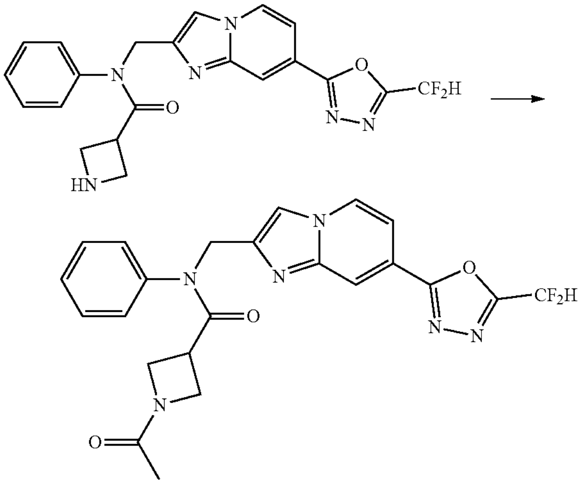

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, acetyl chloride (0.017 mL, 0.236 mmol), and triethylamine (0.049 mL, 0.353 mmol) were dissolved in dichloromethane (4 mL) at room temperature, and the resulting solution was stirred at the same temperature for 18 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 36.4%) as a white solid.

$^1H$ NMR (400 MHz, $CDCl_3$) δ 8.39 (s, 1H), 8.29 (d, J=7.0 Hz, 1H), 7.82 (s, 1H), 7.62 (d, J=7.1 Hz, 1H), 7.42 (dt, J=9.3, 6.4 Hz, 3H), 7.25-7.19 (m, 2H), 6.96 (t, J=51.7 Hz, 1H), 5.13-5.06 (m, 2H), 4.54-4.40 (m, 1H), 4.06 (dd, J=9.6, 6.5 Hz, 1H), 3.93 (t, J=8.5 Hz, 1H), 3.71 (t, J=9.4 Hz, 1H), 3.37 (ddd, J=15.3, 9.0, 6.3 Hz, 1H), 1.83 (s, 3H);

LRMS (ES) m/z 466.9 ($M^+$+1).

Example 123: Synthesis of Compound 4168, N-((7-(5-(difluoromethyl)-1,3,4-oxadiazol-2-yl)imidazo[1,2-a]pyridin-2-yl)methyl)-N-phenyl-1-propionylazetidine-3-carboxamide

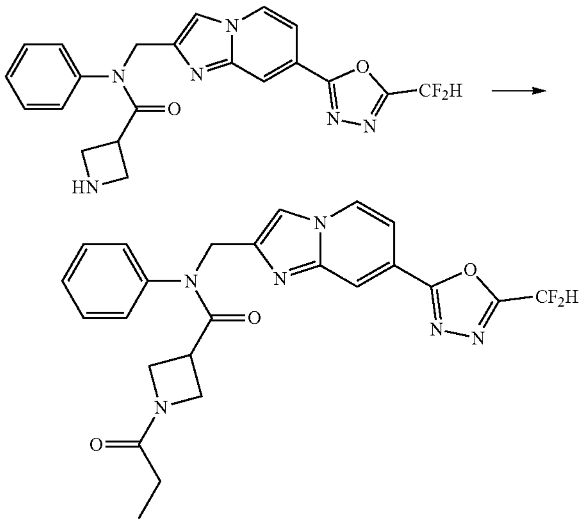

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, propionyl chloride (0.022 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.032 g, 56.5%) as a white solid.

$^1H$ NMR (400 MHz, $CDCl_3$) δ 8.36-8.31 (m, 1H), 8.25 (dd, J=7.1, 1.0 Hz, 1H), 7.80 (d, J=0.7 Hz, 1H), 7.57 (dd, J=7.1, 1.7 Hz, 1H), 7.46-7.36 (m, 3H), 7.20 (dd, J=8.1, 1.6 Hz, 2H), 6.96 (t, J=51.7 Hz, 1H), 5.18-4.96 (m, 2H), 4.45 (dd, J=8.1, 6.2 Hz, 1H), 4.05 (dd, J=9.5, 6.5 Hz, 1H), 3.91 (t, J=8.4 Hz, 1H), 3.71 (t, J=9.3 Hz, 1H), 3.36 (tt, J=9.0, 6.3 Hz, 1H), 2.07 (p, J=7.5 Hz, 2H), 1.09 (t, J=7.5 Hz, 3H);

LRMS (ES) m/z 480.9 ($M^+$+1).

Example 124: Synthesis of Compound 4169, N-((7-(5-(difluoromethyl)-1,3,4-oxadiazol-2-yl)imidazo[1,2-a]pyridin-2-yl)methyl)-1-(2-hydroxyacetyl)-N-phenylazetidine-3-carboxamide

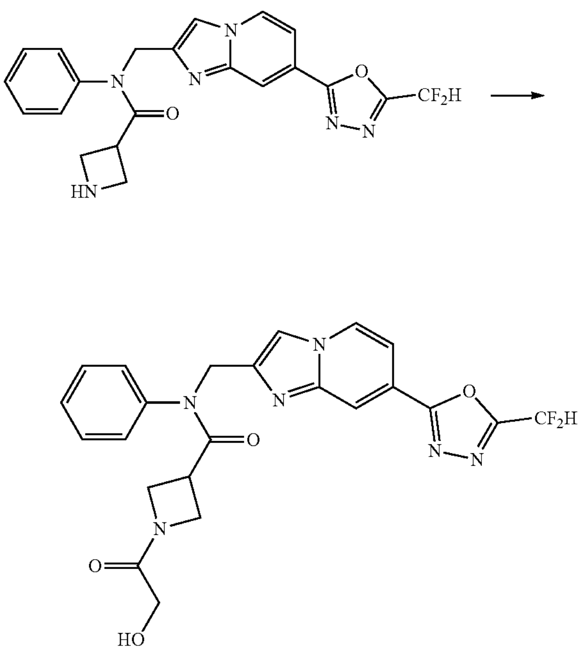

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, 2-hydroxyacetyl chloride (0.022 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.030 g, 52.8%) as a white solid.

$^1H$ NMR (400 MHz, MeOD) δ 8.58 (dd, J=7.1, 1.0 Hz, 1H), 8.23 (dt, J=1.7, 0.8 Hz, 1H), 7.98 (d, J=0.7 Hz, 1H), 7.57 (dd, J=7.2, 1.7 Hz, 1H), 7.48-7.11 (m, 6H), 5.14 (dd, J=2.2, 0.7 Hz, 2H), 4.48 (dd, J=9.0, 6.2 Hz, 1H), 4.22-4.17 (m, 1H), 4.14-4.07 (m, 1H), 3.82 (t, J=9.4 Hz, 1H), 3.57-3.48 (m, 1H), 3.22 (q, J=7.3 Hz, 2H);

LRMS (ES) m/z 483.0 ($M^+$+1).

Example 125: Synthesis of Compound 4170, 1-(cyclobutanecarbonyl)-N-((7-(5-(difluoromethyl)-1,3,4-oxadiazol-2-yl)imidazo[1,2-a]pyridine-2-yl)methyl)-N-phenylazetidine-3-carboxamide

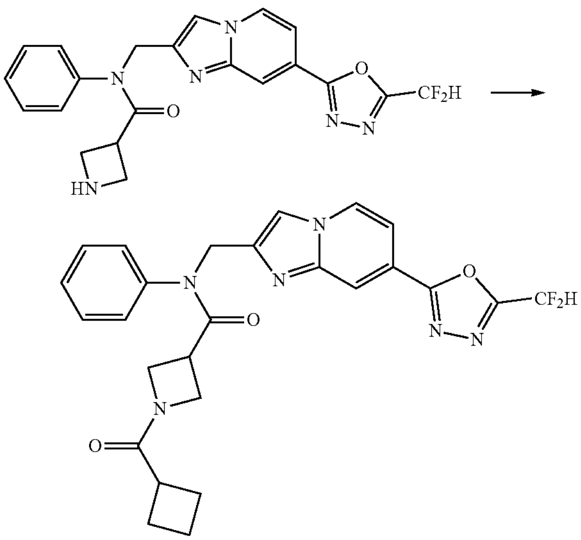

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, cyclobutanecarbonyl chloride (0.028 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.029 g, 48.6%) as a white solid.

$^1H$ NMR (400 MHz, $CDCl_3$) δ 8.35 (s, 1H), 8.25 (dd, J=7.1, 1.0 Hz, 1H), 7.80 (d, J=0.7 Hz, 1H), 7.58 (dd, J=7.2, 1.7 Hz, 1H), 7.47-7.36 (m, 3H), 7.22-7.15 (m, 2H), 6.96 (t, J=51.7 Hz, 1H), 5.15-4.96 (m, 2H), 4.44-4.30 (m, 1H), 4.04 (dd, J=9.5, 6.5 Hz, 1H), 3.85 (t, J=8.4 Hz, 1H), 3.70 (t, J=9.4 Hz, 1H), 3.35 (tt, J=8.9, 6.4 Hz, 1H), 3.09-2.92 (m, 1H), 2.43-2.21 (m, 3H), 2.14-1.89 (m, 3H);

LRMS (ES) m/z 507.4 ($M^+$+1).

Example 126: Synthesis of Compound 4171, N-((7-(5-(difluoromethyl)-1,3,4-oxadiazol-2-yl)imidazo[1,2-a]pyridin-2-yl)methyl)-1-(oxetan-3-carbonyl)-N-phenylazetidine-3-carboxamide

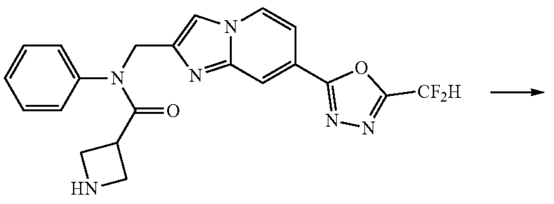

-continued

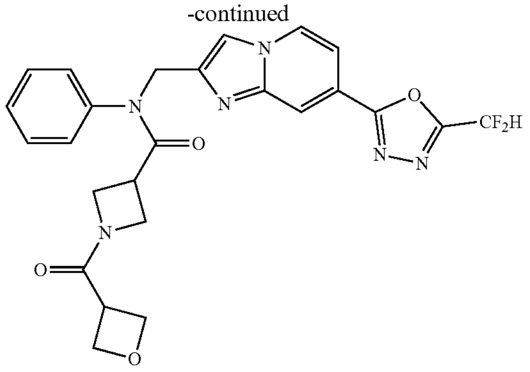

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, oxetane-3-carbonyl chloride (0.028 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.039 g, 65.1%) as a white solid.

$^1H$ NMR (400 MHz, $CDCl_3$) δ 8.38 (s, 1H), 8.26 (dd, J=7.0, 1.0 Hz, 1H), 7.78 (s, 1H), 7.61 (d, J=7.1 Hz, 1H), 7.47-7.38 (m, 3H), 7.24-7.18 (m, 2H), 6.96 (t, J=51.7 Hz, 1H), 5.09 (d, J=2.9 Hz, 2H), 4.90 (dd, J=7.0, 5.8 Hz, 1H), 4.83 (dd, J=7.0, 5.7 Hz, 1H), 4.72 (ddd, J=14.5, 8.6, 5.8 Hz, 2H), 4.40-4.32 (m, 1H), 4.11-4.04 (m, 1H), 3.83 (t, J=8.4 Hz, 1H), 3.79-3.71 (m, 2H), 3.39 (ddd, J=15.1, 8.9, 6.3 Hz, 1H);

LRMS (ES) m/z 509.4 ($M^+$+1).

Example 127: Synthesis of Compound 4172, N-((7-(5-(difluoromethyl)-1,3,4-oxadiazol-2-yl)imidazo[1,2-a]pyridin-2-yl)methyl)-N-phenyl-1-(2,2,2-trifluoroacetyl) azetidine-3-carboxamide

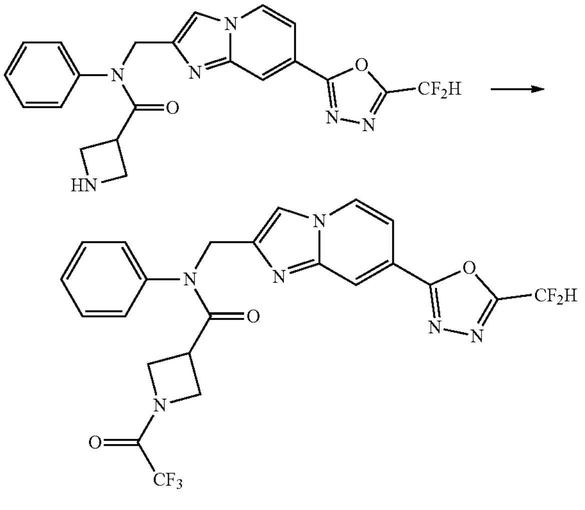

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, 1,1,1,5,5,5-hexafluoropentane-2,4-dione (0.049 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.034 g, 55.5%) as a white solid.

$^1H$ NMR (400 MHz, $CDCl_3$) δ 8.36 (s, 1H), 8.26 (dd, J=7.1, 1.0 Hz, 1H), 7.79 (s, 1H), 7.59 (dd, J=7.1, 1.7 Hz, 1H), 7.51-7.37 (m, 3H), 7.25-7.19 (m, 2H), 6.96 (t, J=51.7 Hz, 1H), 5.09 (d, J=2.9 Hz, 2H), 4.76-4.60 (m, 1H), 4.27 (dd, J=10.4, 6.6 Hz, 1H), 4.22-4.10 (m, 1H), 3.87 (t, J=9.9 Hz, 1H), 3.51 (tt, J=9.1, 6.5 Hz, 1H);

LRMS (ES) m/z 520.9 ($M^+$+1).

Example 128: Synthesis of Compound 4173, N-((7-(5-(difluoromethyl)-1,3,4-oxadiazol-2-yl)imidazo[1,2-a]pyridin-2-yl)methyl)-1-(methylsulfonyl)-N-phenylazetidine-3-carboxamide

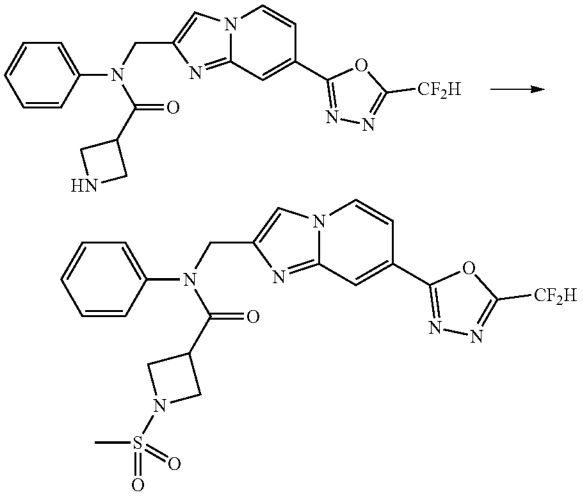

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, methanesulfonyl chloride (0.018 mL, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.032 g, 54.1%) as a white solid.

$^1H$ NMR (400 MHz, $CDCl_3$) δ 8.37 (s, 1H), 8.26 (dd, J=7.2, 1.0 Hz, 1H), 7.80-7.75 (m, 1H), 7.60 (dd, J=7.1, 1.7 Hz, 1H), 7.47-7.38 (m, 3H), 7.24-7.15 (m, 2H), 6.96 (t, J=51.7 Hz, 1H), 5.09 (s, 2H), 4.16 (dd, J=8.1, 7.1 Hz, 2H), 3.71 (t, J=8.3 Hz, 2H), 3.47-3.32 (m, 1H), 2.91 (s, 3H);

LRMS (ES) m/z 503.4 ($M^+$+1).

Example 129: Synthesis of Compound 4174, methyl 3-(((7-(5-(difluoromethyl)-1,3,4-oxadiazol-2-yl)imidazo[1,2-a]pyridin-2-yl)methyl)(phenyl)carbamoyl) azetidine-1-carboxylate

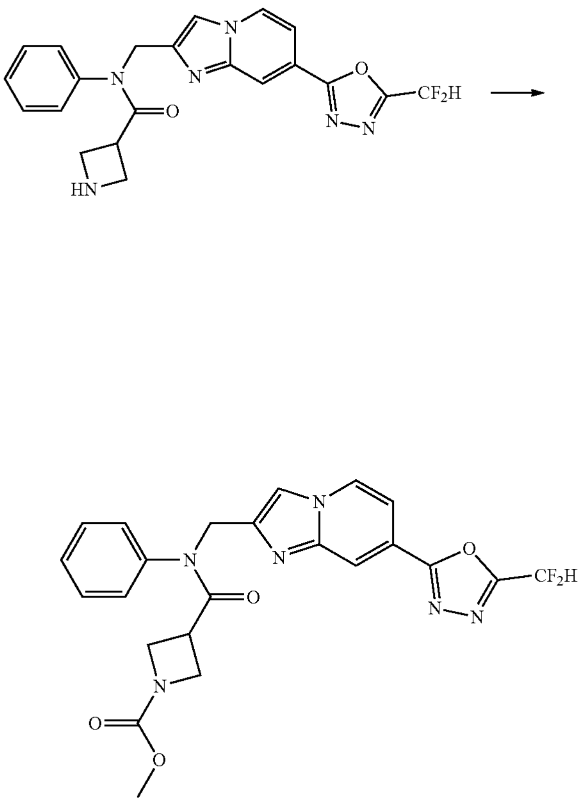

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, methyl carbonochloridate (0.022 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.023 g, 40.5%) as a white solid.

$^1H$ NMR (400 MHz, $CDCl_3$) δ 8.36 (s, 1H), 8.26 (dd, J=7.1, 1.0 Hz, 1H), 7.82 (s, 1H), 7.59 (dd, J=7.2, 1.7 Hz, 1H), 7.46-7.36 (m, 3H), 7.22-7.16 (m, 2H), 6.96 (t, J=51.7 Hz, 1H), 5.08 (s, 2H), 4.19 (s, 2H), 3.74 (t, J=8.6 Hz, 2H), 3.64 (s, 3H), 3.36 (tt, J=8.8, 6.4 Hz, 1H);

LRMS (ES) m/z 482.8 ($M^+$+1).

Example 130: Synthesis of Compound 4175, N3-((7-(5-(difluoromethyl)-1,3,4-oxadiazol-2-yl)imidazo[1,2-a]pyridin-2-yl)methyl)-N1,N1-dimethyl-N3-phenylazetidine-1,3-dicarboxamide

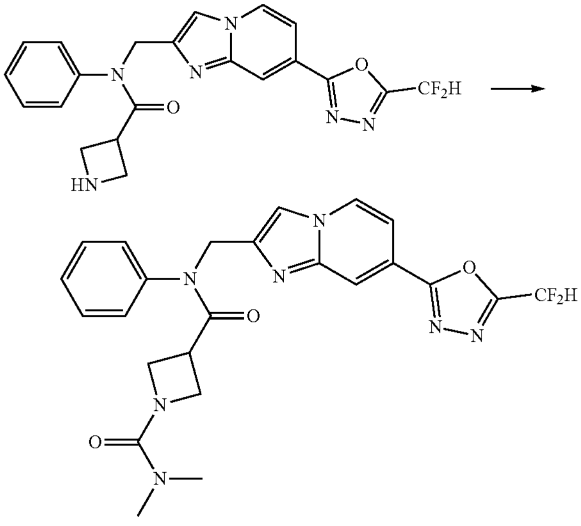

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, dimethylcarbamic chloride (0.025 g, 0.236 mmol), and triethylamine (0.049 mL, 0.353 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.030 g, 51.4%) as a white solid.

$^1H$ NMR (400 MHz, $CDCl_3$) δ 8.34 (s, 1H), 8.26 (dd, J=7.1, 1.0 Hz, 1H), 7.84-7.80 (m, 1H), 7.58 (dd, J=7.1, 1.7 Hz, 1H), 7.45-7.34 (m, 3H), 7.22-7.15 (m, 2H), 6.95 (t, J=51.7 Hz, 1H), 5.08 (s, 2H), 4.18 (dd, J=8.0, 6.8 Hz, 2H), 3.70 (dd, J=9.0, 8.0 Hz, 2H), 3.35 (tt, J=9.0, 6.8 Hz, 1H), 2.82 (s, 6H);

LRMS (ES) m/z 495.9 ($M^+$+1).

Example 131: Synthesis of Compound 4176, N-((7-(5-(difluoromethyl)-1,3,4-oxadiazol-2-yl)imidazo[1,2-a]pyridin-2-yl)methyl)-N-phenyl-1-(pyridin-2-yl) azetidine-3-carboxamide

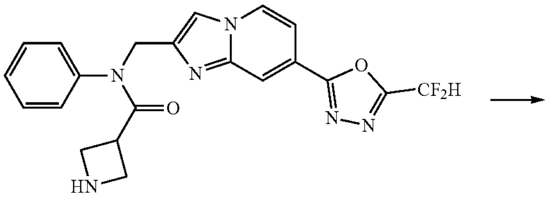

-continued

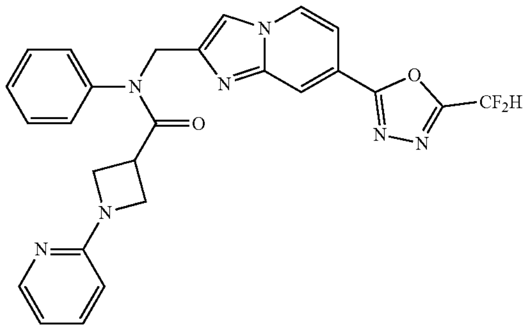

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 2 of Example 113, 2-chloropyridine (0.027 g, 0.236 mmol), cesium carbonate (0.077 g, 0.236 mmol), and RuPhos palladium G2 (0.005 g, 0.006 mmol) were dissolved in 1,4-dioxane (2 mL) at room temperature, and the resulting solution was stirred at 100° C. for 18 hours. Then, the temperature was lowered to room temperature to terminate the reaction. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 30%) and concentrated to obtain the title compound (0.028 g, 47.4%) as a white solid.

$^1H$ NMR (400 MHz, $CDCl_3$) δ 8.31 (dt, J=1.7, 0.8 Hz, 1H), 8.23 (dd, J=7.1, 1.0 Hz, 1H), 8.11 (ddd, J=5.1, 1.8, 0.9 Hz, 1H), 7.82 (d, J=0.7 Hz, 1H), 7.54 (dd, J=7.1, 1.7 Hz, 1H), 7.49-7.35 (m, 4H), 7.25-7.21 (m, 2H), 6.95 (t, J=51.7 Hz, 1H), 6.61 (ddd, J=7.1, 5.1, 1.0 Hz, 1H), 6.35-6.27 (m, 1H), 5.08 (s, 2H), 4.23 (t, J=7.2 Hz, 2H), 3.86 (t, J=8.1 Hz, 2H), 3.61-3.48 (m, 1H);

LRMS (ES) m/z 502.4 ($M^+$+1).

Example 132: Synthesis of Compound 4177, N-((7-(5-(difluoromethyl)-1,3,4-oxadiazol-2-yl)imidazo[1,2-a]pyridin-2-yl)methyl)-N-phenyl-1-(pyrimidin-2-yl) azetidine-3-carboxamide

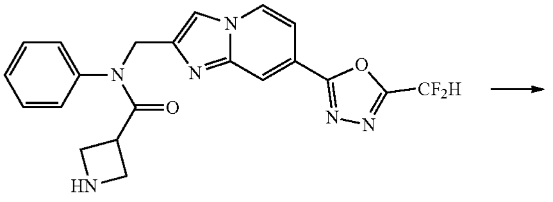

-continued

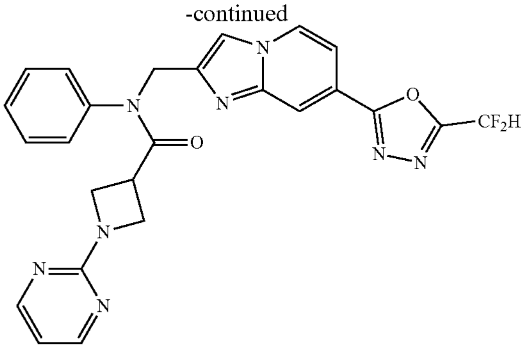

N-((7-(5-(difluoromethyl)-1,3,4-oxadiazol-2-yl)imidazo[1,2-a]pyridin-2-yl)methyl)-N-phenylazetidine-3-carboxamide (0.050 g, 0.118 mmol) prepared in step 3 of Example 113, 2-chloropyrimidine (0.027 g, 0.236 mmol), and potassium carbonate (0.033 g, 0.236 mmol) were dissolved in acetonitrile (2 mL)/N,N-dimethylformamide (2 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.018 g, 30.4%) as a white solid.

$^1$H NMR (400 MHz, $CDCl_3$) δ 8.33-8.28 (m, 3H), 8.23 (dd, J=7.1, 1.0 Hz, 1H), 7.82 (d, J=0.7 Hz, 1H), 7.54 (dd, J=7.2, 1.7 Hz, 1H), 7.47-7.36 (m, 3H), 7.26-7.18 (m, 2H), 6.95 (t, J=51.7 Hz, 1H), 6.54 (t, J=4.8 Hz, 1H), 5.09 (s, 2H), 4.36 (dd, J=8.5, 6.5 Hz, 2H), 3.95 (t, J=8.6 Hz, 2H), 3.51 (tt, J=8.7, 6.5 Hz, 1H);

LRMS (ES) m/z 503.4 ($M^+$+1).

Example 133: Synthesis of Compound 4188, N-((7-(5-(difluoromethyl)-1,3,4-oxadiazol-2-yl)imidazo[1,2-a]pyridin-2-yl)methyl)-N-(3-fluorophenyl)-1-methylazetidine-3-carboxamide

[Step 1] Synthesis of tert-butyl 3-(((7-(5-(difluoromethyl)-1,3,4-oxadiazol-2-yl)imidazo[1,2-a]pyridin-2-yl)methyl)(3-fluorophenyl)carbamoyl) azetidine-1-carboxylate

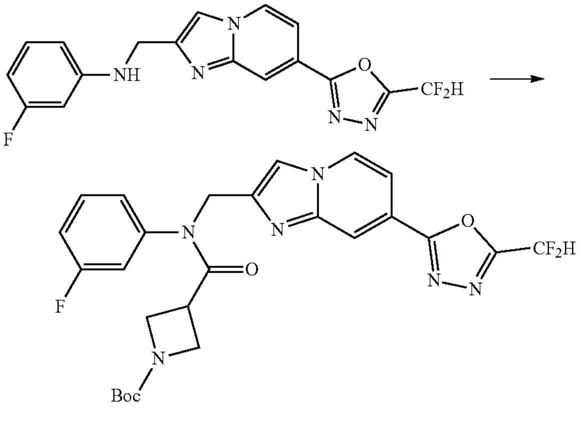

To a solution in which N-((7-(5-(difluoromethyl)-1,3,4-oxadiazol-2-yl)imidazo[1,2-a]pyridin-2-yl)methyl)-3-fluoroaniline (1.500 g, 4.175 mmol) prepared in Example 16 and triethylamine (1.746 mL, 12.524 mmol) were dissolved in dichloromethane (150 mL) at room temperature, tert-butyl 3-(chlorocarbonyl) azetidine-1-carboxylate (1.192 g, 5.427 mmol) prepared in step 1 of Example 113 was added and stirred at the same temperature for 16 hours. A saturated aqueous ammonium chloride solution was poured into the reaction mixture, extracted with dichloromethane, filtered through a plastic filter to remove a solid residue and an aqueous layer, and then concentrated under reduced pressure. The concentrate was purified by column chromatography ($SiO_2$, 40 g cartridge; ethyl acetate/hexane=5% to 60%) and concentrated to obtain the title compound (1.200 g, 53.0%) as a yellow solid.

[Step 2] Synthesis of N-((7-(5-(difluoromethyl)-1,3,4-oxadiazol-2-yl)imidazo[1,2-a]pyridin-2-yl)methyl)-N-(3-fluorophenyl) azetidine-3-carboxamide

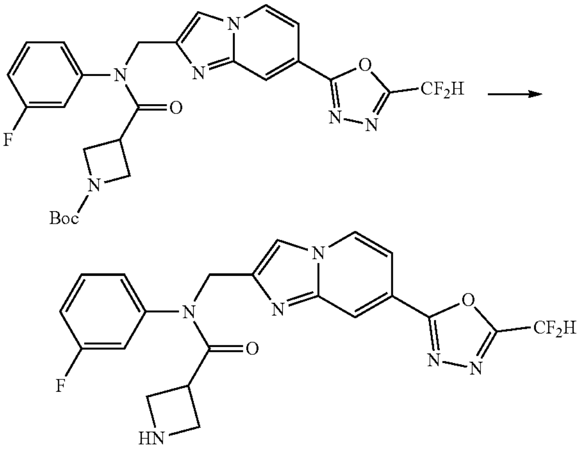

Tert-butyl 4-(((7-(5-(difluoromethyl)-1,3,4-oxadiazol-2-yl)imidazo[1,2-a]pyridin-2-yl)methyl)(3-fluorophenyl)carbamoyl) azetidine-1-carboxylate (0.700 g, 1.290 mmol) prepared in step 1, and trifluoroacetic acid (1.976 mL, 25.806 mmol) were dissolved in dichloromethane (10 mL) at room temperature, and the resulting solution was stirred at the same temperature for 2 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (0.570 g, 99.9%) was obtained as a brown gel without further purification.

[Step 3] Synthesis of Compound 4188

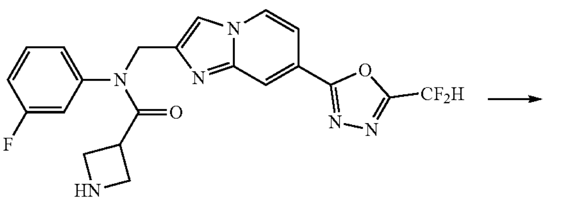

-continued

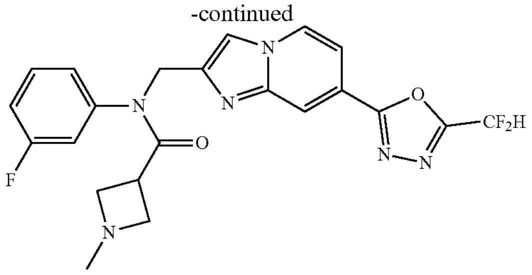

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2, formaldehyde (0.007 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.016 g, 31.0%) as a white solid.

$^1H$ NMR (400 MHz, $CDCl_3$) δ 8.33-8.30 (m, 1H), 8.24 (dd, J=7.1, 1.0 Hz, 1H), 7.79 (s, 1H), 7.55 (dd, J=7.1, 1.7 Hz, 1H), 7.38 (td, J=8.3, 6.3 Hz, 1H), 7.14-6.80 (m, 4H), 5.03 (s, 2H), 3.45 (s, 2H), 3.36 (s, 3H), 2.39 (s, 3H);

LRMS (ES) m/z 457.4 ($M^+$+1).

Example 134: Synthesis of Compound 4189, N-((7-(5-(difluoromethyl)-1,3,4-oxadiazol-2-yl)imidazo[1,2-a]pyridin-2-yl)methyl)-1-ethyl-N-(3-fluorophenyl) azetidine-3-carboxamide

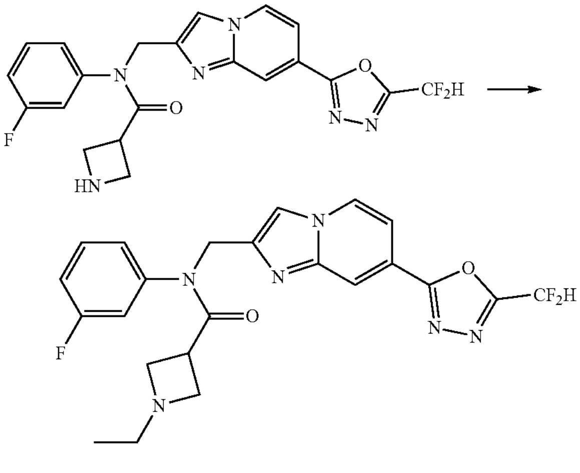

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.060 g, 0.136 mmol) prepared in step 2 of Example 133, acetaldehyde (0.012 g, 0.271 mmol), acetic acid (0.008 mL, 0.136 mmol), and sodium triacetoxyborohydride (0.086 g, 0.407 mmol) were dissolved in dichloromethane (5 mL) at room temperature, and the resulting solution was stirred at the same temperature for 18 hours. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography ($SiO_2$, 12 g cartridge; ethyl acetate/hexane=0% to 30%) and concentrated to obtain the title compound (0.021 g, 32.9%) as a white solid.

$^1H$ NMR (400 MHz, $CDCl_3$) δ 8.33-8.30 (m, 1H), 8.24 (dd, J=7.1, 1.0 Hz, 1H), 7.78 (s, 1H), 7.56 (dd, J=7.1, 1.7 Hz, 1H), 7.43-7.34 (m, 1H), 7.14-6.78 (m, 4H), 5.04 (s, 2H), 3.38 (s, 4H), 2.59 (s, 1H), 1.68 (s, 5H);

LRMS (ES) m/z 471.5 ($M^+$+1).

Example 135: Synthesis of Compound 4190, N-((7-(5-(difluoromethyl)-1,3,4-oxadiazol-2-yl)imidazo[1,2-a]pyridin-2-yl)methyl)-N-(3-fluorophenyl)-1-isopropylazetidine-3-carboxamide

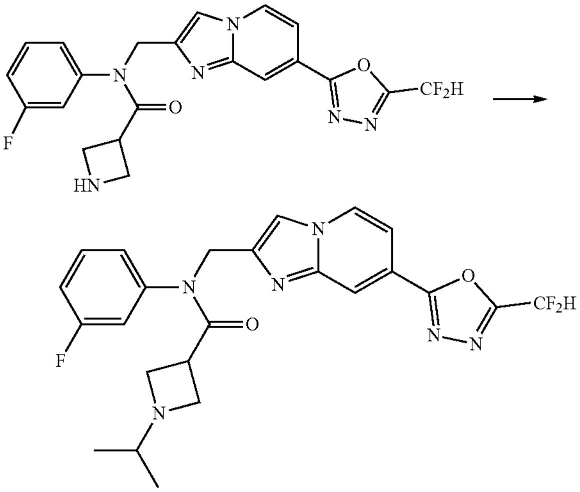

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.060 g, 0.136 mmol) prepared in step 2 of Example 133, propan-2-one (0.016 g, 0.271 mmol), acetic acid (0.008 mL, 0.136 mmol), and sodium triacetoxyborohydride (0.086 g, 0.407 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.025 g, 38.0%) as a white solid.

$^1H$ NMR (400 MHz, $CDCl_3$) δ 8.32 (dd, J=1.7, 0.9 Hz, 1H), 8.24 (dd, J=7.1, 1.0 Hz, 1H), 7.78 (s, 1H), 7.55 (dd, J=7.1, 1.7 Hz, 1H), 7.38 (td, J=8.3, 6.3 Hz, 1H), 7.14-6.80 (m, 4H), 5.03 (s, 2H), 3.43 (s, 2H), 3.35 (s, 3H), 2.54 (s, 1H), 0.97 (d, J=6.3 Hz, 6H);

LRMS (ES) m/z 485.5 ($M^+$+1).

Example 136: Synthesis of Compound 4191, N-((7-(5-(difluoromethyl)-1,3,4-oxadiazol-2-yl)imidazo[1,2-a]pyridin-2-yl)methyl)-N-(3-fluorophenyl)-1-(1-hydroxypropan-2-yl) azetidine-3-carboxamide

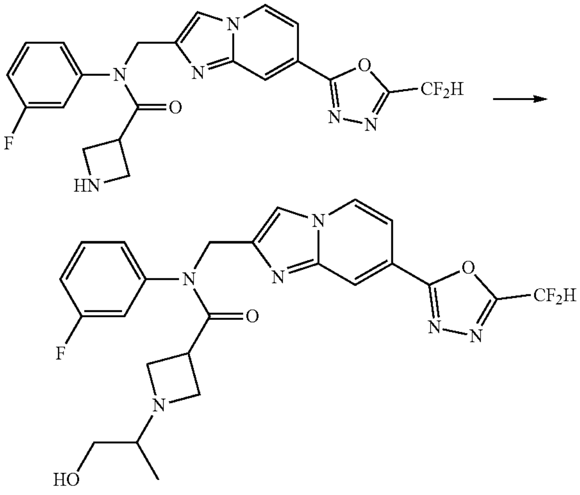

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, 1-hydroxypropan-2-one (0.017 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 35.4%) as a white solid.

$^1H$ NMR (400 MHz, $CDCl_3$) δ 8.32 (dd, J=1.7, 0.9 Hz, 1H), 8.24 (dd, J=7.1, 1.0 Hz, 1H), 7.78 (s, 1H), 7.55 (dd, J=7.1, 1.7 Hz, 1H), 7.43-7.34 (m, 1H), 7.13-6.81 (m, 4H), 5.03 (s, 2H), 3.60-3.45 (m, 4H), 3.43-3.30 (m, 3H), 2.62 (d, J=9.4 Hz, 1H), 1.00 (d, J=6.5 Hz, 3H);

LRMS (ES) m/z 501.4 ($M^+$+1).

Example 137: Synthesis of Compound 4192, 1-cyclobutyl-N-((7-(5-(difluoromethyl)-1,3,4-oxadiazol-2-yl)imidazo[1,2-a]pyridin-2-yl)methyl)-N-(3-fluorophenyl) azetidine-3-carboxamide

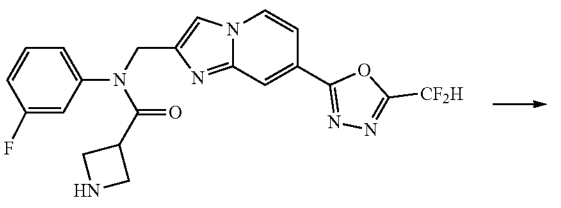

-continued

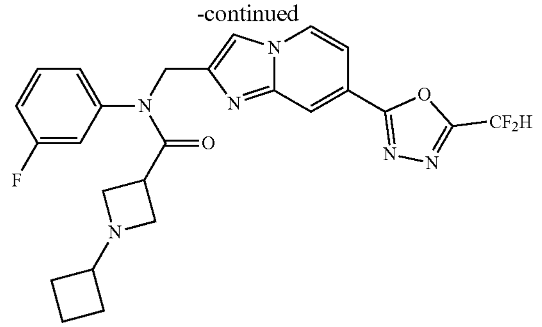

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, cyclobutanone (0.016 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 42.8%) as a white solid.

$^1H$ NMR (400 MHz, $CDCl_3$) δ 8.32 (dt, J=1.7, 0.8 Hz, 1H), 8.24 (dd, J=7.1, 1.0 Hz, 1H), 7.79 (s, 1H), 7.55 (dd, J=7.1, 1.7 Hz, 1H), 7.38 (td, J=8.2, 6.2 Hz, 1H), 7.12-6.81 (m, 4H), 5.03 (s, 2H), 3.23 (d, J=61.3 Hz, 5H), 2.01-1.94 (m, 2H), 1.86-1.59 (m, 5H);

LRMS (ES) m/z 497.4 ($M^+$+1).

Example 138: Synthesis of Compound 4193, N-((7-(5-(difluoromethyl)-1,3,4-oxadiazol-2-yl)imidazo[1,2-a]pyridin-2-yl)methyl)-N-(3-fluorophenyl)-1-(oxetan-3-yl) azetidine-3-carboxamide

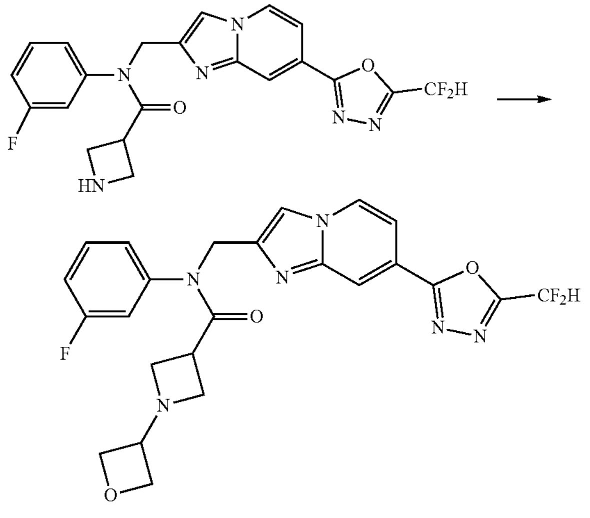

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, oxetan-3-one (0.016 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.032 g, 56.8%) as a white solid.

$^1$H NMR (400 MHz, $CDCl_3$) δ 8.32 (dt, J=1.7, 0.8 Hz, 1H), 8.24 (dd, J=7.1, 1.0 Hz, 1H), 7.79 (s, 1H), 7.55 (dd, J=7.1, 1.7 Hz, 1H), 7.39 (td, J=8.2, 6.2 Hz, 1H), 7.14-6.79 (m, 4H), 5.03 (s, 2H), 4.67 (t, J=6.7 Hz, 2H), 4.49 (dd, J=6.7, 5.2 Hz, 2H), 3.74 (ddd, J=11.9, 6.7, 5.2 Hz, 1H), 3.44-3.32 (m, 3H), 3.28 (d, J=5.6 Hz, 2H);

LRMS (ES) m/z 499.4 ($M^+$+1).

Example 139: Synthesis of Compound 4194, 1-cyclohexyl-N-((7-(5-(difluoromethyl)-1,3,4-oxadiazol-2-yl)imidazo[1,2-a]pyridin-2-yl)methyl)-N-(3-fluorophenyl) azetidine-3-carboxamide

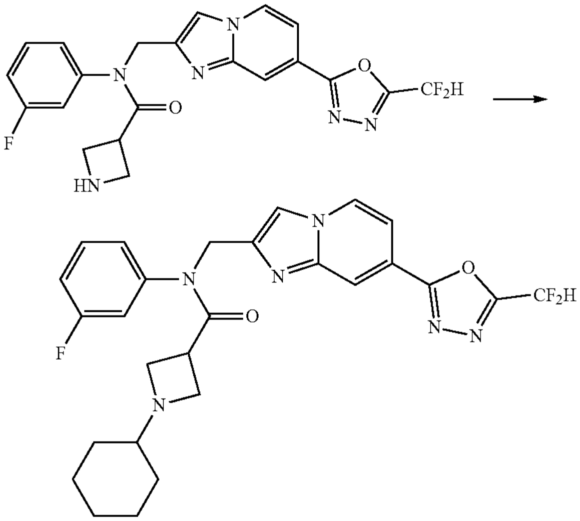

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, cyclohexanone (0.022 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.034 g, 57.4%) as a white solid.

$^1$H NMR (400 MHz, $CDCl_3$) δ 8.32 (dt, J=1.6, 0.8 Hz, 1H), 8.24 (dd, J=7.1, 1.0 Hz, 1H), 7.77 (s, 1H), 7.55 (dd, J=7.1, 1.7 Hz, 1H), 7.38 (td, J=8.3, 6.3 Hz, 1H), 7.14-6.78 (m, 4H), 5.03 (s, 2H), 3.45 (d, J=29.4 Hz, 5H), 2.28 (s, 1H), 1.74 (d, J=10.1 Hz, 4H), 1.61 (s, 1H), 1.23-1.05 (m, 5H);

LRMS (ES) m/z 525.1 ($M^+$+1).

Example 140: Synthesis of Compound 4195, N-((7-(5-(difluoromethyl)-1,3,4-oxadiazol-2-yl)imidazo[1,2-a]pyridin-2-yl)methyl)-N-(3-fluorophenyl)-1-(tetrahydro-2H-pyran-4-yl) azetidine-3-carboxamide

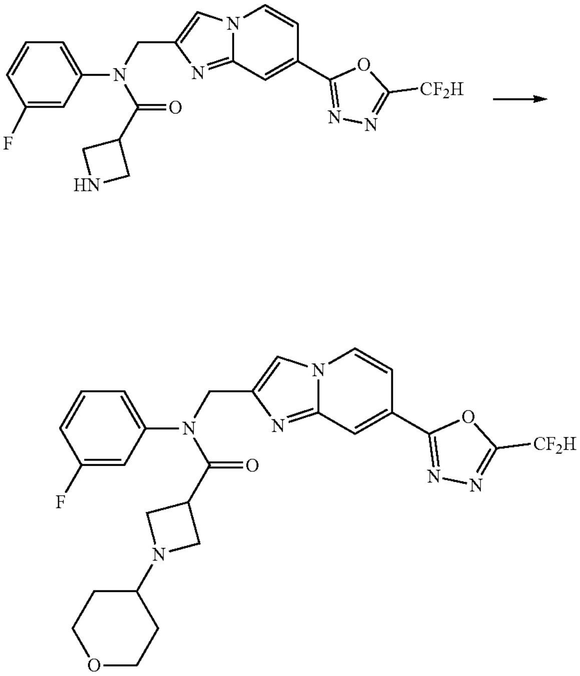

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, tetrahydro-4H-pyran-4-one (0.023 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.015 g, 25.2%) as a white solid.

$^1$H NMR (400 MHz, $CDCl_3$) δ 8.32 (dt, J=1.6, 0.8 Hz, 1H), 8.23 (dd, J=7.1, 1.0 Hz, 1H), 7.78 (s, 1H), 7.55 (dd, J=7.1, 1.7 Hz, 1H), 7.38 (td, J=8.3, 6.3 Hz, 1H), 7.13-6.79 (m, 4H), 5.03 (s, 2H), 3.92 (dt, J=11.6, 3.7 Hz, 2H), 3.41-3.15 (m, 7H), 2.36-2.22 (m, 1H), 1.61 (d, J=13.0 Hz, 2H), 1.31 (d, J=4.3 Hz, 2H);

LRMS (ES) m/z 527.5 ($M^+$+1).

Example 141: Synthesis of Compound 4196, 1-(4,4-Difluorocyclohexyl)-N-((7-(5-(difluoromethyl)-1,3,4-oxadiazol-2-yl)imidazo[1,2-a]pyridin-2-yl)methyl)-N-(3-fluorophenyl) azetidine-3-carboxamide

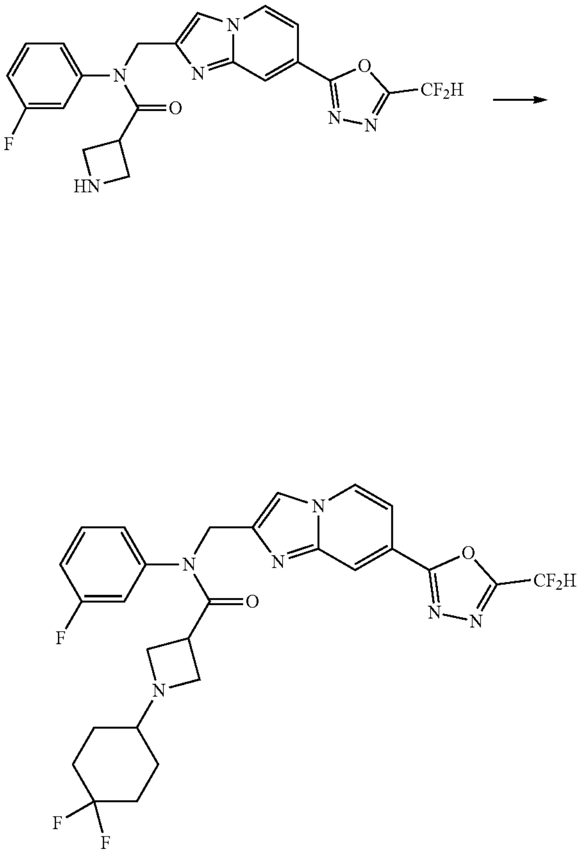

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, 4,4-difluorocyclohexan-1-one (0.030 g, 0.226 mmol), acetic acid (0.006 mL, 0.113 mmol), and sodium triacetoxyborohydride (0.072 g, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.021 g, 33.1%) as a white solid.

$^1H$ NMR (400 MHz, $CDCl_3$) δ 8.32 (dt, J=1.7, 0.8 Hz, 1H), 8.23 (dd, J=7.1, 1.0 Hz, 1H), 7.78 (s, 1H), 7.55 (dd, J=7.1, 1.7 Hz, 1H), 7.38 (td, J=8.4, 6.5 Hz, 1H), 7.15-6.77 (m, 4H), 5.03 (s, 2H), 3.34-3.12 (m, 5H), 2.22 (s, 1H), 2.00 (dd, J=12.7, 5.4 Hz, 2H), 1.69 (q, J=17.0, 15.4 Hz, 4H), 1.40 (d, J=11.4 Hz, 2H);

LRMS (ES) m/z 561.3 ($M^+$+1).

Example 142: Synthesis of Compound 4197, 1-acetyl-N-((7-(5-(difluoromethyl)-1,3,4-oxadiazol-2-yl)imidazo[1,2-a]pyridine-2-yl)methyl)-N-(3-fluorophenyl) azetidine-3-carboxamide

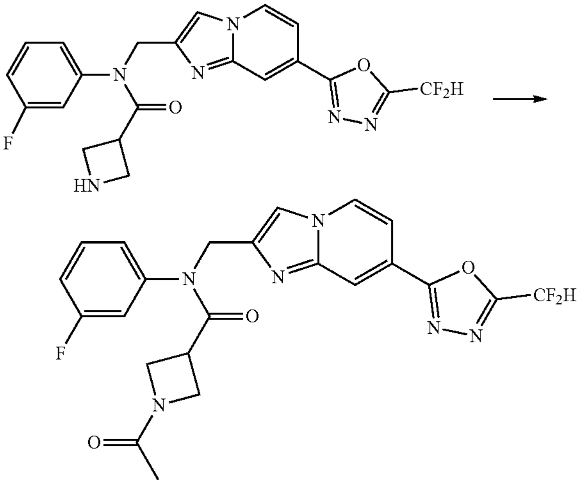

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, acetyl chloride (0.016 mL, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 43.8%) as a white solid.

$^1H$ NMR (400 MHz, $CDCl_3$) δ 8.36 (d, J=1.6 Hz, 1H), 8.26 (dd, J=7.2, 1.0 Hz, 1H), 7.81 (s, 1H), 7.60 (dd, J=7.2, 1.7 Hz, 1H), 7.41 (td, J=8.0, 6.4 Hz, 1H), 7.18-6.77 (m, 4H), 5.15-4.97 (m, 2H), 4.50-4.42 (m, 1H), 4.06 (dd, J=9.5, 6.4 Hz, 1H), 3.97 (t, J=8.5 Hz, 1H), 3.81-3.69 (m, 1H), 3.38 (tt, J=8.9, 6.3 Hz, 1H), 1.84 (s, 3H);

LRMS (ES) m/z 485.0 ($M^+$+1).

Example 143: Synthesis of Compound 4198, N-((7-(5-(difluoromethyl)-1,3,4-oxadiazol-2-yl)imidazo[1,2-a]pyridin-2-yl)methyl)-N-(3-fluorophenyl)-1-isopropylazetidine-3-carboxamide

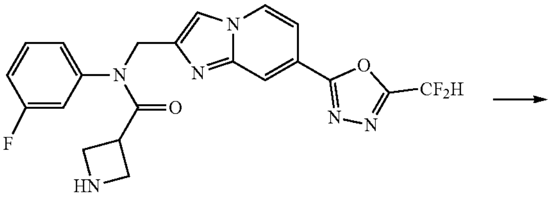

-continued

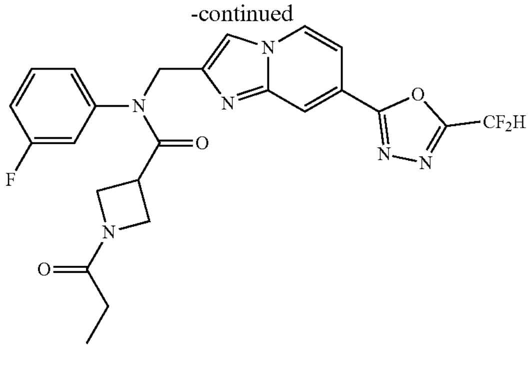

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, propionyl chloride (0.021 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.027 g, 47.9%) as a white solid.

$^1$H NMR (400 MHz, $CDCl_3$) δ 8.35 (s, 1H), 8.26 (d, J=7.1 Hz, 1H), 7.80 (s, 1H), 7.58 (dd, J=7.1, 1.7 Hz, 1H), 7.41 (q, J=7.6 Hz, 1H), 7.17-6.81 (m, 4H), 5.14-4.97 (m, 2H), 4.51-4.38 (m, 1H), 4.06 (dd, J=9.5, 6.5 Hz, 1H), 3.95 (t, J=8.4 Hz, 1H), 3.76 (t, J=9.3 Hz, 1H), 3.38 (tt, J=8.8, 6.2 Hz, 1H), 2.14-2.00 (m, 2H), 1.10 (t, J=7.5 Hz, 3H);

LRMS (ES) m/z 499.5 ($M^+$+1).

Example 144: Synthesis of Compound 4199, N-((7-(5-(difluoromethyl)-1,3,4-oxadiazol-2-yl)imidazo[1,2-a]pyridin-2-yl)methyl)-N-(3-fluorophenyl)-1-(2-hydroxyacetyl) azetidine-3-carboxamide

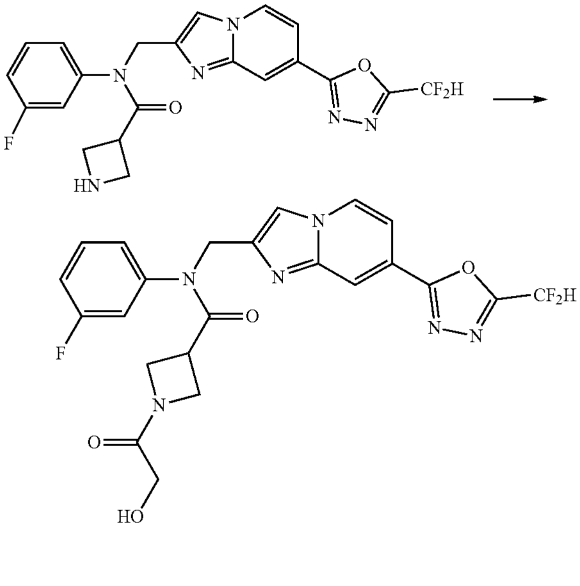

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, 2-hydroxyacetyl chloride (0.021 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.012 g, 21.2%) as a white solid.

$^1$H NMR (400 MHz, $CDCl_3$) δ 8.33 (d, J=2.0 Hz, 1H), 8.25 (dd, J=7.2, 1.1 Hz, 1H), 7.79 (s, 1H), 7.57 (dt, J=7.1, 1.6 Hz, 1H), 7.42 (td, J=8.1, 6.2 Hz, 1H), 7.18-6.79 (m, 4H), 5.05 (d, J=4.0 Hz, 2H), 4.38 (t, J=7.3 Hz, 1H), 4.21-4.14 (m, 1H), 4.03-3.81 (m, 4H), 3.49 (ddd, J=15.2, 8.9, 6.3 Hz, 1H);

LRMS (ES) m/z 501.0 ($M^+$+1).

Example 145: Synthesis of Compound 4200, 1-(cyclobutanecarbonyl)-N-((7-(5-(difluoromethyl)-1,3,4-oxadiazol-2-yl)imidazo[1,2-a]pyridine-2-yl)methyl)-N-(3-fluorophenyl) azetidine-3-carboxamide

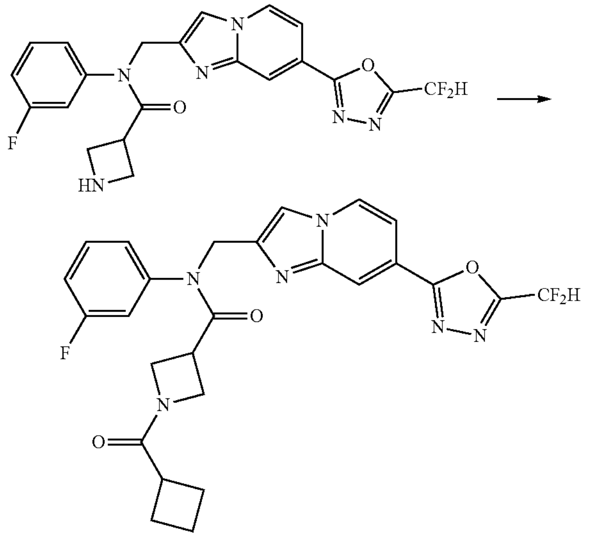

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, cyclobutanecarbonyl chloride (0.027 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.038 g, 64.1%) as a white solid.

$^1$H NMR (400 MHz, $CDCl_3$) δ 8.38 (s, 1H), 8.27 (d, J=7.1 Hz, 1H), 7.81 (s, 1H), 7.62 (d, J=7.1 Hz, 1H), 7.41 (td, J=8.3, 6.2 Hz, 1H), 7.17-6.77 (m, 4H), 5.15-4.96 (m, 2H), 4.43-4.31 (m, 1H), 4.04 (dd, J=9.4, 6.5 Hz, 1H), 3.89 (t, J=8.4 Hz, 1H), 3.75 (t, J=9.3 Hz, 1H), 3.38 (ddd, J=15.1, 8.9, 6.3 Hz, 1H), 3.00 (dd, J=9.4, 7.6 Hz, 1H), 2.28 (dp, J=27.9, 9.2, 8.8 Hz, 3H), 2.13-1.90 (m, 3H);

LRMS (ES) m/z 525.1 ($M^+$+1).

Example 146: Synthesis of Compound 4201, N-((7-(5-(difluoromethyl)-1,3,4-oxadiazol-2-yl)imidazo[1,2-a]pyridin-2-yl)methyl)-N-(3-fluorophenyl)-1-(oxetane-3-carbonyl) azetidine-3-carboxamide

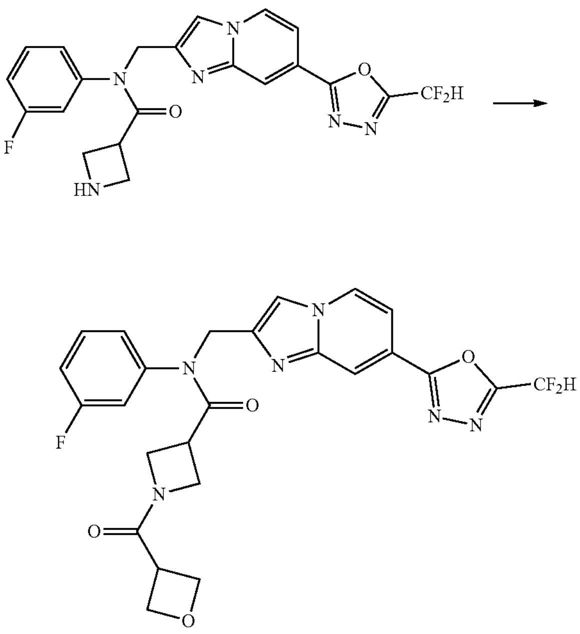

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, oxetane-3-carbonyl chloride (0.027 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.033 g, 55.5%) as a white solid.

$^1$H NMR (400 MHz, $CDCl_3$) δ 8.35 (d, J=1.7 Hz, 1H), 8.25 (dd, J=7.1, 1.0 Hz, 1H), 7.78 (s, 1H), 7.58 (dd, J=7.1, 1.7 Hz, 1H), 7.42 (td, J=8.0, 6.1 Hz, 1H), 7.17-6.79 (m, 4H), 5.14-4.98 (m, 2H), 4.90 (dd, J=7.0, 5.8 Hz, 1H), 4.83 (dd, J=7.0, 5.8 Hz, 1H), 4.72 (ddd, J=12.0, 8.6, 5.8 Hz, 2H), 4.36 (dd, J=8.1, 6.1 Hz, 1H), 4.09 (dd, J=9.7, 6.4 Hz, 1H), 3.89-3.71 (m, 3H), 3.39 (tt, J=8.8, 6.3 Hz, 1H);

LRMS (ES) m/z 527.1 ($M^+$+1).

Example 147: Synthesis of Compound 4202, N-((7-(5-(difluoromethyl)-1,3,4-oxadiazol-2-yl)imidazo[1,2-a]pyridin-2-yl)methyl)-N-(3-fluorophenyl)-1-(2,2,2-trifluoroacetyl) azetidine-3-carboxamide

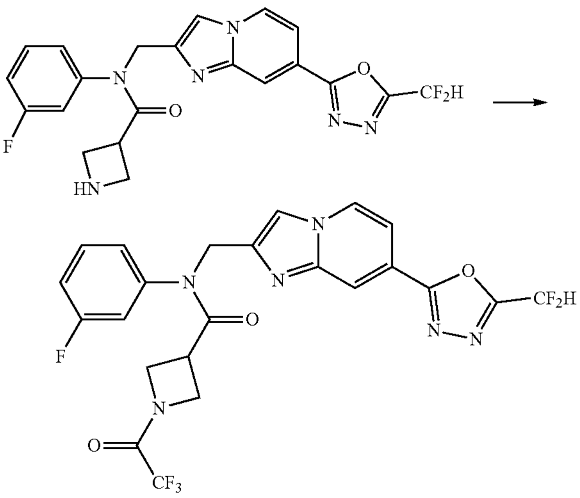

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.060 g, 0.136 mmol) prepared in step 2 of Example 133, 1,1,1,5,5,5-hexafluoropentane-2,4-dione (0.056 g, 0.271 mmol), and triethylamine (0.057 mL, 0.407 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.031 g, 42.5%) as a white solid.

$^1$H NMR (400 MHz, $CDCl_3$) δ 8.37 (s, 1H), 8.27 (dd, J=7.1, 1.0 Hz, 1H), 7.80 (s, 1H), 7.60 (dd, J=7.2, 1.7 Hz, 1H), 7.44 (td, J=8.3, 6.3 Hz, 1H), 7.15 (tdd, J=8.3, 2.5, 1.1 Hz, 1H), 7.11-6.81 (m, 3H), 5.07 (d, J=2.3 Hz, 2H), 4.74-4.62 (m, 1H), 4.33-4.12 (m, 2H), 3.92 (t, J=9.8 Hz, 1H), 3.53 (tt, J=9.1, 6.5 Hz, 1H);

LRMS (ES) m/z 539.0 ($M^+$+1).

Example 148: Synthesis of Compound 4203, N-((7-(5-(difluoromethyl)-1,3,4-oxadiazol-2-yl)imidazo[1,2-a]pyridin-2-yl)methyl)-N-(3-fluorophenyl)-1-(methylsulfonyl) azetidine-3-carboxamide

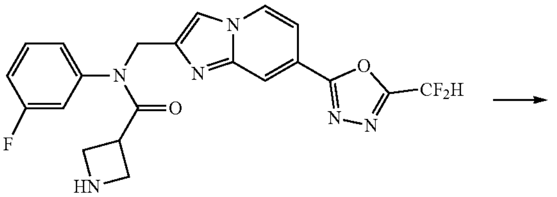

-continued

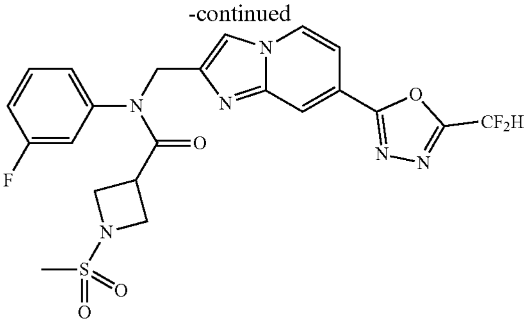

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.060 g, 0.136 mmol) prepared in step 2 of Example 133, methanesulfonyl chloride (0.021 mL, 0.271 mmol), and triethylamine (0.057 mL, 0.407 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.030 g, 42.5%) as a white solid.

$^1H$ NMR (400 MHz, $CDCl_3$) δ 8.37 (s, 1H), 8.27 (dd, J=7.2, 1.0 Hz, 1H), 7.79 (d, J=0.7 Hz, 1H), 7.61 (dd, J=7.1, 1.7 Hz, 1H), 7.50-7.36 (m, 1H), 7.19-7.10 (m, 1H), 7.10-6.79 (m, 3H), 5.07 (s, 2H), 4.17 (dd, J=8.1, 7.1 Hz, 2H), 3.75 (t, J=8.4 Hz, 2H), 3.49-3.35 (m, 1H), 2.91 (s, 3H);

LRMS (ES) m/z 521.1 ($M^+$+1).

Example 149: Synthesis of Compound 4204, methyl 3-(((7-(5-(difluoromethyl)-1,3,4-oxadiazol-2-yl)imidazo[1,2-a]pyridin-2-yl)methyl)(3-fluorophenyl)carbamoyl) azetidine-1-carboxylate

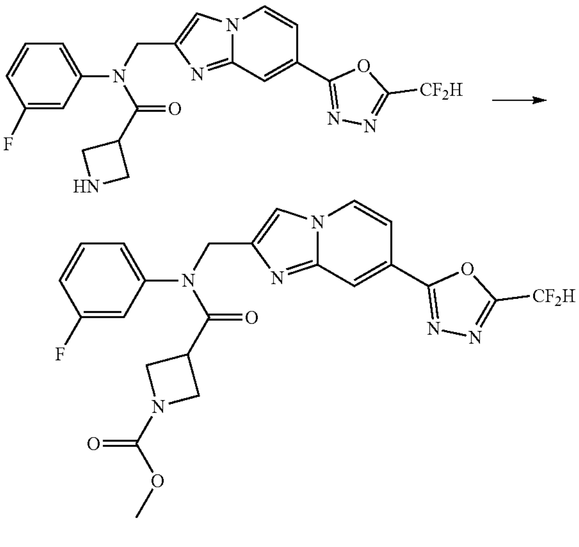

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, methyl carbonochloridate (0.021 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.031 g, 54.8%) as a white solid.

$^1H$ NMR (400 MHz, $CDCl_3$) δ 8.37-8.33 (m, 1H), 8.26 (dd, J=7.1, 1.0 Hz, 1H), 7.82 (s, 1H), 7.59 (dd, J=7.2, 1.8 Hz, 1H), 7.41 (td, J=8.3, 6.2 Hz, 1H), 7.17-6.78 (m, 4H), 5.06 (s, 2H), 4.19 (s, 2H), 3.78 (t, J=8.6 Hz, 2H), 3.65 (s, 3H), 3.37 (tt, J=8.9, 6.4 Hz, 1H);

LRMS (ES) m/z 501.0 ($M^+$+1).

Example 150: Synthesis of Compound 4205, N3-((7-(5-(difluoromethyl)-1,3,4-oxadiazol-2-yl)imidazo[1,2-a]pyridin-2-yl)methyl)-N3-(3-fluorophenyl)-N1,N1-dimethylazetidine-1,3-dicarboxamide

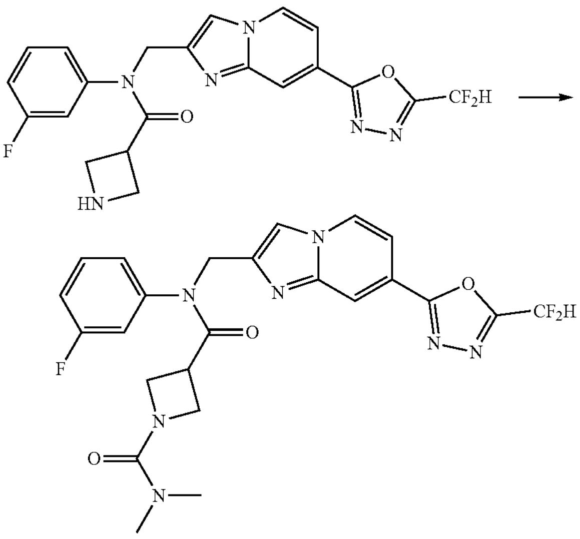

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, dimethylcarbamic chloride (0.024 g, 0.226 mmol), and triethylamine (0.047 mL, 0.339 mmol) were dissolved in dichloromethane (4 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.024 g, 41.4%) as a white solid.

$^1H$ NMR (400 MHz, $CDCl_3$) δ 8.34 (dd, J=1.8, 0.9 Hz, 1H), 8.26 (dd, J=7.1, 1.0 Hz, 1H), 7.82 (s, 1H), 7.58 (dd, J=7.2, 1.7 Hz, 1H), 7.40 (td, J=8.3, 6.3 Hz, 1H), 7.15-6.77

(m, 4H), 5.05 (s, 2H), 4.17 (dd, J=8.0, 6.7 Hz, 2H), 3.74 (t, J=8.5 Hz, 2H), 3.36 (tt, J=8.9, 6.7 Hz, 1H), 2.82 (s, 6H);

LRMS (ES) m/z 514.0 ($M^{+}$+1).

Example 151: Synthesis of Compound 4206, N-((7-(5-(difluoromethyl)-1,3,4-oxadiazol-2-yl)imidazo[1,2-a]pyridin-2-yl)methyl)-N-(3-fluorophenyl)-1-(pyridin-2-yl) azetidine-3-carboxamide

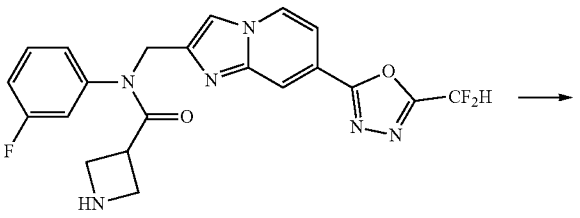

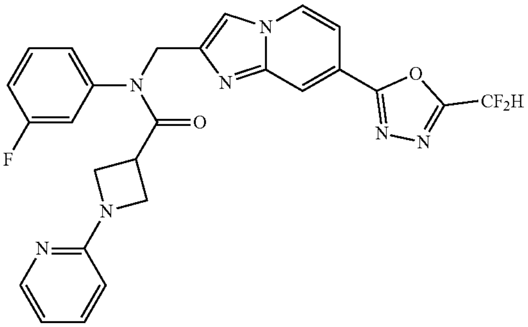

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, 2-chloropyridine (0.026 g, 0.226 mmol), cesium carbonate (0.074 g, 0.226 mmol), and RuPhos palladium G2 (0.004 g, 0.006 mmol) were dissolved in 1,4-dioxane (2 mL) at room temperature, and the resulting solution was stirred at 100° C. for 18 hours. Then, the temperature was lowered to room temperature to terminate the reaction. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 30%) and concentrated to obtain the title compound (0.012 g, 20.4%) as a white solid.

$^1$H NMR (400 MHz, $CDCl_3$) δ 8.36-8.30 (m, 1H), 8.24 (ddd, J=7.1, 6.0, 1.0 Hz, 1H), 8.12 (ddd, J=5.1, 1.9, 0.9 Hz, 1H), 7.80 (d, J=8.0 Hz, 1H), 7.59-7.51 (m, 1H), 7.50-7.37 (m, 2H), 7.15-6.81 (m, 4H), 6.62 (ddd, J=7.2, 5.0, 1.0 Hz, 1H), 6.29 (d, J=8.4 Hz, 1H), 5.06 (s, 2H), 4.21 (t, J=7.1 Hz, 2H); 3.88 (t, J=8.2 Hz, 2H), 3.64-3.54 (m, 1H);

LRMS (ES) m/z 520.5 ($M^{+}$+1).

Example 152: Synthesis of Compound 4207, N-((7-(5-(difluoromethyl)-1,3,4-oxadiazol-2-yl)imidazo[1,2-a]pyridin-2-yl)methyl)-N-(3-fluorophenyl)-1-(pyrimidin-2-yl) azetidine-3-carboxamide

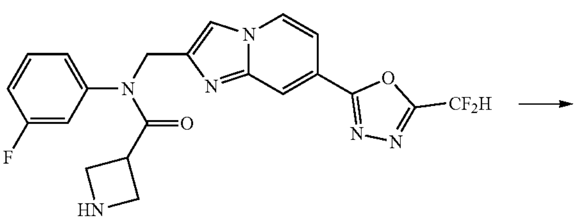

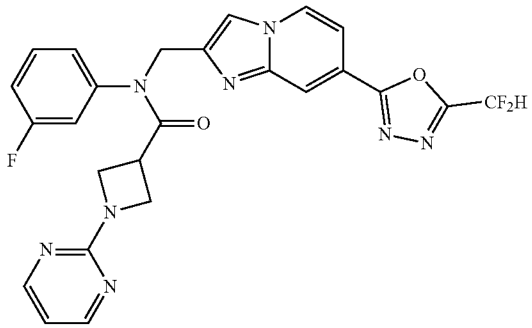

N-((7-(5-(difluoromethyl)-1,3,4-oxadiazol-2-yl)imidazo[1,2-a]pyridin-2-yl)methyl)-N-(3-fluorophenyl) azetidine-3-carboxamide (0.050 g, 0.113 mmol) prepared in step 2 of Example 133, 2-chloropyrimidine (0.026 g, 0.226 mmol), and potassium carbonate (0.031 g, 0.226 mmol) were dissolved in acetonitrile (2 mL)/N,N-dimethylformamide (2 mL) at room temperature, and the resulting solution was stirred at the same temperature for 18 hours. A saturated aqueous ammonium chloride solution was poured into the concentrate obtained by removing the solvent from the reaction mixture under reduced pressure, followed by extraction with dichloromethane. Next, the obtained product was filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.041 g, 69.7%) as a white solid.

$^1$H NMR (400 MHz, $CDCl_3$) δ 8.35-8.29 (m, 3H), 8.24 (dd, J=7.1, 1.0 Hz, 1H), 7.82 (s, 1H), 7.56 (dd, J=7.1, 1.7 Hz, 1H), 7.41 (td, J=8.2, 6.3 Hz, 1H), 7.16-6.80 (m, 4H), 6.56 (t, J=4.8 Hz, 1H), 5.07 (s, 2H), 4.36 (dd, J=8.6, 6.5 Hz, 2H), 4.00 (t, J=8.6 Hz, 2H), 3.54 (tt, J=8.7, 6.4 Hz, 1H);

LRMS (ES) m/z 521.4 ($M^{+}$+1).

Example 153: Synthesis of Compound 4618, N-((7-(5-(difluoromethyl)-1,3,4-oxadiazol-2-yl)imidazo[1,2-a]pyridin-2-yl)methyl)-N-(3-fluorophenyl)-1-(spiro[3.3]heptan-2-yl)piperidine-4-carboxamide

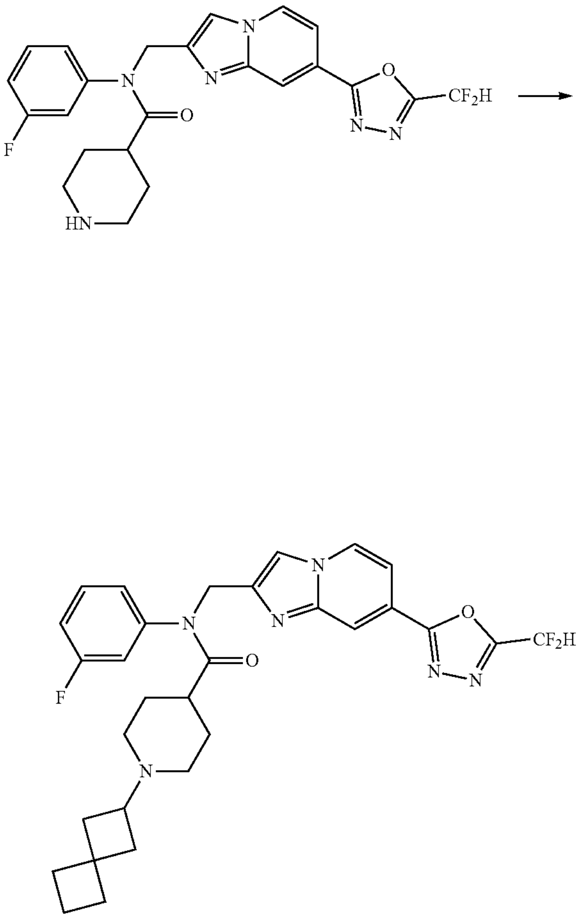

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.040 g, 0.085 mmol) prepared in step 3 of Example 93, spiro[3.3]heptan-2-one (0.019 g, 0.170 mmol), acetic acid (0.011 mL, 0.085 mmol), and sodium triacetoxyborohydride (0.054 g, 0.255 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 41.7%) as a white solid.

$^1H$ NMR (400 MHz, $CDCl_3$) δ 8.30 (s, 1H), 8.23 (d, J=7.1 Hz, 1H), 7.55 (d, J=6.9 Hz, 1H), 7.39 (dd, J=14.6, 8.2 Hz, 1H), 7.14-6.79 (m, 5H), 5.01 (s, 2H), 3.13 (d, J=41.6 Hz, 1H), 2.84 (s, 2H), 2.24 (s, 2H), 1.89 (dt, J=53.6, 40.7 Hz, 12H), 1.57-1.37 (m, 2H);

LRMS (ES) m/z 565.5 ($M^+$+1).

Example 154: Synthesis of Compound 4619, N-((7-(5-(difluoromethyl)-1,3,4-oxadiazol-2-yl)imidazo[1,2-a]pyridin-2-yl)methyl)-N-(3-fluorophenyl)-1-(2-oxaspiro[3.3]heptan-6-yl)piperidine-4-carboxamide

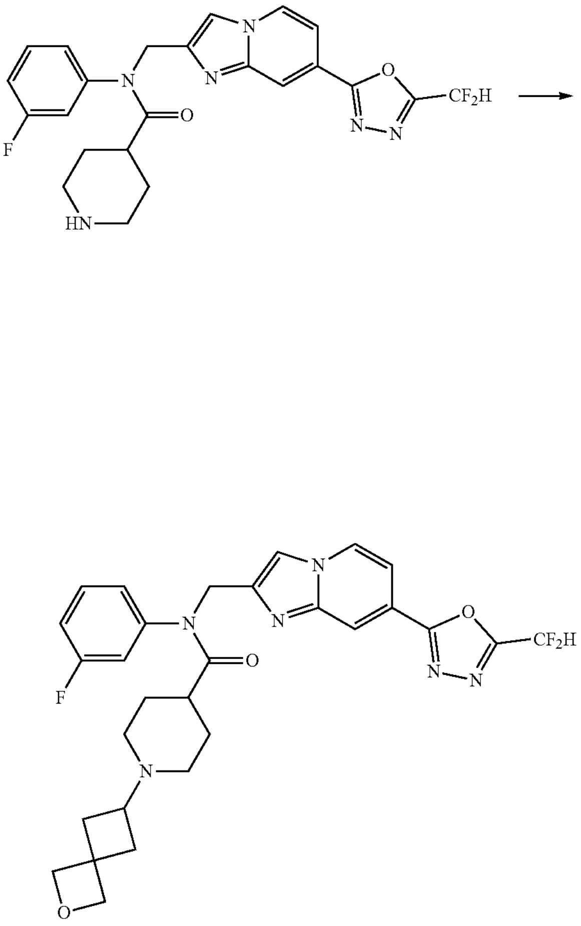

N-((7-(5-(difluoromethyl)-1,3,4-oxadiazol-2-yl)imidazo[1,2-a]pyridin-2-yl)methyl)-N-(3-fluorophenyl)piperidine-4-carboxamide (0.040 g, 0.085 mmol) prepared in step 3 of Example 93, 2-oxaspiro[3.3]heptan-6-one (0.019 g, 0.170 mmol), acetic acid (0.005 mL, 0.085 mmol), and sodium triacetoxyborohydride (0.054 g, 0.255 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 41.5%) as a white solid.

$^1H$ NMR (400 MHz, $CDCl_3$) δ 8.30 (s, 1H), 8.23 (d, J=7.1 Hz, 1H), 7.55 (d, J=7.1 Hz, 1H), 7.39 (dd, J=14.5, 8.1 Hz, 1H), 7.14-6.79 (m, 5H), 5.01 (s, 2H), 4.69 (s, 2H), 4.59 (s, 2H), 3.23 (s, 1H), 2.83 (s, 2H), 2.30 (d, J=47.7 Hz, 4H), 2.04 (s, 2H), 1.96-1.77 (m, 2H), 1.50 (s, 2H);

LRMS (ES) m/z 568.2 ($M^+$+1).

Example 155: Synthesis of Compound 4620, N-((7-(5-(difluoromethyl)-1,3,4-oxadiazol-2-yl)imidazo[1,2-a]pyridin-2-yl)methyl)-N-(3-fluorophenyl)-1-(spiro[3.3]heptan-2-yl)piperidine-4-carboxamide

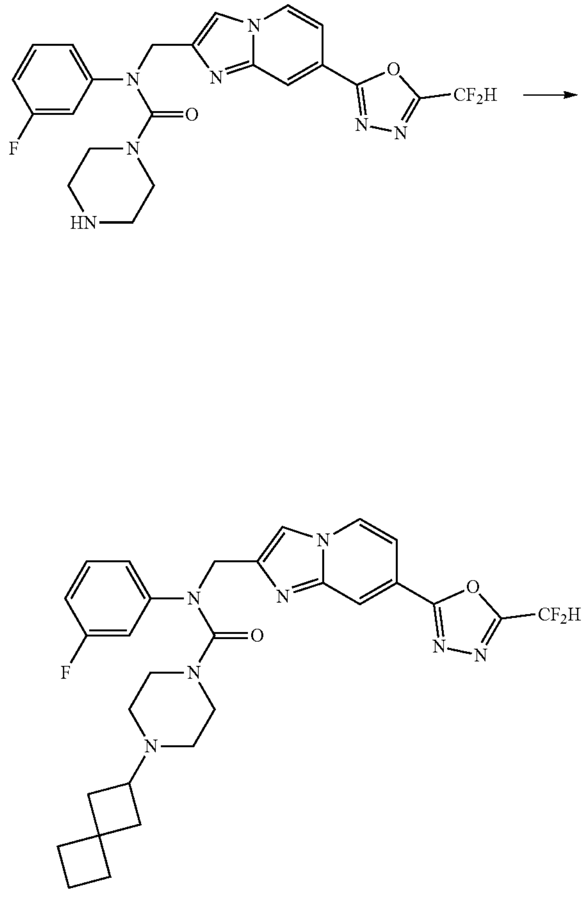

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.040 g, 0.085 mmol) prepared in step 2 of Example 54, spiro[3.3]heptan-2-one (0.019 g, 0.170 mmol), acetic acid (0.005 mL, 0.085 mmol), and sodium triacetoxyborohydride (0.054 g, 0.255 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 41.7%) as a white solid.

$^1$H NMR (400 MHz, $CDCl_3$) δ 8.28 (s, 1H), 8.20 (d, J=7.1 Hz, 1H), 7.74 (s, 1H), 7.51 (dd, J=7.1, 1.6 Hz, 1H), 7.32-7.23 (m, 1H), 7.09-6.76 (m, 4H), 5.06 (s, 2H), 3.33 (s, 4H), 2.14 (d, J=27.7 Hz, 6H), 2.03-1.94 (m, 3H), 1.94-1.86 (m, 2H), 1.82 (dt, J=8.1, 6.0 Hz, 3H);

LRMS (ES) m/z 566.4 ($M^+$+1).

Example 156: Synthesis of Compound 4621, N-((7-(5-(difluoromethyl)-1,3,4-oxadiazol-2-yl)imidazo[1,2-a]pyridin-2-yl)methyl)-N-(3-fluorophenyl)-1-(2-oxaspiro[3.3]heptan-6-yl)piperidine-4-carboxamide

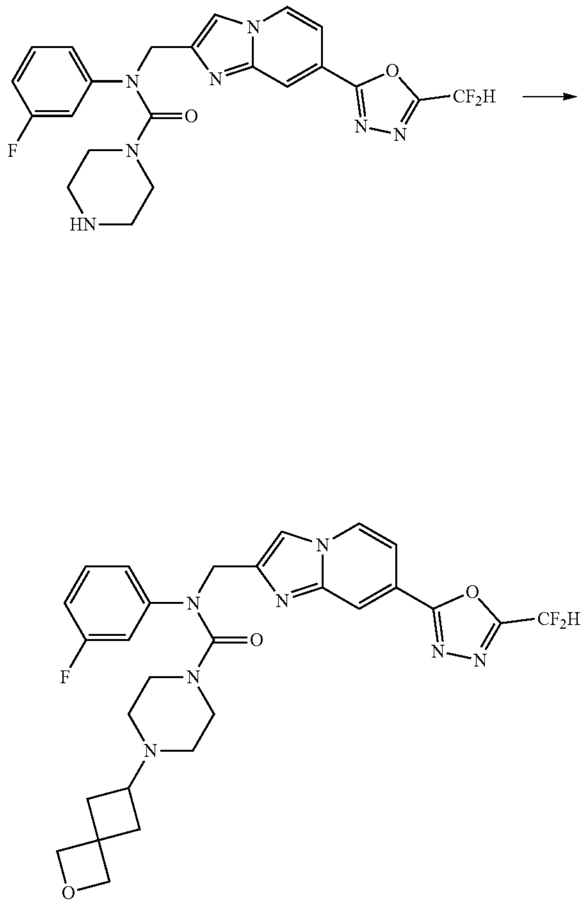

N-((7-(5-(difluoromethyl)-1,3,4-oxadiazol-2-yl)imidazo[1,2-a]pyridin-2-yl)methyl)-N-(3-fluorophenyl)piperazine-1-carboxamide (0.040 g, 0.085 mmol) prepared in step 2 of Example 54, 2-oxaspiro[3.3]heptan-6-one (0.019 g, 0.170 mmol), acetic acid (0.005 mL, 0.085 mmol), and sodium triacetoxyborohydride (0.054 g, 0.255 mmol) were dissolved in dichloromethane (5 mL) at room temperature, and the resulting solution was stirred at the same temperature for 3 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 10%) and concentrated to obtain the title compound (0.020 g, 41.5%) as a white solid.

$^1$H NMR (400 MHz, $CDCl_3$) δ 8.28 (s, 1H), 8.20 (d, J=7.1 Hz, 1H), 7.74 (s, 1H), 7.51 (dd, J=7.1, 1.6 Hz, 1H), 7.33-7.23 (m, 1H), 7.09-6.75 (m, 4H), 5.05 (s, 2H), 4.69 (s, 2H), 4.58 (s, 2H), 3.30 (s, 4H), 2.46 (s, 1H), 2.37 (s, 2H), 2.25-2.04 (m, 3H), 1.95 (d, J=17.0 Hz, 2H);

LRMS (ES) m/z 568.0 ($M^+$+1).

Example 157: Synthesis of Compound 4625, N-((7-(5-(difluoromethyl)-1,3,4-oxadiazol-2-yl)imidazo[1,2-a]pyridin-2-yl)methyl)-6-methyl-N-phenyl-2,6-diazaspiro[3.3]heptan-2-carboxamide

[Step 1] Synthesis of tert-butyl 6-(((7-(5-(difluoromethyl)-1,3,4-oxadiazol-2-yl)imidazo[1,2-a]pyridin-2-yl)methyl)(phenyl)carbamoyl)-2,6-diazaspiro[3.3]heptan-2-carboxylate

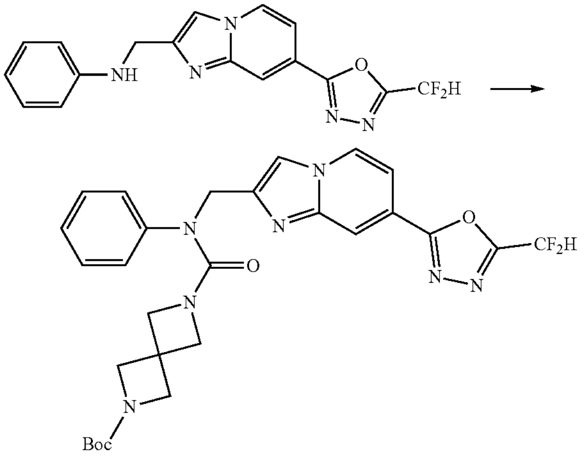

N-((7-(5-(difluoromethyl)-1,3,4-oxadiazol-2-yl)imidazo[1,2-a]pyridin-2-yl)methyl)aniline (0.200 g, 0.586 mmol) prepared in Example 14, tert-butyl 2,6-diazaspiro[3.3]heptan-2-carboxylate (0.081 g, 0.410 mmol), triphosgene (0.174 g, 0.586 mmol), and N,N-diisopropylethylamine (0.510 mL, 2.930 mmol) were dissolved in dichloromethane (10 mL), and the resulting solution was stirred at 0° C. for 1 hour and further stirred at room temperature for 18 hours. Water was poured into the reaction mixture, followed by extraction with dichloromethane. The organic layer was washed with a saturated aqueous water solution, dried over anhydrous magnesium sulfate, filtered, and concentrated under reduced pressure. The concentrate was purified by column chromatography ($SiO_2$, 12 g cartridge; ethyl acetate/hexane=0% to 60%) and concentrated to obtain the title compound (0.210 g, 63.4%) as a brown solid.

[Step 2] Synthesis of N-((7-(5-(difluoromethyl)-1,3,4-oxadiazol-2-yl)imidazo[1,2-a]pyridin-2-yl)methyl)-N-phenyl-2,6-diazaspiro[3.3]heptan-2-carboxamide

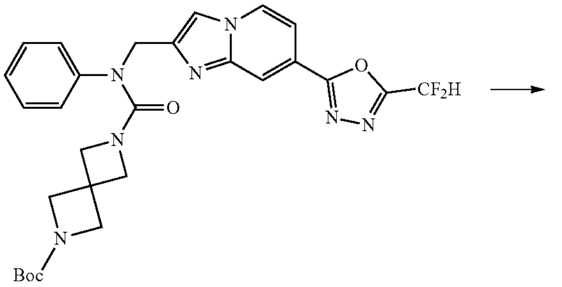

-continued

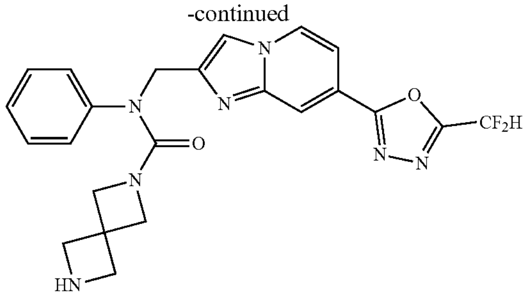

Tert-butyl 6-(((7-(5-(difluoromethyl)-1,3,4-oxadiazol-2-yl)imidazo[1,2-a]pyridin-2-yl)methyl)(phenyl)carbamoyl)-2,6-diazaspiro[3.3]heptan-2-carboxylate (0.210 g, 0.371 mmol) prepared in step 1 and trifluoroacetic acid (0.569 mL, 7.426 mmol) were dissolved in dichloromethane (10 mL) at room temperature, and the resulting solution was stirred at the same temperature for 2 hours. A saturated aqueous sodium hydrogen carbonate solution was poured into the reaction mixture, followed by extraction with dichloromethane. The organic layer was washed with a saturated aqueous water solution, dried over anhydrous magnesium sulfate, filtered, and concentrated under reduced pressure, and the title compound (0.172 g, 99.5%) was obtained as a yellow gel without further purification.

[Step 3] Synthesis of Compound 4625

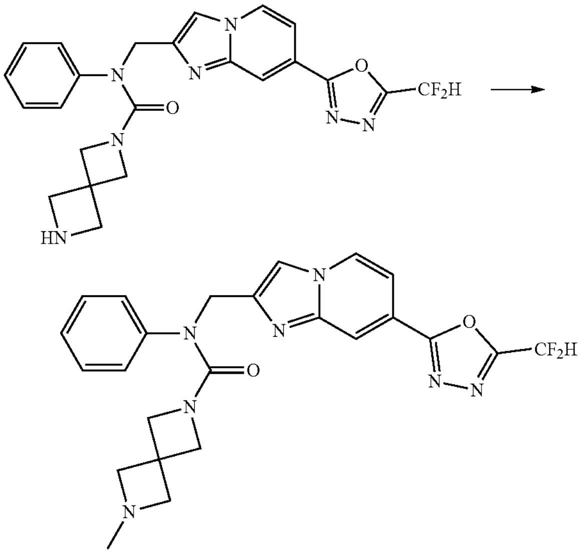

N-((7-(5-(difluoromethyl)-1,3,4-oxadiazol-2-yl)imidazo[1,2-a]pyridin-2-yl)methyl)-N-phenyl-2,6-diazaspiro[3.3]heptan-2-carboxamide (0.172 g, 0.370 mmol) prepared in step 2, formaldehyde (0.022 g, 0.739 mmol), acetic acid (0.021 mL, 0.370 mmol), and sodium triacetoxyborohydride (0.235 g, 1.109 mmol) were dissolved in dichloromethane (5 mL) at room temperature, and the resulting solution was stirred at the same temperature for 18 hours. A saturated aqueous sodium hydrogen carbonate solution was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; dichloromethane/methanol=0% to 20%) and concentrated to obtain the title compound (0.100 g, 56.4%) as a yellow solid.

$^1H$ NMR (400 MHz, $CDCl_3$) δ 8.27 (s, 1H), 8.19 (dt, J=7.8, 3.9 Hz, 1H), 7.81 (s, 1H), 7.50 (dd, J=7.1, 1.7 Hz, 1H), 7.38-7.29 (m, 4H), 7.25-7.19 (m, 1H), 6.94 (dd, J=54.3, 49.1 Hz, 1H), 5.02 (s, 2H), 3.64 (s, 4H), 3.18 (s, 4H), 2.21 (s, 3H);

LRMS (ES) m/z 480.3 ($M^+$+1).

Example 158: Synthesis of Compound 6892, tert-butyl 4-((3-fluorophenyl) ((7-(5-(trifluoromethyl)-1,3,4-oxadiazol-2-yl)imidazo[1,2-a]pyridine-2-yl)methyl)carbamoyl)piperazine-1-carboxylate

[Step 1] Synthesis of tert-butyl (4-(5-(trifluoromethyl)-1,3,4-oxadiazol-2-yl)pyridin-2-yl)carbamate

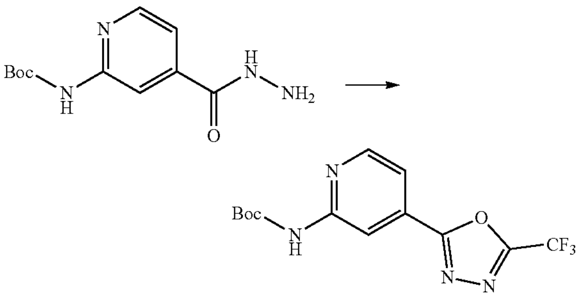

Tert-butyl (4-(hydrazinecarbonyl)pyridin-2-yl)carbamate (2.600 g, 10.306 mmol) prepared in step 2 of Example 2 and triethylamine (14.365 mL, 103.064 mmol) were dissolved in tetrahydrofuran (150 mL), and trifluoroacetic anhydride (7.279 mL, 51.532 mmol) was added at room temperature and heated to reflux for 16 hours. Then, the temperature was lowered to room temperature to terminate the reaction. A saturated aqueous ammonium chloride solution was added to the reaction mixture, followed by extraction with ethyl acetate. The organic layer was washed with a saturated aqueous sodium chloride solution, dried over anhydrous magnesium sulfate, filtered, and concentrated under reduced pressure. Ethyl acetate (30 mL) and hexane (100 mL) were poured into the concentrate, suspended, and filtered to obtain a solid, and the obtained solid was washed with hexane and dried to obtain the title compound (1.500 g, 44.1%) as a white solid.

[Step 2] Synthesis of 4-(5-(trifluoromethyl)-1,3,4-oxadiazol-2-yl)pyridin-2-amine

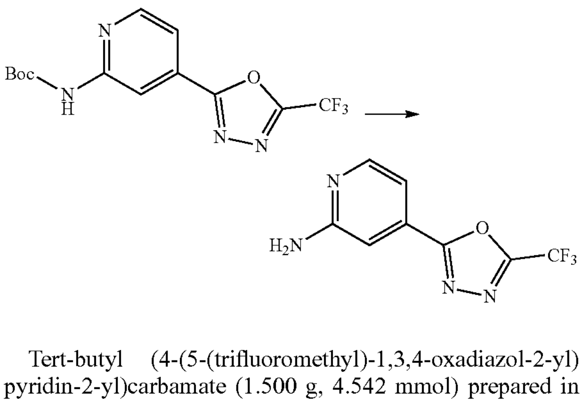

Tert-butyl (4-(5-(trifluoromethyl)-1,3,4-oxadiazol-2-yl) pyridin-2-yl)carbamate (1.500 g, 4.542 mmol) prepared in step 1 was dissolved in dichloromethane (70 mL). Then, trifluoroacetic acid (6.956 mL, 90.835 mmol) was added at 0° C., and the resulting solution was stirred at room temperature for 4 hours. After removing the solvent from the reaction mixture under reduced pressure, a saturated aqueous sodium hydrogen carbonate solution (50 mL) was poured into the concentrate and suspended, followed by filtration to obtain a solid. The obtained solid was washed with water and dried to obtain the title compound (1.030 g, 98.5%) as a yellow solid.

[Step 3] Synthesis of 2-(2-(chloromethyl)imidazo[1,2-a]pyridin-7-yl)-5-(trifluoromethyl)-1,3,4-oxadiazole

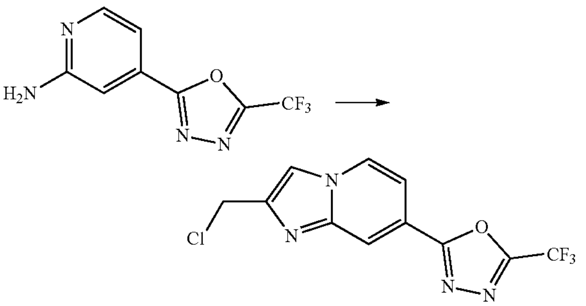

4-(5-(Trifluoromethyl)-1,3,4-oxadiazol-2-yl)pyridin-2-amine (1.100 g, 4.779 mmol) prepared in step 2, 1,3-dichloropropan-2-one (1.214 g, 9.559 mmol), and sodium hydrogen carbonate (2.008 g, 23.897 mmol) were dissolved in 1,4-dioxane (60 mL) at room temperature. The resulting solution was heated to reflux for 16 hours, and then the temperature was lowered to room temperature to terminate the reaction. The reaction mixture was filtered through a plastic filter to remove solids, and the filtrate was purified by column chromatography ($SiO_2$, 40 g cartridge; ethyl acetate/hexane=5% to 70%) and concentrated to obtain the title compound (0.850 g, 58.8%) as a beige solid.

[Step 4] Synthesis of 3-Fluoro-N-((7-(5-(trifluoromethyl)-1,3,4-oxadiazol-2-yl)imidazo[1,2-a]pyridin-2-yl)methyl)aniline

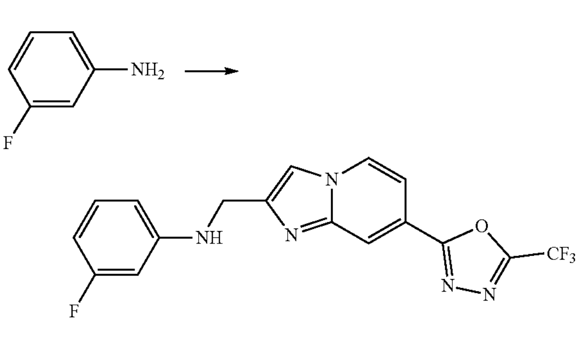

3-(2-(Chloromethyl)imidazo[1,2-a]pyridin-7-yl)-5-(difluoromethyl)-1,3,4-oxadiazole (0.311 g, 1.028 mmol) prepared in step 3, 3-fluoroaniline (0.228 g, 2.055 mmol), potassium carbonate (0.213 g, 1.541 mmol), and potassium iodide (0.085 g, 0.514 mmol) were dissolved in N,N-dimethylformamide (6 mL) at room temperature, and the resulting solution was stirred at 60° C. for 18 hours. Then, the temperature was lowered to room temperature to terminate the reaction. An aqueous N-ammonium chloride solution was poured into the reaction mixture, followed by extraction with ethyl acetate. The organic layer was washed with a saturated aqueous water solution, dried over anhydrous magnesium sulfate, filtered, and concentrated under reduced pressure. The concentrate was purified by chromatography ($SiO_2$ plate, 20×20×1 mm; ethyl acetate/hexane=0% to 50%) and concentrated to obtain the title compound (0.050 g, 12.9%) as a yellow solid.

[Step 5] Synthesis of Compound 6892

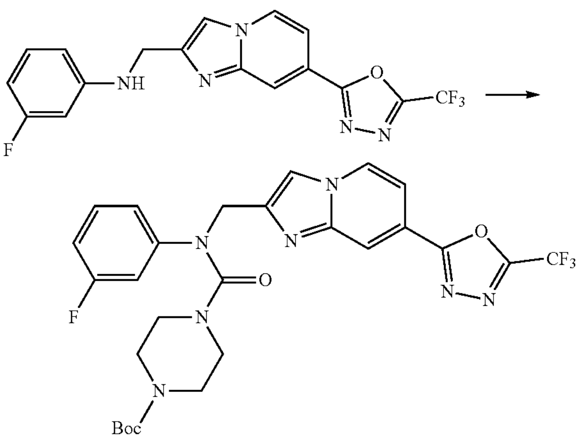

3-Fluoro-N-((7-(5-(trifluoromethyl)-1,3,4-oxadiazol-2-yl)imidazo[1,2-a]pyridin-2-yl)methyl)aniline (0.050 g, 0.133 mmol) prepared in step 4, bis(trichloromethyl)carbonate (0.039 g, 0.133 mmol), and N,N-diisopropylethylamine (0.115 mL, 0.663 mmol) were dissolved in dichloromethane (4 mL), and the resulting solution was stirred at room temperature for 10 minutes. Then, tert-butyl piperazine-1-carboxylate (0.032 g, 0.172 mmol) was added and further stirred at the same temperature for 18 hours. Water was poured into the reaction mixture, extracted with dichloromethane, and filtered through a plastic filter to remove a solid residue and an aqueous layer, and then concentrated under reduced pressure. The concentrate was purified by chromatography ($SiO_2$ plate, 20×20×1 mm; ethyl acetate/hexane=0% to 100%) and concentrated to obtain the title compound (0.040 g, 51.3%) as a brown solid.

$^1H$ NMR (400 MHz, Acetone-d6) δ 8.69 (d, J=7.1 Hz, 1H), 8.25 (d, J=1.7 Hz, 1H), 8.08 (s, 1H), 7.53 (dd, J=7.1, 1.8 Hz, 1H), 7.36 (td, J=8.3, 6.7 Hz, 1H), 7.14 (ddt, J=8.0, 5.3, 2.3 Hz, 2H), 6.86 (td, J=8.4, 2.4 Hz, 1H), 5.09 (s, 2H), 3.28 (qd, J=6.2, 5.0, 2.5 Hz, 8H), 1.42 (s, 10H);

LRMS (ES) m/z 591.1 ($M^+$+1).

Activity Measurement and Analysis Protocol of the Compounds of the Present Invention <Experimental Example 1> In Vitro HDAC Enzyme Activity Inhibition Assay In order to confirm the selectivity of the compounds represented by Chemical Formula I of the present invention to HDAC6 through HDAC1 and HDAC6 enzyme activity inhibition experiments, a comparison experiment was performed using the material that has already been developed as a control group.

HDAC enzyme activity was measured using the HDAC Fluorimetric Drug Discovery Kit (Enzo Life Sciences, Inc., BML-AK511, 516). For the HDAC1 enzyme activity test, human recombinant HDAC1 (BML-SE456) was used as an enzyme source and Fluor de Lys®-SIRT1 (BNL-KI177) was used as a substrate. After dispensing 5-fold diluted compounds into a 96-well plate, 0.3 μg of enzyme and 10 μM substrate were added to each well of the plate and allowed to react at 30° C. for 60 minutes. Next, Fluor de Lys® Developer II (BML-KI176) was added and reacted for 30 minutes to complete the reaction, and then the fluorescence values (Ex 360, Em 460) were measured using a multi-plate reader (Flexstation 3, Molecular Device). The HDAC6 enzymes were tested using human recombinant HDAC6 (382180) from Calbiochem Inc., according to the same protocol as the HDAC1 enzyme activity test method. With respect to the final result values, respective IC50 values were calculated using GraphPad Prism 4.0 program, and results thereof were summarized in Table 5 below.

TABLE 5

Results of HDAC enzyme activity inhibition assay

| Example | Compounds | HDAC1 (nM) | HDAC6 (nM) | HDAC6 Selectivity (fold) |
|---|---|---|---|---|
| 1 | 3009 | >50.000 | 79.2 | 631 |
| 2 | 3585 | >50.000 | 129.5 | 386 |
| 3 | 3586 | >50.000 | 330.4 | 151 |
| 4 | 3587 | >50.000 | 334.4 | 150 |
| 5 | 3588 | >50.000 | 244.1 | 205 |
| 6 | 3589 | >50.000 | 530.3 | 94 |
| 7 | 3590 | >50.000 | 432.0 | 116 |
| 8 | 3591 | >50.000 | 1,064 | 47 |
| 9 | 3592 | >50.000 | 457.4 | 109 |
| 10 | 3593 | >50.000 | 261.4 | 191 |
| 11 | 3594 | >50.000 | 564.4 | 89 |
| 12 | 3595 | >50.000 | 444.5 | 112 |
| 13 | 3596 | >50.000 | 312.9 | 160 |
| 14 | 3668 | >50.000 | 167.4 | 299 |
| 15 | 3669 | >50.000 | 117.4 | 426 |
| 16 | 3670 | >50.000 | 221.2 | 226 |
| 17 | 3671 | >50.000 | 157.0 | 318 |
| 18 | 3672 | >50.000 | 107.7 | 464 |
| 19 | 3673 | >50.000 | 400.2 | 125 |
| 20 | 3674 | >50.000 | 390.8 | 128 |
| 21 | 3675 | >50.000 | 124.8 | 401 |
| 22 | 3676 | >50.000 | 141.4 | 354 |
| 23 | 3677 | >50.000 | 255.0 | 196 |
| 24 | 3678 | >50.000 | 294.0 | 170 |
| 25 | 3679 | >50.000 | 146.8 | 341 |
| 26 | 3719 | >50.000 | 211.1 | 237 |
| 27 | 3720 | >50.000 | 412.6 | 121 |
| 28 | 3721 | >50.000 | 406.5 | 123 |
| 29 | 3722 | >50.000 | 287.3 | 174 |
| 30 | 3723 | >50.000 | 240.1 | 174 |
| 31 | 3724 | >50.000 | 892.7 | 56 |
| 32 | 3725 | >50.000 | 177.4 | 282 |
| 33 | 3782 | >50.000 | 67.6 | 740 |
| 34 | 3783 | >50.000 | 71.8 | 696 |
| 35 | 3784 | >50.000 | 68.8 | 727 |
| 36 | 3785 | >50.000 | 114.3 | 437 |
| 37 | 4033 | >50.000 | 93.0 | 538 |
| 38 | 4034 | >50.000 | 103.0 | 485 |
| 39 | 4035 | >50.000 | 297.5 | 168 |
| 40 | 4036 | >50.000 | 155.7 | 321 |
| 41 | 4037 | >50.000 | 123.9 | 404 |
| 42 | 4038 | >50.000 | 130.8 | 382 |
| 43 | 4039 | >50.000 | 147.8 | 338 |
| 44 | 4040 | >50.000 | 118.8 | 421 |
| 45 | 4041 | >50.000 | 259.2 | 193 |
| 46 | 4042 | >50.000 | 254.2 | 197 |
| 47 | 4043 | >50.000 | 165.6 | 302 |
| 48 | 4044 | >50.000 | 130.2 | 384 |
| 49 | 4045 | >50.000 | 127.5 | 392 |
| 50 | 4046 | >50.000 | 125.0 | 400 |
| 51 | 4047 | >50.000 | 125.0 | 400 |
| 52 | 4048 | >50.000 | 246.8 | 203 |
| 53 | 4049 | >50.000 | 92.8 | 539 |
| 54 | 4083 | >50.000 | 464.9 | 108 |
| 55 | 4084 | >50.000 | 272.5 | 183 |

TABLE 5-continued

Results of HDAC enzyme activity inhibition assay

| Example | Compounds | HDAC1 (nM) | HDAC6 (nM) | HDAC6 Selectivity (fold) |
|---|---|---|---|---|
| 56 | 4085 | >50.000 | 214.2 | 233 |
| 57 | 4086 | >50.000 | 201.1 | 249 |
| 58 | 4087 | >50.000 | 233.4 | 214 |
| 59 | 4088 | >50.000 | 320.3 | 156 |
| 60 | 4089 | >50.000 | 442.8 | 113 |
| 61 | 4090 | >50.000 | 231.9 | 216 |
| 62 | 4091 | >50.000 | 257.3 | 194 |
| 63 | 4092 | >50.000 | 266.8 | 187 |
| 64 | 4093 | >50.000 | 195.2 | 256 |
| 65 | 4094 | >50.000 | 232.4 | 215 |
| 66 | 4095 | >50.000 | 270.4 | 185 |
| 67 | 4096 | >50.000 | 413.4 | 121 |
| 68 | 4097 | >50.000 | 149.4 | 335 |
| 69 | 4098 | >50.000 | 153.8 | 325 |
| 70 | 4099 | >50.000 | 138.7 | 360 |
| 71 | 4100 | >50.000 | 468.4 | 107 |
| 72 | 4101 | >50.000 | 107.8 | 464 |
| 73 | 4102 | >50.000 | 305.3 | 164 |
| 74 | 4103 | >50.000 | 200.8 | 249 |
| 75 | 4115 | >50.000 | 353.6 | 141 |
| 76 | 4116 | >50.000 | 314.0 | 159 |
| 77 | 4117 | >50.000 | 376.9 | 133 |
| 78 | 4118 | >50.000 | 331.8 | 151 |
| 79 | 4119 | >50.000 | 402.4 | 124 |
| 80 | 4120 | >50.000 | 509.1 | 98 |
| 81 | 4121 | >50.000 | 411.4 | 122 |
| 82 | 4122 | >50.000 | 353.0 | 142 |
| 83 | 4123 | >50.000 | 306.6 | 163 |
| 84 | 4124 | >50.000 | 340.9 | 147 |
| 85 | 4125 | >50.000 | 329.2 | 152 |
| 86 | 4126 | >50.000 | 403.8 | 124 |
| 87 | 4127 | >50.000 | 612.2 | 82 |
| 88 | 4128 | >50.000 | 315.3 | 159 |
| 89 | 4129 | >50.000 | 401.5 | 125 |
| 90 | 4130 | >50.000 | 375.4 | 133 |
| 91 | 4131 | >50.000 | 547.0 | 91 |
| 92 | 4132 | >50.000 | 655.2 | 76 |
| 93 | 4137 | >50.000 | 176.9 | 283 |
| 94 | 4138 | >50.000 | 171.2 | 292 |
| 95 | 4139 | >50.000 | 124.0 | 403 |
| 96 | 4140 | >50.000 | 203.1 | 246 |
| 97 | 4141 | >50.000 | 244.8 | 204 |
| 98 | 4142 | >50.000 | 214.1 | 234 |
| 99 | 4143 | >50.000 | 149.3 | 335 |
| 100 | 4144 | >50.000 | 242.7 | 206 |
| 101 | 4145 | >50.000 | 230.1 | 217 |
| 102 | 4146 | >50.000 | 243.0 | 206 |
| 103 | 4147 | >50.000 | 395.9 | 126 |
| 104 | 4149 | >50.000 | 149.4 | 335 |
| 105 | 4150 | >50.000 | 214.0 | 234 |
| 106 | 4151 | >50.000 | 203.9 | 245 |
| 107 | 4152 | >50.000 | 204.1 | 245 |
| 108 | 4153 | >50.000 | 137.9 | 363 |
| 109 | 4154 | >50.000 | 229.1 | 218 |
| 110 | 4155 | >50.000 | 352.0 | 142 |
| 111 | 4156 | >50.000 | 139.1 | 359 |
| 112 | 4157 | >50.000 | 163.5 | 306 |
| 113 | 4158 | >50.000 | 446.7 | 112 |
| 114 | 4159 | >50.000 | 425.0 | 118 |
| 115 | 4160 | >50.000 | 202.1 | 247 |
| 116 | 4161 | >50.000 | 223.2 | 224 |
| 117 | 4162 | >50.000 | 358.3 | 140 |
| 118 | 4163 | >50.000 | 410.5 | 122 |
| 119 | 4164 | >50.000 | 340.3 | 147 |
| 120 | 4165 | >50.000 | 413.2 | 121 |
| 121 | 4166 | >50.000 | 254.0 | 197 |
| 122 | 4167 | >50.000 | 447.0 | 112 |
| 123 | 4168 | >50.000 | 399.6 | 125 |
| 124 | 4169 | >50.000 | 815.3 | 61 |
| 125 | 4170 | >50.000 | 347.2 | 144 |
| 126 | 4171 | >50.000 | 355.3 | 141 |
| 127 | 4172 | >50.000 | 271.8 | 184 |
| 128 | 4173 | >50.000 | 312.2 | 160 |
| 129 | 4174 | >50.000 | 298.4 | 168 |
| 130 | 4175 | >50.000 | 380.6 | 131 |
| 131 | 4176 | >50.000 | 250.8 | 199 |
| 132 | 4177 | >50.000 | 244.4 | 205 |
| 133 | 4188 | >50.000 | 373.3 | 134 |
| 134 | 4189 | >50.000 | 158.6 | 315 |
| 135 | 4190 | >50.000 | 126.5 | 395 |
| 136 | 4191 | >50.000 | 134.1 | 373 |
| 137 | 4192 | >50.000 | 110.6 | 452 |
| 138 | 4193 | >50.000 | 138.6 | 361 |
| 139 | 4194 | >50.000 | 132.0 | 379 |
| 140 | 4195 | >50.000 | 191.9 | 261 |
| 141 | 4196 | >50.000 | 181.0 | 276 |
| 142 | 4197 | >50.000 | 241.9 | 207 |
| 143 | 4198 | >50.000 | 184.6 | 271 |
| 144 | 4199 | >50.000 | 250.1 | 200 |
| 145 | 4200 | >50.000 | 219.7 | 228 |
| 146 | 4201 | >50.000 | 282.7 | 177 |
| 147 | 4202 | >50.000 | 182.4 | 274 |
| 148 | 4203 | >50.000 | 169.7 | 295 |
| 149 | 4204 | >50.000 | 186.8 | 268 |
| 150 | 4205 | >50.000 | 143.8 | 348 |
| 151 | 4206 | >50.000 | 138.5 | 361 |
| 152 | 4207 | >50.000 | 167.8 | 298 |
| 153 | 4618 | >50,000 | 162 | 308 |
| 154 | 4619 | >50,000 | 197 | 253 |
| 155 | 4620 | >50,000 | 263 | 190 |
| 156 | 4621 | >50,000 | 153 | 326 |
| 157 | 4625 | >50,000 | 98 | 510 |
| 158 | 6892 | >50.000 | 2,358 | 21.2 |

As shown in Table 5 above, it was found from the results of the activity inhibition assay for HDAC1 and HDAC6 that the 1,3,4-oxadiazole derivative compounds of the present invention, the optical isomer thereof, or the pharmaceutically acceptable salt thereof exhibited about 21 to about 740 times higher selective HDAC6 inhibitory activity.

<Experimental Example 2> In Vitro Analysis of Effect of HDAC6-Specific Inhibitor on Mitochondrial Axonal Transport The effect of the HDAC6-specific inhibitors on mitochondrial axonal transport was analyzed. Specifically, in order to confirm whether the compounds represented by Chemical Formula I of the present invention selectively inhibit the HDAC6 activity and increase the acetylation of tubulin, which is a major substrate of HDAC6, thereby improving the mitochondrial axonal transport rates reduced by amyloid-beta treatment in neuronal axons, a comparison experiment was performed using the material that has already been developed as a control group.

Hippocampal neurons from Sprague-Dawley (SD) rat embryos at embryonic day 17-18 (E17-18) were cultured for 7 days in an extracellular matrix-coated culture dish for imaging, and then treated with 1M of amyloid-beta peptide fragments. After 24 hours, the compound was treated on the 8th day of in vitro culture, and 3 hours later, treated with MitoTracker Red CMXRos (Life Technologies, NY, USA) for the last 5 minutes to stain the mitochondria. With regard to the axonal transport of the stained neuron mitochondria, the transport rates of each mitochondrion were determined using the IMARIS analysis software (BITPLANE, Zurich, Switzerland) by taking images using a confocal microscope (Leica 5P8; Leica Microsystems, UK) at 1-second intervals for 1 minute.

As a result, it was confirmed that the 1,3,4-oxadiazole derivative compound of the present invention, the optical isomer thereof or the pharmaceutically acceptable salts thereof showed an improvement effect on the rates of mitochondrial axonal transport.

The invention claimed is:

1. A 1,3,4-oxadiazole derivative compound represented by Chemical Formula I below, an optical isomer thereof, or a pharmaceutically acceptable salt thereof:

[Chemical Formula I]

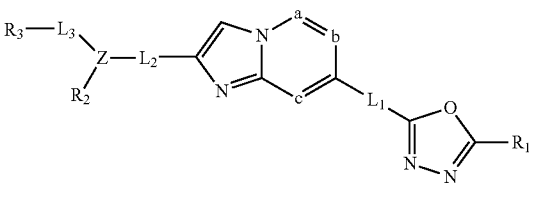

in the Chemical Formula I above, $L_1$, $L_2$ and $L_3$ are each independently —($C_0$-$C_2$alkyl)-;

a, b and c are each independently N or $CR_4$, wherein a, b and c cannot be N at the same time, and $R_4$ is —H, —X or —O($C_1$-$C_4$alkyl);

Z is N, O, S, or nothing (null), wherein when Z is nothing (null), $R_2$ is also nothing (null), and $L_2$ and $L_3$ are directly linked;

$R_1$ is —$CX_2$H or —$CX_3$;

$R_2$ is —H, —($C_1$-$C_4$alkyl), —C(=O)—$R^A$, —C(=O)—$OR^B$ or —C(=O)—$NR^CR^D$, wherein when Z is O or S, $R_2$ is nothing (null);

$R^A$ is —($C_1$-$C_4$alkyl), —($C_1$-$C_4$alkyl)-O—($C_1$-$C_4$alkyl), —($C_1$-$C_4$alkyl)-C(=O)—O($C_1$-$C_4$alkyl), -aryl, -heteroaryl, —$NR^{A1}R^{A2}$,

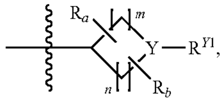

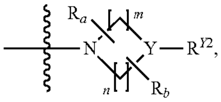

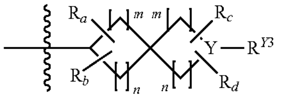

or

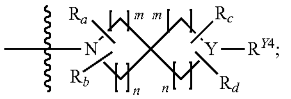

$R^B$ to $R^D$ are each independently —H, —($C_1$-$C_4$alkyl), —($C_1$-$C_4$alkyl)-O—($C_1$-$C_4$alkyl), —($C_1$-$C_4$alkyl)-C(=O)—O($C_1$-$C_4$alkyl), —($C_3$-$C_7$cycloalkyl), -aryl or -heteroaryl;

Y is N, CH, O or S(=O)$_2$, when Y is N or CH, $R^{Y1}$ to $R^{Y4}$ are each independently —H, —X, —OH, —($C_1$-$C_4$alkyl), —($C_3$-$C_7$cycloalkyl), —($C_2$-$C_6$heterocycloalkyl), —($C_1$-$C_4$alkyl)-O—($C_1$-$C_4$alkyl), —($C_1$-$C_4$alkyl)-C(=O)—O($C_1$-$C_4$alkyl), —C(=O)—($C_1$-$C_4$alkyl), —C(=O)—O($C_1$-$C_4$alkyl), —C(=O)—$NR^{A3}R^{A4}$, —C(=O)—($C_3$-$C_7$cycloalkyl), —C(=O)—($C_2$-$C_6$heterocycloalkyl), —S(=O)$_2$—($C_1$-$C_4$alkyl), -aryl, —($C_1$-$C_4$alkyl)-aryl, -heteroaryl, —($C_1$-$C_4$alkyl)-heteroaryl, an amine protecting group, or

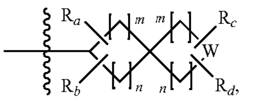

wherein at least one H of —($C_1$-$C_4$alkyl), —($C_3$-$C_7$cycloalkyl), —($C_1$-$C_4$alkyl)-O—($C_1$-$C_4$alkyl), —($C_1$-$C_4$alkyl)-C(=O)—O($C_1$-$C_4$alkyl), —C(=O)—($C_1$-$C_4$alkyl), —C(=O)—($C_3$-$C_7$cycloalkyl), —C(=O)—($C_2$-$C_6$heterocycloalkyl) and —S(=O)$_2$—($C_1$-$C_4$alkyl) may be substituted with —X or —OH; at least one H of the aryl, —($C_1$-$C_4$alkyl)-aryl, heteroaryl and —($C_1$-$C_4$alkyl)-heteroaryl may be substituted with —($C_1$-$C_4$alkyl), —O—($C_1$-$C_4$alkyl), —X, —OH or —$CF_3$; —($C_2$-$C_6$heterocycloalkyl), -heteroaryl, —($C_1$-$C_4$alkyl) heteroaryl may contain N, O or S atoms in the ring; and W is NH, $CH_2$ or O;

when Y is O or S(=O)$_2$, $R^{Y1}$ to $R^{Y4}$ are nothing (null);

m and n are each independently an integer of 1, 2 or 3;

$R_a$ to $R_d$ are each independently —H or —($C_1$-$C_4$alkyl);

$R_3$ is —H, —($C_1$-$C_4$alkyl), —($C_1$-$C_4$alkyl)-O($C_1$-$C_4$alkyl), —($C_1$-$C_4$alkyl)-C(=O)—O($C_1$-$C_4$alkyl), —C(=O)—O($C_1$-$C_4$alkyl), —($C_3$-$C_7$cycloalkyl), —($C_2$-$C_6$heterocycloalkyl), -adamantyl, -aryl or -heteroaryl, wherein at least one H of —($C_1$-$C_4$alkyl) may be substituted with —X or —OH; at least one —H of —($C_3$-$C_7$cycloalkyl), —($C_2$-$C_6$heterocycloalkyl), -adamantyl, -aryl or -heteroaryl may each independently be substituted with —X, —OH, —($C_1$-$C_4$alkyl), —O($C_1$-$C_4$alkyl), —(C=O)—($C_1$-$C_4$alkyl), —C(=O)—O($C_1$-$C_4$alkyl), —$CF_3$, —$CF_2$H, —$OCF_3$, —$NR^{A5}R^{A6}$—S(=O)$_2$—($C_1$-$C_4$alkyl), -aryl and -heteroaryl;

$R^{A1}$ to $R^{A6}$ are each independently —H or —($C_1$-$C_4$alkyl); and

X is F, Cl, Br or I.

2. The 1,3,4-oxadiazole derivative compound represented by Chemical Formula I, the optical isomer thereof, or the pharmaceutically acceptable salt thereof according to claim 1, wherein in the Chemical Formula I above, $L_1$, $L_2$ and $L_3$ are each independently —($C_0$-$C_1$alkyl)-;

a, b and c are each independently N or $CR_4$, wherein a, b and c cannot be N at the same time, and $R_4$ is —H or —X;

Z is N, O, or nothing (null), wherein when Z is nothing (null), $R_2$ is also nothing (null), and $L_2$ and $L_3$ are directly linked;

$R_1$ is —$CX_2$H or —$CX_3$;

$R_2$ is —H, —($C_1$-$C_4$alkyl) or —C(=O)—$R^A$, wherein when Z is O, $R_2$ is nothing (null);

$R^A$ is —$NR^{A1}R^{A2}$,

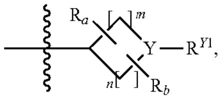

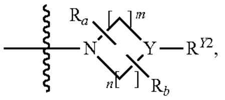

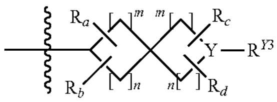

or

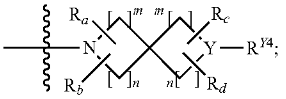

Y is N, CH, O or $S(=O)_2$;

when Y is N or CH, $R^{Y1}$ to $R^{Y4}$ are each independently —H, —($C_1$-$C_4$alkyl), —($C_3$-$C_7$cycloalkyl), —($C_2$-$C_6$heterocycloalkyl), —C(=O)—($C_1$-$C_4$alkyl), —C(=O)—O($C_1$-$C_4$alkyl), —C(=O)—$NR^{A3}R^{A4}$, —C(=O)—($C_3$-$C_7$cycloalkyl), —C(=O)—($C_2$-$C_6$heterocycloalkyl), —$S(=O)_2$—($C_1$-$C_4$alkyl), -aryl, -heteroaryl, or

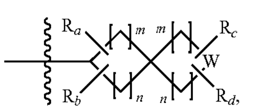

wherein at least one H of —($C_1$-$C_4$alkyl), —($C_3$-$C_7$cycloalkyl), —C(=O)—($C_1$-$C_4$alkyl), —C(=O)—($C_3$-$C_7$cycloalkyl), —C(=O)—($C_2$-$C_6$heterocycloalkyl) and —$S(=O)_2$—($C_1$-$C_4$alkyl) may be substituted with —X or —OH; at least one H of the aryl and heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is NH, $CH_2$ or O;

when Y is O or $S(=O)_2$, $R^{Y1}$ to $R^{Y4}$ are nothing (null);

m or n is each independently an integer of 1 or 2;

$R_a$ to $R_d$ are each independently —H or —($C_1$-$C_4$alkyl);

$R_3$ is —($C_3$-$C_7$cycloalkyl), —($C_2$-$C_6$heterocycloalkyl), -adamantyl, -aryl or -heteroaryl, wherein at least one —H of —($C_3$-$C_7$cycloalkyl), —($C_2$-$C_6$heterocycloalkyl), -adamantyl, -aryl or -heteroaryl may each independently be substituted with —X, —OH, —($C_1$-$C_4$alkyl), —O($C_1$-$C_4$alkyl), —(C=O)—($C_1$-$C_4$alkyl), —C(=O)—O($C_1$-$C_4$alkyl), —$CF_3$, —$CF_2H$, —$OCF_3$, —$NR^{A5}R^{A6}$, —$S(=O)_2$—($C_1$-$C_4$alkyl), -aryl, or -heteroaryl;

$R^{A1}$ to $R^{A6}$ are each independently —H or —($C_1$-$C_4$alkyl); and

X is F, Cl or Br.

3. The 1,3,4-oxadiazole derivative compound represented by Chemical Formula I, the optical isomer thereof, or the pharmaceutically acceptable salt thereof according to claim 2, wherein in the Chemical Formula I above, $L_1$ and $L_3$ are each independently —($C_0$alkyl)-;

$L_2$ is —($C_1$alkyl)-;

a, b and c are $CR_4$, wherein $R_4$ is —H or —X;

Z is N, O, or nothing (null), wherein when Z is nothing (null), $R_2$ is also nothing (null), and $L_2$ and $L_3$ are directly linked;

$R_1$ is —$CF_2H$ or —$CF_3$;

$R_2$ is —H or —C(=O)—$R^A$, wherein Z is O, $R_2$ is nothing (null);

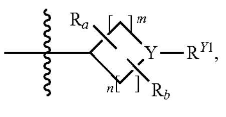,

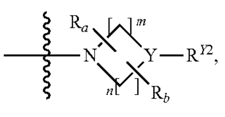,

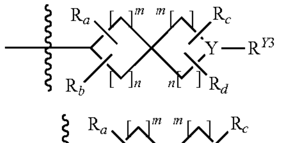

or

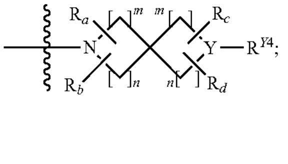;

Y is N;

$R^{Y1}$ to $R^{Y4}$ are each independently —($C_1$-$C_4$alkyl), —($C_3$-$C_7$cycloalkyl), —($C_2$-$C_6$heterocycloalkyl), —C(=O)—($C_1$-$C_4$alkyl), —C(=O)—O($C_1$-$C_4$alkyl), —C(=O)—$NR^{A3}R_{44}$, —C(=O)—($C_3$-$C_7$cycloalkyl), —C(=O)—($C_2$-$C_6$heterocycloalkyl), —$S(=O)_2$—($C_1$-$C_4$alkyl), -heteroaryl, or

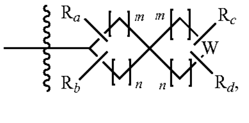

wherein at least one H of —($C_1$-$C_4$alkyl), —($C_3$-$C_7$cycloalkyl), —C(=O)—($C_1$-$C_4$alkyl), —C(=O)—($C_3$-$C_7$cycloalkyl), —C(=O)—($C_2$-$C_6$heterocycloalkyl) and —$S(=O)_2$—($C_1$-$C_4$alkyl) may be substituted with —X or —OH; at least one H of the heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is $CH_2$ or O;

m and n are each independently an integer of 1 or 2;

$R_a$ to $R_d$ are each independently —H or —($C_1$-$C_4$alkyl);

$R_3$ is —($C_3$-$C_7$cycloalkyl), -adamantyl, -aryl or -heteroaryl, wherein at least one —H of —($C_3$-$C_7$cycloalkyl), -adamantyl, -aryl or -heteroaryl may each independently be substituted with —X, —($C_1$-$C_4$alkyl), —O($C_1$-$C_4$alkyl), —(C=O)—($C_1$-$C_4$alkyl), —$CF_3$, or —$S(=O)_2$—($C_1$-$C_4$alkyl);

$R^{A1}$ to $R^{A6}$ are each independently —H or —($C_1$-$C_4$alkyl); and

X is F or Cl.

4. The 1,3,4-oxadiazole derivative compound represented by Chemical Formula I, the optical isomer thereof, or the pharmaceutically acceptable salt thereof according to claim 2, wherein in the Chemical Formula I above, $L_1$, $L_2$ or $L_3$ is each independently —($C_0$-$C_1$alkyl)-;

a, b and c are each independently N or $CR_4$, wherein a, b and c cannot be N at the same time, and $R_4$ is —H or —X;

Z is N;

$R_1$ is —$CX_2H$ or —$CX_3$;

$R_2$ is —C(=O)—$R^A$;

$R^A$ is

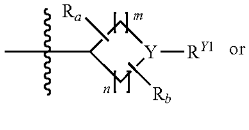

or

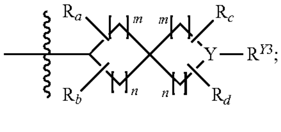;

Y is N, CH, O or $S(=O)_2$;

when Y is N or CH, $R^{Y1}$ and $R^{Y3}$ are each independently —H, —($C_1$-$C_4$alkyl), —($C_3$-$C_7$cycloalkyl), —($C_2$-$C_6$heterocycloalkyl), —C(=O)—($C_1$-$C_4$alkyl), —C(=O)—O($C_1$-$C_4$alkyl), —C(=O)—$NR^{A3}R^{A4}$, —C(=O)—($C_3$-$C_7$cycloalkyl), —C(=O)—($C_2$-$C_6$heterocycloalkyl), —$S(=O)_2$—($C_1$-$C_4$alkyl), -aryl, -heteroaryl, or

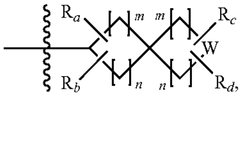

wherein at least one H of —($C_1$-$C_4$alkyl), —($C_3$-$C_7$cycloalkyl), —C(═O)—($C_1$-$C_4$alkyl), —C(═O)—($C_3$-$C_7$cycloalkyl), —C(═O)—($C_2$-$C_6$heterocycloalkyl) and —S(═O)$_2$—($C_1$-$C_4$alkyl) may be substituted with —X or —OH; at least one H of the aryl and heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is NH, $CH_2$ or O;

when Y is O or S(═O)$_2$, $R^{Y1}$ and $R^{Y3}$ are nothing (null);

m and n are each independently an integer of 1 or 2;

$R_a$ to $R_d$ are each independently —H or —($C_1$-$C_4$alkyl);

$R_3$ is —($C_3$-$C_7$cycloalkyl), —($C_2$-$C_6$heterocycloalkyl), -adamantyl, -aryl or -heteroaryl, wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C═O)—($C_1$-$C_4$alkyl), —C(═O)—O($C_1$-$C_4$alkyl), —$CF_3$, —$CF_2$H, —$OCF_3$, —$NR^{A5}R^{A6}$, —S(═O)$_2$—($C_1$-$C_4$alkyl), -aryl, or -heteroaryl;

$R^{A3}$ to $R^{A6}$ are each independently —H or —($C_1$-$C_4$alkyl); and

X is F, Cl or Br.

5. The 1,3,4-oxadiazole derivative compound represented by Chemical Formula I, the optical isomer thereof, or the pharmaceutically acceptable salt thereof according to claim 2, wherein in the Chemical Formula I above, $L_1$, $L_2$ and $L_3$ are each independently —($C_0$-$C_1$alkyl)-;

a, b and c are each independently N or $CR_4$, wherein a, b and c cannot be N at the same time, and $R_4$ is —H or —X;

Z is N;

$R_1$ is —$CX_2$H or —$CX_3$;

$R_2$ is —C(═O)—$R^A$;

$R^A$ is —$NR^{A1}R^{A2}$,

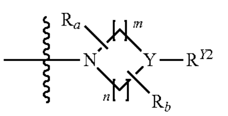

or

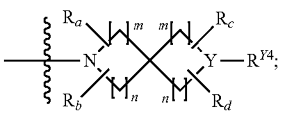

;

Y is N, CH, O or S(═O)$_2$;

when Y is N or CH, $R^{Y2}$ and $R^{Y4}$ are each independently —H, —($C_1$-$C_4$alkyl), —($C_3$-$C_7$cycloalkyl), —($C_2$-$C_6$heterocycloalkyl), —C(═O)—($C_1$-$C_4$alkyl), —C(═O)—O($C_1$-$C_4$alkyl), —C(═O)—$NR^{A3}R^{A4}$, —C(═O)—($C_3$-$C_7$cycloalkyl), —C(═O)—($C_2$-$C_6$heterocycloalkyl), —S(═O)$_2$—($C_1$-$C_4$alkyl), -aryl, -heteroaryl, or

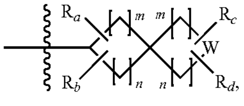

, wherein at least one H of —($C_1$-$C_4$alkyl), —($C_3$-$C_7$cycloalkyl), —C(═O)—($C_1$-$C_4$alkyl), —C(═O)—($C_3$-$C_7$cycloalkyl), —C(═O)—($C_2$-$C_6$heterocycloalkyl) and —S(═O)$_2$—($C_1$-$C_4$alkyl) may be substituted with —X or —OH; at least one H of the aryl or heteroaryl may be substituted with —($C_1$-$C_4$alkyl), —O—($C_1$-$C_4$alkyl), —X, —OH or —$CF_3$; —($C_2$-$C_6$heterocycloalkyl) or -heteroaryl may contain N, O or S atoms in the ring; and W is NH, $CH_2$ or O;

when Y is O or S(═O)$_2$, $R^{Y2}$ and $R^{Y4}$ are nothing (null);

m and n are each independently an integer of 1 or 2;

$R_a$ to $R_d$ are each independently —H or —($C_1$-$C_4$alkyl);

$R_3$ is —($C_3$-$C_7$cycloalkyl), —($C_2$-$C_6$heterocycloalkyl), -adamantyl, -aryl or -heteroaryl, wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C═O)—($C_1$-$C_4$alkyl), —C(═O)—O($C_1$-$C_4$alkyl), —$CF_3$, —$CF_2$H, —$OCF_3$, —$NR^{A5}R^{A6}$, —S(═O)$_2$—($C_1$-$C_4$alkyl), -aryl, or -heteroaryl;

$R^{A1}$ to $R^{A6}$ are each independently —H or —($C_1$-$C_4$alkyl); and

X is F, Cl or Br.

6. The 1,3,4-oxadiazole derivative compound represented by Chemical Formula I, the optical isomer thereof, or the pharmaceutically acceptable salt thereof according to claim 2, wherein in the Chemical Formula I above, $L_1$, $L_2$ are $L_3$ are each independently —($C_0$-$C_1$alkyl)-;

a, b and c are each independently N or $CR_4$, wherein a, b and c cannot be N at the same time, and $R_4$ is —H or —X;

Z is N, O, or nothing (null), wherein when Z is nothing (null), $R_2$ is also nothing (null), and $L_2$ and $L_3$ are directly linked;

$R_1$ is —$CX_2$H or —$CX_3$;

$R_2$ is —H, —($C_1$-$C_4$alkyl), wherein when Z is O, $R_2$ is nothing (null);

$R_3$ is —($C_3$-$C_7$cycloalkyl), —($C_2$-$C_6$heterocycloalkyl), -adamantyl, -aryl or -heteroaryl, wherein at least one —H of —($C_3$-$C_7$cycloalkyl), —($C_2$-$C_6$heterocycloalkyl), -adamantyl, -aryl and -heteroaryl may each independently be substituted with —X, —OH, —($C_1$-$C_4$alkyl), —O($C_1$-$C_4$alkyl), —(C═O)—($C_1$-$C_4$alkyl), —C(═O)—O($C_1$-$C_4$alkyl), —$CF_3$, —$CF_2$H, —$OCF_3$, —$NR^{A5}R^{A6}$, —S(═O)$_2$—($C_1$-$C_4$alkyl), -aryl, or -heteroaryl;

$R^{A5}$ and $R^{A6}$ are each independently —H or —($C_1$-$C_4$alkyl); and

X is F, Cl or Br.

7. The 1,3,4-oxadiazole derivative compound, the optical isomer thereof or the pharmaceutically acceptable salt thereof according to claim 1, wherein it is any one of compounds listed in the following table:

| Ex | Comp | Structure |
|---|---|---|
| 1 | 3009 | 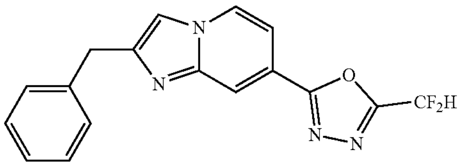 [SMILES: FC(F)c1nnc(-c2ccn3cc(Cc4ccccc4)nc3c2)o1] |
| 2 | 3585 | 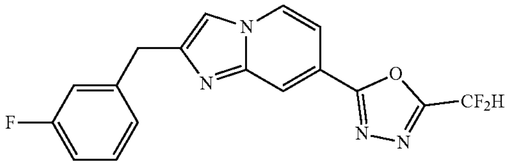 [SMILES: Fc1cccc(Cc2cn3ccc(-c4nnc(C(F)F)o4)cc3n2)c1] |
| 3 | 3586 | 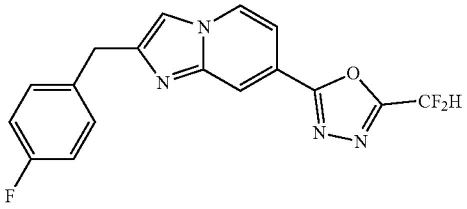 [SMILES: Fc1ccc(Cc2cn3ccc(-c4nnc(C(F)F)o4)cc3n2)cc1] |
| 4 | 3587 | 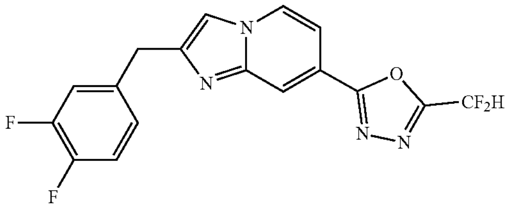 [SMILES: Fc1ccc(Cc2cn3ccc(-c4nnc(C(F)F)o4)cc3n2)cc1F] |
| 5 | 3588 | 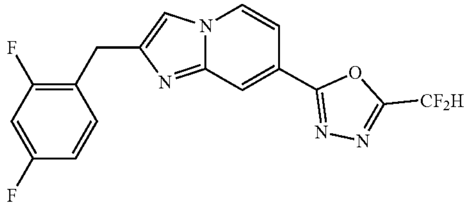 [SMILES: Fc1ccc(Cc2cn3ccc(-c4nnc(C(F)F)o4)cc3n2)c(F)c1] |
| 6 | 3589 | 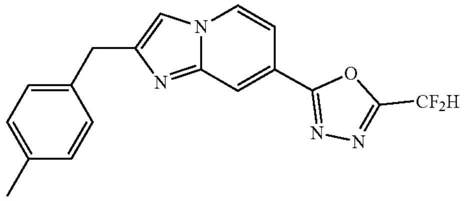 [SMILES: Cc1ccc(Cc2cn3ccc(-c4nnc(C(F)F)o4)cc3n2)cc1] |
| 7 | 3590 | 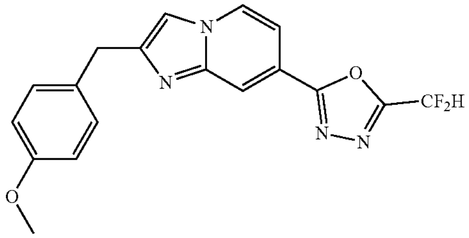 [SMILES: COc1ccc(Cc2cn3ccc(-c4nnc(C(F)F)o4)cc3n2)cc1] |

-continued
| Ex | Comp | Structure |
|---|---|---|
| 8 | 3591 | 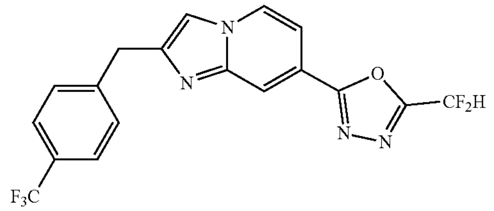 [SMILES: FC(F)c1nnc(-c2ccn3cc(Cc4ccc(C(F)(F)F)cc4)nc3c2)o1] |
| 9 | 3592 | 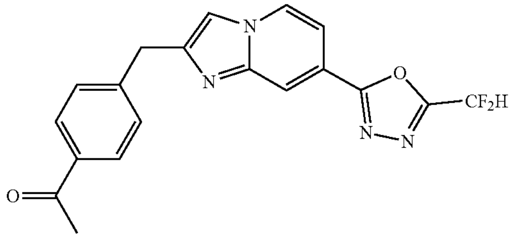 [SMILES: CC(=O)c1ccc(Cc2cn3ccc(-c4nnc(C(F)F)o4)cc3n2)cc1] |
| 10 | 3593 | 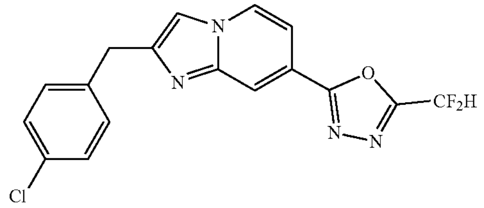 [SMILES: FC(F)c1nnc(-c2ccn3cc(Cc4ccc(Cl)cc4)nc3c2)o1] |
| 11 | 3594 | 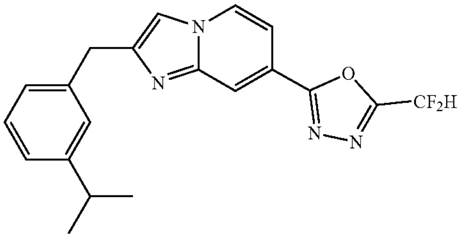 [SMILES: CC(C)c1cccc(Cc2cn3ccc(-c4nnc(C(F)F)o4)cc3n2)c1] |
| 12 | 3595 | 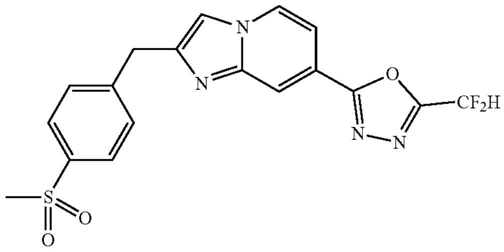 [SMILES: CS(=O)(=O)c1ccc(Cc2cn3ccc(-c4nnc(C(F)F)o4)cc3n2)cc1] |
| 13 | 3596 | 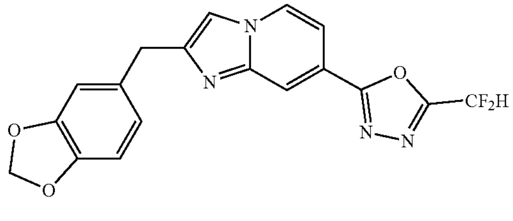 [SMILES: FC(F)c1nnc(-c2ccn3cc(Cc4ccc5c(c4)OCO5)nc3c2)o1] |
| 14 | 3668 | 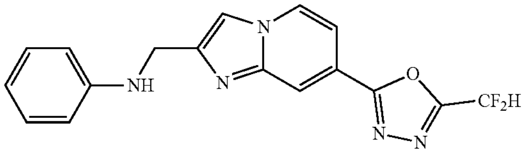 |

-continued
| Ex | Comp | Structure |
|---|---|---|
| 15 | 3669 | 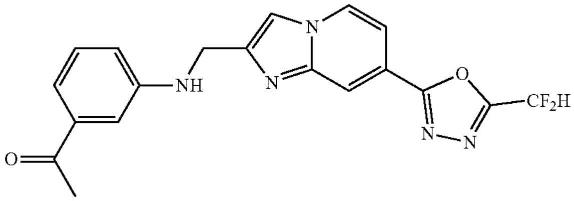 |
| 16 | 3670 | 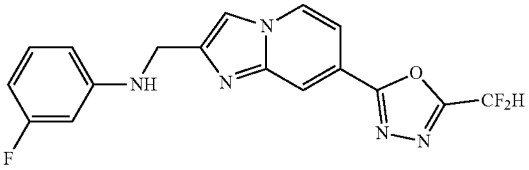 |
| 17 | 3671 | 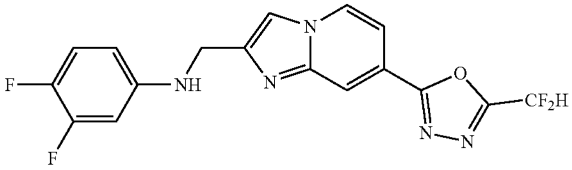 |
| 18 | 3672 | 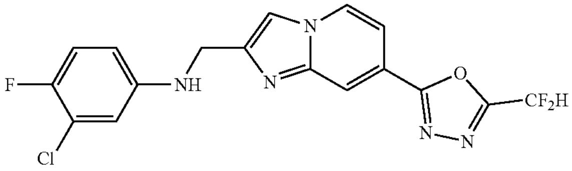 |
| 19 | 3673 | 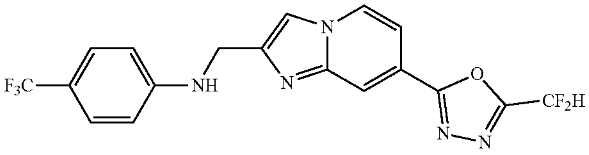 [SMILES: FC(F)c1nnc(-c2ccn3cc(CNc4ccc(C(F)(F)F)cc4)nc3c2)o1] |
| 20 | 3674 | 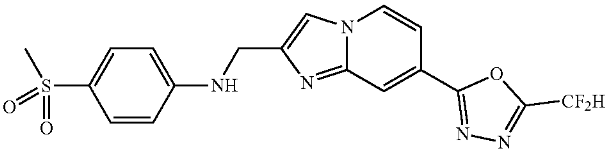 [SMILES: CS(=O)(=O)c1ccc(NCc2cn3ccc(-c4nnc(C(F)F)o4)cc3n2)cc1] |
| 21 | 3675 | 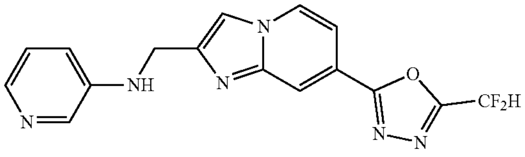 [SMILES: FC(F)c1nnc(-c2ccn3cc(CNc4cccnc4)nc3c2)o1] |
| 22 | 3676 | 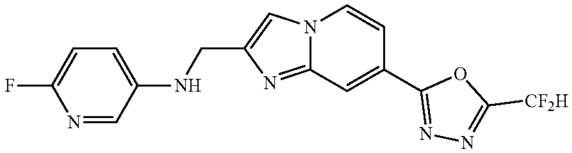 [SMILES: Fc1ccc(NCc2cn3ccc(-c4nnc(C(F)F)o4)cc3n2)cn1] |
| 23 | 3677 | 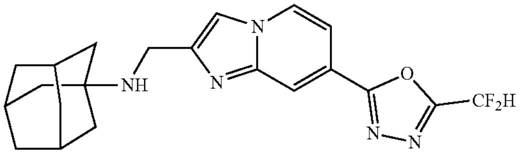 [SMILES: FC(F)c1nnc(-c2ccn3cc(CNC45CC6CC(CC(C6)C4)C5)nc3c2)o1] |

-continued
| Ex | Comp | Structure |
|---|---|---|
| 24 | 3678 | 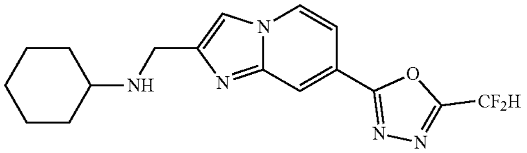 [SMILES: FC(F)c1nnc(-c2ccn3cc(CNC4CCCCC4)nc3c2)o1] |
| 25 | 3679 | 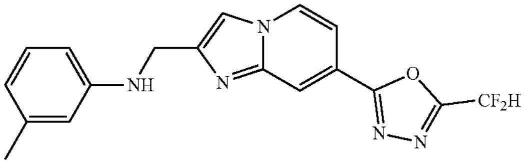 |
| 26 | 3719 | 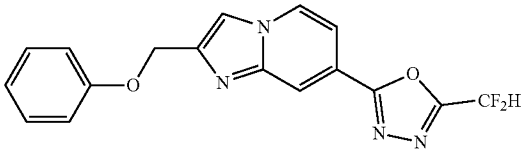 |
| 27 | 3720 | 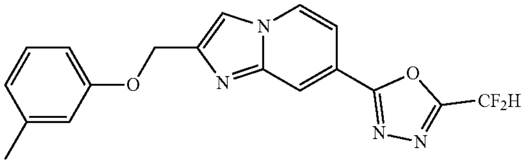 [SMILES: Cc1cccc(OCc2cn3ccc(-c4nnc(C(F)F)o4)cc3n2)c1] |
| 28 | 3721 | 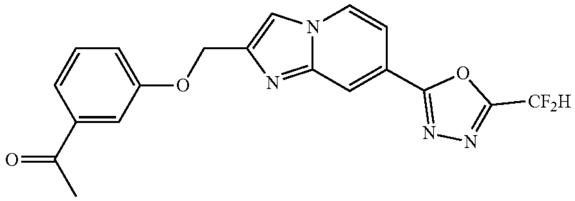 [SMILES: CC(=O)c1cccc(OCc2cn3ccc(-c4nnc(C(F)F)o4)cc3n2)c1] |
| 29 | 3722 | 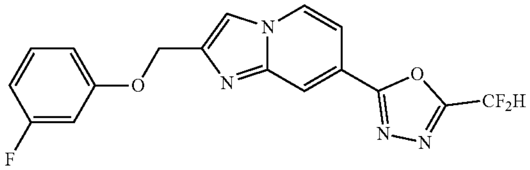 |
| 30 | 3723 | 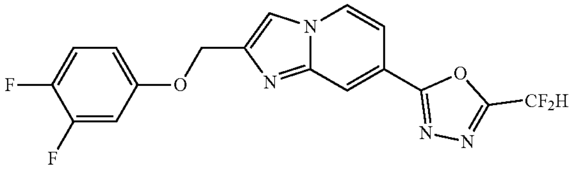 |
| 31 | 3724 | 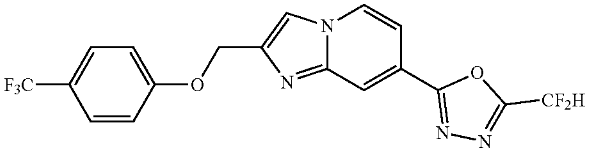 |
| 32 | 3725 | 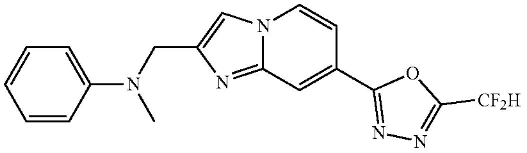 [SMILES: CN(Cc1cn2ccc(-c3nnc(C(F)F)o3)cc2n1)c1ccccc1] |

-continued
| Ex | Comp | Structure |
|---|---|---|
| 33 | 3782 | 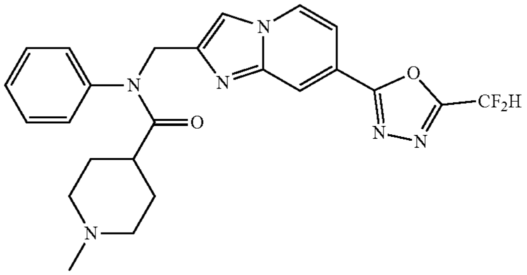 |
| 34 | 3783 | 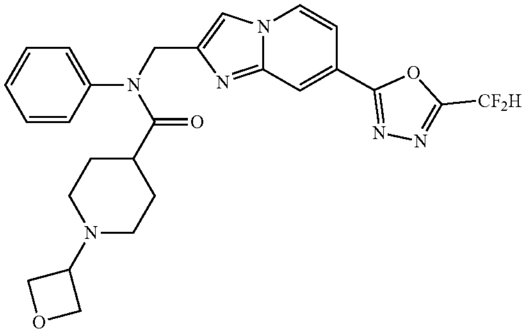 [SMILES: O=C(C1CCN(C2COC2)CC1)N(Cc1cn2ccc(-c3nnc(C(F)F)o3)cc2n1)c1ccccc1] |
| 35 | 3784 | 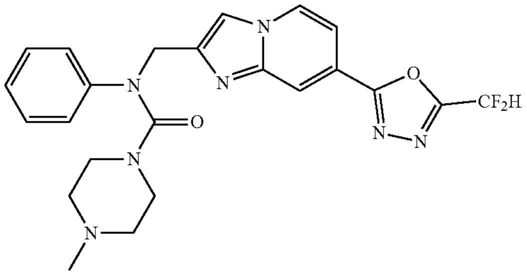 |
| 36 | 3785 | 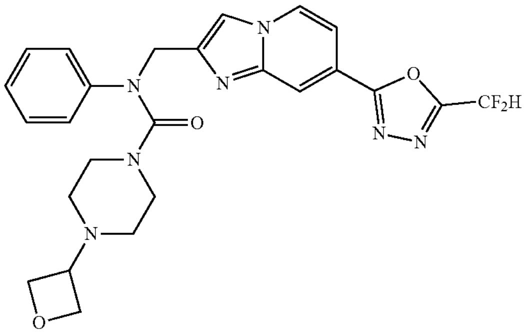 [SMILES: O=C(N1CCN(C2COC2)CC1)N(Cc1cn2ccc(-c3nnc(C(F)F)o3)cc2n1)c1ccccc1] |
| 37 | 4033 | 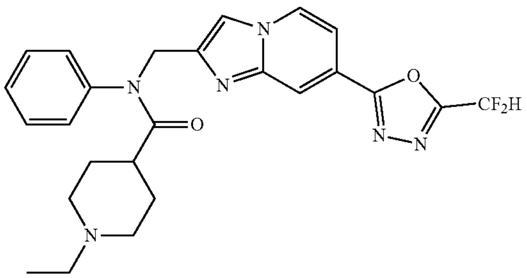 |

-continued
| Ex | Comp | Structure |
| --- | --- | --- |
| 38 | 4034 | 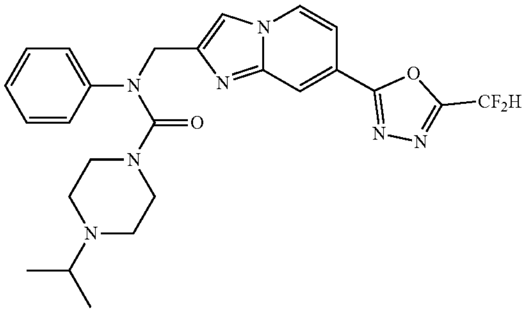 |
| 39 | 4035 | 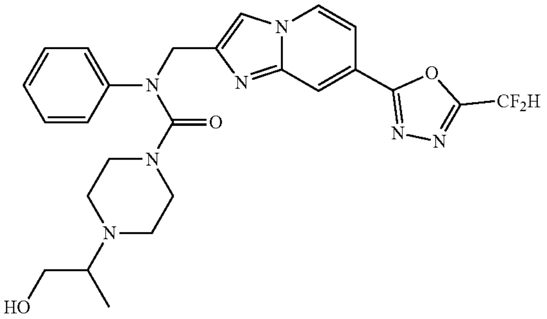 |
| 40 | 4036 | 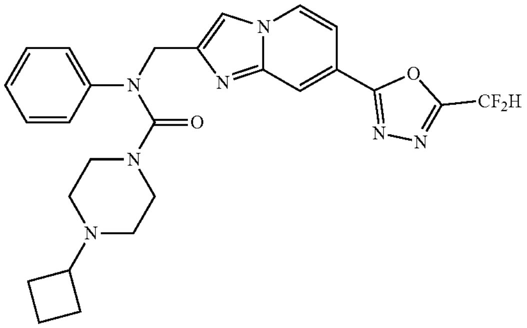 |
| 41 | 4037 | 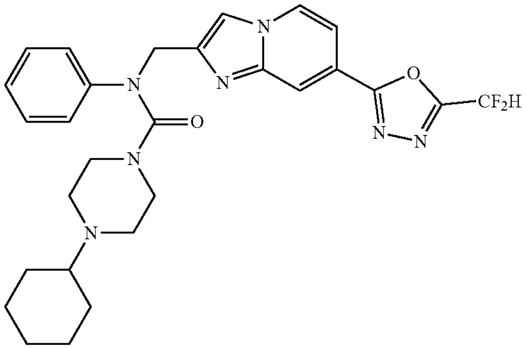 [SMILES: O=C(N1CCN(C2CCCCC2)CC1)N(Cc1cn2ccc(-c3nnc(C(F)F)o3)cc2n1)c1ccccc1] |

-continued
| Ex | Comp | Structure |
|---|---|---|
| 42 | 4038 | 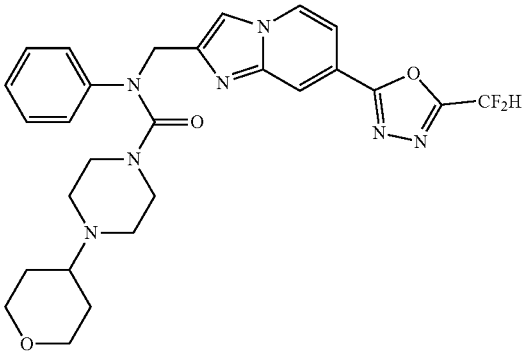 |
| 43 | 4039 | 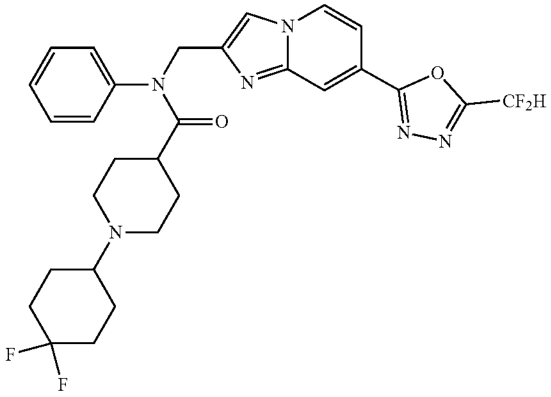 [SMILES: O=C(C1CCN(C2CCC(F)(F)CC2)CC1)N(Cc1cn2ccc(-c3nnc(C(F)F)o3)cc2n1)c1ccccc1] |
| 44 | 4040 | 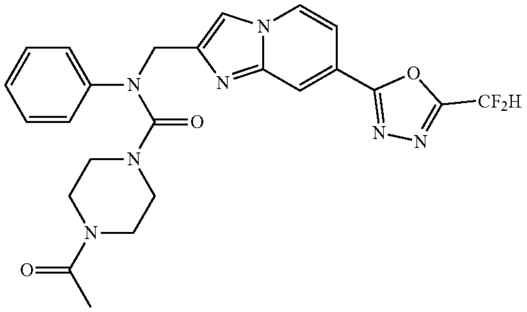 |
| 45 | 4041 | 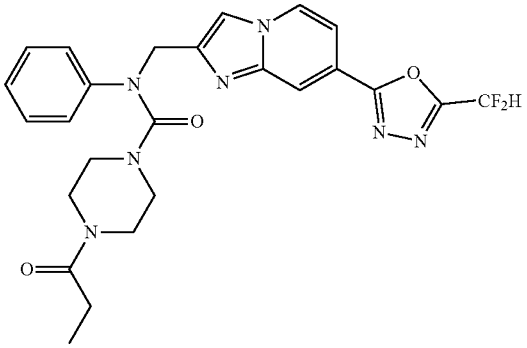 |

-continued
| Ex | Comp | Structure |
|---|---|---|
| 46 | 4042 | 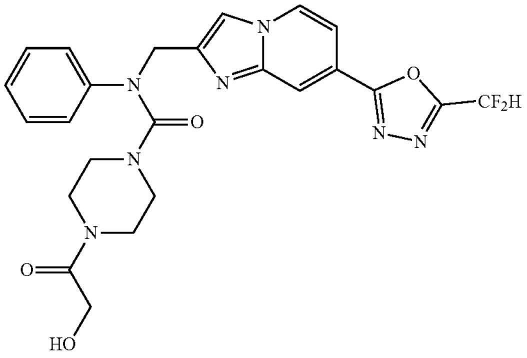 |
| 47 | 4043 | 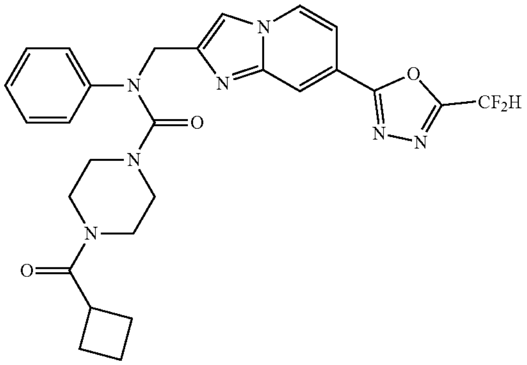 |
| 48 | 4044 | 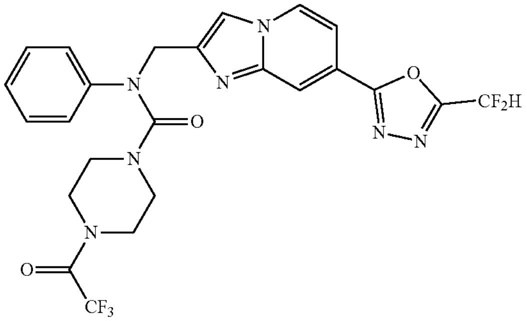 |
| 49 | 4045 | 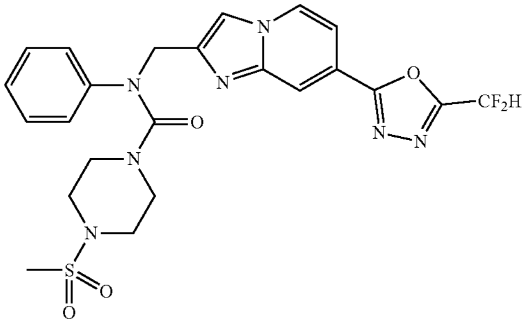 |

-continued
| Ex | Comp | Structure |
| --- | --- | --- |
| 50 | 4046 | 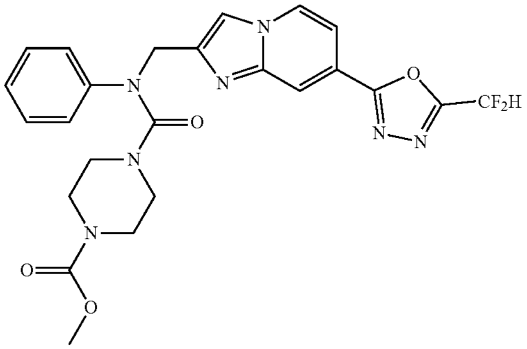 [SMILES: COC(=O)N1CCN(C(=O)N(Cc2cn3ccc(-c4nnc(C(F)F)o4)cc3n2)c2ccccc2)CC1] |
| 51 | 4047 | 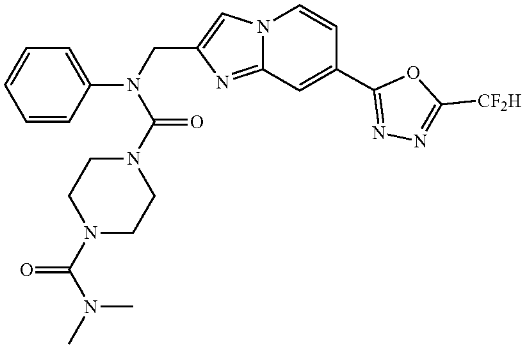 |
| 52 | 4048 | 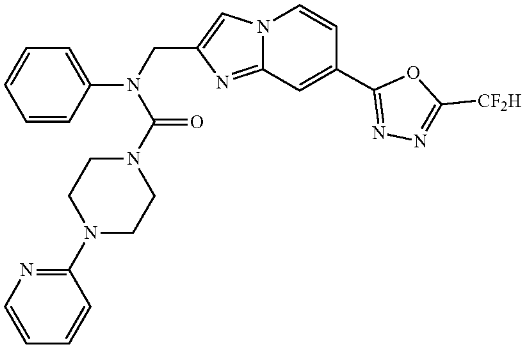 |
| 53 | 4049 | 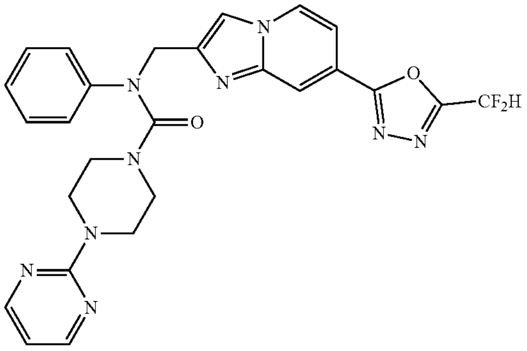 |

-continued
| Ex | Comp | Structure |
|---|---|---|
| 54 | 4083 | 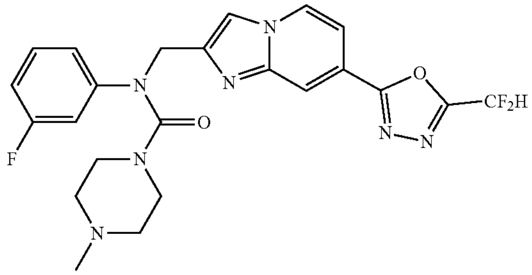 [SMILES: CN1CCN(C(=O)N(Cc2cn3ccc(-c4nnc(C(F)F)o4)cc3n2)c2cccc(F)c2)CC1] |
| 55 | 4084 | 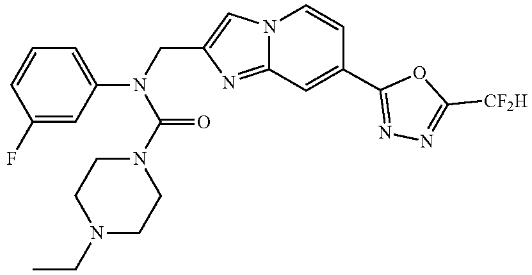 [SMILES: CCN1CCN(C(=O)N(Cc2cn3ccc(-c4nnc(C(F)F)o4)cc3n2)c2cccc(F)c2)CC1] |
| 56 | 4085 | 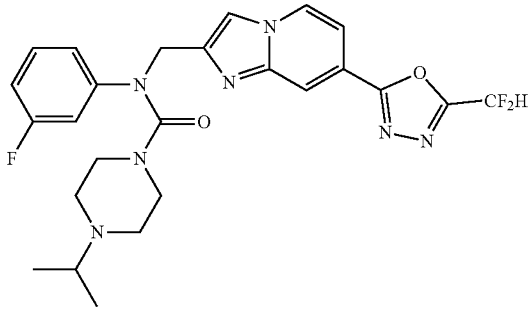 |
| 57 | 4086 | 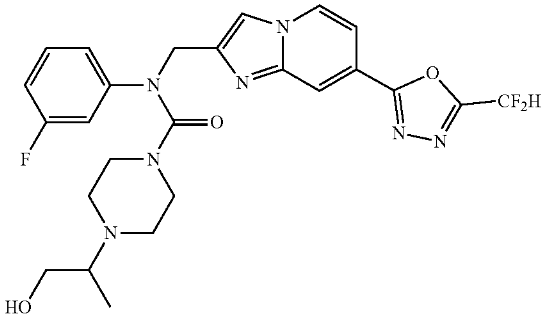 |
| 58 | 4087 | 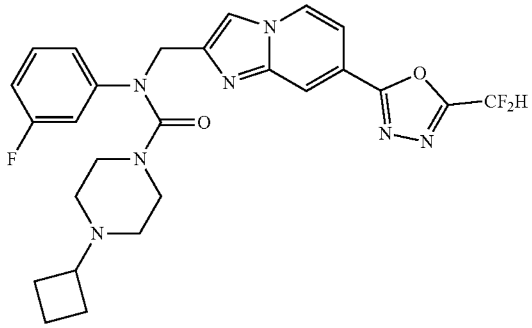 |

-continued
| Ex | Comp | Structure |
| --- | --- | --- |
| 59 | 4088 | 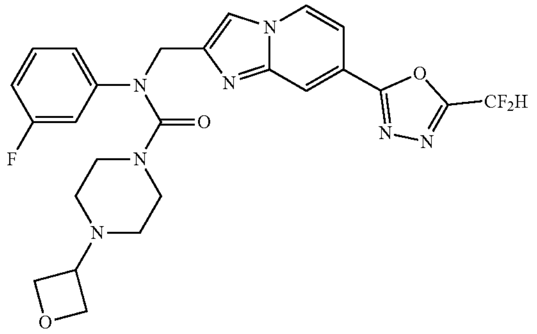 [SMILES: O=C(N1CCN(C2COC2)CC1)N(Cc1cn2ccc(-c3nnc(C(F)F)o3)cc2n1)c1cccc(F)c1] |
| 60 | 4089 | 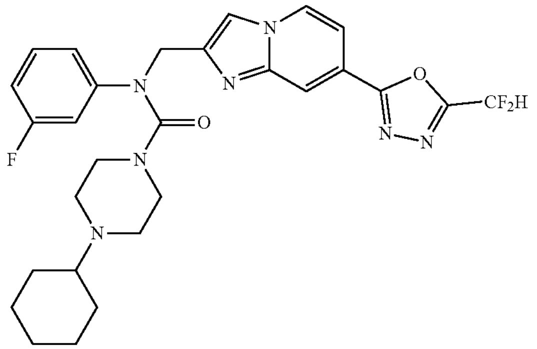 [SMILES: O=C(N1CCN(C2CCCCC2)CC1)N(Cc1cn2ccc(-c3nnc(C(F)F)o3)cc2n1)c1cccc(F)c1] |
| 61 | 4090 | 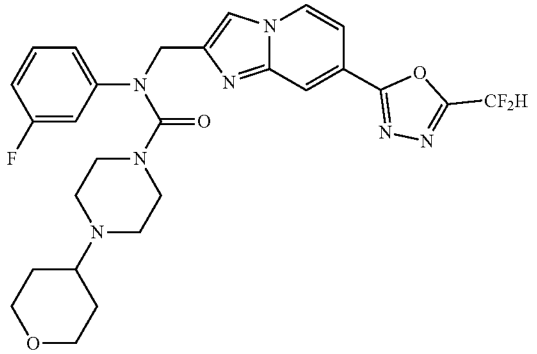 [SMILES: O=C(N1CCN(C2CCOCC2)CC1)N(Cc1cn2ccc(-c3nnc(C(F)F)o3)cc2n1)c1cccc(F)c1] |
| 62 | 4091 | 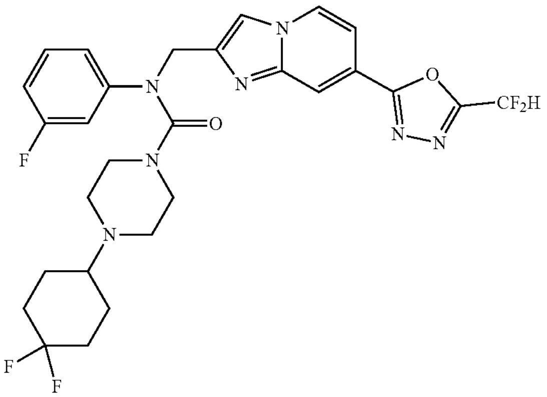 |

-continued
| Ex | Comp | Structure |
|---|---|---|
| 63 | 4092 | 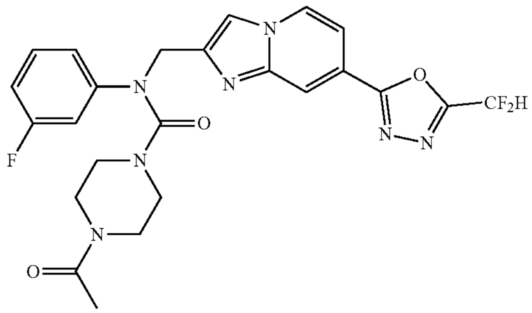 |
| 64 | 4093 | 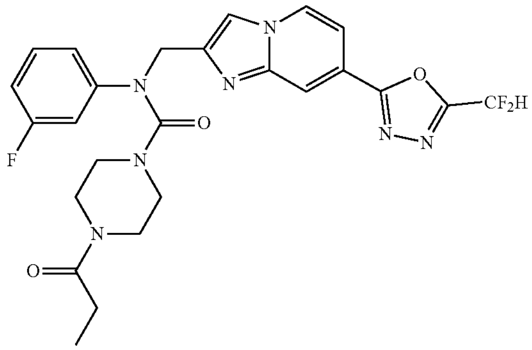 |
| 65 | 4094 | 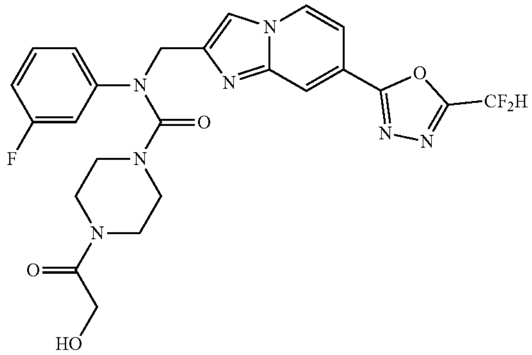 |
| 66 | 4095 | 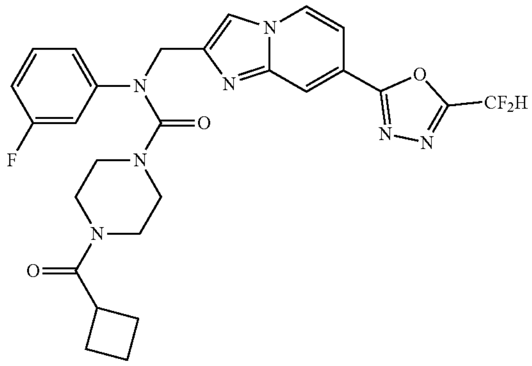 [SMILES: O=C(C1CCC1)N1CCN(C(=O)N(Cc2cn3ccc(-c4nnc(C(F)F)o4)cc3n2)c2cccc(F)c2)CC1] |

-continued
| Ex | Comp | Structure |
|---|---|---|
| 67 | 4096 | 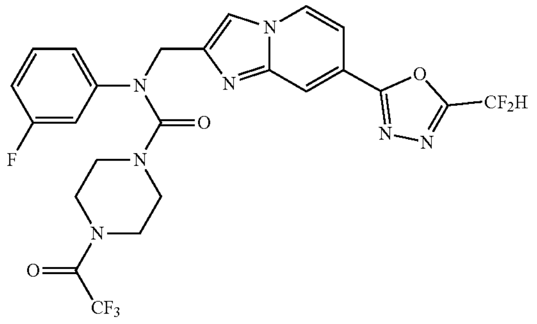 [SMILES: O=C(N1CCN(C(=O)C(F)(F)F)CC1)N(Cc1cn2ccc(-c3nnc(C(F)F)o3)cc2n1)c1cccc(F)c1] |
| 68 | 4097 | 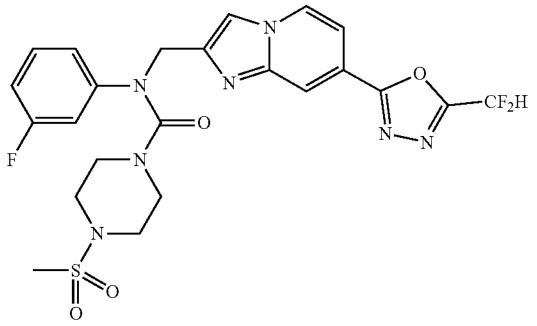 |
| 69 | 4098 | 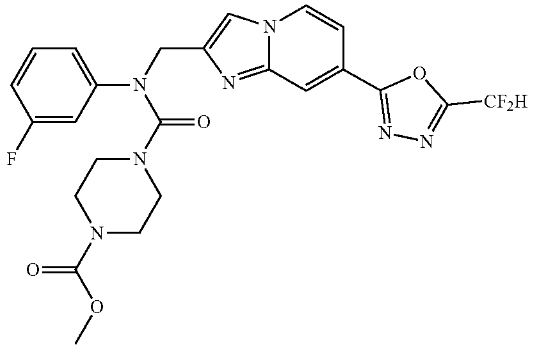 |
| 70 | 4099 | 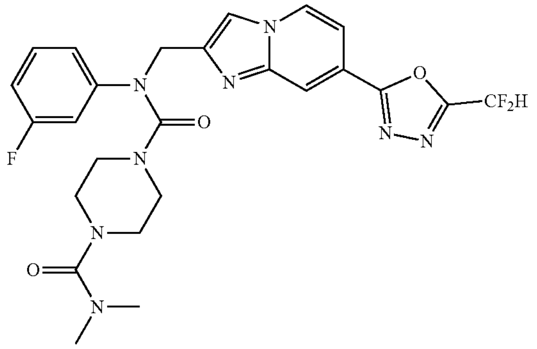 |

-continued
| Ex | Comp | Structure |
|---|---|---|
| 71 | 4100 | 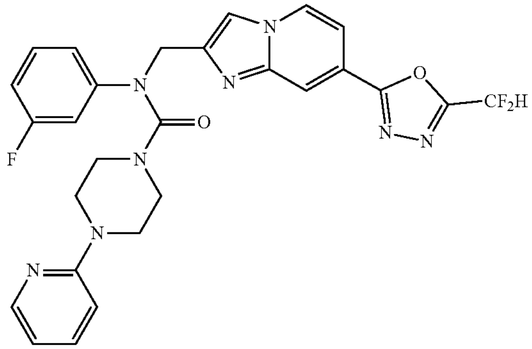 |
| 72 | 4101 | 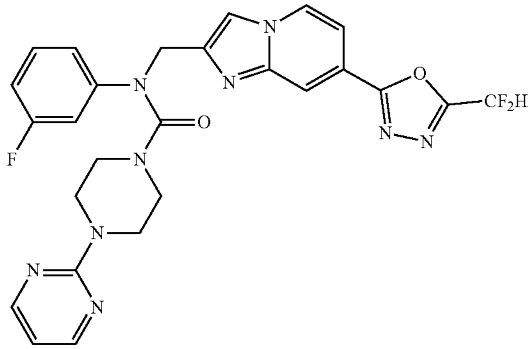 |
| 73 | 4102 | 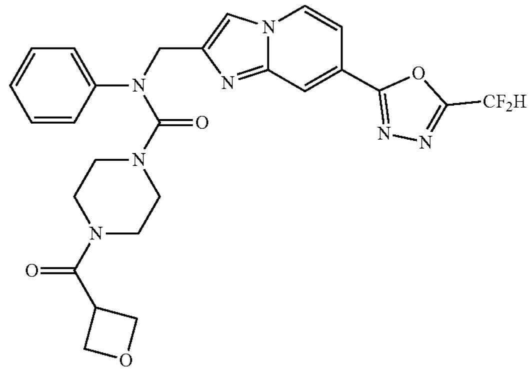 |
| 74 | 4103 | 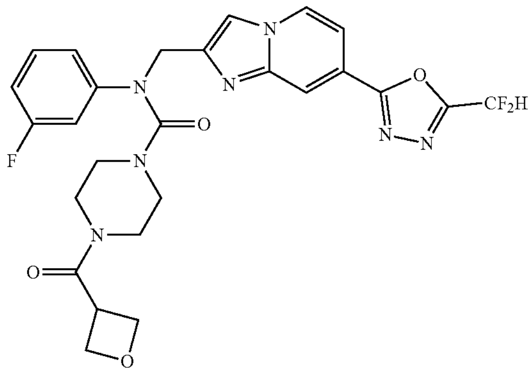 |

-continued
| Ex | Comp | Structure |
| --- | --- | --- |
| 75 | 4115 | 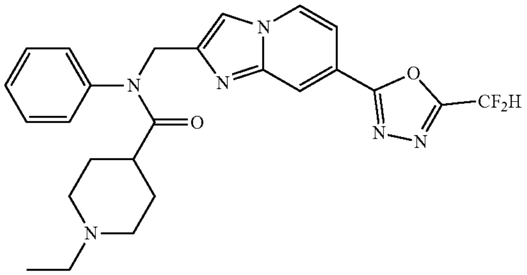 [SMILES: CCN1CCC(C(=O)N(Cc2cn3ccc(-c4nnc(C(F)F)o4)cc3n2)c2ccccc2)CC1] |
| 76 | 4116 | 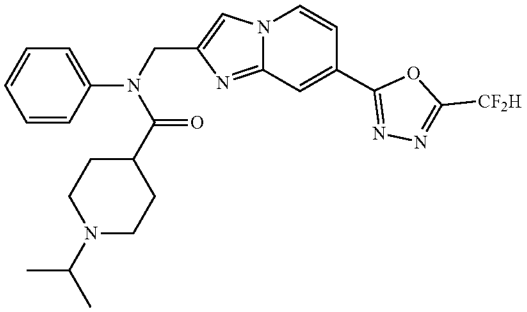 |
| 77 | 4117 | 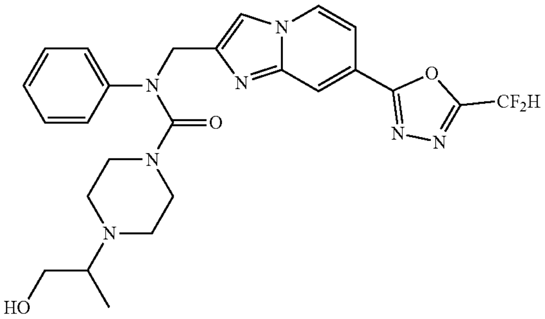 |
| 78 | 4118 | 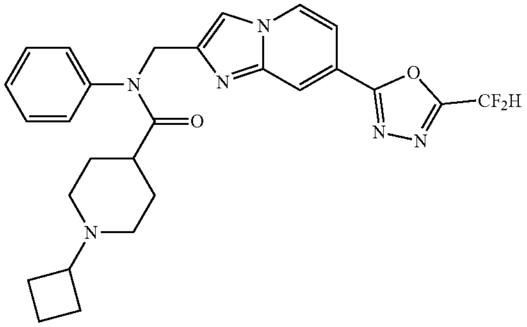 |

-continued
| Ex | Comp | Structure |
|---|---|---|
| 79 | 4119 | 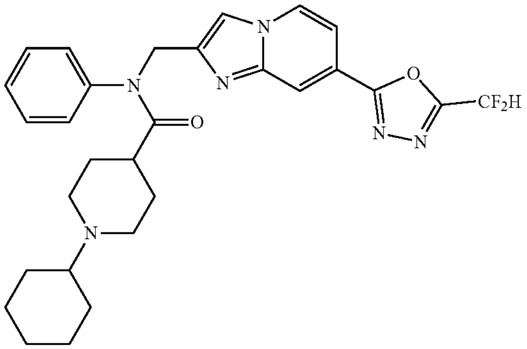 [SMILES: O=C(C1CCN(C2CCCCC2)CC1)N(Cc1cn2ccc(-c3nnc(C(F)F)o3)cc2n1)c1ccccc1] |
| 80 | 4120 | 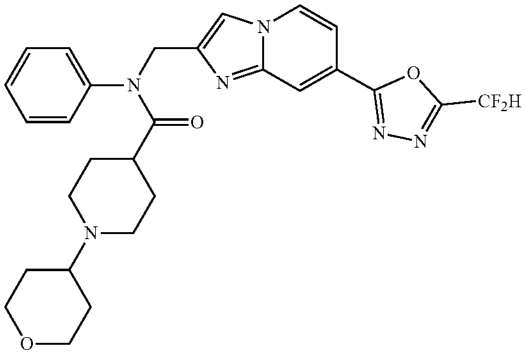 |
| 81 | 4121 | 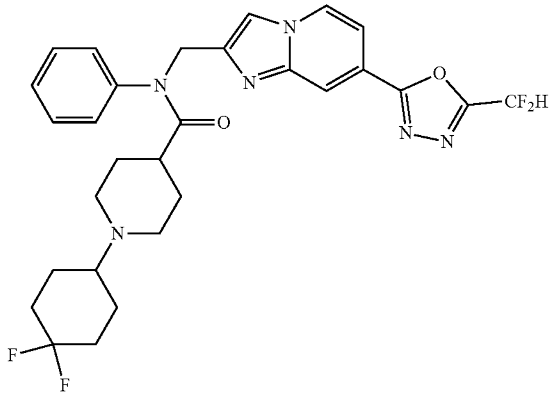 [SMILES: O=C(C1CCN(C2CCC(F)(F)CC2)CC1)N(Cc1cn2ccc(-c3nnc(C(F)F)o3)cc2n1)c1ccccc1] |
| 82 | 4122 | 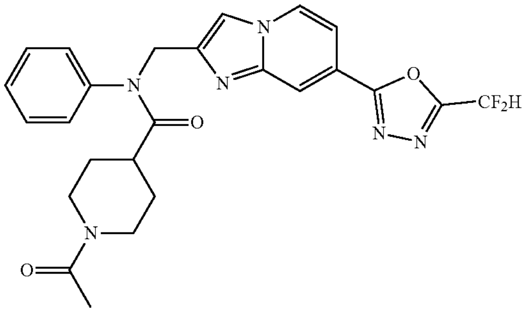 |

-continued
| Ex | Comp | Structure |
|---|---|---|
| 83 | 4123 | 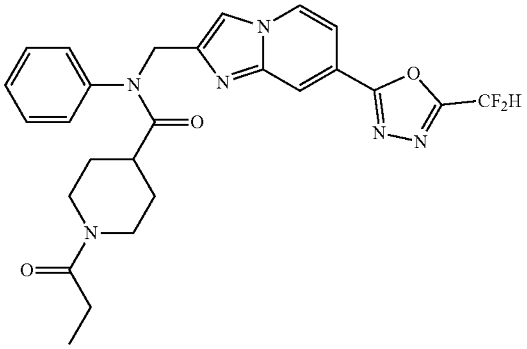 |
| 84 | 4124 | 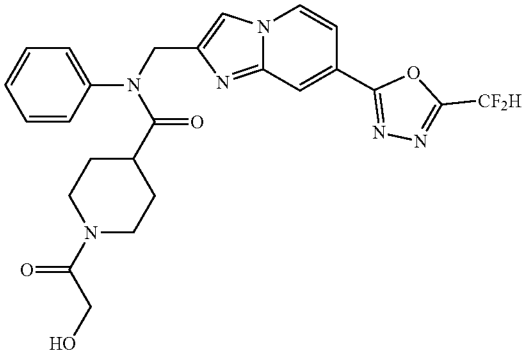 [SMILES: O=C(CO)N1CCC(C(=O)N(Cc2cn3ccc(-c4nnc(C(F)F)o4)cc3n2)c2ccccc2)CC1] |
| 85 | 4125 | 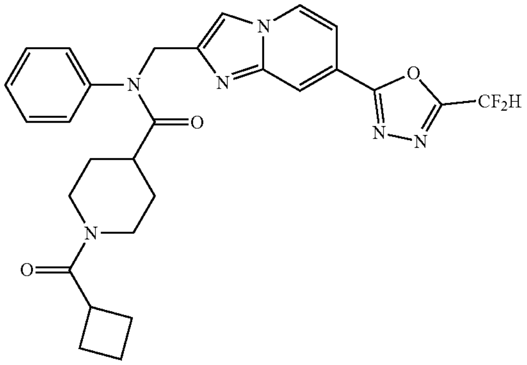 |
| 86 | 4126 | 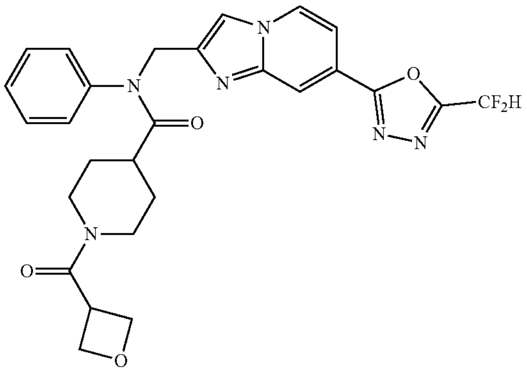 |

-continued
| Ex | Comp | Structure |
|---|---|---|
| 87 | 4127 | 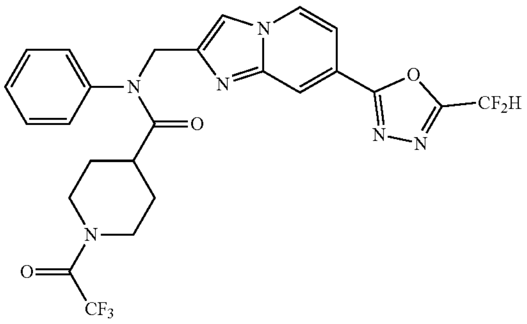 |
| 88 | 4128 | 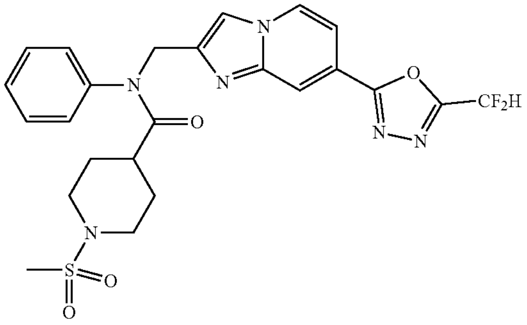 [SMILES: CS(=O)(=O)N1CCC(C(=O)N(Cc2cn3ccc(-c4nnc(C(F)F)o4)cc3n2)c2ccccc2)CC1] |
| 89 | 4129 | 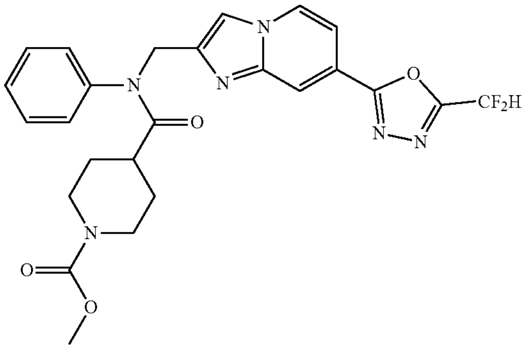 [SMILES: COC(=O)N1CCC(C(=O)N(Cc2cn3ccc(-c4nnc(C(F)F)o4)cc3n2)c2ccccc2)CC1] |
| 90 | 4130 | 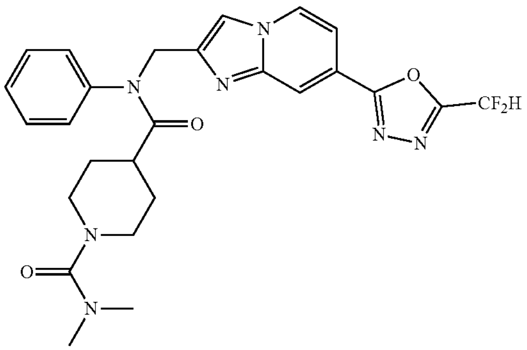 [SMILES: CN(C)C(=O)N1CCC(C(=O)N(Cc2cn3ccc(-c4nnc(C(F)F)o4)cc3n2)c2ccccc2)CC1] |

-continued
| Ex | Comp | Structure |
|---|---|---|
| 91 | 4131 | 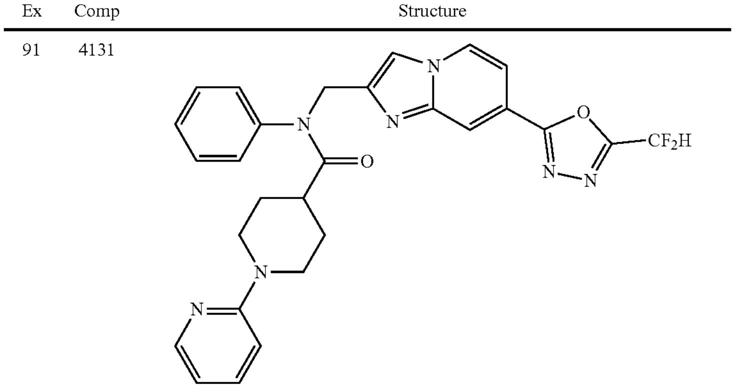 |
| 92 | 4132 | 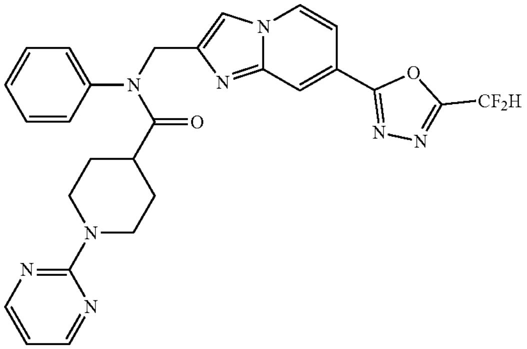 [SMILES: O=C(C1CCN(c2ncccn2)CC1)N(Cc1cn2ccc(-c3nnc(C(F)F)o3)cc2n1)c1ccccc1] |
| 93 | 4137 | 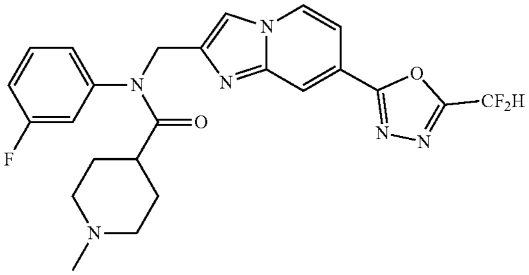 |
| 94 | 4138 | 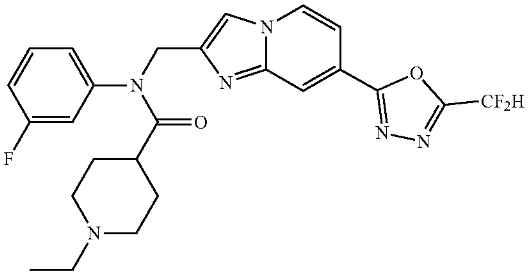 |
| 95 | 4139 | 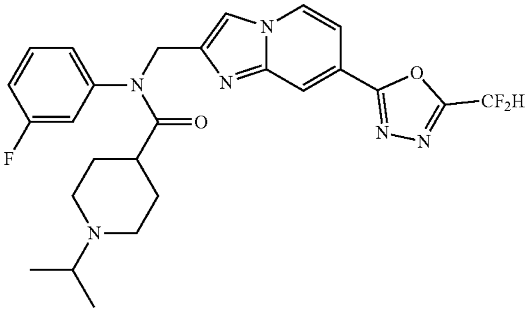 [SMILES: CC(C)N1CCC(C(=O)N(Cc2cn3ccc(-c4nnc(C(F)F)o4)cc3n2)c2cccc(F)c2)CC1] |

-continued
| Ex | Comp | Structure |
|---|---|---|
| 96 | 4140 | 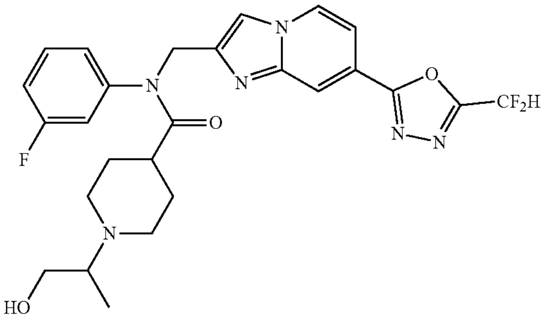 [SMILES: CC(CO)N1CCC(C(=O)N(Cc2cn3ccc(-c4nnc(C(F)F)o4)cc3n2)c2cccc(F)c2)CC1] |
| 97 | 4141 | 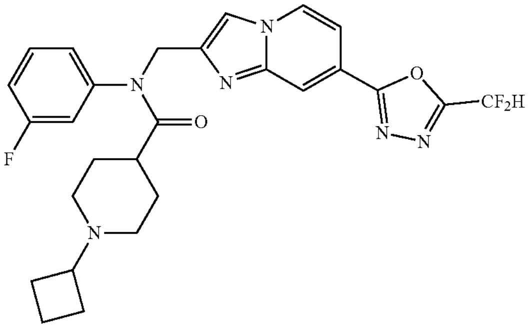 [SMILES: O=C(C1CCN(C2CCC2)CC1)N(Cc1cn2ccc(-c3nnc(C(F)F)o3)cc2n1)c1cccc(F)c1] |
| 98 | 4142 | 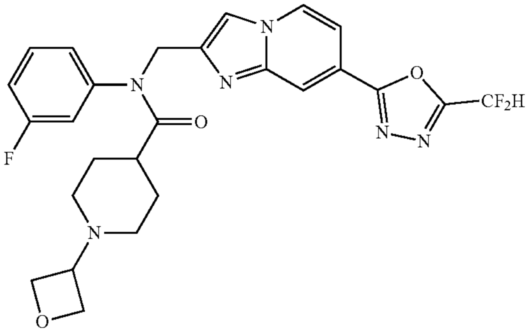 |
| 99 | 4143 | 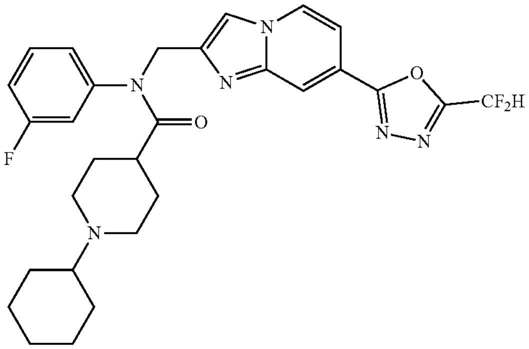 [SMILES: O=C(C1CCN(C2CCCCC2)CC1)N(Cc1cn2ccc(-c3nnc(C(F)F)o3)cc2n1)c1cccc(F)c1] |

-continued
| Ex | Comp | Structure |
| --- | --- | --- |
| 100 | 4144 | 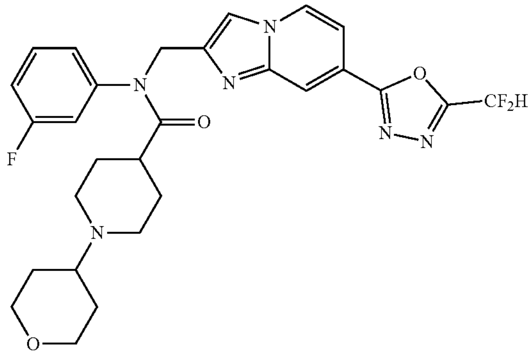 [SMILES: O=C(C1CCN(C2CCOCC2)CC1)N(Cc1cn2ccc(-c3nnc(C(F)F)o3)cc2n1)c1cccc(F)c1] |
| 101 | 4145 | 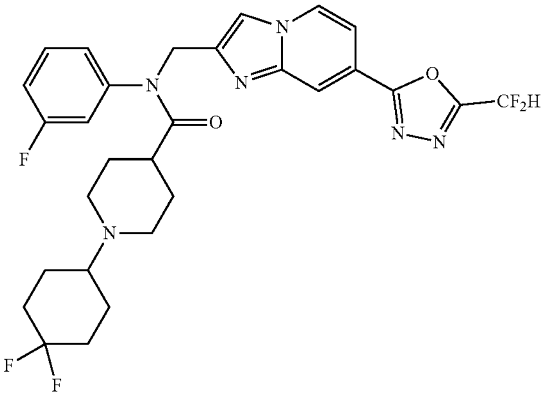 |
| 102 | 4146 | 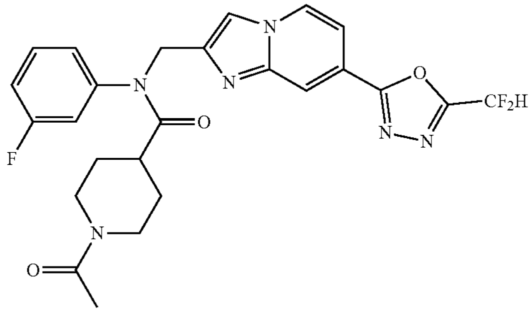 [SMILES: CC(=O)N1CCC(C(=O)N(Cc2cn3ccc(-c4nnc(C(F)F)o4)cc3n2)c2cccc(F)c2)CC1] |
| 103 | 4147 | 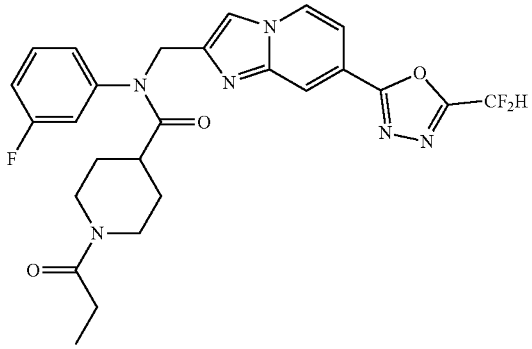 |

-continued
| Ex | Comp | Structure |
| --- | --- | --- |
| 104 | 4149 | 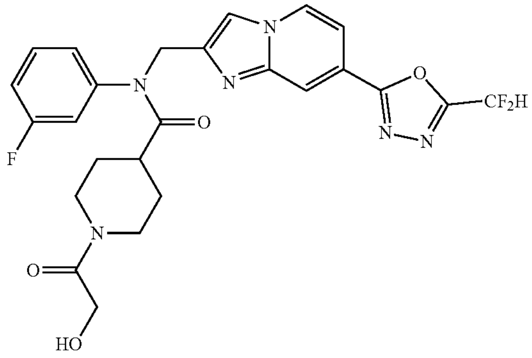 [SMILES: O=C(CO)N1CCC(C(=O)N(Cc2cn3ccc(-c4nnc(C(F)F)o4)cc3n2)c2cccc(F)c2)CC1] |
| 105 | 4150 | 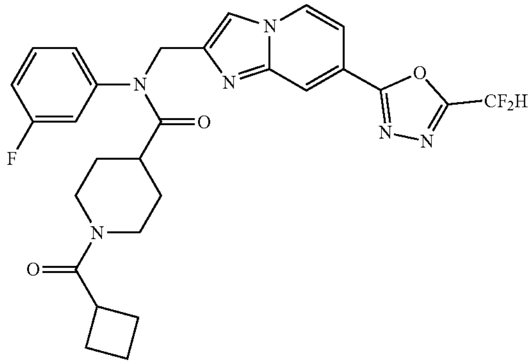 |
| 106 | 4151 | 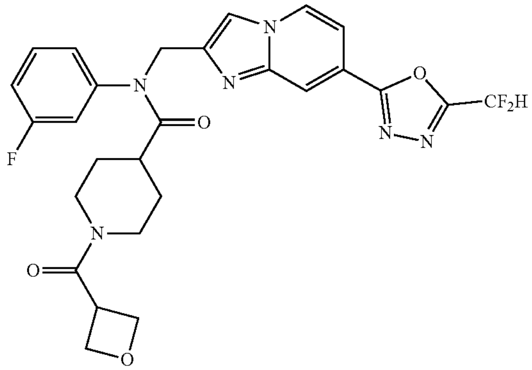 [SMILES: O=C(C1COC1)N1CCC(C(=O)N(Cc2cn3ccc(-c4nnc(C(F)F)o4)cc3n2)c2cccc(F)c2)CC1] |
| 107 | 4152 | 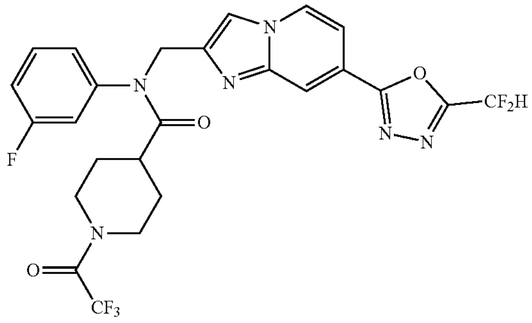 [SMILES: O=C(C1CCN(C(=O)C(F)(F)F)CC1)N(Cc1cn2ccc(-c3nnc(C(F)F)o3)cc2n1)c1cccc(F)c1] |

-continued
| Ex | Comp | Structure |
| --- | --- | --- |
| 108 | 4153 | 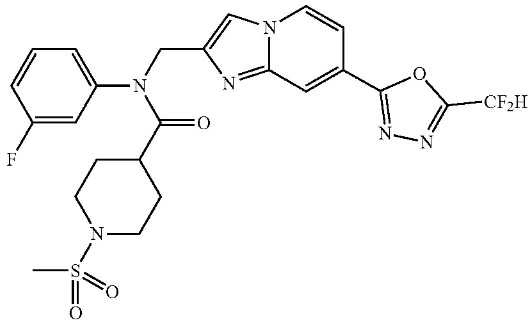 [SMILES: CS(=O)(=O)N1CCC(C(=O)N(Cc2cn3ccc(-c4nnc(C(F)F)o4)cc3n2)c2cccc(F)c2)CC1] |
| 109 | 4154 | 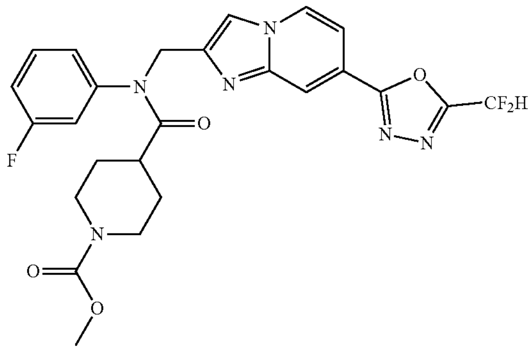 [SMILES: COC(=O)N1CCC(C(=O)N(Cc2cn3ccc(-c4nnc(C(F)F)o4)cc3n2)c2cccc(F)c2)CC1] |
| 110 | 4155 | 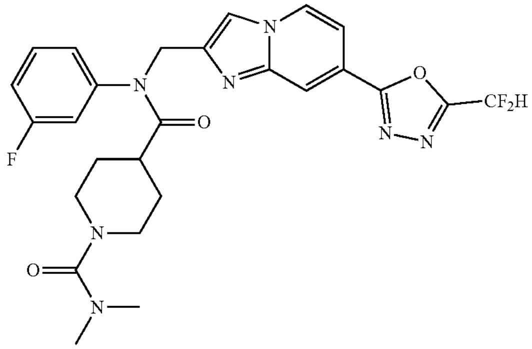 [SMILES: CN(C)C(=O)N1CCC(C(=O)N(Cc2cn3ccc(-c4nnc(C(F)F)o4)cc3n2)c2cccc(F)c2)CC1] |
| 111 | 4156 | 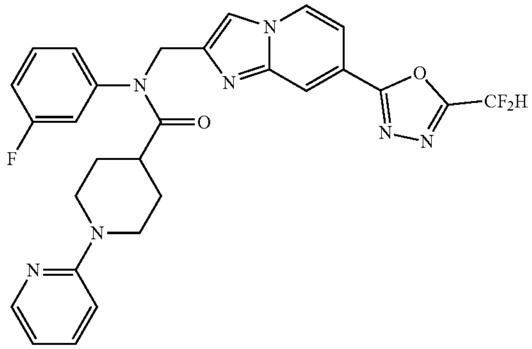 [SMILES: O=C(C1CCN(c2ccccn2)CC1)N(Cc1cn2ccc(-c3nnc(C(F)F)o3)cc2n1)c1cccc(F)c1] |

-continued
| Ex | Comp | Structure |
|---|---|---|
| 112 | 4157 | 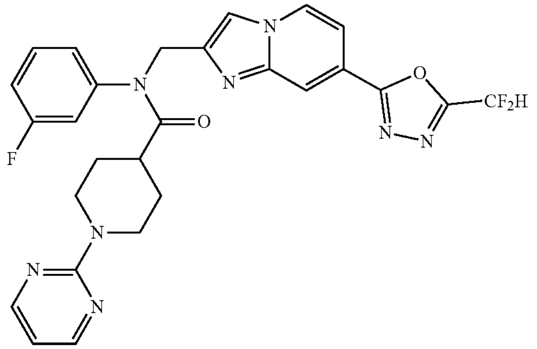 |
| 113 | 4158 | 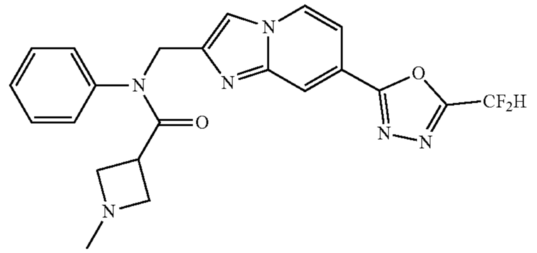 [SMILES: CN1CC(C(=O)N(Cc2cn3ccc(-c4nnc(C(F)F)o4)cc3n2)c2ccccc2)C1] |
| 114 | 4159 | 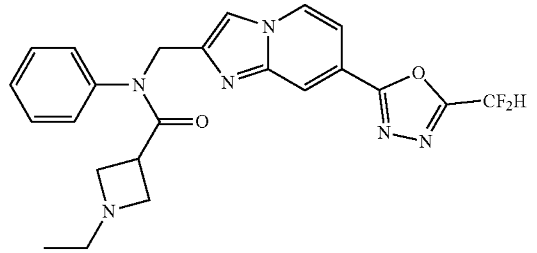 [SMILES: CCN1CC(C(=O)N(Cc2cn3ccc(-c4nnc(C(F)F)o4)cc3n2)c2ccccc2)C1] |
| 115 | 4160 | 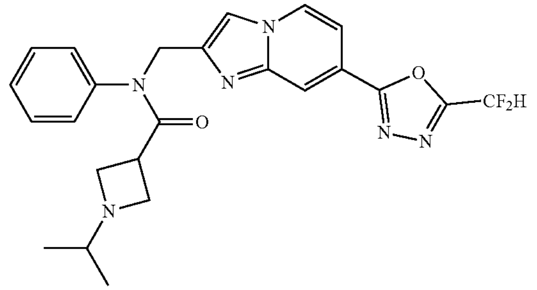 [SMILES: CC(C)N1CC(C(=O)N(Cc2cn3ccc(-c4nnc(C(F)F)o4)cc3n2)c2ccccc2)C1] |
| 116 | 4161 | 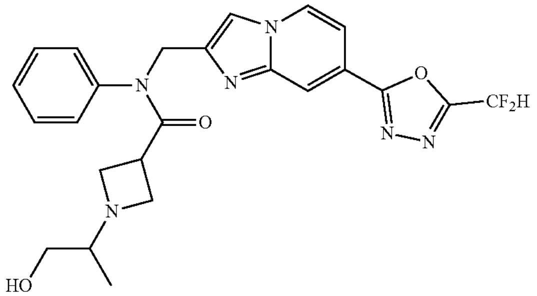 [SMILES: CC(CO)N1CC(C(=O)N(Cc2cn3ccc(-c4nnc(C(F)F)o4)cc3n2)c2ccccc2)C1] |

-continued
| Ex | Comp | Structure |
|---|---|---|
| 117 | 4162 | 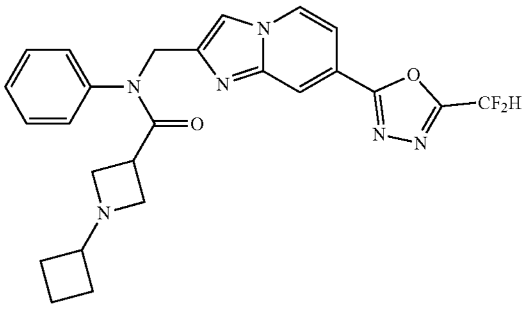 [SMILES: O=C(C1CN(C2CCC2)C1)N(Cc1cn2ccc(-c3nnc(C(F)F)o3)cc2n1)c1ccccc1] |
| 118 | 4163 | 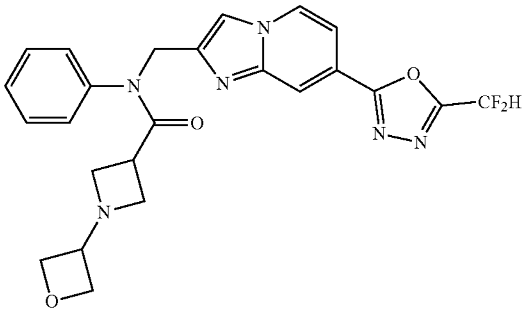 [SMILES: O=C(C1CN(C2COC2)C1)N(Cc1cn2ccc(-c3nnc(C(F)F)o3)cc2n1)c1ccccc1] |
| 119 | 4164 | 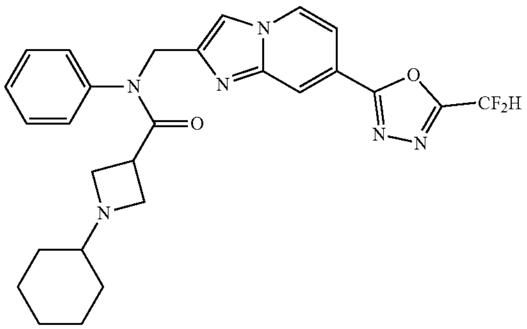 [SMILES: O=C(C1CN(C2CCCCC2)C1)N(Cc1cn2ccc(-c3nnc(C(F)F)o3)cc2n1)c1ccccc1] |
| 120 | 4165 | 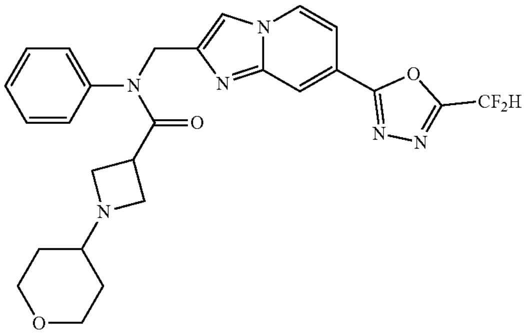 [SMILES: O=C(C1CN(C2CCOCC2)C1)N(Cc1cn2ccc(-c3nnc(C(F)F)o3)cc2n1)c1ccccc1] |

-continued
| Ex | Comp | Structure |
| --- | --- | --- |
| 121 | 4166 | 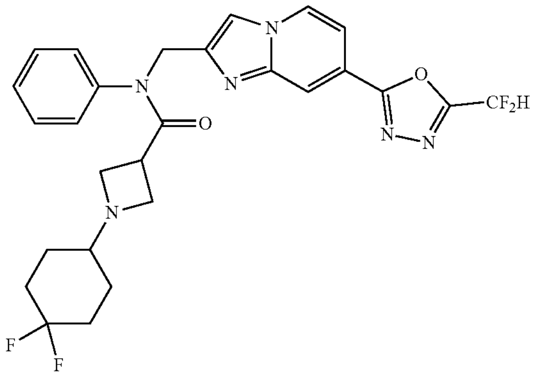 [SMILES: O=C(C1CN(C2CCC(F)(F)CC2)C1)N(Cc1cn2ccc(-c3nnc(C(F)F)o3)cc2n1)c1ccccc1] |
| 122 | 4167 | 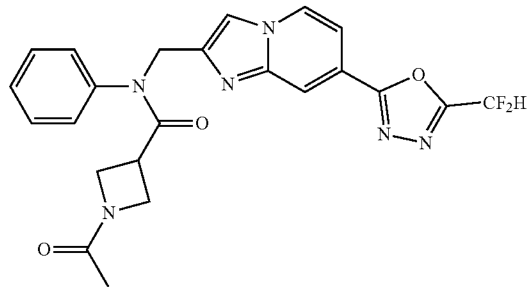 [SMILES: CC(=O)N1CC(C(=O)N(Cc2cn3ccc(-c4nnc(C(F)F)o4)cc3n2)c2ccccc2)C1] |
| 123 | 4168 | 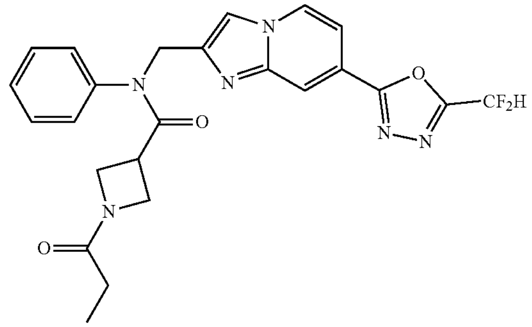 |
| 124 | 4169 | 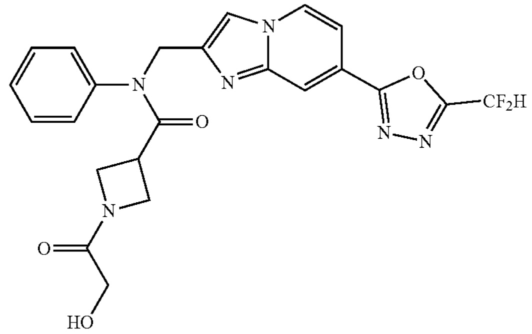 [SMILES: O=C(CO)N1CC(C(=O)N(Cc2cn3ccc(-c4nnc(C(F)F)o4)cc3n2)c2ccccc2)C1] |

-continued
| Ex | Comp | Structure |
|---|---|---|
| 125 | 4170 | 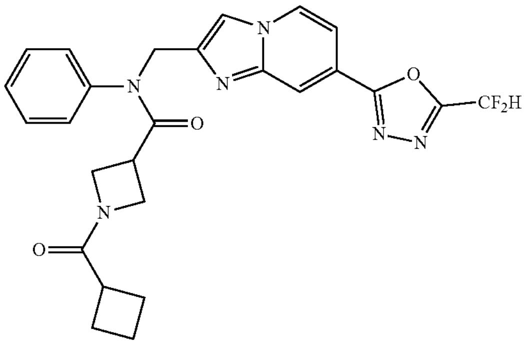 [SMILES: O=C(C1CCC1)N1CC(C(=O)N(Cc2cn3ccc(-c4nnc(C(F)F)o4)cc3n2)c2ccccc2)C1] |
| 126 | 4171 | 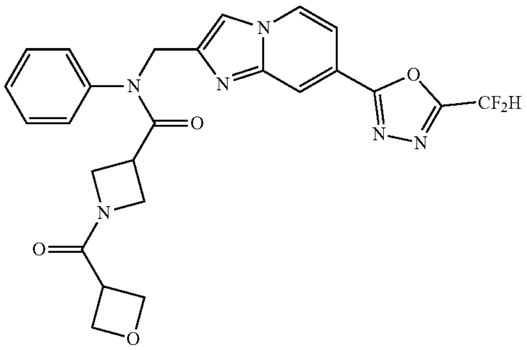 [SMILES: O=C(C1COC1)N1CC(C(=O)N(Cc2cn3ccc(-c4nnc(C(F)F)o4)cc3n2)c2ccccc2)C1] |
| 127 | 4172 | 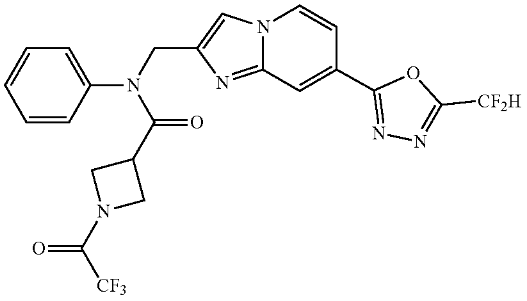 [SMILES: O=C(C1CN(C(=O)C(F)(F)F)C1)N(Cc1cn2ccc(-c3nnc(C(F)F)o3)cc2n1)c1ccccc1] |
| 128 | 4173 | 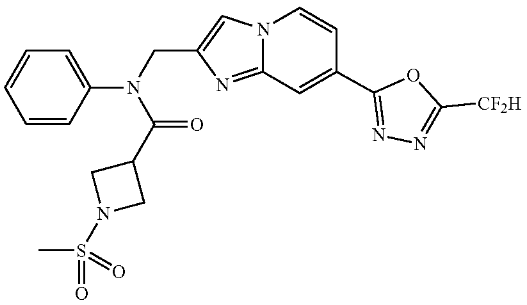 [SMILES: CS(=O)(=O)N1CC(C(=O)N(Cc2cn3ccc(-c4nnc(C(F)F)o4)cc3n2)c2ccccc2)C1] |

-continued
| Ex | Comp | Structure |
| --- | --- | --- |
| 129 | 4174 | 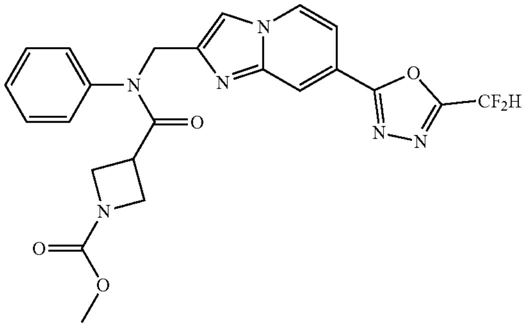 |
| 130 | 4175 | 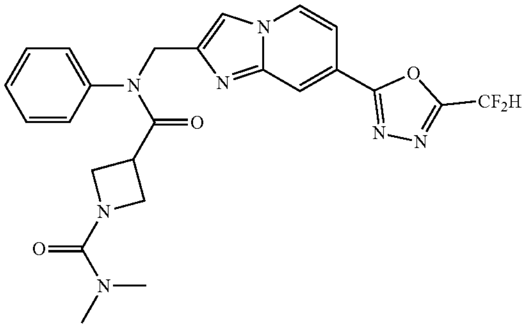 [SMILES: CN(C)C(=O)N1CC(C(=O)N(Cc2cn3ccc(-c4nnc(C(F)F)o4)cc3n2)c2ccccc2)C1] |
| 131 | 4176 | 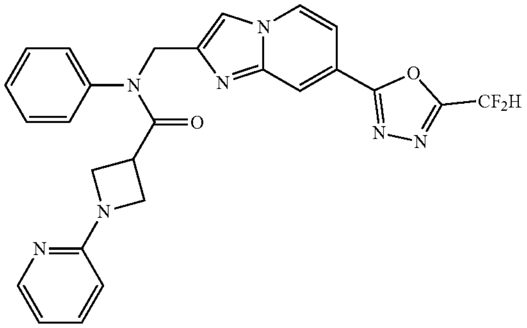 [SMILES: O=C(C1CN(c2ccccn2)C1)N(Cc1cn2ccc(-c3nnc(C(F)F)o3)cc2n1)c1ccccc1] |
| 132 | 4177 | 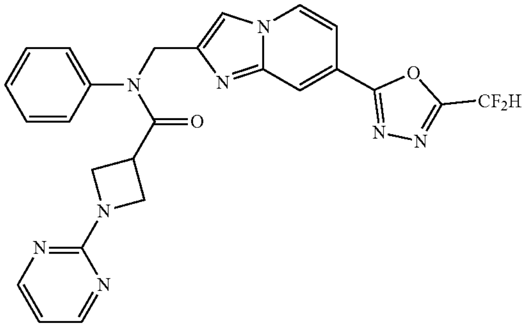 |
| 133 | 4188 | 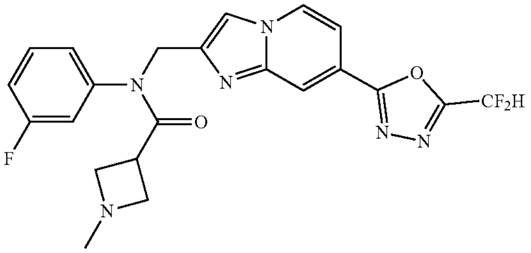 [SMILES: CN1CC(C(=O)N(Cc2cn3ccc(-c4nnc(C(F)F)o4)cc3n2)c2cccc(F)c2)C1] |

-continued
| Ex | Comp | Structure |
|---|---|---|
| 134 | 4189 | 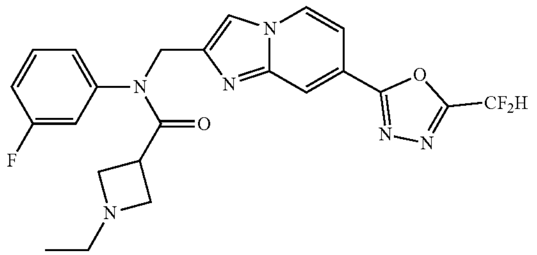 [SMILES: CCN1CC(C(=O)N(Cc2cn3ccc(-c4nnc(C(F)F)o4)cc3n2)c2cccc(F)c2)C1] |
| 135 | 4190 | 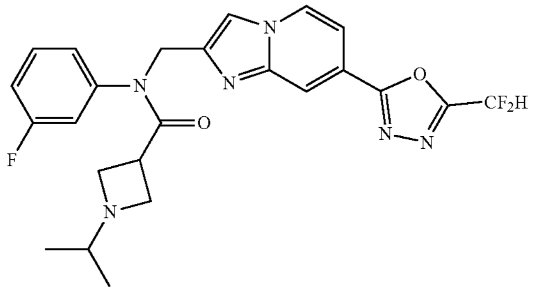 [SMILES: CC(C)N1CC(C(=O)N(Cc2cn3ccc(-c4nnc(C(F)F)o4)cc3n2)c2cccc(F)c2)C1] |
| 136 | 4191 | 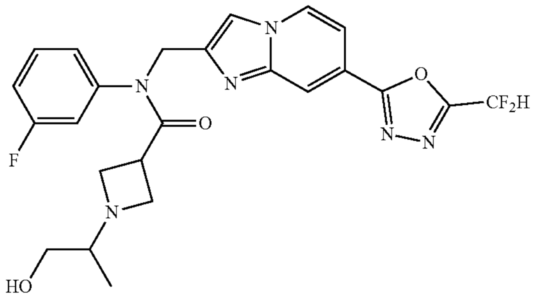 [SMILES: CC(CO)N1CC(C(=O)N(Cc2cn3ccc(-c4nnc(C(F)F)o4)cc3n2)c2cccc(F)c2)C1] |
| 137 | 4192 | 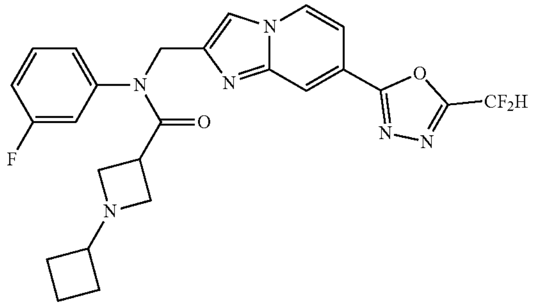 [SMILES: O=C(C1CN(C2CCC2)C1)N(Cc1cn2ccc(-c3nnc(C(F)F)o3)cc2n1)c1cccc(F)c1] |
| 138 | 4193 | 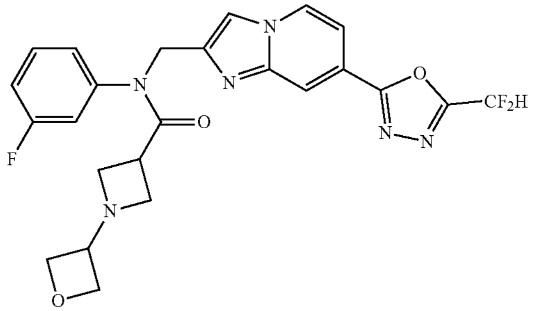 [SMILES: O=C(C1CN(C2COC2)C1)N(Cc1cn2ccc(-c3nnc(C(F)F)o3)cc2n1)c1cccc(F)c1] |

-continued
| Ex | Comp | Structure |
| --- | --- | --- |
| 139 | 4194 | 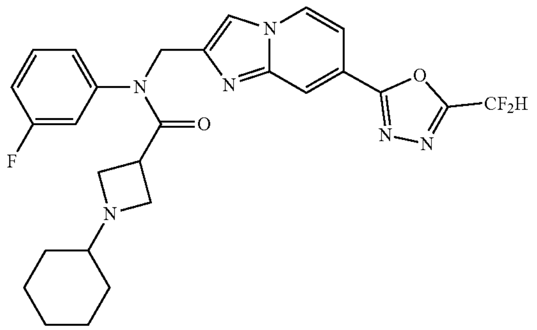 [SMILES: O=C(C1CN(C2CCCCC2)C1)N(Cc1cn2ccc(-c3nnc(C(F)F)o3)cc2n1)c1cccc(F)c1] |
| 140 | 4195 | 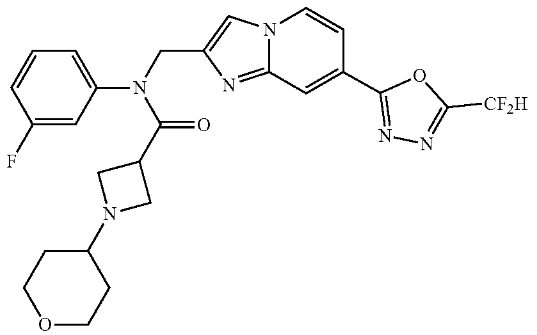 [SMILES: O=C(C1CN(C2CCOCC2)C1)N(Cc1cn2ccc(-c3nnc(C(F)F)o3)cc2n1)c1cccc(F)c1] |
| 141 | 4196 | 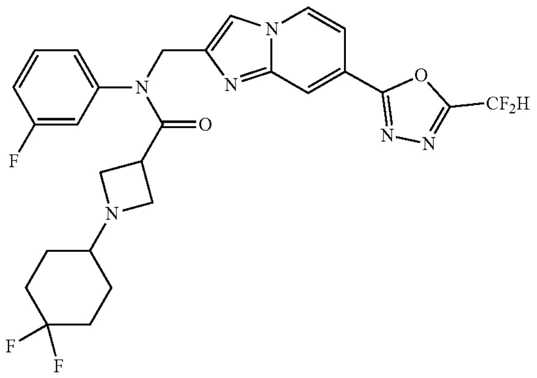 [SMILES: O=C(C1CN(C2CCC(F)(F)CC2)C1)N(Cc1cn2ccc(-c3nnc(C(F)F)o3)cc2n1)c1cccc(F)c1] |
| 142 | 4197 | 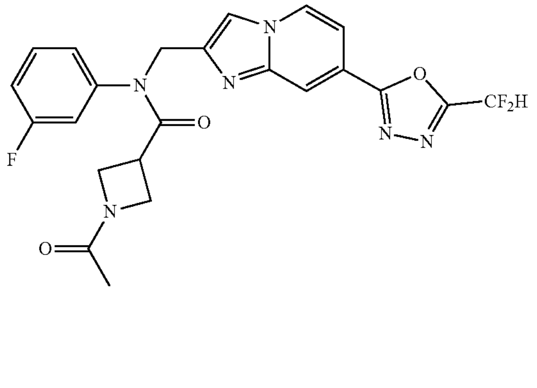 [SMILES: CC(=O)N1CC(C(=O)N(Cc2cn3ccc(-c4nnc(C(F)F)o4)cc3n2)c2cccc(F)c2)C1] |

-continued
| Ex | Comp | Structure |
|---|---|---|
| 143 | 4198 | 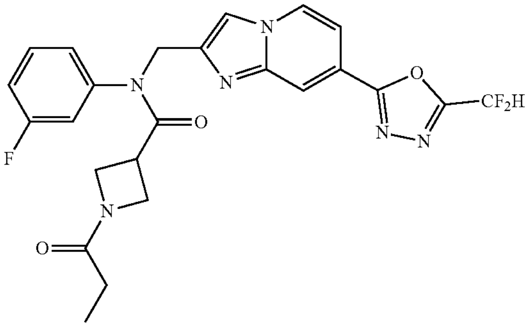 [SMILES: CCC(=O)N1CC(C(=O)N(Cc2cn3ccc(-c4nnc(C(F)F)o4)cc3n2)c2cccc(F)c2)C1] |
| 144 | 4199 | 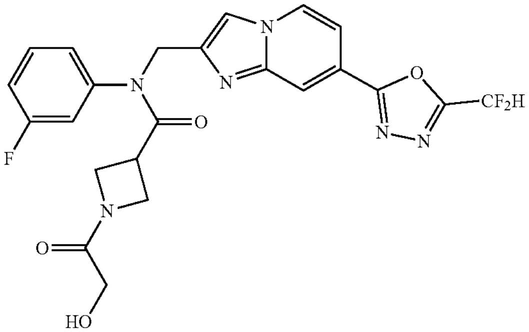 [SMILES: O=C(CO)N1CC(C(=O)N(Cc2cn3ccc(-c4nnc(C(F)F)o4)cc3n2)c2cccc(F)c2)C1] |
| 145 | 4200 | 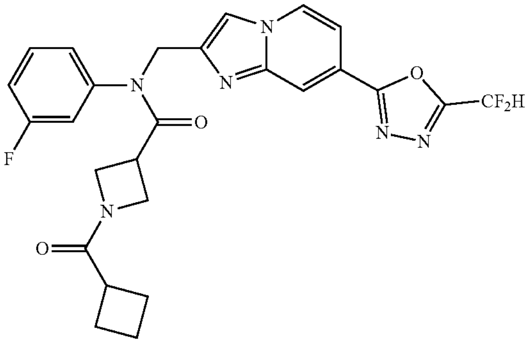 [SMILES: O=C(C1CCC1)N1CC(C(=O)N(Cc2cn3ccc(-c4nnc(C(F)F)o4)cc3n2)c2cccc(F)c2)C1] |
| 146 | 4201 | 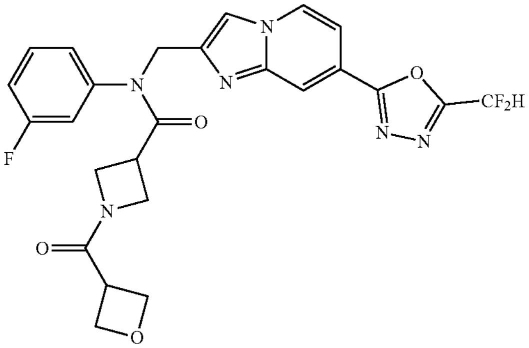 [SMILES: O=C(C1COC1)N1CC(C(=O)N(Cc2cn3ccc(-c4nnc(C(F)F)o4)cc3n2)c2cccc(F)c2)C1] |

-continued
| Ex | Comp | Structure |
|---|---|---|
| 147 | 4202 | 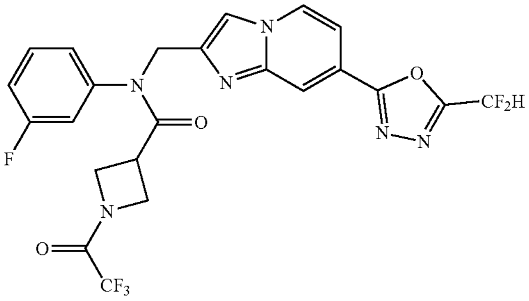 [SMILES: O=C(C1CN(C(=O)C(F)(F)F)C1)N(Cc1cn2ccc(-c3nnc(C(F)F)o3)cc2n1)c1cccc(F)c1] |
| 148 | 4203 | 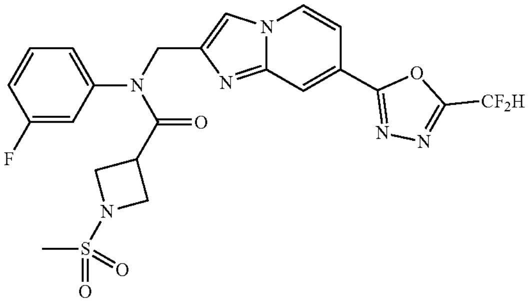 [SMILES: CS(=O)(=O)N1CC(C(=O)N(Cc2cn3ccc(-c4nnc(C(F)F)o4)cc3n2)c2cccc(F)c2)C1] |
| 149 | 4204 | 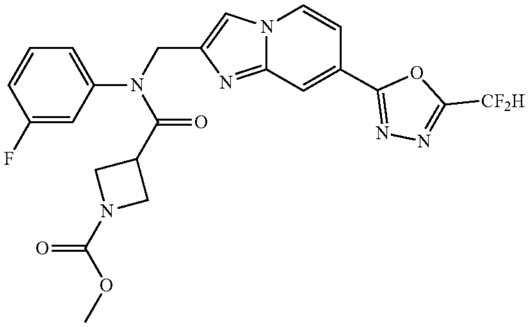 [SMILES: COC(=O)N1CC(C(=O)N(Cc2cn3ccc(-c4nnc(C(F)F)o4)cc3n2)c2cccc(F)c2)C1] |
| 150 | 4205 | 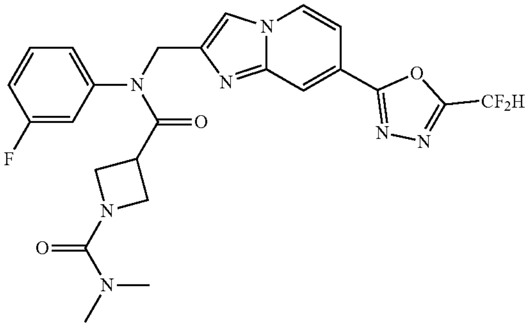 [SMILES: CN(C)C(=O)N1CC(C(=O)N(Cc2cn3ccc(-c4nnc(C(F)F)o4)cc3n2)c2cccc(F)c2)C1] |

-continued
| Ex | Comp | Structure |
|---|---|---|
| 151 | 4206 | 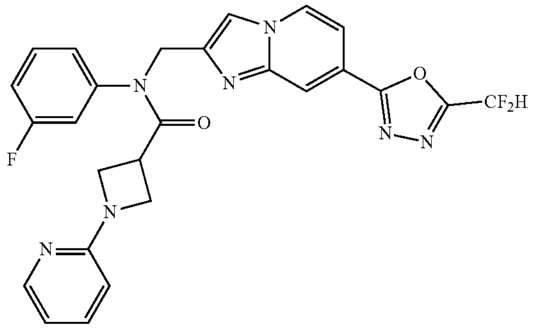 [SMILES: O=C(C1CN(c2ccccn2)C1)N(Cc1cn2ccc(-c3nnc(C(F)F)o3)cc2n1)c1cccc(F)c1] |
| 152 | 4207 | 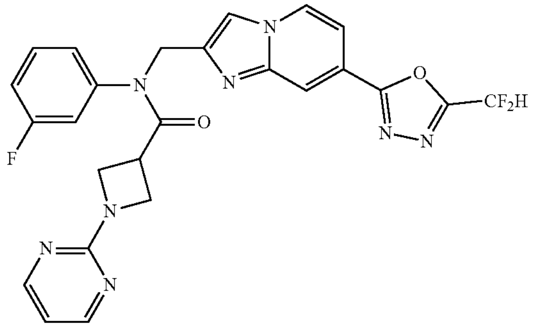 [SMILES: O=C(C1CN(c2ncccn2)C1)N(Cc1cn2ccc(-c3nnc(C(F)F)o3)cc2n1)c1cccc(F)c1] |
| 153 | 4618 | 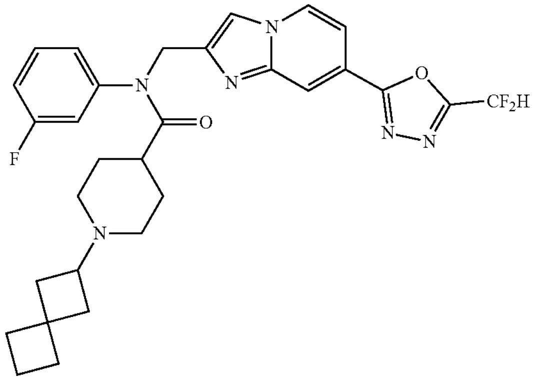 |
| 154 | 4619 | 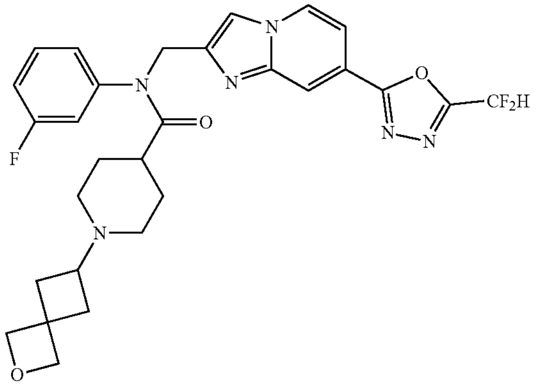 |

-continued
| Ex | Comp | Structure |
|---|---|---|
| 155 | 4620 | 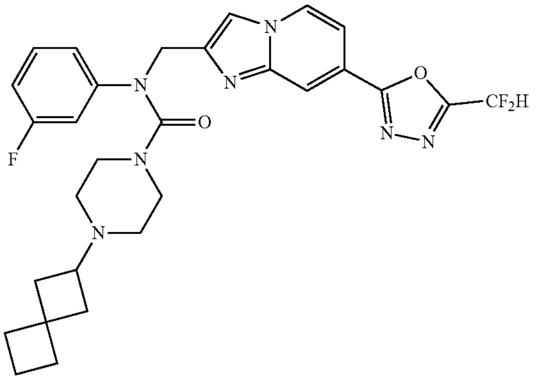 |
| 156 | 4621 | 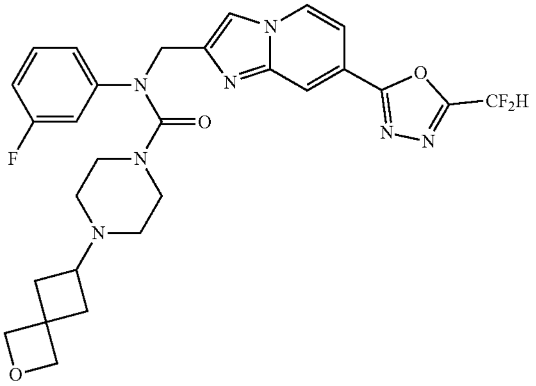 |
| 157 | 4625 | 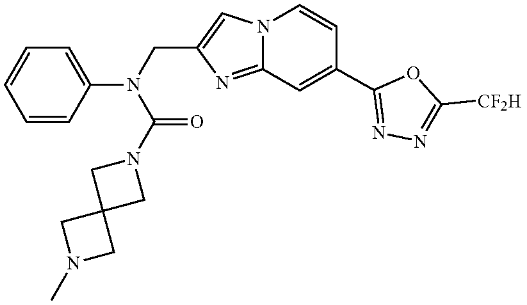 [SMILES: CN1CC2(C1)CN(C(=O)N(Cc1cn3ccc(-c4nnc(C(F)F)o4)cc3n1)c1ccccc1)C2] |
| 158 | 6892 | 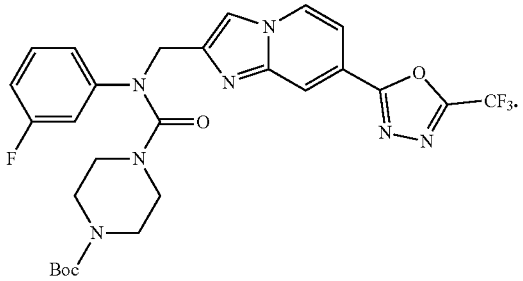 [SMILES: CC(C)(C)OC(=O)N1CCN(C(=O)N(Cc2cn3ccc(-c4nnc(C(F)(F)F)o4)cc3n2)c2cccc(F)c2)CC1] |

8. The 1,3,4-oxadiazole derivative compound, the optical isomer thereof or the pharmaceutically acceptable salt thereof according to claim 7, wherein it is any one of compounds listed in the following table:
| Ex | Comp | Structure |
|---|---|---|
| 33 | 3782 | 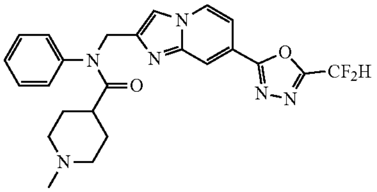 [SMILES: CN1CCC(C(=O)N(Cc2cn3ccc(-c4nnc(C(F)F)o4)cc3n2)c2ccccc2)CC1] |
| 34 | 3783 | 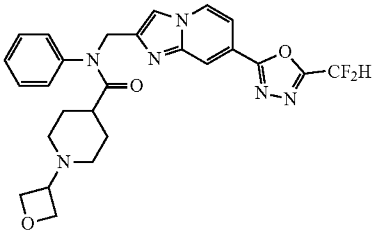 [SMILES: O=C(C1CCN(C2COC2)CC1)N(Cc1cn2ccc(-c3nnc(C(F)F)o3)cc2n1)c1ccccc1] |
| 40 | 4036 | 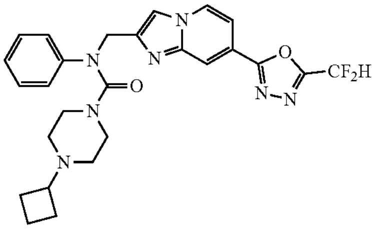 |
| 75 | 4115 | 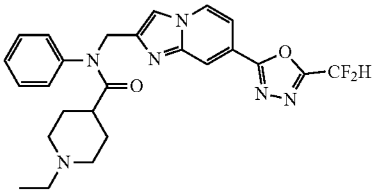 [SMILES: CCN1CCC(C(=O)N(Cc2cn3ccc(-c4nnc(C(F)F)o4)cc3n2)c2ccccc2)CC1] |
| 76 | 4116 | 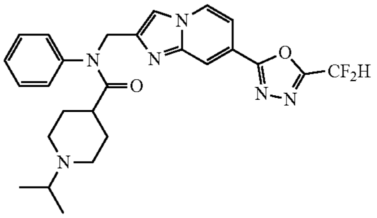 [SMILES: CC(C)N1CCC(C(=O)N(Cc2cn3ccc(-c4nnc(C(F)F)o4)cc3n2)c2ccccc2)CC1] |
| 77 | 4117 | 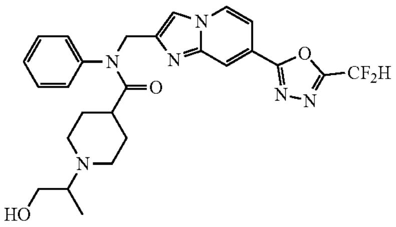 |
-continued
| Ex | Comp | Structure |
|---|---|---|
| 78 | 4118 | 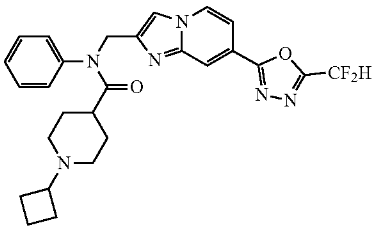 [SMILES: O=C(C1CCN(C2CCC2)CC1)N(Cc1cn2ccc(-c3nnc(C(F)F)o3)cc2n1)c1ccccc1] |
| 79 | 4119 | 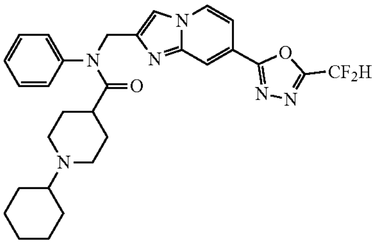 [SMILES: O=C(C1CCN(C2CCCCC2)CC1)N(Cc1cn2ccc(-c3nnc(C(F)F)o3)cc2n1)c1ccccc1] |
| 80 | 4120 | 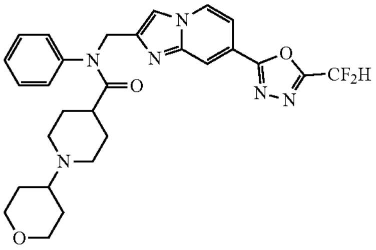 [SMILES: O=C(C1CCN(C2CCOCC2)CC1)N(Cc1cn2ccc(-c3nnc(C(F)F)o3)cc2n1)c1ccccc1] |
| 81 | 4121 | 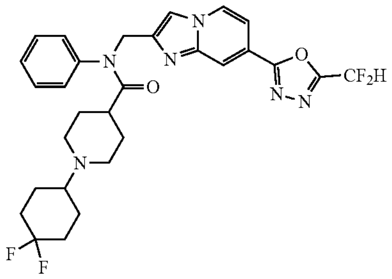 [SMILES: O=C(C1CCN(C2CCC(F)(F)CC2)CC1)N(Cc1cn2ccc(-c3nnc(C(F)F)o3)cc2n1)c1ccccc1] |
| 82 | 4122 | 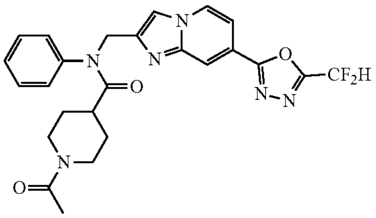 [SMILES: CC(=O)N1CCC(C(=O)N(Cc2cn3ccc(-c4nnc(C(F)F)o4)cc3n2)c2ccccc2)CC1] |
| 83 | 4123 | 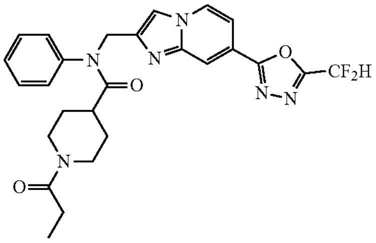 [SMILES: CCC(=O)N1CCC(C(=O)N(Cc2cn3ccc(-c4nnc(C(F)F)o4)cc3n2)c2ccccc2)CC1] |

| Ex | Comp | Structure |
|---|---|---|
| 84 | 4124 | 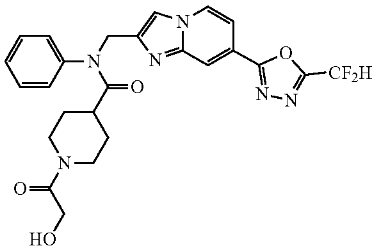 [SMILES: O=C(CO)N1CCC(C(=O)N(Cc2cn3ccc(-c4nnc(C(F)F)o4)cc3n2)c2ccccc2)CC1] |
| 85 | 4125 | 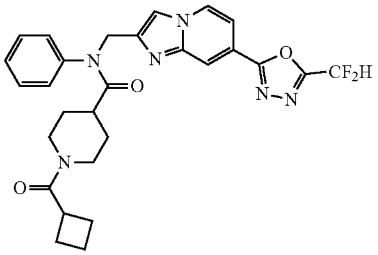 [SMILES: O=C(C1CCC1)N1CCC(C(=O)N(Cc2cn3ccc(-c4nnc(C(F)F)o4)cc3n2)c2ccccc2)CC1] |
| 86 | 4126 | 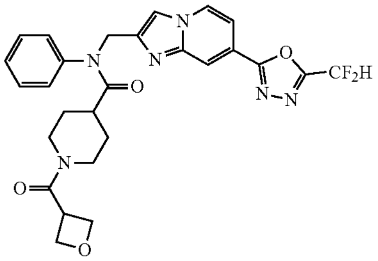 [SMILES: O=C(C1COC1)N1CCC(C(=O)N(Cc2cn3ccc(-c4nnc(C(F)F)o4)cc3n2)c2ccccc2)CC1] |
| 87 | 4127 | 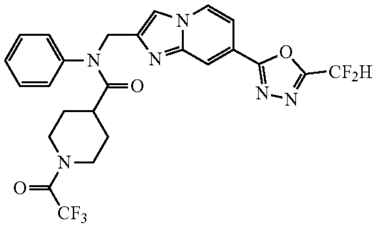 [SMILES: O=C(C1CCN(C(=O)C(F)(F)F)CC1)N(Cc1cn2ccc(-c3nnc(C(F)F)o3)cc2n1)c1ccccc1] |
| 88 | 4128 | 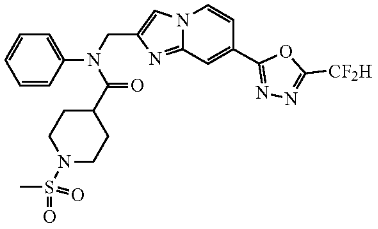 [SMILES: CS(=O)(=O)N1CCC(C(=O)N(Cc2cn3ccc(-c4nnc(C(F)F)o4)cc3n2)c2ccccc2)CC1] |
| 89 | 4129 | 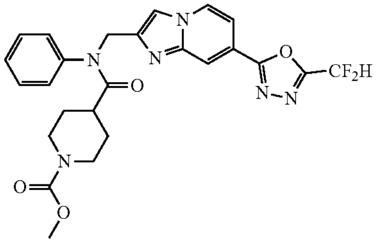 [SMILES: COC(=O)N1CCC(C(=O)N(Cc2cn3ccc(-c4nnc(C(F)F)o4)cc3n2)c2ccccc2)CC1] |
| Ex | Comp | Structure |
|---|---|---|
| 90 | 4130 | 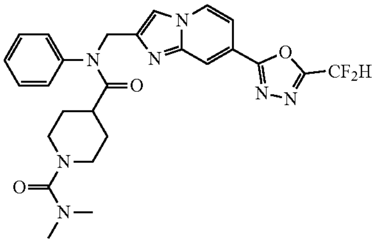 [SMILES: CN(C)C(=O)N1CCC(C(=O)N(Cc2cn3ccc(-c4nnc(C(F)F)o4)cc3n2)c2ccccc2)CC1] |
| 91 | 4131 | 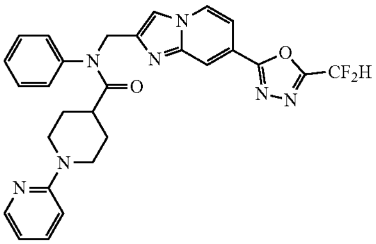 [SMILES: O=C(C1CCN(c2ccccn2)CC1)N(Cc1cn2ccc(-c3nnc(C(F)F)o3)cc2n1)c1ccccc1] |
| 92 | 4132 | 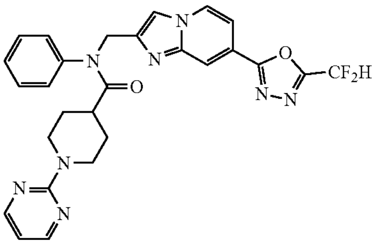 [SMILES: O=C(C1CCN(c2ncccn2)CC1)N(Cc1cn2ccc(-c3nnc(C(F)F)o3)cc2n1)c1ccccc1] |
| 93 | 4137 | 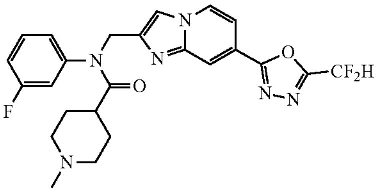 [SMILES: CN1CCC(C(=O)N(Cc2cn3ccc(-c4nnc(C(F)F)o4)cc3n2)c2cccc(F)c2)CC1] |
| 94 | 4138 | 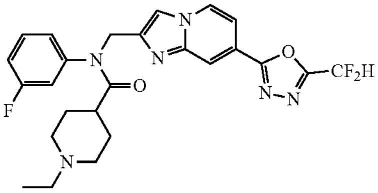 [SMILES: CCN1CCC(C(=O)N(Cc2cn3ccc(-c4nnc(C(F)F)o4)cc3n2)c2cccc(F)c2)CC1] |
| 95 | 4139 | 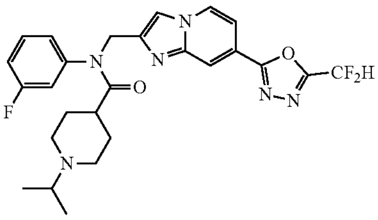 [SMILES: CC(C)N1CCC(C(=O)N(Cc2cn3ccc(-c4nnc(C(F)F)o4)cc3n2)c2cccc(F)c2)CC1] |

-continued
| Ex | Comp | Structure |
| --- | --- | --- |
| 96 | 4140 | 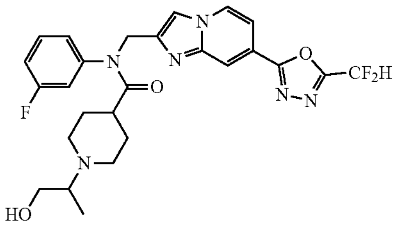 [SMILES: CC(CO)N1CCC(C(=O)N(Cc2cn3ccc(-c4nnc(C(F)F)o4)cc3n2)c2cccc(F)c2)CC1] |
| 97 | 4141 | 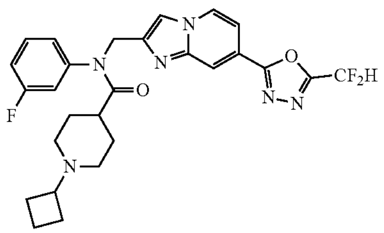 |
| 98 | 4142 | 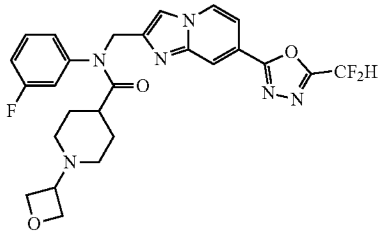 [SMILES: O=C(C1CCN(C2COC2)CC1)N(Cc1cn2ccc(-c3nnc(C(F)F)o3)cc2n1)c1cccc(F)c1] |
| 99 | 4143 | 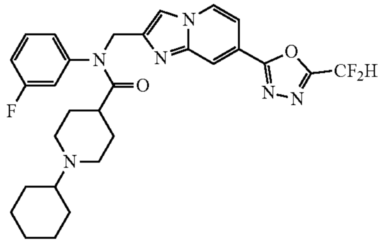 [SMILES: O=C(C1CCN(C2CCCCC2)CC1)N(Cc1cn2ccc(-c3nnc(C(F)F)o3)cc2n1)c1cccc(F)c1] |
| 100 | 4144 | 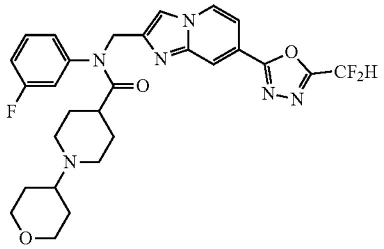 |
| 101 | 4145 | 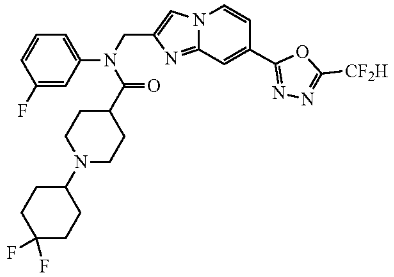 [SMILES: O=C(C1CCN(C2CCC(F)(F)CC2)CC1)N(Cc1cn2ccc(-c3nnc(C(F)F)o3)cc2n1)c1cccc(F)c1] |
| 102 | 4146 | 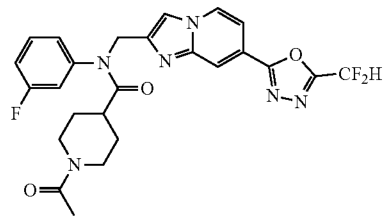 [SMILES: CC(=O)N1CCC(C(=O)N(Cc2cn3ccc(-c4nnc(C(F)F)o4)cc3n2)c2cccc(F)c2)CC1] |
| 103 | 4147 | 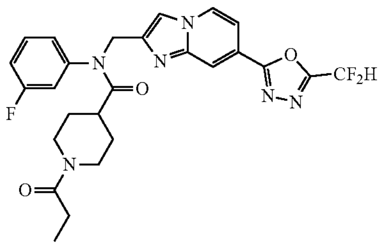 [SMILES: CCC(=O)N1CCC(C(=O)N(Cc2cn3ccc(-c4nnc(C(F)F)o4)cc3n2)c2cccc(F)c2)CC1] |
| 104 | 4149 | 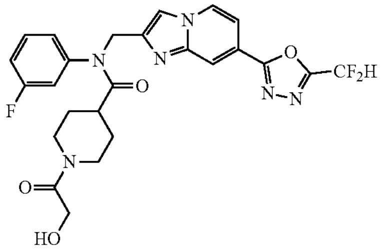 [SMILES: O=C(CO)N1CCC(C(=O)N(Cc2cn3ccc(-c4nnc(C(F)F)o4)cc3n2)c2cccc(F)c2)CC1] |
| 105 | 4150 | 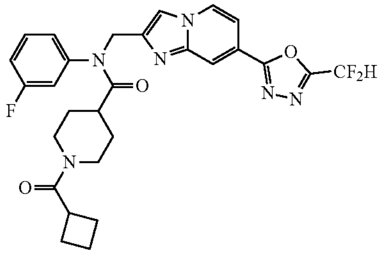 [SMILES: O=C(C1CCC1)N1CCC(C(=O)N(Cc2cn3ccc(-c4nnc(C(F)F)o4)cc3n2)c2cccc(F)c2)CC1] |
| 106 | 4151 | 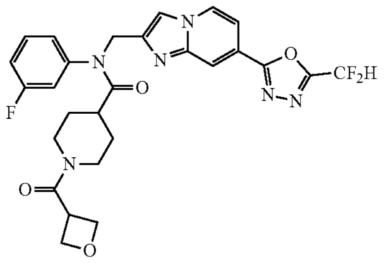 [SMILES: O=C(C1COC1)N1CCC(C(=O)N(Cc2cn3ccc(-c4nnc(C(F)F)o4)cc3n2)c2cccc(F)c2)CC1] |
| 107 | 4152 | 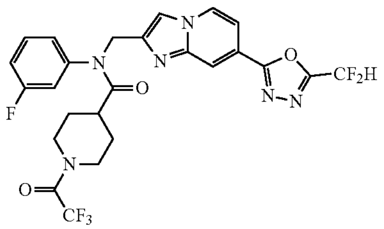 [SMILES: O=C(C1CCN(C(=O)C(F)(F)F)CC1)N(Cc1cn2ccc(-c3nnc(C(F)F)o3)cc2n1)c1cccc(F)c1] |

-continued
| Ex | Comp | Structure |
|---|---|---|
| 108 | 4153 | 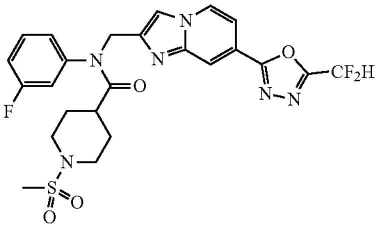 [SMILES: CS(=O)(=O)N1CCC(C(=O)N(Cc2cn3ccc(-c4nnc(C(F)F)o4)cc3n2)c2cccc(F)c2)CC1] |
| 109 | 4154 | 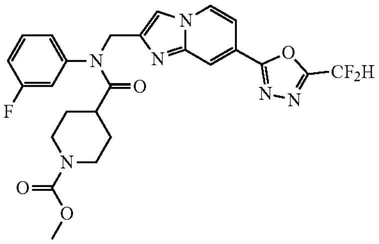 |
| 110 | 4155 | 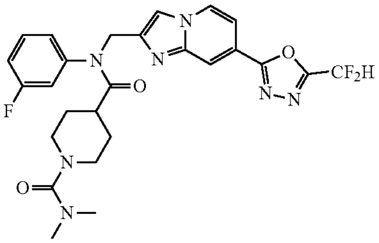 [SMILES: CN(C)C(=O)N1CCC(C(=O)N(Cc2cn3ccc(-c4nnc(C(F)F)o4)cc3n2)c2cccc(F)c2)CC1] |
| 111 | 4156 | 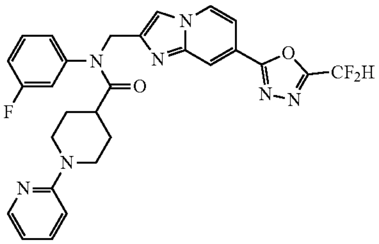 [SMILES: O=C(C1CCN(c2ccccn2)CC1)N(Cc1cn2ccc(-c3nnc(C(F)F)o3)cc2n1)c1cccc(F)c1] |
| 112 | 4157 | 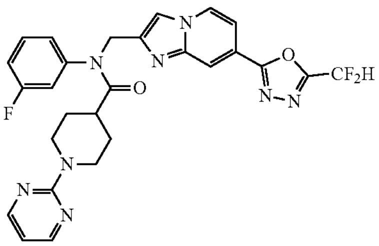 [SMILES: O=C(C1CCN(c2ncccn2)CC1)N(Cc1cn2ccc(-c3nnc(C(F)F)o3)cc2n1)c1cccc(F)c1] |
| 113 | 4158 | 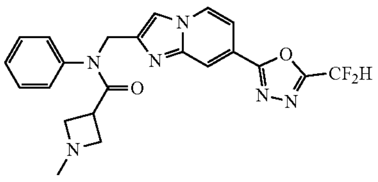 [SMILES: CN1CC(C(=O)N(Cc2cn3ccc(-c4nnc(C(F)F)o4)cc3n2)c2ccccc2)C1] |
| 114 | 4159 | 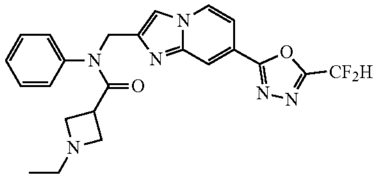 [SMILES: CCN1CC(C(=O)N(Cc2cn3ccc(-c4nnc(C(F)F)o4)cc3n2)c2ccccc2)C1] |
| 115 | 4160 | 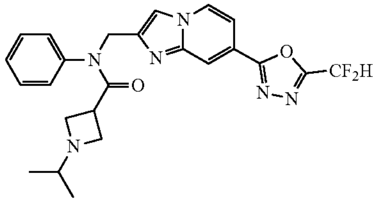 [SMILES: CC(C)N1CC(C(=O)N(Cc2cn3ccc(-c4nnc(C(F)F)o4)cc3n2)c2ccccc2)C1] |
| 116 | 4161 | 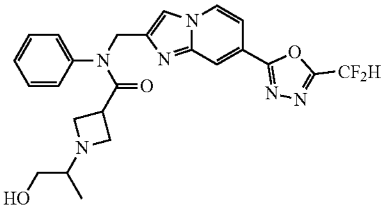 [SMILES: CC(CO)N1CC(C(=O)N(Cc2cn3ccc(-c4nnc(C(F)F)o4)cc3n2)c2ccccc2)C1] |
| 117 | 4162 | 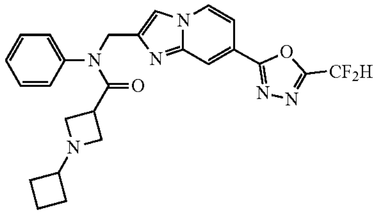 [SMILES: O=C(C1CN(C2CCC2)C1)N(Cc1cn2ccc(-c3nnc(C(F)F)o3)cc2n1)c1ccccc1] |
| 118 | 4163 | 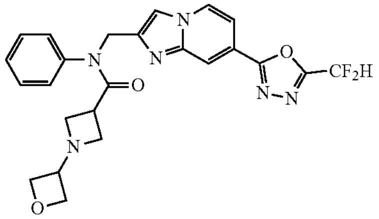 [SMILES: O=C(C1CN(C2COC2)C1)N(Cc1cn2ccc(-c3nnc(C(F)F)o3)cc2n1)c1ccccc1] |
| 119 | 4164 | 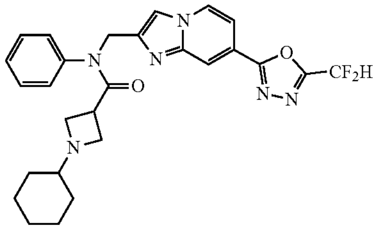 [SMILES: O=C(C1CN(C2CCCCC2)C1)N(Cc1cn2ccc(-c3nnc(C(F)F)o3)cc2n1)c1ccccc1] |
| 120 | 4165 | 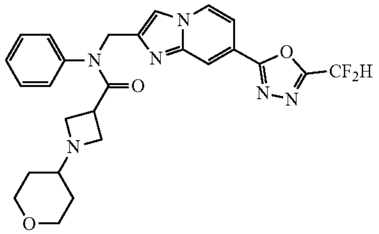 [SMILES: O=C(C1CN(C2CCOCC2)C1)N(Cc1cn2ccc(-c3nnc(C(F)F)o3)cc2n1)c1ccccc1] |

-continued
| Ex | Comp | Structure |
|---|---|---|
| 121 | 4166 | 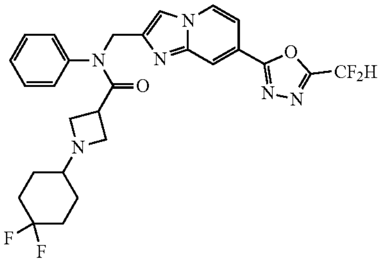 [SMILES: O=C(C1CN(C2CCC(F)(F)CC2)C1)N(Cc1cn2ccc(-c3nnc(C(F)F)o3)cc2n1)c1ccccc1] |
| 122 | 4167 | 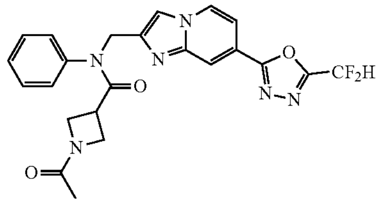 [SMILES: CC(=O)N1CC(C(=O)N(Cc2cn3ccc(-c4nnc(C(F)F)o4)cc3n2)c2ccccc2)C1] |
| 123 | 4168 | 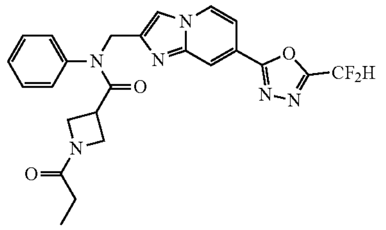 [SMILES: CCC(=O)N1CC(C(=O)N(Cc2cn3ccc(-c4nnc(C(F)F)o4)cc3n2)c2ccccc2)C1] |
| 124 | 4169 | 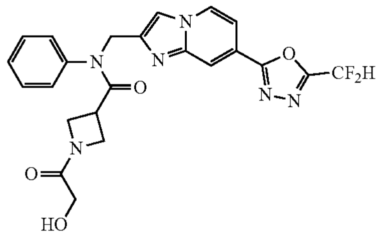 [SMILES: O=C(CO)N1CC(C(=O)N(Cc2cn3ccc(-c4nnc(C(F)F)o4)cc3n2)c2ccccc2)C1] |
| 125 | 4170 | 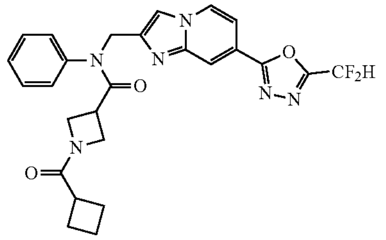 [SMILES: O=C(C1CCC1)N1CC(C(=O)N(Cc2cn3ccc(-c4nnc(C(F)F)o4)cc3n2)c2ccccc2)C1] |
| 126 | 4171 | 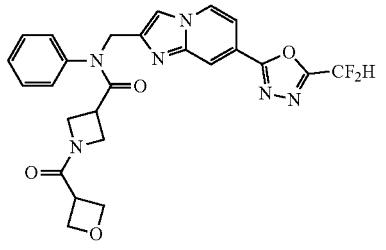 [SMILES: O=C(C1COC1)N1CC(C(=O)N(Cc2cn3ccc(-c4nnc(C(F)F)o4)cc3n2)c2ccccc2)C1] |
-continued
| Ex | Comp | Structure |
|---|---|---|
| 127 | 4172 | 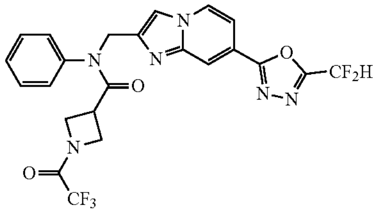 [SMILES: O=C(C1CN(C(=O)C(F)(F)F)C1)N(Cc1cn2ccc(-c3nnc(C(F)F)o3)cc2n1)c1ccccc1] |
| 128 | 4173 | 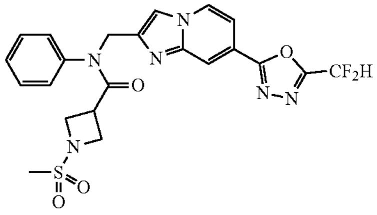 [SMILES: CS(=O)(=O)N1CC(C(=O)N(Cc2cn3ccc(-c4nnc(C(F)F)o4)cc3n2)c2ccccc2)C1] |
| 129 | 4174 | 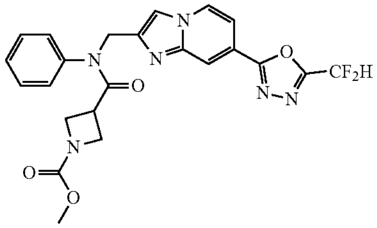 |
| 130 | 4175 | 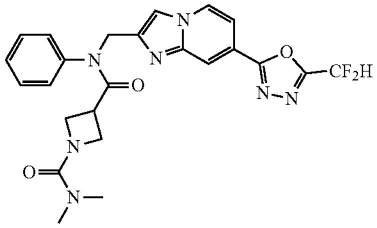 [SMILES: CN(C)C(=O)N1CC(C(=O)N(Cc2cn3ccc(-c4nnc(C(F)F)o4)cc3n2)c2ccccc2)C1] |
| 131 | 4176 | 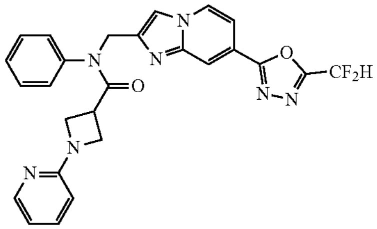 [SMILES: O=C(C1CN(c2ccccn2)C1)N(Cc1cn2ccc(-c3nnc(C(F)F)o3)cc2n1)c1ccccc1] |
| 132 | 4177 | 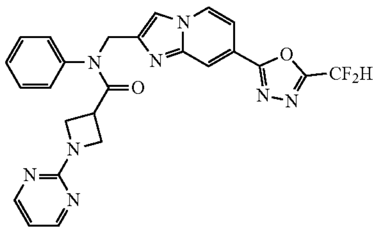 |
| 133 | 4188 | 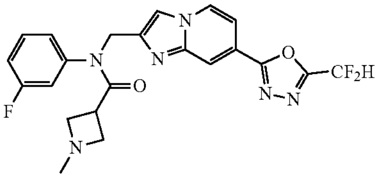 [SMILES: CN1CC(C(=O)N(Cc2cn3ccc(-c4nnc(C(F)F)o4)cc3n2)c2cccc(F)c2)C1] |

-continued
| Ex | Comp | Structure |
|---|---|---|
| 134 | 4189 | 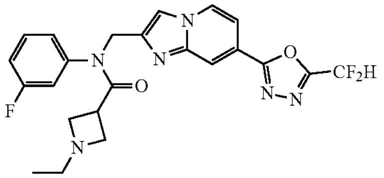 [SMILES: CCN1CC(C(=O)N(Cc2cn3ccc(-c4nnc(C(F)F)o4)cc3n2)c2cccc(F)c2)C1] |
| 135 | 4190 | 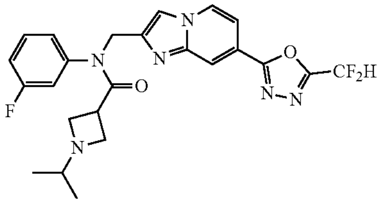 [SMILES: CC(C)N1CC(C(=O)N(Cc2cn3ccc(-c4nnc(C(F)F)o4)cc3n2)c2cccc(F)c2)C1] |
| 136 | 4191 | 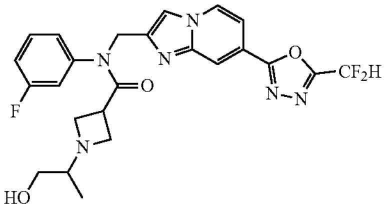 [SMILES: CC(CO)N1CC(C(=O)N(Cc2cn3ccc(-c4nnc(C(F)F)o4)cc3n2)c2cccc(F)c2)C1] |
| 137 | 4192 | 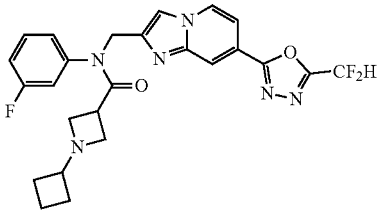 [SMILES: O=C(C1CN(C2CCC2)C1)N(Cc1cn2ccc(-c3nnc(C(F)F)o3)cc2n1)c1cccc(F)c1] |
| 138 | 4193 | 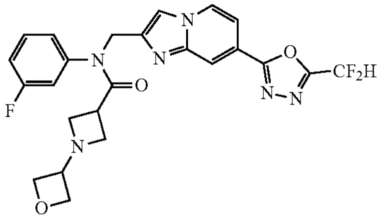 [SMILES: O=C(C1CN(C2COC2)C1)N(Cc1cn2ccc(-c3nnc(C(F)F)o3)cc2n1)c1cccc(F)c1] |
| 139 | 4194 | 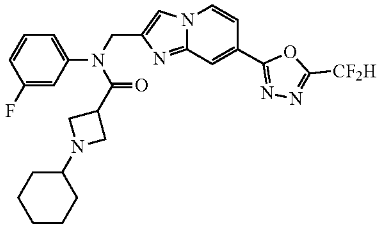 [SMILES: O=C(C1CN(C2CCCCC2)C1)N(Cc1cn2ccc(-c3nnc(C(F)F)o3)cc2n1)c1cccc(F)c1] |
| 140 | 4195 | 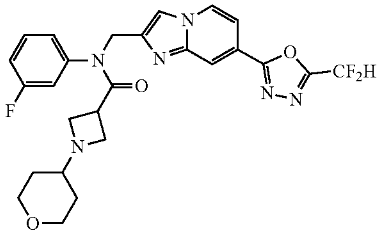 [SMILES: O=C(C1CN(C2CCOCC2)C1)N(Cc1cn2ccc(-c3nnc(C(F)F)o3)cc2n1)c1cccc(F)c1] |
| 141 | 4196 | 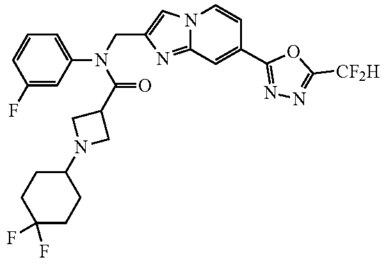 [SMILES: O=C(C1CN(C2CCC(F)(F)CC2)C1)N(Cc1cn2ccc(-c3nnc(C(F)F)o3)cc2n1)c1cccc(F)c1] |
| 142 | 4197 | 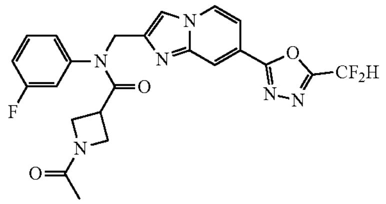 [SMILES: CC(=O)N1CC(C(=O)N(Cc2cn3ccc(-c4nnc(C(F)F)o4)cc3n2)c2cccc(F)c2)C1] |
| 143 | 4198 | 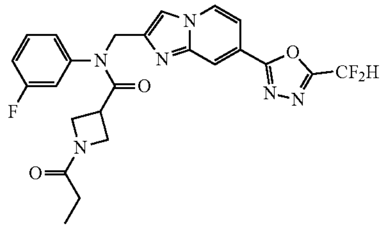 [SMILES: CCC(=O)N1CC(C(=O)N(Cc2cn3ccc(-c4nnc(C(F)F)o4)cc3n2)c2cccc(F)c2)C1] |
| 144 | 4199 | 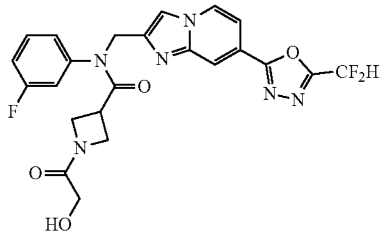 [SMILES: O=C(CO)N1CC(C(=O)N(Cc2cn3ccc(-c4nnc(C(F)F)o4)cc3n2)c2cccc(F)c2)C1] |
| 145 | 4200 | 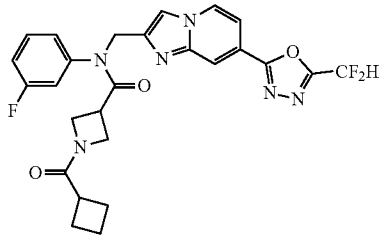 [SMILES: O=C(C1CCC1)N1CC(C(=O)N(Cc2cn3ccc(-c4nnc(C(F)F)o4)cc3n2)c2cccc(F)c2)C1] |
| 146 | 4201 | 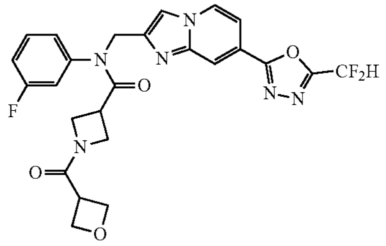 [SMILES: O=C(C1COC1)N1CC(C(=O)N(Cc2cn3ccc(-c4nnc(C(F)F)o4)cc3n2)c2cccc(F)c2)C1] |

-continued
| Ex | Comp | Structure |
|---|---|---|
| 147 | 4202 | 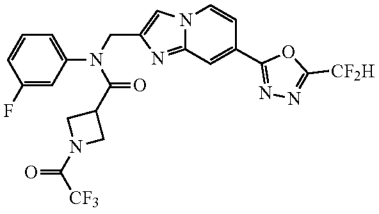 [SMILES: O=C(C1CN(C(=O)C(F)(F)F)C1)N(Cc1cn2ccc(-c3nnc(C(F)F)o3)cc2n1)c1cccc(F)c1] |
| 148 | 4203 | 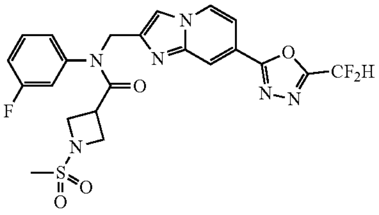 [SMILES: CS(=O)(=O)N1CC(C(=O)N(Cc2cn3ccc(-c4nnc(C(F)F)o4)cc3n2)c2cccc(F)c2)C1] |
| 149 | 4204 | 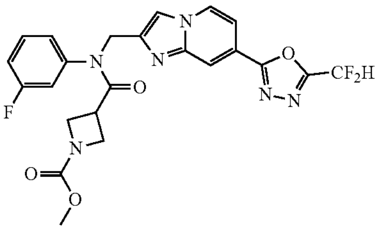 [SMILES: COC(=O)N1CC(C(=O)N(Cc2cn3ccc(-c4nnc(C(F)F)o4)cc3n2)c2cccc(F)c2)C1] |
| 150 | 4205 | 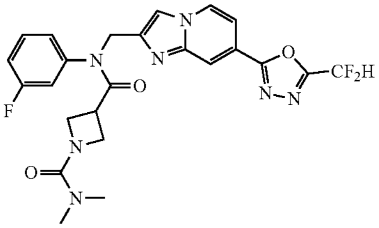 [SMILES: CN(C)C(=O)N1CC(C(=O)N(Cc2cn3ccc(-c4nnc(C(F)F)o4)cc3n2)c2cccc(F)c2)C1] |
| 151 | 4206 | 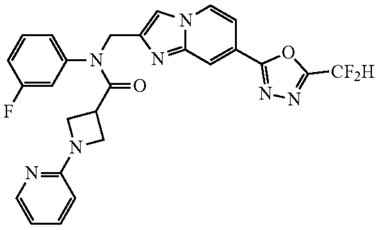 [SMILES: O=C(C1CN(c2ccccn2)C1)N(Cc1cn2ccc(-c3nnc(C(F)F)o3)cc2n1)c1cccc(F)c1] |
| 152 | 4207 | 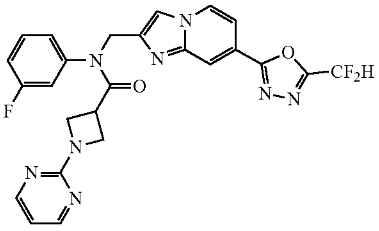 [SMILES: O=C(C1CN(c2ncccn2)C1)N(Cc1cn2ccc(-c3nnc(C(F)F)o3)cc2n1)c1cccc(F)c1] |
-continued
| Ex | Comp | Structure |
|---|---|---|
| 153 | 4618 | 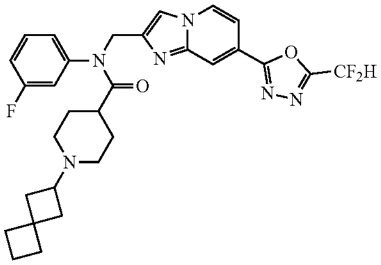 [SMILES: O=C(C1CCN(C2CC3(CCC3)C2)CC1)N(Cc1cn2ccc(-c3nnc(C(F)F)o3)cc2n1)c1cccc(F)c1] |
| 154 | 4619 | 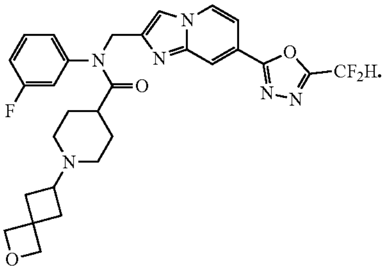 [SMILES: O=C(C1CCN(C2CC3(COC3)C2)CC1)N(Cc1cn2ccc(-c3nnc(C(F)F)o3)cc2n1)c1cccc(F)c1] |
9. The 1,3,4-oxadiazole derivative compound, the optical isomer thereof or the pharmaceutically acceptable salt thereof according to claim 7, wherein it is any one of compounds listed in the following table:
| Ex | Comp | Structure |
|---|---|---|
| 35 | 3784 | 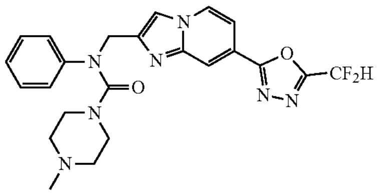 [SMILES: CN1CCN(C(=O)N(Cc2cn3ccc(-c4nnc(C(F)F)o4)cc3n2)c2ccccc2)CC1] |
| 36 | 3785 | 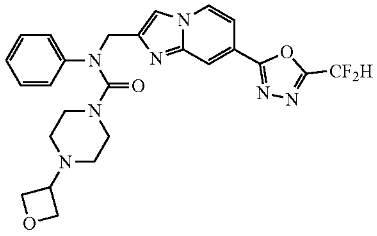 [SMILES: O=C(N1CCN(C2COC2)CC1)N(Cc1cn2ccc(-c3nnc(C(F)F)o3)cc2n1)c1ccccc1] |
| 37 | 4033 | 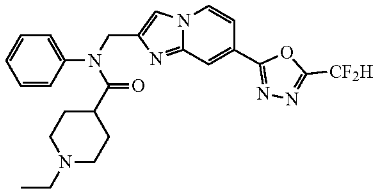 [SMILES: CCN1CCC(C(=O)N(Cc2cn3ccc(-c4nnc(C(F)F)o4)cc3n2)c2ccccc2)CC1] |

-continued
| Ex | Comp | Structure |
|---|---|---|
| 38 | 4034 | 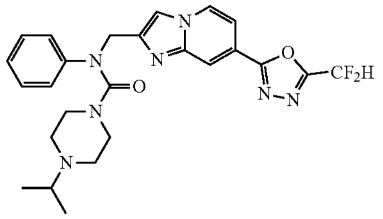 [SMILES: CC(C)N1CCN(C(=O)N(Cc2cn3ccc(-c4nnc(C(F)F)o4)cc3n2)c2ccccc2)CC1] |
| 39 | 4035 | 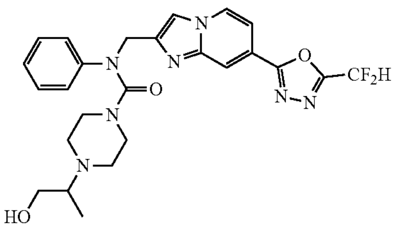 [SMILES: CC(CO)N1CCN(C(=O)N(Cc2cn3ccc(-c4nnc(C(F)F)o4)cc3n2)c2ccccc2)CC1] |
| 41 | 4037 | 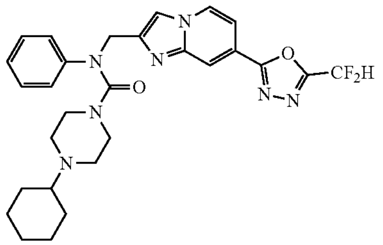 [SMILES: O=C(N1CCN(C2CCCCC2)CC1)N(Cc1cn2ccc(-c3nnc(C(F)F)o3)cc2n1)c1ccccc1] |
| 42 | 4038 | 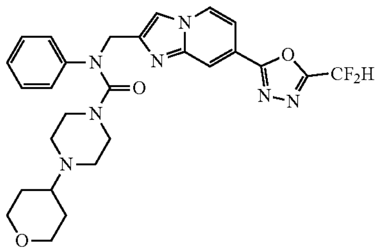 [SMILES: O=C(N1CCN(C2CCOCC2)CC1)N(Cc1cn2ccc(-c3nnc(C(F)F)o3)cc2n1)c1ccccc1] |
| 43 | 4039 | 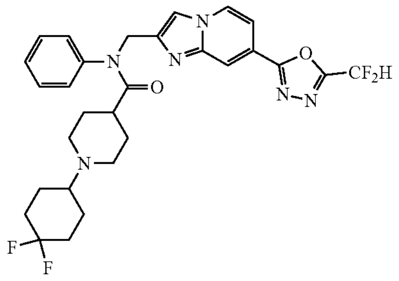 |
| 44 | 4040 | 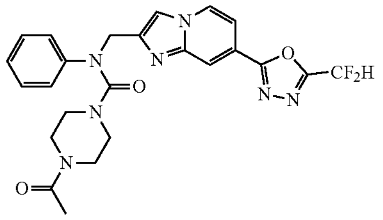 [SMILES: CC(=O)N1CCN(C(=O)N(Cc2cn3ccc(-c4nnc(C(F)F)o4)cc3n2)c2ccccc2)CC1] |
-continued
| Ex | Comp | Structure |
|---|---|---|
| 45 | 4041 | 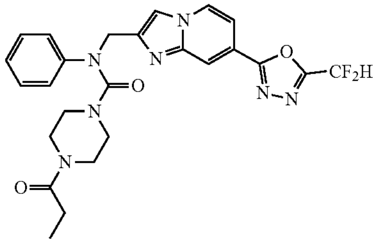 |
| 46 | 4042 | 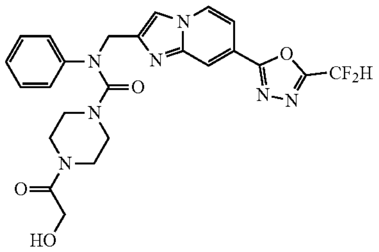 |
| 47 | 4043 | 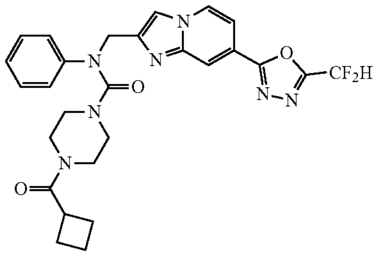 |
| 48 | 4044 | 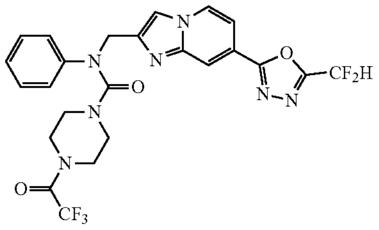 |
| 49 | 4045 | 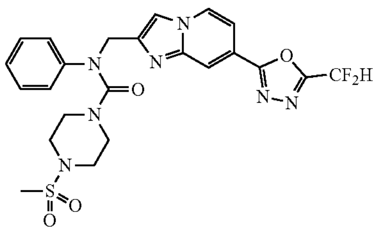 [SMILES: CS(=O)(=O)N1CCN(C(=O)N(Cc2cn3ccc(-c4nnc(C(F)F)o4)cc3n2)c2ccccc2)CC1] |
| 50 | 4046 | 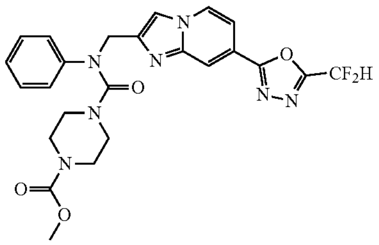 |

-continued
| Ex | Comp | Structure |
|---|---|---|
| 51 | 4047 | 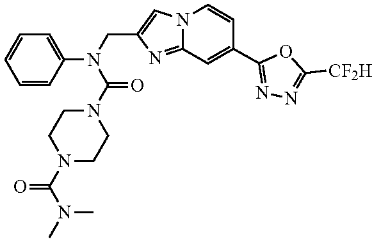 |
| 52 | 4048 | 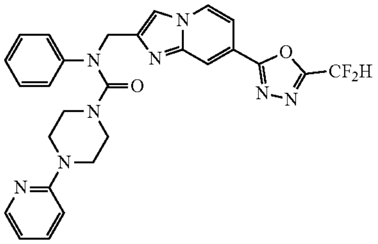 |
| 53 | 4049 | 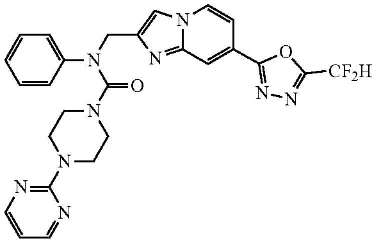 |
| 54 | 4083 | 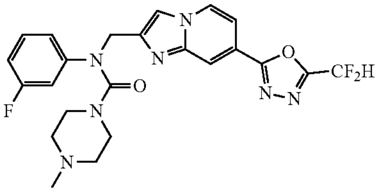 [SMILES: CN1CCN(C(=O)N(Cc2cn3ccc(-c4nnc(C(F)F)o4)cc3n2)c2cccc(F)c2)CC1] |
| 55 | 4084 | 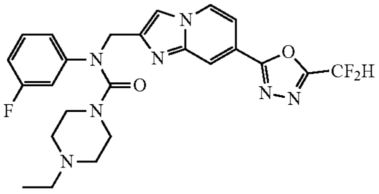 [SMILES: CCN1CCN(C(=O)N(Cc2cn3ccc(-c4nnc(C(F)F)o4)cc3n2)c2cccc(F)c2)CC1] |
| 56 | 4085 | 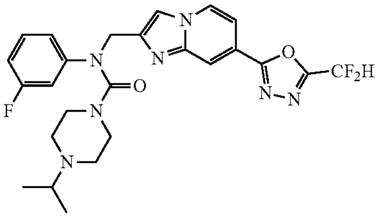 |
-continued
| Ex | Comp | Structure |
|---|---|---|
| 57 | 4086 | 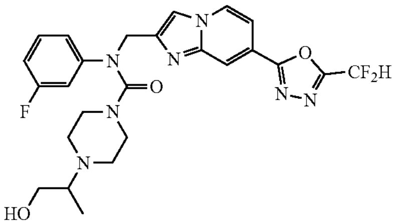 |
| 58 | 4087 | 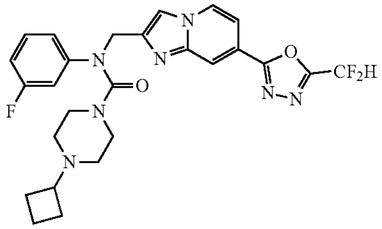 |
| 59 | 4088 | 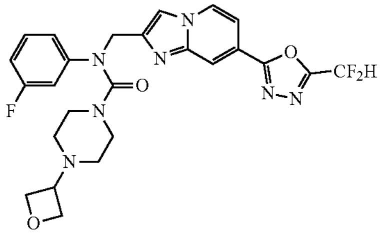 [SMILES: O=C(N1CCN(C2COC2)CC1)N(Cc1cn2ccc(-c3nnc(C(F)F)o3)cc2n1)c1cccc(F)c1] |
| 60 | 4089 | 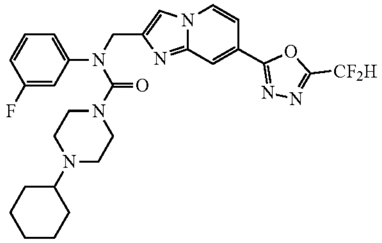 |
| 61 | 4090 | 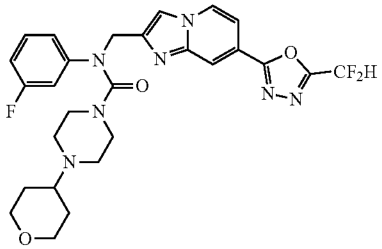 [SMILES: O=C(N1CCN(C2CCOCC2)CC1)N(Cc1cn2ccc(-c3nnc(C(F)F)o3)cc2n1)c1cccc(F)c1] |
| 62 | 4091 | 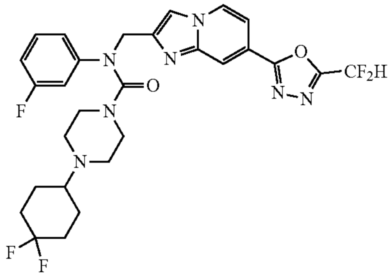 |

-continued
| Ex | Comp | Structure |
|---|---|---|
| 63 | 4092 | 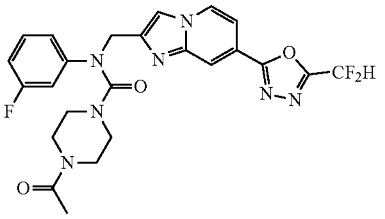 [SMILES: CC(=O)N1CCN(C(=O)N(Cc2cn3ccc(-c4nnc(C(F)F)o4)cc3n2)c2cccc(F)c2)CC1] |
| 64 | 4093 | 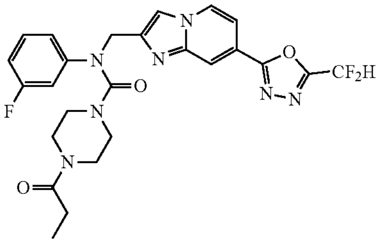 [SMILES: CCC(=O)N1CCN(C(=O)N(Cc2cn3ccc(-c4nnc(C(F)F)o4)cc3n2)c2cccc(F)c2)CC1] |
| 65 | 4094 | 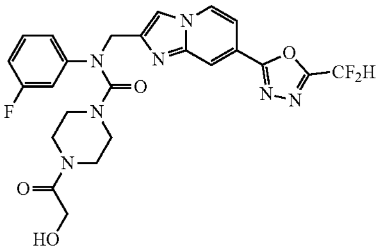 |
| 66 | 4095 | 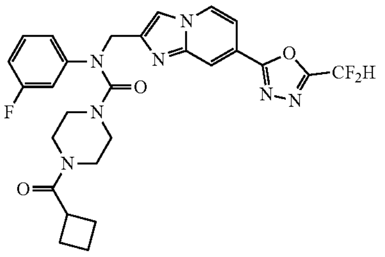 [SMILES: O=C(C1CCC1)N1CCN(C(=O)N(Cc2cn3ccc(-c4nnc(C(F)F)o4)cc3n2)c2cccc(F)c2)CC1] |
| 67 | 4096 | 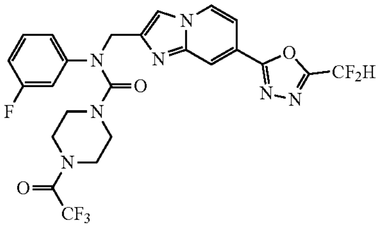 [SMILES: O=C(N1CCN(C(=O)C(F)(F)F)CC1)N(Cc1cn2ccc(-c3nnc(C(F)F)o3)cc2n1)c1cccc(F)c1] |
| 68 | 4097 | 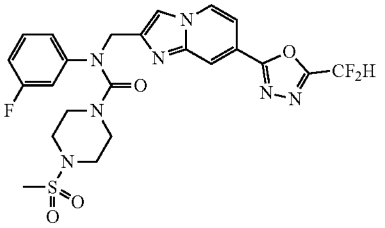 |
-continued
| Ex | Comp | Structure |
|---|---|---|
| 69 | 4098 | 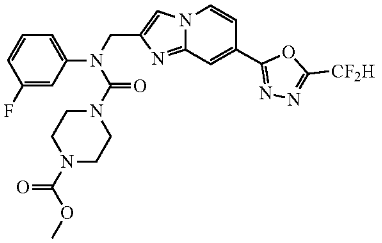 |
| 70 | 4099 | 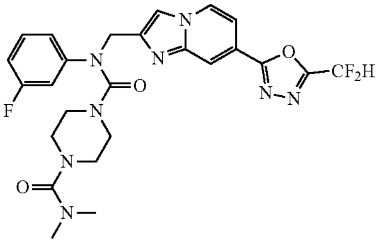 |
| 71 | 4100 | 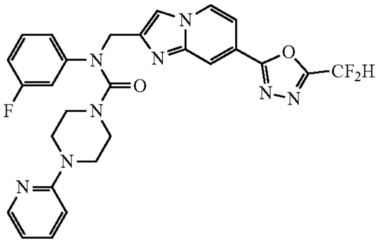 |
| 72 | 4101 | 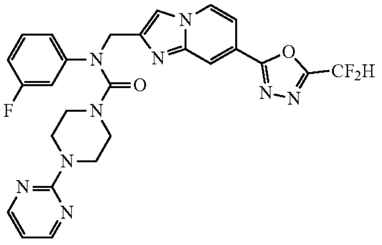 |
| 73 | 4102 | 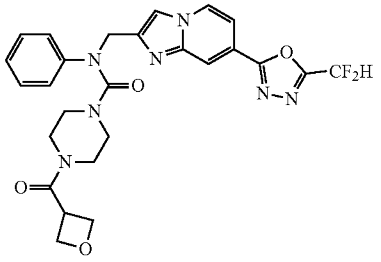 |
| 74 | 4103 | 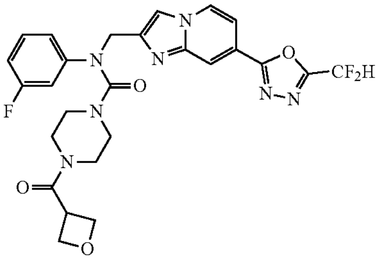 |

-continued
| Ex | Comp | Structure |
|---|---|---|
| 155 | 4620 | 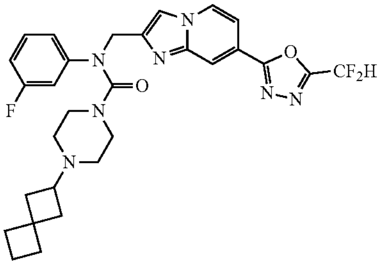 [SMILES: O=C(N1CCN(C2CC3(CCC3)C2)CC1)N(Cc1cn2ccc(-c3nnc(C(F)F)o3)cc2n1)c1cccc(F)c1] |
| 156 | 4621 | 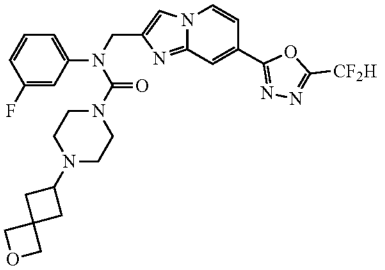 [SMILES: O=C(N1CCN(C2CC3(COC3)C2)CC1)N(Cc1cn2ccc(-c3nnc(C(F)F)o3)cc2n1)c1cccc(F)c1] |
-continued
| Ex | Comp | Structure |
|---|---|---|
| 157 | 4625 | 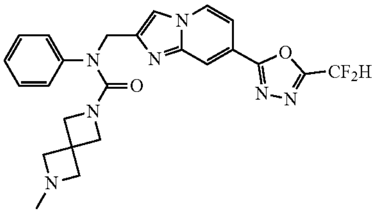 [SMILES: CN1CC2(C1)CN(C(=O)N(Cc1cn3ccc(-c4nnc(C(F)F)o4)cc3n1)c1ccccc1)C2] |
| 158 | 6892 | 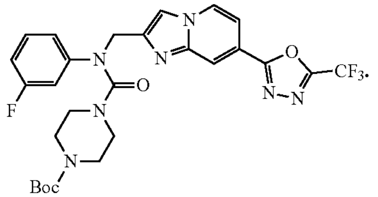 [SMILES: CC(C)(C)OC(=O)N1CCN(C(=O)N(Cc2cn3ccc(-c4nnc(C(F)(F)F)o4)cc3n2)c2cccc(F)c2)CC1] |
10. The 1,3,4-oxadiazole derivative compound, the optical isomer thereof or the pharmaceutically acceptable salt thereof according to claim 7, wherein it is any one of compounds listed in the following table:
| Ex | Comp | Structure |
|---|---|---|
| 1 | 3009 | 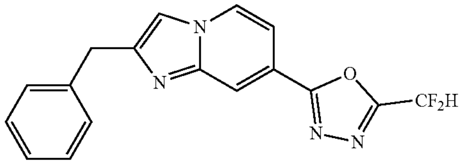 [SMILES: FC(F)c1nnc(-c2ccn3cc(Cc4ccccc4)nc3c2)o1] |
| 2 | 3585 | 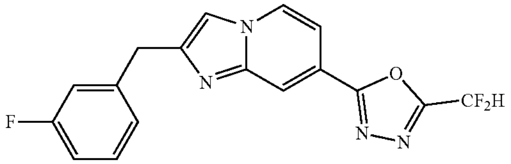 [SMILES: Fc1cccc(Cc2cn3ccc(-c4nnc(C(F)F)o4)cc3n2)c1] |
| 3 | 3586 | 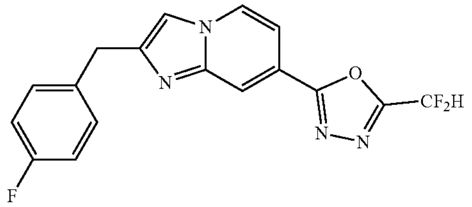 [SMILES: Fc1ccc(Cc2cn3ccc(-c4nnc(C(F)F)o4)cc3n2)cc1] |
| 4 | 3587 | 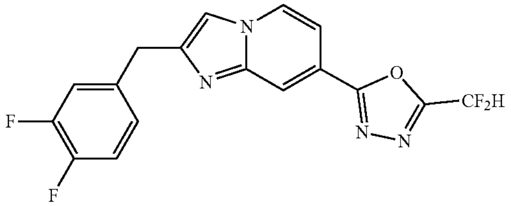 [SMILES: Fc1ccc(Cc2cn3ccc(-c4nnc(C(F)F)o4)cc3n2)cc1F] |

-continued
| Ex | Comp | Structure |
|---|---|---|
| 5 | 3588 | 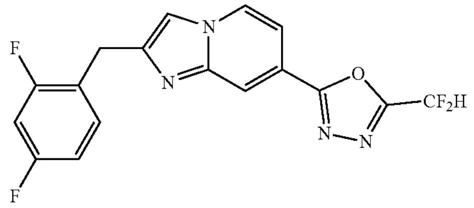 [SMILES: Fc1ccc(Cc2cn3ccc(-c4nnc(C(F)F)o4)cc3n2)c(F)c1] |
| 6 | 3589 | 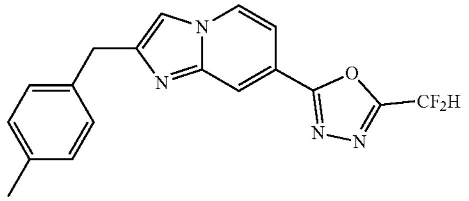 [SMILES: Cc1ccc(Cc2cn3ccc(-c4nnc(C(F)F)o4)cc3n2)cc1] |
| 7 | 3590 | 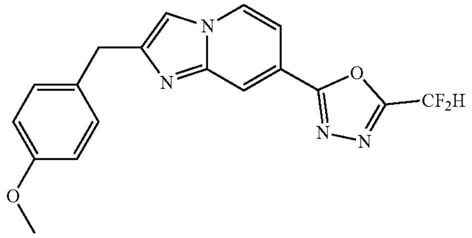 [SMILES: COc1ccc(Cc2cn3ccc(-c4nnc(C(F)F)o4)cc3n2)cc1] |
| 8 | 3591 | 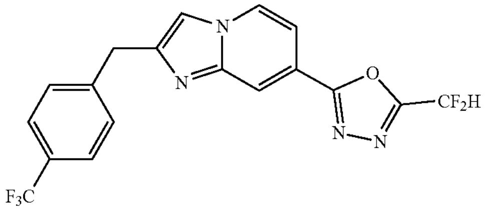 [SMILES: FC(F)c1nnc(-c2ccn3cc(Cc4ccc(C(F)(F)F)cc4)nc3c2)o1] |
| 9 | 3592 | 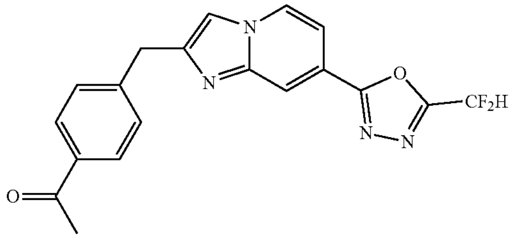 [SMILES: CC(=O)c1ccc(Cc2cn3ccc(-c4nnc(C(F)F)o4)cc3n2)cc1] |
| 10 | 3593 | 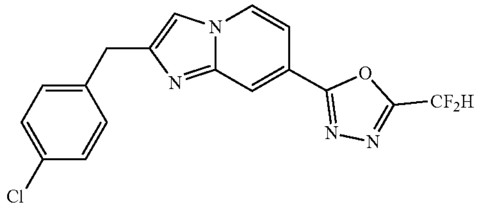 [SMILES: FC(F)c1nnc(-c2ccn3cc(Cc4ccc(Cl)cc4)nc3c2)o1] |
| 11 | 3594 | 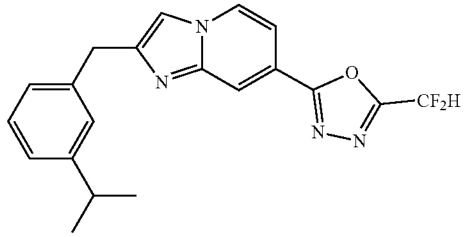 [SMILES: CC(C)c1cccc(Cc2cn3ccc(-c4nnc(C(F)F)o4)cc3n2)c1] |

-continued
| Ex | Comp | Structure |
|---|---|---|
| 12 | 3595 | 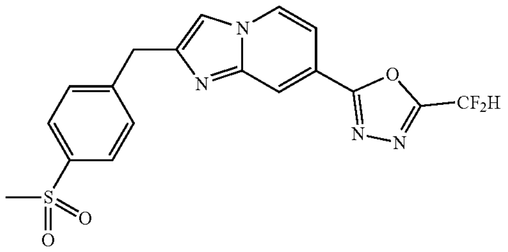 [SMILES: CS(=O)(=O)c1ccc(Cc2cn3ccc(-c4nnc(C(F)F)o4)cc3n2)cc1] |
| 13 | 3596 | 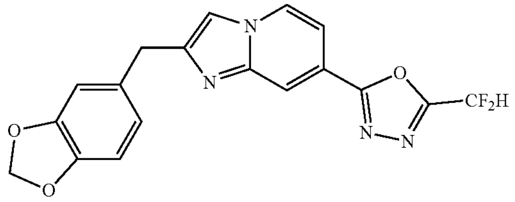 [SMILES: FC(F)c1nnc(-c2ccn3cc(Cc4ccc5c(c4)OCO5)nc3c2)o1] |
| 14 | 3668 | 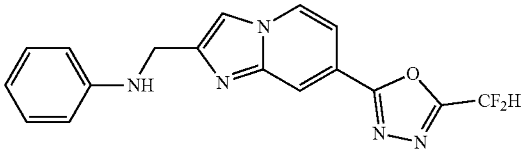 |
| 15 | 3669 | 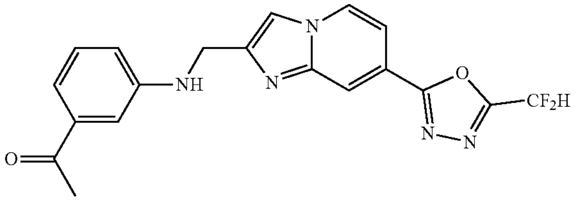 [SMILES: CC(=O)c1cccc(NCc2cn3ccc(-c4nnc(C(F)F)o4)cc3n2)c1] |
| 16 | 3670 | 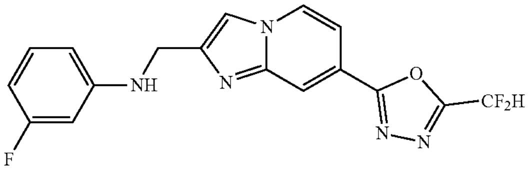 |
| 17 | 3671 | 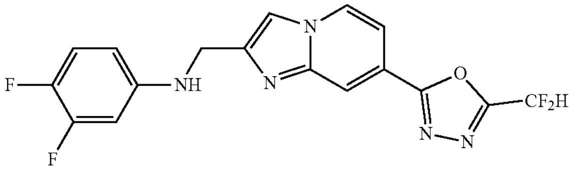 [SMILES: Fc1ccc(NCc2cn3ccc(-c4nnc(C(F)F)o4)cc3n2)cc1F] |
| 18 | 3672 | 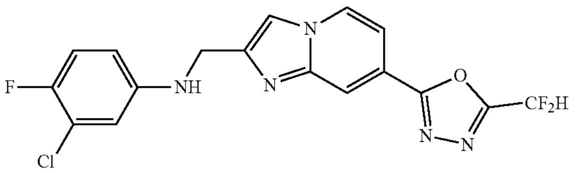 |
| 19 | 3673 | 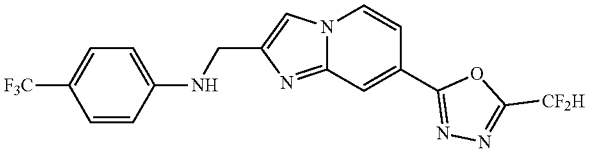 [SMILES: FC(F)c1nnc(-c2ccn3cc(CNc4ccc(C(F)(F)F)cc4)nc3c2)o1] |

-continued
| Ex | Comp | Structure |
|---|---|---|
| 20 | 3674 | 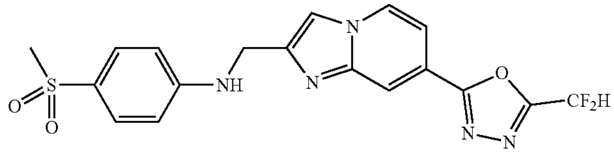 [SMILES: CS(=O)(=O)c1ccc(NCc2cn3ccc(-c4nnc(C(F)F)o4)cc3n2)cc1] |
| 21 | 3675 | 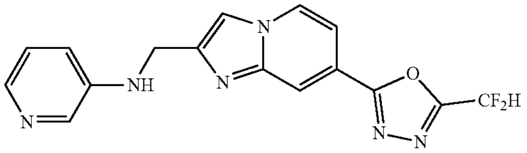 |
| 22 | 3676 | 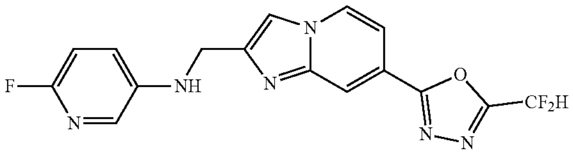 [SMILES: Fc1ccc(NCc2cn3ccc(-c4nnc(C(F)F)o4)cc3n2)cn1] |
| 23 | 3677 | 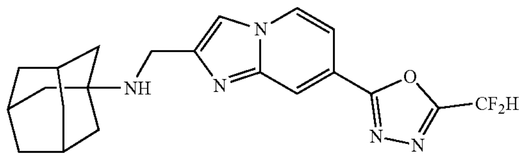 [SMILES: FC(F)c1nnc(-c2ccn3cc(CNC45CC6CC(CC(C6)C4)C5)nc3c2)o1] |
| 24 | 3678 | 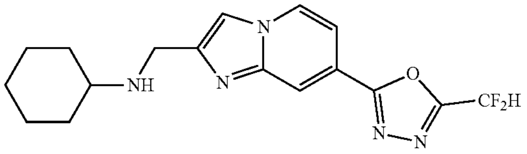 [SMILES: FC(F)c1nnc(-c2ccn3cc(CNC4CCCCC4)nc3c2)o1] |
| 25 | 3679 | 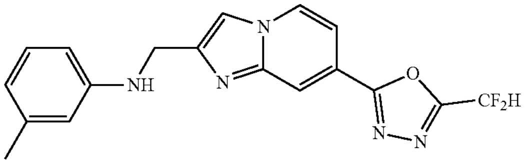 |
| 26 | 3719 | 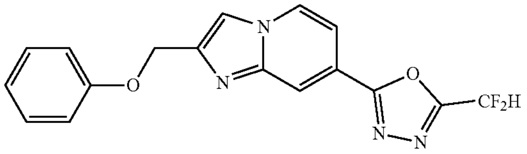 |
| 27 | 3720 | 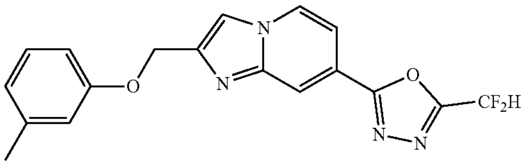 |
| 28 | 3721 | 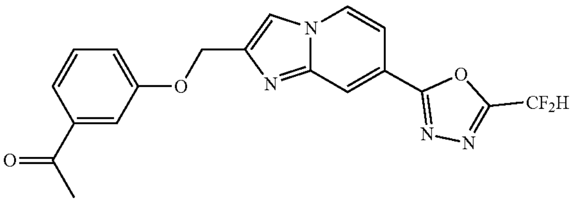 [SMILES: CC(=O)c1cccc(OCc2cn3ccc(-c4nnc(C(F)F)o4)cc3n2)c1] |

-continued

| Ex | Comp | Structure |
|---|---|---|
| 29 | 3722 | 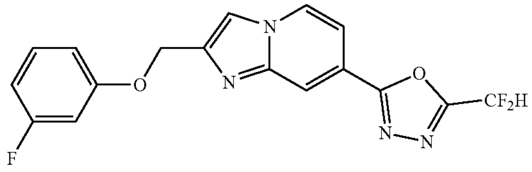 |
| 30 | 3723 | 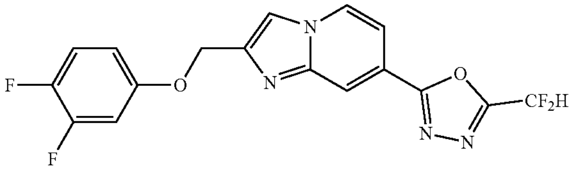 |
| 31 | 3724 | 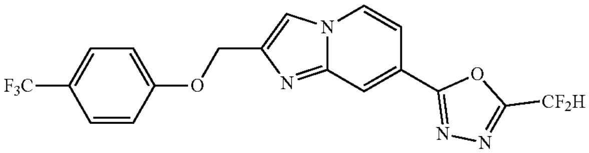 [SMILES: FC(F)c1nnc(-c2ccn3cc(COc4ccc(C(F)(F)F)cc4)nc3c2)o1] |
| 32 | 3725 | 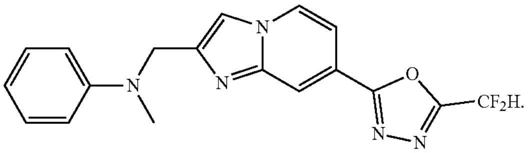 [SMILES: CN(Cc1cn2ccc(-c3nnc(C(F)F)o3)cc2n1)c1ccccc1] |

11. A pharmaceutical composition comprising the compound represented by Chemical Formula I, the optical isomer thereof, or the pharmaceutically acceptable salt thereof according to claim 1 as an active ingredient.

12. The pharmaceutical composition according to claim 11, further comprising a pharmaceutically acceptable carrier.

13. A method for inhibiting histone deacetylase 6 (HDAC6) comprising administering to a patient a therapeutically effective amount of the compound represented by Chemical Formula (I), the optical isomer thereof, or the pharmaceutically acceptable salt thereof according to claim 1 as an active ingredient.

* * * * *